(12) United States Patent
Leonard et al.

(10) Patent No.: US 9,309,222 B2
(45) Date of Patent: Apr. 12, 2016

(54) PHENYL LINKED QUINOLINYL MODULATORS OF RORγT

(71) Applicant: Janssen Pharmaceutica NV, Beerse (BE)

(72) Inventors: Kristi A. Leonard, Lansdale, PA (US); Kent Barbay, Flourtown, PA (US); James P. Edwards, San Diego, CA (US); Kevin D. Kreutter, Plainsboro, NJ (US); David A. Kummer, San Diego, CA (US); Umar Maharoof, North Wales, PA (US); Rachel Nishimura, San Diego, CA (US); Maud Urbanski, Flemington, NJ (US); Hariharan Venkatesan, San Diego, CA (US); Aihua Wang, Jamison, PA (US); Ronald L. Wolin, San Diego, CA (US); Craig R. Woods, San Diego, CA (US); Anne Fourie, San Diego, CA (US); Xiaohua Xue, San Diego, CA (US); Taraneh Mirzadegan, San Diego, CA (US); Kelly Ganamet, Ann Arbor, MI (US)

(73) Assignee: JANSSEN PHARMACEUTICA NV (BE)

( * ) Notice: Subject to any disclaimer, the term of this patent is extended or adjusted under 35 U.S.C. 154(b) by 0 days.

(21) Appl. No.: 14/053,707

(22) Filed: Oct. 15, 2013

(65) Prior Publication Data
US 2014/0107097 A1    Apr. 17, 2014

Related U.S. Application Data

(60) Provisional application No. 61/725,537, filed on Nov. 13, 2012, provisional application No. 61/714,433, filed on Oct. 16, 2012.

(51) Int. Cl.
| | | |
|---|---|---|
| C07D 401/06 | (2006.01) |
| C07D 401/14 | (2006.01) |
| A61K 31/4709 | (2006.01) |
| A61K 45/06 | (2006.01) |
| A61K 31/501 | (2006.01) |
| A61K 31/497 | (2006.01) |
| A61K 31/506 | (2006.01) |
| C07D 413/14 | (2006.01) |
| C07D 413/06 | (2006.01) |
| C07D 417/14 | (2006.01) |
| C07D 409/14 | (2006.01) |

(52) U.S. Cl.
CPC .......... *C07D 401/06* (2013.01); *A61K 31/4709* (2013.01); *A61K 31/497* (2013.01); *A61K 31/501* (2013.01); *A61K 31/506* (2013.01); *A61K 45/06* (2013.01); *C07D 401/14* (2013.01); *C07D 409/14* (2013.01); *C07D 413/06* (2013.01); *C07D 413/14* (2013.01); *C07D 417/14* (2013.01)

(58) Field of Classification Search
CPC .. C07D 417/14; C07D 413/16; C07D 413/14; C07D 409/14; C07D 401/14; C07D 401/06; A61K 45/06; A61K 31/4709
USPC .......................................... 546/159; 514/312
See application file for complete search history.

(56) References Cited

U.S. PATENT DOCUMENTS

| | | | |
|---|---|---|---|
| 3,472,859 A | 10/1969 | Lesher |
| 4,656,283 A | 4/1987 | Doehner, Jr. |
| 4,710,507 A | 12/1987 | Campbell et al. |
| 4,910,327 A | 3/1990 | Doehner, Jr. |
| 4,927,926 A | 5/1990 | Corominas et al. |
| 5,409,930 A | 4/1995 | Spada et al. |

(Continued)

FOREIGN PATENT DOCUMENTS

| | | |
|---|---|---|
| CN | 101143845 | 3/2008 |
| CN | 101899011 | 12/2010 |

(Continued)

OTHER PUBLICATIONS

Codarri, Nature Immunology, vol. 12(6), Jun. 2011, p. 560-568.*

(Continued)

*Primary Examiner* — D M Seaman
(74) *Attorney, Agent, or Firm* — Yuriy P. Stercho

(57) ABSTRACT

The present invention comprises compounds of Formula I.

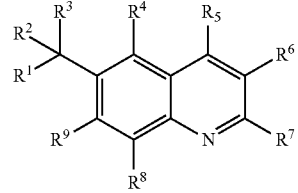

Formula I wherein:

$R^1$, $R^2$, $R^3$, $R^4$, $R^5$, $R^6$, $R^7$, $R^8$, and $R^9$ are defined in the specification.

The invention also comprises a method of treating or ameliorating a syndrome, disorder or disease, wherein said syndrome, disorder or disease is rheumatoid arthritis or psoriasis. The invention also comprises a method of modulating RORγt activity in a mammal by administration of a therapeutically effective amount of at least one compound of claim 1.

25 Claims, No Drawings

(56) References Cited

U.S. PATENT DOCUMENTS

| | | | |
|---|---|---|---|
| 5,780,634 | A | 7/1998 | Inoue et al. |
| 6,248,739 | B1 | 6/2001 | Turner et al. |
| 6,451,812 | B1* | 9/2002 | End et al. .................. 514/312 |
| 6,624,159 | B2 | 9/2003 | Anderson et al. |
| 6,686,356 | B2 | 2/2004 | Strohbach et al. |
| 6,743,805 | B2* | 6/2004 | End et al. .................. 514/312 |
| 7,053,105 | B2 | 5/2006 | Angibaud et al. |
| 7,652,014 | B2 | 1/2010 | Mabire et al. |
| 7,902,225 | B2 | 3/2011 | Guillemont et al. |
| 8,017,606 | B2 | 9/2011 | Andries et al. |
| 8,389,739 | B1 | 3/2013 | Thacher et al. |
| 2003/0166675 | A1 | 9/2003 | Yang |
| 2005/0131014 | A1 | 6/2005 | Collini et al. |
| 2007/0072844 | A1 | 3/2007 | Jones et al. |
| 2008/0188521 | A1 | 8/2008 | Grimm et al. |
| 2009/0197859 | A1 | 8/2009 | Collantes et al. |
| 2009/0286829 | A1 | 11/2009 | Heidelbaugh et al. |
| 2010/0311760 | A1 | 12/2010 | de Vicente Fidalgo et al. |
| 2011/0124870 | A1 | 5/2011 | Guillemont et al. |
| 2012/0322837 | A1 | 12/2012 | Maeba et al. |

FOREIGN PATENT DOCUMENTS

| | | |
|---|---|---|
| EP | 371564 A2 | 6/1990 |
| EP | 709377 A1 | 5/1996 |
| EP | 1106612 A1 | 6/2001 |
| EP | 2368886 A1 | 9/2011 |
| GB | 2095668 A | 10/1982 |
| JP | 48026772 | 4/1973 |
| JP | 2000169451 A | 6/2000 |
| WO | WO 9718208 A1 | 5/1997 |
| WO | WO 9721701 A1 | 6/1997 |
| WO | WO 9744339 A1 | 11/1997 |
| WO | WO 9855124 A1 | 12/1998 |
| WO | WO 9932450 A1 | 7/1999 |
| WO | WO 9950660 A1 | 10/1999 |
| WO | WO 0001386 A1 | 1/2000 |
| WO | WO 0001411 A1 | 1/2000 |
| WO | WO 0001714 A1 | 1/2000 |
| WO | WO 0039082 A2 | 7/2000 |
| WO | WO 0040561 A1 | 7/2000 |
| WO | WO 0040563 A1 | 7/2000 |
| WO | WO 0047574 A1 | 8/2000 |
| WO | WO 0156552 A2 | 8/2001 |
| WO | WO 0162234 A2 | 8/2001 |
| WO | WO 0164194 A2 | 9/2001 |
| WO | WO 0164195 A2 | 9/2001 |
| WO | WO 0164196 A2 | 9/2001 |
| WO | WO 0164197 A2 | 9/2001 |
| WO | WO 0164198 A2 | 9/2001 |
| WO | WO 0164199 A2 | 9/2001 |
| WO | WO 0164217 A2 | 9/2001 |
| WO | WO 0164218 A2 | 9/2001 |
| WO | WO 0164226 A2 | 9/2001 |
| WO | WO 0164246 A2 | 9/2001 |
| WO | WO 0164252 A2 | 9/2001 |
| WO | WO 0202558 A1 | 1/2002 |
| WO | WO 0204445 A1 | 1/2002 |
| WO | WO 0204462 A1 | 1/2002 |
| WO | WO 0224682 A1 | 3/2002 |
| WO | WO 0224686 A2 | 3/2002 |
| WO | WO 0224687 A1 | 3/2002 |
| WO | WO 0228837 A1 | 4/2002 |
| WO | WO 0243733 A1 | 6/2002 |
| WO | WO 02051835 A1 | 7/2002 |
| WO | WO 02064142 A1 | 8/2002 |
| WO | WO 02070487 A1 | 9/2002 |
| WO | WO 02085364 A1 | 10/2002 |
| WO | WO 03/000705 | 1/2003 |
| WO | WO 03053971 A1 | 7/2003 |
| WO | WO 03053972 A1 | 7/2003 |
| WO | WO 03082350 A2 | 10/2003 |
| WO | WO 2004019932 A1 | 3/2004 |
| WO | WO 2004024693 A1 | 3/2004 |
| WO | WO 2004037792 A2 | 5/2004 |
| WO | WO 2005054201 A1 | 6/2005 |
| WO | WO 2005054210 A1 | 6/2005 |
| WO | WO 2005058843 A1 | 6/2005 |
| WO | WO 2005070430 A1 | 8/2005 |
| WO | WO 2005075428 A1 | 8/2005 |
| WO | WO 2006003146 A1 | 1/2006 |
| WO | WO 2006013896 A1 | 2/2006 |
| WO | WO 2006025683 | 3/2006 |
| WO | WO 2006052718 A2 | 5/2006 |
| WO | WO 2007014940 A2 | 2/2007 |
| WO | WO 2007014941 A2 | 2/2007 |
| WO | WO 2007088978 A1 | 8/2007 |
| WO | WO 2008051805 A2 | 5/2008 |
| WO | WO 2008068267 A1 | 6/2008 |
| WO | WO 2008098104 A8 | 8/2008 |
| WO | WO 2008112525 A2 | 9/2008 |
| WO | WO 2008144767 A1 | 11/2008 |
| WO | WO 2009091735 A1 | 7/2009 |
| WO | WO 2009140138 A1 | 11/2009 |
| WO | WO 2010068296 A1 | 6/2010 |
| WO | WO 2010127208 A1 | 11/2010 |
| WO | WO 2010151740 A4 | 12/2010 |
| WO | WO 2011020861 A1 | 2/2011 |
| WO | WO 2011112264 A1 | 9/2011 |
| WO | WO 2011130707 A2 | 10/2011 |
| WO | WO 2012064744 A2 | 5/2012 |
| WO | WO 2012116137 A2 | 8/2012 |
| WO | WO 2012158784 A2 | 11/2012 |
| WO | WO 2013061074 A1 | 5/2013 |
| WO | WO 2013064231 A1 | 5/2013 |
| WO | WO 2013079223 A1 | 6/2013 |

OTHER PUBLICATIONS

U.S. Appl. No. 14/053,736.
U.S. Appl. No. 14/053,773.
U.S. Appl. No. 14/053,797.
U.S. Appl. No. 14/053,906.
U.S. Appl. No. 14/053,682.
U.S. Appl. No. 14/053,653.
International Search Report—PCT/US2013/065007, Jan. 7, 2014.
International Search Report—PCT/US2013/065013, Dec. 16, 2013.
International Search Report—PCT/US2013/065031, Dec. 13, 2013.
International Search Report—PCT/US2013/065040, Dec. 16, 2013.
International Search Report—PCT/US2013/065048, Dec. 3, 2013.
International Search Report—PCT/US2013/065053, Jan. 7, 2014.
International Search Report—PCT/US2013/065026, Feb. 21, 2014.
Bink A, (A fungicidal piperazine-1-carboxamidine induces mitochondrial fission-dependent apoptosis in yeast), FEMS Yeast Research (2010), 10(7), 812-818.
Nieman J, (Modifications of C-2 on the pyrroloquinoline template aimed at the development of potent herpes virus antivirals with improved aqueous solubility), Bioorganic & Medicinal Chemistry Letters (2010), 20(10), 3039-3042.
Tanis S, (The design and development of 2-aryl-2-hydroxy ethylamine substituted 1H,7H-pyrido[1,2,3-de]quinoxaline-6-carboxamides as inhibitors of human cytomegalovirus polymerase), Bioorganic & Medicinal Chemistry Letters (2010), 20(6), 1994-2000.
Mao D, (Synthesis and Na+/H+ Exchanger-1 Inhibitory Activity of Substituted (Quinolinecarbonyl)guanidine Derivatives), Chemistry & Biodiversity (2009), 6(10), 1727-1736.
Sato M, (Quinolone Carboxylic Acids as a Novel Monoketo Acid Class of Human Immunodeficiency Virus Type 1 Integrase Inhibitors), Journal of Medicinal Chemistry (2009), 52(15), 4869-4882.
Aghera V, (Synthesis, spectral and microbial studies of some novel quinoline derivatives via Vilsmeier-Haack reagent) Journal; (online computer file) URL: http://www.arkat-usa.org/get-file/25177/.
Inada T, (One-step synthesis of ethyl quinaldates by Lewis acid-catalyzed three-component coupling reaction of aromatic amines, aliphatic aldehydes, and ethyl glyoxylate), Heterocycles (2005), 66, 611-619.
Zelenin A, (Reaction of polyfluoro carbonyl compounds with 1,2,3,4-tetrahydroquinoline), Izvestiya Akademii Nauk SSSR, Seriya Khimicheskaya (1986), (9), 2074-80 Abstract Only.

(56) References Cited

OTHER PUBLICATIONS

Hirao I, (Studies on the synthesis of quinoline compounds. I. Syntheses of 3,3'-dicarboxy-1,1'-diethyl-4,4'-dioxo-1,1',4,4'-tetrahydrobiquinolines), Memoirs of the Kyushu Institute of Technology, Engineering (1984), 14, 13-16.
Abdul-Ahad P, (Trends in dehydrogenase inhibitory potencies of some quinolones, using quantum chemical indices), European Journal of Medicinal Chemistry (1982), 17(4), 301-6.
Baker B, (Irreversible enzyme inhibitors. 191. Hydrophobic bonding to some dehydrogenases by 6-, 7-, or 8-substituted-4-hydroxyquinoline-3-carboxylic acids), Journal of Medicinal Chemistry (1972), 15(3), 235-7.
Ramachary D, (A novel and green protocol for two-carbon homologation: a direct amino acid/K2CO3-catalyzed four-component reaction of aldehydes, active methylenes, Hantzsch esters and alkyl halides), Tetrahedron Letters (2006) 47, 651-656.
Dong C, (Diversification of T-helper-cell lineages: finding the family root of IL-17-producing cells), Nat Rev Immunol (2006), 6(4), 329-333.
McKenzie B, (Understanding the IL-23-IL-17 immune pathway), Trends Immunol (2006), 27(1), 17-23.
Ivanov II B, (The orphan nuclear receptor RORgammat directs the differentiation program of proinflammatory IL-17+ T helper cells), Cell (2006), 126(6), 1121-33.
Cua, D (Interleukin-23 rather than interleukin-12 is the critical cytokine for autoimmune inflammation of the brain), Nature (2003), 421(6924), 744-748.
Langrish C, (IL-23 drives a pathogenic T cell population that induces autoimmune inflammation), J Exp Med (2005), 201(2), 233-240.
Tonel G, (Cutting edge: A critical functional role for IL-23 in psoriasis), J Immunol (2010), 185(10), 5688-5691.
Barczyk A, (Interleukin-17 in sputum correlates with airway hyperresponsiveness to methacholine), Respir Med (2003), 97(6), 726-733.
Lock C, (Gene-microarray analysis of multiple sclerosis lesions yields new targets validated in autoimmune encephalomyelitis) Nat Med (2002), 8(5), 500-8.
Papp K, (Brodalumab, an anti-interleukin-17-receptor antibody for psoriasis), N Engl J Med (2012), 366(13), 1181-1189.
Leonardi C, (Anti-interleukin-17 monoclonal antibody ixekizumab in chronic plaque psoriasis), N Engl J Med (2012), 366(13), 1190-1199.
Hueber W, (Effects of AIN457, a fully human antibody to interleukin-17A, on psoriasis, rheumatoid arthritis, and uveitis), Sci Transl Med (2010), 2, 5272.
Gao W, (Clean and Convienient One-Pot Synthesis of 4-Hydroxycoumarin and 4-Hydroxy-2-Quinolone Derivatives), Synthetic Communications (2010) 40, 732-738.
Moriarty R, Organic Reactions (2001), 57, 327-415.
Pongratz E, et al., (Ylide von Heterocyclen, VIII Reaktionen von Iodonium-Yliden mit Säuren), Monatshefte fur Chemie (1984) 115(2), 231-242.
Osborne A, (Regioselective Al koxydehalogenation of 2,4-Di halogenoquinolines and a Reinvestigation of the Bromination of 2-Methoxyquinoline), J Chem Soc Perkin Trans 1 (1993), 181-184.
Osborne A, (Further studies of regioselective alkoxydehalogenation of 2,4-dichloroquinolines, 2,6-dichloropyridine and 2,4-dichloronitrobenzene), J Chem Research (S) (2002), 4.
Ramachary D, (Development of Pharmaceutical Drugs, Drug Intermediates and Ingredients by Using Direct Organo-Click Reactions), Eur. J. Org. Chem. (2008), 975-993.
Korn T, (IL-17 and Th17 Cells), Annual Reviews of Immunology (2009), 27, 485-517.
Kolls J, (Interleukin-17 family members and inflammation), Immunity (2004), 21(4), 467-476.
Stamp L, (Interleukin-17: the missing link between T-cell accumulation and effector cell actions in rheumatoid arthritis), Immunol Cell Biol (2004), 82(1), 1-9.
Kamenecka T, (Synthetic modulators of the retinoic acid receptor-related orphan receptors), Med Chem Commun (2013), 4, 764-776.
Yen D, (IL-23 is essential for T cell-mediated colitis and promotes inflammation via IL-17 and IL-6), J Clin Invest (2006), 116(5), 1310-1316.
Fujino S, (Increased expression of interleukin 17 in inflammatory bowel disease) Gut (2003), 52(1), 65-70.
Krueger J, (IL-17A is essential for cell activation and inflammatory gene circuits in subjects with psoriasis) J Allergy Clin Immunol (2012), 130(1), 145-154.
Nunez C, (IL23R: a susceptibility locus for celiac disease and multiple sclerosis?) Genes Immun (2008), 9(4), 289-93.
Bowes J, (The genetics of psoriatic arthritis: lessons from genome-wide association studies), Discov Med (2010), 10(52), 177-83.
Kochi Y, (A regulatory variant in CCR6 is associated with rheumatoid arthritis susceptibility), Nat Genet (2010), 42(6), 515-9.
Garber K, (Psoriasis: from bed to bench and back), Nat Biotech (2011), 29, 563-566.
Madrid P, et al. (Synthesis of ring-substituted 4-aminoquinolines and evaluation of their antimalarial activities), Bioorganic & Medicinal Chemistry Letters (2005), 15, 1015-1018.
Gore T, (Synthesis of substituted 6,6'-biquinolines from ethyl ethoxymethyleneacetoacetate), Indian Journal of Chemistry (1965), 3(2), 90-1.
Gazouli, M, (NOD2/CARD15, ATG16L1 and IL23R gene polymorphisms and childhood-onset of Crohn's disease) World J. Gastroenterol (2010) 16(14), 1753-8.
Knochel P, (Preparation of Polyfunctional Ketones by a Cobalt(II) Mediated Carbonylation of Organozinc Reagents), Tetrahedron Letters (1995), 36(46), 8411-8414.
International Search Report—PCT/US2014/60372, Mar. 27, 2015.
International Search Report—PCT/US2014/60375, Mar. 26, 2015.
U.S. Appl. No. 14/053,653, Office Action dated Sep. 15, 2014.
U.S. Appl. No. 14/053,653, Notice of Allowance dated Mar. 30, 2015.
U.S. Appl. No. 14/053,682, Office Action dated Sep. 12, 2014.
U.S. Appl. No. 14/053,682, Notice of Allowance dated Sep. 12, 2014.
U.S. Appl. No. 14/053,707, Office Action dated Sep. 11, 2014.
U.S. Appl. No. 14/053,707, Notice of Allowance dated Sep. 11, 2014.
U.S. Appl. No. 12/053,736, Office action dated Mar. 26, 2015.
U.S. Appl. No. 14/053,736, Office Action dated Oct. 3, 2014.
U.S. Appl. No. 14/053,773, Office Action dated Apr. 6, 2015.
U.S. Appl. No. 14/053,773, Office Action dated Jan. 9, 2015.
U.S. Appl. No. 14/053,797, Office Action dated Sep. 12, 2014.
U.S. Appl. No. 14/053,797, Notice of Allowance Apr. 7, 2015.
U.S. Appl. No. 14/513,426, Office Action dated Apr. 16, 2015.
U.S. Appl. No. 14/513,455, Office Action dated Apr. 28, 2015.
U.S. Appl. No. 14/053,906, Office Action dated Sep. 12, 2004.
U.S. Appl. No. 14/053,906, Notice of Allowance dated Mar. 23, 2015.
Dorwald F. A. "Slide Reactions in Organic Synthesis", 2005, Wiley: VCH, Weinheim p. IX of Preface pp. 1-15.
Venkatesh, et al. "Role of the Development Scientist in Compound Lead Selection and Optimization", J. Pharm. Sci. vol. 89, No. 2, pp. 145-154 2000.
Hiro, STN Document No. 102: 149081 Abstract of Memoirs of the Kyushu Institute of Technology, Engineering (1984), vol. 14, pp. 13-16.
STN Search Report Mar. 12, 2015, RN 1347913-41-0.

\* cited by examiner

PHENYL LINKED QUINOLINYL MODULATORS OF RORγT

CROSS-REFERENCE TO RELATED APPLICATIONS

This application claims priority from U.S. Application No. 61/714,433, filed on Oct. 16, 2012, and U.S. Application No. 61/725,537, filed on Nov. 13, 2012, each of which is incorporated herein by reference.

FIELD OF THE INVENTION

The invention is directed to substituted quinoline compounds, which are modulators of the nuclear receptor RORγt, pharmaceutical compositions, and methods for use thereof. More particularly, the RORγt modulators are useful for preventing, treating or ameliorating an RORγt mediated inflammatory syndrome, disorder or disease.

BACKGROUND OF THE INVENTION

Retinoic acid-related nuclear receptor gamma t (RORγt) is a nuclear receptor, exclusively expressed in cells of the immune system, and a key transcription factor driving Th17 cell differentiation. Th17 cells are a subset of $CD4^+$ T cells, expressing CCR6 on their surface to mediate their migration to sites of inflammation, and dependent on IL-23 stimulation, through the IL-23 receptor, for their maintenance and expansion. Th17 cells produce several proinflammatory cytokines including IL-17A, IL-17F, IL-21, and IL-22 (Korn, T., E. Bettelli, et al. (2009). "IL-17 and Th17 Cells." Annu Rev Immunol 27: 485-517.), which stimulate tissue cells to produce a panel of inflammatory chemokines, cytokines and metalloproteases, and promote recruitment of granulocytes (Kolls, J. K. and A. Linden (2004). "Interleukin-17 family members and inflammation." Immunity 21(4): 467-76; Stamp, L. K., M. J. James, et al. (2004). "Interleukin-17: the missing link between T-cell accumulation and effector cell actions in rheumatoid arthritis" Immunol Cell Biol 82(1): 1-9). Th17 cells have been shown to be the major pathogenic population in several models of autoimmune inflammation, including collagen-induced arthritis (CIA) and experimental autoimmune encephalomyelitis (EAE) (Dong, C. (2006). "Diversification of T-helper-cell lineages: finding the family root of IL-17-producing cells." Nat Rev Immunol 6(4): 329-33; McKenzie, B. S., R. A. Kastelein, et al. (2006). "Understanding the IL-23-IL-17 immune pathway." Trends Immunol 27(1): 17-23.). RORγt-deficient mice are healthy and reproduce normally, but have shown impaired Th17 cell differentiation in vitro, a significantly reduced Th17 cell population in vivo, and decreased susceptibility to EAE (Ivanov, I I, B. S. McKenzie, et al. (2006). "The orphan nuclear receptor ROR-gammat directs the differentiation program of proinflammatory IL-17+ T helper cells." Cell 126(6): 1121-33.). Mice deficient for IL-23, a cytokine required for Th17 cell survival, fail to produce Th17 cells and are resistant to EAE, CIA, and inflammatory bowel disease (IBD) (Cua, D. J., J. Sherlock, et al. (2003). "Interleukin-23 rather than interleukin-12 is the critical cytokine for autoimmune inflammation of the brain." Nature 421(6924): 744-8.; Langrish, C. L., Y. Chen, et al. (2005). "IL-23 drives a pathogenic T cell population that induces autoimmune inflammation." J Exp Med 201(2): 233-40; Yen, D., J. Cheung, et al. (2006). "IL-23 is essential for T cell-mediated colitis and promotes inflammation via IL-17 and IL-6." J Clin Invest 116(5): 1310-6.). Consistent with these findings, an anti-IL23-specific monoclonal antibody blocks development of psoriasis-like inflammation in a murine disease model (Tonel, G., C. Conrad, et al. "Cutting edge: A critical functional role for IL-23 in psoriasis." J Immunol 185(10): 5688-91).

In humans, a number of observations support the role of the IL-23/Th17 pathway in the pathogenesis of inflammatory diseases. IL-17, the key cytokine produced by Th17 cells, is expressed at elevated levels in a variety of allergic and autoimmune diseases (Barczyk, A., W. Pierzchala, et al. (2003). "Interleukin-17 in sputum correlates with airway hyperresponsiveness to methacholine." Respir Med 97(6): 726-33.; Fujino, S., A. Andoh, et al. (2003). "Increased expression of interleukin 17 in inflammatory bowel disease." Gut 52(1): 65-70.; Lock, C., G. Hermans, et al. (2002). "Gene-microarray analysis of multiple sclerosis lesions yields new targets validated in autoimmune encephalomyelitis." Nat Med 8(5): 500-8.; Krueger, J. G., S. Fretzin, et al. "IL-17A is essential for cell activation and inflammatory gene circuits in subjects with psoriasis." J Allergy Clin Immunol 130(1): 145-154 e9.). Furthermore, human genetic studies have shown association of polymorphisms in the genes for Th17 cell-surface receptors, IL-23R and CCR6, with susceptibility to IBD, multiple sclerosis (MS), rheumatoid arthritis (RA) and psoriasis (Gazouli, M., I. Pachoula, et al. "NOD2/CARD15, ATG16L1 and IL23R gene polymorphisms and childhood-onset of Crohn's disease." World J Gastroenterol 16(14): 1753-8., Nunez, C., B. Dema, et al. (2008). "IL23R: a susceptibility locus for celiac disease and multiple sclerosis?" Genes Immun 9(4): 289-93.; Bowes, J. and A. Barton "The genetics of psoriatic arthritis: lessons from genome-wide association studies." Discov Med 10(52): 177-83; Kochi, Y., Y. Okada, et al. "A regulatory variant in CCR6 is associated with rheumatoid arthritis susceptibility." Nat Genet. 42(6): 515-9.).

Ustekinumab (Stelara®), an anti-p40 monoclonal antibody blocking both IL-12 and IL-23, is approved for the treatment of adult patients (18 years or older), with moderate to severe plaque psoriasis, who are candidates for phototherapy or systemic therapy. Currently, monoclonal antibodies specifically targeting only IL-23, to more selectively inhibit the Th17 subset, are also in clinical development for psoriasis (Garber K. (2011). "Psoriasis: from bed to bench and back" Nat Biotech 29, 563-566), further implicating the important role of the IL-23- and RORγt-driven Th17 pathway in this disease. Results from recent phase II clinical studies strongly support this hypothesis, as anti-IL-17 receptor and anti-IL-17 therapeutic antibodies both demonstrated high levels of efficacy in patients with chronic psoriasis (Papp, K. A., "Brodalumab, an anti-interleukin-17-receptor antibody for psoriasis." N Engl J Med 2012 366(13): 1181-9.; Leonardi, C., R. Matheson, et al. "Anti-interleukin-17 monoclonal antibody ixekizumab in chronic plaque psoriasis." N Engl J Med 366(13): 1190-9.). Anti-IL-17 antibodies have also demonstrated clinically relevant responses in early trials in RA and uveitis (Hueber, W., Patel, D. D., Dryja, T., Wright, A. M., Koroleva, I., Bruin, G., Antoni, C., Draelos, Z., Gold, M. H., Durez, P., Tak, P. P., Gomez-Reino, J. J., Foster, C. S., Kim, R. Y., Samson, C. M., Falk, N. S., Chu, D. S., Callanan, D., Nguyen, Q. D., Rose, K., Haider, A., Di Padova, F. (2010) Effects of AIN457, a fully human antibody to interleukin-17A, on psoriasis, rheumatoid arthritis, and uveitis. Sci Transl Med 2, 5272.).

All the above evidence supports inhibition of the Th17 pathway by modulating RORγt activity as an effective strategy for the treatment of immune-mediated inflammatory diseases.

SUMMARY OF THE INVENTION

The present invention comprises compounds of Formula I.

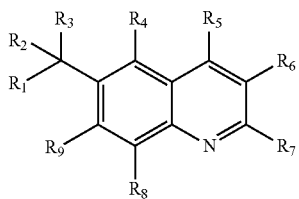

Formula I wherein:

$R^1$ is pyrrolyl, pyrazolyl, imidazolyl, triazolyl, thiazolyl, pyridyl, pyridyl N-oxide, pyrazinyl, pyrimidinyl, pyridazyl, piperidinyl, quinazolinyl, cinnolinyl, benzothiazolyl, indazolyl, tetrahydropyranyl, tetrahydrofuranyl, furanyl, phenyl, oxazolyl, isoxazolyl, thiophenyl, benzoxazolyl, benzimidazolyl, indolyl, thiadiazolyl, oxadiazolyl or quinolinyl; wherein said pyridyl, pyridyl-N-oxide, pyrazinyl, pyrimidinyl, pyridazyl, piperidinyl, quinazolinyl, cinnolinyl, benzothiazolyl, indazolyl, imidazolyl, phenyl, thiophenyl, benzoxazolyl, benzimidazolyl, indolyl, quinolinyl, and pyrazolyl are optionally substituted with $C(O)C_{(1-4)}$alkyl, $C(O)NH_2$, $C(O)NHC_{(1-2)}$alkyl, $C(O)N(C_{(1-2)}$alkyl$)_2$, $NHC(O)C_{(1-4)}$alkyl, $NHSO_2C_{(1-4)}$alkyl, $C_{(1-4)}$alkyl, $CF_3$, $CH_2CF_3$, Cl, F, —CN, $OC_{(1-4)}$alkyl, $N(C_{(1-4)}$alkyl$)_2$, —$(CH_2)_3OCH_3$, $SC_{(1-4)}$alkyl, OH, $CO_2H$, $CO_2C_{(1-4)}$alkyl, $C(O)CF_3$, $SO_2CF_3$, $OCF_3$, $OCHF_2$, $SO_2CH_3$, $SO_2NH_2$, $SO_2NHC_{(1-2)}$alkyl, $SO_2N(C_{(1-2)}$alkyl$)_2$, $C(O)NHSO_2CH_3$, or $OCH_2OCH_3$; and optionally substituted with up to two additional substituents independently selected from the group consisting of Cl, $C_{(1-2)}$alkyl, $SCH_3$, $OC_{(1-2)}$alkyl, $CF_3$, —CN, and F; and wherein said triazolyl, oxazolyl, isoxazolyl, pyrrolyl, and thiazolyl are optionally substituted with up to two substituents independently selected from the group consisting of $SO_2CH_3$, $SO_2NH_2$, $C(O)NH_2$, —CN, $OC_{(1-2)}$alkyl, $(CH_2)_{(2-3)}OCH_3$, $SCH_3$, $CF_3$, F, Cl, and $C_{(1-2)}$alkyl; and said thiadiazolyl and oxadiazolyl are optionally substituted with $C_{(1-2)}$alkyl; and said pyridyl, pyridyl-N-oxide, pyrimidinyl, pyridazyl, and pyrazinyl are optionally substituted with up to three additional substituents independently selected from the group consisting of $C(O)NHC_{(1-2)}$alkyl, $C(O)N(C_{(1-2)}$alkyl$)_2$, NHC(O)$C_{(1-4)}$alkyl, $NHSO_2C_{(1-4)}$alkyl, $C(O)CF_3$, $SO_2CF_3$, $SO_2NHC_{(1-2)}$alkyl, $SO_2N(C_{(1-2)}$alkyl$)_2$, $C(O)NHSO_2CH_3$, $SO_2CH_3$, $SO_2NH_2$, $C(O)NH_2$, —CN, $OC_{(1-4)}$alkyl, $(CH_2)_{(2-3)}OCH_3$ (including —$(CH_2)_3OCH_3$), $SC_{(1-4)}$alkyl, $CF_3$, F, Cl, and $C_{(1-4)}$alkyl;

$R^2$ is triazolyl, pyridyl, pyridyl-N-oxide, pyrazolyl, pyrimidinyl, oxazolyl, isoxazolyl, N-acetyl piperidinyl, 1-H-piperidinyl, N-Boc-piperidinyl, N—$C_{(1-3)}$alkyl-piperidinyl, thiazolyl, pyridazyl, pyrazinyl, 1-(3-methoxypropyl)-imidazolyl, thiadiazolyl, oxadiazolyl, or imidazolyl; wherein said imidazolyl is optionally substituted with up to three additional substituents independently selected from the group consisting of $C_{(1-2)}$alkyl, $SCH_3$, $OC_{(1-2)}$alkyl, $CF_3$, —CN, F, and Cl; and said pyridyl, pyridyl-N-oxide, pyrimidinyl, pyridazyl, and pyrazinyl, are optionally substituted with up to three additional substituents independently selected from the group consisting of $SO_2CH_3$, $SO_2NH_2$, $C(O)NH_2$, —CN, $OC_{(1-2)}$alkyl, $(CH_2)_{(2-3)}OCH_3$, $SCH_3$, $CF_3$, F, Cl, or $C_{(1-2)}$alkyl; and said triazolyl, thiazolyl, oxazolyl and isoxazolyl are optionally substituted with up to two substituents independently selected from the group consisting of $SO_2CH_3$, $SO_2NH_2$, $C(O)NH_2$, —CN, $OC_{(1-2)}$alkyl, $(CH_2)_{(2-3)}OCH_3$, $SCH_3$, $CF_3$, F, Cl, and $C_{(1-2)}$alkyl; and said thiadiazolyl and oxadiazolyl are optionally substituted with $C_{(1-2)}$alkyl; and said pyrazolyl is optionally substituted with up to three $CH_3$ groups;

$R^3$ is H, OH, $OCH_3$, or $NH_2$;

$R^4$ is H, or F;

$R^5$ is H, Cl, —CN, $CF_3$, $SC_{(1-4)}$alkyl, $OC_{(1-4)}$alkyl, OH, $C_{(1-4)}$alkyl, $N(CH_3)OCH_3$, $NH(C_{(1-4)}$alkyl), $N(C_{(1-4)}$alkyl$)_2$, or 4-hydroxy-piperidinyl;

$R^6$ is pyridyl, pyrimidinyl, pyridazyl, pyrazinyl, thiazolyl, isothiazolyl, furanyl, thiophenyl, oxazolyl, isoxazolyl, imidazolyl, pyrazolyl, pyrrolyl, triazolyl, oxadiazolyl, thiadiazolyl, or phenyl, any of which is optionally substituted with up to two substituents independently selected from the group consisting of piperidinyl, pyrrolidinyl, azetidinyl, pyrazolyl, triazolyl, imidazolyl, —CN, $C_{(1-4)}$alkyl (including $CH_3$), $OC_{(1-4)}$alkyl, $C(O)C_{(1-4)}$alkyl, $CO_2H$, $CO_2C_{(1-4)}$alkyl, $NH_2$, $NHC_{(1-2)}$alkyl, $N(C_{(1-2)}$alkyl$)_2$, $SONH_2$, $SON(CH_3)_2$, $SO_2NH_2$, $SO_2NHC_{(1-2)}$alkyl, $SO_2N(C_{(1-2)}$alkyl$)_2$, $SCH_3$, $OCH_2CF_3$, $SO_2CH_3$, $CF_3$, Cl, F, OH, and $OCF_3$;

$R^7$ is H, Cl, —CN, $C_{(1-4)}$alkyl, $OC_{(1-4)}$alkyl$CF_3$, $OCF_3$, $OCHF_2$, $OCH_2CH_2OC_{(1-4)}$alkyl, $CF_3$, $SCH_3$, $C_{(1-4)}$alkyl$NA^1A^2$ (including $CH_2NA^1A^2$), $CH_2OC_{(2-3)}$alkyl$NA^1A^2$, $NA^1A^2$, $C(O)NA^1A^2$, $CH_2NHC_{(2-3)}$alkyl$NA^1A^2$, $CH_2N(CH_3)C_{(2-3)}$alkyl$NA^1A^2$, $NHC_{(2-3)}$alkyl$NA^1A^2$, $N(CH_3)C_{(2-4)}$alkyl$NA^1A^2$, $OC_{(2-4)}$alkyl$NA^1A^2$, $OC_{(1-4)}$alkyl, $OCH_2$-(1-methyl)-imidazol-2-yl, phenyl, thiophenyl, furyl, pyrazolyl, imidazolyl, pyridyl, pyridazyl, pyrazinyl, or pyrimidinyl; wherein said phenyl, thiophenyl, furyl, pyrazolyl, imidazolyl, pyridyl, pyridazyl, pyrazinyl, and pyrimidinyl are optionally substituted with up to three substituents independently selected from the group consisting of F, Cl, $CH_3$, $CF_3$, and $OCH_3$;

$A^1$ is H, or $C_{(1-4)}$alkyl;

$A^2$ is H, $C_{(1-4)}$alkyl, $C_{(1-4)}$alkyl$OC_{(1-4)}$alkyl, $C_{(1-4)}$alkylOH, $C(O)C_{(1-4)}$alkyl, or $OC_{(1-4)}$alkyl; or $A^1$ and $A^2$ may be taken together with their attached nitrogen to form a ring selected from the group consisting of:

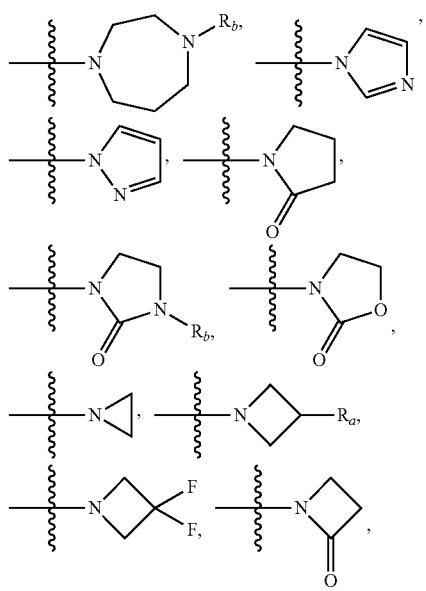

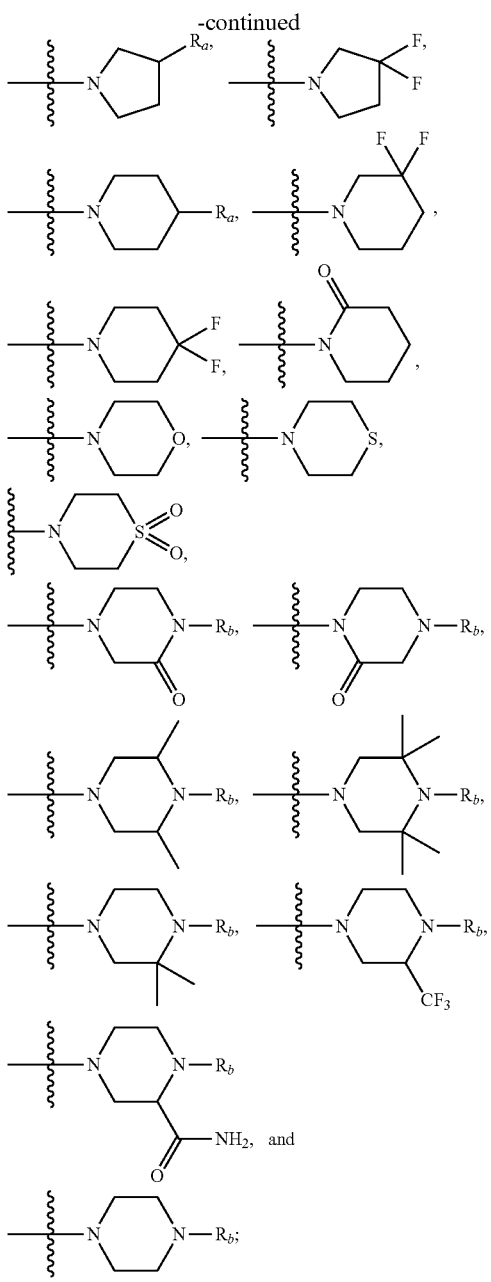

$R_a$ is H, $OC_{(1-4)}$alkyl, $CH_2OH$, $NH(CH_3)$, $N(CH_3)_2$, $NH_2$, $CH_3$, F, $CF_3$, $SO_2CH_3$, or OH;

$R_b$ is H, $CO_2C(CH_3)_3$, $C_{(1-4)}$alkyl, $C(O)C_{(1-4)}$alkyl, $SO_2C_{(1-4)}$alkyl, $CH_2CH_2CF_3$, $CH_2CF_3$, $CH_2$-cyclopropyl, phenyl, $CH_2$-phenyl, or $C_{(3-6)}$cycloalkyl;

$R^8$ is H, $C_{(1-3)}$alkyl (including $CH_3$), $OC_{(1-3)}$alkyl (including $OCH_3$), $CF_3$, $NH_2$, $NHCH_3$, —CN, or F;

$R^9$ is H, or F;

and pharmaceutically acceptable salts thereof;

provided that (4-chloro-3-phenylquinolin-6-yl)(1-methyl-1H-imidazol-5-yl)(pyridin-3-yl)methanamine, (4-chlorophenyl)(2,4-dichloro-3-(2-chlorophenyl)quinolin-6-yl)(1-methyl-1H-imidazol-2-yl)methanol, (2,4-dichloro-3-phenylquinolin-6-yl)(oxazol-2-yl)(phenyl)methanol, (4-chlorophenyl)(2,4-dichloro-3-phenylquinolin-6-yl)(2-methyl-4-(trifluoromethyl)thiazol-5-yl)methanol, (4-chloro-3-phenylquinolin-6-yl)(1-methyl-1H-imidazol-5-yl)(pyridin-4-yl)methanamine, (4-chlorophenyl)(3-(2,6-dichlorophenyl)quinolin-6-yl)(1-methyl-1H-imidazol-5-yl)methanol, (4-chloro-3-phenylquinolin-6-yl)(2-(dimethylamino)pyridin-4-yl)(1-methyl-1H-imidazol-2-yl)methanol, 4-(2-((4-chloro-6-((4-chlorophenyl)(hydroxy)(1-methyl-1H-imidazol-5-yl)methyl)-3-phenylquinolin-2-yl)oxy)ethyl)thiomorpholine 1,1-dioxide, 1-(2-((4-chloro-6-((4-chlorophenyl)(hydroxy)(1-methyl-1H-imidazol-5-yl)methyl)-3-phenylquinolin-2-yl)oxy)ethyl)pyrrolidin-2-one, (2-chloro-4-(dimethylamino)-3-phenylquinolin-6-yl)(pyridin-2-yl)(pyridin-4-yl)methanol, (4-chloro-3-phenylquinolin-6-yl)(2-fluoropyridin-4-yl)(1-methyl-1H-imidazol-2-yl)methanol, (4-chloro-2-(1-methyl-1H-pyrazol-4-yl)-3-phenylquinolin-6-yl)(4-chlorophenyl)(pyridin-3-yl)methanol, (2,4-dichloro-3-phenylquinolin-6-yl)di(pyridin-2-yl)methanol, 6-((3-chlorophenyl)(hydroxy)(2-(trifluoromethyl)pyridin-4-yl)methyl)-3-phenylquinoline-2-carbonitrile, (2,4-dichloro-8-methyl-3-phenylquinolin-6-yl)(1-methyl-1H-imidazol-4-yl)(6-methylpyridin-3-yl)methanol, (4-methoxy-3-phenyl-2-(trifluoromethyl)quinolin-6-yl)(1-methyl-1H-imidazol-5-yl)(pyridin-2-yl)methanol, (4-chlorophenyl)(2,4-dichloro-3-(2-chlorophenyl)quinolin-6-yl)(1-methyl-1H-imidazol-2-yl)methanol, (2,4-dichloro-3-phenylquinolin-6-yl)(phenyl)(pyridin-2-yl)methanol, and the second eluting enantiomer of (4-chloro-2-methoxy-3-phenylquinolin-6-yl)(1-methyl-1H-imidazol-5-yl)pyrimidin-2-ylmethanol (when purified on a chiralcel OD column) are excluded from the embodiment.

DETAILED DESCRIPTION OF THE INVENTION

The present invention comprises compounds of Formula I.

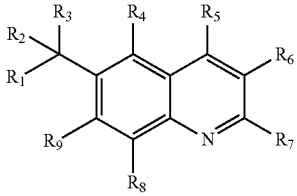

Formula I wherein:

$R^1$ is pyrrolyl, pyrazolyl, imidazolyl, triazolyl, thiazolyl, pyridyl, pyridyl N-oxide, pyrazinyl, pyrimidinyl, pyridazyl, piperidinyl, quinazolinyl, cinnolinyl, benzothiazolyl, indazolyl, tetrahydropyranyl, tetrahydrofuranyl, furanyl, phenyl, oxazolyl, isoxazolyl, thiophenyl, benzoxazolyl, benzimidazolyl, indolyl, thiadiazolyl, oxadiazolyl or quinolinyl; wherein said pyridyl, pyridyl N-oxide, pyrazinyl, pyrimidinyl, pyridazyl, piperidinyl, quinazolinyl, cinnolinyl, benzothiazolyl, indazolyl, imidazolyl, phenyl, thiophenyl, benzoxazolyl, benzimidazolyl, indolyl, quinolinyl, and pyrazolyl are optionally substituted with $C(O)C_{(1-4)}$alkyl, $C(O)NH_2$, $C(O)NHC_{(1-2)}$alkyl, $C(O)N(C_{(1-2)}$alkyl$)_2$, $NHC(O)C_{(1-4)}$alkyl, $NHSO_2C_{(1-4)}$alkyl, $C_{(1-4)}$alkyl, $CF_3$, $CH_2CF_3$, Cl, F, —CN, $OC_{(1-4)}$alkyl, $N(C_{(1-4)}$alkyl$)_2$, —$(CH_2)_3OCH_3$, $SC_{(1-4)}$alkyl, OH, $CO_2H$, $CO_2C_{(1-4)}$alkyl, $C(O)CF_3$, $SO_2CF_3$, $OCF_3$, $OCHF_2$, $SO_2CH_3$, $SO_2NH_2$, $SO_2NHC_{(1-2)}$alkyl, $SO_2N(C_{(1-2)}$alkyl$)_2$, $C(O)NHSO_2CH_3$, or $OCH_2OCH_3$; and optionally substituted with up to two additional substituents independently selected from the group consisting of Cl, $C_{(1-2)}$alkyl, $SCH_3$, $OC_{(1-2)}$alkyl, $CF_3$, —CN, and F; and wherein said triazolyl, oxazolyl, isoxazolyl, pyrrolyl, and thiazolyl are optionally substituted with up to two substituents independently selected from the group consisting of SO$_2$CH$_3$, SO$_2$NH$_2$, C(O)NH$_2$, —CN, OC$_{(1-2)}$alkyl, (CH$_2$)$_{(2-3)}$OCH$_3$, SCH$_3$, CF$_3$, F, Cl, and C$_{(1-2)}$alkyl; and said thiadiazolyl and oxadiazolyl are optionally substituted with C$_{(1-2)}$alkyl; and said pyridyl, pyridyl-N-oxide, pyrimidinyl, pyridazyl, and pyrazinyl are optionally substituted with up to three additional substituents independently selected from the group consisting of C(O)NHC$_{(1-2)}$alkyl, C(O)N(C$_{(1-2)}$alkyl)$_2$, NHC(O)C$_{(1-4)}$alkyl, NHSO$_2$C$_{(1-4)}$alkyl, C(O)CF$_3$, SO$_2$CF$_3$, SO$_2$NHC$_{(1-2)}$alkyl, SO$_2$N(C$_{(1-2)}$alkyl)$_2$, C(O)NHSO$_2$CH$_3$, SO$_2$CH$_3$, SO$_2$NH$_2$, C(O)NH$_2$, —CN, OC$_{(1-4)}$alkyl, (CH$_2$)$_{(2-3)}$OCH$_3$ (including —(CH$_2$)$_3$OCH$_3$), SC$_{(1-4)}$alkyl, CF$_3$, F, Cl, and C$_{(1-4)}$alkyl;

R$^2$ is triazolyl, pyridyl, pyridyl-N-oxide, pyrazolyl, pyrimidinyl, oxazolyl, isoxazolyl, N-acetyl piperidinyl, 1-H-piperidinyl, N-Boc-piperidinyl, N—C$_{(1-3)}$alkyl-piperidinyl, thiazolyl, pyridazyl, pyrazinyl, 1-(3-methoxypropyl)-imidazolyl, thiadiazolyl, oxadiazolyl, or imidazolyl; wherein said imidazolyl is optionally substituted with up to three additional substituents independently selected from the group consisting of C$_{(1-2)}$alkyl, SCH$_3$, OC$_{(1-2)}$alkyl, CF$_3$, —CN, F, and Cl; and said pyridyl, pyridyl-N-oxide, pyrimidinyl, pyridazyl, and pyrazinyl, are optionally substituted with up to three additional substituents independently selected from the group consisting of SO$_2$CH$_3$, SO$_2$NH$_2$, C(O)NH$_2$, —CN, OC$_{(1-2)}$alkyl, (CH$_2$)$_{(2-3)}$OCH$_3$, SCH$_3$, CF$_3$, F, Cl, or C$_{(1-2)}$alkyl; and said triazolyl, thiazolyl, oxazolyl and isoxazolyl are optionally substituted with up to two substituents independently selected from the group consisting of SO$_2$CH$_3$, SO$_2$NH$_2$, C(O)NH$_2$, —CN, OC$_{(1-2)}$alkyl, (CH$_2$)$_{(2-3)}$OCH$_3$, SCH$_3$, CF$_3$, F, Cl, and C$_{(1-2)}$alkyl; and said thiadiazolyl and oxadiazolyl are optionally substituted with C$_{(1-2)}$alkyl; and said pyrazolyl is optionally substituted with up to three CH$_3$ groups;

R$^3$ is H, OH, OCH$_3$, or NH$_2$;

R$^4$ is H, or F;

R$^5$ is H, Cl, —CN, CF$_3$, SC$_{(1-4)}$alkyl, OC$_{(1-4)}$alkyl, OH, C$_{(1-4)}$alkyl, N(CH$_3$)OCH$_3$, NH(C$_{(1-4)}$alkyl), N(C$_{(1-4)}$alkyl)$_2$, or 4-hydroxy-piperidinyl;

R$^6$ is pyridyl, pyrimidinyl, pyridazyl, pyrazinyl, thiazolyl, isothiazolyl, furanyl, thiophenyl, oxazolyl, isoxazolyl, imidazolyl, pyrazolyl, pyrrolyl, triazolyl, oxadiazolyl, thiadiazolyl, or phenyl, any of which is optionally substituted with up to two substituents independently selected from the group consisting of piperidinyl, pyrrolidinyl, azetidinyl, pyrazolyl, triazolyl, imidazolyl, —CN, C$_{(1-4)}$alkyl (including CH$_3$), OC$_{(1-4)}$alkyl, C(O)C$_{(1-4)}$alkyl, CO$_2$H, CO$_2$C$_{(1-4)}$alkyl, NH$_2$, NHC$_{(1-2)}$alkyl, N(C$_{(1-2)}$alkyl)$_2$, SONH$_2$, SON(CH$_3$)$_2$, SO$_2$NH$_2$, SO$_2$NHC$_{(1-2)}$alkyl, SO$_2$N(C$_{(1-2)}$alkyl)$_2$, SCH$_3$, OCH$_2$CF$_3$, SO$_2$CH$_3$, CF$_3$, Cl, F, OH, and OCF$_3$;

R$^7$ is H, Cl, —CN, C$_{(1-4)}$alkyl, OC$_{(1-4)}$alkylCF$_3$, OCF$_3$, OCHF$_2$, OCH$_2$CH$_2$OC$_{(1-4)}$alkyl, CF$_3$, SCH$_3$, C$_{(1-4)}$alkylNA$^1$A$^2$ (including CH$_2$NA$^1$A$^2$), CH$_2$OC$_{(2-3)}$alkylNA$^1$A$^2$, NA$^1$A$^2$, C(O)NA$^1$A$^2$, CH$_2$NHC$_{(2-3)}$alkylNA$^1$A$^2$, CH$_2$N(CH$_3$)C$_{(2-3)}$alkylNA$^1$A$^2$, NHC$_{(2-3)}$alkylNA$^1$A$^2$, N(CH$_3$)C$_{(2-4)}$alkylNA$^1$A$^2$, OC$_{(2-4)}$alkylNA$^1$A$^2$, OC$_{(1-4)}$alkyl, OCH$_2$-(1-methyl)-imidazol-2-yl, phenyl, thiophenyl, furyl, pyrazolyl, imidazolyl, pyridyl, pyridazyl, pyrazinyl, or pyrimidinyl; wherein said phenyl, thiophenyl, furyl, pyrazolyl, imidazolyl, pyridyl, pyridazyl, pyrazinyl, and pyrimidinyl are optionally substituted with up to three substituents independently selected from the group consisting of F, Cl, CH$_3$, CF$_3$, and OCH$_3$;

A$^1$ is H, or C$_{(1-4)}$alkyl;

A$^2$ is H, C$_{(1-4)}$alkyl, C$_{(1-4)}$alkylOC$_{(1-4)}$alkyl, C$_{(1-4)}$alkylOH, C(O)C$_{(1-4)}$alkyl, or OC$_{(1-4)}$alkyl; or A$^1$ and A$^2$ may be taken together with their attached nitrogen to form a ring selected from the group consisting of:

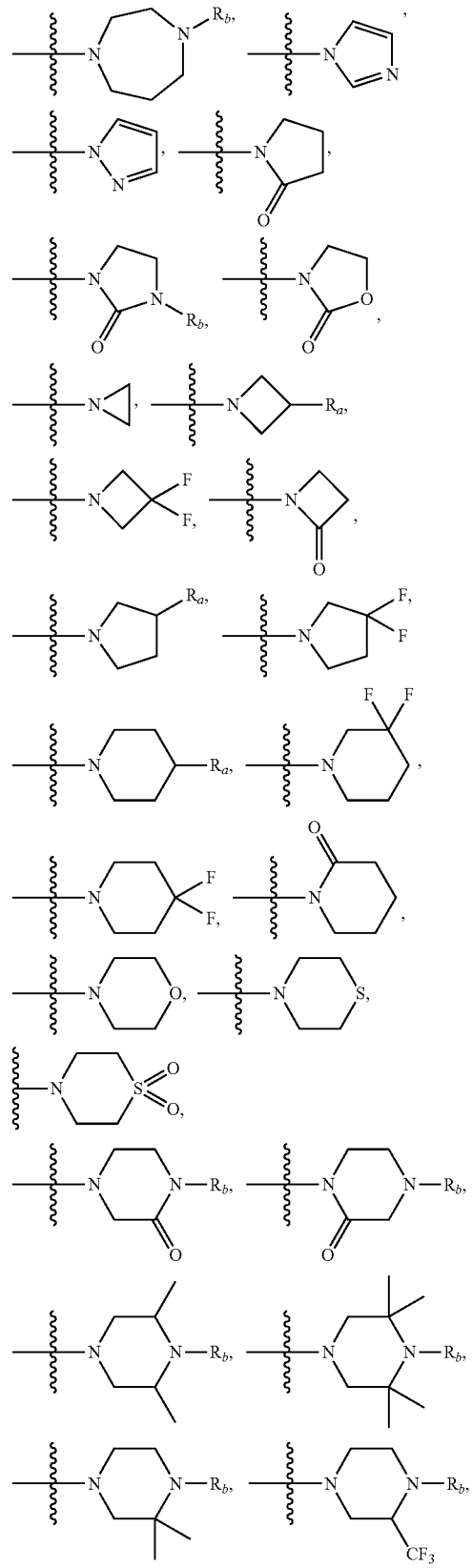

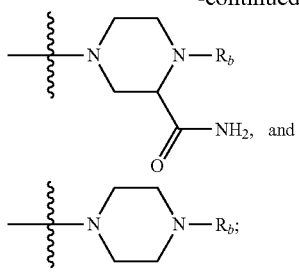

$R_a$ is H, $OC_{(1-4)}$alkyl, $CH_2OH$, $NH(CH_3)$, $N(CH_3)_2$, $NH_2$, $CH_3$, F, $CF_3$, $SO_2CH_3$, or OH;

$R_b$ is H, $CO_2C(CH_3)_3$, $C_{(1-4)}$alkyl, $C(O)C_{(1-4)}$alkyl, $SO_2C_{(1-4)}$alkyl, $CH_2CH_2CF_3$, $CH_2CF_3$, $CH_2$-cyclopropyl, phenyl, $CH_2$-phenyl, or $C_{(3-6)}$cycloalkyl;

$R^8$ is H, $C_{(1-3)}$alkyl (including $CH_3$), $OC_{(1-3)}$alkyl (including $OCH_3$), $CF_3$, $NH_2$, $NHCH_3$, —CN, or F;

$R^9$ is H, or F;

and pharmaceutically acceptable salts thereof;

provided that (4-chloro-3-phenylquinolin-6-yl)(1-methyl-1H-imidazol-5-yl)(pyridin-3-yl)methanamine, (4-chlorophenyl)(2,4-dichloro-3-(2-chlorophenyl)quinolin-6-yl)(1-methyl-1H-imidazol-2-yl)methanol, (2,4-dichloro-3-phenylquinolin-6-yl)(oxazol-2-yl)(phenyl)methanol, (4-chlorophenyl)(2,4-dichloro-3-phenylquinolin-6-yl)(2-methyl-4-(trifluoromethyl)thiazol-5-yl)methanol, (4-chloro-3-phenylquinolin-6-yl)(1-methyl-1H-imidazol-5-yl)(pyridin-4-yl)methanamine, (4-chlorophenyl)(3-(2,6-dichlorophenyl)quinolin-6-yl)(1-methyl-1H-imidazol-5-yl)methanol, (4-chloro-3-phenylquinolin-6-yl)(2-(dimethylamino)pyridin-4-yl)(1-methyl-1H-imidazol-2-yl)methanol, 4-(2-((4-chloro-6-((4-chlorophenyl)(hydroxy)(1-methyl-1H-imidazol-5-yl)methyl)-3-phenylquinolin-2-yl)oxy)ethyl)thiomorpholine 1,1-dioxide, 1-(2-((4-chloro-6-((4-chlorophenyl)(hydroxy)(1-methyl-1H-imidazol-5-yl)methyl)-3-phenylquinolin-2-yl)oxy)ethyl)pyrrolidin-2-one, (2-chloro-4-(dimethylamino)-3-phenylquinolin-6-yl)(pyridin-2-yl)(pyridin-4-yl)methanol, (4-chloro-3-phenylquinolin-6-yl)(2-fluoropyridin-4-yl)(1-methyl-1H-imidazol-2-yl)methanol, (4-chloro-2-(1-methyl-1H-pyrazol-4-yl)-3-phenylquinolin-6-yl)(4-chlorophenyl)(pyridin-3-yl)methanol, (2,4-dichloro-3-phenylquinolin-6-yl)di(pyridin-2-yl)methanol, 6-((3-chlorophenyl)(hydroxy)(2-(trifluoromethyl)pyridin-4-yl)methyl)-3-phenylquinoline-2-carbonitrile, (2,4-dichloro-8-methyl-3-phenylquinolin-6-yl)(1-methyl-1H-imidazol-4-yl)(6-methylpyridin-3-yl)methanol, (4-methoxy-3-phenyl-2-(trifluoromethyl)quinolin-6-yl)(1-methyl-1H-imidazol-5-yl)(pyridin-2-yl)methanol, (4-chlorophenyl)(2,4-dichloro-3-(2-chlorophenyl)quinolin-6-yl)(1-methyl-1H-imidazol-2-yl)methanol, (2,4-dichloro-3-phenylquinolin-6-yl)(phenyl)(pyridin-2-yl)methanol, and the second eluting enantiomer of (4-chloro-2-methoxy-3-phenylquinolin-6-yl)(1-methyl-1H-imidazol-5-yl)pyrimidin-2-ylmethanol (when purified on a chiralcel OD column) are excluded from the embodiment.

In another embodiment of the invention:

$R^1$ is pyrrolyl, pyrazolyl, imidazolyl, triazolyl, thiazolyl, pyridyl, pyridyl N-oxide, pyrazinyl, pyrimidinyl, pyridazyl, piperidinyl, tetrahydropyranyl, phenyl, oxazolyl, isoxazolyl, thiophenyl, benzoxazolyl, or quinolinyl; wherein said piperidinyl, imidazolyl, phenyl, thiophenyl, benzoxazolyl, pyrazolyl, pyridyl, pyridyl N-oxide, pyrazinyl, pyrimidinyl, pyridazyl, or quinolinyl are optionally substituted with C(O)$C_{(1-4)}$alkyl, $C(O)NH_2$, $C_{(1-4)}$alkyl, $CF_3$, $CH_2CF_3$, Cl, F, —CN, $OC_{(1-4)}$alkyl, $N(C_{(1-4)}$alkyl$)_2$, —$(CH_2)_3OCH_3$, $SC_{(1-4)}$alkyl, OH, $CO_2H$, $CO_2C_{(1-4)}$alkyl, $OCF_3$, $OCHF_2$, $SO_2CH_3$, $SO_2NH_2$, or $OCH_2OCH_3$; and optionally substituted with up to two additional substituents independently selected from the group consisting of Cl, $C_{(1-2)}$alkyl (including $CH_3$), $SCH_3$, $OC_{(1-2)}$alkyl (including $OCH_3$), $CF_3$, —CN, and F; and wherein said triazolyl, oxazolyl, isoxazolyl, pyrrolyl, and thiazolyl are optionally substituted with up to two substituents independently selected from the group consisting of $SO_2CH_3$, $SO_2NH_2$, $C(O)NH_2$, —CN, $OC_{(1-2)}$alkyl, $(CH_2)_{(2-3)}OCH_3$, $SCH_3$, $CF_3$, F, Cl, and $C_{(1-2)}$alkyl (including $CH_3$); and said pyridyl, and pyridyl-N-oxide are optionally substituted with up to three additional substituents independently selected from the group consisting of $SO_2CH_3$, $SO_2NH_2$, $C(O)NH_2$, —CN, $OC_{(1-4)}$alkyl, $(CH_2)_{(2-3)}OCH_3$ (including —$(CH_2)_3OCH_3$), $SC_{(1-4)}$alkyl, $CF_3$, F, Cl, and $C_{(1-4)}$alkyl;

$R^2$ is 1-methyl triazolyl, pyridyl, pyridyl-N-oxide, 1-methylpyrazolyl, pyrimidinyl, oxazolyl, isoxazolyl, N-acetyl piperidinyl, 1-H-piperidinyl, N-Boc-piperidinyl, N—$C_{(1-3)}$alkyl-piperidinyl (including N—$C_{(1-2)}$alkyl-piperidinyl), thiazolyl, pyridazyl, pyrazinyl, 1-(3-methoxypropyl)-imidazolyl, or 1-$C_{(1-2)}$alkyl imidazolyl; wherein said 1-$C_{(1-2)}$alkyl imidazolyl is optionally substituted with up to two additional substituents independently selected from the group consisting of $C_{(1-2)}$alkyl (including $CH_3$), $SCH_3$, $OC_{(1-2)}$alkyl, $CF_3$, —CN, F, and Cl; and said pyridyl, and pyridyl-N-oxide are optionally substituted with up to three additional substituents independently selected from the group consisting of $SO_2CH_3$, $SO_2NH_2$, $C(O)NH_2$, —CN, $OC_{(1-2)}$alkyl (including $OCH_3$), $(CH_2)_{(2-3)}OCH_3$, $SCH_3$, $CF_3$, F, Cl, and $C_{(1-2)}$alkyl (including $CH_3$); and said thiazolyl, oxazolyl and isoxazolyl are optionally substituted with up to two substituents independently selected from the group consisting of $SO_2CH_3$, $SO_2NH_2$, $C(O)NH_2$, —CN, $OC_{(1-2)}$alkyl, $(CH_2)_{(2-3)}OCH_3$, $SCH_3$, $CF_3$, F, Cl, and $C_{(1-2)}$alkyl (including $CH_3$); and said 1-methyl pyrazolyl is optionally substituted with up to two additional $CH_3$ groups;

$R^3$ is H, OH, $OCH_3$, or $NH_2$;

$R^4$ is H, or F;

$R^5$ is H, Cl, —CN, $CF_3$, $SC_{(1-4)}$alkyl, $OC_{(1-4)}$alkyl, OH, $C_{(1-4)}$alkyl, $N(CH_3)OCH_3$, $NH(C_{(1-4)}$alkyl), $N(C_{(1-4)}$alkyl$)_2$, or 4-hydroxy-piperidinyl;

$R^6$ is pyridyl, pyrimidinyl, pyridazyl, pyrazinyl, or phenyl, any of which is optionally substituted with —CN, $CH_3$, $OC_{(1-4)}$alkyl (including $OCH_3$), $N(C_{(1-2)}$alkyl$)_2$ (including $N(CH_3)_2$), $SONH_2$, $SON(CH_3)_2$, $OCH_2CF_3$, $SO_2CH_3$, $CF_3$, Cl, F, or $OCF_3$;

$R^7$ is H, Cl, —CN, $C_{(1-4)}$alkyl, $OC_{(1-4)}$alkylCF$_3$, $OCH_2CH_2OC_{(1-4)}$alkyl, $CF_3$, $SCH_3$, $CH_2NA^1A^2$, $CH_2OC_{(2-3)}$alkylNA$^1$A$^2$, NA$^1$A$^2$, $C(O)NA^1A^2$, $N(CH_3)C_{(2-4)}$alkylNA$^1$A$^2$, $OC_{(2-4)}$alkylNA$^1$A$^2$, $OC_{(1-4)}$alkyl, $OCH_2$-(1-methyl)-imidazol-2-yl, furyl, pyrazolyl, imidazolyl, pyridyl, pyridazyl, pyrazinyl, or pyrimidinyl; wherein said imidazolyl or pyrazolyl is optionally substituted with one $CH_3$ group;

$A^1$ is H, or $C_{(1-4)}$alkyl;

$A^2$ is H, $C_{(1-4)}$alkyl, $C_{(1-4)}$alkylOC$_{(1-4)}$alkyl, $C_{(1-4)}$alkylOH, $C(O)C_{(1-4)}$alkyl, or $OC_{(1-4)}$alkyl; or $A^1$ and $A^2$ may be taken together with their attached nitrogen to form a ring selected from the group consisting of:

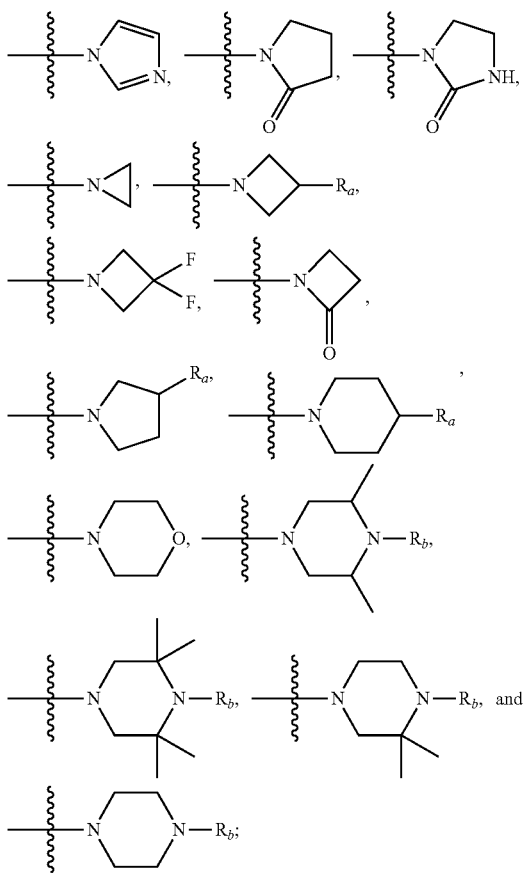

$R_a$ is H, $OC_{(1-4)}$alkyl, $CH_2OH$, $NH(CH_3)$, $N(CH_3)_2$, $NH_2$, $CH_3$, F, or OH;

$R_b$ is H, $CO_2C(CH_3)_3$, $C_{(1-4)}$alkyl, $C(O)C_{(1-4)}$alkyl (including $C(O)CH_3$), $SO_2C_{(1-4)}$alkyl, $CH_2CH_2CF_3$, $CH_2CF_3$, $CH_2$-cyclopropyl, phenyl, $CH_2$-phenyl, or $C_{(3-6)}$cycloalkyl;

$R^8$ is H, $CH_3$, $OCH_3$, or F;

$R^9$ is H, or F;

and pharmaceutically acceptable salts thereof;

provided that (4-chloro-3-phenylquinolin-6-yl)(1-methyl-1H-imidazol-5-yl)(pyridin-3-yl)methanamine, (4-chlorophenyl)(2,4-dichloro-3-(2-chlorophenyl)quinolin-6-yl)(1-methyl-1H-imidazol-2-yl)methanol, (2,4-dichloro-3-phenylquinolin-6-yl)(oxazol-2-yl)(phenyl)methanol, (4-chlorophenyl)(2,4-dichloro-3-phenylquinolin-6-yl)(2-methyl-4-(trifluoromethyl)thiazol-5-yl)methanol, (4-chloro-3-phenylquinolin-6-yl)(1-methyl-1H-imidazol-5-yl)(pyridin-4-yl)methanamine, (4-chlorophenyl)(3-(2,6-dichlorophenyl)quinolin-6-yl)(1-methyl-1H-imidazol-5-yl)methanol, (4-chloro-3-phenylquinolin-6-yl)(2-(dimethylamino)pyridin-4-yl)(1-methyl-1H-imidazol-2-yl)methanol, 4-(2-((4-chloro-6-((4-chlorophenyl)(hydroxy)(1-methyl-1H-imidazol-5-yl)methyl)-3-phenylquinolin-2-yl)oxy)ethyl)thiomorpholine 1,1-dioxide, 1-(2-((4-chloro-6-((4-chlorophenyl)(hydroxy)(1-methyl-1H-imidazol-5-yl)methyl)-3-phenylquinolin-2-yl)oxy)ethyl)pyrrolidin-2-one, (2-chloro-4-(dimethylamino)-3-phenylquinolin-6-yl)(pyridin-2-yl)(pyridin-4-yl)methanol, (4-chloro-3-phenylquinolin-6-yl)(2-fluoropyridin-4-yl)(1-methyl-1H-imidazol-2-yl)methanol, (4-chloro-2-(1-methyl-1H-pyrazol-4-yl)-3-phenylquinolin-6-yl)(4-chlorophenyl)(pyridin-3-yl)methanol, (2,4-dichloro-3-phenylquinolin-6-yl)di(pyridin-2-yl)methanol, 6-((3-chlorophenyl)(hydroxy)(2-(trifluoromethyl)pyridin-4-yl)methyl)-3-phenylquinoline-2-carbonitrile, (2,4-dichloro-8-methyl-3-phenylquinolin-6-yl)(1-methyl-1H-imidazol-4-yl)(6-methylpyridin-3-yl)methanol, (4-methoxy-3-phenyl-2-(trifluoromethyl)quinolin-6-yl)(1-methyl-1H-imidazol-5-yl)(pyridin-2-yl)methanol, (4-chlorophenyl)(2,4-dichloro-3-(2-chlorophenyl)quinolin-6-yl)(1-methyl-1H-imidazol-2-yl)methanol, (2,4-dichloro-3-phenylquinolin-6-yl)(phenyl)(pyridin-2-yl)methanol, and the second eluting enantiomer of (4-chloro-2-methoxy-3-phenylquinolin-6-yl)(1-methyl-1H-imidazol-5-yl)pyrimidin-2-ylmethanol (when purified on a chiralcel OD column) are excluded from the claim.

In another embodiment of the invention:

$R^1$ is pyrrolyl, pyrazolyl, imidazolyl, triazolyl, thiazolyl, pyridyl, pyridyl N-oxide, pyrazinyl, pyrimidinyl, pyridazyl, piperidinyl, tetrahydropyranyl, phenyl, oxazolyl, isoxazolyl, thiophenyl, benzoxazolyl, or quinolinyl; wherein said piperidinyl, pyridyl, pyridyl N-oxide, imidazolyl, phenyl, thiophenyl, benzoxazolyl, and pyrazolyl are optionally substituted with $C(O)C_{(1-4)}$alkyl (including $C(O)CH_3$), $C(O)NH_2$, $C_{(1-4)}$alkyl (including $CH_3$, and $CH_2CH_3$), $CF_3$, $CH_2CF_3$, Cl, F, —CN, $OC_{(1-4)}$alkyl (including $OCH_3$), $N(C_{(1-4)}$alkyl$)_2$ (including $N(CH_3)_2$), —$(CH_2)_3OCH_3$, $SC_{(1-4)}$alkyl (including $SCH_3$), OH, $CO_2H$, $CO_2C_{(1-4)}$alkyl (including $CO_2C(CH_3)_3$), $OCF_3$, $OCHF_2$, $SO_2CH_3$, $SO_2NH_2$, or $OCH_2OCH_3$; and optionally substituted with up to two additional substituents independently selected from the group consisting of Cl, $OCH_3$, and $CH_3$; and wherein said triazolyl, oxazolyl, isoxazolyl, and thiazolyl are optionally substituted with one or two $CH_3$ groups;

$R^2$ is 1-methyl triazolyl, pyridyl, pyridyl-N-oxide, 1-methylpyrazolyl, pyrimidinyl, pyrazinyl, oxazolyl, isoxazolyl, N-acetyl piperidinyl, 1-H-piperidinyl, N-Boc-piperidinyl, N—$C_{(1-2)}$alkyl-piperidinyl, thiazolyl, pyridazyl, 1-(3-methoxypropyl)-imidazolyl, or 1-$C_{(1-2)}$alkyl imidazolyl; wherein said 1-$C_{(1-2)}$alkyl imidazolyl is optionally substituted with up to two additional $CH_3$ groups, or one substituent selected from the group consisting of $SCH_3$, and Cl; and said pyridyl, and pyridyl-N-oxide are optionally substituted with up to two substituents independently selected from the group consisting of $SO_2CH_3$, $SO_2NH_2$, $C(O)NH_2$, —CN, $OCH_3$, $CF_3$, Cl, and $CH_3$; and said thiazolyl, oxazolyl and isoxazolyl are optionally substituted with up to two $CH_3$ groups; and said 1-methylpyrazolyl is optionally substituted with up to two additional $CH_3$ groups;

$R^3$ is H, OH, $OCH_3$, or $NH_2$;

$R^4$ is H, or F;

$R^5$ is H, Cl, —CN, $CF_3$, $SC_{(1-4)}$alkyl (including $SCH_3$), $OC_{(1-4)}$alkyl (including $OC_{(1-3)}$alkyl), OH, $C_{(1-4)}$alkyl, $N(CH_3)OCH_3$, $NH(C_{(1-4)}$alkyl) (including $NH(C_{(1-2)}$alkyl)), $N(C_{(1-4)}$alkyl$)_2$ (including $N(C_{(1-2)}$alkyl$)_2$), or 4-hydroxy-piperidinyl;

$R^6$ is pyridyl or phenyl, either of which is optionally substituted with —CN, $CH_3$, $OCH_3$, $N(CH_3)_2$, $SONH_2$, $SO_2CH_3$, $CF_3$, Cl, F, or $OCF_3$;

$R^7$ is H, Cl, —CN, $C_{(1-4)}$alkyl, $OC_{(1-4)}$alkylCF$_3$ (including $OCH_2CF_3$), $OCH_2CH_2OC_{(1-4)}$alkyl (including $OCH_2CH_2OCH_3$), $CF_3$, $SCH_3$, $NA^1A^2$, $C(O)NA^1A^2$ (including $C(O)NHCH_3$), $N(CH_3)C_{(2-4)}$alkyl$NA^1A^2$ (including $N(CH_3)CH_2CH_2NA^1A^2$), $OC_{(2-4)}$alkyl$NA^1A^2$ (including $OCH_2CH_2NA^1A^2$), $OC_{(1-4)}$alkyl (including $OC_{(1-3)}$alkyl), $OCH_2$-(1-methyl)-imidazol-2-yl, imidazolyl, furyl, pyrazolyl, pyridyl, or pyrimidinyl; wherein said imidazolyl or pyrazolyl is optionally substituted with one $CH_3$ group;

$A^1$ is H, or $C_{(1-4)}$alkyl;

$A^2$ is H, $C_{(1-4)}$alkyl, $C_{(1-4)}$alkyl$OC_{(1-4)}$alkyl, $C_{(1-4)}$alkylOH, $C(O)C_{(1-4)}$alkyl (including $C(O)C_{(1-2)}$alkyl), or $OC_{(1-4)}$alkyl (including $OCH_3$); or $A^1$ and $A^2$ may be taken together with their attached nitrogen to form a ring selected from the group consisting of:

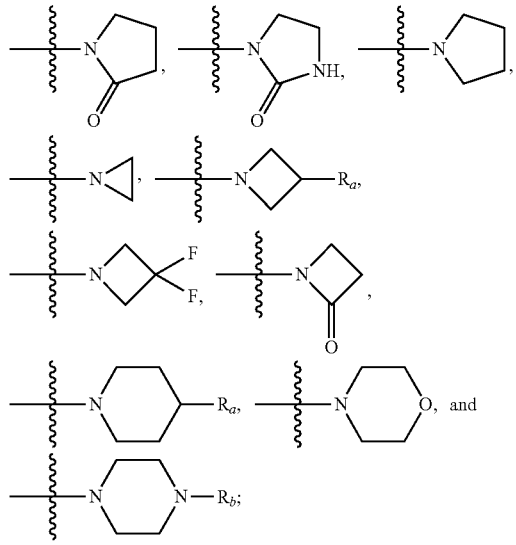

$R_a$ is H, F, $OC_{(1-4)}$alkyl (including $OCH_3$), or OH;
$R_b$ is $C_{(1-4)}$alkyl (including $CH_3$), $C(O)CH_3$, or phenyl;
$R^8$ is H, $CH_3$, $OCH_3$, or F;
$R^9$ is H, or F;
and pharmaceutically acceptable salts thereof;
provided that (4-chloro-3-phenylquinolin-6-yl)(1-methyl-1H-imidazol-5-yl)(pyridin-3-yl)methanamine, (4-chlorophenyl)(2,4-dichloro-3-(2-chlorophenyl)quinolin-6-yl)(1-methyl-1H-imidazol-2-yl)methanol, (2,4-dichloro-3-phenylquinolin-6-yl)(oxazol-2-yl)(phenyl)methanol, (4-chloro-3-phenylquinolin-6-yl)(1-methyl-1H-imidazol-5-yl)(pyridin-4-yl)methanamine, (4-chlorophenyl)(3-(2,6-dichlorophenyl)quinolin-6-yl)(1-methyl-1H-imidazol-5-yl)methanol, (4-chloro-3-phenylquinolin-6-yl)(2-(dimethylamino)pyridin-4-yl)(1-methyl-1H-imidazol-2-yl)methanol, 4-(2-((4-chloro-6-((4-chlorophenyl)(hydroxy)(1-methyl-1H-imidazol-5-yl)methyl)-3-phenylquinolin-2-yl)oxy)ethyl)thiomorpholine 1,1-dioxide, 1-(2-((4-chloro-6-((4-chlorophenyl)(hydroxy)(1-methyl-1H-imidazol-5-yl)methyl)-3-phenylquinolin-2-yl)oxy)ethyl)pyrrolidin-2-one, (2-chloro-4-(dimethylamino)-3-phenylquinolin-6-yl)(pyridin-2-yl)(pyridin-4-yl)methanol, (4-chloro-3-phenylquinolin-6-yl)(2-fluoropyridin-4-yl)(1-methyl-1H-imidazol-2-yl)methanol, (4-chloro-2-(1-methyl-1H-pyrazol-4-yl)-3-phenylquinolin-6-yl)(4-chlorophenyl)(pyridin-3-yl)methanol, (2,4-dichloro-3-phenylquinolin-6-yl)di(pyridin-2-yl)methanol, 6-((3-chlorophenyl)(hydroxy)(2-(trifluoromethyl)pyridin-4-yl)methyl)-3-phenylquinoline-2-carbonitrile, (2,4-dichloro-8-methyl-3-phenylquinolin-6-yl)(1-methyl-1H-imidazol-4-yl)(6-methylpyridin-3-yl)methanol, (4-methoxy-3-phenyl-2-(trifluoromethyl)quinolin-6-yl)(1-methyl-1H-imidazol-5-yl)(pyridin-2-yl)methanol, (4-chlorophenyl)(2,4-dichloro-3-(2-chlorophenyl)quinolin-6-yl)(1-methyl-1H-imidazol-2-yl)methanol, (2,4-dichloro-3-phenylquinolin-6-yl)(phenyl)(pyridin-2-yl)methanol, and the second eluting enantiomer of (4-chloro-2-methoxy-3-phenylquinolin-6-yl)(1-methyl-1H-imidazol-5-yl)pyrimidin-2-ylmethanol (when purified on a chiralcel OD column) are excluded from the claim.

In another embodiment of the invention:

$R^1$ is pyrrolyl, pyrazolyl, imidazolyl, triazolyl, thiazolyl, pyridyl, pyridyl N-oxide, pyrazinyl, pyrimidinyl, pyridazyl, piperidinyl, tetrahydropyranyl, phenyl, oxazolyl, isoxazolyl, thiophenyl, benzoxazolyl, or quinolinyl; wherein said piperidinyl, pyridyl, pyridyl N-oxide, imidazolyl, phenyl, thiophenyl, benzoxazolyl, and pyrazolyl are optionally substituted with $SO_2CH_3$, $C(O)CH_3$, $C(O)NH_2$, $CH_3$, $CH_2CH_3$, $CF_3$, Cl, F, —CN, $OCH_3$, $N(CH_3)_2$, —$(CH_2)_3OCH_3$, $SCH_3$, OH, $CO_2H$, $CO_2C(CH_3)_3$, or $OCH_2OCH_3$; and optionally substituted with up to two additional substituents independently selected from the group consisting of Cl, $OCH_3$, and $CH_3$; and wherein said triazolyl, oxazolyl, isoxazolyl, and thiazolyl are optionally substituted with one or two $CH_3$ groups;

$R^2$ is 1-methyl-1,2,3-triazolyl, pyridyl, pyridyl-N-oxide, 1-methylpyrazol-4-yl, pyrimidin-5-yl, pyridazyl, pyrazin-2-yl, isoxazolyl, N-acetyl piperidinyl, 1-H-piperidinyl, N-Boc-piperidinyl, N—$C_{(1-2)}$alkyl-piperidinyl, thiazol-5-yl, 1-(3-methoxypropyl)-imidazol-5-yl, or 1-$C_{(1-2)}$alkyl imidazol-5-yl (including 1-ethyl imidazol-5-yl and 1-methyl imidazol-5-yl); wherein said 1-$C_{(1-2)}$alkyl imidazol-5-yl (including 1-methyl imidazol-5-yl) is optionally substituted with up to two additional $CH_3$ groups, or one substituent selected from the group consisting of $SCH_3$, and Cl; and said pyridyl, and pyridyl-N-oxide are optionally substituted with up to two substitutents independently selected from the group consisting of $C(O)NH_2$, —CN, $OCH_3$, $CF_3$, Cl, and $CH_3$; and said thiazol-5-yl, and said isoxazolyl are optionally substituted with up to two $CH_3$ groups; and said 1-methylpyrazol-4-yl is optionally substituted with up to two additional $CH_3$ groups;

$R^3$ is H, OH, $OCH_3$, or $NH_2$;

$R^4$ is H, or F;

$R^5$ is H, Cl, —CN, $CF_3$, $SCH_3$, $OC_{(1-3)}$alkyl, OH, $C_{(1-4)}$alkyl, $N(CH_3)OCH_3$, $NH(C_{(1-2)}$alkyl), $N(C_{(1-2)}$alkyl)$_2$, or 4-hydroxy-piperidinyl;

$R^6$ is pyridyl or phenyl, either of which is optionally substituted with Cl, F, $CF_3$, $SO_2CH_3$, —CN, or $OCF_3$;

$R^7$ is H, Cl, —CN, $C_{(1-4)}$alkyl (including $C_{(1-3)}$alkyl), $OCH_2CF_3$, $OCH_2CH_2OCH_3$, $CF_3$, $SCH_3$, $NA^1A^2$, $C(O)NHCH_3$, $N(CH_3)CH_2CH_2NA^1A^2$, $OCH_2CH_2NA^1A^2$, $OC_{(1-3)}$alkyl, $OCH_2$-(1-methyl)-imidazol-2-yl, imidazol-2-yl, fur-2-yl, pyrazol-4-yl, pyrid-3-yl, or pyrimidin-5-yl; wherein said imidazolyl or pyrazolyl is optionally substituted with one $CH_3$ group;

$A^1$ is H, or $C_{(1-4)}$alkyl;

$A^2$ is H, $C_{(1-4)}$alkyl, $C_{(1-4)}$alkyl$OC_{(1-4)}$alkyl, $C_{(1-4)}$alkylOH, $C(O)C_{(1-2)}$alkyl, or $OCH_3$; or $A^1$ and $A^2$ may be taken together with their attached nitrogen to form a ring selected from the group consisting of:

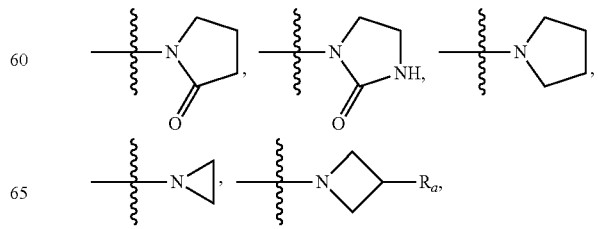

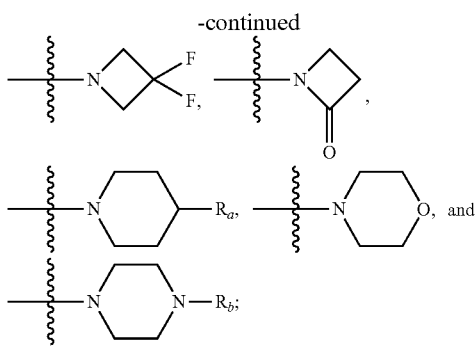

$R_a$ is H, F, OCH$_3$, or OH;
$R_b$ is CH$_3$, or phenyl;
$R^8$ is H, CH$_3$, OCH$_3$, or F;
$R^9$ is H, or F;
and pharmaceutically acceptable salts thereof;
provided that (4-chloro-3-phenylquinolin-6-yl)(1-methyl-1H-imidazol-5-yl)(pyridin-3-yl)methanamine, (4-chlorophenyl)(2,4-dichloro-3-(2-chlorophenyl)quinolin-6-yl)(1-methyl-1H-imidazol-2-yl)methanol, (4-chloro-3-phenylquinolin-6-yl)(1-methyl-1H-imidazol-5-yl)(pyridin-4-yl)methanamine, (4-chlorophenyl)(3-(2,6-dichlorophenyl)quinolin-6-yl)(1-methyl-1H-imidazol-5-yl)methanol, (4-chloro-3-phenylquinolin-6-yl)(2-(dimethylamino)pyridin-4-yl)(1-methyl-1H-imidazol-2-yl)methanol, 4-(2-((4-chloro-6-((4-chlorophenyl)(hydroxy)(1-methyl-1H-imidazol-5-yl)methyl)-3-phenylquinolin-2-yl)oxy)ethyl)thiomorpholine 1,1-dioxide, 1-(2-((4-chloro-6-((4-chlorophenyl)(hydroxy)(1-methyl-1H-imidazol-5-yl)methyl)-3-phenylquinolin-2-yl)oxy)ethyl)pyrrolidin-2-one, (2-chloro-4-(dimethylamino)-3-phenylquinolin-6-yl)(pyridin-2-yl)(pyridin-4-yl)methanol, (4-chloro-3-phenylquinolin-6-yl)(2-fluoropyridin-4-yl)(1-methyl-1H-imidazol-2-yl)methanol, (4-chloro-2-(1-methyl-1H-pyrazol-4-yl)-3-phenylquinolin-6-yl)(4-chlorophenyl)(pyridin-3-yl)methanol, (2,4-dichloro-3-phenylquinolin-6-yl)di(pyridin-2-yl)methanol, 6-((3-chlorophenyl)(hydroxy)(2-(trifluoromethyl)pyridin-4-yl)methyl)-3-phenylquinoline-2-carbonitrile, (2,4-dichloro-8-methyl-3-phenylquinolin-6-yl)(1-methyl-1H-imidazol-4-yl)(6-methylpyridin-3-yl)methanol, (4-methoxy-3-phenyl-2-(trifluoromethyl)quinolin-6-yl)(1-methyl-1H-imidazol-5-yl)(pyridin-2-yl)methanol, (4-chlorophenyl)(2,4-dichloro-3-(2-chlorophenyl)quinolin-6-yl)(1-methyl-1H-imidazol-2-yl)methanol, (2,4-dichloro-3-phenylquinolin-6-yl)(phenyl)(pyridin-2-yl)methanol, and the second eluting enantiomer of (4-chloro-2-methoxy-3-phenylquinolin-6-yl)(1-methyl-1H-imidazol-5-yl)pyrimidin-2-ylmethanol (when purified on a chiralcel OD column) are excluded from the embodiment.
In another embodiment of the invention:
$R^1$ is pyrrolyl, triazolyl, imidazolyl, thiazolyl, pyridyl, pyridyl N-oxide, pyrazinyl, pyrimidinyl, pyridazyl, piperidinyl, phenyl, isoxazolyl, thiophenyl, benzoxazolyl, pyrazolyl or quinolinyl; wherein said piperidinyl, pyridyl, imidazolyl, phenyl, thiophenyl, benzoxazolyl, and pyrazolyl are optionally substituted with C(O)CH$_3$, C(O)NH$_2$, CH$_3$, CH$_2$CH$_3$, CF$_3$, Cl, F, —CN, OCH$_3$, N(CH$_3$)$_2$, —(CH$_2$)$_3$OCH$_3$, SCH$_3$, OH, CO$_2$H, CO$_2$C(CH$_3$)$_3$, or OCH$_2$OCH$_3$; and optionally substituted with up to two additional CH$_3$ groups, or one additional chloro group; and wherein said triazolyl, isoxazolyl, and thiazolyl are optionally substituted with one or two CH$_3$ groups;

$R^2$ is 1-methyl-1,2,3-triazolyl, pyridyl, pyridyl-N-oxide, 1-methylpyrazol-4-yl, pyrimidin-5-yl, pyridazyl, pyrazin-2-yl, isoxazol-4-yl, isoxazol-5-yl, N-acetyl piperidin-3-yl, N-acetyl piperidin-4-yl, 1-H-piperidin-3-yl, 1-H-piperidin-4-yl, N-Boc-piperidin-3-yl, N-Boc-piperidin-4-yl, N—C$_{(1-2)}$alkyl-piperidin-3-yl, N—C$_{(1-2)}$alkyl-piperidin-4-yl, thiazol-5-yl, 1-(3-methoxypropyl)-imidazol-5-yl, or 1-C$_{(1-2)}$alkyl imidazol-5-yl; wherein said 1-C$_{(1-2)}$alkyl imidazol-5-yl is optionally substituted with up to two additional CH$_3$ groups, or one substituent selected from the group consisting of SCH$_3$, and Cl; and said pyridyl is optionally substituted with up to two substitutents selected from the group consisting of C(O)NH$_2$, —CN, OCH$_3$, CF$_3$, Cl, and CH$_3$; and said thiazol-5-yl, isoxazol-4-yl, and isoxazol-5-yl are optionally substituted with up to two CH$_3$ groups; and said 1-methylpyrazol-4-yl is optionally substituted with up to two additional CH$_3$ groups;
$R^3$ is H, OH, OCH$_3$, or NH$_2$;
$R^4$ is H, F;
$R^5$ is H, Cl, —CN, CF$_3$, SCH$_3$, OC$_{(1-3)}$alkyl, OH, C$_{(1-4)}$alkyl, N(CH$_3$)OCH$_3$, NH(C$_{(1-2)}$alkyl) (including NH(CH$_3$)), N(C$_{(1-2)}$alkyl)$_2$, or 4-hydroxy-piperidinyl;
$R^6$ is phenyl, or pyridyl, wherein said phenyl is optionally substituted with Cl, F, CF$_3$, SO$_2$CH$_3$, or OCF$_3$;
$R^7$ is H, Cl, —CN, C$_{(1-3)}$alkyl, OCH$_2$CF$_3$, OCH$_2$CH$_2$OCH$_3$, CF$_3$, SCH$_3$, NA$^1$A$^2$, N(CH$_3$)CH$_2$CH$_2$N(CH$_3$)$_2$, OCH$_2$CH$_2$NH$_2$, OCH$_2$CH$_2$—N-aziridinyl, OCH$_2$CH$_2$NHC(O)CH$_3$, OC$_{(1-3)}$alkyl, OCH$_2$-(1-methyl)-imidazol-2-yl, pyrid-3-yl, or pyrimidin-5-yl;
$A^1$ is H, or C$_{(1-4)}$alkyl;
$A^2$ is H, C$_{(1-4)}$alkyl, C$_{(1-4)}$alkylOC$_{(1-4)}$alkyl, C$_{(1-4)}$alkylOH, C(O)C$_{(1-2)}$alkyl, or OCH$_3$; or A$^1$ and A$^2$ may be taken together with their attached nitrogen to form a ring selected from the group consisting of:

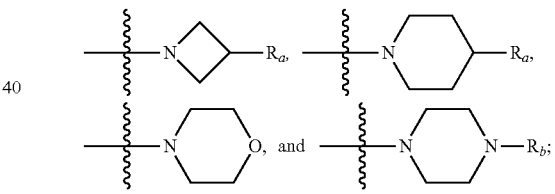

$R_a$ is H, OCH$_3$, or OH;
$R_b$ is CH$_3$, or phenyl;
$R^8$ is H, CH$_3$, or F;
$R^9$ is H, F;
and pharmaceutically acceptable salts thereof;
provided that (4-chloro-3-phenylquinolin-6-yl)(1-methyl-1H-imidazol-5-yl)(pyridin-3-yl)methanamine, (4-chlorophenyl)(2,4-dichloro-3-(2-chlorophenyl)quinolin-6-yl)(1-methyl-1H-imidazol-2-yl)methanol, (4-chloro-3-phenylquinolin-6-yl)(1-methyl-1H-imidazol-5-yl)(pyridin-4-yl)methanamine, (4-chlorophenyl)(3-(2,6-dichlorophenyl)quinolin-6-yl)(1-methyl-1H-imidazol-5-yl)methanol, (4-chloro-3-phenylquinolin-6-yl)(2-(dimethylamino)pyridin-4-yl)(1-methyl-1H-imidazol-2-yl)methanol, (2-chloro-4-(dimethylamino)-3-phenylquinolin-6-yl)(pyridin-2-yl)(pyridin-4-yl)methanol, (4-chloro-3-phenylquinolin-6-yl)(2-fluoropyridin-4-yl)(1-methyl-1H-imidazol-2-yl)methanol, (2,4-dichloro-3-phenylquinolin-6-yl)di(pyridin-2-yl)methanol, 6-((3-chlorophenyl)(hydroxy)(2-(trifluoromethyl)pyridin-4-yl)methyl)-3-phenylquinoline-2-carbonitrile, (2,4-dichloro-8-methyl-3-phenylquinolin-6-yl)(1-methyl-1H-imidazol-4-yl)(6-methylpyridin-3-yl)methanol, (4-methoxy- 3-phenyl-2-(trifluoromethyl)quinolin-6-yl)(1-methyl-1H-imidazol-5-yl)(pyridin-2-yl)methanol, (4-chlorophenyl)(2,4-dichloro-3-(2-chlorophenyl)quinolin-6-yl)(1-methyl-1H-imidazol-2-yl)methanol, (2,4-dichloro-3-phenylquinolin-6-yl)(phenyl)(pyridin-2-yl)methanol, and the second eluting enantiomer of (4-chloro-2-methoxy-3-phenylquinolin-6-yl)(1-methyl-1H-imidazol-5-yl)pyrimidin-2-ylmethanol (when purified on a chiralcel OD column) are excluded from the embodiment.

In another embodiment of the invention:

$R^1$ is pyrrolyl, triazolyl, imidazolyl, thiazolyl, pyridyl, pyrazinyl, pyrimidinyl, pyridazyl, piperidinyl, phenyl, isoxazolyl, thiophenyl, benzoxazolyl, or quinolinyl; wherein said piperidinyl, pyridyl, phenyl, thiophenyl, and benzoxazolyl, are optionally substituted with $C(O)CH_3$, $CH_3$, $CF_3$, Cl, F, $OCH_3$, $N(CH_3)_2$, OH, or $OCH_2OCH_3$; and optionally substituted with $CH_3$; and wherein said triazolyl, imidazolyl, isoxazolyl, and thiazolyl are optionally substituted with one or two $CH_3$ groups;

$R^2$ is 1-methyl-1,2,3-triazolyl, pyridyl, pyridyl-N-oxide, 1-methylpyrazol-4-yl, pyrimidin-5-yl, pyridazyl, pyrazin-2-yl, isoxazol-4-yl, isoxazol-5-yl, N-acetyl piperidin-3-yl, N-acetyl piperidin-4-yl, 1-H-piperidin-3-yl, 1-H-piperidin-4-yl, N-Boc-piperidin-3-yl, N-Boc-piperidin-4-yl, N—$C_{(1-2)}$alkyl-piperidin-3-yl, N—$C_{(1-2)}$alkyl-piperidin-4-yl, thiazol-5-yl, 1-(3-methoxypropyl)-imidazol-5-yl, or 1-$C_{(1-2)}$alkyl imidazol-5-yl; wherein said 1-$C_{(1-2)}$alkyl imidazol-5-yl is optionally substituted with up to two additional $CH_3$ groups, or one substituent selected from the group consisting of $SCH_3$, and Cl; and said pyridyl is optionally substituted with up to two substitutents selected from the group consisting of $C(O)NH_2$, —CN, $OCH_3$, $CF_3$, Cl, and $CH_3$; and said thiazol-5-yl, isoxazol-4-yl, and isoxazol-5-yl are optionally substituted with up to two $CH_3$ groups; and said 1-methylpyrazol-4-yl is optionally substituted with up to two additional $CH_3$ groups;

$R^3$ is H, OH, $OCH_3$, or $NH_2$;

$R^4$ is H, or F;

$R^5$ is H, Cl, —CN, $CF_3$, $OC_{(1-3)}$alkyl, OH, $C_{(1-4)}$alkyl, $NH(CH_3)$, $N(C_{(1-2)}alkyl)_2$, or 4-hydroxy-piperidinyl;

$R^6$ is phenyl, or pyridyl, wherein said phenyl is optionally substituted with Cl, F, or $OCF_3$;

$R^7$ is H, Cl, —CN, $C_{(1-2)}$alkyl, $CF_3$, $NA^1A^2$, $N(CH_3)CH_2CH_2N(CH_3)_2$, $OC_{(1-3)}$alkyl, pyrid-3-yl, or pyrimidin-5-yl;

$A^1$ is $C_{(1-2)}$alkyl;

$A^2$ is $C_{(1-4)}$alkyl, or $CH_2CH_2OCH_3$; or $A^1$ and $A^2$ may be taken together with their attached nitrogen to form a ring selected from the group consisting of:

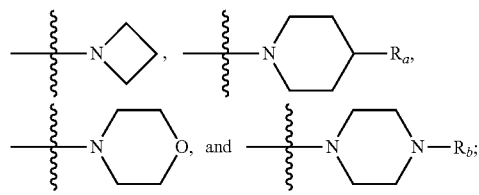

$R_a$ is $OCH_3$, or OH;
$R_b$ is $CH_3$, or phenyl;
$R^8$ is H, $CH_3$, or F;
$R^9$ is H, or F;

and pharmaceutically acceptable salts thereof;
provided that (4-chloro-3-phenylquinolin-6-yl)(1-methyl-1H-imidazol-5-yl)(pyridin-3-yl)methanamine, (4-chlorophenyl)(2,4-dichloro-3-(2-chlorophenyl)quinolin-6-yl)(1-methyl-1H-imidazol-2-yl)methanol, (4-chloro-3-phenylquinolin-6-yl)(1-methyl-1H-imidazol-5-yl)(pyridin-4-yl)methanamine, (4-chlorophenyl)(3-(2,6-dichlorophenyl)quinolin-6-yl)(1-methyl-1H-imidazol-5-yl)methanol, (4-chloro-3-phenylquinolin-6-yl)(2-(dimethylamino)pyridin-4-yl)(1-methyl-1H-imidazol-2-yl)methanol, (2-chloro-4-(dimethylamino)-3-phenylquinolin-6-yl)(pyridin-2-yl)(pyridin-4-yl)methanol, (4-chloro-3-phenylquinolin-6-yl)(2-fluoropyridin-4-yl)(1-methyl-1H-imidazol-2-yl)methanol, (2,4-dichloro-3-phenylquinolin-6-yl)di(pyridin-2-yl)methanol, 6-((3-chlorophenyl)(hydroxy)(2-(trifluoromethyl)pyridin-4-yl)methyl)-3-phenylquinoline-2-carbonitrile, (2,4-dichloro-8-methyl-3-phenylquinolin-6-yl)(1-methyl-1H-imidazol-4-yl)(6-methylpyridin-3-yl)methanol, (4-methoxy-3-phenyl-2-(trifluoromethyl)quinolin-6-yl)(1-methyl-1H-imidazol-5-yl)(pyridin-2-yl)methanol, (4-chlorophenyl)(2,4-dichloro-3-(2-chlorophenyl)quinolin-6-yl)(1-methyl-1H-imidazol-2-yl)methanol, (2,4-dichloro-3-phenylquinolin-6-yl)(phenyl)(pyridin-2-yl)methanol, and the second eluting enantiomer of (4-chloro-2-methoxy-3-phenylquinolin-6-yl)(1-methyl-1H-imidazol-5-yl)pyrimidin-2-ylmethanol (when purified on a chiralcel OD column) are excluded from the embodiment.

Another embodiment of the invention is a compound selected from the group consisting of:

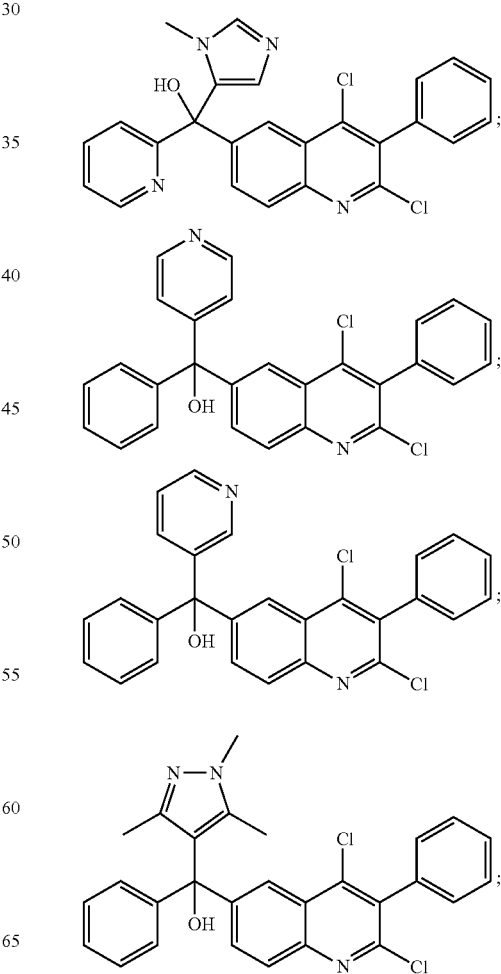

-continued
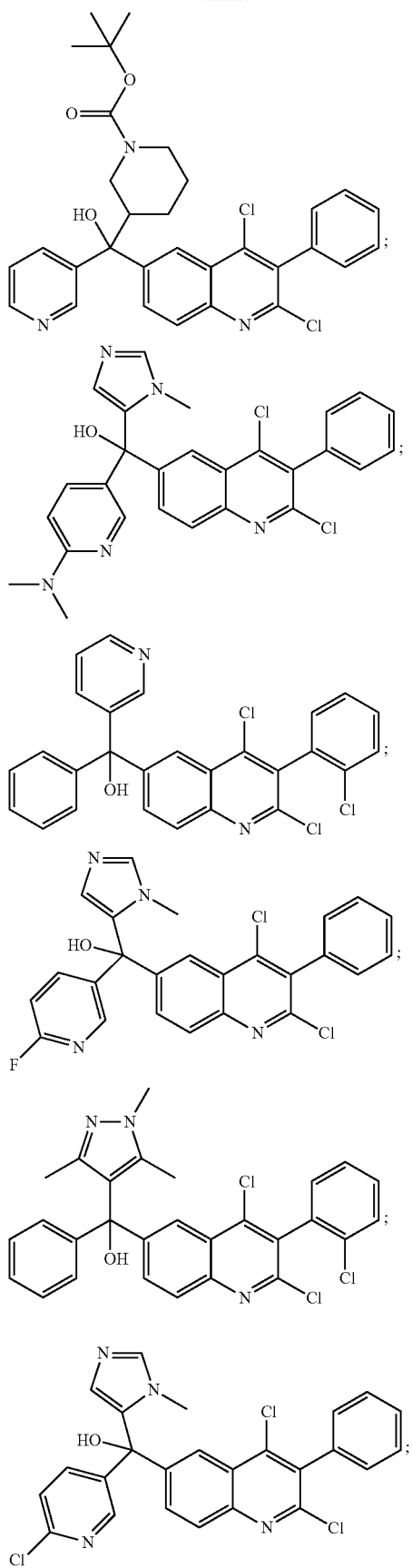
-continued
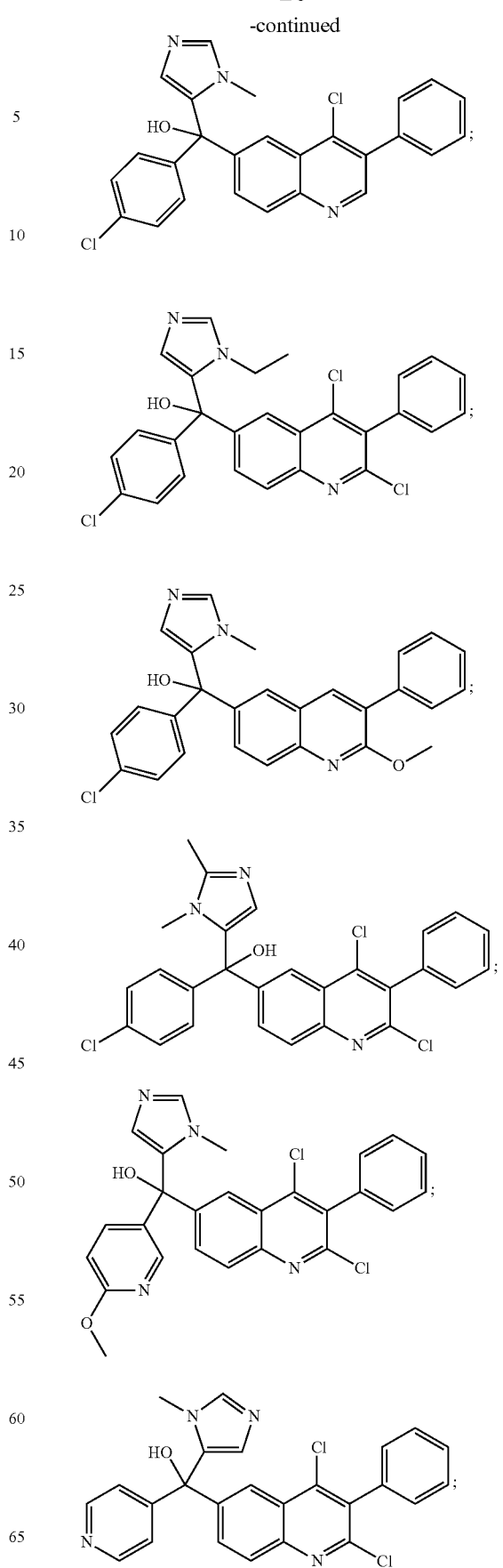

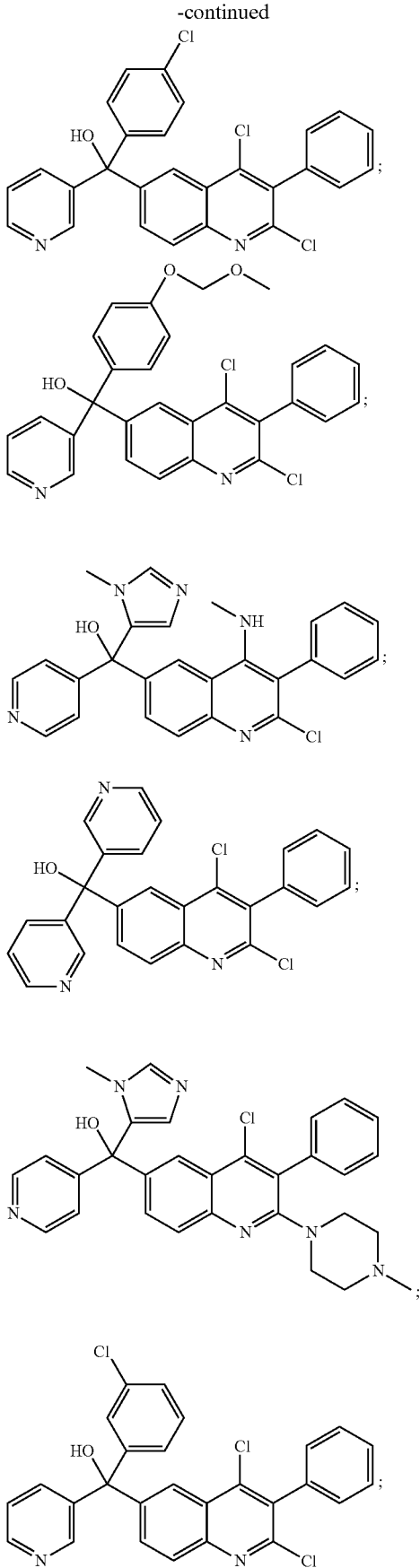
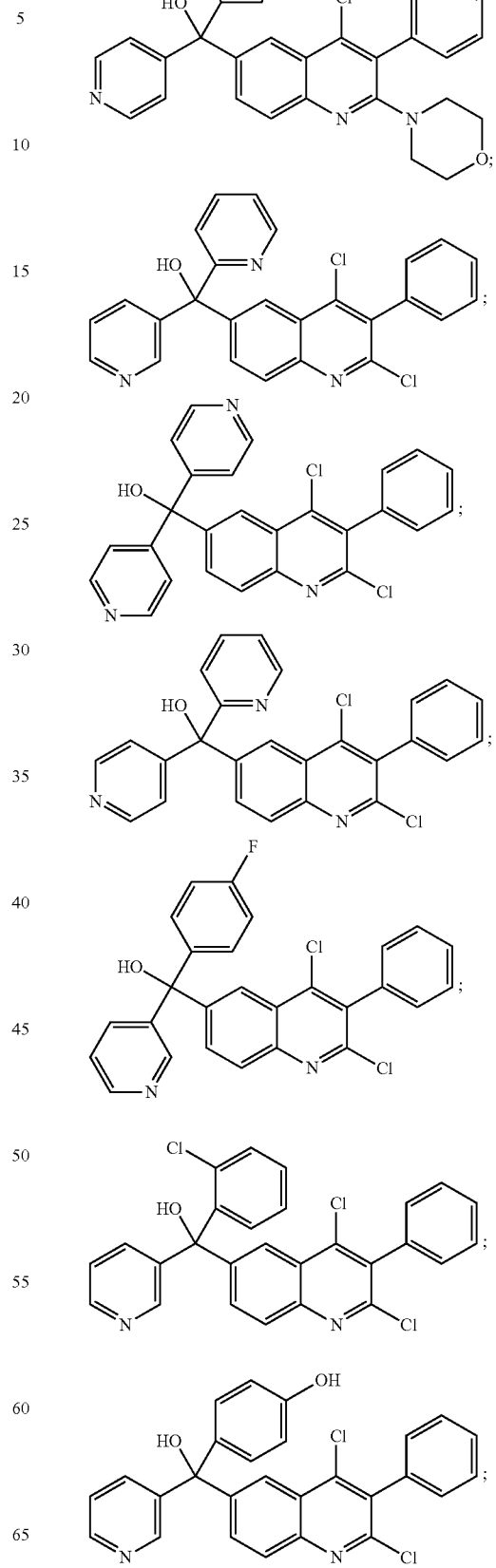

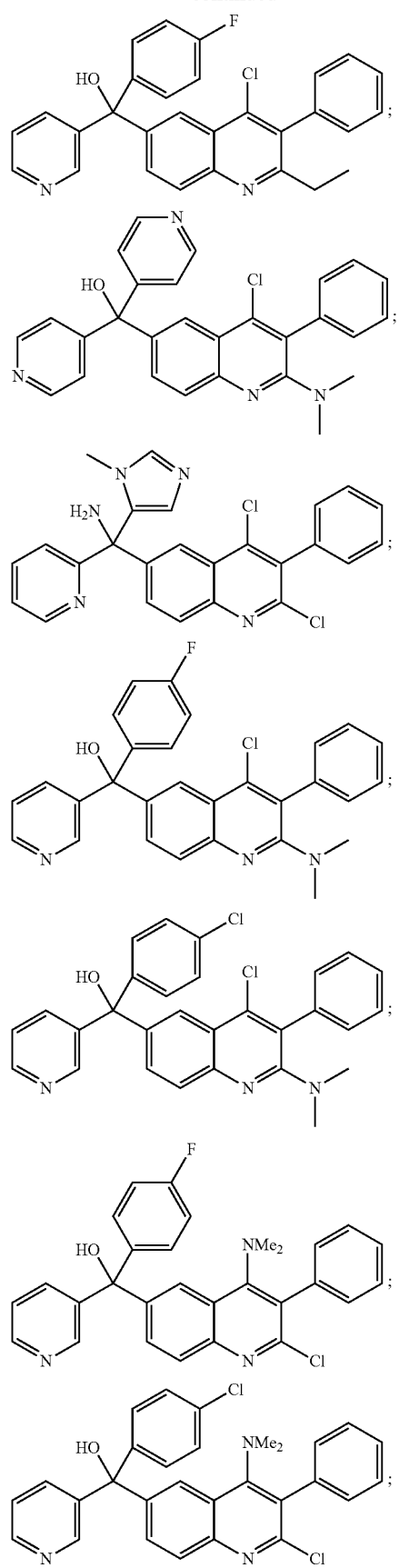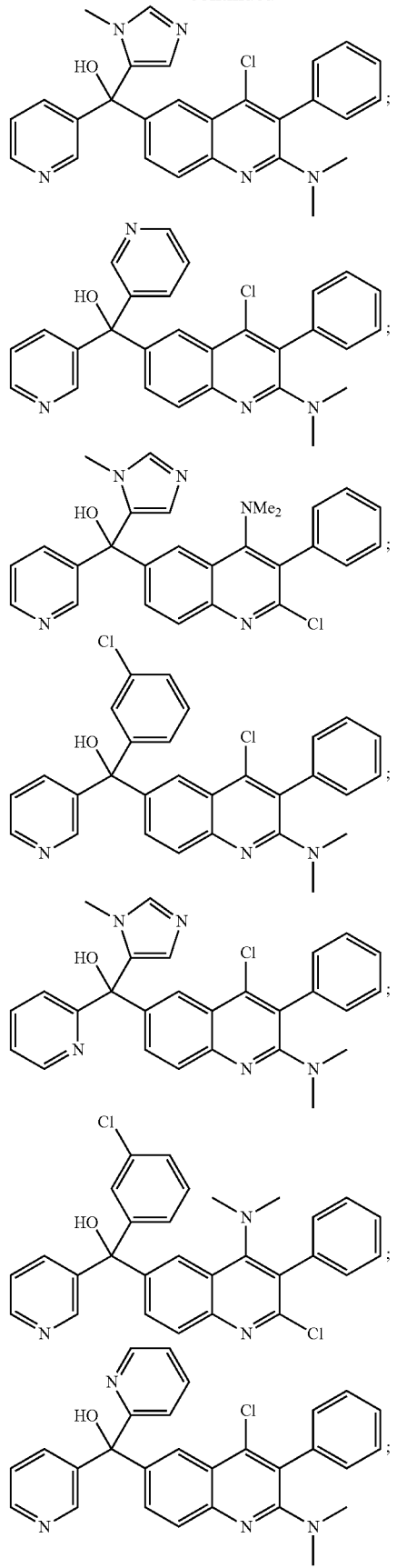

-continued
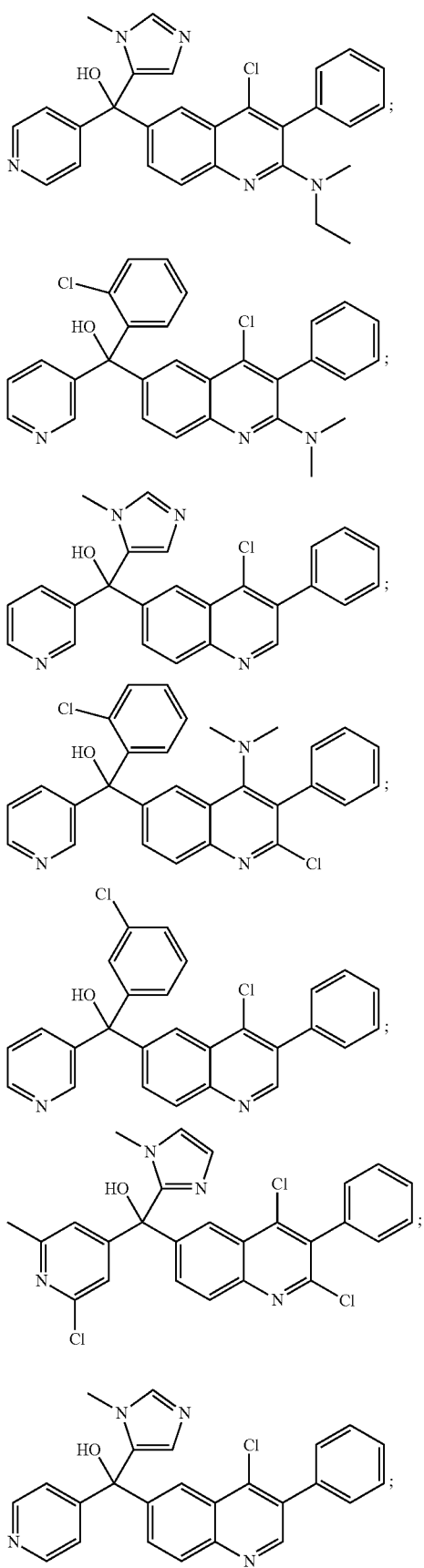
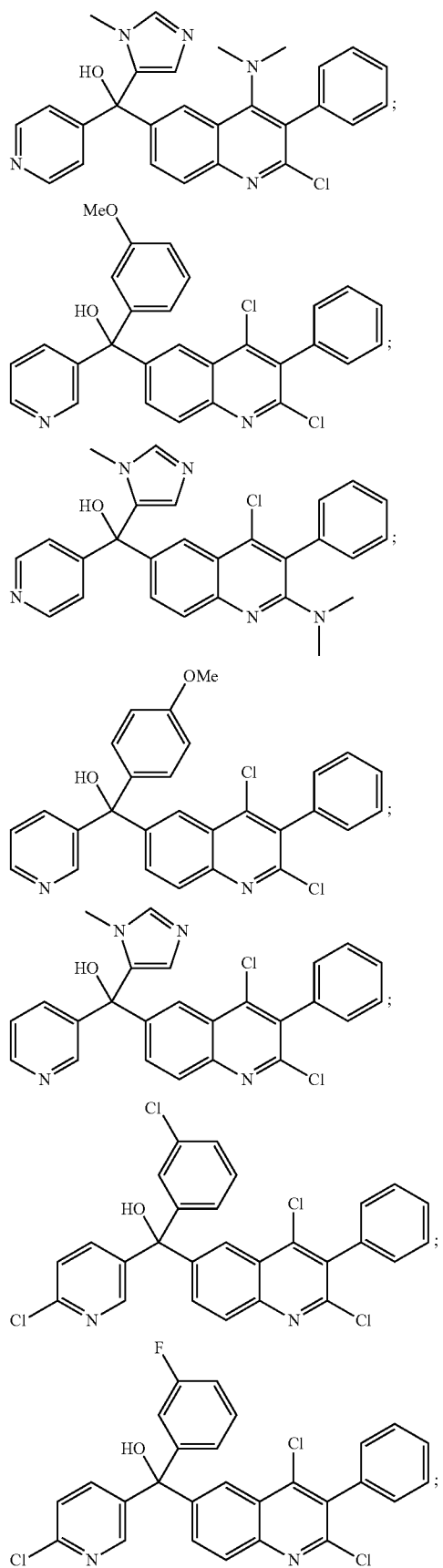

27
-continued
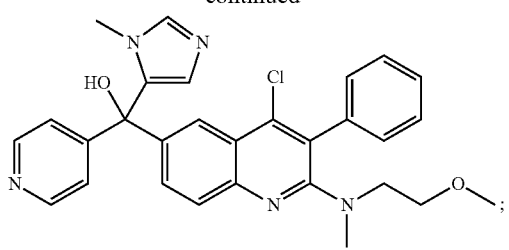
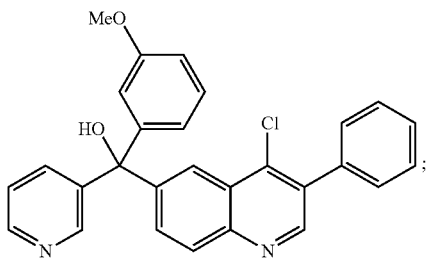
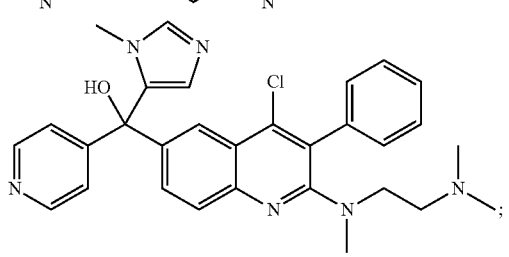
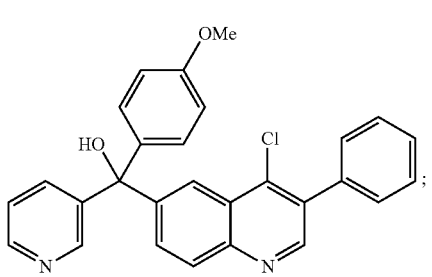
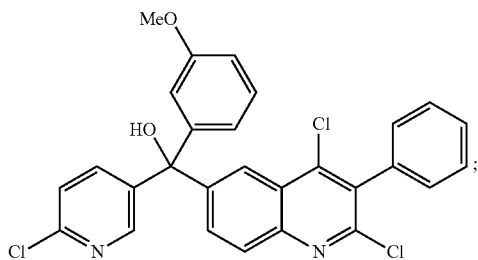
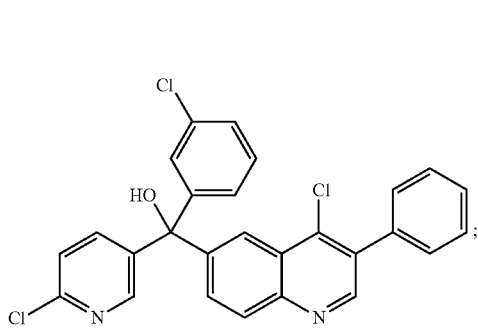
28
-continued
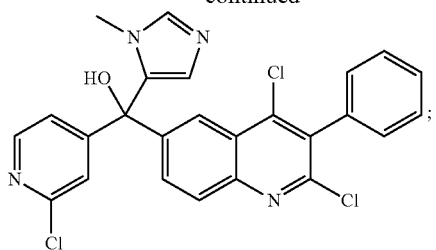
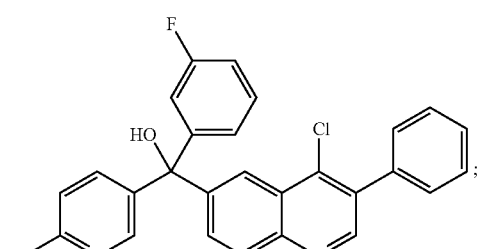
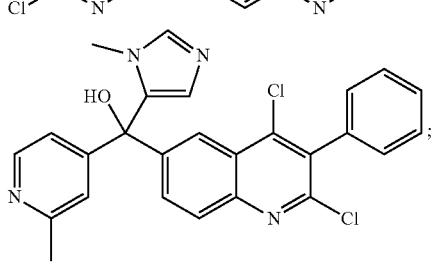
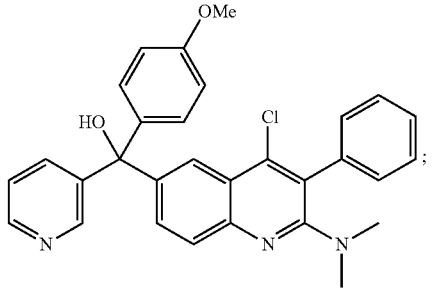
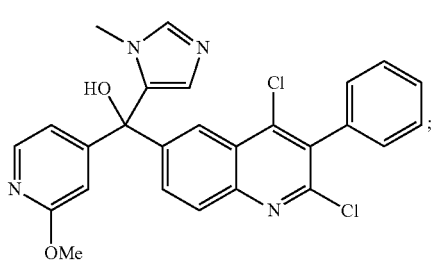
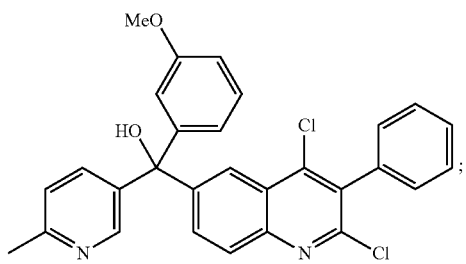

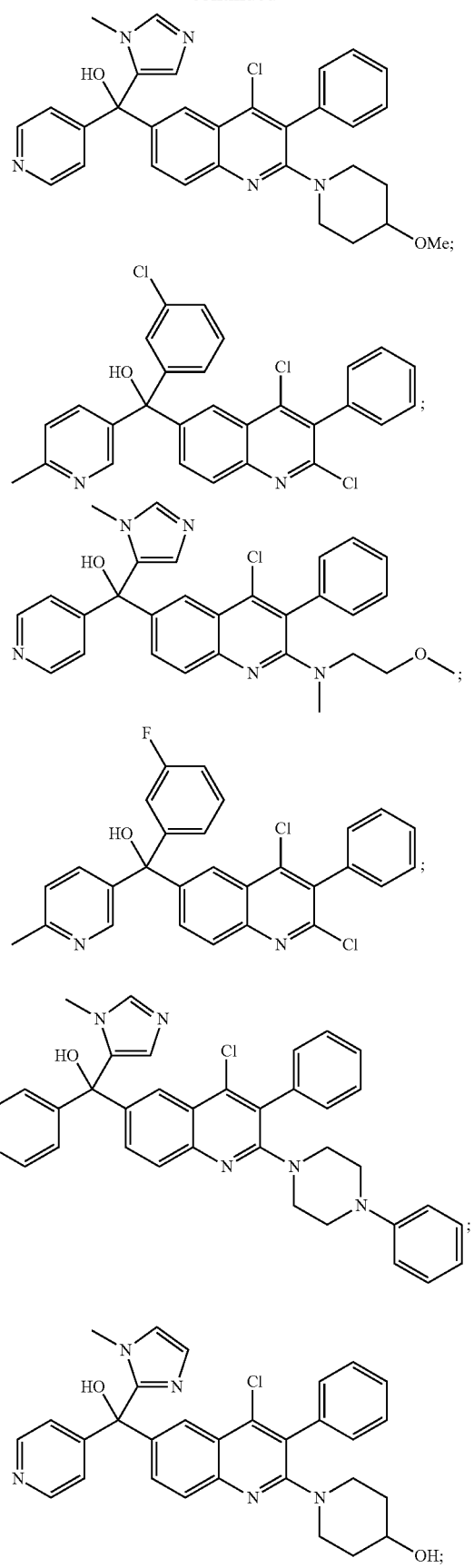
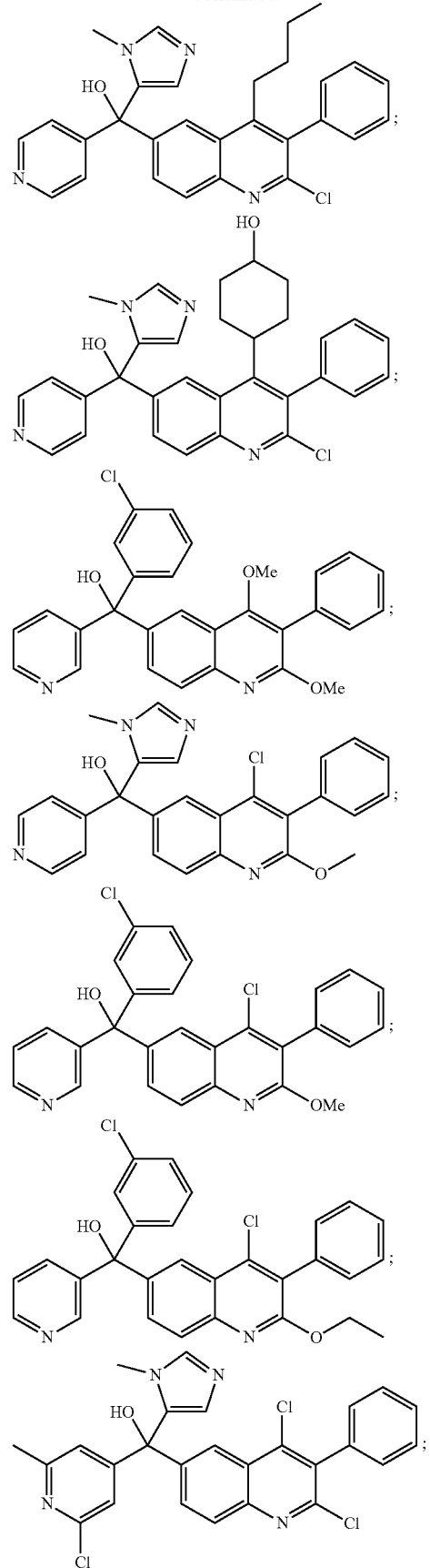

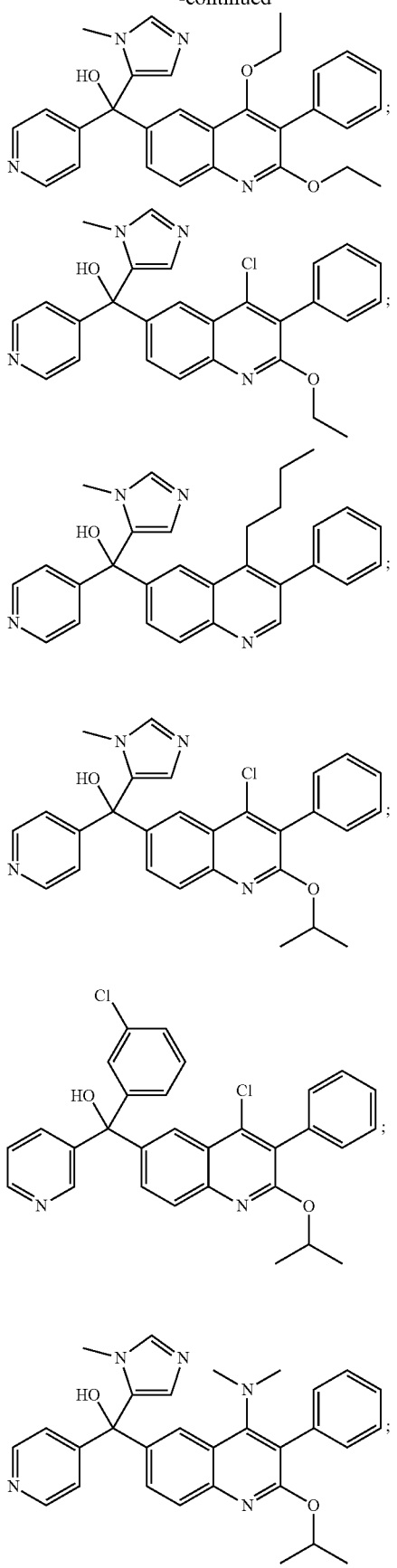
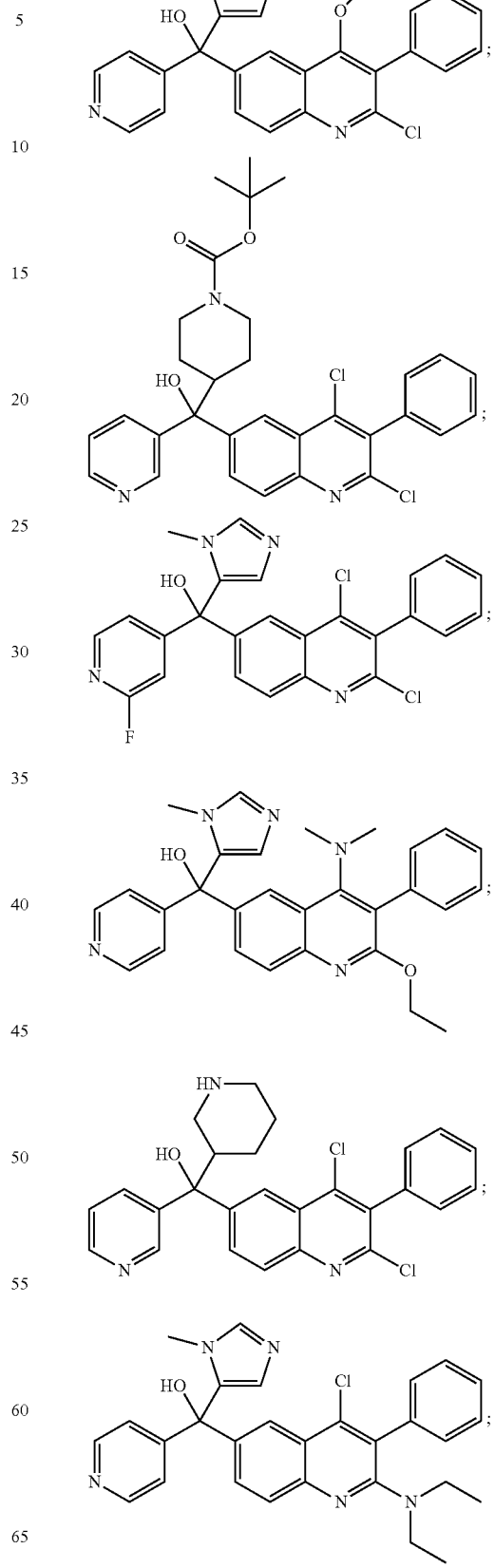

33
-continued
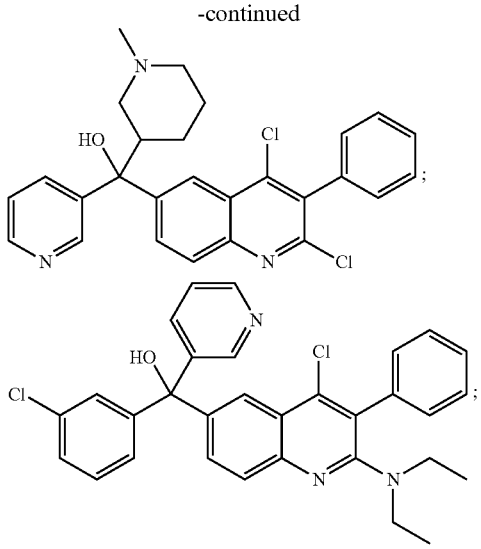
34
-continued
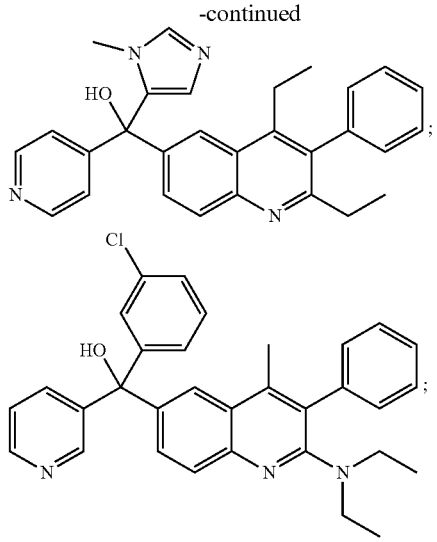
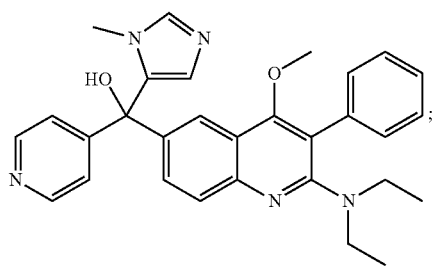
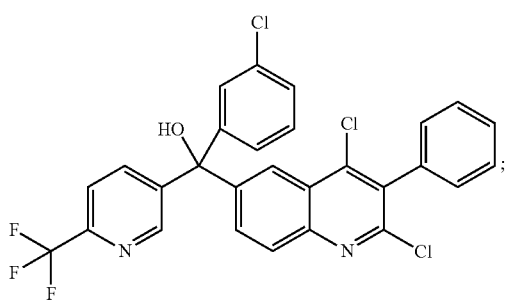

-continued
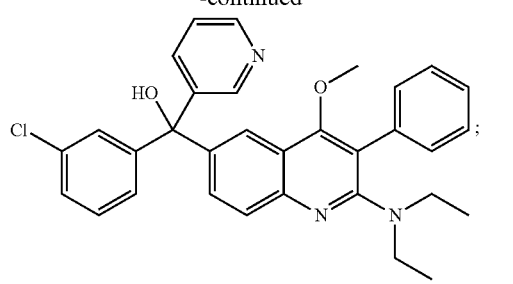
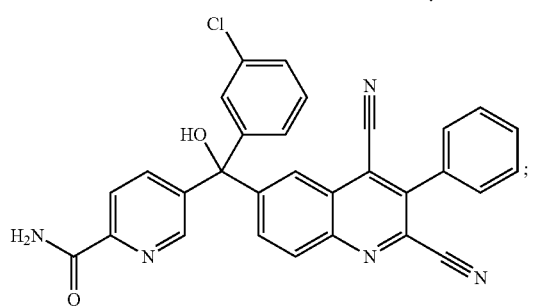
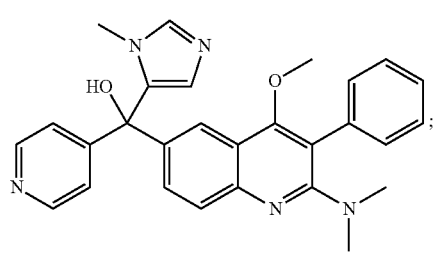
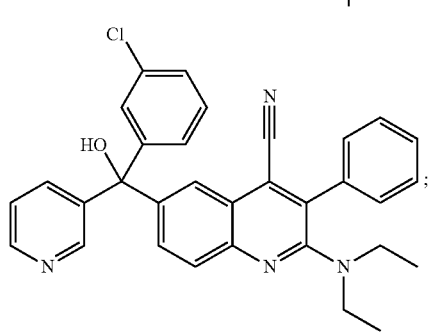
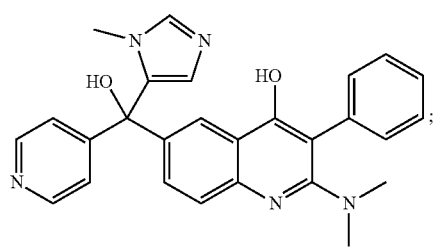
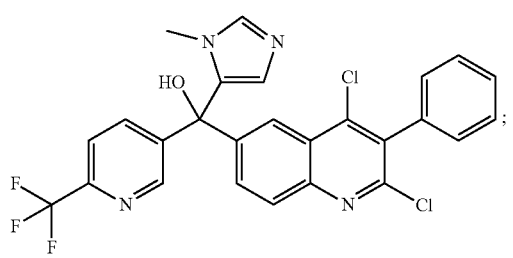
-continued
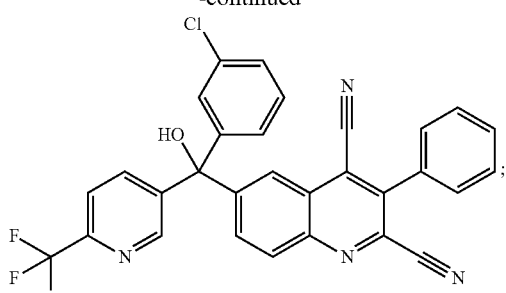
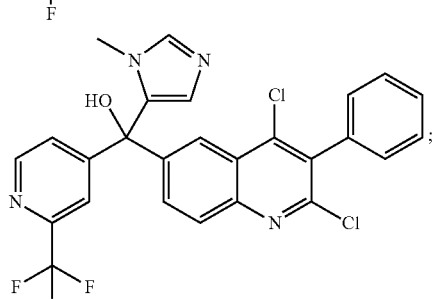
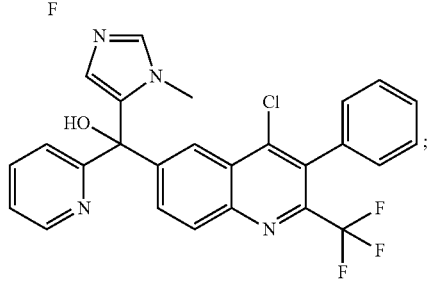
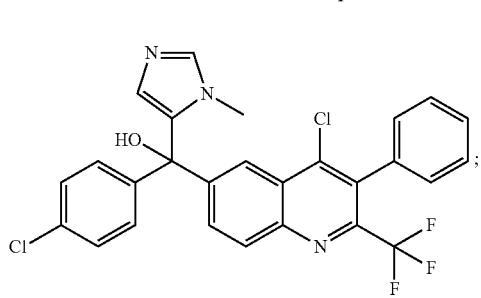
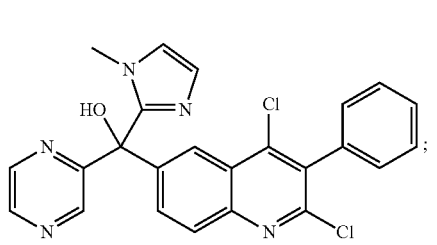
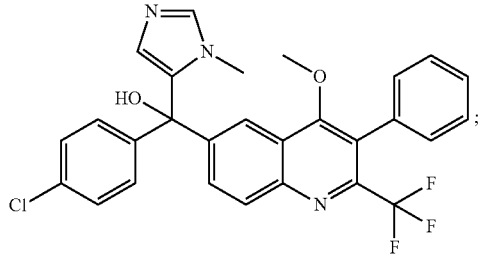

-continued
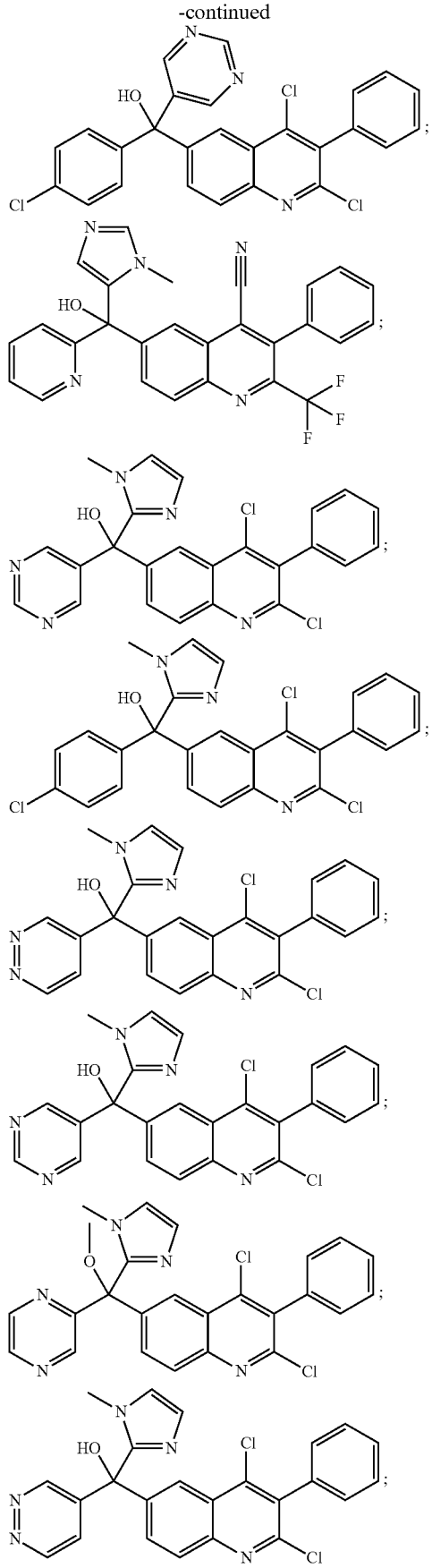
-continued
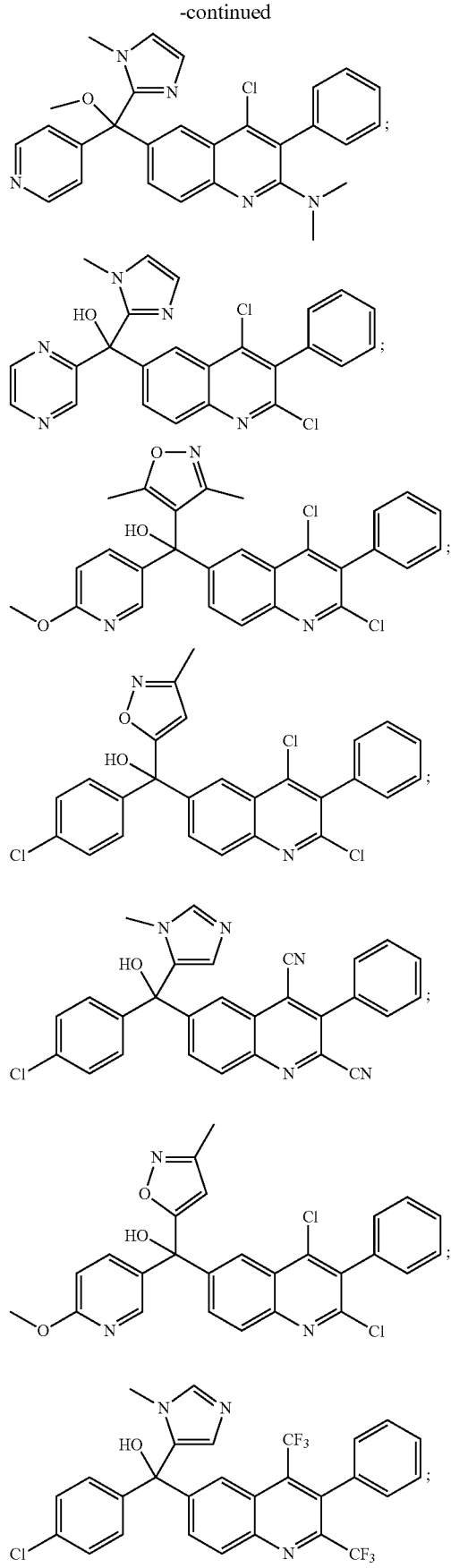

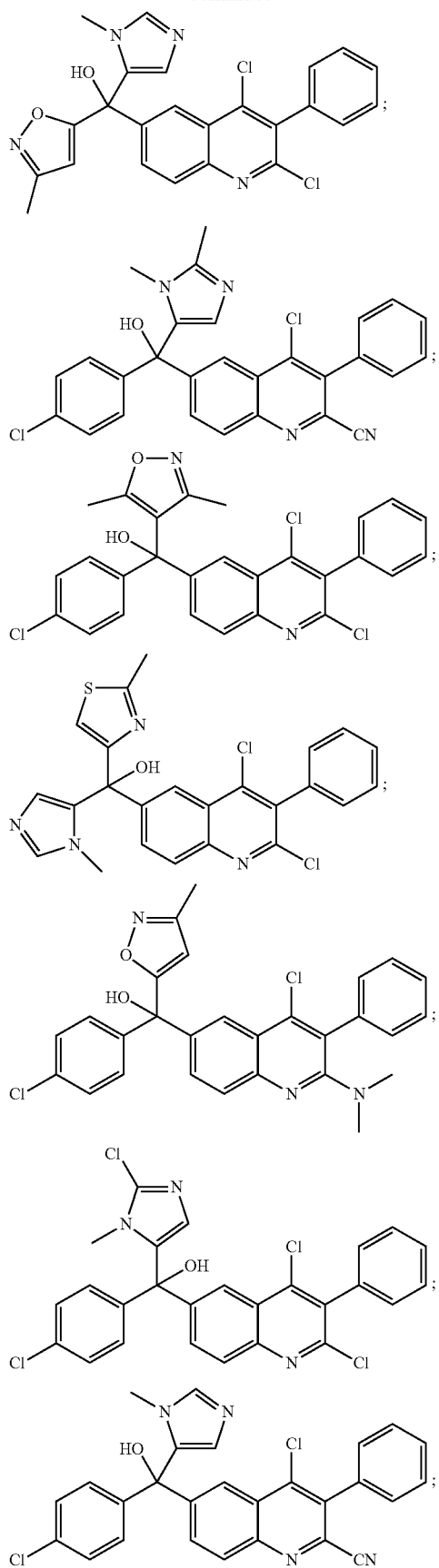
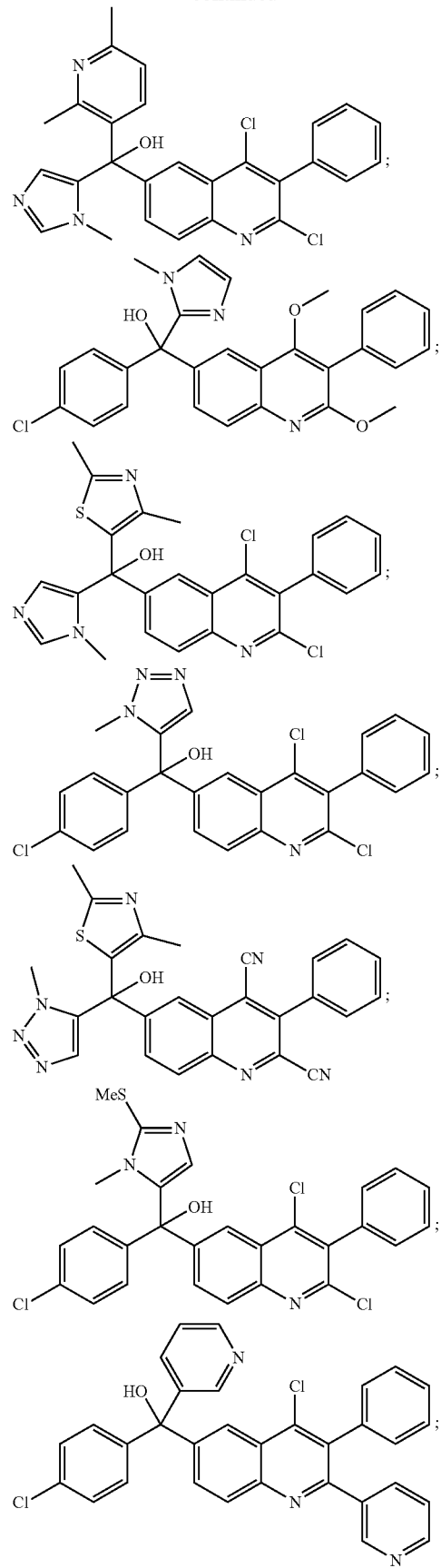

-continued
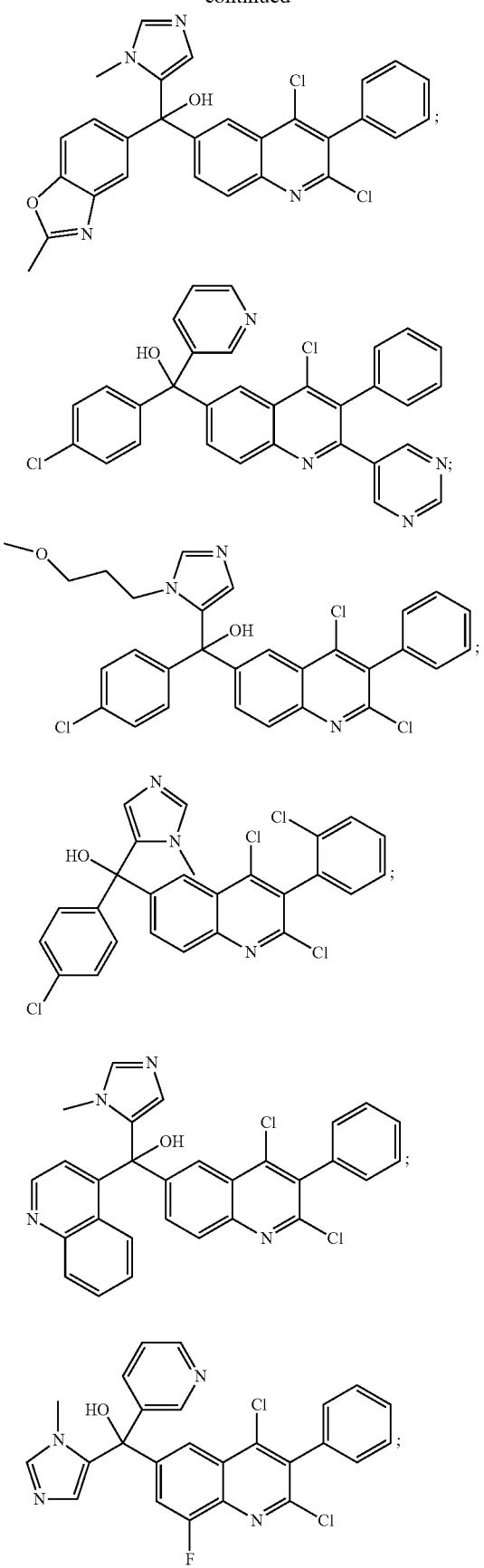
-continued
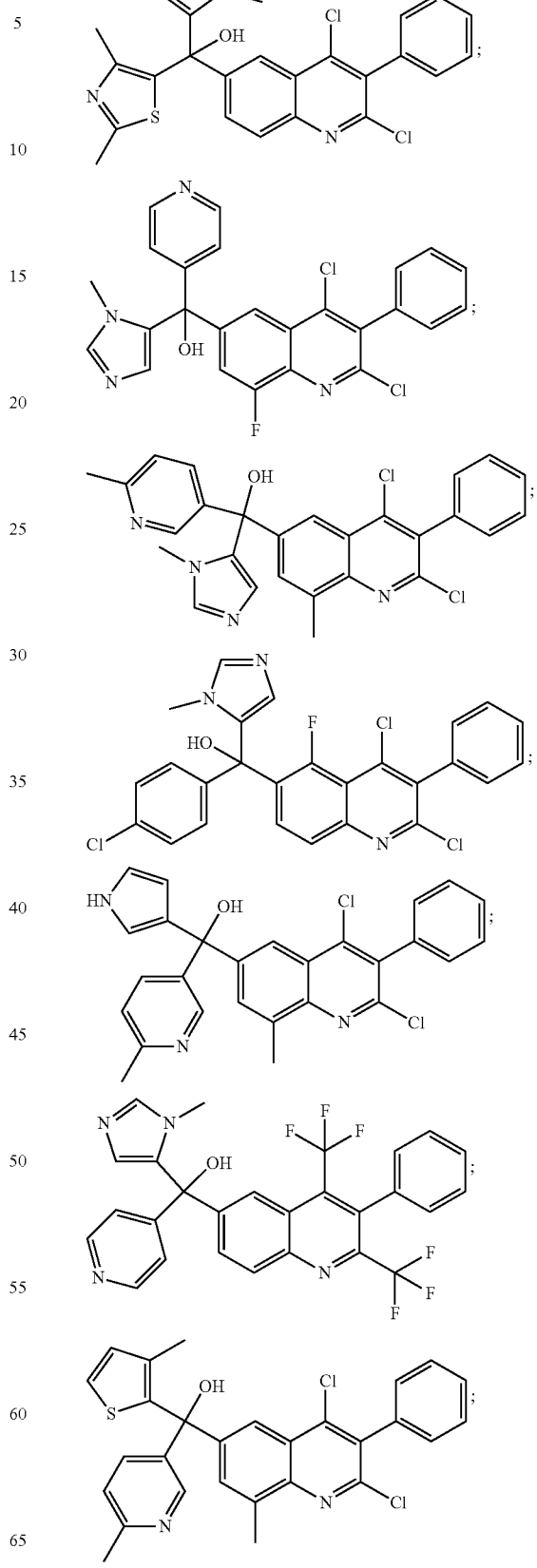

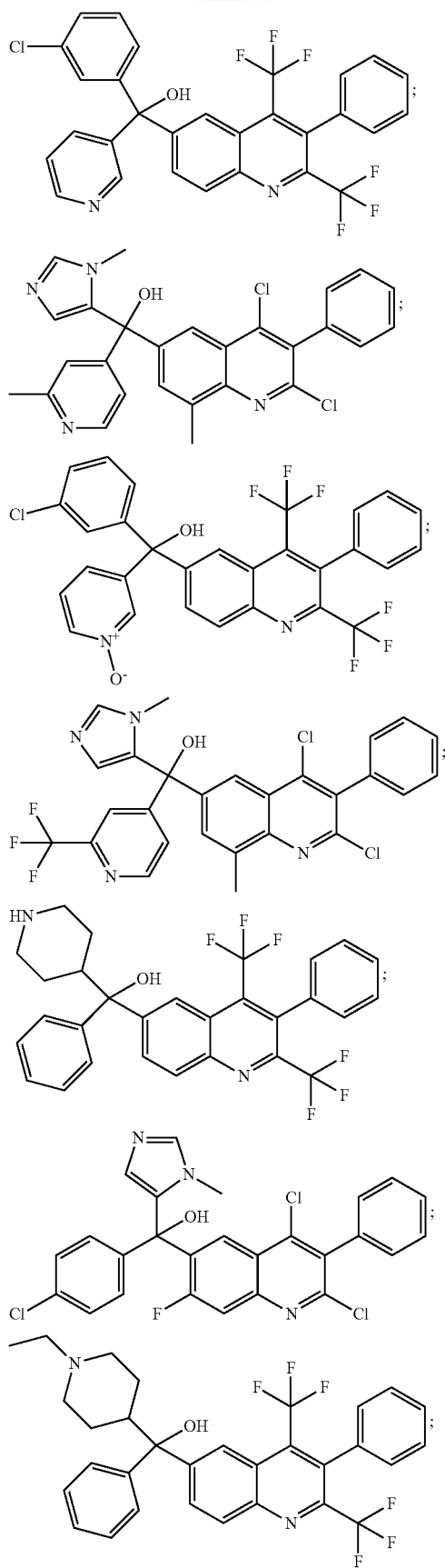
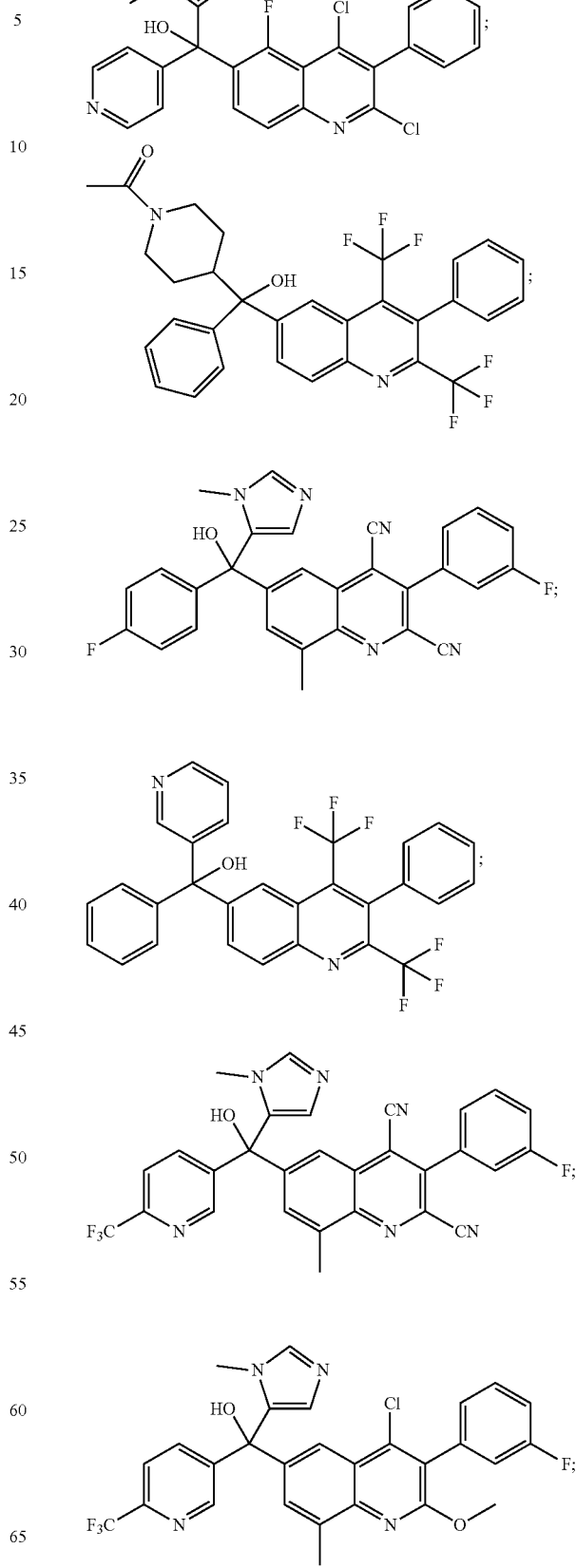

45
-continued
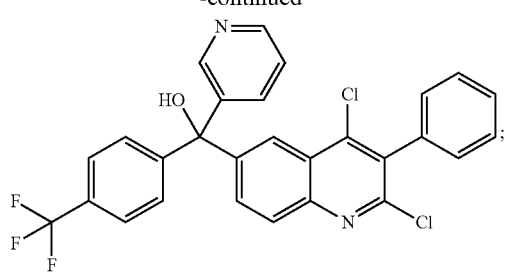
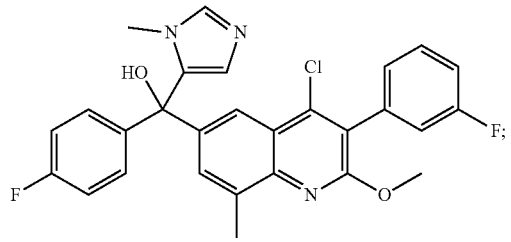
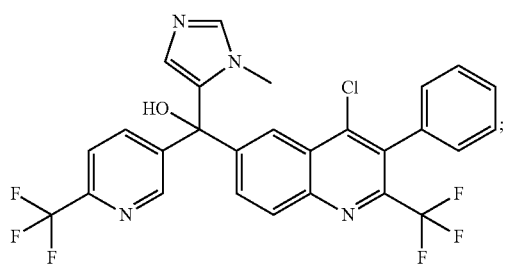
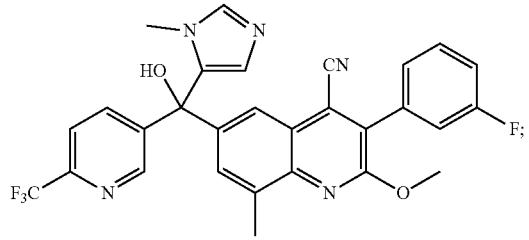
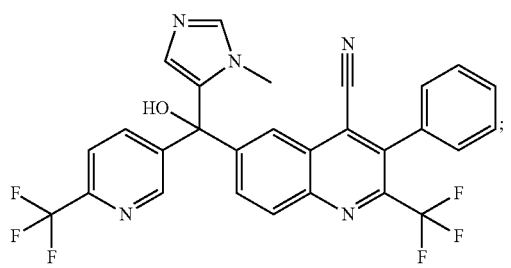
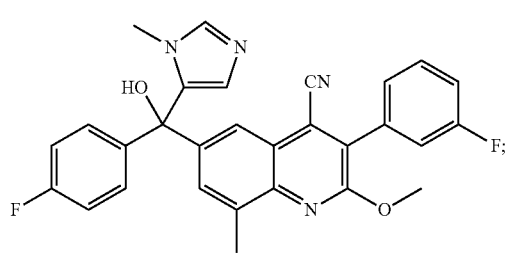
46
-continued
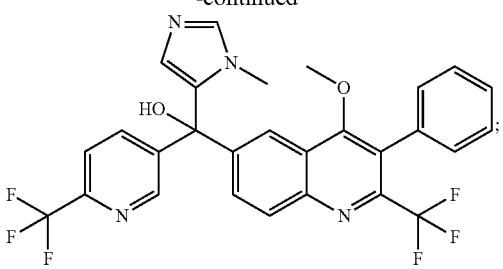
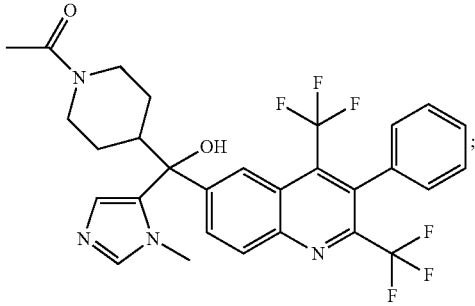
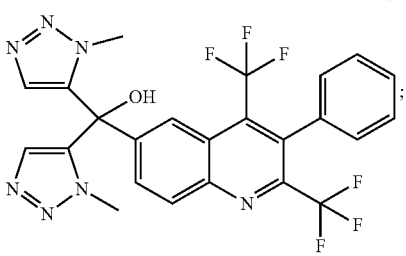
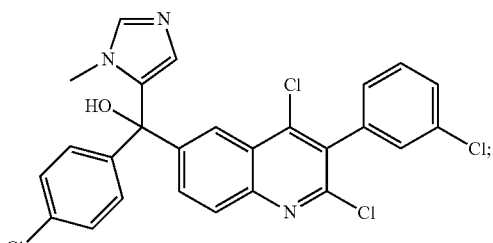
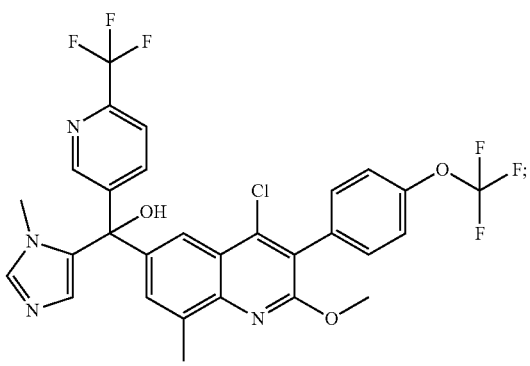
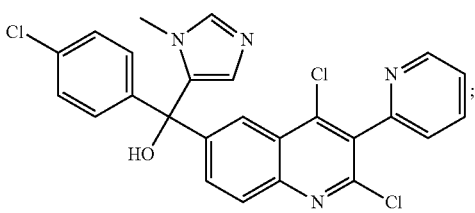

-continued

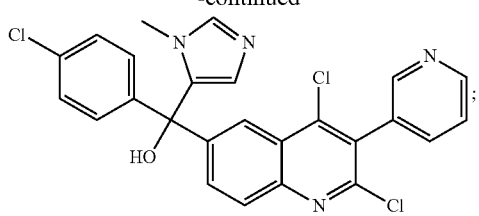

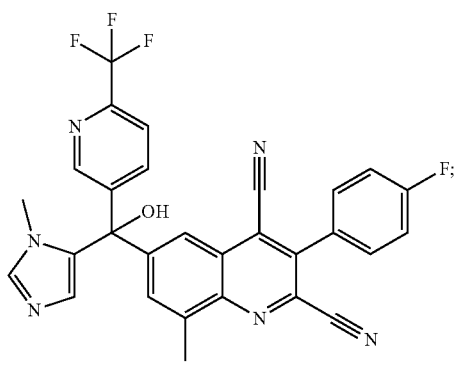

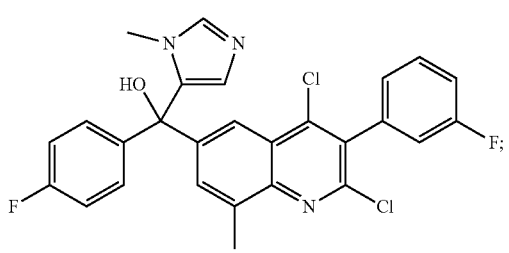

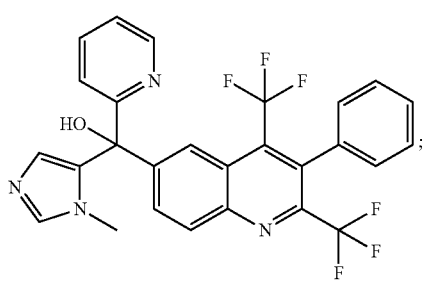

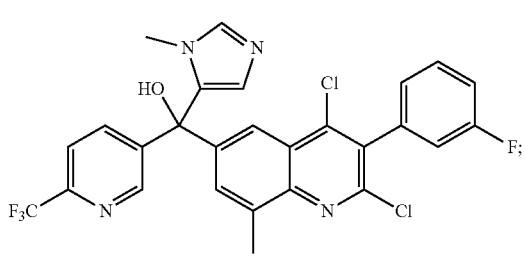

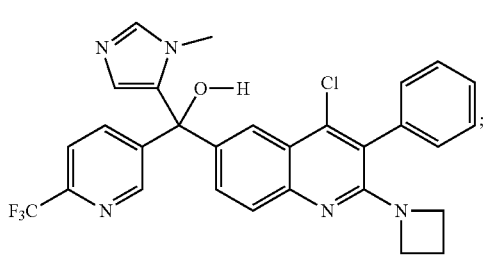

-continued

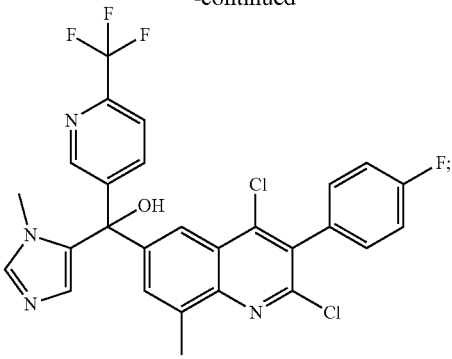

and pharmaceutically acceptable salts thereof.

Another embodiment of the invention comprises a compound of Formula I and a pharmaceutically acceptable carrier.

The present invention also provides a method for treating or ameliorating an RORγt mediated inflammatory syndrome, disorder or disease comprising administering to a subject in need thereof an effective amount of a compound of Formula I or a form, composition or medicament thereof.

The present invention provides a method of preventing, treating or ameliorating a syndrome, disorder or disease, wherein said syndrome, disorder or disease is selected from the group consisting of: ophthalmic disorders, uveitis, atherosclerosis, rheumatoid arthritis, psoriasis, psoriatic arthritis, atopic dermatitis, multiple sclerosis, Crohn's Disease, ulcerative colitis, ankylosing spondylitis, nephritis, organ allograft rejection, fibroid lung, systic fibrosis, renal insufficiency, diabetes and diabetic complications, diabetic nephropathy, diabetic retinopathy, diabetic retinitis, diabetic microangiopathy, tuberculosis, chronic obstructive pulmonary disease, sarcoidosis, invasive staphylococcia, inflammation after cataract surgery, allergic rhinitis, allergic conjunctivitis, chronic urticaria, systemic lupus erythematosus, asthma, allergic asthma, steroid resistant asthma, neutrophilic asthma, periodontal diseases, periodonitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, or stomach comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, neutrophilic asthma, steroid resistant asthma, multiple sclerosis, systemic lupus erythematosus, and ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, and psoriasis comprising administering to a subject in need thereof an effective amount of a compound of Formula I or a form, composition or medicament thereof.

The present invention provides a method of treating or ameliorating a syndrome, disorder or disease, in a subject in need thereof comprising administering to the subject an effective amount of the compound of Formula I or composition or medicament thereof in a combination therapy with one or more anti-inflammatory agents, or immunosuppressive agents, wherein said syndrome, disorder or disease is selected from the group consisting of: rheumatoid arthritis, and psoriasis.

The present invention provides a method of treating or ameliorating a syndrome, disorder or disease, wherein said syndrome, disorder or disease is rheumatoid arthritis, comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriasis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is chronic obstructive pulmonary disorder comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriatic arthritis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is ankylosing spondylitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is Crohn's disease comprising administering to a subject in need thereof an effective amount of a compound of Formula I or a form, composition or medicament thereof.

The present invention provides a method of treating or ameliorating a syndrome, disorder or disease, wherein said syndrome, disorder or disease is ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is neutrophilic asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is steroid resistant asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is multiple sclerosis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is systemic lupus erythematosus comprising administering to a subject in need thereof an effective amount of a compound of Formula I or a form, composition or medicament thereof.

The invention also relates to methods of modulating RORγt activity in a mammal by administration of an effective amount of at least one compound of Formula I.

The present invention provides a method of treating or ameliorating a syndrome, disorder or disease, wherein said syndrome, disorder or disease is selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, and systemic lupus erythematosus comprising administering to a subject in need thereof an effective amount of a compound of Formula I or a form, composition or medicament thereof.

The present invention provides a method of treating or ameliorating an inflammatory bowel disease, wherein said inflammatory bowel disease is Crohn's disease comprising administering to a subject in need thereof an effective amount of a compound of Formula I or a form, composition or medicament thereof.

The present invention provides a method of treating or ameliorating an inflammatory bowel diseases, wherein said inflammatory bowel disease is ulcerative colitis comprising administering to a subject in need thereof an effective amount of a compound of Formula I or a form, composition or medicament thereof.

Definitions

The term "administering" with respect to the methods of the invention, means a method for therapeutically or prophylactically preventing, treating or ameliorating a syndrome, disorder or disease as described herein by using a compound of Formula I or a form, composition or medicament thereof. Such methods include administering an effective amount of said compound, compound form, composition or medicament at different times during the course of a therapy or concurrently in a combination form. The methods of the invention are to be understood as embracing all known therapeutic treatment regimens.

The term "subject" refers to a patient, which may be animal, typically a mammal, typically a human, which has been the object of treatment, observation or experiment and is at risk of (or susceptible to) developing a syndrome, disorder or disease that is associated with abberant RORγt expression or RORγt overexpression, or a patient with an inflammatory condition that accompanies syndromes, disorders or diseases associated with abberant RORγt expression or RORγt overexpression.

The term "effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

As used herein, the term "composition" is intended to encompass a product comprising the specified ingredients in the specified amounts, as well as any product which results, directly or indirectly, from combinations of the specified ingredients in the specified amounts.

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl. Any alkyl group may be optionally substituted with one $OCH_3$, one OH, or up to two fluorine atoms.

The term "$C_{(a-b)}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{(1-4)}$ denotes a radical containing 1, 2, 3 or 4 carbon atoms.

The term "cycloalkyl" refers to a saturated or partially unsaturated monocyclic or bicyclic hydrocarbon ring radical derived by the removal of one hydrogen atom from a single ring carbon atom. Typical cycloalkyl radicals include cyclopropyl, cyclobutyl, cyclopentyl, cyclopentenyl, cyclohexyl, cyclohexenyl, cycloheptyl and cyclooctyl. Additional examples include $C_{(3-6)}$cycloalkyl, $C_{(5-8)}$cycloalkyl, decahydronaphthalenyl, and 2,3,4,5,6,7-hexahydro-1H-indenyl. Any cycloalkyl group may be optionally substituted with one $OCH_3$, one OH, or up to two fluorine atoms.

As used herein, the term "thiophenyl" is intended to describe the radical formed by removing a hydrogen atom from the molecule with the structure:

Pharmaceutically Acceptable Salts

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate, sodium hydroxide, triethanolamine or zinc.

Methods of Use

The present invention is directed to a method for preventing, treating or ameliorating a RORγt mediated inflammatory syndrome, disorder or disease comprising administering to a subject in need thereof an effective amount of a compound of Formula I or a form, composition or medicament thereof.

Since RORγt is an N-terminal isoform of RORγ, it is recognized that compounds of the present invention which are modulators of RORγt are likely to be modulators of RORγ as well. Therefore the mechanistic description "RORγt modulators" is intended to encompass RORγ modulators as well.

When employed as RORγt modulators, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula I may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the compounds of the present invention. Thus, in the methods of treatment of the present invention, the term "administering" shall encompass the means for treating, ameliorating or preventing a syndrome, disorder or disease described herein with the compounds of the present invention or a polymorph or solvate thereof, which would obviously be included within the scope of the invention albeit not specifically disclosed.

In another embodiment, the invention relates to a compound as described in Formula I for use as a medicament.

In another embodiment, the invention relates to the use of a compound as described in Formula I for the preparation of a medicament for the treatment of a disease associated with an elevated or aberrant RORγt activity.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", Ed. H. Bundgaard, Elsevier, 1985.

Furthermore, it is intended that within the scope of the present invention, any element, in particular when mentioned in relation to a compound of Formula (I), shall comprise all isotopes and isotopic mixtures of said element, either naturally occurring or synthetically produced, either with natural abundance or in an isotopically enriched form. For example, a reference to hydrogen includes within its scope $^1H$, $^2H$ (D), and $^3H$ (T). Similarly, references to carbon and oxygen include within their scope respectively $^{13}C$ and $^{14}C$ and $^{16}O$ and $^{18}O$. The isotopes may be radioactive or non-radioactive. Radiolabelled compounds of formula (I) may comprise a radioactive isotope selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^3H$, $^{11}C$ and $^{18}F$.

Some compounds of the present invention may exist as atropisomers. Atropisomers are stereoisomers resulting from hindered rotation about single bonds where the steric strain barrier to rotation is high enough to allow for the isolation of the conformers. It is to be understood that all such conformers and mixtures thereof are encompassed within the scope of the present invention.

Where the compounds according to this invention have at least one stereo center, they may accordingly exist as enantiomers or diastereomers. It is to be understood that all such isomers and mixtures thereof are encompassed within the scope of the present invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Abbreviations

Herein and throughout the application, the following abbreviations may be used.

Å angstrom
Ac acetyl
Ac$_2$O acetic anhydride
BHT butylated hydroxytoluene
Boc tert-butyloxycarbonyl
br broad
Bu butyl
n-BuLi n-butyl lithium
t-BuOH tert-butanol
d doublet dba dibenzylideneacetone
DCE dichloroethane
DCM dichloromethane
Dess-Martin periodinane 1,1,1-tris(acetyloxy)-1,1-dihydro-1,2-benziodoxol-3-(1H)-one
DIEA N,N-diisopropylethylamine
DMA dimethylacetamide
DME dimethylacetamide
DMF N,N-dimethylformamide
DMSO dimethyl sulfoxide
dppf (diphenylphosphino)ferrocene
Eaton's Reagent 7.7 wt % phosphorus pentoxide solution in methanesulfonic acid
EDCI N-(3-dimethylaminopropyl)-N'-ethylcarbodiimide hydrochloride
EtMgBr ethylmagnesium bromide
ESI electrospray ionization
Et ethyl
$Et_2O$ diethyl ether
EtOAc ethyl acetate
EtOH ethyl alcohol
$Et_3SiCl$ chlorotriethylsilane
HATU O-(7-azabenzotriazol-1-yl)-N,N,N',N'-tetramethyluronium hexafluorophosphate
HPLC high pressure liquid chromatography
Hz hertz
i-PrOH isopropyl alcohol
LCMS liquid chromatography-mass spectrometry
m multiplet
M molar (moles/liter)
mCPBA 3-chloroperbenzoic acid
Meldrum's acid 2,2-dimethyl-1,3-dioxane-4,6-dione
MeOH methanol
MeONa sodium methoxide
MHz megahertz
min minutes
mL milliliters
MTBE methyl tertiary butyl ether
nm nanometers
NaOiPr sodium isopropoxide
NBS N-bromosuccinimide
NMR nuclear magnetic resonance
Ph phenyl
ppm parts per million
Pr propyl
q quartet
RP-HPLC reverse phase high pressure liquid chromatography
s singlet
TBAF tetrabutylammonium fluoride
TEA triethylamine
TEMPO (2,2,6,6-tetramethylpiperidin-1-yl)oxidanyl
TFA trifluoroacetic acid
THF tetrahydrofuran
TLC thin layer chromatography
UV ultra-violet
X-Phos 2-dicyclohexylphosphino-2',4',6'-triisopropylbiphenyl General Schemes:

Compounds of Formula I in the present invention can be synthesized in accordance with the general synthetic methods known to those who are skilled in the art. The following reaction schemes are only meant to represent examples of the invention and are in no way meant to be a limit of the invention.

Scheme 1

PATH 1

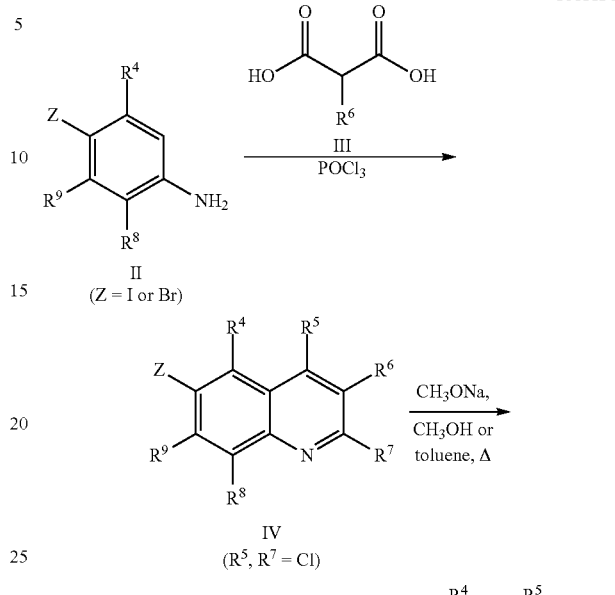

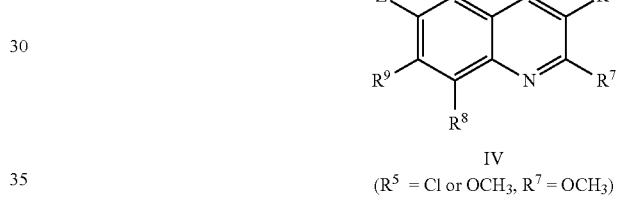

PATH 2

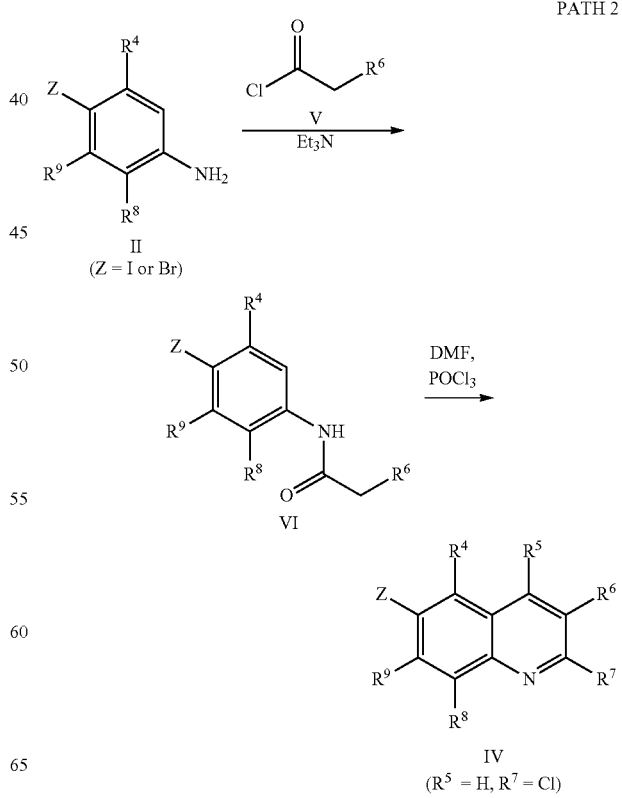

PATH 3

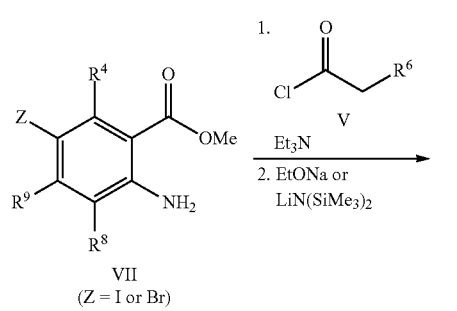

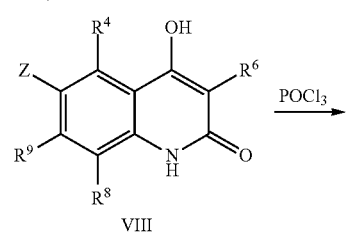

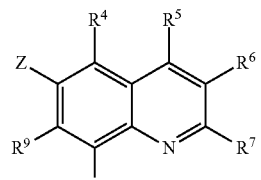

PATH 4

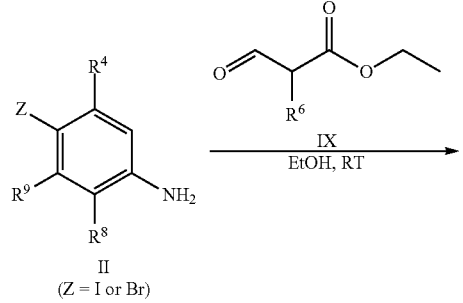

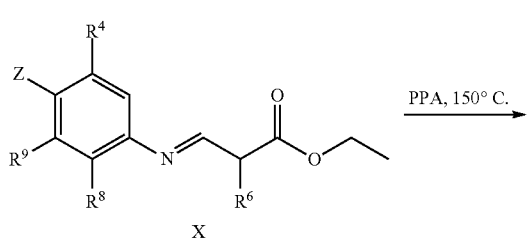

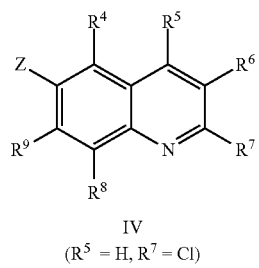

Scheme 1 describes the preparation of 6-bromo or 6-iodo-quinolines of Formula IV by various methods (path 1 to 4). In path 1, cyclization of 4-haloanilines II with 2-substituted malonic acids III can be done in refluxing phosphorus oxychloride to provide 6-haloquinolines IV, wherein $R^5$ and $R^7$ are Cl. Nucleophilic displacement of 2-chloro substitution with sodium methoxide in hot MeOH or toluene gives 6-halo-2-methoxyquinolines IV. Path 2 illustrates the cyclization of amides VI, derived from acylation of 4-haloanilines II with substituted acid chlorides V, in the presence of DMF in hot phosphorus oxychloride to generate 6-haloquinolines IV, wherein $R^5$ is H and $R^7$ is Cl. In path 3, methyl 2-aminobenzoates VII can undergo acylation with acid chlorides V to form an amide intermediate, which can be further treated with a base, such as sodium ethoxide or lithium bis(trimethylsilyl) amide, to afford 6-halo-4-hydroxyquinolin-2(1H)-ones VIII. Conversion of hydroxyquinolin-2(1H)-ones VIII to 2,4-dichloroquinolines IV can be carried out in refluxing phosphorus oxychloride. Path 4 describes the condensation of anilines II and aldehydes IX in ethanol to form compound X which can be further cyclized in polyphosphoric acid at high temperatures to give quinolinones XI. Convertion to the 4-chloroquinolines IV wherein $R^7$ is H can be accomplished in phosphorus oxychloride as previously described.

Scheme 2

PATH 1

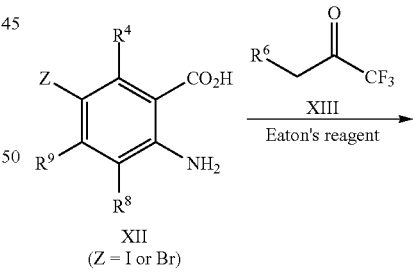

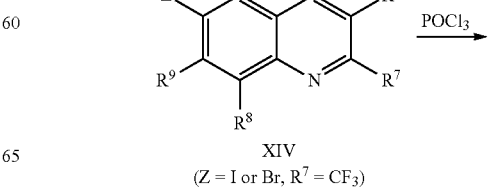

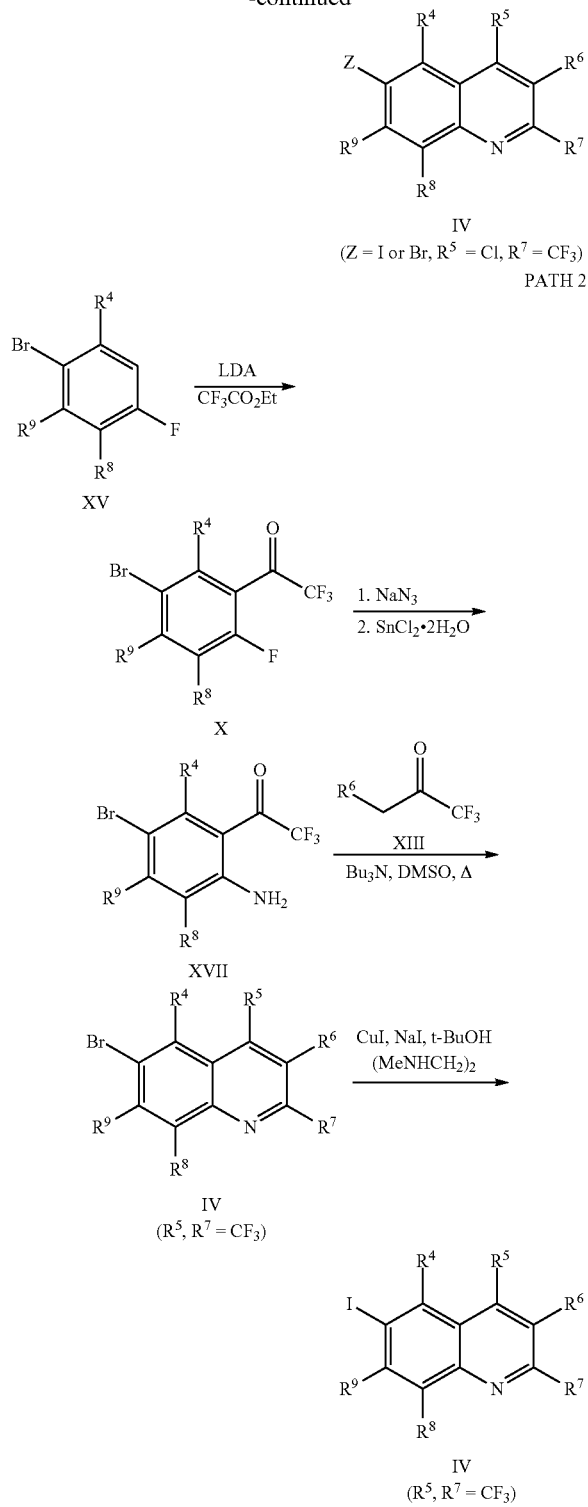
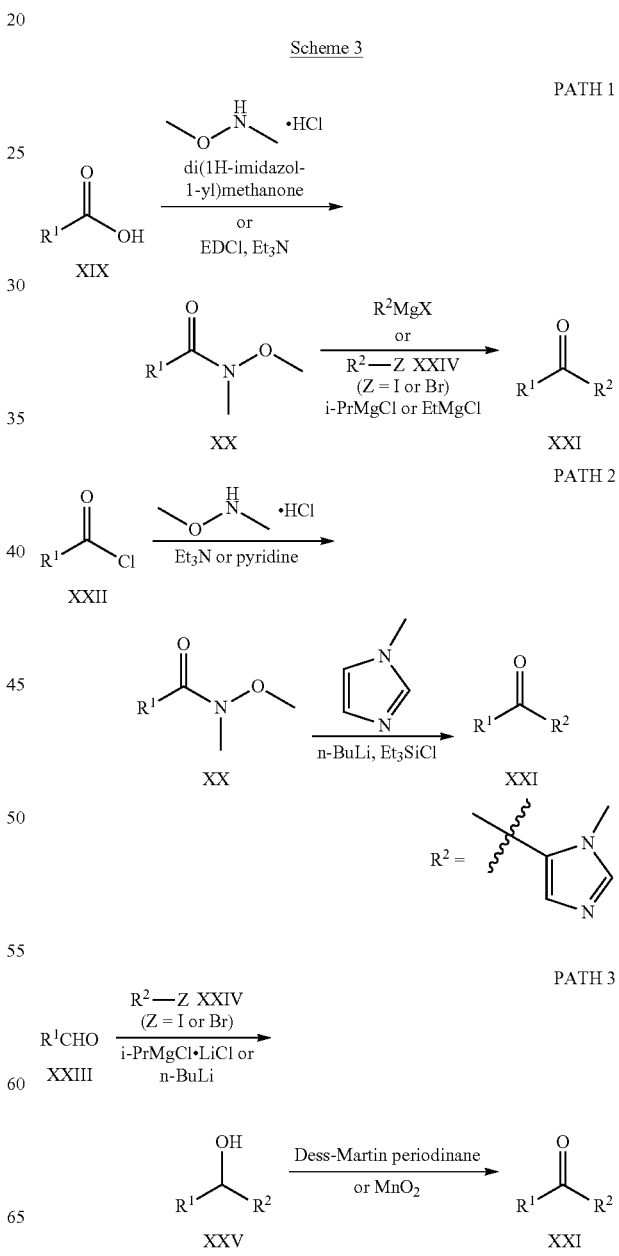

C. gives 6-bromo or 6-iodoquinolines IV, wherein $R^5$ is Cl and $R^7$ is $CF_3$. 6-Iodo-2,4-bis(trifluoromethyl)quinolines IV can be formed by the reaction sequence illustrated in path 2. Treatment of 1-bromo-4-fluorobenzenes XV with lithium diisopropylamide at −78° C. followed by addition of ethyl trifluoroacetate provides 2-fluorophenyl-2,2,2-trifluoroethanones XVI. Anilines XVII can be prepared by displacing 2-fluoro in XVI with sodium azide followed by reduction with tin (II) chloride dihydrate. Cyclization of XVII with 1,1,1-trifluoropropan-2-ones XIII in the presence of tributylamine in a polar solvent, such as DMF or DMSO, at high temperatures can provide 6-bromo-2,4-bis(trifluoromethyl)quinolines IV. The 6-iodo-2,4-bis(trifluoromethyl)quinolines XVIII can then be subsequently obtained by conversion of 6-bromoquinoline IV, where $R^5$ and $R^7$ are $CF_3$, with NaI, CuI, and N,N'-dimethylethylenediamine in t-BuOH at high temperatures under microwave condition.

Scheme 2 illustrates the synthesis leading to 6-bromo or 6-iodoquinolines of Formula IV wherein $R^5$ is Cl and $R^7$ is $CF_3$ (path 1), and 6-iodoquinolines of Formula XVIII where $R^5$ and $R^7$ are $CF_3$ (path 2). In path 1, cyclization of 2-aminobenzoic acids XII with 1,1,1-trifluoropropan-2-ones XIII in Eaton's reagent at elevated temperatures yields 4-hydroxy-2-trifluoromethylquinolines XIV, which upon heating in phosphorus oxychloride at temperatures between 100-120°

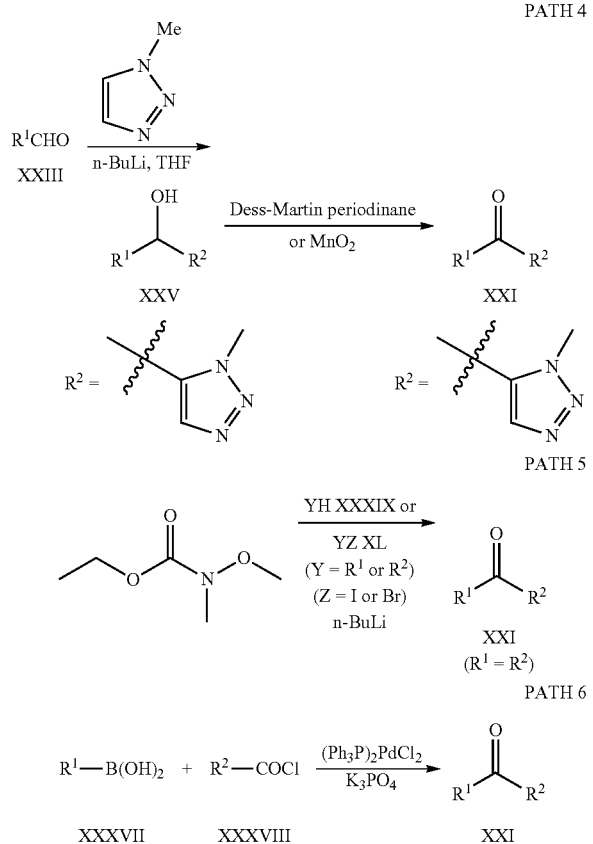

ence of a base such as triethylamine or Hunig's base and a coupling reagent such as EDCI. The amides XX can be further treated with Grignard reagents such as $R^2MgX$ (X is Br or Cl) that can be obtained commercially or preformed by treatment of $R^2Z$ with organometallic reagents such as i-PrMgCl or EtMgCl in THF. Alternatively, Weinreb amides XX can be obtained from acyl chlorides XXII and N,O-dimethylhydroxylamine hydrochloride by using triethylamine or pyridine as a base. 1-Methyl-1H-imidazole can be treated with one equivalent of n-BuLi and one equivalent of chlorotriethylsilane at −78° C. followed by an additional equivalent of n-BuLi, to which the Weinreb amides XX can be added to yield ketones XXI wherein $R^2$ is imidazolyl (path 2).

In path 3, halogen and metal exchange of bromides or iodides XXIV with i-PrMgCl.LiCl or n-BuLi, followed by addition of aldehydes XXIII affords alcohols XXV. Oxidation of XXV with Dess-Martin periodinane or $MnO_2$ can provide ketones XXI. In path 4, ketones XXI, where $R^2$ is triazolyl, can be prepared by treatment of 1-methyl-1H-1,2,3-triazole with n-BuLi followed by reaction with aldehydes XXIII to yield alcohols XXV, which could undergo oxidation with Dess-Martin periodinane or $MnO_2$. Path 5 exemplifies the preparation of symmetrical ketones XXI, wherein $R^1$ and $R^2$ are the same. As illustrated, an aryl or heteroaryl group containing an acidic proton XXXIX ($Y=R^1$ or $R^2$) can be deprotonated in the presence of a strong base such as n-butyllithium once solubilized in a preferred solvent such as tetrahydrofuran at temperatures between 0 and −78° C. then added in excess to ethyl methoxy(methyl)carbamate to provide ketones XXI wherein $R^1$ and $R^2$ are the same. Aryl or heteroaryl bromide or iodide XL can also be lithiated through a lithium/halogen exchange with n-butyllithium before adding in excess to ethyl methoxy(methyl)carbamate as previously described to provide symmetrical ketones XXI. Path 6, which employs palladium catalyzed cross-coupling of arylboronic acids XXXVII with acid chlorides XXXVIII using $K_3PO_4$ as a base and $(Ph_3P)_2PdCl_2$ as a catalyst in a high boiling non-polar solvent such as toluene, can also be used to generate ketones XXI.

Scheme 3 illustrates synthetic routes (path 1 to 6) to ketones of Formula XXI. In path 1, Weinreb amide XX can be prepared from acids XIX by reacting with N,O-dimethylhydroxylamine hydrochloride and 1,1-carbonyldiimidazole or with N,O-dimethylhydroxylamine hydrochloride in the pres-

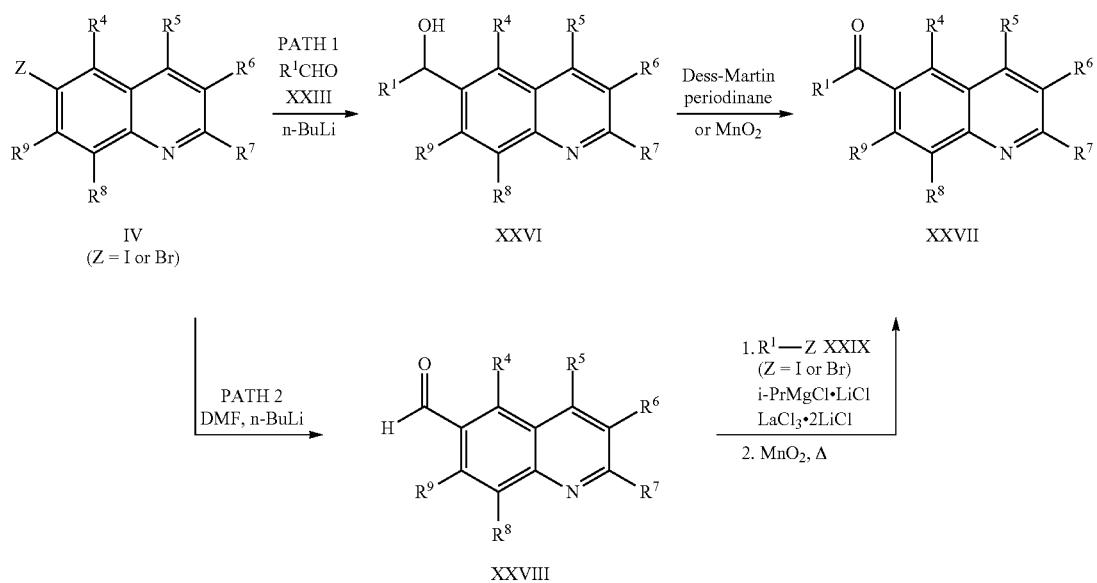

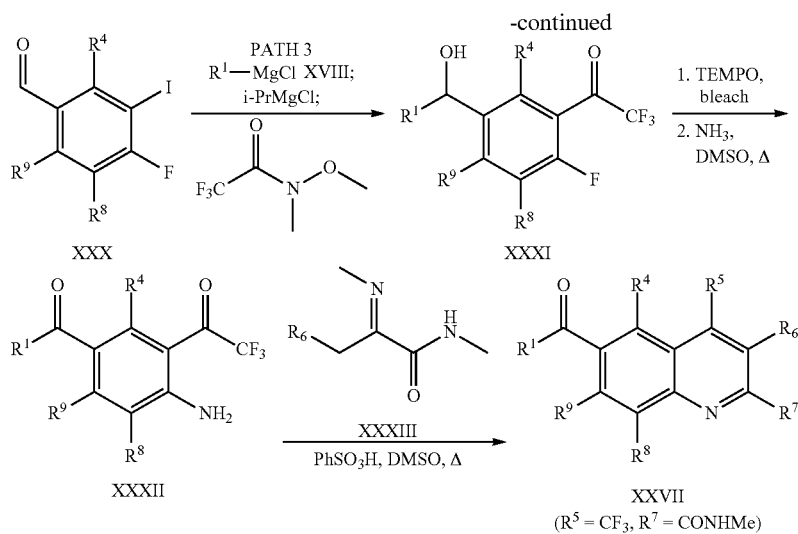

Synthesis leading to intermediate ketones XXVII may also be achieved via chemical routes shown in Scheme 4. In path 1, treatment of 6-bromo or 6-iodoquinolines IV with n-BuLi at −78° C. followed by addition of aldehydes XXIII provides secondary alcohol quinolines XXVI, which can be oxidized to ketones XXVII with Dess-Martin periodinane or $MnO_2$. Alternatively, ketones XXVII may also be prepared by treatment of 6-haloquinolines IV with n-BuLi at −78° C. followed by quenching with DMF affording carboxaldehydes XXVIII. Ketones XXVII can be obtained in a two-step process by addition of aldehyde XXVIII to a reaction mixture of aryl iodides or bromides XXIX and i-PrMgCl·LiCl followed by oxidation with $MnO_2$ (path 2).

As illustrated in Path 3, a one-pot reaction of aldehydes XXX and Grignard reagents such as $R^1$—MgCl XVIII followed by treatment with i-PrMgCl and addition of 2,2,2-trifluoro-N-methoxy-N-methylacetamide yields hydroxyl compounds XXXI. The hydroxyl group can be oxidized using bleach and TEMPO. Fluoro displacement can then be achieved with ammonia in hot DMSO to provide anilines XXXII. In the presence of benzenesulfonic acid, condensation of anilines XXXII and 2-(methylimino)butanamides XXXIII in hot DMSO furnishes ketoquinolines XXVII wherein $R^5$ is $CF_3$ and $R^7$ is CONHMe.

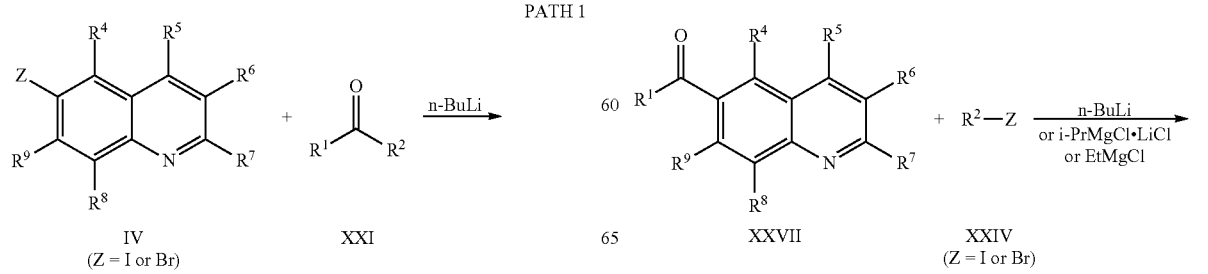

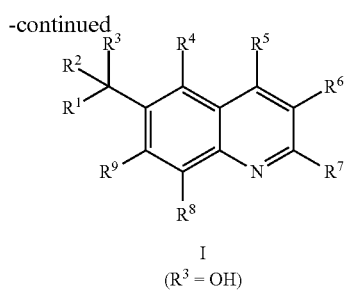

Scheme 5 illustrates synthetic routes leading to compounds of Formula I (path 1 to 3). As illustrated in path 1, a mixture of the 6-bromo or 6-iodoquinolines IV in an appropriate solvent such as THF can be either premixed with the ketones XXI at −78° C. followed by addition of BuLi or can be pretreated with BuLi at −78° C. prior to the addition of the ketones XXI to afford the tertiary alcohols of Formula I, wherein $R^3$ is OH. In path 2,6-iodoquinolines IV can be treated with i-PrMgCl followed by addition of ketone XXI to yield compounds of Formula I wherein $R^3$ is OH. As shown in Path 3, halogen-metal exchange of aryl halides (iodide or bromide) XXIV with an organometallic reagent, such as n-BuLi, i-PrMgCl.LiCl, or EtMgCl, at an appropriate temperature, such as −78° C. or 0° C., followed by reaction with ketones XXVII may afford tertiary alcohol quinolines of Formula I.

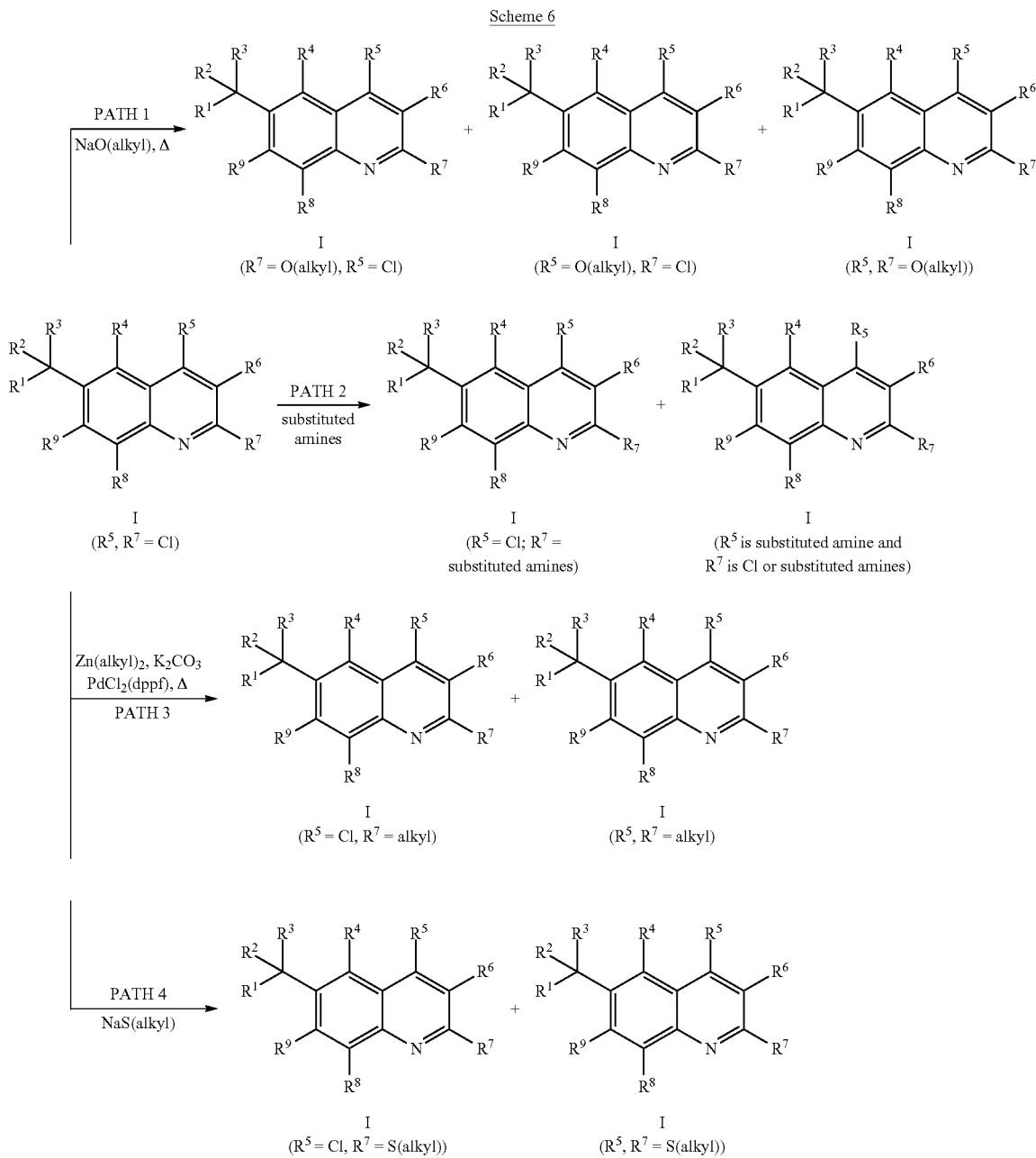

Scheme 6 illustrates methods used to synthesize compounds of Formula I wherein either the chlorine at $R^7$ or at both $R^5$ and $R^7$ positions are replaced with nitrogen, oxygen, sulfur or alkyl groups. In path 1 and 4, nucleophilic displacement of 2,4-dichloroquinolines I ($R^5$ and $R^7$ are Cl) with NaO(alkyl), NaS(alkyl), such as NaOMe, NaSMe, NaOEt, or NaO$^i$Pr, in an appropriate solvent, such as MeOH, EtOH, i-PrOH or DMF at elevated temperatures or with substituted hydroxy reagents such as 2-methoxyethanol in the presence of a base like sodium hydride in a non-polar solvent such as toluene provides compounds of Formula I wherein $R^5$ is Cl and $R^7$ is O(alkyl), O(CH$_2$)$_2$OCH$_3$ or S(alkyl) and compounds of Formula I wherein $R^5$ and $R^7$ are O(alkyl) or S(alkyl). Likewise, nucleophilic displacement of 2,4-dichloroquinolines I ($R^5$ and $R^7$ are Cl) with primary or secondary alkyl amines, heterocycle amines, or N,O-dimethylhydroxylamine in polar solvents such as MeOH, EtOH, or Et$_2$NCHO, or DMF provides quinolines of Formula I (path 2) wherein $R^5$ is NH(alkyl), N(alkyl)$_2$, N(CH$_3$)OCH$_3$, or Cl, and $R^7$ is NH(alkyl), N(alkyl)$_2$, N(CH$_3$)OCH$_3$, NA$^1$A$^2$, NHC$_{(2-3)}$alkylNA$^1$A$^2$ or N(CH$_3$)C$_{(2-4)}$alkylNA$^1$A$^2$, wherein A$_1$ and A$_2$ are as defined above. Replacement of chlorine at positions 2 and 4 of quinolines I ($R^5$ and $R^7$ are Cl) with alkyl groups could be carried out using Zn(alkyl)$_2$ in the presence of K$_2$CO$_3$ and a palladium catalyst, such as PdCl$_2$(dppf), to afford 2-alkyl and 2,4-dialkylquinolines I (path 3).

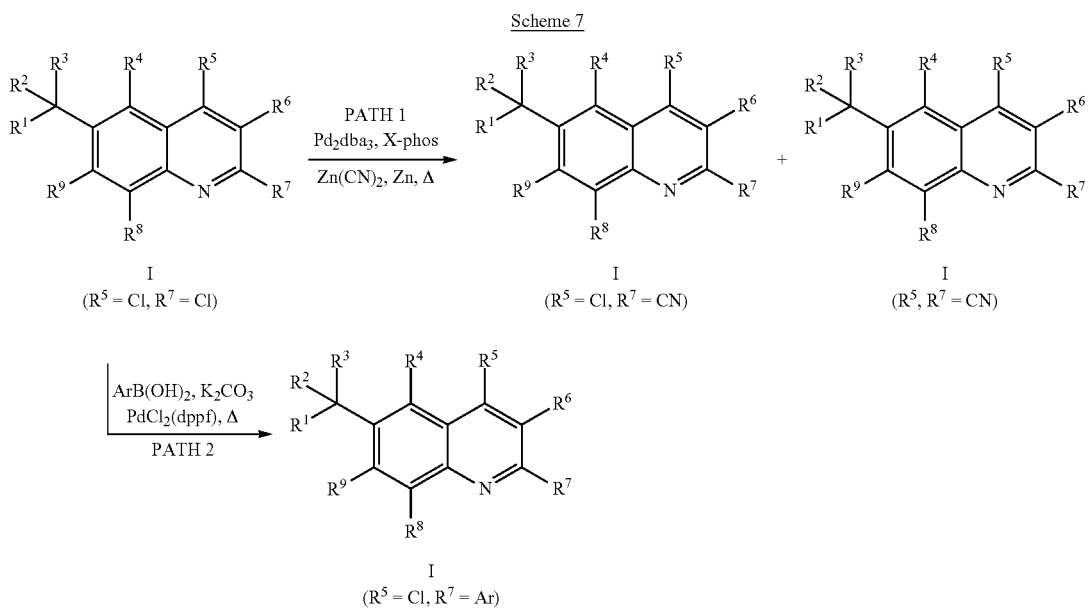

Scheme 7

Synthetic routes to compounds of Formula I, wherein $R^5$ is Cl or CN, and $R^7$ is CN or aryl, are illustrated in Scheme 7. In path 1, cyanation of the 2,4-dichloroquinolines I with Zn(CN)$_2$ in the presence of Zn, a palladium catalyst, such as Pd$_2$dba$_3$, and a ligand, such as dppf or X-phos, at high temperatures can provide 2-CN and 2,4-diCN quinolines I. The 2,4-dichloroquinolines I can also undergo a Suzuki reactions with ArB(OH)$_2$ or ArB(OR)$_2$ and a palladium catalyst, such as PdCl$_2$(dppf), yielding compounds of Formula I wherein $R^7$ is phenyl, substituted phenyl and five or six-membered heteroaryls such as furan, pyridine, pyridazine, pyrazine, pyrimidine, pyrrol, pyrazole or imidazole (path 2).

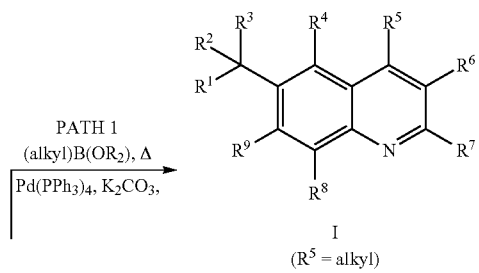

Scheme 8

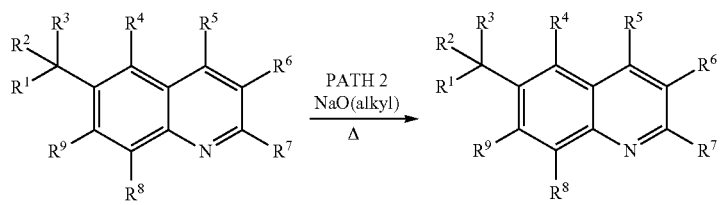

As illustrated in Scheme 8, compounds of Formula I wherein $R^5$ is a chlorine can be further substituted by treatment with alkylboronic acids or esters under Suzuki reaction conditions (path 1), with sodium alkoxides (path 2), or with zinc cyanide (path 3) using conditions previously described to provide compounds of Formula I wherein $R^5$ is alkyl, O(alkyl) or CN and $R^7$ is as described above.

Scheme 9

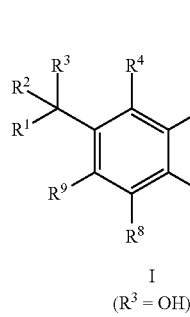

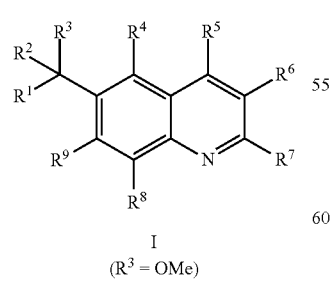

In scheme 9, tertiary alcohols I can be treated with base, such as NaH, and alkylated with MeI in DMF to provide compounds of Formula I wherein $R^3$ is OMe.

Scheme 10

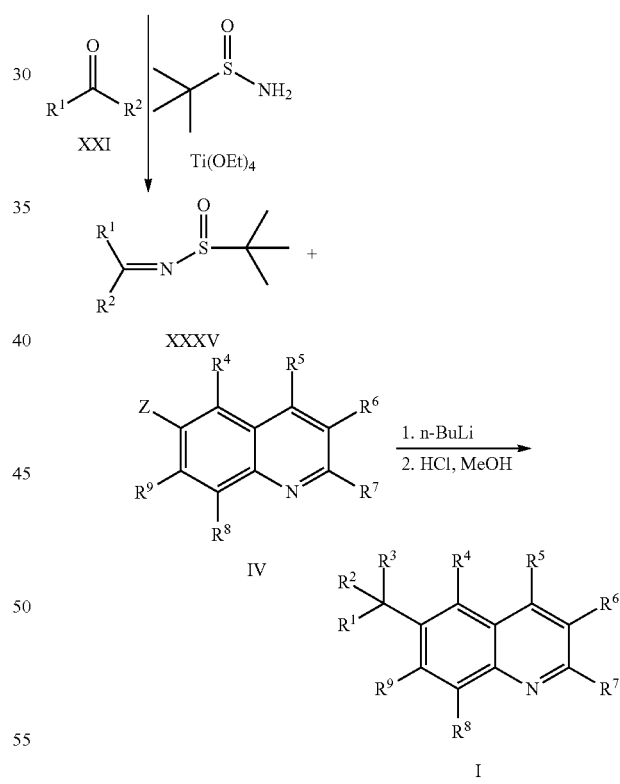

Synthetic routes to compounds of Formula I, wherein $R^3$ is $NH_2$, are illustrated in Scheme 10. Ketimines XXXV may be prepared by $Ti(OEt)_4$ mediated condensation of ketones XXI with 2-methylpropane-2-sulfinamide in refluxing THF. Addition of n-BuLi to the reaction mixture of ketimines XXXV and 6-bromo or 6-iodoquinolines IV at −78° C. followed by cleavage of tert-butanesulfinyl group with HCl in MeOH liberates amines I.

Scheme 11

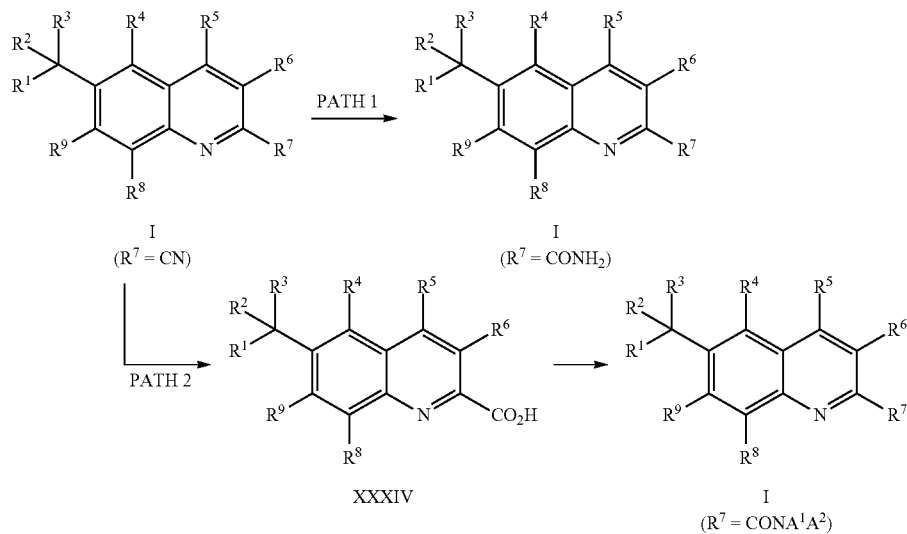

As shown in Scheme 11, the quinolines of Formula I wherein $R^7$ is CN can be hydrolyzed as described in US20080188521 by treatment with sodium carbonate and hydrogen peroxide to provide compounds of Formula I wherein $R^7$ is $CONH_2$ (Path 1) or can be treated with a strong acid like HCl to convert CN to a carboxylic acid XXXIV (Path 2). Once formed the acid can be further coupled to substituted amines using appropriated coupling reagents such as EDCI or HATU in the presence of a base such as triethylamine or Hunig's base to provide compounds of Formula I wherein $R^7$ is $CONA^1A^2$.

Synthesis of compounds of Formula I, wherein $R^7$ is an aminoalkylaminomethylene or an aminoalkoxymethylene can be prepared from 2-methylquinolines as shown in Scheme 12. Bromination of 2-methylquinolines of Formula I can accomplished with N-Bromosuccinamide in acetic acid at elevated temperatures as described in WO2010151740, to provide the methylbromide intermediate XXXVI. Nucleophilic displacement of the bromide under basic conditions using procedures known in the art could afford compounds of Formula I wherein $R^7$ is $-CH_2NHC_{(2-3)}alkylNA^1A^2$ or $CH_2N(CH_3)C_{(2-3)}alkylNA^1A^2$ (Path 1) or $CH_2OC_{(2-3)}alkylNA^1A^2$ (Path 2) and $A^1$ and $A^2$ are defined above.

Scheme 12

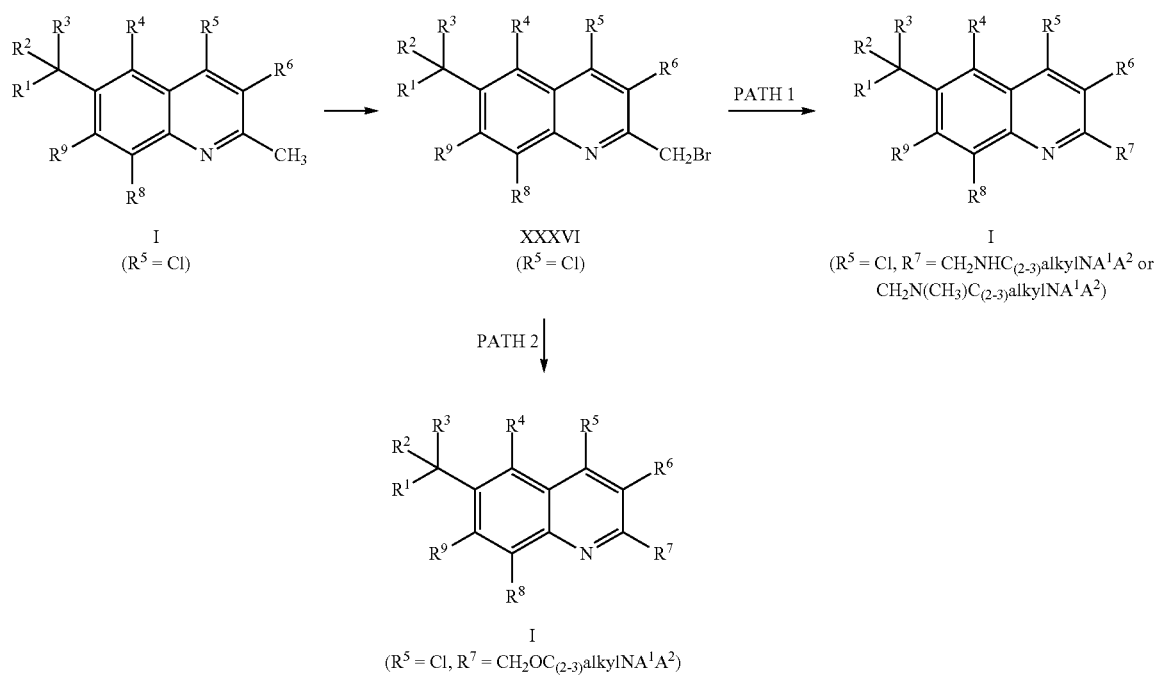

Compounds of Formula I wherein $R^1$, $R^2$ or $R^6$ are pyridyl can be treated with m-chloroperbenzoic acid in a chlorinated solvent at ambient to 40° C. to form the pyridyl-N-oxides of Formula I.

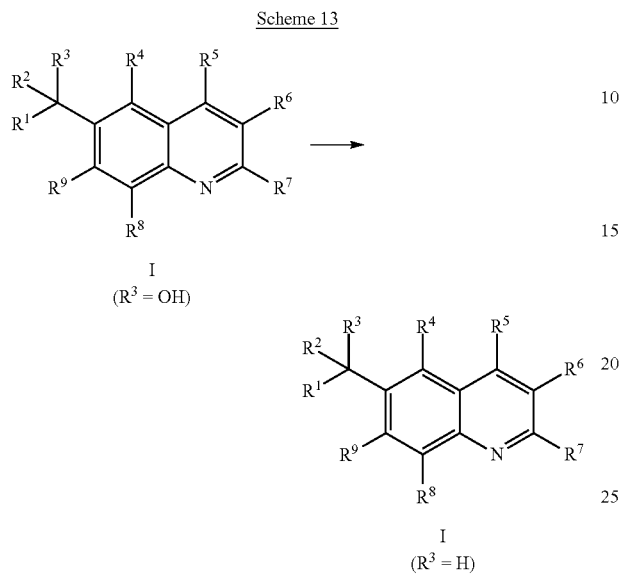

Scheme 13

I
($R^3$ = OH)

I
($R^3$ = H)

As shown in Scheme 13, compounds of the Formula I wherein $R^3$ is H can be prepared by treating compounds of Formula I wherein $R^3$ is OH with an acid such as trifluoroacetic acid in a solvent such as dichloromethane at room temperature or with heating (WO2009091735).

EXAMPLES

Compounds of the present invention can be prepared by methods known to those who are skilled in the art. The following examples are only meant to represent examples of the invention and are in no way meant to be a limit of the invention.

Intermediate 1: Step a

Methyl 5-bromo-2-(2-phenylacetamido)benzoate

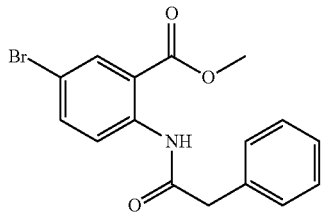 [SMILES: COC(=O)c1cc(Br)ccc1NC(=O)Cc1ccccc1]

To a mixture of methyl 2-amino-5-bromobenzoate (9.00 g, 39.1 mmol) and $Et_3N$ (7.6 mL, 54.8 mmol) in $CH_2Cl_2$ (90 mL) was added 2-phenylacetyl chloride (7.26 g, 46.9 mmol) at 4° C. dropwise. After completion of the addition, the cooling bath was removed and the mixture was stirred for 27 hours. TLC showed some of the starting material methyl 2-amino-5-bromobenzoate still remained. More 2-phenylacetyl chloride (1.88 g, 12.2 mmol) and $Et_3N$ (2.2 mL, 15.9 mmol) were added, and the mixture was stirred overnight. $K_2CO_3$ (aqueous) was added, the organic layer was separated, and the aqueous layer was extracted with $CH_2Cl_2$. The combined organic layers were washed with water, dried ($Na_2SO_4$), filtered, and concentrated in vacuo. $CH_3CN$ (100 mL) was added, and the precipitated solid was filtered, washed with $Et_2O$, and dried to give the title compound. The filtrate was concentrated in vacuo, and the solid was filtered, washed with $Et_2O$, and dried to give more title compound.

Intermediate 1: Step b

6-Bromo-4-hydroxy-3-phenylquinolin-2(1H)-one

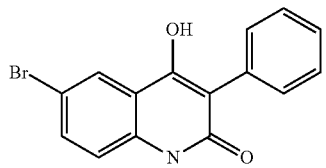 [SMILES: O=c1[nH]c2ccc(Br)cc2c(O)c1-c1ccccc1]

To a solution of methyl 5-bromo-2-(2-phenylacetamido)benzoate (7.71 g, 22.1 mmol, Intermediate 1, step a) in THF (50 mL) at −78° C. was added 1.0 M lithium bis(trimethylsilyl)amide in hexane (48.7 mL, 48.7 mmol) slowly, and the color changed from clear to clear red. The mixture was stirred at −78° C. to room temperature for 4 hours, during which time the color changed to cloudy yellow. The reaction was quenched with water, and acidified with 37% HCl until pH ~5. The precipitated solid was filtered, washed with water and $Et_2O$, and air dried to give the title compound. More solid was precipitated from the filtrate after standing overnight. The solid was collected by filtering, washing with water and $Et_2O$, and air drying to afford more title compound.

Intermediate 1: Step c

6-Bromo-2,4-dichloro-3-phenylquinoline

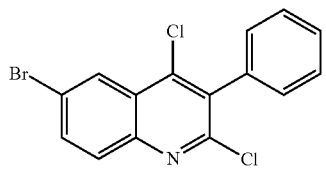 [SMILES: Clc1nc2ccc(Br)cc2c(Cl)c1-c1ccccc1]

A solution of 6-bromo-4-hydroxy-3-phenylquinolin-2(1H)-one (8.50 g, 26.9 mmol, Intermediate 1, step b) in phosphoryl trichloride (51 mL, 547 mmol) was heated at 107° C. for 3.5 hours, and then cooled to room temperature. After evaporation of $POCl_3$ in vacuo, concentrated $NH_4OH$ (aqueous) was added dropwise at 4° C. until pH 9. The precipitated solid was filtered, washed with water, and dried at 50° C. under vacuum overnight to provide the title compound.

The title compound was also prepared using the following procedure:

A mixture of 4-bromoaniline (10.0 g, 58.1 mmol), 2-phenylmalonic acid (11.0 g, 61.0 mmol), and phosphorus oxychloride (54.0 mL, 581 mmol) was heated in a 90° C. oil bath for 20 hours. The mixture was allowed to cool to room temperature and was diluted with $CH_2Cl_2$ in a large beaker (ca. 200 mL final volume). Ice (ca. 100 mL) was added and the mixture was stirred while monitoring the internal temperature; an ice bath was used to cool the mixture when the internal temperature reached 35° C. When the temperature of the mixture fell, the phases were separated and the aqueous phase was extracted once with CH$_2$Cl$_2$. The organic extract was concentrated onto silica gel and the title compound was isolated by flash column chromatography (silica gel, 20-55% CH$_2$Cl$_2$-heptane).

Intermediate 2: Step a

Methyl 5-bromo-2-(2-(2-chlorophenyl)acetamido)benzoate

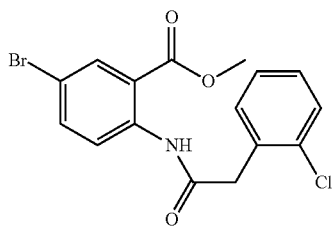 [SMILES: COC(=O)c1cc(Br)ccc1NC(=O)Cc1ccccc1Cl]

The title compound was prepared using 2-chlorophenylacetyl chloride in place of phenylacetyl chloride using the procedure described for Intermediate 1, step a.

Intermediate 2: Step b

6-Bromo-3-(2-chlorophenyl)-4-hydroxyquinolin-2(1H)-one

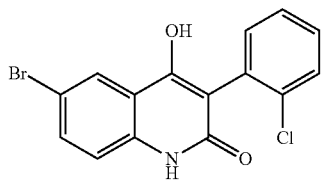 [SMILES: O=c1[nH]c2ccc(Br)cc2c(O)c1-c1ccccc1Cl]

The title compound was prepared using methyl 5-bromo-2-(2-(2-chlorophenyl)acetamido)benzoate (Intermediate 2, step a) in place of 5-bromo-2-(2-phenylacetamido)benzoate using the procedure described for Intermediate 1, step b.

Intermediate 2: Step c

6-Bromo-2,4-dichloro-3-(2-chlorophenyl)quinoline

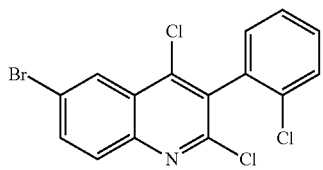 [SMILES: Clc1ccccc1-c1c(Cl)nc2ccc(Br)cc2c1Cl]

The title compound was prepared using 6-bromo-3-(2-chlorophenyl)-4-hydroxyquinolin-2(1H)-one (Intermediate 2, step b) in place of 6-bromo-4-hydroxy-3-phenylquinolin-2(1H)-one using the procedure described for Intermediate 1, step c.

Intermediate 3: Step a

Ethyl 3-((4-bromophenyl)imino)-2-phenylpropanoate

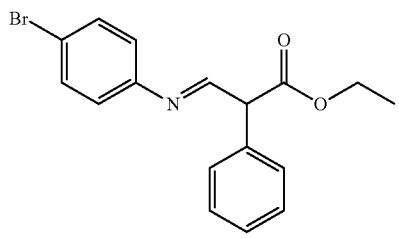 [SMILES: CCOC(=O)C(/C=N/c1ccc(Br)cc1)c1ccccc1]

A solution of ethyl 3-oxo-2-phenylpropanoate (3.50 g, 18.2 mmol) and 4-bromoaniline (2.60 g, 15.1 mmol) in EtOH (25 mL) was stirred at room temperature overnight and concentrated to give the title compound as an oil.

Intermediate 3: Step b

6-Bromo-3-phenylquinolin-4(1H)-one

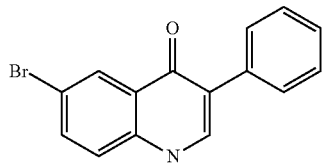 [SMILES: O=c1c(-c2ccccc2)c[nH]c2ccc(Br)cc12]

A mixture of ethyl 3-((4-bromophenyl)imino)-2-phenylpropanoate (6.18 g, 17.8 mmol, Intermediate 3, step a) and polyphosphoric acid (8.90 g) was heated at 150° C. for 1.5 hours. After cooling to room temperature, 3 N NaOH was added at 4° C. until basic. The solid was filtered, washed with water, and dried under vacuum overnight to give the title compound.

Intermediate 3: Step c

6-Bromo-4-chloro-3-phenylquinoline

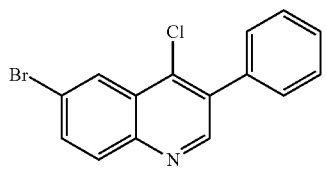 [SMILES: Clc1c(-c2ccccc2)cnc2ccc(Br)cc12]

The title compound was prepared using 6-bromo-3-phenylquinolin-4(1H)-one (Intermediate 3, step b) in place of 6-bromo-4-hydroxy-3-phenylquinolin-2(1H)-one according to the procedure described in Intermediate 1, step c, with the exception of flash column chromatography purification (silica gel, 5-10% EtOAc in heptanes).

Intermediate 4: Step a

N-(4-Bromophenyl)-2-phenylacetamide

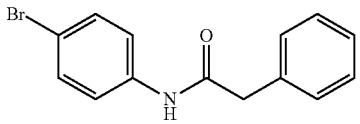 [SMILES: O=C(Cc1ccccc1)Nc1ccc(Br)cc1]

In a 250-mL round-bottom flask was placed a mixture of 4-bromoaniline (6.90 g, 40.1 mmol), triethylamine (16.8 g, 166 mmol), 4-dimethylaminopyridine (200 mg, 1.64 mmol), and 2-phenylacetyl chloride (6.50 g, 42.1 mmol) in dichloromethane (150 mL). The resulting mixture was stirred for 12 hours at 25° C. The reaction was then quenched by the addition of 50 mL of water. The organic layer was separated, and the aqueous layer was extracted with 2×50 mL of dichloromethane. The combined organic layers were dried over anhydrous sodium sulfate, filtered, and concentrated under vacuum. The residue was purified by flash column chromatography (silica gel column, 100:1 to 10:1 CH$_2$Cl$_2$/MeOH) to provide the title compound as a light yellow solid.

Intermediate 4: Step b

6-Bromo-2-chloro-3-phenylquinoline

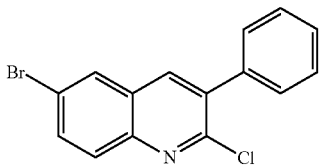 [SMILES: Clc1nc2ccc(Br)cc2cc1-c1ccccc1]

N,N-dimethylformamide (2.10 g, 28.7 mmol) was placed in a 100-mL round-bottom flask, and POCl$_3$ (20.3 g, 132 mmol) was added. After stirring for 30 min, N-(4-bromophenyl)-2-phenylacetamide (5.50 g, 19.0 mmol, Intermediate 4, step a) was added. The resulting mixture was stirred for 12 hours at 80° C. The reaction was then quenched by the addition of 50 mL of water. The organic layer was separated, and the aqueous layer was extracted with 3×200 mL of ethyl acetate. The combined organic layers were dried over anhydrous sodium sulfate, filtered, and concentrated under vacuum. The residue was purified by chromatography (silica gel column, 1:10 EtOAc/petroleum ether) to provide the title compound as a white solid.

Intermediate 4: Step c

6-Bromo-2-methoxy-3-phenylquinoline

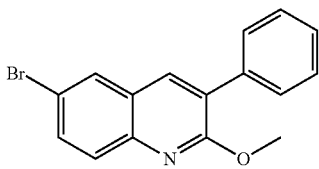 [SMILES: COc1nc2ccc(Br)cc2cc1-c1ccccc1]

In a 100-mL round-bottom flask was placed a mixture of 6-bromo-2-chloro-3-phenylquinoline (550 mg, 1.73 mmol, Intermediate 4, step b) and NaOCH$_3$ (931 mg, 17.2 mmol) in methanol (50 mL). The resulting mixture was refluxed for 5 hours and concentrated under vacuum. The residue was purified by chromatography (silica gel column, 1:5 EtOAc/petroleum ether) to provide the title compound as a white solid.

Intermediate 5: Step a

6-Iodo-3-phenyl-2-(trifluoromethyl)quinolin-4-ol

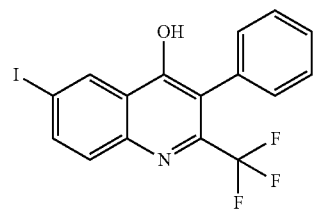 [SMILES: Oc1c(-c2ccccc2)c(C(F)(F)F)nc2ccc(I)cc12]

A mixture of 2-amino-5-iodobenzoic acid (5.20 g, 19.8 mmol), 1,1,1-trifluoro-3-phenylpropan-2-one (3.95 g, 21.0 mmol), and Eaton's reagent (12 mL) in a sealed tube was heated at 100° C. for 2 hours. More 1,1,1-trifluoro-3-phenylpropan-2-one (1.60 g, 8.50 mmol) was added and the mixture was heated for another 2 hours. The reaction was then cooled to room temperature, ice water was added, and the mixture was stirred vigorously for about 20 min. 50% NaOH and conc. NH$_4$OH solution were added until pH was 9. Some gummy dark brown material formed. After the addition of CH$_2$Cl$_2$, the gummy material became fluffy solid. This solid was filtered, washed with water and Et$_2$O, and air dried to give the title compound.

Intermediate 5: Step b

4-Chloro-6-iodo-3-phenyl-2-(trifluoromethyl)quinoline

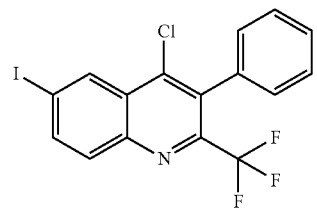 [SMILES: FC(F)(F)c1nc2ccc(I)cc2c(Cl)c1-c1ccccc1]

A solution of 6-iodo-3-phenyl-2-(trifluoromethyl)quinolin-4-ol (1.54 g, 3.71 mmol, Intermediate 5, step a) in phosphoryl trichloride (5 mL, 53.8 mmol) was heated at 110° C. for 1 hour 45 min, and then cooled to room temperature. Ice-water was added, and the mixture was basified at 4° C. with 50% NaOH and conc. NH$_4$OH until pH 9. The precipitated solid was filtered, washed with water and Et$_2$O, and dried to provide the title compound. The filtrate was separated and the aqueous layer was extracted with CH$_2$Cl$_2$. The combined organic phases were dried (Na$_2$SO$_4$), filtered, concentrated, and purified by flash column chromatography (80 g silica gel column, 0-5% EtOAc in heptane), affording a mixture of the title compound and des-iodo by-product in about 8:1 ratio as a thick oil, which solidified overnight.

Intermediate 6

6-Bromo-2,4-dichloro-7-fluoro-3-phenylquinoline

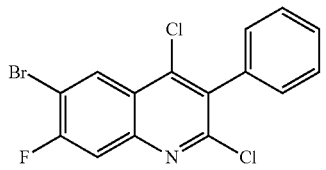 [SMILES: Fc1cc2nc(Cl)c(-c3ccccc3)c(Cl)c2cc1Br]

A mixture of 4-bromo-3-fluoroaniline (6.54 g, 34.4 mmol), 2-phenylmalonic acid (7.44 g, 41.3 mmol), and POCl$_3$ (32.0 mL, 344 mmol) was stirred at reflux (130° C. aluminum block temperature) for 3 hours. The dark solution was then allowed to cool to room temperature and diluted with DCM (70 mL). This was treated with 100 mL ice and stirred on an ice bath for ~5 min, and was then treated with 15 M NH$_4$OH dropwise (6 mL) and removed from the ice bath. Stirring at room temperature caused the reaction to warm to a gentle reflux (42° C.), and the reaction was chilled on an ice bath intermittently. After ~10 min stirring at room temperature the exotherm moderated, the aqueous layer was extracted with DCM (30 mL), and the combined dark clear organic layers were concentrated to provide a brown solid. This was dry load flash chromatographed with a 20% DCM/heptane to 100% DCM gradient to afford a ~2:1 mol ratio of the title compound and the 5-fluoro regioisomer as a light yellow solid. A portion of this was dry load flash chromatographed with a 20% toluene/heptane to 100% toluene gradient to provide the title compound eluting at 60-70% toluene/heptane.

Intermediate 7

6-Bromo-2,4-dichloro-5-fluoro-3-phenylquinoline

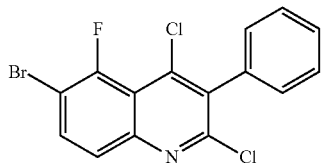 [SMILES: Fc1c(Br)ccc2nc(Cl)c(-c3ccccc3)c(Cl)c12]

After successful flash chromatographic isolation of Intermediate 6, further elution at 80-95% toluene/heptane provided the title compound.

Intermediate 8: Step a 1-(5-Bromo-2-fluorophenyl)-2,2,2-trifluoroethanone

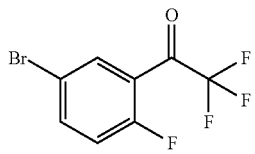 [SMILES: O=C(c1cc(Br)ccc1F)C(F)(F)F]

A solution of diisopropylamine (22.1 mL, 157 mmol) in 140 mL THF was stirred under argon at –68° C. while n-BuLi (57.9 mL, 2.59 M in hexane, 150 mmol) was added in a fine stream in 2 portions over 6 min. The resulting pale yellow homogeneous solution was removed from the acetone/dry ice bath and stirred at ambient conditions for 9 min, and was then cooled back down to –68° C. and a solution of 1-bromo-4-fluorobenzene (15.6 mL, 143 mmol) in THF (30 mL) was added rapidly dropwise over 5 min. The reaction was then stirred in the cold bath for another 6 min, and the pale yellow reaction was then treated rapidly dropwise with a solution of ethyl trifluoroacetate (18.7 mL, 157 mmol) in THF (30 mL) over ~8 min (internal temp rose to –47° C.). The pale yellow reaction was then stirred overnight as the acetone/dry ice bath expired (15 hrs). The resulting yellow homogeneous solution was washed with 5 M NH$_4$Cl (2×50 mL), and the organic layer was dried (Na$_2$SO$_4$), filtered, and concentrated to provide the crude title compound as a clear dark yellow oil.

Intermediate 8: Step b 1-(2-Amino-5-bromophenyl)-2,2,2-trifluoroethanone

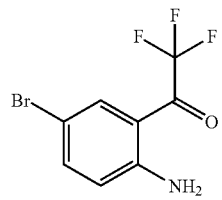

A solution of 1-(5-bromo-2-fluorophenyl)-2,2,2-trifluoroethanone (6.67 g, 24.6 mmol, Intermediate 8, step a) in DMSO (6.2 mL) was treated with NaN$_3$ (1.76 g, 27.0 mmol) and stirred under air (lightly capped) at 95° C. for 1 hour. The brownish-red opaque reaction was then cooled to room temperature on an ice bath, diluted with EtOAc (49 mL), treated with SnCl$_2$-dihydrate (6.66 g, 29.5 mmol) in several portions over ~30 sec followed by water (1.33 mL, 73.8 mmol), and the mixture was stirred at room temperature for 30 min. The reddish solution with heavy off-white particulates was then treated with anhydrous Na$_2$SO$_4$ (~6 g; ~40 mmol; ~400 mmol water capacity) and stirred vigorously for a few minutes. The mixture was then filtered over a bed of Celite®, and the cloudy orange filtrate was dry load flash chromatographed (~60 g silica gel) with a heptane to 50% DCM/heptane gradient to provide the title compound as an orange oil that crystallized upon standing.

Intermediate 8: Step c

6-Bromo-3-phenyl-2,4-bis(trifluoromethyl)quinoline

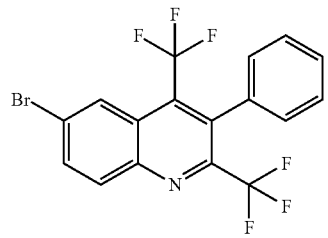 [SMILES: FC(F)(F)c1nc2ccc(Br)cc2c(C(F)(F)F)c1-c1ccccc1]

A yellow solution of 1-(2-amino-5-bromophenyl)-2,2,2-trifluoroethanone (1.32 g, 4.94 mmol, Intermediate 8, step b)

and 1,1,1-trifluoro-3-phenylpropan-2-one (0.980 g, 5.21 mmol) in DMF (4.95 mL) was treated with tributylamine (1.23 mL, 5.19 mmol) and stirred at 130° C. under air (capped) for 2 hours. The homogeneous orange solution was then cooled to room temperature and partitioned with ether (8 mL) and 1 M $NaH_2PO_4$ (8 mL). The organic layer was washed with 1 M $NaH_2PO_4$ (1×8 mL), dried ($Na_2SO_4$), filtered, and concentrated, and the residue was flash chromatographed with a heptane to 30% DCM/heptane gradient to yield the title compound as a nearly colorless oil.

Intermediate 8: Step d

6-Iodo-3-phenyl-2,4-bis(trifluoromethyl)quinoline

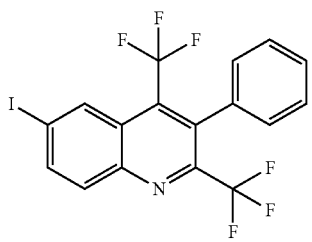 [SMILES: FC(F)(F)c1nc2ccc(I)cc2c(C(F)(F)F)c1-c1ccccc1]

A mixture of 6-bromo-3-phenyl-2,4-bis(trifluoromethyl)quinoline (273 mg, 0.650 mmol, Intermediate 8, step c), CuI (14 mg, 0.074 mmol), N,N'-dimethylethylenediamine (0.0158 mL, 0.147 mmol), t-BuOH (0.65 mL), and NaI (200 mg, 1.33 mmol) was microwaved at 150° C. for 30 min (Biotage). The reaction was diluted with DCM (10 mL), filtered through Celite® and a 0.45 um filter, and concentrated. The residue was flash chromatographed with a heptane to 20% EtOAc/heptane gradient to afford the title compound as a light yellow oil that crystallized upon standing.

Intermediate 9: Step a

N-Methoxy-N-methylisonicotinamide

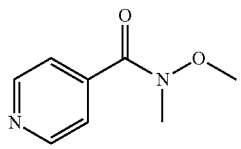

A suspension of 4-picolinic acid (3.00 g, 24.4 mmol) and 1,1-carbonyldiimidazole (4.74 g, 29.2 mmol) in $CH_2Cl_2$ (35 mL) was stirred for ~40 min and became a clear solution. After the addition of N,O-dimethylhydroxylamine hydrochloride (2.85 g, 29.2 mmol), the mixture was stirred at room temperature for 22 hours. Water was added, the organic layer was separated, and the aqueous layer was extracted with $CH_2Cl_2$. The combined organic layers were washed with water once, and the aqueous layer was back extracted with $CH_2Cl_2$. The organic phase was dried ($Na_2SO_4$), filtered, concentrated, and purified by flash column chromatography (80 g silica gel column, 100% EtOAc) to give the title compound as a clear oil.

Intermediate 9: Step b (1-Methyl-1H-imidazol-5-yl)(pyridin-4-yl)methanone

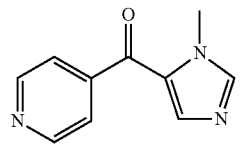

To a heat-gun dried flask containing 1-methyl-1H-imidazole (2.2 mL, 27.7 mmol) and THF (13 mL) at −78° C. was added 1.6 M n-BuLi in hexane (18.5 mL, 29.6 mmol). After stirring at −78° C. for 40 min, chlorotriethylsilane (4.9 mL, 29.2 mmol) in neat was introduced slowly. The mixture was stirred at −78° C. for 1 hour. 1.6 M n-BuLi in hexane (18 mL, 28.8 mmol) was added, and stirring became very difficult. The cooling bath was removed, and stirring was continued for a while before the temperature reached around 10° C. The mixture was recooled to −78° C., a solution of N-methoxy-N-methylisonicotinamide (3.82 g, 23.0 mmol, Intermediate 9, step a) in THF (28 mL) was added via cannula, and stirring stopped. The cooling bath was removed, and the stirring was continued for 40 min before room temperature was reached. The reaction was quenched with a few drops of MeOH. Brine was added, the organic layer was separated, and the aqueous layer was extracted with $CH_2Cl_2$. The combined organic phases were dried ($Na_2SO_4$), filtered, concentrated, and purified by flash column chromatography (silica gel, 50-100% EtOAc in heptane, then 5-10% MeOH in $CH_2Cl_2$) to obtain the title compound as an off-white solid.

Intermediate 10: Step a

N-Methoxy-N-methylnicotinamide

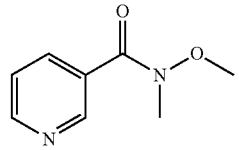

The title compound was prepared using nicotinic acid in place of 4-picolinic acid using the procedure described for Intermediate 9, step a.

Intermediate 10: Step b (1-Methyl-1H-imidazol-5-yl)(pyridin-3-yl)methanone

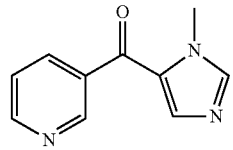

To a heat-gun dried flask containing 1-methyl-1H-imidazole (1.55 mL, 19.5 mmol) and THF (20 mL) at −78° C. was added 1.6 M n-BuLi in hexane (12.8 mL, 20.5 mmol). After stirring at −78° C. for 30 min, chlorotriethylsilane (3.3 mL, 19.7 mmol) in neat was introduced slowly. The mixture was stirred at −78° C. for 30 min. 1.6 M n-BuLi in hexane (12.8 mL, 20.5 mmol) was added, and the mixture was stirred for 45 min. A solution of N-methoxy-N-methylnicotinamide (2.70 g, 16.2 mmol, Intermediate 10, step a) in THF (20 mL) was added via cannula, and the mixture was stirred at −78° C. to room temperature for 2 hours. The reaction was quenched with NH$_4$Cl (aqueous), the organic layer was separated, and the aqueous layer was extracted with CH$_2$Cl$_2$. The combined organic phases were dried (Na$_2$SO$_4$), filtered, concentrated, and purified by flash column chromatography (40 g silica gel column, 50-100% EtOAc in heptane, then 5-10% MeOH in CH$_2$Cl$_2$) to obtain the title compound as an off-white solid.

Intermediate 11: Step a

N-Methoxy-N-methylpicolinamide

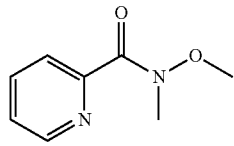

The title compound was prepared using picolinic acid in place of 4-picolinic acid using the procedure described for Intermediate 9, step a.

Intermediate 11: Step b (1-Methyl-1H-imidazol-5-yl)(pyridin-2-yl)methanone

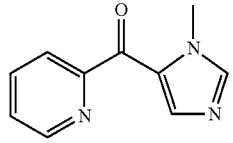

The title compound was prepared using N-methoxy-N-methylpicolinamide (Intermediate 11, step a) in place of N-methoxy-N-methylnicotinamide using the procedure described for Intermediate 10, step b.

Intermediate 11: Step c (2-Methyl-N-((1-methyl-1H-imidazol-5-yl)(pyridin-2-yl)methylene)propane-2-sulfinamide

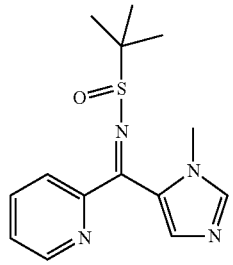 [SMILES: Cn1cncc1C(=NS(=O)C(C)(C)C)c1ccccn1]

To a mixture of (1-methyl-1H-imidazol-5-yl)(pyridin-2-yl)methanone (202 mg, 1.08 mmol, Intermediate 11, step b) and Ti(OEt)$_4$ (0.45 mL, 2.2 mmol) in THF (3 mL) was added 2-methylpropane-2-sulfinamide (145 mg, 1.20 mmol) and then heated at 70° C. for 4.5 days. After cooling to room temperature, NH$_4$Cl (aqueous) was added. The precipitated solid was filtered off. The filtrate was separated, and the aqueous layer was extracted with CH$_2$Cl$_2$. The combined organic phases were dried (Na$_2$SO$_4$), filtered, concentrated, and purified by reverse phase HPLC (water/acetonitrile/0.1% TFA). The collected TFA salt was worked up between aqueous NaHCO$_3$ and CH$_2$Cl$_2$. The organic layer was dried (Na$_2$SO$_4$), filtered, and concentrated to obtain the title compound as a yellow oil.

Intermediate 12: Step a

2-Chloro-N-methoxy-N,6-dimethylisonicotinamide

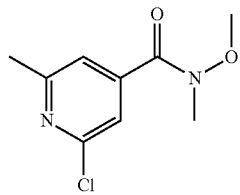

The title compound was prepared using 2-chloro-6-methylisonicotinic acid in place of 4-picolinic acid using the procedure described for Intermediate 9, step a.

Intermediate 12: Step b (2-Chloro-6-methylpyridin-4-yl)(1-methyl-1H-imidazol-2-yl)methanone

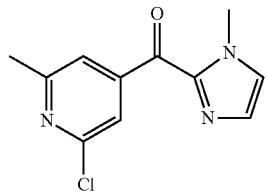 [SMILES: Cc1cc(C(=O)c2nccn2C)cc(Cl)n1]

The title compound was prepared using 2-chloro-N-methoxy-N,6-dimethylisonicotinamide (Intermediate 12, step a) in place of N-methoxy-N-methylnicotinamide using the procedure described for Intermediate 10, step b.

Intermediate 13: Step a

2-Fluoro-N-methoxy-N-methylisonicotinamide

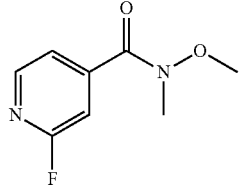

The title compound was prepared using 2-fluoroisonicotinic acid in place of 4-picolinic acid using the procedure described for Intermediate 9, step a.

Intermediate 13: Step b (2-Fluoropyridin-4-yl)(1-methyl-1H-imidazol-5-yl)methanone

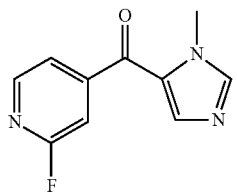

To a solution of 5-bromo-1-methyl-1H-imidazole (0.964 g, 5.99 mmol) in CH$_2$Cl$_2$ (6 mL) at room temperature was added 3.0 Methylmagnesium bromide in Et$_2$O (2.0 mL, 6.00 mmol) dropwise. The mixture changed to a white suspension briefly then to clear yellow. After 15 min stirring, the mixture was cooled to 4° C. A solution of 2-fluoro-N-methoxy-N-methylisonicotinamide (1.05 g, 5.70 mmol, Intermediate 13, step a) in CH$_2$Cl$_2$ (6 mL) was introduced via cannula and some hard solid formed. The cooling bath was removed, and the mixture was stirred for 2 days. NH$_4$Cl (aqueous) was added, the organic layer was separated, and the aqueous layer was extracted with EtOAc. The combined organic layers were dried (Na$_2$SO$_4$), filtered, and concentrated. The residue was diluted with small amount of CH$_2$Cl$_2$. The undissolved solid was filtered, washed with Et$_2$O, and dried under vacuum to provide the title compound as a white solid. The filtrate was concentrated and purified by flash column chromatography (40 g silica gel column, 100% EtOAc) to give more title compound.

Intermediate 14

(2-Chloro-6-methylpyridin-4-yl)(1-methyl-1H-imidazol-5-yl)methanone

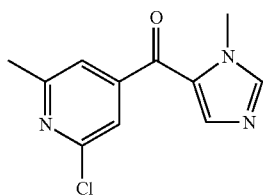 [SMILES: Cc1cc(C(=O)c2cncn2C)cc(Cl)n1]

The title compound was prepared using 2-chloro-N-methoxy-N,6-dimethylisonicotinamide (Intermediate 12, step a) in place of 2-fluoro-N-methoxy-N-methylisonicotinamide using the procedure described for Intermediate 13, step b.

Intermediate 15: Step a 6-(Trifluoromethyl)nicotinoyl chloride

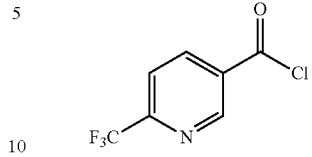

To a 1 L 3-neck flask equipped with an overhead stirrer, Claisen adaptor, nitrogen bubbler, 60 mL addition funnel, and thermocouple was added 6-(trifluoromethyl)nicotinic acid (45 g, 235.5 mmol), dichloromethane (540 mL) and DMF (0.910 mL, 11.77 mmol) via syringe. To this solution was added oxalyl chloride (24.51 mL, 282.56 mmol) and the reaction was allowed to stir at ambient temperature overnight. The reaction was then filtered and the clear filtrate was concentrated in vacuo to afford the title compound as a brownish semisolid.

Intermediate 15: Step b

N-Methoxy-N-methyl-6-(trifluoromethyl)nicotinamide

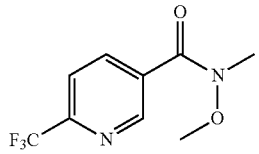

To a 1 L 3-neck flask equipped with an overhead stirrer, Claisen adaptor, nitrogen bubbler, 125 mL addition funnel, and thermocouple was added 6-(trifluoromethyl)nicotinoyl chloride (49.3 g, 235.2 mmol, Intermediate 15, step a), dichloromethane (493 mL), and N,O-dimethylhydroxylamine hydrochloride (25.63 g, 258.8 mmol). After the mixture was cooled to 7° C., diisopropylethylamine (90.263 mL, 517.6 mmol) was added such that the addition temperature did not exceed 16° C. After the addition, the reaction was allowed to warm to room temperature. The reaction was then transferred to a separatory funnel and the organic layer was washed with saturated NaHCO$_3$ (2×100 mL) followed by water (100 mL) and then dried over sodium sulfate, and filtered. Solvent removal afforded the title compound as a brownish oil.

Intermediate 15: Step c (1-Methyl-1H-imidazol-5-yl)(6-(trifluoromethyl)pyridin-3-yl)methanone

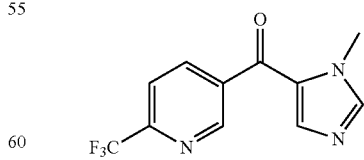

To a 3 L 4-neck flask equipped with an overhead stirrer, nitrogen bubbler, and thermocouple was added 5-bromo-1-methyl-1H-imidazole (47.96 g, 297.9 mmol), followed by THF (537 mL). To this room temperature solution was added isopropylmagnesium chloride/lithium chloride complex [1.3

M] (246.8 mL, 320.8 mmol) (addition temperature maintained between 16.6 and 25° C.) to afford a milky suspension and the reaction was stirred for 60 minutes and then cooled to 5.3° C. in an ice bath. To this mixture was added a solution of N-methoxy-N-methyl-6-(trifluoromethyl)nicotinamide (53.66 g, 229.14 mmol, Intermediate 15, step b) in THF (268.3 mL) (addition temperature between 5.3 and 5.6° C.) to afford an orange mixture. After addition, the reaction was warmed to room temperature over 2 hours. After stirring at room temperature for 18 hours, THF (200 mL) was added and the reaction was stirred for 2 hours. The reaction was then cooled to 4° C. with an ice bath and carefully quenched with 2N HCl to a pH=7, quenching temperature reached 12° C. The mixture was diluted with ethyl acetate (500 mL), phase split and the organic layer was washed with brine (2×200 mL) and dried over sodium sulfate, filtered, and the solvent was removed. Hot ether was added and then filtered to give the title compound as a solid.

Intermediate 16: Step a

N-Methoxy-N-methyl-2-(trifluoromethyl)isonicotinamide

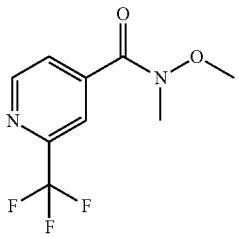 [SMILES: CON(C)C(=O)c1ccnc(C(F)(F)F)c1]

To a suspension of 2-(trifluoromethyl)isonicotinic acid (1.03 g, 5.39 mmol), N,O-dimethylhydroxylamine hydrochloride (0.800 g, 8.20 mmol), N'(ethylcarbonimidoyl)-N,N-dimethyl-1,3-propanediamine hydrochloride (EDCI, 1.35 g, 7.04 mmol) and CH₂Cl₂ was added Et₃N (1.90 mL, 13.7 mmol), and the mixture immediately turned to clear. After stirring at room temperature overnight, NH₄Cl (aqueous) was added. The mixture was stirred vigorously for a while, and white solid was filtered off. The organic layer was separated, and the aqueous layer was extracted with CH₂Cl₂. The combined organic phases were washed with brine, and the aqueous layer was back extracted with CH₂Cl₂. The organic phase was dried (Na₂SO₄), filtered, concentrated, and purified by flash column chromatography (40 g silica gel column, 40-70% EtOAc in heptanes) to give the title compound as a clear oil.

Intermediate 16: Step b (1-Methyl-1H-imidazol-5-yl)(2-(trifluoromethyl)pyridin-4-yl)methanone

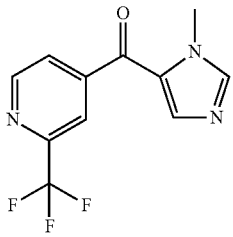 [SMILES: Cn1cncc1C(=O)c1ccnc(C(F)(F)F)c1]

The title compound was prepared using N-methoxy-N-methyl-2-(trifluoromethyl)isonicotinamide (Intermediate 16, step a) in place of 2-fluoro-N-methoxy-N-methylisonicotinamide using the procedure described for Intermediate 13, step b.

Intermediate 17

(3-Chlorophenyl)(6-(trifluoromethyl)pyridin-3-yl)methanone

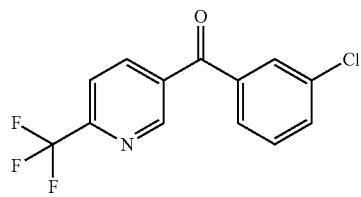 [SMILES: O=C(c1ccc(C(F)(F)F)nc1)c1cccc(Cl)c1]

To a solution of N-methoxy-N-methyl-6-(trifluoromethyl)nicotinamide (1.23 g, 5.25 mmol, Intermediate 15, step b) in THF (12 mL) at 4° C. was added 0.5 M (3-chlorophenyl)magnesium bromide in THF (12.7 mL, 6.35 mmol). The mixture was stirred at 4° C. to room temperature overnight, and quenched with NH₄Cl (aqueous). The organic layer was separated, and the aqueous layer was extracted with CH₂Cl₂. The combined organic phases were dried (Na₂SO₄), filtered, concentrated, and purified by flash column chromatography (40 g silica gel column, 0-70% EtOAc in heptanes) to give the title compound as an oil, which solidified upon standing.

Intermediate 18: Step a

4-Chloro-N-methoxy-N-methylbenzamide

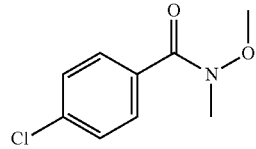

Pyridine (27.6 mL, 343 mmol) was added to N,O-dimethylhydroxylamine hydrochloride (16.7 g, 172 mmol) in DCM (400 mL). 4-Chlorobenzoyl chloride (20 mL, 156 mmol) was then added and the mixture was stirred at room temperature for 3 days. Solids were removed by vacuum filtration, washing with DCM. The filtrate was washed with 1 N HCl followed by water. The organic phase was dried (Na₂SO₄), filtered, and concentrated, affording the crude title compound as a colorless liquid which was used without purification in the next step.

Intermediate 18: Step b (4-Chlorophenyl)(1-methyl-1H-imidazol-5-yl)methanone

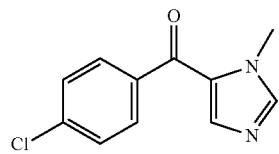

Ethyl magnesium bromide (3.0 M in diethyl ether, 21.5 mL, 64.4 mmol) was added via syringe over a few minutes to a clear colorless solution of 5-bromo-1-methyl-1H-imidazole (10.4 g, 64.4 mmol) in THF (100 mL) under a nitrogen atmosphere in an ice bath. A white precipitate formed during the addition. The mixture was removed from the ice bath and was stirred for 20 min, then was again cooled in an ice bath before addition of 4-chloro-N-methoxy-N-methylbenzamide (10.7 g, 53.6 mmol, Intermediate 18, step a). The resulting white suspension was stirred overnight at room temperature. The reaction was quenched by addition of saturated aqueous NH$_4$Cl and diluted with water. The mixture was partially concentrated to remove THF and was diluted with DCM. The mixture was acidified to pH 1 with 1 N aqueous HCl, then neutralized with saturated aqueous NaHCO$_3$. The phases were separated and the aqueous phase was further extracted with DCM. The organic extracts were washed with water, then were dried (Na$_2$SO$_4$), filtered, and concentrated, affording a white solid. The crude product was triturated with a mixture of EtOAc:heptanes (1:1, 150 mL). The precipitated solid was collected by vacuum filtration, washing with heptanes, to afford the title compound.

Intermediate 19

2-Methoxy-5-[(1-methyl-1H-imidazol-5-yl)carbonyl]pyridine

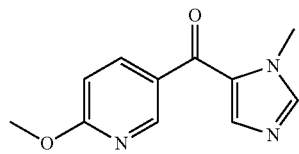 [SMILES: COc1ccc(C(=O)c2cncn2C)cn1]

In a 50-mL round-bottom flask was placed a solution of Na (260 mg, 11.3 mmol) in methanol (15 mL) and the solution was stirred for 30 min at room temperature. Then 2-chloro-5-[(1-methyl-1H-imidazol-5-yl)carbonyl]pyridine (250 mg, 1.13 mmol, Intermediate 22, step c) was added. The resulting mixture was stirred for 4 hours at 75° C. and concentrated under vacuum. The residue was purified by flash column chromatography (silica gel column, 100:0-20:1 CH$_2$Cl$_2$/MeOH) to give the title compound as a light yellow solid.

Intermediate 20

N,N-Dimethyl-5-[(1-methyl-1H-imidazol-5-yl)carbonyl]pyridin-2-amine

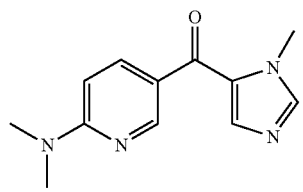 [SMILES: CN(C)c1ccc(C(=O)c2cncn2C)cn1]

In a 50-mL round-bottom flask was placed a solution of 2-chloro-5-[(1-methyl-1H-imidazol-5-yl)carbonyl]pyridine (250 mg, 1.13 mmol, Intermediate 22, step c), dimethylamine hydrochloride (96 mg, 1.2 mmol), and Et$_3$N (342 mg, 3.39 mmol) in methanol (15 mL). The resulting mixture was heated at 75° C. overnight and concentrated under vacuum. The residue was purified by flash column chromatography (silica gel column, 100:0-20:1 CH$_2$Cl$_2$/MeOH) to give the title compound as a light yellow solid.

Intermediate 21: Step a

6-Fluoropyridine-3-carbonyl chloride

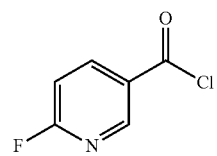

In a 100-mL round-bottom flask was placed a solution of 6-fluoropyridine-3-carboxylic acid (5.0 g, 35.4 mmol) in thionyl chloride (20 mL). The resulting solution was heated at 80° C. for 2 hours and concentrated under vacuum to give the title compound as a yellow oil.

Intermediate 21: Step b

6-Fluoro-N-methoxy-N-methylpyridine-3-carboxamide

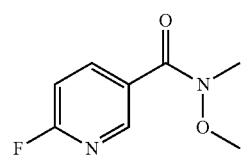

To a 250-mL round-bottom flask containing N,O-dimethyl hydroxylamine hydrochloride (3.5 g, 35.9 mmol) and triethylamine (15.0 mL, 108 mmol) was added a solution of 6-fluoropyridine-3-carbonyl chloride (5.70 g, 35.7 mmol, Intermediate 21, step a) in dichloromethane (200 mL) dropwise. The resulting mixture was stirred for 12 hours at room temperature, and 20 mL of water was added. The organic layer was separated, and the aqueous layer was extracted with 2×100 mL of dichloromethane. The combined organic layers were dried over anhydrous sodium sulfate, filtered, and concentrated under vacuum. The residue was purified by chromatography (silica gel column, 100:1 CHCl$_3$/MeOH) to give the title compound as a white solid.

Intermediate 21: Step c (6-Fluoropyridin-3-yl)(1-methyl-1H-imidazol-5-yl)methanone

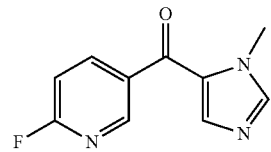

To a 250-mL round-bottom flask containing 1-methyl-1H-imidazole (1.74 g, 21.2 mmol) and THF (50 mL) at −78° C. under nitrogen was added n-BuLi in hexane (2.5 M, 9.8 mL, 24.5 mmol) dropwise. The resulting mixture was stirred for 1 hour at −78° C., and Et$_3$SiCl (3.20 g, 21.2 mmol) was added.

The mixture was stirred for an additional 1 hour at −78° C., and a second portion of n-BuLi (2.5 M, 8.5 mL, 21.3 mmol) was added. After stirring for an additional 1 hour at −78° C., 6-fluoro-N-methoxy-N-methylpyridine-3-carboxamide (3.00 g, 16.3 mmol, Intermediate 21, step b) was added. The mixture was stirred at −78° C. and then allowed to warm up to room temperature. The stirring was continued for 1 hour at room temperature, and then the reaction was quenched by the addition of 20 mL of water. The mixture was diluted with 100 mL of water. The organic layer was separated, and the aqueous layer was extracted with 3×50 mL of ethyl acetate. The combined organic layers were dried over anhydrous sodium sulfate, filtered, and concentrated under vacuum. The residue was purified by chromatography (silica gel column, 1:4 EtOAc/petroleum ether) to give the title compound as a white solid.

Intermediate 22: Step a

6-Chloropyridine-3-carbonyl chloride

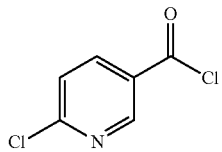

The title compound was prepared using 6-chloropyridine-3-carboxylic acid in place of 6-fluoropyridine-3-carboxylic acid according to the procedure described for Intermediate 21, step a.

Intermediate 22: Step b

6-Chloro-N-methoxy-N-methylpyridine-3-carboxamide

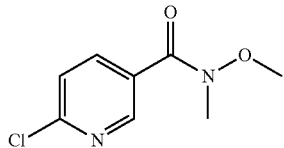

The title compound was prepared using 6-chloropyridine-3-carbonyl chloride (Intermediate 22, step a) in place of 6-fluoropyridine-3-carbonyl chloride according to the procedure described for Intermediate 21, step b.

Intermediate 22: Step c

2-Chloro-5-[(1-methyl-1H-imidazol-5-yl)carbonyl]pyridine

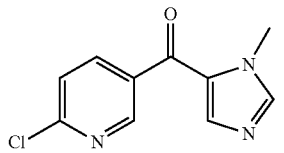

The title compound was prepared using 6-chloro-N-methoxy-N-methylpyridine-3-carboxamide (Intermediate 22, step b) in place of 6-fluoro-N-methoxy-N-methylpyridine-3-carboxamide according to the procedure described for Intermediate 21, step c.

Intermediate 23

(4-Chlorophenyl)(1-ethyl-1H-imidazol-5-yl)methanone

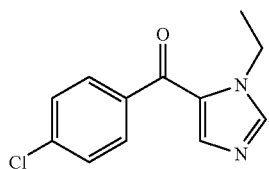 [SMILES: CCn1cncc1C(=O)c1ccc(Cl)cc1]

The title compound was prepared using 1-ethyl-1H-imidazole and 4-chloro-N-methoxy-N-methylbenzamide (Intermediate 18, step a) in place of 1-methyl-1H-imidazole and 6-fluoro-N-methoxy-N-methylpyridine-3-carboxamide, respectively, according to the procedure described for Intermediate 21, step c.

Intermediate 24: Step a

5-Bromo-1,2-dimethyl-1H-imidazole

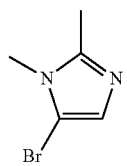

A mixture of 1,2-dimethyl-1H-imidazole (2.80 g, 29.1 mmol) and NBS (5.40 g, 30.3 mmol) in dichloromethane (100 mL) was stirred for 2 hours at 0° C. and diluted with 100 mL of dichloromethane. The mixture was washed with 3×200 mL of $H_2O$, dried over anhydrous sodium sulfate, filtered, and concentrated under vacuum. The residue was purified by flash column chromatography (silica gel column, 10:1 $CH_2Cl_2$/MeOH) to give the title compound as a pink solid.

Intermediate 24: Step b

5-[(4-Chlorophenyl)carbonyl]-1,2-dimethyl-1H-imidazole

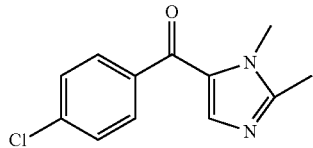 [SMILES: Cc1ncc(C(=O)c2ccc(Cl)cc2)n1C]

To a 50-mL round-bottom flask containing a solution of 5-bromo-1,2-dimethyl-1H-imidazole (440 mg, 2.51 mmol, Intermediate 24, step a) and THF (20 mL) under nitrogen was added isopropylmagnesium chloride in THF (2.0 M, 1.2 mL, 2.4 mmol) dropwise. The mixture was stirred for 0.5 hours at room temperature, and a solution of 4-chloro-N-methoxy-N-methylbenzamide (500 mg, 2.50 mmol, Intermediate 18, step a) in THF (5 mL) was introduced. After stirring for 7.5 hours at room temperature, the reaction was quenched by addition of 10 mL of EtOH, and concentrated under vacuum. The residue was purified by flash column chromatography (silica gel, 50% EtOAc in petroleum, 0-10% MeOH in $CH_2Cl_2$) to give the title compound as a white solid.

Intermediate 25 tert-Butyl 4-nicotinoylpiperidine-1-carboxylate

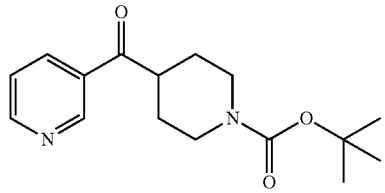 [SMILES: CC(C)(C)OC(=O)N1CCC(C(=O)c2cccnc2)CC1]

A mixture of piperidin-4-yl(pyridin-3-yl)methanone hydrochloride (397 mg, 1.75 mmol), di-tert-butyl dicarbonate (710 mg, 3.25 mmol), N,N-dimethylpyridin-4-amine (28 mg, 0.23 mmol) and $Et_3N$ (1.2 mL, 8.6 mmol) in THF (15 mL) and $CH_2Cl_2$ (5 mL) was stirred for 3 days and concentrated. The residue was purified by flash column chromatography (40 g silica gel column, 50-70% EtOAc in heptane) to give the title compound as a clear oil.

Intermediate 26 tert-Butyl 3-nicotinoylpiperidine-1-carboxylate

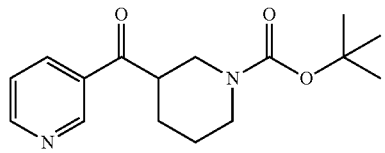 [SMILES: CC(C)(C)OC(=O)N1CCCC(C(=O)c2cccnc2)C1]

The title compound was prepared using piperidin-3-yl(pyridin-3-yl)methanone hydrochloride in place of piperidin-4-yl(pyridin-3-yl)methanone hydrochloride using the procedure described for Intermediate 25.

Intermediate 27

1-(4-Benzoylpiperidin-1-yl)ethanone

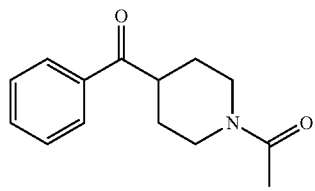 [SMILES: CC(=O)N1CCC(C(=O)c2ccccc2)CC1]

A mixture of phenyl(piperidin-4-yl)methanone hydrochloride (743 mg, 3.29 mmol, Apollo Scientific) in DCM (13.2 mL) and TEA (1.10 mL, 7.90 mmol) was treated with $Ac_2O$ (0.373 mL, 3.95 mmol) dropwise over 1 min on an ice bath under argon, and the resulting translucent mixture was immediately removed from the ice bath and stirred at room temperature overnight. The reaction was then partitioned with 1 M HCl (1×8 mL) and 1 M NaOH (1×8 mL), and the organic layer was dried ($Na_2SO_4$), filtered, and concentrated to provide the title compound as a translucent beige oil that crystallized upon standing.

Intermediate 28: Step a

N-Methoxy-N-methylpyrimidine-5-carboxamide

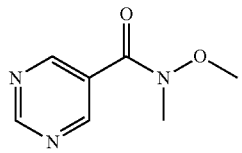

1,1'-carbonyldiimidazole (1.23 g, 7.57 mmol) was added to a suspension of pyrimidine-5-carboxylic acid (783 mg, 6.31 mmol) in DCM (20 mL) and the mixture was stirred at room temperature for 15 min before addition of N,O-dimethylhydroxylamine hydrochloride (739 mg, 7.57 mmol). The mixture was stirred at room temperature for 5 d, then was diluted with saturated aqueous $NH_4Cl$ and water and extracted with DCM. The organic phase was washed with water, and the aqueous phases were back-extracted with DCM. The organic phase was dried ($Na_2SO_4$), filtered, and concentrated, affording the crude title compound as a light yellow oil which was used without further purification in the next reaction.

Intermediate 28: Step b (1-Methyl-1H-imidazol-5-yl)(pyrimidin-5-yl)methanone

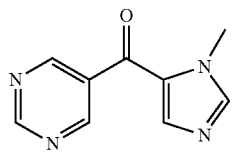

n-BuLi (1.6 M in hexane, 3.71 mL, 5.94 mmol) was added to a solution of 1-methylimidazole (0.452 mL, 5.7 mmol) in THF (10 mL) at −78° C. The mixture was stirred at −78° C. for 30 min. Chlorotriethylsilane (0.957 mL, 5.7 mmol) was added slowly. The mixture was stirred at −78° C. for 30 min. A second portion of n-BuLi (1.6 M in hexane, 3.71 mL, 5.94 mmol) was added. The mixture was stirred at −78° C. for 30 min. Crude N-methoxy-N-methylpyrimidine-5-carboxamide (794 mg, 4.75 mmol, Intermediate 28, step a) was added via cannula as a solution in THF (5 mL). The mixture was stirred at −78° C. for 5 min and was removed from the cold bath and stirred at room temperature overnight. Saturated aqueous $NH_4Cl$ was added and the phases were separated. The aqueous phase was extracted twice with DCM. The organic phase was dried ($Na_2SO_4$), filtered, and concentrated. The residue was purified by flash column chromatography (silica gel, gradient 10-100% EtOAc-heptanes, then 0-10% MeOH- EtOAc) to afford impure title compound, which was further purified by flash column chromatography (silica gel, 4-5% MeOH-DCM).

Intermediate 29: Step a

N-Methoxy-N-methylpyridazine-4-carboxamide

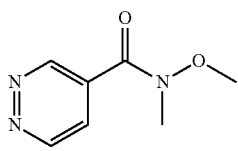

The title compound was prepared using pyridazine-4-carboxylic acid in place of pyrimidine-5-carboxylic acid using the procedure described for Intermediate 28, step a, except that the reaction was run for 2 days and the crude product was purified by flash column chromatography (silica gel, gradient 0-3% MeOH-DCM).

Intermediate 29: Step b (1-Methyl-1H-imidazol-2-yl)(pyridazin-4-yl)methanone

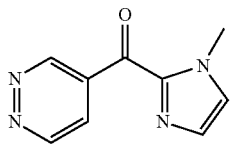

n-BuLi (1.6 M in hexane, 3.65 mL, 5.84 mmol) was added to a solution of 1-methylimidazole (0.452 mL, 5.7 mmol) in THF (30 mL) at −78° C. The mixture was stirred at −78° C. for 15 min. Chlorotriethylsilane (0.955 mL, 5.7 mmol) was added slowly. The mixture was removed from the dry ice/acetone bath and was stirred for 30 min. The mixture was again cooled in a dry ice/acetone bath before addition of a second portion of n-BuLi (1.6 M in hexane, 3.65 mL, 5.84 mmol). The mixture was stirred at −78° C. for 1 hour, then transferred to an ice bath and stirred 10 min. The mixture was again cooled in a dry ice/acetone bath before addition of a solution of N-methoxy-N-methylpyridazine-4-carboxamide (793 mg, 4.74 mmol, Intermediate 29, step a) in THF (15 mL) via cannula. The reaction mixture was stirred at −78° C. for 30 min, then was transferred to a slurry of CH$_3$CN/dry ice and stirred for 15 min. The reaction was quenched by addition of water (50 mL) and the mixture was extracted with EtOAc three times. The organic phase was dried (Na$_2$SO$_4$), filtered, and concentrated. The residue was purified by flash column chromatography (silica gel, gradient 0-4% MeOH-DCM first column, 75-100% EtOAc-heptanes second column) to afford the title compound.

Intermediate 30: Step a

N-Methoxy-N-methylpyrazine-2-carboxamide

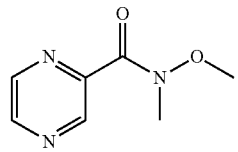

The title compound was prepared using pyrazine-2-carboxylic acid in place of pyrimidine-5-carboxylic acid using the procedure described for Intermediate 28, step a, except that the reaction was run for 1 day and the crude product was purified by flash column chromatography (silica gel, gradient 0-3% MeOH-DCM first column, 50-70% EtOAc-heptane second column).

Intermediate 30: Step b (1-Methyl-1H-imidazol-2-yl)(pyrazin-2-yl)methanone

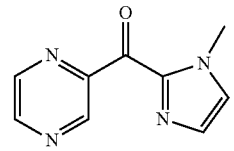

The title compound was prepared using N-methoxy-N-methylpyrazine-2-carboxamide (Intermediate 30, step a) in place of N-methoxy-N-methylpyridazine-4-carboxamide using the procedure described for Intermediate 29, step b, except for the gradients used during normal phase chromatography (75-100% EtOAc-heptane first column, 25-55% acetone-DCM second column).

Intermediate 31

(1-Methyl-1H-imidazol-5-yl)(pyrazin-2-yl)methanone

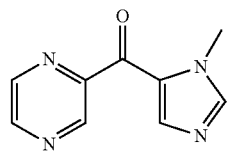

The title compound was also isolated from the reaction that formed Intermediate 30, step b.

Intermediate 32

(4-Chlorophenyl)(pyrimidin-5-yl)methanone

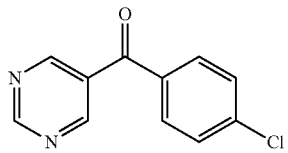 [SMILES: O=C(c1ccc(Cl)cc1)c1cncnc1]

4-chlorophenylmagnesium bromide (1 M in Et₂O, 4.53 mL, 4.53 mmol) was added to a solution of crude N-methoxy-N-methylpyrimidine-5-carboxamide (505 mg, 3.02 mmol, Intermediate 28, step a) in THF at 0° C. The reaction mixture was allowed to warm to room temperature and was stirred overnight. The reaction was quenched by addition of saturated aqueous NH₄Cl, diluted with water, and extracted three times with EtOAc. The organic phase was dried (Na₂SO₄), filtered, and concentrated. The residue was purified by flash column chromatography (silica gel, gradient 1-5% MeOH-DCM), affording impure title compound which was used without further purification.

Intermediate 33

(1-Methyl-1H-imidazol-2-yl)(pyrimidin-5-yl)methanone

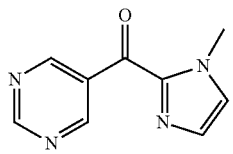

Ethylmagnesium bromide (3 M in Et₂O, 1.05 mL, 3.14 mmol) was added dropwise to a solution of 2-bromo-1-methyl-1H-imidazole (505 mg, 3.14 mmol) in DCM (6 mL) under a nitrogen atmosphere. The mixture was stirred at room temperature 30 min, then was cooled in an ice bath prior to addition of a solution of N-methoxy-N-methylpyrimidine-5-carboxamide (419 mg, 2.51 mmol, Intermediate 28, step a) in DCM (1 mL). The resulting suspension was stirred at room temperature for 24 hours. The reaction was quenched by addition of saturated aqueous NH₄Cl, diluted with water, and extracted three times with DCM. The organic phase was dried (Na₂SO₄), filtered, and concentrated. The residue was purified by flash column chromatography (silica gel, gradient 0-60% CH₃CN-DCM), affording the title compound.

Intermediate 34: Step a

6-Bromo-3-phenyl-2-(trifluoromethyl)quinolin-4-ol

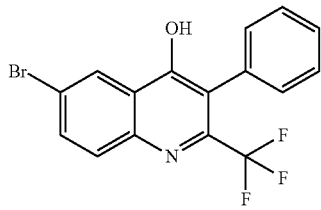 [SMILES: Oc1c(-c2ccccc2)c(C(F)(F)F)nc2ccc(Br)cc12]

A mixture of 2-amino-5-bromobenzoic acid (3.01 g, 13.9 mmol), 1,1,1-trifluoro-3-phenylpropan-2-one (3.11 g, 16.5 mmol), and Eaton's reagent (9.3 mL) in a sealed tube was heated at 100° C. for 4 hours. The reaction mixture was then allowed to cool to room temperature, water was added slowly, and the mixture was stirred vigorously for about 15 min. The precipitated solid was filtered, washed with water, and dried to give the title compound.

Intermediate 34: Step b

6-Bromo-4-chloro-3-phenyl-2-(trifluoromethyl)quinoline

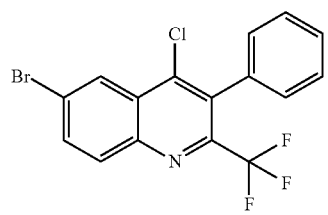

A solution of 6-bromo-3-phenyl-2-(trifluoromethyl)quinolin-4-ol (8.29 g, 22.5 mmol, Intermediate 34, step a) in phosphoryl trichloride (25 mL, 269 mmol) was heated at 110° C. for 2 hours, and concentrated in vacuo. Dichloromethane and ice-water were added, and the mixture was basified at 4° C. with conc. NH₄OH until pH ~10. The organic layer was separated and the aqueous layer was extracted with CH₂Cl₂. The combined organic phases were dried (Na₂SO₄), filtered, concentrated, and purified by flash column chromatography (120 g silica gel column, 2-9% EtOAc in heptane) to give the title compound as a light yellow solid.

Intermediate 35

(1-Methyl-1H-imidazol-5-yl)(pyridazin-4-yl)methanone

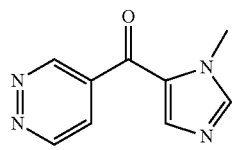

Ethylmagnesium bromide (3 M in Et₂O, 1.04 mL, 3.11 mmol) was added dropwise to a solution of 5-bromo-1-methyl-1H-imidazole (500 mg, 3.11 mmol) in DCM (6 mL) under a nitrogen atmosphere. The mixture was stirred at room temperature 15 min, then was cooled in an ice bath prior to addition of N-methoxy-N-methylpyridazine-4-carboxamide (419 mg, 2.51 mmol, Intermediate 29, step a). The resulting suspension was stirred at room temperature for 2 hours. The reaction was quenched by addition of saturated aqueous NH₄Cl, diluted with water, and extracted three times with EtOAc. The aqueous phase was saturated with NaCl and back-extracted with DCM (three times). The organic phase was dried (Na₂SO₄), filtered, and concentrated. The residue was purified by flash column chromatography (silica gel, gradient 30-100% CH₃CN-DCM, followed by isocratic 5% MeOH-acetone), affording title compound contaminated with 1-methyl-1H-imidazole, the mixture of which was used in the next reaction without further purification.

Intermediate 36

(2,4-Dichloro-3-phenylquinolin-6-yl)(3,5-dimethyl-isoxazol-4-yl)methanone

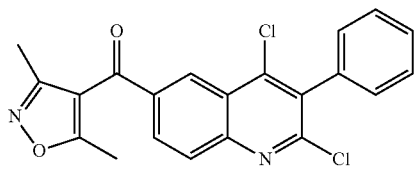 [SMILES: Cc1noc(C)c1C(=O)c1ccc2nc(Cl)c(-c3ccccc3)c(Cl)c2c1]

THF (5 mL) was added to a mixture of 6-bromo-2,4-dichloro-3-phenylquinoline (363 mg, 1.03 mmol, Intermediate 1, step c) and 3,5-dimethylisoxazole-4-carbaldehyde (180 mg, 1.44 mmol) under a nitrogen atmosphere. The resulting colorless solution was cooled in a dry ice/acetone bath. n-BuLi (1.6 M in hexane, 0.771 mL, 1.23 mmol) was added dropwise and the mixture was stirred at −78° C. for 30 min, then moved to an ice bath and stirred for 30 min. The reaction was quenched by addition of saturated aqueous NH₄Cl and was diluted with water. The mixture was extracted three times with EtOAc. The organic phase was dried (Na₂SO₄), filtered, and concentrated to afford crude (2,4-dichloro-3-phenylquinolin-6-yl)(3,5-dimethylisoxazol-4-yl)methanol which was used without further purification in the next step. 1,4-dioxane (7.5 mL) and manganese (IV) dioxide (447 mg, 5.14 mmol) were added to the crude alcohol from the prior step. The resulting black suspension was heated in a 100° C. oil bath in a sealed tube overnight. The mixture was allowed to cool, was diluted with DCM, and was filtered through Celite®. The filtrate was concentrated and the residue was purified by flash column chromatography—(silica gel, 3-15% EtOAc-heptane) to isolate the title compound.

Intermediate 37: Step a (2,4-Dichloro-3-phenylquinolin-6-yl)(3-methylisoxazol-5-yl)methanol

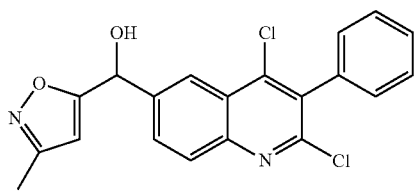 [SMILES: Cc1cc(C(O)c2ccc3nc(Cl)c(-c4ccccc4)c(Cl)c3c2)on1]

To a mixture of 6-bromo-2,4-dichloro-3-phenylquinoline (363 mg, 1.03 mmol, Intermediate 1, step c) and 3-methylisoxazole-5-carbaldehyde (149 mg, 1.34 mmol) in THF (5 mL) at −78° C. was added n-BuLi (1.6 M in hexane, 0.707 mL, 1.13 mmol) dropwise. The mixture was stirred at −78° C. for 30 min, then moved to an ice bath and stirred for 30 min. The reaction was quenched by addition of saturated aqueous NH₄Cl and was diluted with water. The mixture was extracted three times with EtOAc. The organic phase was dried (Na₂SO₄), filtered, and concentrated to afford the crude title compound which was used without further purification in the next reaction.

Intermediate 37: Step b (2,4-Dichloro-3-phenylquinolin-6-yl)(3-methylisoxazol-5-yl)methanone

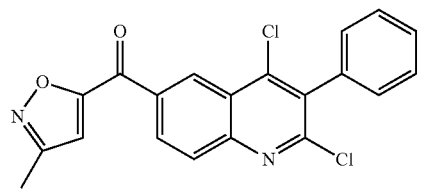 [SMILES: Cc1cc(C(=O)c2ccc3nc(Cl)c(-c4ccccc4)c(Cl)c3c2)on1]

1,4-dioxane (7.5 mL) and manganese (IV) dioxide (447 mg, 5.14 mmol) were added to crude (2,4-dichloro-3-phenylquinolin-6-yl)(3-methylisoxazol-5-yl)methanol (Intermediate 37, step a, 1.03 mmol assuming theoretical yield in prior step). The resulting black suspension was heated in a 100° C. oil bath in a sealed tube for 3 hours. The mixture was allowed to cool, was diluted with DCM, and was filtered through Celite®. The filtrate was concentrated and the residue was purified by flash column chromatography (silica gel, 3-15% EtOAc-heptane) to afford slightly impure title compound which was used without further purification.

Intermediate 38: Step a

N-Methoxy-N,2-dimethylthiazole-4-carboxamide

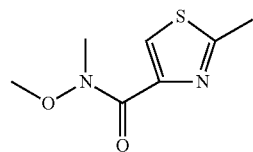

Analogous to the general method described in *J. Med. Chem.*, (2005), 48(6), 2134-2153. To a flask containing 2-methylthiazole-4-carboxylic acid (1.10 g, 7.68 mmol) was added DCM (30 mL) and the homogeneous solution was stirred at room temperature as carbonyldiimidazole (1.30 g, 8.02 mmol) was added. A white opaque suspension resulted. After the mixture was stirred at room temperature for 2.25 hours a colorless homogeneous solution resulted and then N,O-dimethylhydroxylamine hydrochloride (820 mg, 8.41 mmol) was added which caused an opaque solution to result once again. The mixture was stirred at room temperature for 18 hours, then diluted with water and 1 N NaOH (to pH ~9) and extracted with DCM (4×50 mL). The combined organics were washed with brine, dried over Na₂SO₄, filtered and concentrated to give a colorless oil, which was passed through a plug of silica gel eluting with (20% THF-DCM) to provide the title compound as a colorless oil.

Intermediate 38: Step b (1-Methyl-1H-imidazol-5-yl)(2-methylthiazol-4-yl)methanone

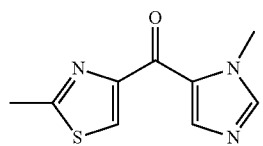

To a flask containing 5-bromo-1-methyl-1H-imidazole (345 mg, 2.14 mmol) was added THF (8 mL) and the solution was cooled to 0° C. To this clear homogeneous solution was added isopropylmagnesium chloride-LiCl complex (1.3 M, 2.0 mL, 2.6 mmol) which resulted in a white suspension. The reaction was stirred at 0° C. for 30 min, then a THF (2 mL) solution of N-methoxy-N,2-dimethylthiazole-4-carboxamide (250 mg, 1.34 mmol, Intermediate 38, step a) was introduced and the mixture became more viscous and was allowed to warm to room temperature. After 3 hours the mixture was quenched with saturated NH₄Cl solution and extracted with EtOAc (4×50 mL). The combined organics were washed with brine, dried over Na₂SO₄, filtered and concentrated. Flash chromatography on silica gel (20-40% EtOAc-DCM increasing gradient to 5% MeOH-DCM) provided the title compound as an off-white solid.

Intermediate 39

(2-Chloro-1-methyl-1H-imidazol-5-yl)(4-chlorophenyl)methanone

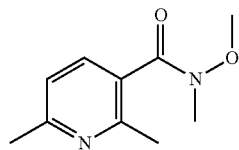

The title compound was prepared by the method described in *J. Org. Chem.* 2004, 69 (23), 8115.

Intermediate 40: Step a

N-Methoxy-N,2,6-trimethylnicotinamide

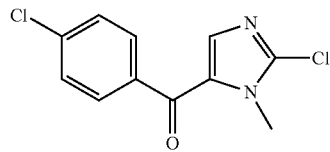 [SMILES: Cn1c(C(=O)c2ccc(Cl)cc2)cnc1Cl]

To a flask containing 2,6-dimethylnicotinic acid (2.80 g, 18.5 mmol) was added CH₂Cl₂ and DMF (6 mL). The suspension was stirred at room temperature as carbonyl diimidazole (3.50 g, 21.6 mmol) was added. The suspension remained throughout the day and was allowed to stir overnight at room temperature. After 18 hours, N,O-dimethylhydroxylamine hydrochloride (3.00 g, 30.8 mmol) was introduced and the mixture was stirred at room temperature again for 24 hours. The reaction mixture was quenched with water and 1 N NaOH, and extracted with CH₂Cl₂ (4×50 mL). The combined organics were washed with brine, dried over Na₂SO₄, filtered and concentrated to give a colorless oil. Flash chromatography on silica gel (50% EtOAc-hexane) afforded the title compound as a colorless oil.

Intermediate 40: Step b (2,6-Dimethylpyridin-3-yl)(1-methyl-1H-imidazol-5-yl)methanone

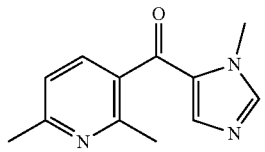 [SMILES: Cc1ccc(C(=O)c2cncn2C)c(C)n1]

To a flask containing 5-bromo-1-methyl-1H-imidazole (360 mg, 2.24 mmol) was added THF and the solution was cooled to 0° C. To this clear homogeneous solution was added isopropyl magnesium chloride-LiCl complex (1.3 M, 2.3 mL, 2.98 mmol) which resulted in a white suspension. The reaction mixture was stirred at 0° C. for 30 min, and a THF (2 mL) solution of N-methoxy-N,2,6-trimethylnicotinamide (522 mg, 2.69 mmol, Intermediate 40, step a) was introduced and the mixture was allowed to warm to room temperature for 3 hours and then heated to 50° C. for 20 hours. The contents were cooled to room temperature, poured into a saturated NH₄Cl solution and extracted with EtOAc (4×50 mL). The combined organics were washed with brine, dried over MgSO₄, filtered and concentrated. Flash chromatography on silica gel (25-50% Acetonitrile-DCM increasing gradient to 5% MeOH-DCM) afforded the title compound as a pale yellowish solid.

Intermediate 41: Step a

N-Methoxy-N,2,4-trimethylthiazole-5-carboxamide

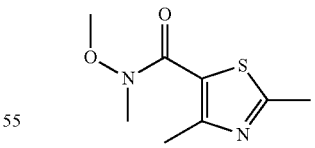

To a flask containing 2,4-dimethylthiazole-5-carboxylic acid (2.50 g, 15.9 mmol) was added DCM (75 mL) and DMF (3 mL) to afford a homogeneous solution. Then, carbonyldiimidazole (2.84 g, 17.5 mmol) was added and the mixture was stirred at room temperature for 2 hours. N,O-dimethylhydroxylamine hydrochloride (1.90 g, 19.9 mmol) was then added and the reaction mixture was stirred at room temperature for 18 hours, then diluted with water and 1 N NaOH and extracted with DCM (4×50 mL). The combined organics were washed with brine, dried over Na₂SO₄, filtered and

Intermediate 41: Step b (2,4-Dimethylthiazol-5-yl)(1-methyl-1H-imidazol-5-yl)methanone

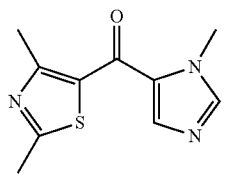

To a flask containing 5-bromo-1-methyl-1H-imidazole (390 mg, 2.42 mmol) was added THF (8 mL) and the solution was cooled to 0° C. To this clear homogeneous solution was added isopropyl magnesium chloride-LiCl complex (1.3 M in THF, 2.5 mL, 3.25 mmol) which resulted in a white suspension. The mixture was stirred at 0° C. for 30 min, then a THF solution (2 mL) of N-methoxy-N,2,4-trimethylthiazole-5-carboxamide (550 mg, 2.75 mmol, Intermediate 41, step a) was introduced and the mixture was allowed to warm to room temperature. After 3 hours at room temperature the mixture was heated to 50° C. for 18 hours, followed by quenching with NH$_4$Cl solution. The aqueous portion was extracted with DCM (4×50 mL). The combined organics were washed with brine, dried over Na$_2$SO$_4$, filtered and concentrated. Flash chromatography on silica gel (25-50% EtOAc-DCM increasing gradient to 5% MeOH-DCM) provided the title compound as an amber solid.

Intermediate 42: Step a

1-Methyl-1H-1,2,3-triazole

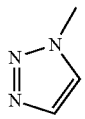

The title compound was prepared by the method described in WO2008/98104.

Intermediate 42: Step b (4-Chlorophenyl)(1-methyl-1H-1,2,3-triazol-5-yl)methanol

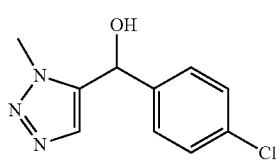

Analogous to the general method described in *J. Org. Chem.* 2004, 69, 8115, and *Chem. Pharm. Bull,* 1997, 1145. To a 2-necked flask containing 1-methyl-1H-1,2,3-triazole (1.00 g, 12.0 mmol, Intermediate 42, step a) was added THF (75 mL) and the solution was cooled between −40 to −20° C. To this colorless homogeneous solution was added n-BuLi (2.5 M in hexanes, 5.0 mL, 11.4 mmol) dropwise which afforded a dark brown viscous mixture. After stirring at 0° C. for 1 hours, a THF (10 mL) solution of 4-chlorobenzaldehyde (1.60 g, 11.4 mmol) was introduced and the reaction mixture began to be stirred freely and remained brownish. After 3 hours the reaction mixture was quenched by pouring into a saturated solution of NH$_4$Cl and the aqueous portion was extracted with EtOAc (4×50 mL). The combined organics were washed with brine, dried over MgSO$_4$, filtered and concentrated to give a brown oil which solidified upon standing. The crude material was triturated with Et$_2$O to provide the title compound as a brown solid.

Intermediate 42: Step c (4-Chlorophenyl)(1-methyl-1H-1,2,3-triazol-5-yl)methanone

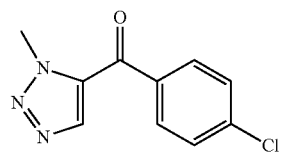

Similar to the procedure described in *J. Am. Chem. Soc.* 1991, 7277, a flask containing Dess-Martin reagent (1.50 g, 3.54 mmol) in DCM (30 mL) was cooled to 0° C. and then a solution of (4-chlorophenyl)(1-methyl-1H-1,2,3-triazol-5-yl)methanol (500 mg, 2.24 mmol, Intermediate 42, step b) in 10 mL of DCM was added. After 5 min, the ice bath was removed and the mixture was allowed to stir at room temperature for 45 min, at which time TLC (20% EtOAc-DCM) indicated the reaction was complete. The mixture was quenched with a saturated NaHCO$_3$ solution and 2 mL of 1 N NaOH and the aqueous portion (pH ~9) was extracted with DCM (3×75 mL). The combined organics were washed with brine, dried over MgSO$_4$, filtered and concentrated to give a light amber solid. Flash chromatography on silica gel (10% EtOAc-DCM) afforded the title compound as a white solid.

Intermediate 43: Step a

N-Methoxy-N,2-dimethylbenzo[d]oxazole-5-carboxamide

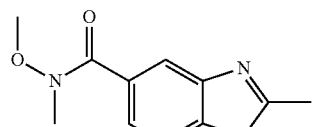

To a flask containing 2-methylbenzo[d]oxazole-5-carboxylic acid (1.00 g, 5.64 mmol) was added DCM (40 mL) to give a suspension. Carbonyldiimidazole (1.01 g, 6.21 mmol) was added and the mixture remained homogeneous and was stirred at room temperature for 17 hours, then N,O-dimethylhydroxylamine hydrochloride (688 mg, 7.06 mmol) was added and the mixture was stirred at room temperature for 18 hours. The contents were diluted with water and 1 N NaOH and extracted with DCM (4×50 mL). The combined organics were washed with brine, dried over Na₂SO₄, filtered and concentrated. Flash chromatography on silica gel (10-40% EtOAc-DCM) gave the title compound as an amber oil.

Intermediate 43: Step b (1-Methyl-1H-imidazol-5-yl)(2-methylbenzo[d]ox-azol-5-yl)methanone

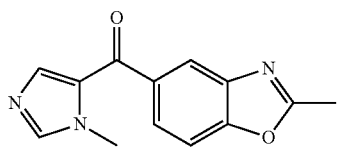 [SMILES: Cc1nc2cc(C(=O)c3cncn3C)ccc2o1]

To a flask containing 5-bromo-1-methyl-1H-imidazole (700 mg, 4.35 mmol) was added THF (14 mL) and the solution was cooled to 0° C. To this clear homogeneous solution was added isopropylmagnesium chloride-LiCl complex (1.3 M in THF, 3.4 mL, 4.38 mmol) which resulted in a white suspension. The reaction was stirred at 0° C. for 25 min, then a THF solution (5 mL) of (N-methoxy-N,2-dimethylbenzo[d]oxazole-5-carboxamide (700 mg, 3.20 mmol, Intermediate 43, step a) was introduced and the mixture was allowed to warm to room temperature. The reaction was heated to 40° C. for 20 hours and then quenched with a saturated NH₄Cl solution. The aqueous portion was extracted with EtOAc (4×50 mL). The combined organics were washed with brine, dried over Na₂SO₄, filtered and concentrated. The crude material was triturated with DCM-Et₂O (1:10) to afford the title compound as an amber solid. The mother liquors were concentrated and again triturated with Et₂O to provide a second crop of the material. Finally, the mother liquors were concentrated and chromatographed on silica gel (10-50% acetone-DCM increasing gradient to 5% MeOH-DCM) to provide the title compound as a pale yellow solid.

Intermediate 44: Step a (1-Methyl-1H-imidazol-5-yl)(quinolin-4-yl)methanol

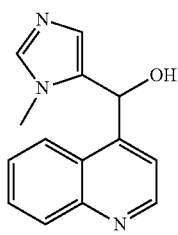 [SMILES: Cn1cncc1C(O)c1ccnc2ccccc12]

Analogous to the general method described in *J. Org. Chem.* 2004, 69, 8115 and *Chem. Pharm. Bull* 1997, 1145. To a 2-necked flask containing 5-bromo-1-methyl-1H-imidazole (2.05 g, 12.7 mmol) was added THF (50 mL) and the solution was cooled to 0° C. To this clear homogeneous solution was added isopropyl magnesium chloride-LiCl complex (1.3 M, 10.5 mL, 13.6 mmol) which initially resulted in a white suspension, but became grayish once the addition of the Grignard reagent was complete. The reaction was stirred in an ice bath for 30 min, then a THF solution (20 mL) of quinoline-4-carbaldehyde (1.00 g, 6.36 mmol) was introduced and the reaction mixture became a greenish-grey color, and was subsequently allowed to warm to room temp. After 2 hours, the reaction mixture became brown in color and still remained heterogeneous. The reaction was quenched after 2 hours with saturated NH₄Cl solution and the aqueous portion was extracted with EtOAc (4×75 mL). The combined organics were washed with brine, dried over MgSO₄, filtered and concentrated to give an amber oil which solidified to a white solid upon standing. The crude material was triturated with DCM and then MeOH leaving behind the title compound as a white solid. The mother liquors were concentrated and chromatographed on silica gel (30% EtOAc-DCM increasing gradient to 10% MeOH-DCM) to provide more title compound as an off-white solid.

Intermediate 44: Step b (1-Methyl-1H-imidazol-5-yl)(quinolin-4-yl)methanone

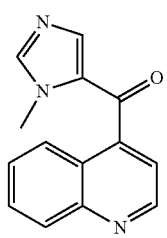 [SMILES: Cn1cncc1C(=O)c1ccnc2ccccc12]

To a flask containing 1-methyl-1H-imidazol-5-yl)(quinolin-4-yl)methanol (525 mg, 2.19 mmol, Intermediate 44, step a) was added 1,4-dioxane (10 ml) followed by manganese dioxide (700 mg, 6.84 mmol). The dark black mixture was heated to reflux using an aluminum heating mantle. TLC (10% MeOH-DCM) after 1.5 hours showed the reaction to be complete. The reaction mixture was filtered through a Celite® pad and rinsed with THF and EtOAc. The filtrate was concentrated to give the product as a light amber foam. Purification through a short column of silica gel (10% MeOH-DCM) gave the title compound as light tan foam/gum. After 2 days under vacuum, the gum solidified.

Intermediate 45: Step a (2,4-Dimethylthiazol-5-yl)(1-methyl-1H-1,2,3-triazol-5-yl)methanol

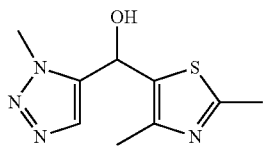

To a flask containing 1-methyl-1H-1,2,3-triazole (1.60 g, 19.3 mmol, Intermediate 42, step a) was added THF (200 mL) and the solution was cooled to −40° C. To this colorless homogeneous solution was added n-BuLi (2.5 M in hexanes, 7.7 mL, 19.2 mmol) dropwise which immediately afforded a dark brown viscous mixture. The mixture was kept between −10 to −20° C. for 60 min, then 2,4-dimethylthiazole-5-carbaldehyde (3.03 g, 21.5 mmol) in THF (5 mL) was introduced and the reaction mixture began to stir much more easily, but still remained brownish. Once the aldehyde was added the reaction was placed in an ice-bath and maintained there until it warmed to room temp. After 3 hours the reaction was quenched by pouring into a saturated solution of NH₄Cl at room temperature. The aqueous portion was extracted with EtOAc (5×100 mL). The combined organics were washed with brine, dried over MgSO₄, filtered and concentrated to give a brown oil-foam. Flash chromatography on silica gel (10-30% acetone increasing gradient to 10% MeOH-DCM) gave the title compound as a light orange foam.

Intermediate 45: Step b (2,4-Dimethylthiazol-5-yl)(1-methyl-1H-1,2,3-triazol-5-yl)methanone

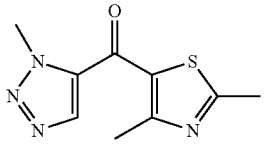

A flask containing Dess-Martin reagent (7.50 g, 17.7 mmol) in DCM (200 mL) was cooled to 0° C. and then a solution of (2,4-dimethylthiazol-5-yl)(1-methyl-1H-1,2,3-triazol-5-yl)methanol (3.00 g, 13.4 mmol, Intermediate 45, step a) in 100 mL of DCM was added. After 5 min, the ice bath was removed and the reaction was allowed to stir at room temperature for 45 min, at which time TLC (30% acetone-DCM) indicated the reaction was complete. The reaction was quenched with saturated NaHCO₃ solution and about 2 mL of 1 N NaOH and the aqueous portion (pH~9) was extracted with DCM (3×75 mL). The combined organic layers were washed with brine, dried over MgSO₄, filtered and concentrated to give an amber oil. Flash chromatography on silica gel (10-40% EtOAc-DCM) afforded the title compound as a yellow solid.

Intermediate 46: Step a

6-Bromo-2,4-dichloro-8-fluoro-3-phenylquinoline

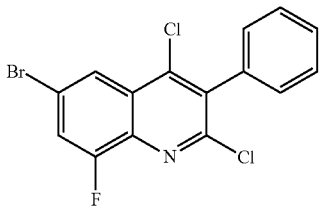 [SMILES: Fc1cc(Br)cc2c(Cl)c(-c3ccccc3)c(Cl)nc12]

A mixture of 4-bromo-2-fluoroaniline (6.53 g, 34.4 mmol), 2-phenylmalonic acid (7.43 g, 41.2 mmol), and POCl₃ (31.9 mL, 344 mmol) was stirred at reflux (130° C. aluminum block temp) for 45 min. The resulting homogeneous dark solution was chilled on an ice bath, diluted with DCM (50 mL) and ice (100 mL), and stirred on the ice bath while 15 M NH₄OH (30 mL) was added intermittently with swirling over ~5 min (delayed exotherm). The aqueous layer was extracted with DCM (1×25 mL), and the combined organic layers were dried (Na₂SO₄), filtered, and concentrated. The residue was flash chromatographed with a 20% to 50% DCM/heptane gradient to provide the title compound as a light yellow solid.

Intermediate 46: Step b 2,4-Dichloro-8-fluoro-3-phenylquinoline-6-carbaldehyde

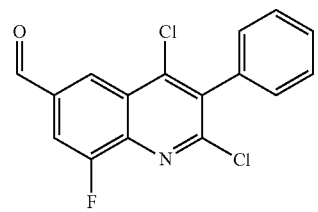 [SMILES: O=Cc1cc(F)c2nc(Cl)c(-c3ccccc3)c(Cl)c2c1]

A yellow solution of 6-bromo-2,4-dichloro-8-fluoro-3-phenylquinoline (1.01 g, 2.72 mmol, Intermediate 46, step a) in THF (10 mL) was stirred at −72° C. while n-BuLi (1.15 mL, 2.59 M in hexane, 2.99 mmol) was added dropwise under argon. The resulting homogeneous dark solution was stirred at −72° C. for 20 min, and was then treated with DMF (0.273 mL, 3.53 mmol) dropwise. The homogeneous dark reaction was stirred at −72° C. for 25 min, and was then removed from the cold bath and stirred under ambient conditions for 30 min. The dark homogeneous solution was quenched with 5 M NH₄Cl (10 mL) and the aqueous layer was extracted with EtOAc (3×8 mL). The combined organic layers were dried (Na₂SO₄), filtered, and concentrated, and the residue was flash chromatographed with a 20% DCM/heptane to 100% DCM gradient to provide the title compound as a yellow powder.

Intermediate 46: Step c (2,4-Dichloro-8-fluoro-3-phenylquinolin-6-yl)(1-methyl-1H-imidazol-5-yl)methanone

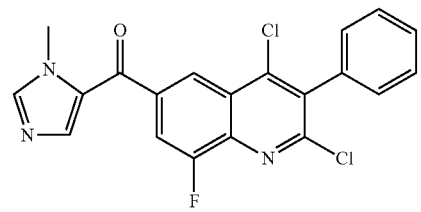 [SMILES: Cn1cncc1C(=O)c1cc(F)c2nc(Cl)c(-c3ccccc3)c(Cl)c2c1]

A solution of 5-bromo-1-methyl-1H-imidazole (95.7 mg, 0.594 mmol) in DCM (0.6 mL) was stirred on an ice bath while iPrMgCl—LiCl (0.495 mL, 1.2 M in THF, 0.593 mmol) was added dropwise over 2.5 min under argon. After 15 min stirring at room temperature, the Grignard solution was added dropwise over 2.5 min to a slurry of 2,4-dichloro-8-fluoro-3-phenylquinoline-6-carbaldehyde (140 mg, 0.436 mmol, Intermediate 46, step b) in LaCl₃-2LiCl (0.779 mL, 0.56 M in THF, 0.436 mmol) on an ice bath. The red-colored reaction was removed from the ice bath immediately following Grignard addition, and after 15 min stirring under ambient conditions, the reaction was partitioned with DCM (5 mL) and 1M NaHCO₃ (0.6 mL). The mixture was filtered and the filter cake washed with 3 mL DCM. The combined clear yellow filtrates were dried (Na₂SO₄), filtered, and concentrated, and the crude secondary alcohol was dissolved in DCM (2 mL), treated with MnO₂ (379 mg, 4.36 mmol), and stirred at 40° C. for 2 hours. The reaction was then diluted with DCM (4 mL) and filtered, and the clear yellow filtrate was concentrated and flash chromatographed with a 5% acetone/heptane to 100% acetone gradient to yield the title compound as a white solid.

Intermediate 47: Step a

6-Bromo-2,4-dichloro-8-methyl-3-phenylquinoline

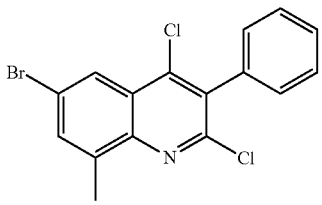 [SMILES: Cc1cc(Br)cc2c(Cl)c(-c3ccccc3)c(Cl)nc12]

A mixture of 2-phenylmalonic acid (7.62 g, 42.3 mmol) and POCl₃ (32.8 mL, 352 mmol) was stirred at reflux (130° C. aluminum block temp) for 10 min, and the resulting homogeneous yellow solution was cooled on an ice bath. 4-Bromo-2-methylaniline (6.56 g, 35.2 mmol) was added in one portion and the mixture was refluxed for 2 hours. The dark solution was allowed to cool to room temperature and was diluted with DCM (70 mL) and ice (100 mL), and stirred under ambient conditions for ~5-10 min at which point exothermic POCl₃ hydrolysis commenced (ice bath cooling), and was then stirred at room temperature for another 30 min. The light yellow aqueous layer was extracted with DCM (1×30 mL), and the combined dark homogeneous organic layers were dried (Na₂SO₄), filtered, and concentrated with silica gel. The silica-adsorbed residue was dry load flash chromatographed with a 20% DCM/heptane to 100% DCM gradient to provide the title compound as an off-white solid.

Intermediate 47: Step b 2,4-Dichloro-8-methyl-3-phenylquinoline-6-carbaldehyde

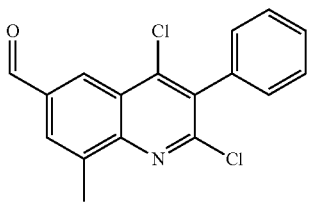 [SMILES: Cc1cc(C=O)cc2c(Cl)c(-c3ccccc3)c(Cl)nc12]

A −71° C. solution of n-BuLi (6.14 mL, 1.59 M in hexane, 9.77 mmol) under argon was treated with a solution of 6-bromo-2,4-dichloro-8-methyl-3-phenylquinoline (3.26 g, 8.81 mmol, Intermediate 47, step a) in THF (27 mL) as an intermittent fine stream over 28 min. After a few minutes, DMF (1.38 mL, 17.8 mmol) was added dropwise over 2 min to the reddish-brown reaction, and the resulting greenish-black mixture was stirred at −72° C. for 30 min. The reaction was removed from the cold bath and allowed to stir under ambient conditions for 10 min, and was then quenched in one portion with 5 M NH₄Cl (7 mL), partitioned with 4:1 EtOAc/heptane (50 mL) and 5:3 4 M NaCl/5 M NaBr (40 mL), and filtered. The filter cake was dissolved in 9:1 DCM/MeOH (15 mL), and this was combined with the clear yellow organic layer filtrate and dried (Na₂SO₄), filtered, and concentrated. The residue was dry load flash chromatographed with a 20% DCM/heptane to 100% DCM gradient to afford the title compound as a white solid.

Intermediate 47: Step c (2,4-Dichloro-8-methyl-3-phenylquinolin-6-yl)(6-methylpyridin-3-yl)methanone

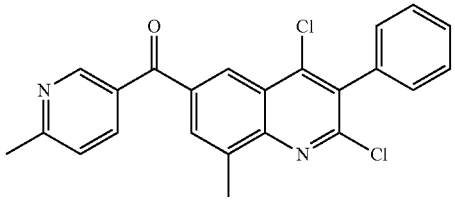 [SMILES: Cc1ccc(C(=O)c2cc(C)c3nc(Cl)c(-c4ccccc4)c(Cl)c3c2)cn1]

A solution of 5-bromo-2-methylpyridine (380 mg, 2.21 mmol) in DCM (2.2 mL) was stirred on an ice bath while iPrMgCl—LiCl (1.84 mL, 1.2 M in THF, 2.21 mmol) was added dropwise over 1-2 min under argon. After 30 min stirring at room temperature, the dark brown Grignard solution was added dropwise over 1-2 min to a slurry of 2,4-dichloro-8-methyl-3-phenylquinoline-6-carbaldehyde (460 mg, 1.46 mmol, Intermediate 47, step b) in LaCl₃-2LiCl (2.60 mL, 0.56 M in THF, 1.46 mmol) on an ice bath under argon. The homogeneous reddish-amber reaction was removed from the ice bath immediately following Grignard addition and stirred at room temperature overnight. The resulting homogeneous brown amber solution was diluted with 9:1 DCM/MeOH (14 mL) and 5 M NH₄Cl (0.72 mL), shaken with Celite® and filtered, and the filter cake was washed with 9:1 DCM/MeOH (1×5 mL). The combined clear amber filtrates were dried (Na₂SO₄), filtered, and concentrated repeatedly from DCM. The residue was taken up in DCM (15 mL) and the resulting slurry was stirred with MnO₂ (1.27 g, 14.5 mmol) under air (capped) at 40° C. for 32 hours. The reaction was diluted with 9:1 DCM/MeOH (10 mL) and Celite®, and filtered on a bed of Celite®. The filtrate was concentrated and flash chromatographed with a DCM to 30% EtOAc/DCM gradient to provide the title compound as a colorless film.

Intermediate 48: Step a (2,4-Dichloro-8-methyl-3-phenylquinolin-6-yl)(1-methyl-1H-imidazol-5-yl)methanol

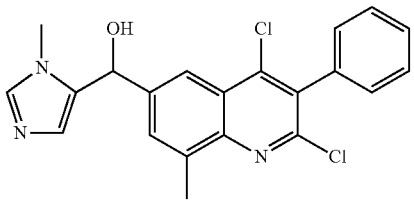 [SMILES: Cc1cc(C(O)c2cncn2C)cc2c(Cl)c(-c3ccccc3)c(Cl)nc12]

A solution of 5-bromo-1-methyl-1H-imidazole (342 mg, 2.12 mmol) in DCM (2.2 mL) was stirred on an ice bath while iPrMgCl—LiCl (1.77 mL, 1.2 M in THF, 2.1 mmol) was added dropwise over 1-2 min under argon. After 10 min stirring at room temperature, the homogeneous amber reaction was added dropwise over 1-2 min to a slurry of 2,4-dichloro-8-methyl-3-phenylquinoline-6-carbaldehyde (460 mg, 1.46 mmol, Intermediate 47, step b) in LaCl$_3$-2LiCl (7.60 mL, 0.56 M in THF, 1.46 mmol) on an ice bath. The reaction was removed from the ice bath immediately following Grignard addition and stirred for 45 min at ambient temperature, and was then partitioned with 9:1 DCM/MeOH (14 mL) and 5 M NH$_4$Cl (0.72 mL). This was filtered over Celite®, and the filter cake washed with 9:1 DCM/MeOH (1×5 mL). The combined clear dark yellow filtrates were dried (Na$_2$SO$_4$), filtered, and concentrated to provide a beige foam. This was concentrated from DCM (3×15 mL) in prelude to MnO$_2$ oxidation.

Intermediate 48: Step b (2,4-Dichloro-8-methyl-3-phenylquinolin-6-yl)(1-methyl-1H-imidazol-5-yl)methanone

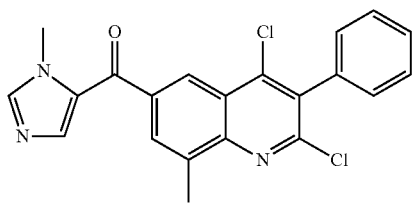 [SMILES: Cc1cc(C(=O)c2cncn2C)cc2c(Cl)c(-c3ccccc3)c(Cl)nc12]

A suspension of crude (2,4-dichloro-8-methyl-3-phenylquinolin-6-yl)(1-methyl-1H-imidazol-5-yl)methanol (801 mg, assume 1.46 mmol, Intermediate 48, step a) in DCE (15 mL) was stirred at 70° C. until a milky mixture resulted with no visible particulates. This was cooled to room temperature and treated with MnO$_2$ (1.27 g, 14.5 mmol), and stirred under air (capped) at 70° C. for 35 hours. The reaction was diluted with 9:1 DCM/MeOH (10 mL) and Celite®, filtered on a bed of Celite®, and concentrated to provide an oil. This was flash chromatographed with a DCM to 100% EtOAc gradient to afford the title compound as a white foam.

Intermediate 49: Step a

4-Fluoro-N-methoxy-N-methylbenzamide

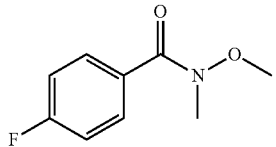

To N,O-dimethylhydroxylamine hydrochloride (27.7 g, 284 mmol) in DCM (660 mL) was added pyridine (45.8 mL, 569 mmol) followed by 4-fluorobenzoyl chloride (31.0 mL, 258 mmol). The resulting suspension was stirred at room temperature for 20 hours, then was filtered to remove a white solid precipitate. The solid was washed with DCM and the filtrate was washed with 1 N aqueous HCl (2×), then water. The organic phase was dried (Na$_2$SO$_4$), filtered, and concentrated, yielding the crude title compound which was used without further purification.

Intermediate 49: Step b (4-Fluorophenyl)(1-methyl-1H-imidazol-5-yl)methanone

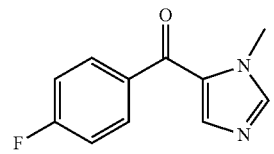

A clear colorless solution of 5-bromo-N-methyl-imidazole (47.7 g, 296 mmol) in THF (500 mL) was placed in an ice bath and ethylmagnesium bromide in diethyl ether (3.0 M, 98.7 mL, 296 mmol) was added via syringe fairly rapidly, over 17 min. The thick suspension was stirred at room temperature for 20 min. The mixture was again cooled in an ice water bath before addition of neat 4-fluoro-N-methoxy-N-methylbenzamide (45.2 g, 247 mmol, Intermediate 49, step a). The resulting suspension was stirred overnight at room temperature. To the reaction mixture was added saturated aqueous NH$_4$Cl (100 mL) followed by water (200 mL). The pH was adjusted to 7 by addition of 1 N aqueous HCl, the mixture was partially concentrated to remove THF, and was extracted with EtOAc (3×). The organic phase was dried (Na$_2$SO$_4$), filtered, and concentrated. The crude product was triturated with EtOAc:heptane(1:1, 150 mL) to afford the title compound as a white crystalline solid.

Intermediate 50: Step a

Diethyl 2-(3-fluorophenyl)malonate

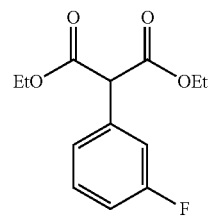 [SMILES: CCOC(=O)C(C(=O)OCC)c1cccc(F)c1]

A round bottom flask was charged with copper (I) iodide (571 mg, 3.0 mmol), 2-picolinic acid (739 mg, 6.0 mmol), and Cs$_2$CO$_3$ (58.6 g, 180 mmol). The flask was evacuated and re-filled with argon (3 times). 1,4-dioxane (60 mL), diethylmalonate (18.2 mL, 120 mmol), and 3-fluoroiodobenzene (7.05 mL, 60 mmol) were then added in sequence. The resulting yellow suspension was stirred at room temperature overnight. To the mixture was added sat aqueous NH$_4$Cl and the mixture was extracted with EtOAc (3×). The organic phase was washed once with water. The organic phase was dried (Na$_2$SO$_4$), filtered, and concentrated to yield the crude title compound as a colorless liquid, which was used without further purification.

Intermediate 50: Step b 2-(3-Fluorophenyl)malonate

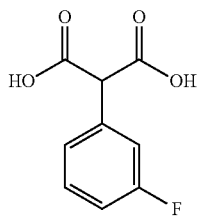

Crude diethyl 2-(3-fluorophenyl)malonate (19.8 g, Intermediate 50, step a) was added to 20 wt. % aqueous NaOH (600 mL) and the mixture was heated in a 65° C. oil bath with vigorous stirring for 10 min, then was cooled in an ice water bath. Ice was added to the reaction mixture and it was acidified to pH 2 by addition of 6 N aqueous HCl, keeping the internal temperature below 30° C. by adding ice as needed. The mixture was extracted with EtOAc (3×). The organic phase was dried (Na$_2$SO$_4$), filtered, and concentrated to yield the title compound as a white solid.

Intermediate 50: Step c

6-Bromo-2,4-dichloro-3-(3-fluorophenyl)-8-methylquinoline

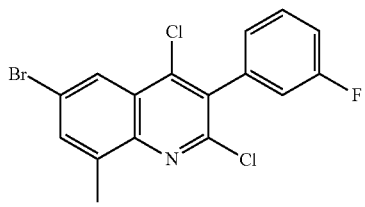 [SMILES: Cc1cc(Br)cc2c(Cl)c(-c3cccc(F)c3)c(Cl)nc12]

A mixture of 2-(3-fluorophenyl)malonate (9.84 g, 49.7 mmol, Intermediate 50, step b) and POCl$_3$ (44 mL, 473 mmol) was heated at 70° C. for 1 hour. The mixture was allowed to cool for 10 min before addition of 2-methyl-4-bromoaniline (8.80 g, 47.3 mmol) portionwise over 5 min. The mixture was stirred at 105° C. for 3 hours. The mixture was concentrated and was added to stirred ice water in a flask immersed in an ice water bath. The mixture was basified to pH 9 by addition of concentrated aqueous NH$_4$OH and was filtered to collect the yellow precipitate. The solid was dried by concentrating from toluene, and then heptane, and further dried under vacuum, then was purified by flash column chromatography (silica gel, gradient 30-60% DCM-heptanes, dry pack loading) to afford the title compound.

Intermediate 51: Step a

Methyl 5-bromo-2-[2-(pyridin-3-yl)acetamido]benzoate

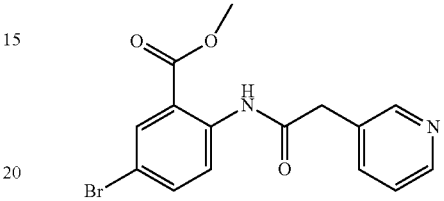

Into a 250-mL round-bottom flask was placed a solution of methyl 2-amino-5-bromobenzoate (5 g, 21.73 mmol, 1.00 equivalent), 2-(pyridin-3-yl)acetic acid hydrochloride (4.5 g, 25.92 mmol, 1.20 equivalents), HATU (10 g, 26.30 mmol, 1.20 equivalents), and DIEA (8.5 g, 65.77 mmol, 3.00 equivalents) in N,N-dimethylformamide (100 mL). After stirring overnight at 20° C., the reaction was quenched with 100 mL of water and extracted with 3×100 mL of dichloromethane. The combined organic layer was dried over anhydrous sodium sulfate, filtered, and concentrated under vacuum. The residue was applied onto a silica gel column and eluted with ethyl acetate/petroleum ether (1:2-1:1) to give the title compound as a yellow solid.

Intermediate 51: Step b

6-Bromo-3-(pyridin-3-yl)-1,2,3,4-tetrahydroquinoline-2,4-dione

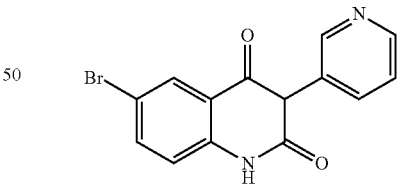

Into a 100-mL round-bottom flask was placed a solution of methyl 5-bromo-2-[2-(pyridin-3-yl)acetamido]benzoate (3 g, 7.73 mmol, 1.00 equivalent, purity 90%, Intermediate 51, step a) in tetrahydrofuran (30 mL). A 2.38 M solution of MeONa in MeOH (freshly prepared by dissolving 2.74 g of Na in 50 mL of anhydrous MeOH solution, 11.7 mL, 27.85 mmol, 4.00 equivalents) was then added. The resulting solution was stirred overnight at 20° C., and the precipitate was collected by filtration to give the title compound as a white solid.

Intermediate 51: Step c

6-Bromo-2,4-dichloro-3-(pyridin-3-yl)quinoline

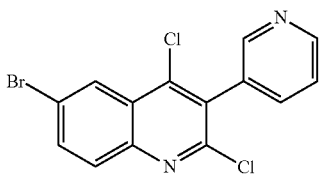 [SMILES: Clc1nc2ccc(Br)cc2c(Cl)c1-c1cccnc1]

Into a 100-mL round-bottom flask was placed a solution of 6-bromo-3-(pyridin-3-yl)-1,2,3,4-tetrahydroquinoline-2,4-dione (700 mg, 1.99 mmol, 1.00 equivalents, purity 90%, Intermediate 51, step b) in POCl$_3$ (20 mL). The resulting solution was stirred for 3 hours at 120° C., then concentrated under vacuum. It was then diluted with 20 mL of water, and extracted with 3×20 mL of ethyl acetate. The combined organic layer was dried over anhydrous sodium sulfate, filtered, and concentrated to give the crude title compound as a white solid.

Intermediate 52

6-Bromo-4-chloro-3-(3-fluorophenyl)-2-methoxy-8-methylquinoline

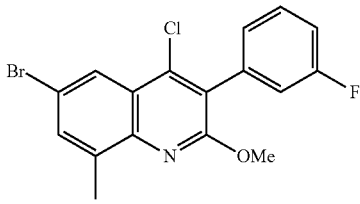

Sodium methoxide (4.29 g, 79.5 mmol) was added to a suspension of 6-bromo-2,4-dichloro-3-(3-fluorophenyl)-8-methylquinoline (3.06 g, 7.95 mmol, Intermediate 50, step c) in toluene (30 mL) in a pressure tube. The vessel was sealed and was heated in a 100° C. oil bath for 24 hours. To the mixture was added 10 wt. % aqueous NaHCO$_3$ (60 mL), the mixture was stirred for several minutes, and the phases were separated. The organic phase was washed once with saturated aqueous NaCl. The organic phase was dried (Na$_2$SO$_4$), filtered, and concentrated to yield the title compound as a light yellow solid.

Intermediate 53: Step a tert-Butyl 4-(hydroxy(1-methyl-1H-imidazol-5-yl)methyl)piperidine-1-carboxylate

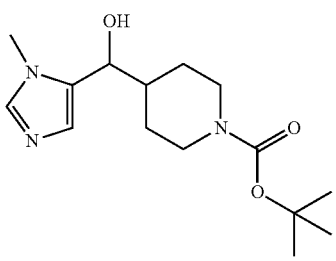 [SMILES: Cn1cncc1C(O)C1CCN(C(=O)OC(C)(C)C)CC1]

A solution of 5-bromo-1-methyl-1H-imidazole (25.0 g, 155 mmol; dried over 3 Å MS, then filtered) in DCM (310 mL) was stirred on an ice bath while iPrMgCl (72 mL, 2.01 M solution in THF, 145 mmol) was added rapidly dropwise under argon via pressure-equalizing addition funnel. Residual iPrMgCl was rinsed down with 50 mL THF, and the ice bath was removed and the reaction stirred for 25 min. A solution of tert-butyl 4-formylpiperidine-1-carboxylate (27.6 g, 130 mmol) (PharmaCore) in THF (65 mL) was added dropwise over ~5 min via pressure-equalizing addition funnel at room temperature. After stirring 1 hour at rt, the yellow mixture was quenched with 5 M NH$_4$Cl (250 mL) in one portion. The organic layer was dried (Na$_2$SO$_4$), filtered, and concentrated to provide the crude title compound as a clear light amber oil.

Intermediate 53: Step b tert-Butyl 4-(1-methyl-1H-imidazole-5-carbonyl)piperidine-1-carboxylate

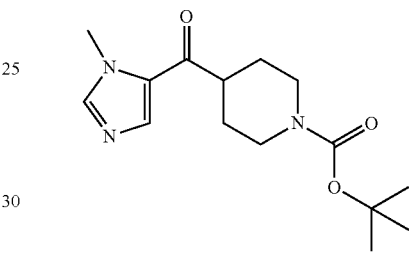

A homogeneous solution of tert-butyl 4-(hydroxy(1-methyl-1H-imidazol-5-yl)methyl)piperidine-1-carboxylate (32.2 g, 109 mmol; Intermediate 53, step a) in dioxane (436 mL) was treated with MnO$_2$ (47.6 g, 547 mmol) and stirred at 100° C. under air overnight (17 hrs). Since the reaction was only ~50% complete by NMR, the reaction was cooled to room temperature and additional MnO$_2$ was added (48.0 g, 552 mmol) and the reaction stirred under air at 100° C. for 6.5 hours, then at room temperature for 18 days, then filtered through a pad of Celite® and the black filter cake washed with EtOAc. The crude filtrate was treated with a third portion of MnO$_2$ (28.5 g, 327 mmol) and stirred at room temperature overnight. The reaction was then filtered as above and concentrated to provide the crude title compound as a clear dark yellow oil. This was flash chromatographed with an EtOAc to 50% acetone/EtOAc gradient to provide the title compound as a clear dark yellow oil.

Intermediate 53: Step c

1-(4-(1-Methyl-1H-imidazole-5-carbonyl)piperidin-1-yl)ethanone

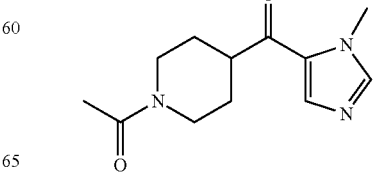

A homogeneous yellow solution of tert-butyl 4-(1-methyl-1H-imidazole-5-carbonyl)piperidine-1-carboxylate (10.1 g, 34.4 mmol; Intermediate 53, step b) in DCM (172 mL) was treated with TFA (26.4 mL, 344 mmol) and stirred at room temperature for 2.5 hours. The reaction was concentrated, toluene (2×100 mL) was added and the mixture concentrated again and the resulting clear light amber residue was taken up in DCM (344 mL) and TEA (23.9 mL, 172 mmol). Acetic anhydride (3.91 mL, 41.3 mmol) was added dropwise and the reaction stirred at room temperature for 1 hour. The reaction was concentrated under high vacuum and the residue flash chromatographed using 95:5 DCM/MeOH with 2% TEA as eluent. The combined fractions were concentrated, dissolved in DCM (200 mL), and washed with water (2×200 mL) to remove TEA. The organic layer was dried (Na$_2$SO$_4$), filtered, and concentrated, and the residue was triturated with MTBE (75 mL) at reflux for 15 min and then allowed to cool to room temperature. The mixture was filtered and the off-white filter cake was washed with MTBE (2×3 mL) to provide, after air drying at 100° C., the title compound as an off-white fine powder.

Intermediate 54: Step a

2-Chloro-N-methoxy-N-methylisonicotinamide

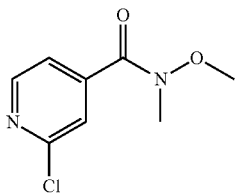

The title compound was prepared using 2-chloroisonicotinic acid in place of 4-picolinic acid using the procedure described for Intermediate 9, step a.

Intermediate 54: Step b (2-Chloropyridin-4-yl)(1-methyl-1H-imidazol-5-yl)methanone

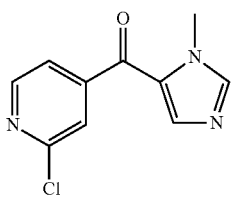

The title compound was prepared using 2-chloro-N-methoxy-N-methylisonicotinamide (Intermediate 54, step a) in place of N-methoxy-N-methylnicotinamide using the procedure described for Intermediate 10, step b.

Intermediate 55: Step a

N-Methoxy-N,2-dimethylisonicotinamide

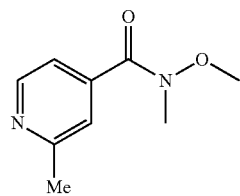

The title compound was prepared using 2-methylisonicotinic acid in place of 4-picolinic acid using the procedure described for Intermediate 9, step a.

Intermediate 55: Step b (1-Methyl-1H-imidazol-5-yl)(2-methylpyridin-4-yl)methanone

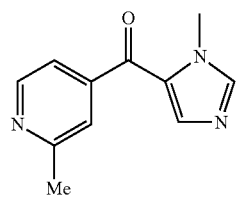

The title compound was prepared using N-methoxy-N,2-dimethylisonicotinamide (Intermediate 55, step a) in place of N-methoxy-N-methylnicotinamide using the procedure described for Intermediate 10, step b.

Intermediate 56: Step a

N,2-Dimethoxy-N-methylisonicotinamide

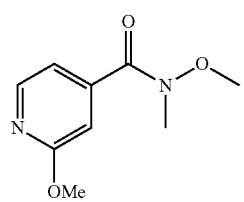

The title compound was prepared using 2-methoxyisonicotinic acid in place of 4-picolinic acid using the procedure described for Intermediate 9, step a.

Intermediate 56: Step b (2-Methoxypyridin-4-yl)(1-methyl-1H-imidazol-5-yl)methanone

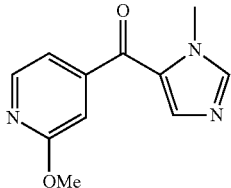 [SMILES: COc1cc(C(=O)c2cncn2C)ccn1]

The title compound was prepared using N,2-dimethoxy-N-methylisonicotinamide (Intermediate 56, step a) in place of N-methoxy-N-methylnicotinamide using the procedure described for Intermediate 10, step b.

Intermediate 57 bis(1-Methyl-1H-1,2,3-triazol-5-yl)methanone

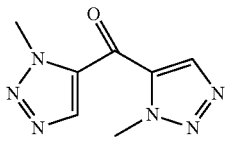

A solution of 1-methyl-1H-1,2,3-triazole (0.954 g, 11.4 mmol) (PCT Int. Appl., 2008098104; also commercially available from Matrix Scientific) in THF (22 mL) was stirred at ~−70° C. under argon while n-BuLi (2.56 M in hexanes; 4.29 mL, 11.0 mmol) was added dropwise over 5 min. After stirring for another 5 min, a solution of ethyl methoxy(methyl)carbamate (0.665 g, 4.99 mmol) (commercially available from Aldrich) in THF (3 mL) was added dropwise over 5 min. After stirring at ~−70° C. for an additional 5 min, the cold bath was removed and the light slurry was allowed to warm to room temperature with stirring for 1 hour 20 min. The reaction was then quenched at room temperature with 5 M NH$_4$Cl (3 mL) and the aqueous layer was extracted with THF (1×6 mL). The combined organic layers were dried (Na$_2$SO$_4$), filtered, and concentrated. A portion of the residue was crystallized from ~30 mL toluene to provide, after washing the filter cake with ether (1×3 mL) and heptane (1×3 mL), the title compound as blunt needles.

Intermediate 58: Step a

Diethyl 2-(4-(trifluoromethoxy)phenyl)malonate

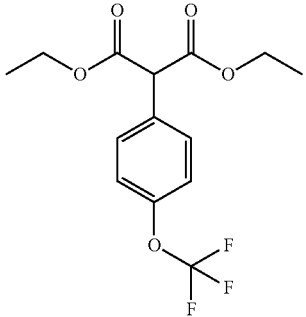 [SMILES: CCOC(=O)C(C(=O)OCC)c1ccc(OC(F)(F)F)cc1]

CuI (0.26 g, 1.378 mmol), 2-picolinic acid (0.24 g, 1.969 mmol), and cesium carbonate (19.24 g, 59.061 mmol) were combined, evacuated and filled with argon (3 times). 1,4-Dioxane was then added followed by diethylmalonate (6 mL, 39.374 mmol) and 1-iodo-4-(trifluoromethoxy)benzene (3 mL, 19.687 mmol). The resulting yellow suspension was stirred at room temperature for 48 hours and quenched with saturated NH$_4$Cl. The mixture was extracted with EtOAc (2×). The combined organic extracts were dried over Na$_2$SO$_4$, filtered, and concentrated to provide the title compound.

Intermediate 58: Step b 2-(4-(Trifluoromethoxy)phenyl)malonic acid

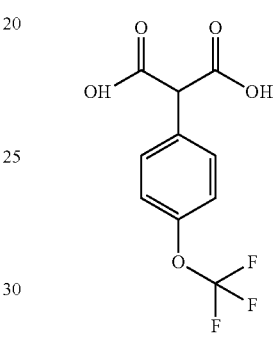

A mixture of diethyl 2-(4-(trifluoromethoxy)phenyl)malonate (5.6 g, 17.486 mmol, Intermediate 58, step a) and an aqueous 3 M NaOH solution were stirred in a 100° C. oil bath for 1 hour, cooled to RT, poured into ice water and acidified with 6N HCl. The aqueous mixture was extracted with EtOAc. The EtOAc extract was dried over Na$_2$SO$_4$, filtered, and evaporated in vacuo to provide the title compound.

Intermediate 58: Step c

6-Bromo-2,4-dichloro-8-methyl-3-(4-(trifluoromethoxy)phenyl)quinoline

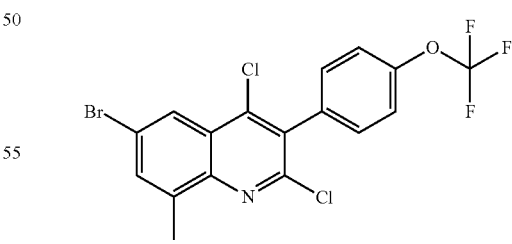

A mixture of 2-(4-(trifluoromethoxy)phenyl)malonic acid (3.1 g, 11.735 mmol, Intermediate 58, step b), 4-bromo-2-methylaniline (2.18 g, 11.735 mmol) and POCl$_3$ (10 mL) was heated at 105° C. for 3 hours, cooled to RT, concentrated under reduced pressure then slowly poured into ice water. A NH$_4$OH solution was added to a basic pH (pH 8-9). The precipitates were collected by filtration, rinsed with H$_2$O and dried under high vacuum pressure. The resulting tan solids were dissolved in DCM and chromatographed (Heptane/DCM) to provide the title compound.

Intermediate 58: Step d 6-Bromo-4-chloro-2-methoxy-8-methyl-3-(4-(trifluoromethoxy)phenyl)quinoline

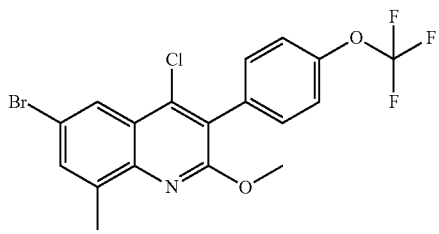 [SMILES: COc1nc2c(C)cc(Br)cc2c(Cl)c1-c1ccc(OC(F)(F)F)cc1]

A mixture of 6-bromo-2,4-dichloro-8-methyl-3-(4-(trifluoromethoxy)phenyl)quinoline (1.97 g, 4.367 mmol, Intermediate 58, step c) and sodium methoxide (1.18 g, 21.837 mmol) in toluene (20 mL) was heated in a sealed tube at 110° C. for 24 hours, cooled to RT, diluted with DCM, stirred at room temperature for 30 min, and filtered through Celite® rinsing several times with DCM. The solvents were removed under reduced pressure and the off-white solid product precipitated from MeOH, filtered and dried to provide the title compound.

Intermediate 59: Step a

Diethyl 2-(4-fluorophenyl)malonate

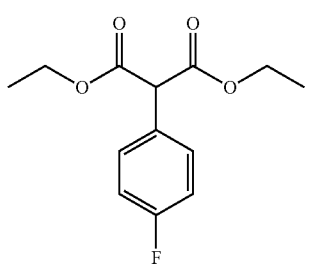 [SMILES: CCOC(=O)C(C(=O)OCC)c1ccc(F)cc1]

CuI (0.13 g, 0.669 mmol), 2-picolinic acid (0.16 g, 1.338 mmol), and cesium carbonate (13.1 g, 40.135 mmol) were combined, evacuated and filled with argon (3 times). 1,4-dioxane (10 mL) was then added followed by diethylmalonate (2.8 g, 17.392 mmol) and 1-iodo-4-fluorobenzene (3 g, 13.378 mmol). The resulting mixture was stirred at room temperature for 24 hours and quenched with saturated NH$_4$Cl. The mixture was extracted with EtOAc (2×). The combined organic extracts were dried over Na$_2$SO$_4$, filtered, concentrated and chromatographed (Heptane/EtOAc) to provide the title compound.

Intermediate 59: Step b 2-(4-Fluorophenyl)malonic acid

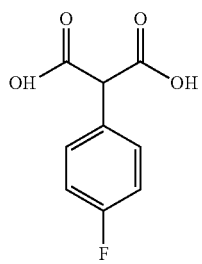 [SMILES: O=C(O)C(C(=O)O)c1ccc(F)cc1]

A mixture of diethyl 2-(4-fluorophenyl)malonate (2.98 g, 8.204 mmol, Intermediate 59, step a) and an aqueous 3 M NaOH solution (5 mL) were stirred in a 50° C. oil bath for 48 hours, cooled to RT, poured into ice water and acidified with 6N HCl. The aqueous mixture was extracted with EtOAc. The EtOAc extract was dried over Na$_2$SO$_4$, filtered, and evaporated in vacuo to provide the title compound.

Intermediate 59: Step c

6-Bromo-2,4-dichloro-3-(4-fluorophenyl)-8-methylquinoline

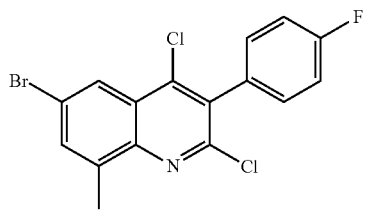 [SMILES: Cc1cc(Br)cc2c(Cl)c(-c3ccc(F)cc3)c(Cl)nc12]

A mixture of 2-(4-fluorophenyl)malonic acid (1 g, 5.047 mmol, Intermediate 59, step b), 4-bromo-2-methylaniline (0.608 g, 3.27 mmol) and POCl$_3$ (3 mL) was heated at 105° C. for 3 hours, cooled to room temperature, concentrated under reduced pressure then slowly poured into ice water. A NH$_4$OH solution was added to a basic pH (pH 8-9). The precipitates were collected by filtration, rinsed with H$_2$O and dried under high vacuum pressure. The resulting tan solids were dissolved in DCM and chromatographed (Heptane/DCM) to provide the title compound.

Intermediate 60: Step a

Methyl 5-bromo-2-(2-(3-chlorophenyl)acetamido)benzoate

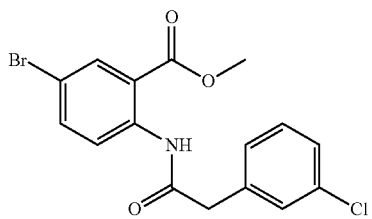 [SMILES: COC(=O)c1cc(Br)ccc1NC(=O)Cc1cccc(Cl)c1]

Triethylamine (18 mL, 130 mmol) was added to methyl 2-amino-5-bromobenzoate (25 g, 110 mmol) in DCM (150 mL). The mixture was cooled to 0° C. and 2-(3-chlorophenyl)acetyl chloride (24.3 g, 130 mmol) in DCM (100 mL) was added. The mixture was allowed to warm to room temperature overnight with stirring. Aqueous $K_2CO_3$ (10 wt. %) was added and the mixture was extracted with DCM. The organic phase was dried ($MgSO_4$), filtered, and concentrated to yield the title compound.

Intermediate 60: Step b

6-Bromo-3-(3-chlorophenyl)-4-hydroxyquinolin-2(1H)-one

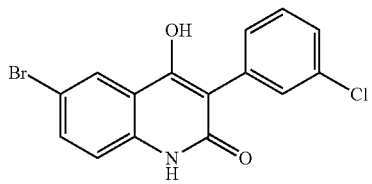 [SMILES: O=c1[nH]c2ccc(Br)cc2c(O)c1-c1cccc(Cl)c1]

n-BuLi (1.6 M in hexane, 79 mL, 126 mmol) was added dropwise to a mixture of hexamethyldisilazane (26.7 mL, 126 mmol) in THF (150 mL) at −78° C. under nitrogen. The mixture was stirred for 1 hour, then was warmed to −40° C. A solution of methyl 5-bromo-2-(2-(3-chlorophenyl)acetamido)benzoate (21.1 g, 55 mmol, Intermediate 60, step a) in THF (150 mL) was added. The mixture was allowed to warm to room temperature and ice was added. The aqueous phase was acidified with 6 N aqueous HCl. The precipitate was collected by filtration, washed with DCM, and air-dried to yield the title compound.

Intermediate 60: Step c

6-Bromo-2,4-dichloro-3-(3-chlorophenyl)quinoline

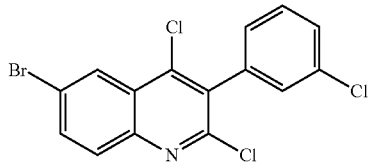 [SMILES: Clc1cccc(-c2c(Cl)nc3ccc(Br)cc3c2Cl)c1]

A mixture of 6-bromo-3-(3-chlorophenyl)-4-hydroxyquinolin-2(1H)-one (35 g, 99 mmol, Intermediate 60, step b) and $POCl_3$ (100 mL) was refluxed for 2 hours, then was concentrated. The residue was poured into ice water, basified with conc. aqueous $NH_4OH$ and extracted with DCM. The organic phase was dried ($MgSO_4$), filtered, and concentrated. The residue was triturated with $CH_3CN$ and the precipitate was collected by filtration and air-dried to afford the title compound.

Intermediate 61: Step a

Methyl 5-bromo-2-[2-(pyridin-2-yl)acetamido]benzoate

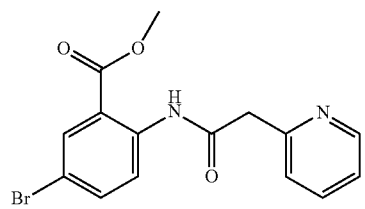 [SMILES: COC(=O)c1cc(Br)ccc1NC(=O)Cc1ccccn1]

Into a 250-mL round-bottom flask was placed a solution of methyl 2-amino-5-bromobenzoate (5 g, 21.73 mmol, 1.00 equivalent), 2-(pyridin-2-yl)acetic acid hydrochloride (4.5 g, 25.92 mmol, 1.20 equivalent), HATU (10 g, 26.30 mmol, 1.20 equivalents), and DIEA (8.5 g, 65.77 mmol, 3.00 equivalents) in N,N-dimethylformamide (100 mL). After stirring overnight at 20° C., the reaction was quenched with 100 mL of water and extracted with 3×100 mL of dichloromethane. The combined organic layer was dried over anhydrous sodium sulfate, filtered, and concentrated under vacuum. The residue was applied onto a silica gel column eluted with dichloromethane/methanol (1:50) to give the title compound as a red solid.

Intermediate 61: Step b

6-Bromo-3-(pyridin-2-yl)-1,2,3,4-tetrahydroquinoline-2,4-dione

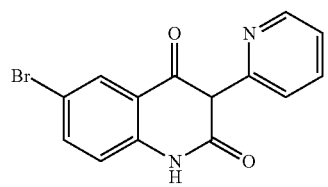 [SMILES: O=C1Nc2ccc(Br)cc2C(=O)C1c1ccccn1]

Into a 250-mL round-bottom flask were placed a solution of methyl 5-bromo-2-[2-(pyridin-2-yl)acetamido]benzoate (3 g, 7.73 mmol, 1.00 equivalent, 90%, Intermediate 61, step a) in tetrahydrofuran (30 mL). A 2.38 M solution of MeONa in MeOH (freshly prepared from dissolving 2.74 g of Na in 50 mL of anhydrous MeOH solution, 11.7 mL, 27.85 mmol, 4.00 equivalents) was then added. The resulting solution was stirred overnight at 20° C., and the precipitate was collected by filtration to give the title compound as a white solid.

Intermediate 61: Step c

6-Bromo-2,4-dichloro-3-(pyridin-2-yl)quinoline

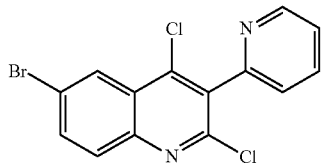 [SMILES: Clc1nc2ccc(Br)cc2c(Cl)c1-c1ccccn1]

Into a 100-mL round-bottom flask was placed a solution of 6-bromo-3-(pyridin-2-yl)-1,2,3,4-tetrahydroquinoline-2,4-dione (2.54 g, 7.21 mmol, 1.00 equivalent, purity 90%, Intermediate 61, step b) in POCl$_3$ (50 mL). The resulting solution was stirred at 120° C. for 3 hours, and then quenched with 50 mL of water, and extracted with 3×50 mL of ethyl acetate. The combined organic layer was dried over anhydrous sodium sulfate, filtered, and concentrated to afford the title compound as a white solid.

Example 1

(2,4-Dichloro-3-phenylquinolin-6-yl)(1-methyl-1H-imidazol-5-yl)(pyridin-2-yl)methanol

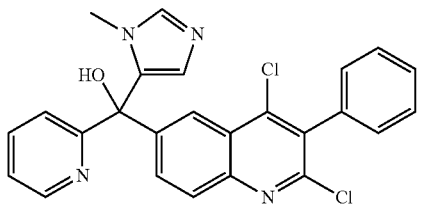 [SMILES: Cn1cncc1C(O)(c1ccc2nc(Cl)c(-c3ccccc3)c(Cl)c2c1)c1ccccn1]

A solution of n-BuLi (2.5 M in hexanes, 0.34 mL, 0.85 mmol) was added dropwise by syringe to a solution of 6-bromo-2,4-dichloro-3-phenylquinoline (305.4 mg, 0.865 mmol, Intermediate 1, step c) in dry THF (4.4 mL) at −78° C. After 1.5 min, a solution of (1-methyl-1H-imidazol-5-yl)(pyridin-2-yl)methanone (0.175 g, 0.936 mmol, Intermediate 11, step b) in dry THF (1.8 mL) was added dropwise. The reaction mixture was stirred for 5 min at −78° C., then the reaction flask was placed into an ice-water bath. After 10 min, the mixture was warmed to room temperature and the reaction was quenched with methanol and water. The mixture was partitioned between water and DCM. The separated aqueous phase was further extracted with DCM. The organic phase was dried (Na$_2$SO$_4$), filtered, and concentrated. The crude product was purified by flash column chromatography (silica gel, 0-10% MeOH-DCM) to provide the title compound as a white solid. $^1$H NMR (500 MHz, CDCl$_3$) δ 8.65 (ddd, J=4.9, 1.6, 1.0 Hz, 1H), 8.30 (d, J=1.7 Hz, 1H), 8.06 (d, J=8.8 Hz, 1H), 7.86 (dd, J=8.8, 2.0 Hz, 1H), 7.73 (td, J=7.7, 1.7 Hz, 1H), 7.55-7.47 (m, 4H), 7.36-7.29 (m, 3H), 7.23 (d, J=8.0 Hz, 1H), 6.37 (d, J=1.1 Hz, 1H), 3.44 (s, 3H). MS m/e 461.1 [M+H]$^+$.

Example 2

(2,4-Dichloro-3-phenylquinolin-6-yl)(phenyl)(pyridin-3-yl)methanol

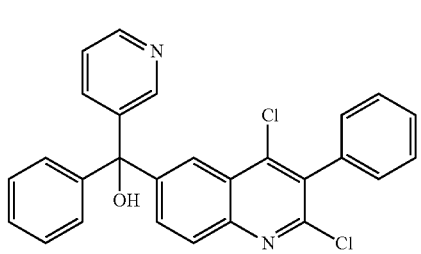 [SMILES: OC(c1ccccc1)(c1cccnc1)c1ccc2nc(Cl)c(-c3ccccc3)c(Cl)c2c1]

A solution of 6-bromo-2,4-dichloro-3-phenylquinoline (353 mg, 1.0 mmol, Intermediate 1, step c) in THF (15 mL) was stirred at −70° C. under N$_2$ (g) for 15 min before the addition of n-BuLi (1.6 M in hexane, 0.81 mL, 1.3 mmol). After the addition, the reaction mixture was allowed to stir at −70° C. for 15 min. A solution of phenyl(pyridin-3-yl)methanone (183 mg, 1.00 mmol) in THF (20 mL) was added, and the resulting reaction mixture continued to stir at low temperature for 30 min. The cold bath was removed, and the reaction mixture was warmed to room temperature and stirred for 2 hours. The mixture was quenched with water and extracted with CH$_2$Cl$_2$. The organic phase was dried, filtered and concentrated. The crude product was purified by flash column chromatography (silica gel, 1:40 CH$_3$OH/CH$_2$Cl$_2$) affording the title compound. $^1$H NMR (300 MHz, CD$_3$OD) δ 8.52 (d, J=2.3 Hz, 1H), 8.48 (d, J=4.6 Hz, 1H), 8.21 (d, J=2.0 Hz, 1H), 8.00 (d, J=8.9 Hz, 1H), 7.88-7.85 (m, 1H), 7.81 (dt, J=7.8, 2.0 Hz, 1H), 7.54-7.42 (m, 4H), 7.38-7.31 (m, 7H). MS m/e 457.1 [M+H]$^+$.

Example 3

(2,4-Dichloro-3-phenylquinolin-6-yl)(phenyl)(pyridin-4-yl)methanol

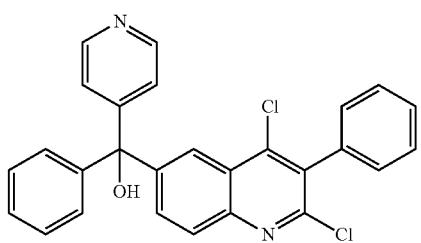 [SMILES: OC(c1ccccc1)(c1ccncc1)c1ccc2nc(Cl)c(-c3ccccc3)c(Cl)c2c1]

The title compound was prepared using phenyl(pyridin-4-yl)methanone in place of phenyl(pyridin-3-yl)methanone according to the procedure described in Example 2. $^1$H NMR (300 MHz, CD$_3$OD) δ 8.53-8.51 (m, 2H), 8.21 (d, J=2.0 Hz, 1H), 8.00 (d, J=8.9 Hz, 1H), 7.86 (dd, J=8.8, 1.9 Hz, 1H), 7.53-7.44 (m, 5H), 7.38-7.31 (m, 7H). MS m/e 457.1 [M+H]⁺.

Example 4

(2,4-Dichloro-3-phenylquinolin-6-yl)(phenyl)(1,3,5-trimethyl-1H-pyrazol-4-yl)methanol

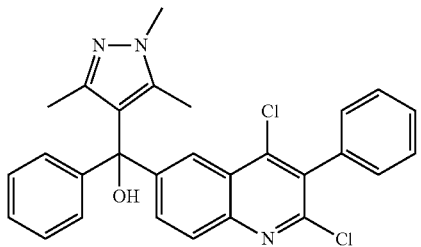 [SMILES: Cc1nn(C)c(C)c1C(O)(c1ccccc1)c1ccc2nc(Cl)c(-c3ccccc3)c(Cl)c2c1]

The title compound was prepared using phenyl(1,3,5-trimethyl-1H-pyrazol-4-yl)methanone in place of phenyl(pyridin-3-yl)methanone according to the procedure described in Example 2. ¹H NMR (300 MHz, CD₃OD) δ 8.25 (d, J=1.9 Hz, 1H), 7.96 (dd, J=13.8, 5.3 Hz, 2H), 7.56-7.44 (m, J=7.4 Hz, 3H), 7.39-7.25 (m, 7H), 3.68 (s, 3H), 1.75 (s, 3H), 1.64 (s, 3H). MS m/e 488.1 [M+H]⁺.

Example 5 tert-Butyl 3-((2,4-Dichloro-3-phenylquinolin-6-yl)(hydroxy)(pyridin-3-yl)methyl)piperidine-1-carboxylate

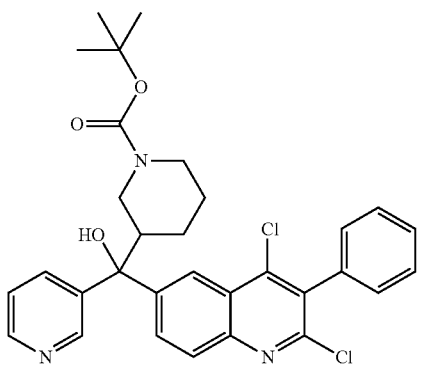 [SMILES: CC(C)(C)OC(=O)N1CCCC(C(O)(c2cccnc2)c2ccc3nc(Cl)c(-c4ccccc4)c(Cl)c3c2)C1]

To a solution of 6-bromo-2,4-dichloro-3-phenylquinoline (122 mg, 0.346 mmol, Intermediate 1, step c) and tert-butyl 3-nicotinoylpiperidine-1-carboxylate (100 mg, 0.344 mmol, Intermediate 26) in THF (4 mL) at −78° C. was added 1.6 M n-BuLi in hexane (0.33 mL, 0.53 mmol). The mixture was stirred at −78 to 0° C. for 3 hours, and quenched with NH₄Cl (aqueous). The organic layer was separated, and the aqueous layer was extracted with CH₂Cl₂. The combined organic phases were dried (Na₂SO₄), filtered, concentrated, and purified by reverse phase HPLC (water/acetonitrile/0.1% TFA) to give the title compound. ¹H NMR (400 MHz, MeOH-d₄) δ 9.06 (s, 1H), 8.57-8.77 (m, 3H), 8.09-8.29 (m, 1H), 7.99-8.09 (m, 1H), 7.89 (dd, J=5.31, 8.34 Hz, 1H), 7.44-7.63 (m, 3H), 7.24-7.43 (m, 2H), 4.00-4.22 (m, 1H), 3.77-3.96 (m, 1H), 2.85-3.00 (m, 1H), 2.54-2.86 (m, 2H), 1.69-1.84 (m, 1H), 1.50-1.69 (m, 3H), 1.30 (br. s., 9H); MS m/e 564.4 [M+H]⁺.

Example 6

(2,4-Dichloro-3-(2-chlorophenyl)quinolin-6-yl)(phenyl)(pyridin-3-yl)methanol

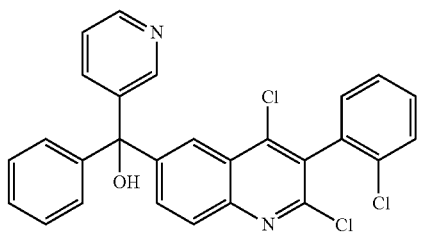 [SMILES: OC(c1ccccc1)(c1cccnc1)c1ccc2nc(Cl)c(-c3ccccc3Cl)c(Cl)c2c1]

The title compound was prepared using 6-bromo-2,4-dichloro-3-(2-chlorophenyl)quinoline (Intermediate 2, step c) in place of 6-bromo-2,4-dichloro-3-phenylquinoline according to the procedure described in Example 2. ¹H NMR (300 MHz, CD₃OD) δ 8.55-8.45 (m, 2H), 8.21 (t, J=1.5 Hz, 1H), 8.02 (d, J=8.9 Hz, 1H), 7.89 (dd, J=8.9, 2.1 Hz, 1H), 7.84-7.76 (m, 1H), 7.63-7.56 (m, 1H), 7.54-7.30 (m, 9H). MS m/e 491.0 [M+H]⁺.

Example 7

(2,4-Dichloro-3-(2-chlorophenyl)quinolin-6-yl)(phenyl)(1,3,5-trimethyl-1H-pyrazol-4-yl)methanol

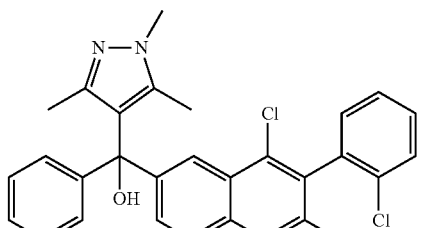

The title compound was prepared using 6-bromo-2,4-dichloro-3-(2-chlorophenyl)quinoline (Intermediate 2, step c) and phenyl(1,3,5-trimethyl-1H-pyrazol-4-yl)methanone in place of 6-bromo-2,4-dichloro-3-phenylquinoline and phenyl(pyridin-3-yl)methanone, respectively, according to the procedure described in Example 2. ¹H NMR (300 MHz, CD₃OD) δ 8.25 (dd, J=9.5, 1.8 Hz, 1H), 8.01-7.91 (m, 2H), 7.60-7.44 (m, 3H), 7.37-7.28 (m, 6H), 3.67 (s, 3H), 1.75 (s, 3H), 1.64 (s, 3H). MS m/e 522.1 [M+H]+.

Example 8

(4-Chloro-3-phenylquinolin-6-yl)(4-chlorophenyl)(1-methyl-1H-imidazol-5-yl)methanol

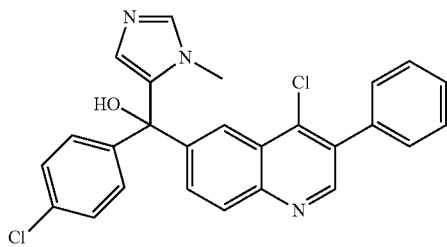 [SMILES: Cn1cncc1C(O)(c1ccc(Cl)cc1)c1ccc2ncc(-c3ccccc3)c(Cl)c2c1]

In a 100-mL round-bottom flask purged and maintained with an inert atmosphere of nitrogen was placed a solution of 6-bromo-4-chloro-3-phenylquinoline (460 mg, 1.44 mmol, Intermediate 3, step c), (4-chlorophenyl)(1-methyl-1H-imidazol-5-yl)methanone (266 mg, 1.21 mmol, Intermediate 18, step b) in tetrahydrofuran (20 mL). This solution was cooled to −78° C., followed by the addition of n-BuLi (0.624 mL, 1.56 mmol, 2.5M in hexane) dropwise. The mixture was gradually warmed to room temperature. After 4 hours stirring, 1.0 M HCl was added until pH 6-7. After removal of solvent under vacuum, the residue was purified by flash column chromatography (silica gel column, 100:0~15:1 EtOAc/petroleum ether) to give the title compound as a white solid. $^1$H NMR (300 MHz, MeOH-$d_4$) δ=8.83 (s, 1H), 8.39 (d, J=1.5 Hz, 1H), 8.12 (d, J=9.0 Hz, 1H), 7.88 (dd, J=1.9, 8.9 Hz, 1H), 7.75 (s, 1H), 7.46-7.62 (m, 5H), 7.41 (s, 4H), 6.35 (s, 1H), 3.51 (s, 3H); MS m/e 460 [M+H]+.

Example 9

(3-Benzyl-2,4-dichloroquinolin-6-yl)(4-chlorophenyl)(1-methyl-1H-imidazol-5-yl)methanol

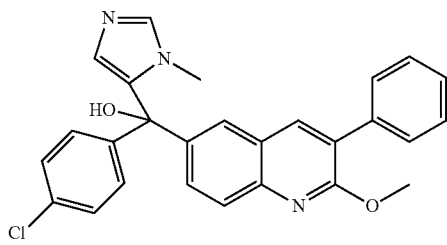 [SMILES: COc1nc2ccc(C(O)(c3ccc(Cl)cc3)c3cncn3C)cc2cc1-c1ccccc1]

In a 100-mL round-bottom flask purged and maintained with an inert atmosphere of nitrogen was placed a solution of 6-bromo-2-methoxy-3-phenylquinoline (440 mg, 1.99 mmol, Intermediate 4, step c) in tetrahydrofuran (10 mL), and n-BuLi (0.67 mL, 1.68 mmol, 2.5 M in hexane) was added at −78° C. After stirring for 10 min at −78° C., (4-chlorophenyl)(1-methyl-1H-imidazol-5-yl)methanone (372 mg, 1.18 mmol, Intermediate 18, step b) was added. The resulting mixture was allowed to warm to room temperature and stirred for an additional 8 hours, and then quenched with 20 mL of water. The organic layer was separated, and the aqueous layer was extracted with 2×50 mL of EtOAc. The combined organic layers were dried over anhydrous sodium sulfate, filtered, and concentrated under vacuum. The residue was purified by flash chromatography (silica gel column, 100:1 dichloromethane/methanol) to give the title compound as a white solid. $^1$H NMR (300 MHz, DMSO-$d_6$) δ=8.25 (s, 1H), 7.73-7.85 (m, 2H), 7.70 (s, 1H), 7.56-7.67 (m, 3H), 7.39-7.51 (m, 5H), 7.29-7.36 (m, 2H), 6.96 (s, 1H), 6.15 (s, 1H), 4.00 (s, 3H), 3.34 (s, 3H); MS m/e 456 [M+H]+.

Example 10

(2,4-Dichloro-3-phenylquinolin-6-yl)(6-methoxypyridin-3-yl)(1-methyl-1H-imidazol-5-yl)methanol•TFA

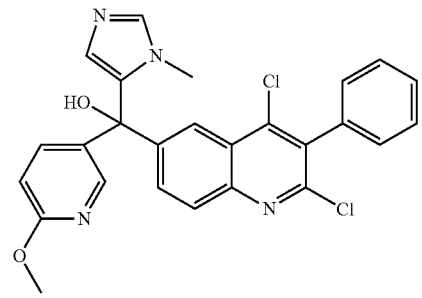

In a 50-mL round-bottom flask purged and maintained with an inert atmosphere of nitrogen was placed a solution of 6-bromo-2,4-dichloro-3-phenylquinoline (340 mg, 0.96 mmol, Intermediate 1, step c) in tetrahydrofuran (10 mL), and n-BuLi (0.413 mL, 1.03 mmol, 2.5 M in hexane) was added at −78° C. After stirring for 30 min at −78° C., a solution of 2-methoxy-5-[(1-methyl-1H-imidazol-5-yl)carbonyl]pyridine (140 mg, 0.64 mmol, Intermediate 19) in tetrahydrofuran (5 mL) was added. The resulting mixture was allowed to warm to room temperature and stirred for an additional 5 hours, and then quenched with 1.0 M HCl until pH 6-7. After removal of solvent under vacuum, the residue was purified by Prep-HPLC (water/acetonitrile/0.05% TFA) to give the title compound as a white solid. $^1$H NMR (400 MHz, CDCl$_3$) δ=8.60 (br. s., 1H), 8.30 (s, 1H), 8.02-8.19 (m, 2H), 7.77 (d, J=9.0 Hz, 1H), 7.70 (d, J=8.0 Hz, 1H), 7.46-7.60 (m, 3H), 7.34 (d, J=7.5 Hz, 2H), 6.68-6.89 (m, 2H), 3.95 (s, 3H), 3.70 (s, 3H); MS m/e 491 [M+H]+.

Example 11

(2,4-Dichloro-3-phenylquinolin-6-yl)[6-(dimethylamino)pyridin-3-yl](1-methyl-1H-imidazol-5-yl)methanol•TFA

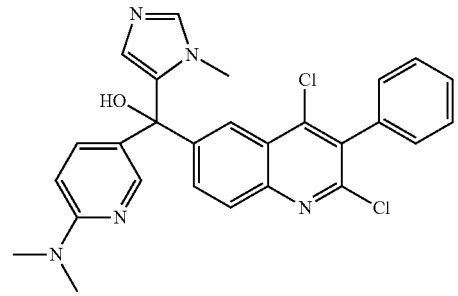 [SMILES: CN(C)c1ccc(C(O)(c2ccc3nc(Cl)c(-c4ccccc4)c(Cl)c3c2)c2cncn2C)cn1]

In a 50-mL round-bottom flask purged and maintained with an inert atmosphere of nitrogen was placed a solution of 6-bromo-2,4-dichloro-3-phenylquinoline (250 mg, 0.71 mmol, Intermediate 1, step c) in tetrahydrofuran (10 mL), and n-BuLi (0.304 mL, 0.76 mmol, 2.5 M in hexane) was added at −78° C. After stirring for 30 min at −78° C., a solution of N,N-dimethyl-5-[(1-methyl-1H-imidazol-5-yl)carbonyl]pyridin-2-amine (109 mg, 0.47 mmol, Intermediate 20) in tetrahydrofuran (5 mL) was introduced. The resulting mixture was allowed to warm to room temperature and stirred for 5 hours, and then quenched with 1.0 M HCl until pH 6-7. After removal of solvent under vacuum, the residue was purified by Prep-HPLC (water/acetonitrile/0.05% TFA) to give the title compound as a white solid. $^1$H NMR (400 MHz, CDCl$_3$) δ=8.75 (br. s., 1H), 8.37 (s, 1H), 8.31 (s, 1H), 8.10 (d, J=8.5 Hz, 1H), 7.78 (d, J=8.8 Hz, 2H), 7.45-7.62 (m, 3H), 7.33 (d, J=6.0 Hz, 2H), 7.11 (br. s., 1H), 6.87 (d, J=9.5 Hz, 1H), 3.66 (s, 3H), 3.30 (s, 6H); MS m/e 504 [M+H]$^+$.

Example 12

(2,4-Dichloro-3-phenylquinolin-6-yl)(6-fluoropyridin-3-yl)(1-methyl-1H-imidazol-5-yl)methanol•TFA

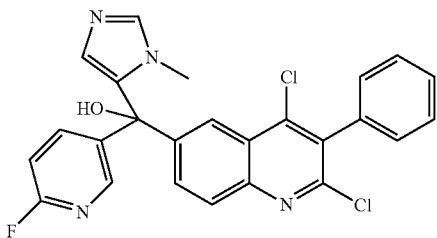 [SMILES: Cn1cncc1C(O)(c1ccc(F)nc1)c1ccc2nc(Cl)c(-c3ccccc3)c(Cl)c2c1]

In a 100-mL round-bottom flask purged and maintained with an inert atmosphere of nitrogen was placed 6-bromo-2,4-dichloro-3-phenylquinoline (675 mg, 1.91 mmol, Intermediate 1, step c) and THF, and n-BuLi (0.80 mL, 2.0 mmol, 2.5 M in hexane) was added at −78° C. The resulting mixture was stirred for 10 min at −78° C., and a solution of (6-fluoropyridin-3-yl)(1-methyl-1H-imidazol-5-yl)methanone (300 mg, 1.46 mmol, Intermediate 21, step c) in tetrahydrofuran (10 mL) was added. The mixture was allowed to warm to room temperature and stirred for an additional 8 hours, and then quenched with 40 mL of water. The organic layer was separated, and the aqueous layer was extracted with 3×20 mL of ethyl acetate. The combined organic layers were dried over anhydrous sodium sulfate, filtered, and concentrated under vacuum. The residue was purified by Prep-HPLC (water/acetonitrile/0.05% TFA) to give the title compound as a white solid. $^1$H NMR (400 MHz, DMSO-d$_6$) δ=9.04 (br. s., 1H), 8.31 (s, 1H), 8.22 (s, 1H), 8.14 (d, J=9.0 Hz, 1H), 7.99 (t, J=8.2 Hz, 1H), 7.89 (s, 1H), 7.83 (d, J=8.8 Hz, 1H), 7.49-7.63 (m, 3H), 7.41-7.50 (m, 2H), 7.27 (d, J=8.5 Hz, 1H), 7.06 (s, 1H), 3.55 (s, 3H); MS m/e 479 [M+H]$^+$.

Example 13

(6-Chloropyridin-3-yl)(6,8-dichloro-7-phenylnaphthalen-2-yl)(1-methyl-1H-imidazol-5-yl)methanol•TFA

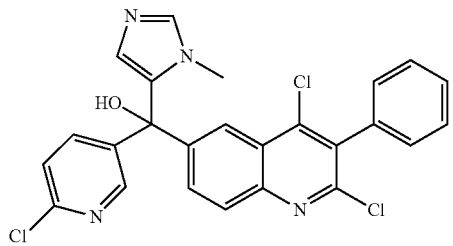 [SMILES: Cn1cncc1C(O)(c1ccc(Cl)nc1)c1ccc2nc(Cl)c(-c3ccccc3)c(Cl)c2c1]

In a 50-mL round-bottom flask purged and maintained with an inert atmosphere of nitrogen was placed a solution of 6-bromo-2,4-dichloro-3-phenylquinoline (524 mg, 1.49 mmol, Intermediate 1, step c) in tetrahydrofuran (15 mL). A solution of n-BuLi (0.64 mL, 1.6 mmol, 2.5 M in hexane) was added at −78° C. After stirring for 30 min at −78° C., a solution of 2-chloro-5-[(1-methyl-1H-imidazol-5-yl)carbonyl]pyridine (200 mg, 0.90 mmol, Intermediate 22, step c) in tetrahydrofuran (5 mL) was added. The mixture was allowed to warm to room temperature and stirred for an additional 4 hours, and then quenched with 1.0 M HCl until pH 6-7. After removal of solvent under vacuum, the residue was purified by Prep-HPLC (water/acetonitrile/0.05% TFA) to give the title compound as a white solid. $^1$H NMR (400 MHz, CDCl$_3$) δ=8.62 (br. s., 1H), 8.54 (br. s., 1H), 8.32 (s, 1H), 8.12 (d, J=8.8 Hz, 1H), 7.80 (d, J=8.5 Hz, 1H), 7.72 (d, J=8.3 Hz, 1H), 7.48-7.62 (m, 3H), 7.30-7.40 (m, 3H), 6.82 (br. s., 1H), 3.69 (s, 3H); MS m/e 495 [M+H]$^+$.

Example 14

(4-Chlorophenyl)(2,4-dichloro-3-phenylquinolin-6-yl)(1-ethyl-1H-imidazol-5-yl)methanol•TFA

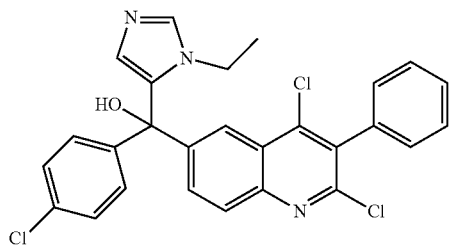 [SMILES: CCn1cncc1C(O)(c1ccc(Cl)cc1)c1ccc2nc(Cl)c(-c3ccccc3)c(Cl)c2c1]

In a 50-mL round-bottom flask purged and maintained with an inert atmosphere of nitrogen was placed a solution of 6-bromo-2,4-dichloro-3-phenylquinoline (225 mg, 0.64 mmol, Intermediate 1, step c) in tetrahydrofuran (10 mL). n-BuLi (0.28 mL, 0.70 mmol, 2.5 M in hexane) was added at −78° C. After stirring for 20 min at −78° C., a solution of (4-chlorophenyl)(1-ethyl-1H-imidazol-5-yl)methanone (100 mg, 0.43 mmol, Intermediate 23) in tetrahydrofuran (5 mL) was added. The mixture was allowed to warm to room temperature and stirred for an additional 3 hours, and then quenched with 1.0 M HCl until pH 6-7. After removal of solvent under vacuum, the residue was purified by Prep-HPLC (water/acetonitrile/0.05% TFA) to give the title compound as a white solid. $^1$H NMR (400 MHz, CDCl$_3$) δ=8.39 (br. s., 1H), 8.22 (s, 1H), 8.08 (d, J=8.8 Hz, 1H), 7.78 (d, J=8.3 Hz, 1H), 7.48-7.63 (m, 3H), 7.31-7.45 (m, 6H), 6.47 (s, 1H), 4.05 (m, 2H), 1.32 (t, J=7.2 Hz, 3H); MS m/e 508 [M+H]$^+$.

Example 15

(4-Chlorophenyl)(2,4-dichloro-3-phenylquinolin-6-yl)(1,2-dimethyl-1H-imidazol-5-yl)methanol

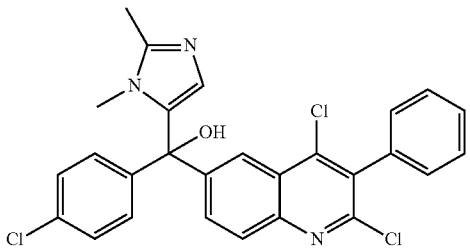 [SMILES: Cc1ncc(C(O)(c2ccc(Cl)cc2)c2ccc3nc(Cl)c(-c4ccccc4)c(Cl)c3c2)n1C]

In a 100-mL round-bottom flask purged and maintained with an inert atmosphere of nitrogen was placed a solution of 6-bromo-2,4-dichloro-3-phenylquinoline (237 mg, 0.67 mmol, Intermediate 1, step c) in tetrahydrofuran (10 mL). n-BuLi (0.54 mL, 0.86 mmol, 1.6 M in hexane) was added at −78° C. After stirring for 30 min, 5-[(4-chlorophenyl)carbonyl]-1,2-dimethyl-1H-imidazole (130 mg, 0.55 mmol, Intermediate 24, step b) was added. The mixture was stirred for 2 hours at −78° C., then quenched with 2 mL of water. After removal of solvent under vacuum, the residue was partitioned between ethyl acetate and H$_2$O. The organic layer was dried (Na$_2$SO$_4$), filtered, concentrated, and purified by flash chromatography (silica gel, 0-10% MeOH/CH$_2$Cl$_2$) to give the title compound as a white solid. $^1$H NMR (400 MHz, CDCl$_3$) δ=8.33 (s, 1H), 8.02 (d, J=8.8 Hz, 1H), 7.75 (dd, J=1.6, 8.9 Hz, 1H), 7.48-7.61 (m, 3H), 7.30-7.43 (m, 6H), 6.19 (s, 1H), 3.33 (s, 3H), 2.32 (s, 3H); MS m/e 508 [M+H]$^+$.

Example 16

(2,4-Dichloro-3-phenylquinolin-6-yl)(1-methyl-1H-imidazol-5-yl)(pyridin-4-yl)methanol

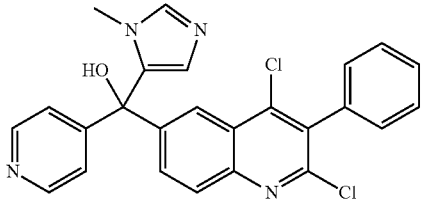 [SMILES: Cn1cncc1C(O)(c1ccncc1)c1ccc2nc(Cl)c(-c3ccccc3)c(Cl)c2c1]

To a solution of 6-bromo-2,4-dichloro-3-phenylquinoline (500 mg, 1.42 mmol, Intermediate 1, step c) and THF (12 mL) at −78° C. was added 1.6 M n-BuLi in hexane (1.15 mL, 1.84 mmol). After stirring at −78° C. for 30 min, a solution of (1-methyl-1H-imidazol-5-yl)(pyridin-4-yl)methanone (292 mg, 1.56 mmol, Intermediate 9, step b) in THF (13 mL) was added via cannula. The mixture was stirred at −78° C. for 10 min, and the cooling bath was removed. After the mixture reached room temperature, it was quenched with NH$_4$Cl (aqueous). The organic layer was separated, and the aqueous layer was extracted with CH$_2$Cl$_2$. The combined organic phases were dried (Na$_2$SO$_4$), filtered, concentrated, and purified by flash column chromatography (40 g silica gel column, 100% EtOAc, then 5-10% MeOH in CH$_2$Cl$_2$) to obtain the title compound as a white solid. $^1$H NMR (400 MHz, CDCl$_3$) δ 8.42 (d, J=4.65 Hz, 2H), 8.35 (d, J=1.96 Hz, 1H), 8.01 (d, J=9.05 Hz, 1H), 7.75 (dd, J=2.08, 8.93 Hz, 1H), 7.48-7.57 (m, 3H), 7.38 (d, J=6.11 Hz, 2H), 7.29-7.35 (m, 2H), 7.26 (s, 1H), 6.30 (s, 1H), 3.45 (s, 1H), 3.35 (s, 3H); MS m/e 461.1 [M+H]$^+$.

Example 17

(4-Chlorophenyl)(2,4-dichloro-3-phenylquinolin-6-yl)(pyridin-3-yl)methanol

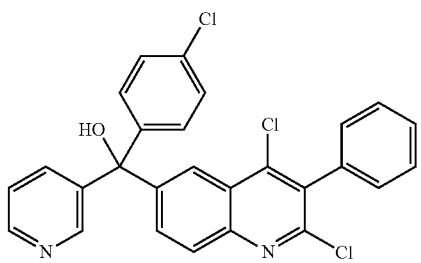 [SMILES: OC(c1ccc(Cl)cc1)(c1cccnc1)c1ccc2nc(Cl)c(-c3ccccc3)c(Cl)c2c1]

The title compound was prepared using (4-chlorophenyl)(pyridin-3-yl)methanone in place of (1-methyl-1H-imidazol-5-yl)(pyridin-4-yl)methanone according to the procedure described in Example 16. $^1$H NMR (400 MHz, CDCl$_3$) δ 8.54-8.60 (m, 2H), 8.26 (d, J=1.96 Hz, 1H), 8.04 (d, J=9.05 Hz, 1H), 7.65-7.74 (m, 2H), 7.47-7.56 (m, 4H), 7.23-7.38 (m, 6H), 3.28 (br. s., 1H); MS m/e 491.0.

Example 18

[2-Chloro-4-(methylamino)-3-phenylquinolin-6-yl](1-methyl-1H-imidazol-5-yl)pyridin-4-ylmethanol•TFA

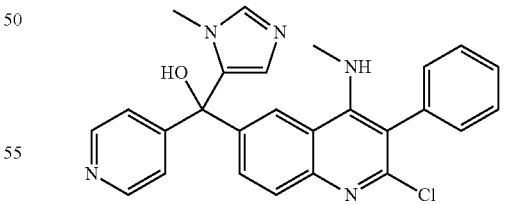

A mixture of (2,4-dichloro-3-phenylquinolin-6-yl)(1-methyl-1H-imidazol-5-yl)pyridin-4-ylmethanol (28 mg, 0.0607 mmol, Example 16), 33% MeNH$_2$ in EtOH (0.8 mL), and trifluoroacetic acid (0.050 mL, 0.653 mmol) was heated at 80° C. for 17 hours. After cooling to room temperature, the mixture was diluted with DMF and purified by reverse phase HPLC (water/acetonitrile/0.1% TFA) to give the title compound. $^1$H NMR (400 MHz, MeOH-d$_4$) δ 9.08 (s, 1H), 8.74-8.83 (m, 2H), 8.49 (d, J=1.71 Hz, 1H), 7.98 (dt, J=1.93, 6.91

Hz, 3H), 7.86 (d, J=8.80 Hz, 1H), 7.47-7.55 (m, 3H), 7.35-7.46 (m, 2H), 7.25 (d, J=1.47 Hz, 1H), 3.69 (s, 3H), 2.58 (s, 3H); MS m/e 456.1 [M+H]⁺.

Example 19

[4-Chloro-2-(4-methylpiperazin-1-yl)-3-phenylquinolin-6-yl](1-methyl-1H-imidazol-5-yl)pyridin-4-ylmethanol•TFA

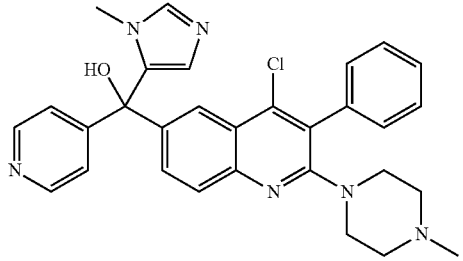 [SMILES: CN1CCN(c2nc3ccc(C(O)(c4ccncc4)c4cncn4C)cc3c(Cl)c2-c2ccccc2)CC1]

A mixture of (2,4-dichloro-3-phenylquinolin-6-yl)(1-methyl-1H-imidazol-5-yl)pyridin-4-ylmethanol (28 mg, 0.0607 mmol, Example 16) and 1-methylpiperazine (35 mg, 0.35 mmol) in MeOH (1 mL) was heated at 80° C. for 12.5 hours. More 1-methylpiperazine (135 mg, 1.35 mmol) was added and the mixture was heated at 80° C. for 18 hours. LCMS of the reaction mixture showed the presence of starting material and title compound in ~1:1 ratio. Trifluoroacetic acid (0.040 mL, 0.523 mmol) was added and the mixture was heated at 80° C. for 22 hours. Purification by reverse phase HPLC (water/acetonitrile/0.1% TFA) provided the title compound. ¹H NMR (400 MHz, MeOH-d₄) δ 9.09 (s, 1H), 8.85 (d, J=5.87 Hz, 2H), 8.33 (s, 1H), 8.08 (d, J=5.87 Hz, 2H), 7.96 (d, J=9.05 Hz, 1H), 7.77 (d, J=8.80 Hz, 1H), 7.52-7.61 (m, 2H), 7.41-7.52 (m, 3H), 7.22 (s, 1H), 3.78 (d, J=13.94 Hz, 2H), 3.71 (s, 3H), 3.35 (d, J=11.98 Hz, 2H), 3.09 (t, J=13.20 Hz, 2H), 2.87-3.00 (m, 2H), 2.85 (s, 3H); MS m/e 525.2 [M+H]⁺.

Example 20

(4-Chloro-2-morpholin-4-yl-3-phenylquinolin-6-yl)(1-methyl-1H-imidazol-5-yl)pyridin-4-ylmethanol•TFA

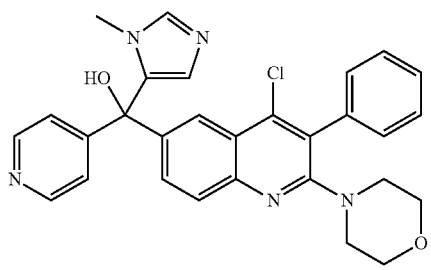 [SMILES: Cn1cncc1C(O)(c1ccncc1)c1ccc2nc(N3CCOCC3)c(-c3ccccc3)c(Cl)c2c1]

The title compound was prepared using morpholine in place of 1-methylpiperazine according to the procedure described in Example 19. ¹H NMR (400 MHz, MeOH-d₄) δ 9.08 (s, 1H), 8.84 (d, J=6.11 Hz, 2H), 8.29 (s, 1H), 8.04 (d, J=6.11 Hz, 2H), 7.94 (d, J=8.80 Hz, 1H), 7.70-7.77 (m, 1H), 7.49-7.57 (m, 2H), 7.42-7.49 (m, 3H), 7.21 (s, 1H), 3.70 (s, 3H), 3.44-3.54 (m, 4H), 3.14-3.21 (m, 4H); MS m/e 512.1 [M+H]⁺.

Example 21

(2,4-Dichloro-3-phenylquinolin-6-yl)(dipyridin-4-yl)methanol•TFA

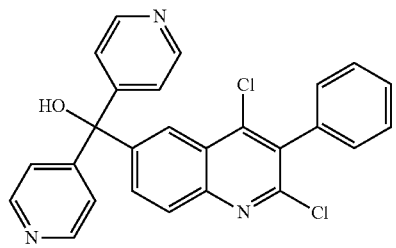 [SMILES: OC(c1ccncc1)(c1ccncc1)c1ccc2nc(Cl)c(-c3ccccc3)c(Cl)c2c1]

To a solution of 6-bromo-2,4-dichloro-3-phenylquinoline (200 mg, 0.567 mmol, Intermediate 1, step c) and THF (7 mL) at −78° C. was added 1.6 M n-BuLi in hexane (0.50 mL, 0.80 mmol). After stirring at −78° C. for 20 min, di(pyridin-4-yl)methanone (105 mg, 0.570 mmol) was added. The mixture was stirred at −78° C. for 10 min, and the cooling bath was removed. After the mixture reached room temperature, it was quenched with NH₄Cl (aqueous). The organic layer was separated, and the aqueous layer was extracted with CH₂Cl₂. The combined organic phases were dried (Na₂SO₄), filtered, concentrated, and purified by reverse phase HPLC (water/acetonitrile/0.1% TFA) to give the title compound as a white solid. ¹H NMR (400 MHz, MeOH-d₄) δ 8.74-8.82 (m, 4H), 8.29 (d, J=1.96 Hz, 1H), 8.08 (d, J=8.80 Hz, 1H), 7.88-7.98 (m, 4H), 7.84 (dd, J=2.20, 9.05 Hz, 1H), 7.46-7.60 (m, 3H), 7.28-7.37 (m, 2H); MS m/e 458.0 [M+H]⁺.

Example 22

(2,4-Dichloro-3-phenylquinolin-6-yl)(4-fluorophenyl)pyridin-3-ylmethanol

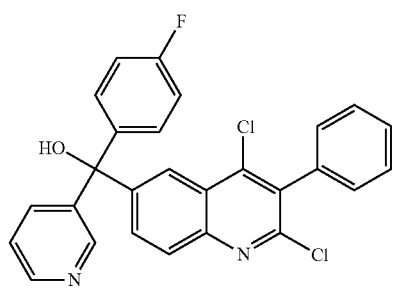 [SMILES: OC(c1ccc(F)cc1)(c1cccnc1)c1ccc2nc(Cl)c(-c3ccccc3)c(Cl)c2c1]

The title compound was prepared using (4-fluorophenyl)(pyridin-3-yl)methanone in place of (1-methyl-1H-imidazol-5-yl)(pyridin-4-yl)methanone according to the procedure described in Example 16. ¹H NMR (400 MHz, CDCl₃) δ 8.58 (td, J=1.71, 5.01 Hz, 2H), 8.26 (d, J=1.71 Hz, 1H), 8.04 (d, J=9.05 Hz, 1H), 7.65-7.81 (m, 2H), 7.43-7.58 (m, 3H), 7.27-7.35 (m, 5H), 7.03-7.10 (m, 2H); MS m/e 475.0 [M+H]⁺.

Example 23

(2,4-Dichloro-3-phenylquinolin-6-yl)[4-(methoxymethoxy)phenyl]pyridin-3-ylmethanol

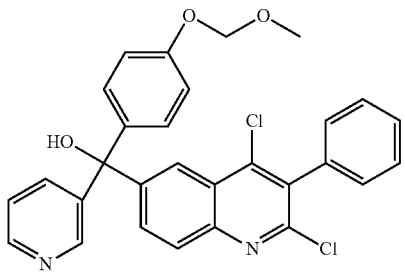 [SMILES: COCOc1ccc(C(O)(c2cccnc2)c2ccc3nc(Cl)c(-c4ccccc4)c(Cl)c3c2)cc1]

The title compound was prepared using (4-(methoxymethoxy)phenyl)(pyridin-3-yl)methanone in place of (1-methyl-1H-imidazol-5-yl)(pyridin-4-yl)methanone according to the procedure described in Example 16. ¹H NMR (400 MHz, CDCl₃) δ 8.62 (d, J=2.45 Hz, 1H), 8.54-8.58 (m, 1H), 8.31 (d, J=1.96 Hz, 1H), 8.03 (d, J=8.80 Hz, 1H), 7.72-7.76 (m, 1H), 7.72 (d, J=1.96 Hz, 1H), 7.48-7.54 (m, 3H), 7.27-7.36 (m, 3H), 7.16-7.20 (m, 2H), 7.01-7.05 (m, 2H), 5.19 (s, 2H), 3.48 (s, 3H); MS m/e 517.0 [M+H]⁺.

Example 24

(2,4-Dichloro-3-phenylquinolin-6-yl)(dipyridin-3-yl)methanol•TFA

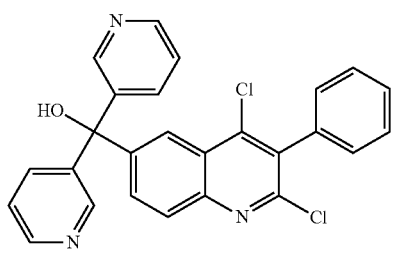 [SMILES: OC(c1cccnc1)(c1cccnc1)c1ccc2nc(Cl)c(-c3ccccc3)c(Cl)c2c1]

To a solution of 6-bromo-2,4-dichloro-3-phenylquinoline (180 mg, 0.510 mmol, Intermediate 1, step c) and di(pyridin-3-yl)methanone (94 mg, 0.51 mmol) in THF (7 mL) at −78° C. was added 1.6 M n-BuLi in hexane (0.50 mL, 0.80 mmol). The mixture was stirred at −78° C. for 10 min, and the cooling bath was removed. After the mixture reached to room temperature, it was quenched with NH₄Cl (aqueous). The organic layer was separated, and the aqueous layer was extracted with CH₂Cl₂. The combined organic phases were dried (Na₂SO₄), filtered, concentrated, and purified by reverse phase HPLC (water/acetonitrile/0.1% TFA) to give the title compound as a white solid. ¹H NMR (400 MHz, MeOH-d₄) δ 8.92 (br. s., 2H), 8.82 (d, J=4.89 Hz, 2H), 8.45 (dt, J=1.59, 8.56 Hz, 2H), 8.34 (d, J=1.71 Hz, 1H), 8.07 (d, J=8.80 Hz, 1H), 7.95 (dd, J=5.38, 8.31 Hz, 2H), 7.88 (dd, J=2.08, 8.93 Hz, 1H), 7.48-7.57 (m, 3H), 7.29-7.35 (m, 2H); MS m/e 458.0 [M+H]⁺.

Example 25

(3-Chlorophenyl)(2,4-dichloro-3-phenylquinolin-6-yl)(pyridin-3-yl)methanol

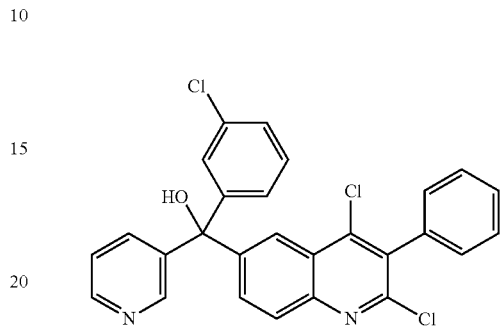

To a solution of 6-bromo-2,4-dichloro-3-phenylquinoline (130 mg, 0.368 mmol, Intermediate 1, step c) and (3-chlorophenyl)(pyridin-3-yl)methanone (81 mg, 0.372 mmol) in THF (8 mL) at −78° C. was added 1.6 M n-BuLi in hexane (0.35 mL, 0.56 mmol). The mixture was stirred at −78° C. for 10 min, and the cooling bath was removed. After the mixture reached room temperature, it was quenched with NH₄Cl (aqueous). The organic layer was separated, and the aqueous layer was extracted with CH₂Cl₂. The combined organic phases were dried (Na₂SO₄), filtered, concentrated, and purified by flash column chromatography (24 g silica gel column, 30-40% EtOAc in heptane) to obtain the title compound as a white solid. ¹H NMR (400 MHz, CDCl₃) δ 8.53 (br. s., 2H), 8.26 (d, J=1.96 Hz, 1H), 8.04 (d, J=8.80 Hz, 1H), 7.64-7.73 (m, 2H), 7.49-7.54 (m, 3H), 7.30-7.38 (m, 4H), 7.27-7.30 (m, 2H), 7.16 (dt, J=1.80, 7.09 Hz, 1H); MS m/e 491.0 [M+H]⁺.

Example 26

(2,4-Dichloro-3-phenylquinolin-6-yl)(pyridin-2-yl)pyridin-3-ylmethanol•TFA

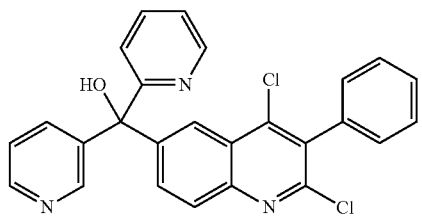 [SMILES: OC(c1cccnc1)(c1ccc2nc(Cl)c(-c3ccccc3)c(Cl)c2c1)c1ccccn1]

The title compound was prepared using pyridin-2-yl(pyridin-3-yl)methanone in place of di(pyridin-3-yl)methanone according to the procedure described in Example 24. ¹H NMR (400 MHz, MeOH-d₄) δ 8.93 (d, J=1.96 Hz, 1H), 8.75 (d, J=4.65 Hz, 1H), 8.64 (dt, J=1.77, 8.44 Hz, 1H), 8.58-8.62 (m, 1H), 8.22 (d, J=1.71 Hz, 1H), 8.02 (d, J=8.80 Hz, 1H), 7.93-8.00 (m, 2H), 7.89-7.93 (m, 1H), 7.86 (dd, J=2.08, 8.93

Hz, 1H), 7.48-7.55 (m, 3H), 7.41 (ddd, J=1.47, 4.89, 7.34 Hz, 1H), 7.30-7.36 (m, 2H); MS m/e 458.0 [M+H]⁺.

Example 27

(2,4-Dichloro-3-phenylquinolin-6-yl)(pyridin-2-yl)pyridin-4-ylmethanol•TFA

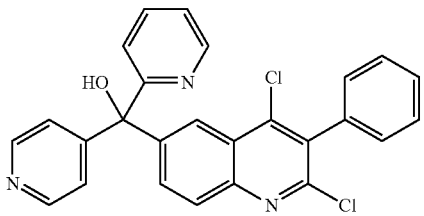 [SMILES: OC(c1ccncc1)(c1ccc2nc(Cl)c(-c3ccccc3)c(Cl)c2c1)c1ccccn1]

The title compound was prepared using pyridin-2-yl(pyridin-4-yl)methanone in place of di(pyridin-3-yl)methanone according to the procedure described in Example 24. $^1$H NMR (400 MHz, MeOH-d$_4$) δ 8.80 (d, J=6.85 Hz, 2H), 8.60 (d, J=4.65 Hz, 1H), 8.25 (dd, J=2.32, 4.52 Hz, 3H), 8.02 (d, J=8.80 Hz, 1H), 7.93-8.00 (m, 1H), 7.88-7.93 (m, 1H), 7.85 (dd, J=2.08, 8.93 Hz, 1H), 7.47-7.57 (m, 3H), 7.42 (ddd, J=1.22, 4.89, 7.34 Hz, 1H), 7.28-7.35 (m, 2H); MS m/e 458.0 [M+H]⁺.

Example 28

(2-Chlorophenyl)(2,4-dichloro-3-phenylquinolin-6-yl)pyridin-3-ylmethanol•TFA

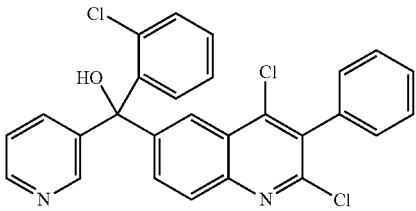 [SMILES: OC(c1cccnc1)(c1ccc2nc(Cl)c(-c3ccccc3)c(Cl)c2c1)c1ccccc1Cl]

The title compound was prepared using (2-chlorophenyl)(pyridin-3-yl)methanone in place of di(pyridin-3-yl)methanone according to the procedure described in Example 24. $^1$H NMR (400 MHz, MeOH-d$_4$) δ 8.86 (s, 1H), 8.76 (d, J=5.62 Hz, 1H), 8.48-8.54 (m, 1H), 8.35 (d, J=2.20 Hz, 1H), 8.06 (d, J=9.05 Hz, 1H), 7.97 (dd, J=5.62, 8.31 Hz, 1H), 7.89 (dd, J=2.08, 8.93 Hz, 1H), 7.47-7.56 (m, 4H), 7.36-7.48 (m, 3H), 7.31-7.36 (m, 2H); MS m/e 491.0 [M+H]⁺.

Example 29

4-[(2,4-Dichloro-3-phenylquinolin-6-yl)(hydroxy)pyridin-3-ylmethyl]phenol•HCl

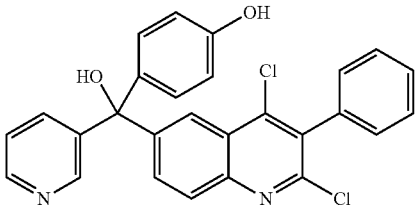 [SMILES: Oc1ccc(C(O)(c2cccnc2)c2ccc3nc(Cl)c(-c4ccccc4)c(Cl)c3c2)cc1]

(2,4-Dichloro-3-phenylquinolin-6-yl)[4-(methoxymethoxy)phenyl]pyridin-3-ylmethanol (20 mg, 0.039 mmol, Example 23) in MeOH (2 mL) was treated with 37% HCl (1 mL) at room temperature for 18 hours, and concentrated. The residue was purified by reverse phase HPLC (water/acetonitrile/0.1% TFA) to give the title compound as an off-white solid. $^1$H NMR (400 MHz, MeOH-d$_4$) δ 8.85 (d, J=2.20 Hz, 1H), 8.75 (d, J=4.89 Hz, 1H), 8.48 (dt, J=1.80, 8.13 Hz, 1H), 8.31 (d, J=1.96 Hz, 1H), 8.02 (d, J=9.05 Hz, 1H), 7.95 (dd, J=5.62, 8.31 Hz, 1H), 7.86 (dd, J=1.96, 8.80 Hz, 1H), 7.48-7.57 (m, 3H), 7.33 (dd, J=1.47, 7.83 Hz, 2H), 7.08-7.16 (m, 2H), 6.77-6.84 (m, 2H); MS m/e 473.0 [M+H]⁺.

Example 30

(4-Chloro-2-ethyl-3-phenylquinolin-6-yl)(4-fluorophenyl)pyridin-3-ylmethanol•TFA

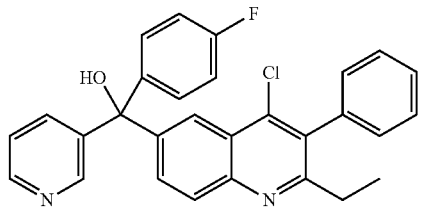 [SMILES: CCc1nc2ccc(C(O)(c3ccc(F)cc3)c3cccnc3)cc2c(Cl)c1-c1ccccc1]

A sealed tube containing (2,4-dichloro-3-phenylquinolin-6-yl)(4-fluorophenyl)pyridin-3-ylmethanol (30 mg, 0.063 mmol, Example 22), PdCl$_2$(dppf)$_2$.CH$_2$Cl$_2$ (6.0 mg, 0.0074 mmol), K$_2$CO$_3$ (29 mg, 0.21 mmol), and THF (1 mL) was bubbled with N$_2$ for 3 min, and 1.0 M Zn(Et)$_2$ in heptane (0.070 mL, 0.070 mmol) was then added. After heating at 66° C. for 16 hours, more PdCl$_2$(dppf)$_2$.CH$_2$Cl$_2$ (4.6 mg, 0.0056 mmol) and 1.0 M Zn(Et)$_2$ in heptane (0.070 mL, 0.070 mmol) were added, and the mixture was heated for another 6 hours. NH$_4$Cl (aqueous) was added, the organic layer was separated, and the aqueous layer was extracted with CH$_2$Cl$_2$. The combined organic phases were dried (Na$_2$SO$_4$), filtered, concentrated, and purified by reverse phase HPLC (water/acetonitrile/0.1% TFA) to give the title compound as a white solid. $^1$H NMR (400 MHz, MeOH-d$_4$) δ 8.83-8.88 (m, 1H), 8.76 (d, J=5.62 Hz, 1H), 8.43-8.50 (m, 1H), 8.30 (d, J=1.71 Hz, 1H), 8.12 (d, J=8.80 Hz, 1H), 7.95 (dd, J=5.62, 8.31 Hz, 1H), 7.88 (dd, J=2.08, 8.93 Hz, 1H), 7.50-7.59 (m, 3H), 7.36-7.43 (m, 2H), 7.28-7.36 (m, 2H), 7.11-7.20 (m, 2H), 2.81 (q, J=7.58 Hz, 2H), 1.18 (t, J=7.58 Hz, 3H); MS m/e 469.0 [M+H]⁺.

Example 31

1-(2,4-Dichloro-3-phenylquinolin-6-yl)-1-(1-methyl-1H-imidazol-5-yl)-1-pyridin-2-ylmethanamine•HCl

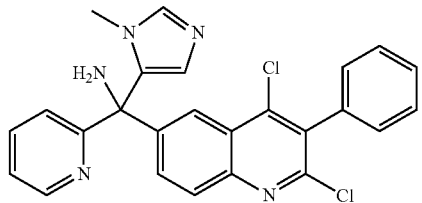 [SMILES: Cn1cncc1C(N)(c1ccc2nc(Cl)c(-c3ccccc3)c(Cl)c2c1)c1ccccn1]

To a solution of 6-bromo-2,4-dichloro-3-phenylquinoline (112 mg, 0.317 mmol, Intermediate 1, step c) and (2-methyl- N-((1-methyl-1H-imidazol-5-yl)(pyridin-2-yl)methylene)propane-2-sulfinamide (46 mg, 0.16 mmol, Intermediate 11, step c) in THF (5 mL) at −78° C. was added 1.6 M n-BuLi in hexane (0.40 mL, 0.64 mmol). The mixture was stirred at −78° C. to room temperature overnight and quenched with NH$_4$Cl (aqueous). The organic layer was separated, and the aqueous layer was extracted with CH$_2$Cl$_2$. The combined organic phases were dried (Na$_2$SO$_4$), filtered, and concentrated. The residue was diluted with MeOH (3 mL), treated with 4 M HCl in dioxane (3 mL) overnight, and concentrated. The residue was purified by reverse phase HPLC (water/acetonitrile/0.1% TFA) to give the title compound as a white solid. $^1$H NMR (400 MHz, MeOH-d$_4$) δ 8.88 (s, 1H), 8.77 (d, J=4.89 Hz, 1H), 8.26 (d, J=2.20 Hz, 1H), 8.15 (d, J=8.80 Hz, 1H), 7.97 (td, J=1.71, 7.83 Hz, 1H), 7.87 (dd, J=2.32, 8.93 Hz, 1H), 7.42-7.63 (m, 5H), 7.34 (dd, J=1.71, 7.83 Hz, 2H), 7.05 (d, J=1.47 Hz, 1H), 3.59 (s, 3H); MS m/e 460.0 [M+H]$^+$.

Example 32

[4-Chloro-2-(dimethylamino)-3-phenylquinolin-6-yl](4-chlorophenyl)pyridin-3-ylmethanol•TFA

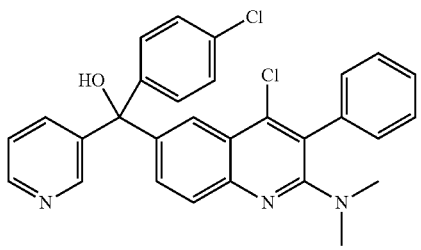 [SMILES: CN(C)c1nc2ccc(C(O)(c3ccc(Cl)cc3)c3cccnc3)cc2c(Cl)c1-c1ccccc1]

A mixture of (4-chlorophenyl)(2,4-dichloro-3-phenylquinolin-6-yl)pyridin-3-ylmethanol (25 mg, 0.051 mmol, Example 17) and 2 M NHMe$_2$ in MeOH (0.8 mL, 1.6 mmol) was heated at 80° C. for 4.5 days. After evaporation of the solvent in vacuo, the residue was purified by reverse phase HPLC (water/acetonitrile/0.1% TFA) to give the title compound. $^1$H NMR (400 MHz, MeOH-d$_4$) δ 8.85 (s, 1H), 8.79 (d, J=5.38 Hz, 1H), 8.47 (dt, J=1.77, 8.19 Hz, 1H), 8.25 (d, J=1.96 Hz, 1H), 8.06 (d, J=8.80 Hz, 1H), 7.95-8.03 (m, 2H), 7.83 (dd, J=2.08, 8.93 Hz, 1H), 7.51-7.61 (m, 4H), 7.40-7.49 (m, 3H), 7.32-7.39 (m, 2H), 2.99 (s, 6H); MS m/e 499.8 [M+H]$^+$.

Example 33

[2-Chloro-4-(dimethylamino)-3-phenylquinolin-6-yl](4-chlorophenyl)pyridin-3-ylmethanol•TFA

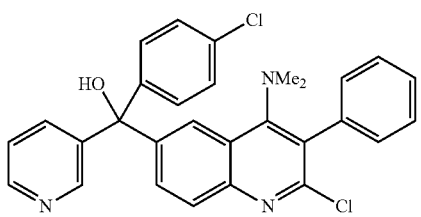 [SMILES: CN(C)c1c(-c2ccccc2)c(Cl)nc2ccc(C(O)(c3ccc(Cl)cc3)c3cccnc3)cc12]

The title compound was isolated from the reaction that formed Example 32. $^1$H NMR (400 MHz, MeOH-d$_4$) δ 8.85 (br. s., 1H), 8.74-8.79 (m, 1H), 8.44-8.49 (m, 1H), 7.98 (d, J=1.96 Hz, 2H), 7.89 (d, J=8.80 Hz, 1H), 7.70 (dd, J=2.20, 8.80 Hz, 1H), 7.45-7.53 (m, 3H), 7.41-7.45 (m, 2H), 7.35-7.41 (m, 2H), 7.29 (d, J=7.58 Hz, 2H), 2.53 (s, 6H); MS m/e 499.9 [M+H]$^+$.

Example 34

[4-Chloro-2-(dimethylamino)-3-phenylquinolin-6-yl](1-methyl-1H-imidazol-5-yl)pyridin-3-ylmethanol•TFA

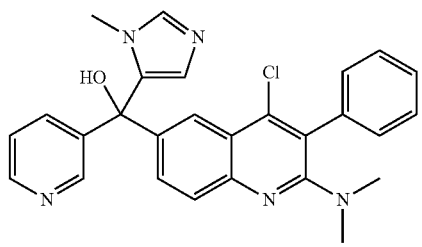 [SMILES: CN(C)c1nc2ccc(C(O)(c3cccnc3)c3cncn3C)cc2c(Cl)c1-c1ccccc1]

The title compound was prepared using (2,4-dichloro-3-phenylquinolin-6-yl)(1-methyl-1H-imidazol-5-yl)(pyridin-3-yl)methanol (Example 49) in place of (4-chlorophenyl)(2,4-dichloro-3-phenylquinolin-6-yl)pyridin-3-ylmethanol according to the procedure described in Example 32. $^1$H NMR (400 MHz, MeOH-d$_4$) δ 9.08 (s, 1H), 8.91 (s, 1H), 8.83 (d, J=4.89 Hz, 1H), 8.46 (dt, J=1.59, 8.56 Hz, 1H), 8.37 (d, J=1.96 Hz, 1H), 8.15 (d, J=8.80 Hz, 1H), 7.95 (dd, J=5.38, 8.07 Hz, 1H), 7.88 (dd, J=2.20, 8.80 Hz, 1H), 7.51-7.65 (m, 3H), 7.40-7.50 (m, 2H), 7.20 (d, J=1.47 Hz, 1H), 3.72 (s, 3H), 3.01 (s, 6H); MS m/e 470.0 [M+H]$^+$.

Example 35

[2-Chloro-4-(dimethylamino)-3-phenylquinolin-6-yl](1-methyl-1H-imidazol-5-yl)pyridin-3-ylmethanol•TFA

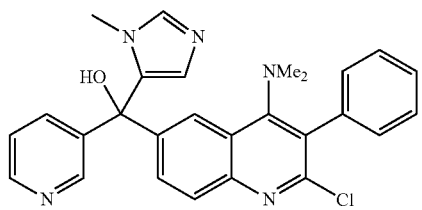 [SMILES: CN(C)c1c(-c2ccccc2)c(Cl)nc2ccc(C(O)(c3cccnc3)c3cncn3C)cc12]

The title compound was isolated from the reaction that formed Example 34. $^1$H NMR (400 MHz, MeOH-d$_4$) δ 9.03 (s, 1H), 8.63-8.77 (m, 2H), 8.07-8.14 (m, 2H), 7.96 (d, J=8.80 Hz, 1H), 7.76 (dd, J=2.20, 8.80 Hz, 1H), 7.69 (dd, J=5.14, 8.07 Hz, 1H), 7.41-7.56 (m, 3H), 7.24-7.34 (m, 2H), 7.07 (d, J=1.47 Hz, 1H), 3.72 (s, 3H), 2.57 (s, 6H); MS m/e 470.0 [M+H]⁺.

Example 36

[4-Chloro-2-(dimethylamino)-3-phenylquinolin-6-yl](1-methyl-1H-imidazol-5-yl)pyridin-2-ylmethanol•TFA

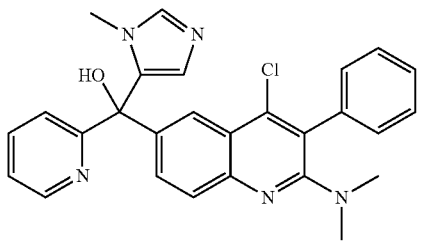

The title compound was prepared using (2,4-dichloro-3-phenylquinolin-6-yl)(1-methyl-1H-imidazol-5-yl)(pyridin-2-yl)methanol (Example 1) in place of (4-chlorophenyl)(2,4-dichloro-3-phenylquinolin-6-yl)pyridin-3-ylmethanol according to the procedure described in Example 32. ¹H NMR (400 MHz, MeOH-d₄) δ 8.96 (s, 1H), 8.60 (d, J=4.16 Hz, 1H), 8.45 (d, J=1.71 Hz, 1H), 7.98-8.11 (m, 2H), 7.92 (td, J=1.83, 7.76 Hz, 1H), 7.79 (d, J=7.83 Hz, 1H), 7.50-7.65 (m, 3H), 7.36-7.50 (m, 3H), 7.08 (d, J=1.71 Hz, 1H), 3.62 (s, 3H), 2.99 (s, 6H); MS m/e 470.0 [M+H]⁺.

Example 37

[4-Chloro-2-(dimethylamino)-3-phenylquinolin-6-yl](dipyridin-4-yl)methanol•TFA

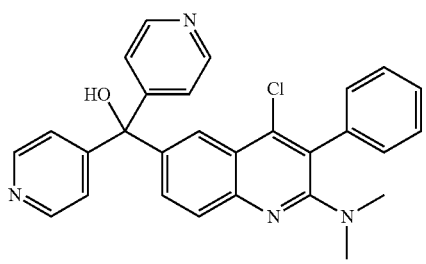 [SMILES: CN(C)c1nc2ccc(C(O)(c3ccncc3)c3ccncc3)cc2c(Cl)c1-c1ccccc1]

The title compound was prepared using (2,4-dichloro-3-phenylquinolin-6-yl)(dipyridin-4-yl)methanol•TFA (Example 21) in place of (4-chlorophenyl)(2,4-dichloro-3-phenylquinolin-6-yl)pyridin-3-ylmethanol according to the procedure described in Example 32. ¹H NMR (400 MHz, MeOH-d₄) δ 8.85 (d, J=5.87 Hz, 4H), 8.25 (d, J=1.96 Hz, 1H), 8.10 (d, J=8.80 Hz, 1H), 8.05 (d, J=6.60 Hz, 4H), 7.81 (dd, J=2.20, 8.80 Hz, 1H), 7.51-7.60 (m, 3H), 7.41-7.47 (m, 2H), 2.99 (s, 6H); MS m/e 467.0 [M+H]⁺.

Example 38

[4-Chloro-2-(dimethylamino)-3-phenylquinolin-6-yl](4-fluorophenyl)pyridin-3-ylmethanol•TFA

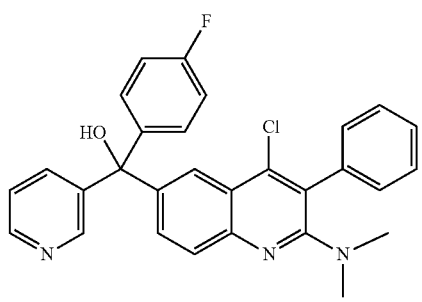 [SMILES: CN(C)c1nc2ccc(C(O)(c3ccc(F)cc3)c3cccnc3)cc2c(Cl)c1-c1ccccc1]

The title compound was prepared using (2,4-dichloro-3-phenylquinolin-6-yl)(4-fluorophenyl)pyridin-3-ylmethanol (Example 22) in place of (4-chlorophenyl)(2,4-dichloro-3-phenylquinolin-6-yl)pyridin-3-ylmethanol according to the procedure described in Example 32. ¹H NMR (400 MHz, MeOH-d₄) δ 8.85 (d, J=1.96 Hz, 1H), 8.84-8.84 (m, 1H), 8.79 (d, J=4.89 Hz, 1H), 8.48 (dt, J=1.74, 8.25 Hz, 1H), 8.25 (d, J=1.96 Hz, 1H), 8.06 (d, J=9.05 Hz, 1H), 7.98 (dd, J=5.50, 8.19 Hz, 1H), 7.83 (dd, J=2.20, 8.80 Hz, 1H), 7.51-7.61 (m, 2H), 7.42-7.47 (m, 2H), 7.32-7.40 (m, 2H), 7.11-7.19 (m, 2H), 2.99 (s, 6H); MS m/e 483.9 [M+H]⁺.

Example 39

[2-Chloro-4-(dimethylamino)-3-phenylquinolin-6-yl](4-fluorophenyl)pyridin-3-ylmethanol•TFA

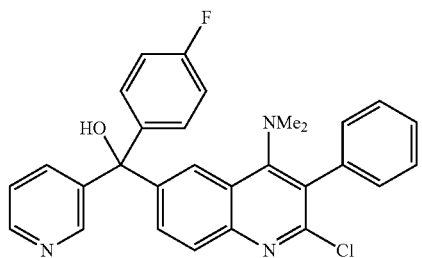 [SMILES: CN(C)c1c(-c2ccccc2)c(Cl)nc2ccc(C(O)(c3ccc(F)cc3)c3cccnc3)cc12]

The title compound was isolated from the reaction that formed Example 38. ¹H NMR (400 MHz, MeOH-d₄) δ 8.84 (s, 1H), 8.74 (s, 1H), 8.44 (dt, J=1.71, 8.31 Hz, 1H), 7.97 (d, J=1.96 Hz, 1H), 7.94 (dd, J=5.62, 8.07 Hz, 1H), 7.88 (d, J=8.80 Hz, 1H), 7.71 (dd, J=2.20, 8.80 Hz, 1H), 7.37-7.54 (m, 5H), 7.25-7.32 (m, 2H), 7.12-7.21 (m, 2H), 2.52 (s, 6H); MS m/e 483.9 [M+H]+.

Example 40

[4-Chloro-2-(dimethylamino)-3-phenylquinolin-6-yl] (dipyridin-3-yl)methanol•TFA

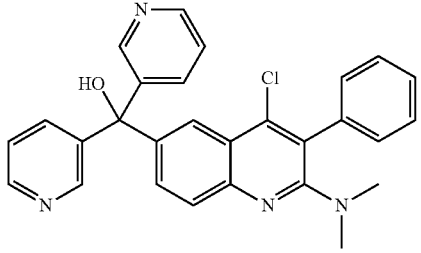 [SMILES: CN(C)c1nc2ccc(C(O)(c3cccnc3)c3cccnc3)cc2c(Cl)c1-c1ccccc1]

The title compound was prepared using (2,4-dichloro-3-phenylquinolin-6-yl)(dipyridin-3-yl)methanol•TFA (Example 24) in place of (4-chlorophenyl)(2,4-dichloro-3-phenylquinolin-6-yl)pyridin-3-ylmethanol according to the procedure described in Example 32. $^1$H NMR (400 MHz, MeOH-d$_4$) δ 8.86-8.95 (m, 2H), 8.82 (d, J=3.42 Hz, 2H), 8.44 (d, J=8.31 Hz, 2H), 8.28 (d, J=1.96 Hz, 1H), 8.11 (d, J=8.80 Hz, 1H), 7.95 (dd, J=5.38, 8.07 Hz, 2H), 7.85 (dd, J=2.08, 8.93 Hz, 1H), 7.52-7.63 (m, 3H), 7.41-7.49 (m, 2H), 3.00 (s, 6H); MS m/e 467.0 [M+H]+.

Example 41

[4-Chloro-2-(dimethylamino)-3-phenylquinolin-6-yl] (3-chlorophenyl)pyridin-3-ylmethanol•TFA

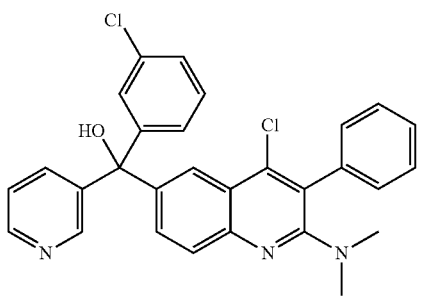 [SMILES: CN(C)c1nc2ccc(C(O)(c3cccnc3)c3cccc(Cl)c3)cc2c(Cl)c1-c1ccccc1]

The title compound was prepared using (3-chlorophenyl) (2,4-dichloro-3-phenylquinolin-6-yl)pyridin-3-ylmethanol (Example 25) in place of (4-chlorophenyl)(2,4-dichloro-3-phenylquinolin-6-yl)pyridin-3-ylmethanol according to the procedure described in Example 32. $^1$H NMR (400 MHz, MeOH-d$_4$) δ 8.84 (s, 1H), 8.79 (d, J=5.14 Hz, 1H), 8.46 (dt, J=1.62, 8.50 Hz, 1H), 8.24 (d, J=1.96 Hz, 1H), 8.07 (d, J=9.05 Hz, 1H), 7.97 (dd, J=5.62, 8.31 Hz, 1H), 7.83 (dd, J=2.20, 8.80 Hz, 1H), 7.51-7.57 (m, 3H), 7.42-7.46 (m, 3H), 7.38-7.42 (m, 2H), 7.23-7.28 (m, 1H), 2.99 (s, 6H); MS m/e 499.8 [M+H]+.

Example 42

[2-Chloro-4-(dimethylamino)-3-phenylquinolin-6-yl] (3-chlorophenyl)pyridin-3-ylmethanol•TFA

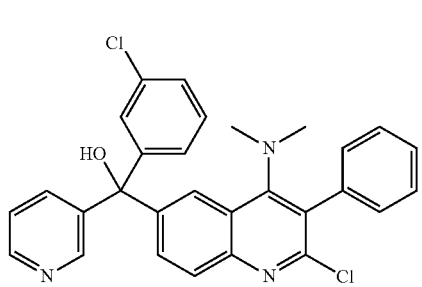 [SMILES: CN(C)c1c(-c2ccccc2)c(Cl)nc2ccc(C(O)(c3cccnc3)c3cccc(Cl)c3)cc12]

The title compound was isolated from the reaction that formed Example 41. $^1$H NMR (400 MHz, MeOH-d$_4$) δ 8.83 (s, 1H), 8.75 (d, J=4.89 Hz, 1H), 8.38-8.44 (m, 1H), 7.95 (d, J=1.96 Hz, 1H), 7.91-7.94 (m, 1H), 7.89 (d, J=9.05 Hz, 1H), 7.70 (dd, J=2.20, 8.80 Hz, 1H), 7.43-7.53 (m, 4H), 7.38-7.43 (m, 2H), 7.26-7.32 (m, 3H), 2.52 (s, 6H); MS m/e 499.9 [M+H]+.

Example 43

[4-Chloro-2-(dimethylamino)-3-phenylquinolin-6-yl] (pyridin-2-yl)pyridin-3-ylmethanol•TFA

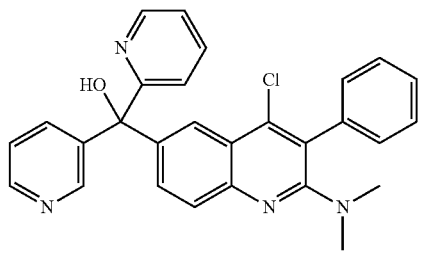 [SMILES: CN(C)c1nc2ccc(C(O)(c3cccnc3)c3ccccn3)cc2c(Cl)c1-c1ccccc1]

The title compound was prepared using (2,4-dichloro-3-phenylquinolin-6-yl)(pyridin-2-yl)pyridin-3-ylmethanol•TFA (Example 26) in place of (4-chlorophenyl) (2,4-dichloro-3-phenylquinolin-6-yl)pyridin-3-ylmethanol according to the procedure described in Example 32. $^1$H NMR (400 MHz, MeOH-d$_4$) δ 8.94 (s, 1H), 8.78 (d, J=5.38 Hz, 1H), 8.63-8.70 (m, 1H), 8.59 (d, J=4.89 Hz, 1H), 8.21 (d, J=1.96 Hz, 1H), 7.97-8.10 (m, 2H), 7.89-7.97 (m, 2H), 7.86 (dd, J=2.08, 8.93 Hz, 1H), 7.51-7.61 (m, 3H), 7.37-7.48 (m, 3H), 2.99 (s, 6H); MS m/e 467.0 [M+H]+.

Example 44

[4-Chloro-2-(dimethylamino)-3-phenylquinolin-6-yl](2-chlorophenyl)pyridin-3-ylmethanol•TFA

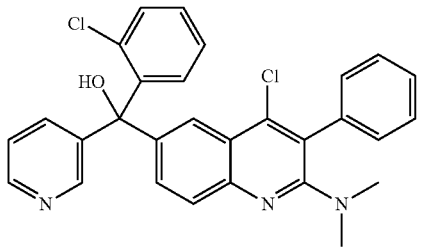 [SMILES: CN(C)c1nc2ccc(C(O)(c3cccnc3)c3ccccc3Cl)cc2c(Cl)c1-c1ccccc1]

The title compound was prepared using (2-chlorophenyl)(2,4-dichloro-3-phenylquinolin-6-yl)pyridin-3-ylmethanol•TFA (Example 28) in place of (4-chlorophenyl)(2,4-dichloro-3-phenylquinolin-6-yl)pyridin-3-ylmethanol according to the procedure described in Example 32. $^1$H NMR (400 MHz, MeOH-d$_4$) δ 8.85 (d, J=1.96 Hz, 1H), 8.78 (d, J=4.89 Hz, 1H), 8.50 (dt, J=1.59, 8.56 Hz, 1H), 8.29 (d, J=1.96 Hz, 1H), 8.08 (d, J=8.80 Hz, 1H), 7.99 (dd, J=5.62, 8.31 Hz, 1H), 7.87 (dd, J=2.20, 8.80 Hz, 1H), 7.47-7.60 (m, 4H), 7.42-7.47 (m, 4H), 7.35-7.42 (m, 1H), 2.99 (s, 6H); MS m/e 499.8 [M+H]$^+$.

Example 45

[2-Chloro-4-(dimethylamino)-3-phenylquinolin-6-yl](2-chlorophenyl)pyridin-3-ylmethanol•TFA

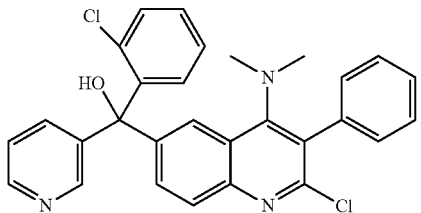 [SMILES: CN(C)c1c(-c2ccccc2)c(Cl)nc2ccc(C(O)(c3cccnc3)c3ccccc3Cl)cc12]

The title compound was isolated from the reaction that formed Example 44. $^1$H NMR (400 MHz, MeOH-d$_4$) δ 8.81-8.87 (m, 1H), 8.73-8.79 (m, 1H), 8.51 (d, J=8.31 Hz, 1H), 8.04 (d, J=1.96 Hz, 1H), 7.98 (dd, J=5.62, 7.83 Hz, 1H), 7.91 (d, J=8.80 Hz, 1H), 7.77 (dd, J=2.20, 8.80 Hz, 1H), 7.37-7.53 (m, 7H), 7.25-7.34 (m, 2H), 2.53 (s, 6H); MS m/e 499.9 [M+H]$^+$.

Example 46

(2-Chloro-6-methylpyridin-4-yl)(2,4-dichloro-3-phenylquinolin-6-yl)(1-methyl-1H-imidazol-2-yl)methanol

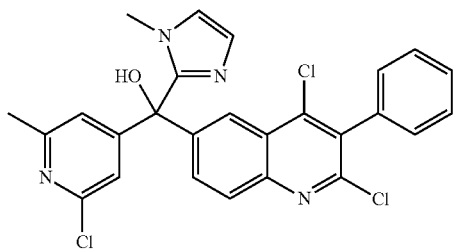 [SMILES: Cc1cc(C(O)(c2ccc3nc(Cl)c(-c4ccccc4)c(Cl)c3c2)c2nccn2C)cc(Cl)n1]

The title compound was prepared using (2-chloro-6-methylpyridin-4-yl)(1-methyl-1H-imidazol-2-yl)methanone (Intermediate 12, step b) in place of (3-chlorophenyl)(pyridin-3-yl)methanone according to the procedure described in Example 25. $^1$H NMR (400 MHz, CDCl$_3$) δ 8.17 (d, J=1.96 Hz, 1H), 8.05 (d, J=8.80 Hz, 1H), 7.70 (d, J=8.80 Hz, 1H), 7.43-7.58 (m, 3H), 7.28-7.37 (m, 2H), 7.15 (s, 1H), 7.08 (s, 1H), 6.82-6.97 (m, 2H), 3.37 (s, 3H), 2.49 (s, 3H); MS m/e 508.8 [M+H]$^+$.

Example 47

(2-Chloro-4-(dimethylamino)-3-phenylquinolin-6-yl)(1-methyl-1H-imidazol-5-yl)pyridin-4-ylmethanol•TFA

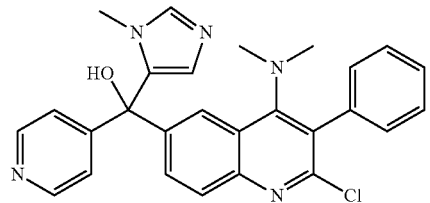 [SMILES: CN(C)c1c(-c2ccccc2)c(Cl)nc2ccc(C(O)(c3ccncc3)c3cncn3C)cc12]

The title compound was prepared using (2,4-dichloro-3-phenylquinolin-6-yl)(1-methyl-1H-imidazol-5-yl)pyridin-4-ylmethanol (Example 16) in place of (4-chlorophenyl)(2,4-dichloro-3-phenylquinolin-6-yl)pyridin-3-ylmethanol according to the procedure described in Example 32. $^1$H NMR (400 MHz, MeOH-d$_4$) δ 9.09 (s, 1H), 8.86 (d, J=6.60 Hz, 2H), 8.24 (d, J=1.96 Hz, 1H), 8.07 (d, J=6.85 Hz, 2H), 7.95 (d, J=9.05 Hz, 1H), 7.78 (dd, J=2.20, 8.80 Hz, 1H), 7.43-7.57 (m, 3H), 7.29 (dd, J=1.96, 5.62 Hz, 2H), 7.24 (d, J=1.47 Hz, 1H), 3.72 (s, 3H), 2.61 (s, 6H); MS m/e 470.0 [M+H]$^+$.

Example 48a (4-Chloro-2-(dimethylamino)-3-phenylquinolin-6-yl)(1-methyl-1H-imidazol-5-yl)pyridin-4-ylmethanol•TFA

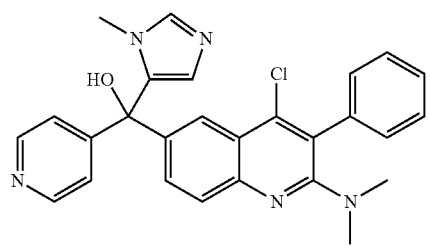

The title compound was isolated from the reaction that formed Example 47. $^1$H NMR (400 MHz, MeOH) δ 9.07 (s, 1H), 8.78 (d, J=6.36 Hz, 2H), 8.32 (d, J=1.96 Hz, 1H), 8.04 (d, J=8.80 Hz, 1H), 7.86-7.93 (m, 2H), 7.79-7.85 (m, 1H), 7.48-7.62 (m, 3H), 7.40-7.46 (m, 2H), 7.18 (d, J=1.47 Hz, 1H), 3.69 (s, 3H), 2.93 (s, 6H); MS m/e 470.0 [M+H]$^+$.

Example 48a was purified by chiral HPLC Jasco Preparative SFC System (Lux-2 Cellulose, EtOH/0.2% isopropylamine, CO$_2$) to give 2 pure enantiomers Example 48b and Example 48c (elution order: Example 48b first, Example 48c second).

Example 48b

MS m/e 470.0 [M+H]$^+$.

Example 48c

MS m/e 470.0 [M+H]$^+$.

Example 49

(2,4-Dichloro-3-phenylquinolin-6-yl)(1-methyl-1H-imidazol-5-yl)(pyridin-3-yl)methanol

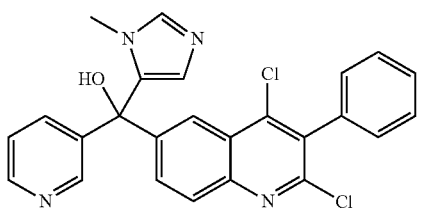 [SMILES: Cn1cncc1C(O)(c1cccnc1)c1ccc2nc(Cl)c(-c3ccccc3)c(Cl)c2c1]

The title compound was prepared using (1-methyl-1H-imidazol-5-yl)(pyridin-3-yl)methanone (Intermediate 10, step b) in place of (1-methyl-1H-imidazol-5-yl)(pyridin-4-yl)methanone according to the procedure described in Example 16. $^1$H NMR (400 MHz, CDCl$_3$) δ 8.58 (d, J=1.96 Hz, 1H), 8.47 (dd, J=1.34, 4.77 Hz, 1H), 8.34 (d, J=1.96 Hz, 1H), 8.02 (d, J=8.80 Hz, 1H), 7.73 (dd, J=1.96, 8.80 Hz, 1H), 7.67 (dt, J=1.96, 8.07 Hz, 1H), 7.48-7.54 (m, 3H), 7.29-7.36 (m, 2H), 7.21-7.26 (m, 2H), 6.27 (s, 1H), 3.36 (s, 3H); MS m/e 460.8 [M+H]$^+$.

Example 50

{4-Chloro-2-[ethyl(methyl)amino]-3-phenylquinolin-6-yl}(1-methyl-1H-imidazol-5-yl)pyridin-4-ylmethanol•TFA

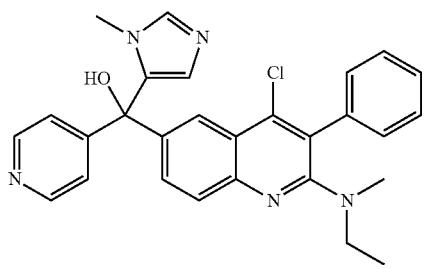

The title compound was prepared using (2,4-dichloro-3-phenylquinolin-6-yl)(1-methyl-1H-imidazol-5-yl)pyridin-4-ylmethanol (Example 16) and NHMeEt in place of (4-chlorophenyl)(2,4-dichloro-3-phenylquinolin-6-yl)pyridin-3-ylmethanol and NHMe$_2$, respectively, according to the procedure described in Example 32. $^1$H NMR (400 MHz, MeOH-d$_4$) δ 9.05 (s, 1H), 8.72-8.82 (m, 2H), 8.26 (d, J=2.20 Hz, 1H), 7.97 (d, J=8.80 Hz, 1H), 7.86 (dd, J=1.47, 5.14 Hz, 2H), 7.77 (dd, J=2.20, 9.05 Hz, 1H), 7.45-7.59 (m, 3H), 7.34-7.45 (m, 2H), 7.15 (d, J=1.71 Hz, 1H), 3.70 (s, 3H), 3.26 (q, J=7.09 Hz, 2H), 2.90 (s, 3H), 0.90 (t, J=7.09 Hz, 3H); MS m/e 483.9 [M+H]$^+$.

Example 51

(4-Chloro-3-phenylquinolin-6-yl)(1-methyl-1H-imidazol-5-yl)pyridin-3-ylmethanol•TFA

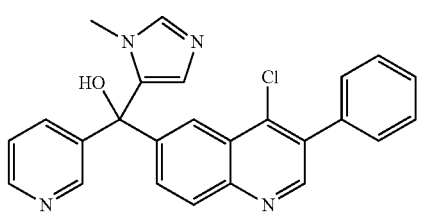 [SMILES: Cn1cncc1C(O)(c1cccnc1)c1ccc2ncc(-c3ccccc3)c(Cl)c2c1]

The title compound was prepared using 6-bromo-4-chloro-3-phenylquinoline (Intermediate 3, step c) and (1-methyl-1H-imidazol-5-yl)(pyridin-3-yl)methanone (Intermediate 10, step b) in place of 6-bromo-2,4-dichloro-3-phenylquinoline and di(pyridin-3-yl)methanone, respectively, according to the procedure described in Example 24. $^1$H NMR (400 MHz, MeOH-d$_4$) δ 9.06 (s, 1H), 8.90 (s, 1H), 8.78 (d, J=1.71 Hz, 1H), 8.71 (dd, J=1.47, 5.13 Hz, 1H), 8.49 (d, J=2.20 Hz, 1H), 8.10-8.28 (m, 2H), 7.88 (dd, J=2.20, 9.05 Hz, 1H), 7.73 (dd, J=5.14, 8.07 Hz, 1H), 7.46-7.62 (m, 5H), 7.13 (d, J=1.47 Hz, 1H), 3.73 (s, 3H); MS m/e 426.9 [M+H]$^+$.

Example 52

(3-Chlorophenyl)(4-chloro-3-phenylquinolin-6-yl)pyridin-3-ylmethanol

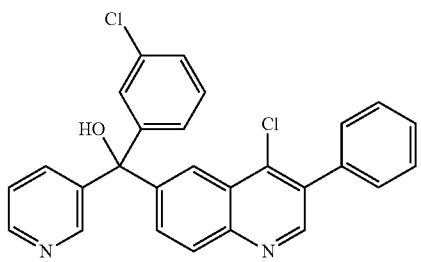

The title compound was prepared using 6-bromo-4-chloro-3-phenylquinoline (Intermediate 3, step c) in place of 6-bromo-2,4-dichloro-3-phenylquinoline according to the procedure described in Example 25. $^1$H NMR (400 MHz, CDCl$_3$) δ 8.79 (s, 1H), 8.51-8.57 (m, 1H), 8.49 (dd, J=1.47, 4.89 Hz, 1H), 8.32 (d, J=1.96 Hz, 1H), 8.07 (d, J=8.80 Hz, 1H), 7.63-7.71 (m, 2H), 7.46-7.53 (m, 4H), 7.37-7.41 (m, 1H), 7.23-7.31 (m, 4H), 7.18 (dt, J=1.74, 7.27 Hz, 1H); MS m/e 456.7 [M+H]$^+$.

Example 53

(4-Chloro-3-phenylquinolin-6-yl)(1-methyl-1H-imidazol-5-yl)pyridin-4-ylmethanol•TFA

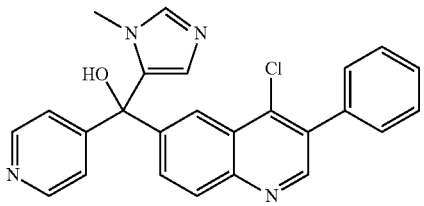 [SMILES: Cn1cncc1C(O)(c1ccncc1)c1ccc2ncc(-c3ccccc3)c(Cl)c2c1]

The title compound was prepared using 6-bromo-4-chloro-3-phenylquinoline (Intermediate 3, step c) and (1-methyl-1H-imidazol-5-yl)(pyridin-4-yl)methanone (Intermediate 9, step b) in place of 6-bromo-2,4-dichloro-3-phenylquinoline and di(pyridin-3-yl)methanone, respectively, according to the procedure described in Example 24. $^1$H NMR (400 MHz, MeOH-$d_4$) δ 9.08 (s, 1H), 8.90 (s, 1H), 8.78-8.82 (m, 2H), 8.53 (d, J=1.96 Hz, 1H), 8.21 (d, J=9.05 Hz, 1H), 7.93-7.96 (m, 2H), 7.54-7.60 (m, 6H), 7.21 (d, J=1.71 Hz, 1H), 3.71 (s, 3H); MS m/e 426.9 [M+H]$^+$.

Example 54

(2,4-Dichloro-3-phenylquinolin-6-yl)(3-methoxyphenyl)pyridin-3-ylmethanol

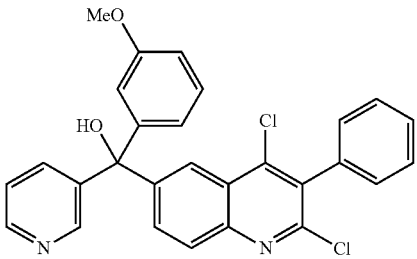 [SMILES: COc1cccc(C(O)(c2cccnc2)c2ccc3nc(Cl)c(-c4ccccc4)c(Cl)c3c2)c1]

The title compound was prepared using (3-methoxyphenyl)(pyridin-3-yl)methanone in place of (3-chlorophenyl)(pyridin-3-yl)methanone according to the procedure described in Example 25. $^1$H NMR (400 MHz, CDCl$_3$) δ 8.55 (d, J=2.45 Hz, 1H), 8.49 (dd, J=1.59, 4.77 Hz, 1H), 8.30 (d, J=1.96 Hz, 1H), 8.01 (d, J=8.80 Hz, 1H), 7.67-7.77 (m, 2H), 7.48-7.57 (m, 3H), 7.30-7.37 (m, 2H), 7.22-7.30 (m, 2H), 6.83-6.91 (m, 2H), 6.78-6.83 (m, 1H), 3.74 (s, 3H); MS m/e 486.7 [M+H]$^+$.

Example 55

(2,4-Dichloro-3-phenylquinolin-6-yl)(4-methoxyphenyl)(pyridin-3-yl)methanol

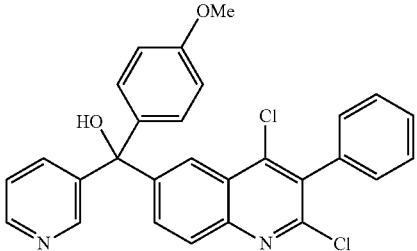

The title compound was prepared using (4-methoxyphenyl)(pyridin-3-yl)methanone in place of (3-chlorophenyl)(pyridin-3-yl)methanone according to the procedure described in Example 25. $^1$H NMR (400 MHz, CDCl$_3$) δ 8.58 (d, J=2.20 Hz, 1H), 8.51 (dd, J=1.47, 4.89 Hz, 1H), 8.31 (d, J=1.96 Hz, 1H), 8.01 (d, J=9.05 Hz, 1H), 7.68-7.75 (m, 2H), 7.48-7.56 (m, 3H), 7.32 (dd, J=1.71, 7.58 Hz, 2H), 7.24-7.30 (m, 1H), 7.14-7.21 (m, 2H), 6.84-6.91 (m, 2H), 3.81 (s, 3H); MS m/e 486.7 [M+H]$^+$.

Example 56

(3-Chlorophenyl)(6-chloropyridin-3-yl)(2,4-dichloro-3-phenylquinolin-6-yl)methanol

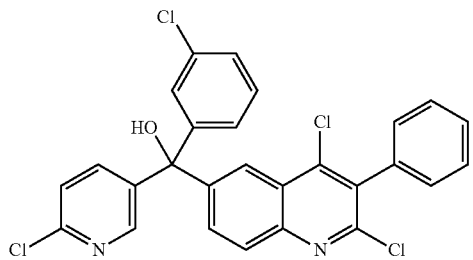 [SMILES: OC(c1ccc(Cl)nc1)(c1cccc(Cl)c1)c1ccc2nc(Cl)c(-c3ccccc3)c(Cl)c2c1]

The title compound was prepared using (3-chlorophenyl)(6-chloropyridin-3-yl)methanone in place of (3-chlorophenyl)(pyridin-3-yl)methanone according to the procedure described in Example 25. $^1$H NMR (400 MHz, CDCl$_3$) δ 8.37 (d, J=2.69 Hz, 1H), 8.25 (d, J=1.96 Hz, 1H), 8.06 (d, J=9.05 Hz, 1H), 7.68 (dd, J=2.20, 8.80 Hz, 2H), 7.48-7.58 (m, 3H), 7.30-7.39 (m, 6H), 7.13-7.19 (m, 1H); MS m/e 526.7 [M+H]$^+$.

Example 57

(6-Chloropyridin-3-yl)(2,4-dichloro-3-phenylquinolin-6-yl)(3-fluorophenyl)methanol

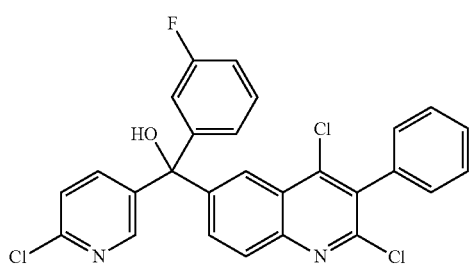

The title compound was prepared using (3-fluorophenyl)(6-chloropyridin-3-yl)methanone in place of (3-chlorophenyl)(pyridin-3-yl)methanone according to the procedure described in Example 25. $^1$H NMR (400 MHz, CDCl$_3$) δ 8.35 (d, J=2.69 Hz, 1H), 8.25 (d, J=1.96 Hz, 1H), 8.05 (d, J=8.80

Hz, 1H), 7.68 (dt, J=2.26, 8.68 Hz, 2H), 7.48-7.55 (m, 4H), 7.30-7.35 (m, 3H), 7.05 (d, J=8.80 Hz, 3H); MS m/e 508.8 [M+H]+.

Example 58

(4-Chloro-3-phenylquinolin-6-yl)(3-methoxyphenyl)pyridin-3-ylmethanol

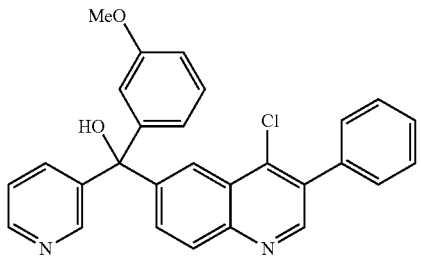 [SMILES: COc1cccc(C(O)(c2cccnc2)c2ccc3ncc(-c4ccccc4)c(Cl)c3c2)c1]

The title compound was prepared using 6-bromo-4-chloro-3-phenylquinoline (Intermediate 3, step c) and (3-methoxyphenyl)(pyridin-3-yl)methanone in place of 6-bromo-2,4-dichloro-3-phenylquinoline and (3-chlorophenyl)(pyridin-3-yl)methanone, respectively, according to the procedure described in Example 25. $^1$H NMR (400 MHz, CDCl$_3$) δ 8.83 (s, 1H), 8.61-8.65 (m, 1H), 8.53-8.57 (m, 1H), 8.37 (d, J=1.96 Hz, 1H), 8.09 (d, J=9.05 Hz, 1H), 7.68-7.75 (m, 2H), 7.50-7.55 (m, 5H), 7.26-7.30 (m, 2H), 6.83-6.91 (m, 3H), 3.75 (s, 3H); MS m/e 452.9 [M+H]+.

Example 59

(4-Chloro-3-phenylquinolin-6-yl)(4-methoxyphenyl)pyridin-3-ylmethanol

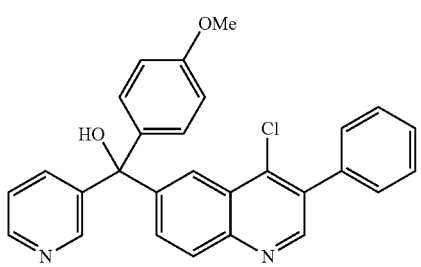 [SMILES: COc1ccc(C(O)(c2cccnc2)c2ccc3ncc(-c4ccccc4)c(Cl)c3c2)cc1]

The title compound was prepared using 6-bromo-4-chloro-3-phenylquinoline (Intermediate 3, step c) and (4-methoxyphenyl)(pyridin-3-yl)methanone in place of 6-bromo-2,4-dichloro-3-phenylquinoline and (3-chlorophenyl)(pyridin-3-yl)methanone, respectively, according to the procedure described in Example 25. $^1$H NMR (400 MHz, CDCl$_3$) δ 8.81 (s, 1H), 8.60-8.68 (m, 1H), 8.51-8.57 (m, 1H), 8.38 (d, J=1.96 Hz, 1H), 8.08 (d, J=8.80 Hz, 1H), 7.67-7.78 (m, 2H), 7.44-7.57 (m, 5H), 7.25-7.32 (m, 1H), 7.20 (d, J=8.80 Hz, 2H), 6.88 (d, J=8.80 Hz, 2H), 3.81 (s, 3H); MS m/e 452.9 [M+H]+.

Example 60

(3-Chlorophenyl)(4-chloro-3-phenylquinolin-6-yl)(6-chloropyridin-3-yl)methanol

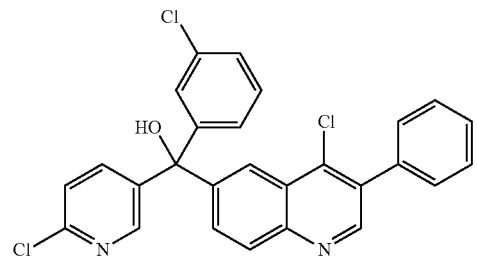 [SMILES: OC(c1ccc(Cl)nc1)(c1cccc(F)c1)c1ccc2ncc(-c3ccccc3)c(Cl)c2c1]

The title compound was prepared using 6-bromo-4-chloro-3-phenylquinoline (Intermediate 3, step c) and (3-chlorophenyl)(6-chloropyridin-3-yl)methanone in place of 6-bromo-2,4-dichloro-3-phenylquinoline and (3-chlorophenyl)(pyridin-3-yl)methanone, respectively, according to the procedure described in Example 25. $^1$H NMR (400 MHz, CDCl$_3$) δ 8.81 (s, 1H), 8.40 (d, J=2.69 Hz, 1H), 8.29 (d, J=2.20 Hz, 1H), 8.10 (d, J=9.05 Hz, 1H), 7.70 (dd, J=2.69, 8.31 Hz, 1H), 7.65 (dd, J=2.08, 8.93 Hz, 1H), 7.47-7.54 (m, 5H), 7.37 (d, J=1.47 Hz, 1H), 7.31-7.35 (m, 3H), 7.18 (dt, J=1.80, 7.15 Hz, 1H); MS m/e 490.8 [M+H]+.

Example 61

(4-Chloro-3-phenylquinolin-6-yl)(6-chloropyridin-3-yl)(3-fluorophenyl)methanol

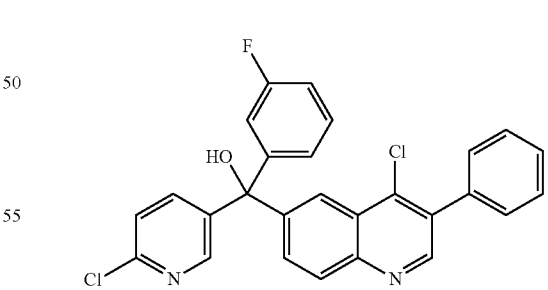

The title compound was prepared using 6-bromo-4-chloro-3-phenylquinoline (Intermediate 3, step c) and (3-fluorophenyl)(6-chloropyridin-3-yl)methanone in place of 6-bromo-2,4-dichloro-3-phenylquinoline and (3-chlorophenyl)(pyridin-3-yl)methanone, respectively, according to the procedure described in Example 25. $^1$H NMR (400 MHz, CDCl$_3$) δ 8.81 (s, 1H), 8.40 (d, J=2.69 Hz, 1H), 8.30 (d, J=2.20 Hz, 1H), 8.10

(d, J=8.80 Hz, 1H), 7.68 (ddd, J=2.20, 8.62, 17.55 Hz, 2H), 7.46-7.54 (m, 5H), 7.33 (d, J=8.56 Hz, 2H), 7.05-7.11 (m, 3H); MS m/e 474.9 [M+H]⁺.

Example 62

[4-Chloro-2-(dimethylamino)-3-phenylquinolin-6-yl](4-methoxyphenyl)pyridin-3-ylmethanol•TFA

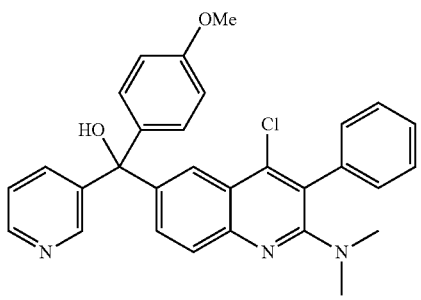 [SMILES: COc1ccc(C(O)(c2cccnc2)c2ccc3nc(N(C)C)c(-c4ccccc4)c(Cl)c3c2)cc1]

The title compound was prepared using (2,4-dichloro-3-phenylquinolin-6-yl)(4-methoxyphenyl)(pyridin-3-yl)methanol (Example 55) in place of (4-chlorophenyl)(2,4-dichloro-3-phenylquinolin-6-yl)pyridin-3-ylmethanol according to the procedure described in Example 32 except heating of the reaction mixture at 80° C. for 16 hours. ¹H NMR (400 MHz, MeOH-d₄) δ 8.91 (s, 1H), 8.77-8.85 (m, 1H), 8.74 (d, J=4.55 Hz, 1H), 8.68 (d, J=5.56 Hz, 1H), 8.57 (d, J=8.08 Hz, 1H), 8.41 (d, J=8.59 Hz, 1H), 8.24 (d, J=2.02 Hz, 1H), 8.01 (d, J=8.59 Hz, 1H), 7.95-7.98 (m, 1H), 7.81 (dd, J=2.02, 9.09 Hz, 1H), 7.50-7.59 (m, 1H), 7.40-7.47 (m, 2H), 7.22 (d, J=9.09 Hz, 1H), 6.94 (d, J=9.09 Hz, 1H), 6.87-6.92 (m, 1H), 3.80 (s, 3H), 3.76 (s, 3H), 2.96 (s, 3H); MS m/e 495.9 [M+H]⁺.

Example 63

{4-Chloro-2-[(2-methoxyethyl)(methyl)amino]-3-phenylquinolin-6-yl}(1-methyl-1H-imidazol-5-yl)pyridin-4-ylmethanol•TFA

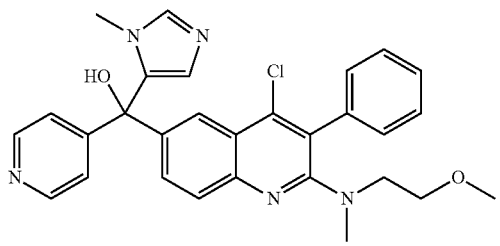 [SMILES: COCCN(C)c1nc2ccc(C(O)(c3ccncc3)c3cncn3C)cc2c(Cl)c1-c1ccccc1]

The title compound was prepared using (2,4-dichloro-3-phenylquinolin-6-yl)(1-methyl-1H-imidazol-5-yl)(pyridin-4-yl)methanol (Example 16) and 2-methoxy-N-methylethanamine in place of (4-chlorophenyl)(2,4-dichloro-3-phenylquinolin-6-yl)pyridin-3-ylmethanol and NHMe₂, respectively, according to the procedure described in Example 32 except heating of the reaction mixture at 80° C. for 16 hours in the absence of MeOH. ¹H NMR (400 MHz, MeOH-d₄) δ 9.07 (s, 1H), 8.82 (br. s., 2H), 8.33 (d, J=2.02 Hz, 1H), 7.92-8.01 (m, 3H), 7.80-7.87 (m, 1H), 7.49-7.59 (m, 3H), 7.38-7.46 (m, 2H), 7.20 (s, 1H), 3.69 (s, 3H), 3.48-3.57 (m, 4H), 3.33 (s, 3H), 2.87 (s, 3H); MS m/e 513.9 [M+H]⁺.

Example 64

(4-Chloro-2-{[2-(dimethylamino)ethyl](methyl)amino}-3-phenylquinolin-6-yl)(1-methyl-1H-imidazol-5-yl)pyridin-4-ylmethanol•TFA

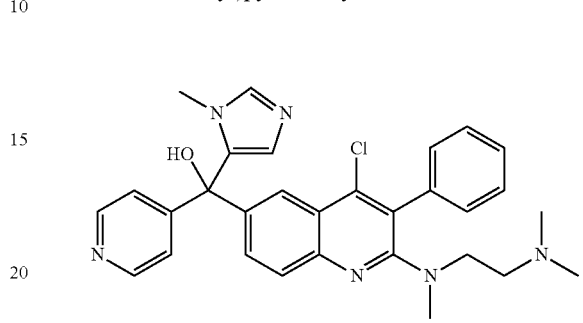

The title compound was prepared using (2,4-dichloro-3-phenylquinolin-6-yl)(1-methyl-1H-imidazol-5-yl)(pyridin-4-yl)methanol (Example 16) and N¹,N¹,N²-trimethylethane-1,2-diamine in place of (4-chlorophenyl)(2,4-dichloro-3-phenylquinolin-6-yl)pyridin-3-ylmethanol and NHMe₂, respectively, according to the procedure described in Example 32 except heating of the reaction mixture at 80° C. for 16 hours in the absence of MeOH. ¹H NMR (400 MHz, MeOH-d₄) δ 9.08 (s, 1H), 8.78-8.90 (m, 2H), 8.25 (d, J=2.02 Hz, 1H), 7.99-8.07 (m, 2H), 7.84 (d, J=8.59 Hz, 1H), 7.71-7.76 (m, 1H), 7.50-7.57 (m, 2H), 7.48 (d, J=7.07 Hz, 1H), 7.38 (d, J=6.57 Hz, 2H), 7.19 (s, 1H), 3.80 (t, J=5.81 Hz, 2H), 3.70 (s, 3H), 3.33 (t, J=6.06 Hz, 2H), 3.00 (s, 6H), 2.54 (s, 3H); MS m/e 527.0 [M+H]⁺.

Example 65

(6-Chloropyridin-3-yl)(2,4-dichloro-3-phenylquinolin-6-yl)(3-methoxyphenyl)methanol

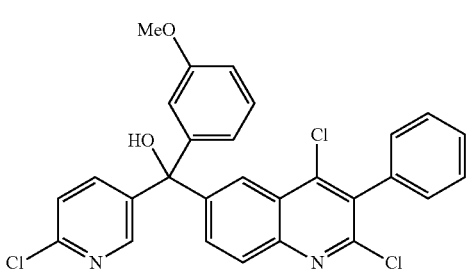 [SMILES: COc1cccc(C(O)(c2ccc(Cl)nc2)c2ccc3nc(Cl)c(-c4ccccc4)c(Cl)c3c2)c1]

The title compound was prepared using (6-chloropyridin-3-yl)(3-methoxyphenyl)methanone in place of (3-chlorophenyl)(pyridin-3-yl)methanone according to the procedure described in Example 25. ¹H NMR (400 MHz, CDCl₃) δ 8.40 (d, J=2.53 Hz, 1H), 8.29 (d, J=2.02 Hz, 1H), 8.04 (d, J=8.59 Hz, 1H), 7.70 (td, J=2.27, 6.19 Hz, 2H), 7.49-7.54 (m, 3H), 7.32 (dd, J=4.29, 8.34 Hz, 4H), 6.90 (d, J=9.09 Hz, 1H), 6.78-6.83 (m, 2H), 3.76 (s, 3H); MS m/e 520.8 [M+H]⁺.

Example 66

(2-Chloropyridin-4-yl)(2,4-dichloro-3-phenylquinolin-6-yl)(1-methyl-1H-imidazol-5-yl)methanol•TFA

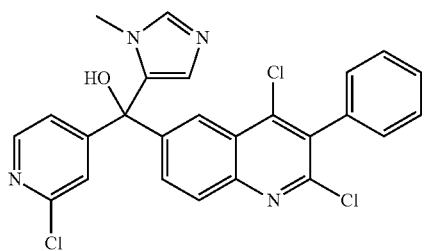

The title compound was prepared using (2-chloropyridin-4-yl)(1-methyl-1H-imidazol-5-yl)methanone (Intermediate 54, step b) in place of di(pyridin-3-yl)methanone according to the procedure described in Example 24. ¹H NMR (400 MHz, MeOH-d₄) δ 9.07 (s, 1H), 8.44 (d, J=5.05 Hz, 1H), 8.39 (d, J=2.02 Hz, 1H), 8.11 (d, J=9.09 Hz, 1H), 7.91 (dd, J=2.27, 8.84 Hz, 1H), 7.63 (s, 1H), 7.48-7.58 (m, 3H), 7.40-7.48 (m, 1H), 7.29-7.40 (m, 2H), 7.16 (s, 1H), 3.70 (s, 3H); MS m/e 494.9 [M+H]⁺.

Example 67

(2,4-Dichloro-3-phenylquinolin-6-yl)(1-methyl-1H-imidazol-5-yl)(2-methylpyridin-4-yl)methanol•TFA

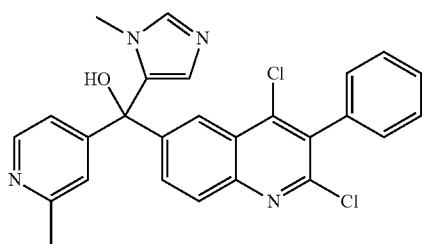 [SMILES: Cc1cc(C(O)(c2ccc3nc(Cl)c(-c4ccccc4)c(Cl)c3c2)c2cncn2C)ccn1]

The title compound was prepared using (1-methyl-1H-imidazol-5-yl)(2-methylpyridin-4-yl)methanone (Intermediate 55, step b) in place of di(pyridin-3-yl)methanone according to the procedure described in Example 24. ¹H NMR (400 MHz, MeOH-d₄) δ 9.07 (s, 1H), 8.68 (d, J=6.06 Hz, 1H), 8.48 (s, 1H), 8.11 (d, J=8.59 Hz, 1H), 7.89-7.95 (m, 2H), 7.85 (d, J=5.56 Hz, 1H), 7.49-7.58 (m, 3H), 7.34 (d, J=6.06 Hz, 2H), 7.24 (s, 1H), 3.70 (s, 3H); MS m/e 474.9 [M+H]⁺.

Example 68

(2,4-Dichloro-3-phenylquinolin-6-yl)(2-methoxypyridin-4-yl)(1-methyl-1H-imidazol-5-yl)methanol•TFA

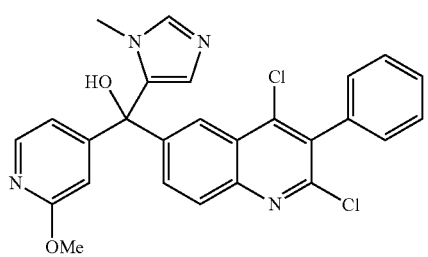 [SMILES: COc1cc(C(O)(c2ccc3nc(Cl)c(-c4ccccc4)c(Cl)c3c2)c2cncn2C)ccn1]

The title compound was prepared using (2-methoxypyridin-4-yl)(1-methyl-1H-imidazol-5-yl)methanone (Intermediate 56, step b) in place of di(pyridin-3-yl)methanone according to the procedure described in Example 24. ¹H NMR (400 MHz, MeOH-d₄) δ 9.02 (s, 1H), 8.37 (s, 1H), 8.20 (d, J=5.56 Hz, 1H), 8.09 (d, J=9.09 Hz, 1H), 7.91 (dd, J=2.02, 9.09 Hz, 1H), 7.48-7.58 (m, 3H), 7.31-7.38 (m, 2H), 7.07 (s, 1H), 6.96-7.04 (m, 1H), 6.89 (s, 1H), 3.92 (s, 3H), 3.71 (s, 3H); MS m/e 490.8 [M+H]⁺.

Example 69

(2,4-Dichloro-3-phenylquinolin-6-yl)(3-methoxyphenyl)(6-methylpyridin-3-yl)methanol•TFA

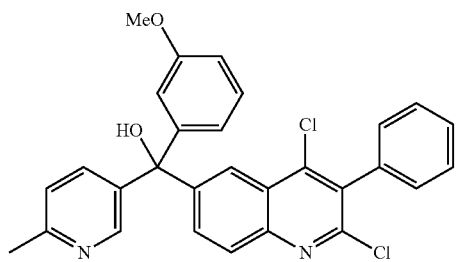 [SMILES: COc1cccc(C(O)(c2ccc(C)nc2)c2ccc3nc(Cl)c(-c4ccccc4)c(Cl)c3c2)c1]

The title compound was prepared using (3-methoxyphenyl)(6-methylpyridin-3-yl)methanone in place of di(pyridin-3-yl)methanone according to the procedure described in Example 24. ¹H NMR (400 MHz, MeOH-d₄) δ 8.67 (s, 1H), 8.42 (dd, J=2.27, 8.34 Hz, 1H), 8.30 (d, J=2.02 Hz, 1H), 8.03 (d, J=9.09 Hz, 1H), 7.83-7.89 (m, 2H), 7.48-7.57 (m, 3H), 7.28-7.38 (m, 3H), 6.92-6.99 (m, 2H), 6.85 (d, J=6.57 Hz, 1H), 3.75 (s, 3H), 2.79 (s, 3H); MS m/e 500.9 [M+H]⁺.

Example 70

(3-Chlorophenyl)(2,4-dichloro-3-phenylquinolin-6-yl)(6-methylpyridin-3-yl)methanol•TFA

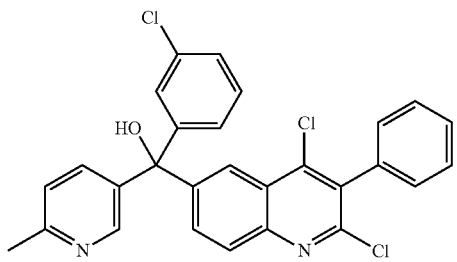

The title compound was prepared using (3-chlorophenyl)(6-methylpyridin-3-yl)methanone in place of di(pyridin-3-yl)methanone according to the procedure described in Example 24. $^1$H NMR (400 MHz, MeOH-d$_4$) δ 8.70 (d, J=2.53 Hz, 1H), 8.43 (dd, J=2.27, 8.34 Hz, 1H), 8.29 (s, 1H), 8.04 (d, J=8.59 Hz, 1H), 7.82-7.92 (m, 2H), 7.48-7.58 (m, 3H), 7.46 (s, 1H), 7.41 (d, J=5.05 Hz, 2H), 7.33 (d, J=6.57 Hz, 2H), 7.27 (dt, J=2.27, 4.55 Hz, 1H), 2.79 (s, 3H); MS m/e 504.8 [M+H]⁺.

Example 71

(2,4-Dichloro-3-phenylquinolin-6-yl)(3-fluorophenyl)(6-methylpyridin-3-yl)methanol•TFA

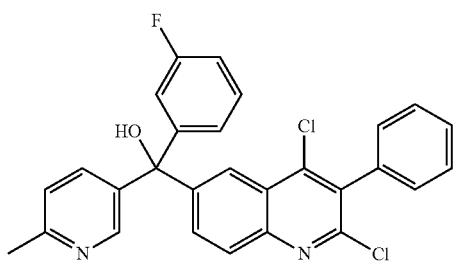 [SMILES: Cc1ccc(C(O)(c2cccc(F)c2)c2ccc3nc(Cl)c(-c4ccccc4)c(Cl)c3c2)cn1]

The title compound was prepared using (3-fluorophenyl)(6-methylpyridin-3-yl)methanone in place of di(pyridin-3-yl)methanone according to the procedure described in Example 24. $^1$H NMR (400 MHz, MeOH-d$_4$) δ 8.68 (d, J=2.02 Hz, 1H), 8.41 (dd, J=2.02, 8.59 Hz, 1H), 8.28 (d, J=2.02 Hz, 1H), 8.04 (d, J=9.09 Hz, 1H), 7.85 (dt, J=2.08, 8.97 Hz, 2H), 7.48-7.58 (m, 3H), 7.40-7.48 (m, 1H), 7.33 (d, J=6.57 Hz, 2H), 7.10-7.22 (m, 3H), 2.78 (s, 3H); MS m/e 488.9 [M+H]⁺.

Example 72

1-{4-Chloro-6-[hydroxy(1-methyl-1H-imidazol-5-yl)pyridin-4-ylmethyl]-3-phenylquinolin-2-yl}piperidin-4-ol•TFA

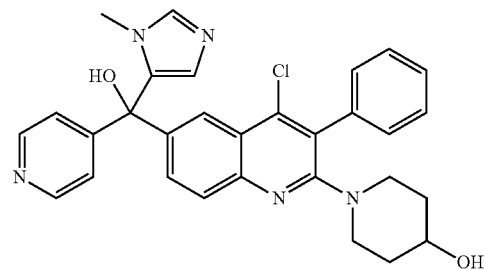 [SMILES: Cn1cncc1C(O)(c1ccncc1)c1ccc2nc(N3CCC(O)CC3)c(-c3ccccc3)c(Cl)c2c1]

The title compound was prepared using (2,4-dichloro-3-phenylquinolin-6-yl)(1-methyl-1H-imidazol-5-yl)(pyridin-4-yl)methanol (Example 16) and piperidin-4-ol in place of (4-chlorophenyl)(2,4-dichloro-3-phenylquinolin-6-yl)pyridin-3-ylmethanol and NHMe$_2$, respectively, according to the procedure described in Example 32 except heating of the reaction mixture at 90° C. for 64 hours. $^1$H NMR (400 MHz, MeOH-d$_4$) δ 9.07 (s, 1H), 8.81 (d, J=6.57 Hz, 2H), 8.30 (d, J=2.02 Hz, 1H), 7.93-8.02 (m, 3H), 7.77 (dd, J=2.27, 8.84 Hz, 1H), 7.51-7.60 (m, 2H), 7.40-7.51 (m, 3H), 7.20 (s, 1H), 3.70 (s, 3H), 3.68-3.70 (m, 1H), 3.60 (dd, J=4.80, 8.84 Hz, 2H), 2.96-3.09 (m, 2H), 1.61-1.72 (m, 2H), 1.24-1.38 (m, 2H); MS m/e 525.9 [M+H]⁺.

Example 73

1-{2-Chloro-6-[hydroxy(1-methyl-1H-imidazol-5-yl)pyridin-4-ylmethyl]-3-phenylquinolin-4-yl}piperidin-4-ol•TFA

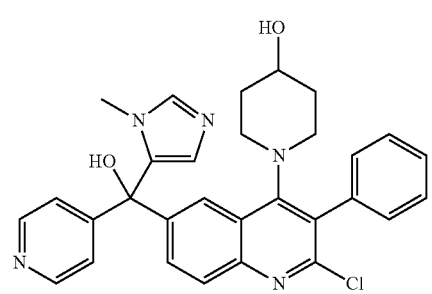 [SMILES: Cn1cncc1C(O)(c1ccncc1)c1ccc2nc(Cl)c(-c3ccccc3)c(N3CCC(O)CC3)c2c1]

The title compound was isolated from the reaction that formed Example 72. $^1$H NMR (400 MHz, MeOH-d$_4$) δ 9.03-9.11 (m, 1H), 8.76 (d, J=6.57 Hz, 2H), 8.09 (d, J=2.02 Hz, 1H), 7.93-8.02 (m, 1H), 7.88 (d, J=2.53 Hz, 1H), 7.75-7.88 (m, 2H), 7.40-7.57 (m, 3H), 7.23-7.35 (m, 2H), 7.09-7.23 (m, 1H), 3.72 (s, 3H), 3.44-3.57 (m, 1H), 2.97-3.09 (m, 2H), 2.32-2.54 (m, 2H), 1.57-1.72 (m, 2H), 1.30 (m, 2H); MS m/e 525.9 [M+H]⁺.

Example 74

(4-Chloro-2-methoxy-3-phenylquinolin-6-yl)(1-methyl-1H-imidazol-5-yl)pyridin-4-ylmethanol•TFA

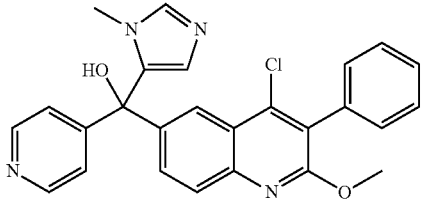 [SMILES: COc1nc2ccc(C(O)(c3ccncc3)c3cncn3C)cc2c(Cl)c1-c1ccccc1]

The title compound was isolated from the reaction that formed Example 72. ¹H NMR (400 MHz, MeOH-d₄) δ 9.04 (s, 1H), 8.73 (d, J=6.06 Hz, 2H), 8.27 (d, J=2.02 Hz, 1H), 7.97 (d, J=9.09 Hz, 1H), 7.79 (d, J=6.57 Hz, 2H), 7.75 (dd, J=2.27, 8.84 Hz, 1H), 7.41-7.50 (m, 3H), 7.28-7.33 (m, 2H), 7.12 (s, 1H), 3.99 (s, 3H), 3.70 (s, 3H); MS m/e 456.9 [M+H]⁺.

Example 75

[4-Chloro-2-(4-methoxypiperidin-1-yl)-3-phenylquinolin-6-yl](1-methyl-1H-imidazol-5-yl)pyridin-4-ylmethanol•TFA

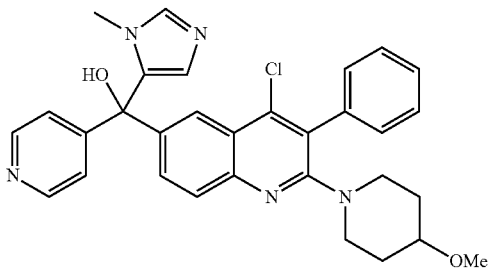 [SMILES: COC1CCN(c2nc3ccc(C(O)(c4ccncc4)c4cncn4C)cc3c(Cl)c2-c2ccccc2)CC1]

The title compound was prepared using (2,4-dichloro-3-phenylquinolin-6-yl)(1-methyl-1H-imidazol-5-yl)(pyridin-4-yl)methanol (Example 16) and 4-methoxypiperidine in place of (4-chlorophenyl)(2,4-dichloro-3-phenylquinolin-6-yl)pyridin-3-ylmethanol and NHMe₂, respectively, according to the procedure described in Example 32 except heating of the reaction mixture at 90° C. for 66 hours. ¹H NMR (400 MHz, MeOH-d₄) δ 9.06 (s, 1H), 8.79 (d, J=6.57 Hz, 2H), 8.27 (d, J=2.02 Hz, 1H), 7.90-7.97 (m, 3H), 7.75 (dd, J=2.02, 8.59 Hz, 1H), 7.50-7.58 (m, 2H), 7.41-7.50 (m, 3H), 7.17 (s, 1H), 3.71 (s, 3H), 3.48-3.57 (m, 2H), 3.35-3.37 (m, 1H), 3.28 (s, 3H), 2.97-3.08 (m, 2H), 1.64-1.76 (m, 2H), 1.31-1.39 (m, 2H); MS m/e 539.8 [M+H]⁺.

Example 76

{2-[Butyl(methyl)amino]-4-chloro-3-phenylquinolin-6-yl}(1-methyl-1H-imidazol-5-yl)pyridin-4-ylmethanol•TFA

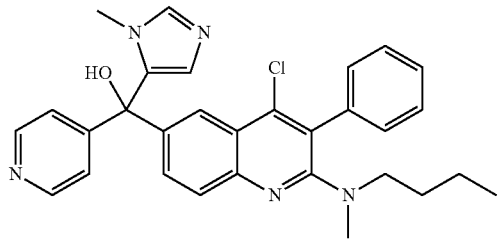 [SMILES: CCCCN(C)c1nc2ccc(C(O)(c3ccncc3)c3cncn3C)cc2c(Cl)c1-c1ccccc1]

The title compound was prepared using (2,4-dichloro-3-phenylquinolin-6-yl)(1-methyl-1H-imidazol-5-yl)(pyridin-4-yl)methanol (Example 16) and N-methylbutan-1-amine in place of (4-chlorophenyl)(2,4-dichloro-3-phenylquinolin-6-yl)pyridin-3-ylmethanol and NHMe₂, respectively, according to the procedure described in Example 32. ¹H NMR (400 MHz, MeOH-d₄) δ 9.07 (s, 1H), 8.81 (d, J=6.57 Hz, 2H), 8.32 (d, J=2.02 Hz, 1H), 8.03 (d, J=9.09 Hz, 1H), 7.98 (d, J=6.57 Hz, 2H), 7.82 (dd, J=2.02, 9.09 Hz, 1H), 7.48-7.61 (m, 3H), 7.41 (d, J=6.57 Hz, 2H), 7.20 (s, 1H), 3.70 (s, 3H), 3.13-3.21 (m, 2H), 3.01 (s, 3H), 1.23-1.40 (m, 2H), 0.98-1.08 (m, 2H), 0.74-0.84 (m, 3H); MS m/e 512.0 [M+H]⁺.

Example 77

[4-Chloro-3-phenyl-2-(4-phenylpiperazin-1-yl)quinolin-6-yl](1-methyl-1H-imidazol-5-yl)pyridin-4-ylmethanol•TFA

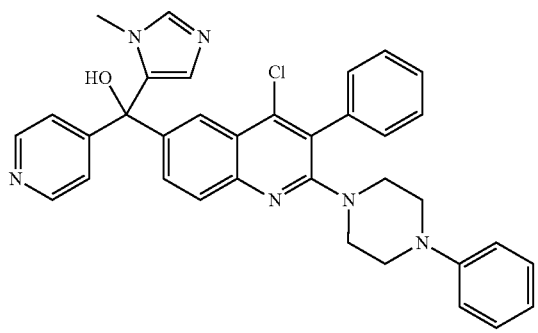 [SMILES: Cn1cncc1C(O)(c1ccncc1)c1ccc2nc(N3CCN(c4ccccc4)CC3)c(-c3ccccc3)c(Cl)c2c1]

The title compound was prepared using (2,4-dichloro-3-phenylquinolin-6-yl)(1-methyl-1H-imidazol-5-yl)(pyridin-4-yl)methanol (Example 16) and 1-phenylpiperazine in place of (4-chlorophenyl)(2,4-dichloro-3-phenylquinolin-6-yl)pyridin-3-ylmethanol and NHMe₂, respectively, according to the procedure described in Example 32 except heating of the reaction mixture at 90° C. for 66 hours. ¹H NMR (400 MHz, MeOH-d₄) δ 9.07 (s, 1H), 8.80 (d, J=6.57 Hz, 2H), 8.30 (d, J=2.02 Hz, 1H), 7.90-8.06 (m, 3H), 7.75 (dd, J=2.27, 8.84 Hz, 1H), 7.41-7.62 (m, 5H), 7.28-7.39 (m, 2H), 7.04-7.22 (m, 4H), 3.71 (s, 3H), 3.41-3.51 (m, 4H), 3.13-3.22 (m, 4H); MS m/e 587.0 [M+H]⁺.

Example 78

(4-Butyl-2-chloro-3-phenylquinolin-6-yl)(1-methyl-1H-imidazol-5-yl)pyridin-4-ylmethanol•TFA

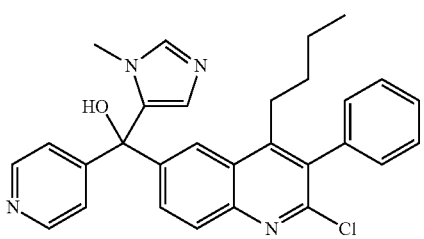 [SMILES: CCCCc1c(-c2ccccc2)c(Cl)nc2ccc(C(O)(c3ccncc3)c3cncn3C)cc12]

The title compound was isolated from the reaction that formed Example 16. ¹H NMR (400 MHz, MeOH-d₄) δ 9.08 (s, 1H), 8.79 (d, J=6.57 Hz, 2H), 8.10 (d, J=2.02 Hz, 1H), 8.06 (d, J=9.09 Hz, 1H), 7.88 (d, J=6.57 Hz, 3H), 7.46-7.57 (m, 3H), 7.27 (d, J=6.06 Hz, 2H), 7.18 (s, 1H), 3.71 (s, 3H), 2.74-2.84 (m, 2H), 1.37-1.47 (m, 2H), 1.13-1.22 (m, 2H), 0.73 (t, J=7.33 Hz, 3H); MS m/e 483.2 [M+H]⁺.

Example 79

(3-Chlorophenyl)(2,4-dimethoxy-3-phenylquinolin-6-yl)pyridin-3-ylmethanol•TFA

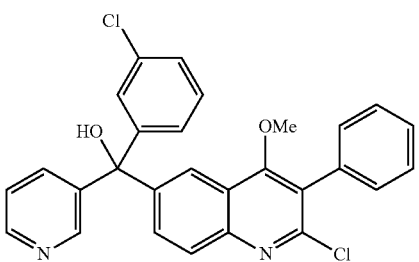

A mixture of (3-chlorophenyl)(2,4-dichloro-3-phenylquinolin-6-yl)(pyridin-3-yl)methanol (20 mg, 0.041 mmol, Example 25) and NaOMe (50 mg, 0.93 mmol) in MeOH (1 mL) was heated in a sealed tube at 82° C. for 24 hours and purified by reverse phase HPLC (water/acetonitrile/0.1% TFA) to provide the title compound as a white solid. ¹H NMR (400 MHz, MeOH-d₄) δ 8.89 (s, 1H), 8.80 (d, J=5.38 Hz, 1H), 8.56 (d, J=8.31 Hz, 1H), 8.00-8.07 (m, 1H), 7.97 (s, 1H), 7.85 (d, J=8.80 Hz, 1H), 7.56-7.61 (m, 1H), 7.35-7.50 (m, 8H), 7.25-7.32 (m, 1H), 3.97 (s, 3H), 3.43 (s, 3H); MS m/e 483.1 [M+H]⁺.

Example 80

(4-Chloro-2-methoxy-3-phenylquinolin-6-yl)(3-chlorophenyl)pyridin-3-ylmethanol•TFA

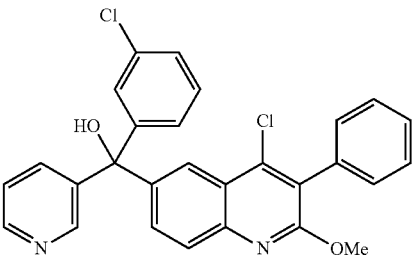 [SMILES: COc1nc2ccc(C(O)(c3cccnc3)c3cccc(Cl)c3)cc2c(Cl)c1-c1ccccc1]

The title compound was isolated from the reaction that formed Example 79. ¹H NMR (400 MHz, MeOH-d₄) δ 8.86 (s, 1H), 8.77 (d, J=5.38 Hz, 1H), 8.50 (d, J=8.31 Hz, 1H), 8.12 (s, 1H), 7.95-8.02 (m, 1H), 7.92 (d, J=8.80 Hz, 1H), 7.67 (dd, J=1.47, 8.56 Hz, 1H), 7.36-7.50 (m, 6H), 7.22-7.34 (m, 3H), 3.98 (s, 3H); MS m/e 487.2 [M+H]⁺.

Example 81

(4-Chloro-2-ethoxy-3-phenylquinolin-6-yl)(3-chlorophenyl)pyridin-3-ylmethanol•TFA

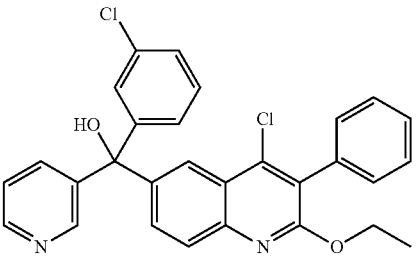 [SMILES: CCOc1nc2ccc(C(O)(c3cccnc3)c3cccc(Cl)c3)cc2c(Cl)c1-c1ccccc1]

The title compound was prepared using NaOEt in EtOH in place of NaOMe in MeOH according to the procedure described in Example 79. ¹H NMR (400 MHz, MeOH-d₄) δ 8.83-8.94 (m, 1H), 8.75-8.83 (m, 1H), 8.51 (d, 1H), 8.11 (s, 1H), 7.97-8.06 (m, 1H), 7.89 (d, J=9.05 Hz, 1H), 7.66 (s, 1H), 7.36-7.51 (m, 6H), 7.31 (d, J=6.85 Hz, 2H), 7.27 (d, J=4.16 Hz, 1H), 4.48 (q, J=7.09 Hz, 2H), 1.28 (t, J=7.09 Hz, 3H); MS m/e 501.1 [M+H]⁺.

Example 82

(2,4-Diethoxy-3-phenylquinolin-6-yl)(1-methyl-1H-imidazol-5-yl)pyridin-4-ylmethanol•TFA

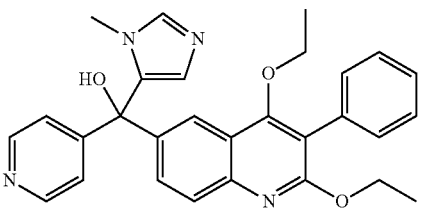 [SMILES: CCOc1nc2ccc(C(O)(c3ccncc3)c3cncn3C)cc2c(OCC)c1-c1ccccc1]

The title compound was prepared using (2,4-dichloro-3-phenylquinolin-6-yl)(1-methyl-1H-imidazol-5-yl)(pyridin-4-yl)methanol (Example 16) and NaOEt in EtOH in place of (3-chlorophenyl)(2,4-dichloro-3-phenylquinolin-6-yl)(pyridin-3-yl)methanol and NaOMe in MeOH, respectively, according to the procedure described in Example 79. $^1$H NMR (400 MHz, MeOH-d$_4$) δ 9.04 (s, 1H), 8.76 (d, J=5.38 Hz, 2H), 8.04 (d, J=2.20 Hz, 1H), 7.87 (d, J=8.80 Hz, 1H), 7.82 (dd, J=1.71, 4.89 Hz, 2H), 7.68 (dd, J=2.20, 8.80 Hz, 1H), 7.37-7.46 (m, 5H), 7.10 (d, J=1.47 Hz, 1H), 4.47 (q, J=6.93 Hz, 2H), 3.71 (s, 3H), 3.60 (q, J=6.93 Hz, 2H), 1.29 (t, J=7.09 Hz, 3H), 1.01 (t, J=6.97 Hz, 3H); MS m/e 481.2 [M+H]$^+$.

Example 83

(4-Butyl-3-phenylquinolin-6-yl)(1-methyl-1H-imidazol-5-yl)pyridin-4-ylmethanol•TFA

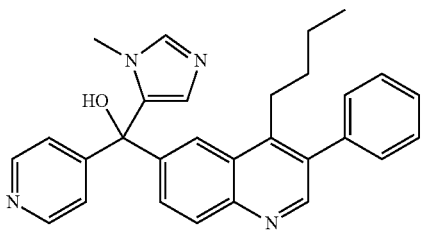 [SMILES: CCCCc1c(-c2ccccc2)cnc2ccc(C(O)(c3ccncc3)c3cncn3C)cc12]

A mixture of (4-butyl-2-chloro-3-phenylquinolin-6-yl)(1-methyl-1H-imidazol-5-yl)pyridin-4-ylmethanol•TFA (16 mg, 0.023 mmol, Example 78) and NaOiPr (19 mg, 0.23 mmol) in iPrOH (0.4 mL) was heated in a sealed tube at 80° C. for 17 hours, and more NaOiPr (7 mg, 0.085 mmol) was added. The mixture was heated for 64 hours and purified by reverse phase HPLC (water/acetonitrile/0.1% TFA) to provide the title compound. $^1$H NMR (400 MHz, MeOH-d$_4$) δ 9.08 (s, 1H), 8.90 (s, 1H), 8.77 (d, J=6.57 Hz, 3H), 8.29 (d, J=2.02 Hz, 1H), 8.24 (d, J=8.59 Hz, 1H), 8.03 (dd, J=2.02, 9.09 Hz, 1H), 7.83 (d, J=6.57 Hz, 2H), 7.53-7.58 (m, 2H), 7.43 (d, J=6.06 Hz, 2H), 7.18 (s, 1H), 3.72 (s, 3H), 3.06-3.12 (m, 2H), 1.45-1.55 (m, 2H), 1.19-1.28 (m, 2H), 0.78 (t, J=7.33 Hz, 3H); MS m/e 449.2 [M+H]$^+$.

Example 84

[4-Chloro-2-(1-methylethoxy)-3-phenylquinolin-6-yl](3-chlorophenyl)pyridin-3-ylmethanol•TFA

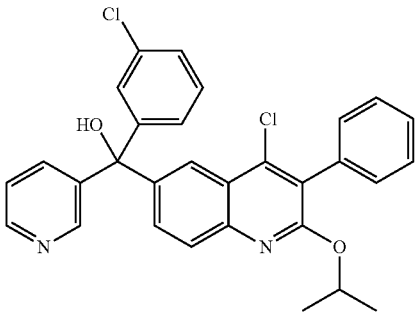 [SMILES: CC(C)Oc1nc2ccc(C(O)(c3cccnc3)c3cccc(Cl)c3)cc2c(Cl)c1-c1ccccc1]

The title compound was prepared using NaO$^i$Pr in iPrOH in place of NaOMe in MeOH according to the procedure described in Example 79. $^1$H NMR (400 MHz, MeOH-d$_4$) δ 8.88 (d, J=2.20 Hz, 1H), 8.79 (d, J=5.62 Hz, 1H), 8.52-8.55 (m, 1H), 8.10 (d, J=2.20 Hz, 1H), 8.01 (dd, J=5.62, 8.31 Hz, 1H), 7.87 (d, J=8.80 Hz, 1H), 7.65 (dd, J=2.20, 8.80 Hz, 1H), 7.37-7.50 (m, 7H), 7.24-7.32 (m, 2H), 5.49-5.57 (m, 1H), 1.27 (d, J=6.36 Hz, 6H); MS m/e 515.1 [M+H]$^+$.

Example 85

[2-Chloro-4-(1-methylethoxy)-3-phenylquinolin-6-yl](1-methyl-1H-imidazol-5-yl)pyridin-4-ylmethanol•TFA

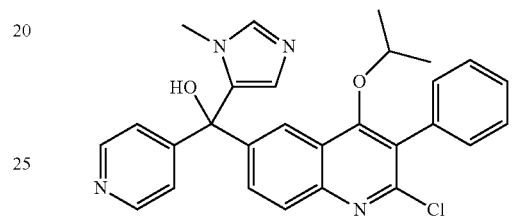

The title compound was prepared using (2,4-dichloro-3-phenylquinolin-6-yl)(1-methyl-1H-imidazol-5-yl)(pyridin-4-yl)methanol (Example 16) and NaO$^i$Pr in iPrOH in place of (3-chlorophenyl)(2,4-dichloro-3-phenylquinolin-6-yl)(pyridin-3-yl)methanol and NaOMe in MeOH, respectively, according to the procedure described in Example 79. $^1$H NMR (400 MHz, MeOH-d$_4$) δ 9.04 (s, 1H), 8.73 (d, J=6.11 Hz, 2H), 8.13 (d, J=2.20 Hz, 1H), 8.02 (d, J=8.80 Hz, 1H), 7.90 (dd, J=2.20, 9.05 Hz, 1H), 7.73 (dd, J=1.47, 4.89 Hz, 2H), 7.47-7.57 (m, 3H), 7.40-7.45 (m, 2H), 7.11 (d, J=1.47 Hz, 1H), 3.93-4.00 (m, 1H), 3.71 (s, 3H), 0.90 (dd, J=6.11, 11.74 Hz, 6H); MS m/e 485.0 [M+H]$^+$.

Example 86

(2,4-Dichloro-3-phenylquinolin-6-yl)(2-fluoropyridin-4-yl)(1-methyl-1H-imidazol-5-yl)methanol•TFA

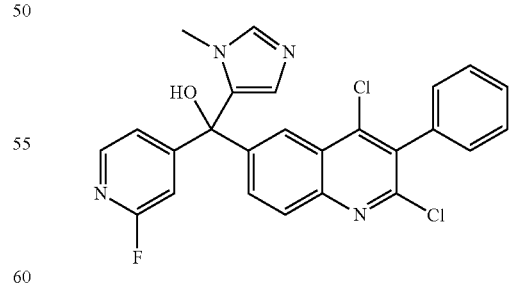

The title compound was prepared using (2-fluoropyridin-4-yl)(1-methyl-1H-imidazol-5-yl)methanone (Intermediate 13, step b) in place of di(pyridin-3-yl)methanone according to the procedure described in Example 24. $^1$H NMR (400 MHz, MeOH-d$_4$) δ 9.04 (s, 1H), 8.39 (s, 1H), 8.29 (d, J=5.38 Hz, 1H), 8.11 (d, J=9.05 Hz, 1H), 7.92 (dd, J=1.71, 8.80 Hz, 1H), 7.45-7.61 (m, 3H), 7.41 (d, J=5.14 Hz, 1H), 7.34 (d, J=6.60 Hz, 2H), 7.24 (s, 1H), 7.15 (s, 1H), 3.70 (s, 3H); MS m/e 478.8 [M+H]⁺.

Example 87

(2-Chloro-6-methylpyridin-4-yl)(2,4-dichloro-3-phenylquinolin-6-yl)(1-methyl-1H-imidazol-5-yl)methanol•TFA

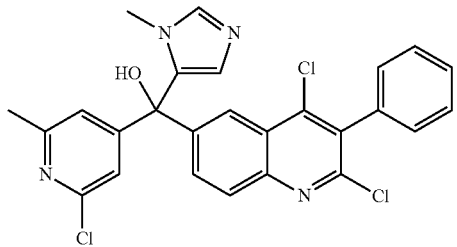

The title compound was prepared using (2-chloro-6-methylpyridin-4-yl)(1-methyl-1H-imidazol-5-yl)methanone (Intermediate 14) in place of di(pyridin-3-yl)methanone according to the procedure described in Example 24. $^1$H NMR (400 MHz, MeOH-d$_4$) δ 8.96 (s, 1H), 8.39 (d, J=1.71 Hz, 1H), 8.10 (d, J=8.80 Hz, 1H), 7.89 (dd, J=1.83, 8.93 Hz, 1H), 7.48-7.60 (m, 3H), 7.38 (s, 1H), 7.35 (d, J=6.60 Hz, 2H), 7.31 (s, 1H), 7.10 (s, 1H), 3.69 (s, 3H), 2.51 (s, 3H); MS m/e 509.1 [M+H]⁺.

Example 88

(4-Chloro-2-ethoxy-3-phenylquinolin-6-yl)(1-methyl-1H-imidazol-5-yl)pyridin-4-ylmethanol•TFA

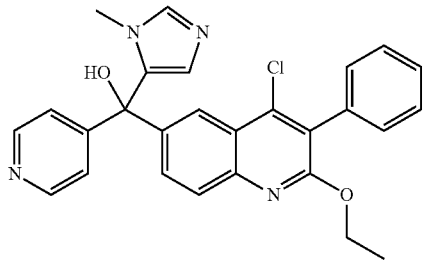 [SMILES: CCOc1nc2ccc(C(O)(c3ccncc3)c3cncn3C)cc2c(Cl)c1-c1ccccc1]

The title compound was isolated from the reaction that formed Example 82. $^1$H NMR (400 MHz, MeOH-d$_4$) δ 9.03 (s, 1H), 8.72 (d, J=5.38 Hz, 2H), 8.25 (s, 1H), 7.93 (d, J=8.80 Hz, 1H), 7.77 (d, J=5.38 Hz, 2H), 7.73 (d, J=9.05 Hz, 1H), 7.39-7.49 (m, 3H), 7.31 (d, J=7.34 Hz, 2H), 7.10 (s, 1H), 4.48 (q, J=7.09 Hz, 2H), 3.70 (s, 3H), 1.28 (t, J=7.09 Hz, 3H); MS m/e 471.1 [M+H]⁺.

Example 89

[4-Chloro-2-(1-methylethoxy)-3-phenylquinolin-6-yl](1-methyl-1H-imidazol-5-yl)pyridin-4-ylmethanol•TFA

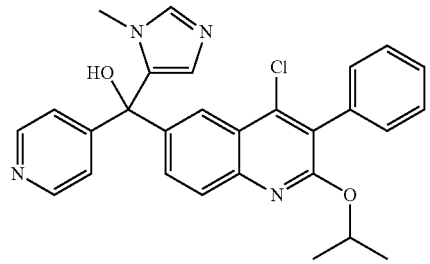 [SMILES: CC(C)Oc1nc2ccc(C(O)(c3ccncc3)c3cncn3C)cc2c(Cl)c1-c1ccccc1]

The title compound was isolated from the reaction that formed Example 85. $^1$H NMR (400 MHz, MeOH-d$_4$) δ 9.05 (s, 1H), 8.77 (d, J=5.13 Hz, 2H), 8.26 (br. s., 1H), 7.83-7.98 (m, 3H), 7.73 (d, J=8.56 Hz, 1H), 7.37-7.52 (m, 3H), 7.30 (d, J=6.85 Hz, 2H), 7.14 (s, 1H), 5.41-5.63 (m, 1H), 3.71 (s, 3H), 1.27 (d, J=5.87 Hz, 6H); MS m/e 485.2 [M+H]⁺.

Example 90

[4-(Dimethylamino)-2-(1-methylethoxy)-3-phenylquinolin-6-yl](1-methyl-1H-imidazol-5-yl)pyridin-4-ylmethanol•TFA

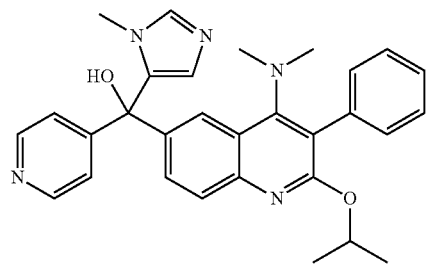

The title compound was prepared using (2-chloro-4-(dimethylamino)-3-phenylquinolin-6-yl)(1-methyl-1H-imidazol-5-yl)(pyridin-4-yl)methanol (Example 47) and NaOiPr in iPrOH in place of (3-chlorophenyl)(2,4-dichloro-3-phenylquinolin-6-yl)(pyridin-3-yl)methanol and NaOMe in MeOH, respectively, according to the procedure described in Example 79. $^1$H NMR (400 MHz, MeOH-d$_4$) δ 9.08 (s, 1H), 8.84 (d, J=6.11 Hz, 2H), 8.11 (s, 1H), 8.05 (d, J=6.11 Hz, 2H), 7.87 (d, J=8.80 Hz, 1H), 7.64 (d, J=8.80 Hz, 1H), 7.33-7.50 (m, 3H), 7.16-7.27 (m, 3H), 5.32-5.50 (m, 1H), 3.72 (s, 3H), 2.59 (s, 6H), 1.23 (d, J=6.11 Hz, 6H); MS m/e 494.2 [M+H]⁺.

Example 91 tert-Butyl 4-[(2,4-dichloro-3-phenylquinolin-6-yl)(hydroxy)pyridin-3-ylmethyl]piperidine-1-carboxylate

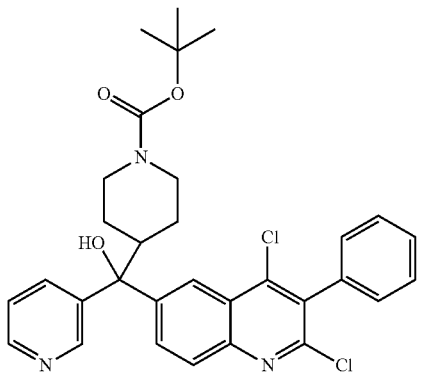 [SMILES: CC(C)(C)OC(=O)N1CCC(C(O)(c2cccnc2)c2ccc3nc(Cl)c(-c4ccccc4)c(Cl)c3c2)CC1]

The title compound was prepared using tert-butyl 4-nicotinoylpiperidine-1-carboxylate (Intermediate 25) in place of (3-chlorophenyl)(pyridin-3-yl)methanone according to the procedure described in Example 25. $^1$H NMR (400 MHz, CDCl$_3$) δ 8.83 (s, 1H), 8.40-8.55 (m, 2H), 8.03 (d, J=9.05 Hz, 1H), 7.78-7.93 (m, 2H), 7.46-7.61 (m, 3H), 7.19-7.39 (m, 3H), 4.12-4.33 (m, 2H), 2.66-2.87 (m, 3H), 1.51-1.74 (m, 2H), 1.33-1.50 (m, 2H), 1.43 (s, 9H); MS m/e 564.2 [M+H]$^+$.

Example 92

[4-(Dimethylamino)-2-ethoxy-3-phenylquinolin-6-yl](1-methyl-1H-imidazol-5-yl)pyridin-4-ylmethanol•TFA

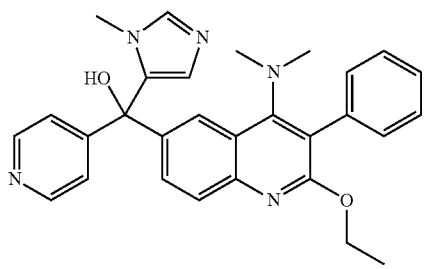 [SMILES: CCOc1nc2ccc(C(O)(c3ccncc3)c3cncn3C)cc2c(N(C)C)c1-c1ccccc1]

The title compound was prepared using (2-chloro-4-(dimethylamino)-3-phenylquinolin-6-yl)(1-methyl-1H-imidazol-5-yl)(pyridin-4-yl)methanol (Example 47) and NaOEt in EtOH in place of (3-chlorophenyl)(2,4-dichloro-3-phenylquinolin-6-yl)(pyridin-3-yl)methanol and NaOMe in MeOH, respectively, according to the procedure described in Example 79. $^1$H NMR (400 MHz, MeOH-d$_4$) δ 9.07 (s, 1H), 8.82 (d, J=5.62 Hz, 2H), 8.09 (s, 1H), 7.99 (d, J=5.38 Hz, 2H), 7.87 (d, J=8.56 Hz, 1H), 7.63 (dd, J=1.96, 8.56 Hz, 1H), 7.41-7.48 (m, 2H), 7.39 (d, J=7.09 Hz, 1H), 7.24 (d, J=7.82 Hz, 2H), 7.17 (s, 1H), 4.42 (q, J=7.01 Hz, 2H), 3.72 (s, 3H), 2.57 (s, 6H), 1.24 (t, J=6.97, 3H); MS m/e 480.3 [M+H]$^+$.

Example 93

(2,4-Dichloro-3-phenylquinolin-6-yl)(piperidin-3-yl)pyridin-3-ylmethanol•TFA

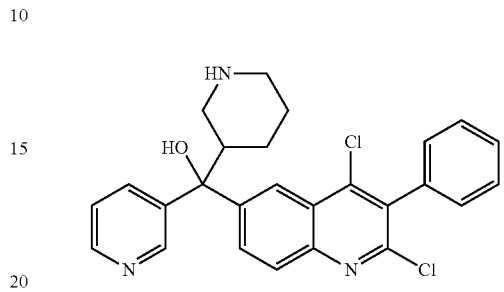

tert-Butyl 3-((2,4-dichloro-3-phenylquinolin-6-yl)(hydroxy)(pyridin-3-yl)methyl)piperidine-1-carboxylate (88 mg, 0.11 mmol, Example 5) was treated with TFA (0.8 mL) at room temperature for 1 hour and concentrated to give the title compound. $^1$H NMR (400 MHz, MeOH-d$_4$) δ 9.05 (s, 1H), 8.56-8.72 (m, 3H), 8.02-8.09 (m, 2H), 7.91 (dd, J=5.56, 8.08 Hz, 1H), 7.49-7.58 (m, 2H), 7.29-7.37 (m, 2H), 7.10-7.22 (m, 1H), 3.37-3.46 (m, 1H), 3.27-3.34 (m, 1H), 3.11 (d, J=11.12 Hz, 1H), 3.01 (d, J=12.13 Hz, 1H), 2.84-2.98 (m, 1H), 1.96-2.08 (m, 1H), 1.78-1.96 (m, 1H), 1.64-1.74 (m, 2H); MS m/e 464.4 [M+H]$^+$.

Example 94

(2,4-Dichloro-3-phenylquinolin-6-yl)(1-methylpiperidin-3-yl)pyridin-3-ylmethanol•TFA

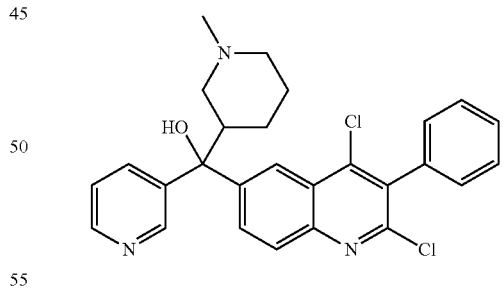

To a mixture of (2,4-dichloro-3-phenylquinolin-6-yl)(piperidin-3-yl)pyridin-3-ylmethanol•TFA (15 mg, 0.022 mmol, Example 93), 37% formaldehyde in water (0.010 mL, 0.13 mmol) and MeOH (1 mL) was added NaBH$_3$CN (4.0 mg, 0.064 mmol). The mixture was stirred overnight and concentrated. The residue was purified by reverse phase HPLC (water/acetonitrile/0.1% TFA) to provide the title compound as a white solid. $^1$H NMR (400 MHz, MeOH-d$_4$) δ 8.95 (s, 1H), 8.54-8.68 (m, 2H), 8.41 (d, J=7.58 Hz, 1H), 7.96-8.13 (m, 2H), 7.72 (dd, J=5.14, 7.58 Hz, 1H), 7.53 (d, J=7.09 Hz, 3H), 7.33 (d, J=6.85 Hz, 2H), 3.48-3.64 (m, 1H), 3.10-3.21 (m, 1H), 2.96-3.10 (m, 1H), 2.83-2.97 (m, 1H), 2.80 (s, 3H), 2.66 (s, 1H), 2.01-2.13 (m, 1H), 1.82-2.01 (m, 1H), 1.54-1.82 (m, 2H); MS m/e 478.0 [M+H]+.

Example 95

(1-Acetylpiperidin-4-yl)(2,4-dichloro-3-phenylquinolin-6-yl)pyridin-3-ylmethanol•TFA

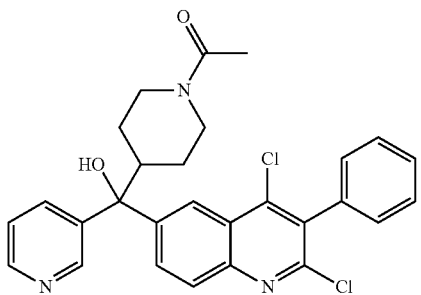 [SMILES: CC(=O)N1CCC(C(O)(c2cccnc2)c2ccc3nc(Cl)c(-c4ccccc4)c(Cl)c3c2)CC1]

tert-Butyl 4-[(2,4-dichloro-3-phenylquinolin-6-yl)(hydroxy)pyridin-3-ylmethyl]piperidine-1-carboxylate (149 mg, 0.264 mmol, Example 91) was treated with TFA (1 mL) at room temperature for 1 hour and concentrated. A part of the residue (10 mg, 0.027 mmol), acetyl chloride (10 mg, 0.13 mmol), and Et$_3$N (0.030 mL, 0.22 mmol) in CH$_2$Cl$_2$ (1 mL) was stirred overnight and concentrated. The residue was purified by reverse phase HPLC (water/acetonitrile/0.1% TFA) to provide the title compound as a white solid. $^1$H NMR (400 MHz, MeOH-d$_4$) δ 9.11 (s, 1H), 8.80 (t, J=7.33 Hz, 1H), 8.70 (d, J=5.56 Hz, 1H), 8.59-8.65 (m, 1H), 8.08-8.15 (m, 1H), 8.01-8.06 (m, 1H), 7.94-8.01 (m, 1H), 7.47-7.57 (m, 3H), 7.33 (t, J=6.57 Hz, 2H), 4.59 (d, J=13.14 Hz, 1H), 3.97 (d, J=13.14 Hz, 1H), 3.10-3.28 (m, 2H), 2.63-2.76 (m, 1H), 1.37-1.67 (m, 4H); MS m/e 506.1 [M+H]+.

Example 96

(1-Acetylpiperidin-3-yl)(2,4-dichloro-3-phenylquinolin-6-yl)pyridin-3-ylmethanol•TFA

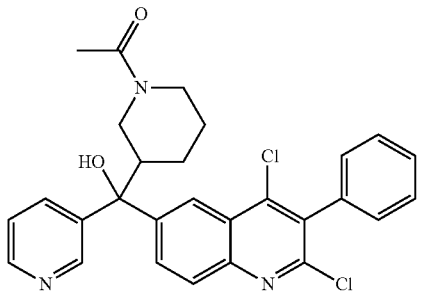 [SMILES: CC(=O)N1CCCC(C(O)(c2cccnc2)c2ccc3nc(Cl)c(-c4ccccc4)c(Cl)c3c2)C1]

A mixture of 2,4-dichloro-3-phenylquinolin-6-yl)(piperidin-3-yl)pyridin-3-ylmethanol•TFA (19 mg, 0.027 mmol, Example 93), acetyl chloride (10 mg, 0.13 mmol), and Et$_3$N (0.030 mL, 0.22 mmol) in CH$_2$Cl$_2$ (1 mL) was stirred overnight and concentrated. The residue was purified by reverse phase HPLC (water/acetonitrile/0.1% TFA) to provide the title compound as a white solid. $^1$H NMR (400 MHz, MeOH-d$_4$) δ 9.06-9.14 (m, 1H), 8.67-8.77 (m, 3H), 8.02-8.20 (m, 2H), 7.96 (dd, J=5.56, 8.08 Hz, 1H), 7.46-7.58 (m, 3H), 7.30-7.38 (m, 2H), 4.48-4.63 (m, 1H), 3.94 (d, J=13.14 Hz, 0.6H), 3.65 (d, J=9.60 Hz, 0.4H), 2.88-3.16 (m, 2H), 2.45-2.67 (m, 1H), 2.10 (s, 2H), 1.90 (s, 1H), 1.49-1.88 (m, 4H); MS m/e 506.1 [M+H]+.

Example 97

(2,4-Diethyl-3-phenylquinolin-6-yl)(1-methyl-1H-imidazol-5-yl)pyridin-4-ylmethanol•TFA

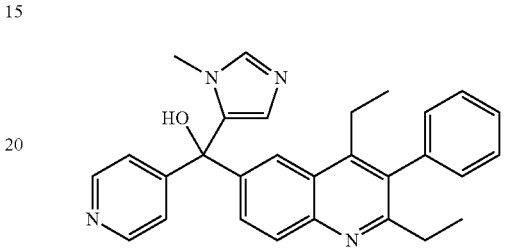

The title compound was prepared using (2,4-dichloro-3-phenylquinolin-6-yl)(1-methyl-1H-imidazol-5-yl)(pyridin-4-yl)methanol (Example 16) in place of (2,4-dichloro-3-phenylquinolin-6-yl)(4-fluorophenyl)pyridin-3-ylmethanol according to the procedure described in Example 30. $^1$H NMR (400 MHz, MeOH-d$_4$) δ 9.07 (s, 1H), 8.76 (d, J=4.55 Hz, 2H), 8.49 (s, 1H), 8.30 (d, J=9.09 Hz, 1H), 8.10-8.15 (m, 1H), 7.81-7.89 (m, 2H), 7.59-7.64 (m, 3H), 7.40 (d, J=7.58 Hz, 2H), 7.22 (s, 1H), 3.70 (s, 3H), 3.01 (dq, J=2.53, 7.58 Hz, 2H), 2.92 (q, J=7.58 Hz, 2H), 1.22 (t, J=7.58 Hz, 3H), 1.15 (t, J=7.58 Hz, 3H); MS m/e 449.2 [M+H]+.

Example 98

[4-(Dimethylamino)-2-ethyl-3-phenylquinolin-6-yl](1-methyl-1H-imidazol-5-yl)pyridin-4-ylmethanol•TFA

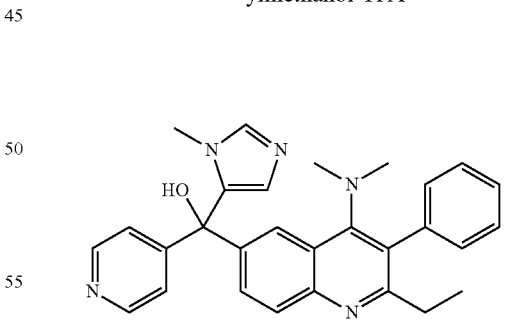

The title compound was prepared using (2-chloro-4-(dimethylamino)-3-phenylquinolin-6-yl)(1-methyl-1H-imidazol-5-yl)pyridin-4-ylmethanol•TFA (Example 47) in place of (2,4-dichloro-3-phenylquinolin-6-yl)(4-fluorophenyl)pyridin-3-ylmethanol according to the procedure described in Example 30. $^1$H NMR (400 MHz, MeOH-d$_4$) δ 9.04 (s, 1H), 8.73 (d, J=5.05 Hz, 2H), 8.30 (s, 1H), 8.01 (d, J=5.56 Hz, 1H), 7.71-7.77 (m, 2H), 7.54-7.59 (m, 3H), 7.38 (d, J=7.07 Hz, 3H), 7.20 (s, 1H), 3.71 (s, 3H), 2.87 (s, 6H), 2.76 (q, J=7.58 Hz, 2H), 1.16 (t, J=7.58 Hz, 3H); MS m/e 464.2 [M+H]⁺.

Example 99

(4-Chloro-2-(diethylamino)-3-phenylquinolin-6-yl)(1-methyl-1H-imidazol-5-yl)pyridin-4-ylmethanol•TFA

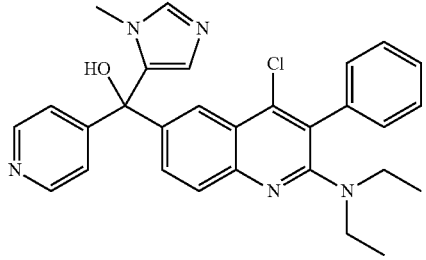 [SMILES: CCN(CC)c1nc2ccc(C(O)(c3ccncc3)c3cncn3C)cc2c(Cl)c1-c1ccccc1]

A mixture of (2,4-dichloro-3-phenylquinolin-6-yl)(1-methyl-1H-imidazol-5-yl)(pyridin-4-yl)methanol (114 mg, 0.165 mmol, Example 16) and NHEt₂ (0.50 mL, 4.8 mmol) in N,N-diethylformamide (0.5 mL) was heated at 130° C. for 64 hours and purified by reverse phase HPLC (water/acetonitrile/0.1% TFA) to give the title compound. ¹H NMR (400 MHz, MeOH-d₄) δ 9.03 (s, 1H), 8.75 (d, J=6.57 Hz, 2H), 8.21 (d, J=2.02 Hz, 1H), 7.91 (d, J=9.09 Hz, 1H), 7.83 (d, J=6.57 Hz, 2H), 7.71 (dd, J=2.27, 8.84 Hz, 1H), 7.48-7.58 (m, 2H), 7.45-7.47 (m, 1H), 7.37 (d, J=7.07 Hz, 2H), 7.12 (s, 1H), 3.70 (s, 3H), 3.28 (q, J=7.07 Hz, 4H), 0.93 (t, J=7.07 Hz, 6H); MS m/e 498.1 [M+H]⁺.

Example 100

(4-Chloro-2-(diethylamino)-3-phenylquinolin-6-yl)(3-chlorophenyl)pyridin-3-ylmethanol•TFA

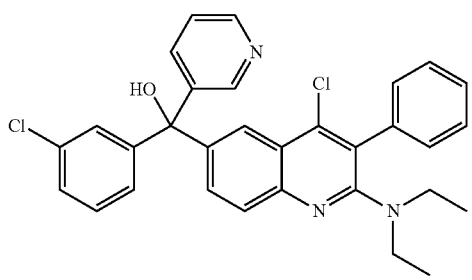 [SMILES: CCN(CC)c1nc2ccc(C(O)(c3cccnc3)c3cccc(Cl)c3)cc2c(Cl)c1-c1ccccc1]

The title compound was prepared using (3-chlorophenyl)(2,4-dichloro-3-phenylquinolin-6-yl)(pyridin-3-yl)methanol (Example 25) in place of (2,4-dichloro-3-phenylquinolin-6-yl)(1-methyl-1H-imidazol-5-yl)(pyridin-4-yl)methanol according to the procedure described in Example 99. ¹H NMR (400 MHz, MeOH-d₄) δ 8.76 (s, 1H), 8.71 (d, J=4.04 Hz, 1H), 8.32 (d, J=8.59 Hz, 1H), 8.10 (d, J=2.02 Hz, 1H), 7.90 (d, J=8.59 Hz, 1H), 7.85 (dd, J=5.56, 8.08 Hz, 1H), 7.69 (dd, J=2.02, 8.59 Hz, 1H), 7.49-7.55 (m, 2H), 7.47 (d, J=7.58 Hz, 1H), 7.43 (s, 1H), 7.36-7.42 (m, 4H), 7.21-7.28 (m, 1H), 3.28-3.33 (m, 4H), 0.95 (t, J=7.07 Hz, 6H); MS m/e 527.8 [M+H]⁺.

Example 101

[2-Chloro-4-(diethylamino)-3-phenylquinolin-6-yl](3-chlorophenyl)pyridin-3-ylmethanol•TFA

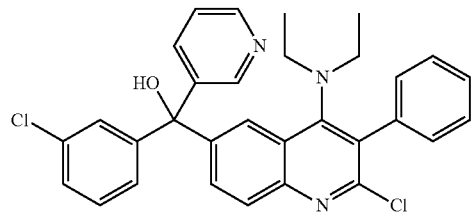 [SMILES: CCN(CC)c1c(-c2ccccc2)c(Cl)nc2ccc(C(O)(c3cccnc3)c3cccc(Cl)c3)cc12]

The title compound was isolated from the reaction that formed Example 100. ¹H NMR (400 MHz, MeOH-d₄) δ 8.89 (s, 1H), 8.80 (d, J=5.05 Hz, 1H), 8.49 (d, J=8.08 Hz, 1H), 8.00 (dd, J=5.56, 8.08 Hz, 1H), 7.90-7.97 (m, 2H), 7.71-7.78 (m, 1H), 7.37-7.55 (m, 6H), 7.27-7.36 (m, 3H), 2.73-2.84 (q, J=7.07 Hz, 4H), 0.83 (t, J=7.07 Hz, 6H); MS m/e 527.8 [M+H]⁺.

Example 102

[2-(Diethylamino)-4-methyl-3-phenylquinolin-6-yl](1-methyl-1H-imidazol-5-yl)pyridin-4-ylmethanol•TFA

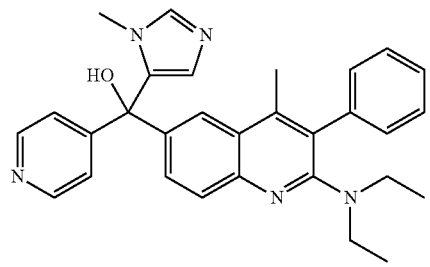 [SMILES: CCN(CC)c1nc2ccc(C(O)(c3ccncc3)c3cncn3C)cc2c(C)c1-c1ccccc1]

A sealed tube containing [4-chloro-2-(diethylamino)-3-phenylquinolin-6-yl](1-methyl-1H-imidazol-5-yl)pyridin-4-ylmethanol•TFA (21 mg, 0.029 mmol, Example 99), Pd(PPh₃)₄ (5.0 mg, 0.0043 mmol), 2,4,6-trimethyl-1,3,5,2,4,6-trioxatriborinane (0.010 mL, 0.072 mmol), 2.0 M K₂CO₃ in water (0.050 mL, 0.10 mmol), and 1,2-dimethoxyethane (1.2 mL) was bubbled with N₂ for 3 min. After heating at 90° C. for 17 hours, more Pd(PPh₃)₄ (5.0 mg, 0.0043 mmol), 2.0 M K₂CO₃ in water (0.040 mL, 0.080 mmol), and 1,4-dioxane (1 mL) were added. The mixture was heated at 130° C. for 16 hours. NH₄Cl (aqueous) was added, the organic layer was separated, and the aqueous layer was extracted with CH₂Cl₂. The combined organic phases were dried (Na₂SO₄), filtered, concentrated, and purified by reverse phase HPLC (water/acetonitrile/0.1% TFA) to give the title compound. ¹H NMR (400 MHz, MeOH-d₄) δ 9.06 (s, 1H), 8.79 (d, J=6.57 Hz, 2H), 8.25 (d, J=2.02 Hz, 1H), 8.14 (d, J=9.09 Hz, 1H), 7.94 (d, J=6.57 Hz, 2H), 7.88 (dd, J=2.02, 9.09 Hz, 1H), 7.51-7.64 (m, 3H), 7.40 (d, J=6.57 Hz, 2H), 7.20 (s, 1H), 3.69 (s, 3H), 3.46 (q, J=7.07 Hz, 4H), 2.41 (s, 3H), 1.04 (t, J=7.07 Hz, 6H); MS m/e 478.0 [M+H]+.

Example 103

(3-Chlorophenyl)[2-(diethylamino)-4-methyl-3-phenylquinolin-6-yl]pyridin-3-ylmethanol•TFA

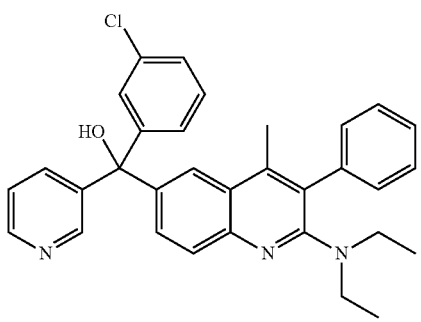 [SMILES: CCN(CC)c1nc2ccc(C(O)(c3cccnc3)c3cccc(Cl)c3)cc2c(C)c1-c1ccccc1]

The title compound was prepared using [4-chloro-2-(diethylamino)-3-phenylquinolin-6-yl](3-chlorophenyl)pyridin-3-ylmethanol•TFA (Example 100) in place of [4-chloro-2-(diethylamino)-3-phenylquinolin-6-yl](1-methyl-1H-imidazol-5-yl)pyridin-4-ylmethanol•TFA according to the procedure described in Example 102. $^1$H NMR (400 MHz, MeOH-d$_4$) δ 8.71 (s, 1H), 8.69 (d, J=5.56 Hz, 1H), 8.23 (d, J=8.08 Hz, 1H), 8.13 (d, J=2.02 Hz, 1H), 8.06 (d, J=8.59 Hz, 1H), 7.75-7.82 (m, 3H), 7.51-7.63 (m, 3H), 7.40 (t, J=4.80 Hz, 4H), 7.22-7.27 (m, 1H), 3.44 (q, J=7.07 Hz, 4H), 2.35 (s, 3H), 1.04 (t, J=7.58 Hz, 6H); MS m/e 508.2 [M+H]+.

Example 104

6-[(3-Chlorophenyl)(6-cyanopyridin-3-yl)hydroxymethyl]-3-phenylquinoline-2,4-dicarbonitrile•TFA

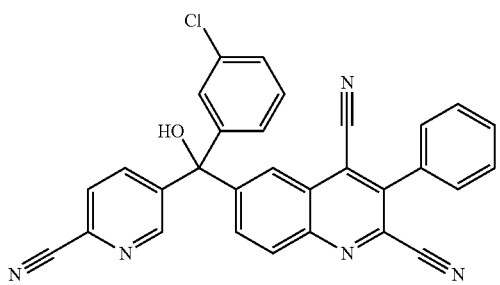 [SMILES: N#Cc1ccc(C(O)(c2cccc(Cl)c2)c2ccc3nc(C#N)c(-c4ccccc4)c(C#N)c3c2)cn1]

A pressure tube containing (3-chlorophenyl)(6-chloropyridin-3-yl)(2,4-dichloro-3-phenylquinolin-6-yl)methanol (70 mg, 0.13 mmol, Example 56), Pd$_2$ dba$_3$ (8.0 mg, 0.0087 mmol), 1,1'-bis(diphenylphosphino)ferrocene (dppf, 10 mg, 0.018 mmol), zinc cyanide (32 mg, 0.27 mmol), and zinc nanopowder (3.5 mg, 0.054 mmol) in N,N-dimethylacetamide (1 mL) was purged with nitrogen for 5 min, and then heated at 120° C. for 5 hours. The mixture was allowed to cool to room temperature and filtered through a syringe filter. The filtrate was concentrated in vacuo, EtOAc and NH$_4$OH (aqueous) were added. The organic layer was separated, and the aqueous layer was extracted with EtOAc. The combined organic layers were dried (Na$_2$SO$_4$), filtered, and concentrated. The residue was purified by flash column chromatography (12 g silica gel column, 30-70% EtOAc in heptane) and then by reverse phase HPLC (water/acetonitrile/0.1% TFA) to give the title compound. $^1$H NMR (400 MHz, MeOH-d$_4$) δ 8.74-8.75 (m, 1H), 8.27-8.31 (m, 2H), 7.99 (ddd, J=2.27, 6.32, 8.59 Hz, 2H), 7.87-7.91 (m, 1H), 7.68-7.73 (m, 2H), 7.62-7.67 (m, 3H), 7.44 (s, 1H), 7.39 (d, J=5.05 Hz, 2H), 7.22-7.27 (m, 1H); MS m/e 498.1 [M+H]+.

Example 105

[2-(Diethylamino)-4-methoxy-3-phenylquinolin-6-yl](1-methyl-1H-imidazol-5-yl)pyridin-4-ylmethanol•TFA

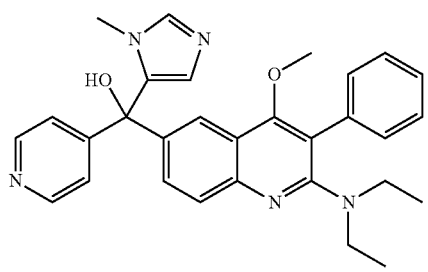 [SMILES: CCN(CC)c1nc2ccc(C(O)(c3ccncc3)c3cncn3C)cc2c(OC)c1-c1ccccc1]

The title compound was prepared using (4-chloro-2-(diethylamino)-3-phenylquinolin-6-yl)(1-methyl-1H-imidazol-5-yl)(pyridin-4-yl)methanol (Example 99) in place of (3-chlorophenyl)(2,4-dichloro-3-phenylquinolin-6-yl)(pyridin-3-yl)methanol according to the procedure described in Example 79. $^1$H NMR (400 MHz, MeOH-d$_4$) δ 9.03 (s, 1H), 8.73 (d, J=6.06 Hz, 2H), 8.16 (d, J=2.02 Hz, 1H), 8.10 (d, J=8.59 Hz, 1H), 7.88 (dd, J=2.27, 8.84 Hz, 1H), 7.78 (d, J=6.57 Hz, 2H), 7.52-7.61 (m, 3H), 7.50 (m, 2H), 7.15 (s, 1H), 3.69 (s, 3H), 3.49 (s, 3H), 3.44 (q, J=7.07 Hz, 4H), 1.07 (t, J=7.07 Hz, 6H); MS m/e 494.2 [M+H]+.

Example 106

(3-Chlorophenyl)[2-(diethylamino)-4-methoxy-3-phenylquinolin-6-yl]pyridin-3-ylmethanol•TFA

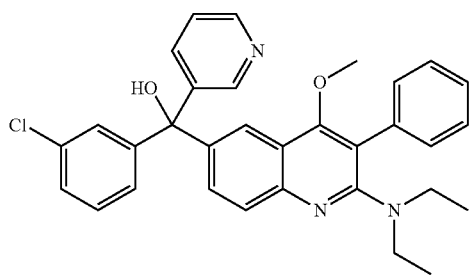 [SMILES: CCN(CC)c1nc2ccc(C(O)(c3cccnc3)c3cccc(Cl)c3)cc2c(OC)c1-c1ccccc1]

The title compound was prepared using [4-chloro-2-(diethylamino)-3-phenylquinolin-6-yl](3-chlorophenyl)pyridin-3-ylmethanol (Example 100) in place of (3-chlorophenyl)(2,4-dichloro-3-phenylquinolin-6-yl)(pyridin-3-yl) methanol according to the procedure described in Example 79. ¹H NMR (400 MHz, MeOH-d₄) δ 8.63-8.70 (m, 2H), 8.16 (d, J=8.59 Hz, 1H), 8.04 (d, J=8.59 Hz, 1H), 8.00 (d, J=2.02 Hz, 1H), 7.83 (dd, J=2.02, 9.09 Hz, 1H), 7.74 (dd, J=5.31, 8.34 Hz, 1H), 7.46-7.60 (m, 5H), 7.37-7.43 (m, 3H), 7.21-7.27 (m, 1H), 3.45 (s, 3H), 3.44 (q, J=7.07 Hz, 4H), 1.08 (t, J=7.07 Hz, 6H); MS m/e 524.3 [M+H]⁺.

Example 107

[2-(Dimethylamino)-4-methoxy-3-phenylquinolin-6-yl](1-methyl-1H-imidazol-5-yl)pyridin-4-ylmethanol•TFA

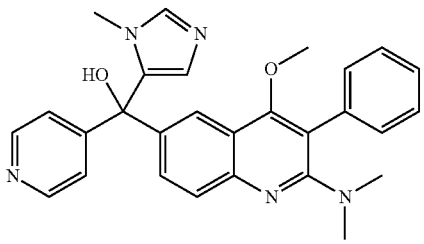 [SMILES: COc1c(-c2ccccc2)c(N(C)C)nc2ccc(C(O)(c3ccncc3)c3cncn3C)cc12]

The title compound was prepared using (4-chloro-2-(dimethylamino)-3-phenylquinolin-6-yl)(1-methyl-1H-imidazol-5-yl)(pyridin-4-yl)methanol (Example 48a) in place of (3-chlorophenyl)(2,4-dichloro-3-phenylquinolin-6-yl)(pyridin-3-yl)methanol according to the procedure described in Example 79. ¹H NMR (400 MHz, MeOH-d₄) δ 9.06 (s, 1H), 8.78 (d, J=4.55 Hz, 2H), 8.17 (d, J=2.02 Hz, 1H), 8.10 (d, J=9.09 Hz, 1H), 7.84-7.92 (m, 3H), 7.45-7.60 (m, 5H), 7.18 (s, 1H), 3.69 (s, 3H), 3.49 (s, 3H), 3.02 (s, 6H); MS m/e 466.2 [M+H]⁺.

Example 108

2-(Dimethylamino)-6-[hydroxy(1-methyl-1H-imidazol-5-yl)pyridin-4-ylmethyl]-3-phenylquinolin-4-ol•TFA

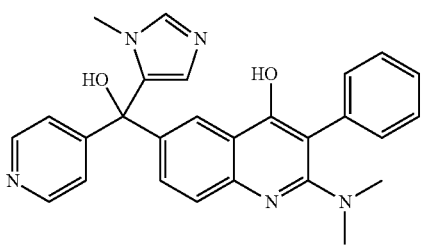 [SMILES: CN(C)c1nc2ccc(C(O)(c3ccncc3)c3cncn3C)cc2c(O)c1-c1ccccc1]

The title compound was isolated from the reaction that formed Example 107. ¹H NMR (400 MHz, MeOH-d₄) δ 9.03 (s, 1H), 8.73 (d, J=4.55 Hz, 2H), 8.17 (d, J=2.02 Hz, 1H), 7.86-7.95 (m, 1H), 7.76-7.85 (m, 3H), 7.46-7.54 (m, 2H), 7.34-7.46 (m, 3H), 7.11 (s, 1H), 3.68 (s, 3H), 2.87 (s, 6H); MS m/e 452.2 [M+H]⁺.

Example 109

(2,4-Dichloro-3-phenylquinolin-6-yl)(1-methyl-1H-imidazol-5-yl)[6-(trifluoromethyl)pyridin-3-yl]methanol•TFA

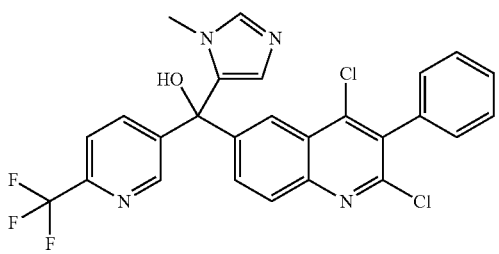 [SMILES: Cn1cncc1C(O)(c1ccc(C(F)(F)F)nc1)c1ccc2nc(Cl)c(-c3ccccc3)c(Cl)c2c1]

The title compound was prepared using (1-methyl-1H-imidazol-5-yl)(6-(trifluoromethyl)pyridin-3-yl)methanone (Intermediate 15, step c) in place of di(pyridin-3-yl)methanone according to the procedure described in Example 24. ¹H NMR (400 MHz, MeOH-d₄) δ 9.02 (s, 1H), 8.84 (d, J=2.53 Hz, 1H), 8.40 (d, J=2.02 Hz, 1H), 8.06-8.15 (m, 2H), 7.84-7.94 (m, 2H), 7.46-7.59 (m, 3H), 7.35 (d, J=8.08 Hz, 2H), 7.13 (s, 1H), 3.71 (s, 3H); MS m/e 529.0 [M+H]⁺.

Example 110

(2,4-Dichloro-3-phenylquinolin-6-yl)(1-methyl-1H-imidazol-5-yl)[2-(trifluoromethyl)pyridin-4-yl]methanol•TFA

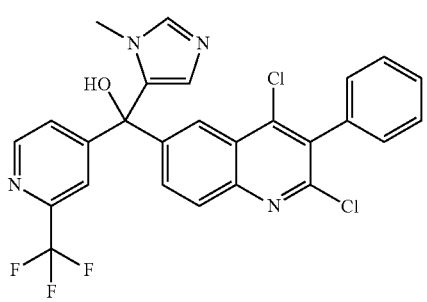 [SMILES: Cn1cncc1C(O)(c1ccnc(C(F)(F)F)c1)c1ccc2nc(Cl)c(-c3ccccc3)c(Cl)c2c1]

The title compound was prepared using (1-methyl-1H-imidazol-5-yl)(2-(trifluoromethyl)pyridin-4-yl)methanone (Intermediate 16, step b) in place of di(pyridin-3-yl)methanone according to the procedure described in Example 24. ¹H NMR (400 MHz, MeOH-d₄) δ 9.06 (s, 1H), 8.79 (d, J=5.05 Hz, 1H), 8.39 (d, J=2.02 Hz, 1H), 8.11 (d, J=8.59 Hz, 1H), 8.01 (s, 1H), 7.91 (dd, J=2.02, 9.09 Hz, 1H), 7.69 (d, J=5.05 Hz, 1H), 7.48-7.58 (m, 3H), 7.32-7.37 (m, 2H), 7.16 (s, 1H), 3.69 (s, 3H); MS m/e 529.0 [M+H]⁺.

Example 111

(3-Chlorophenyl)(2,4-dichloro-3-phenylquinolin-6-yl)(6-(trifluoromethyl)pyridin-3-yl)methanol

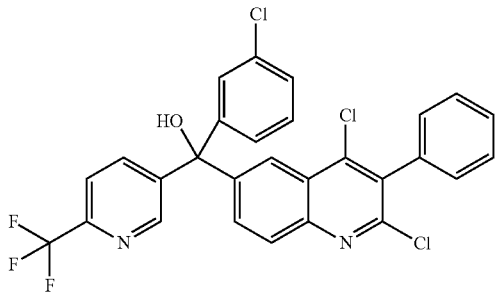 [SMILES: OC(c1ccc(C(F)(F)F)nc1)(c1cccc(Cl)c1)c1ccc2nc(Cl)c(-c3ccccc3)c(Cl)c2c1]

The title compound was prepared using (3-chlorophenyl)(6-(trifluoromethyl)pyridin-3-yl)methanone (Intermediate 17) in place of (3-chlorophenyl)(pyridin-3-yl)methanone according to the procedure described in Example 25. $^1$H NMR (400 MHz, CDCl$_3$) δ 8.76 (d, J=2.02 Hz, 1H), 8.26 (d, J=2.02 Hz, 1H), 8.07 (d, J=8.59 Hz, 1H), 7.93 (dd, J=2.27, 8.34 Hz, 1H), 7.66-7.73 (m, 2H), 7.48-7.55 (m, 3H), 7.29-7.40 (m, 5H), 7.14-7.16 (m, 1H); MS m/e 559.0 [M+H]$^+$.

Example 112

5-[(3-Chlorophenyl)(2,4-dicyano-3-phenylquinolin-6-yl)hydroxymethyl]pyridine-2-carboxamide•TFA

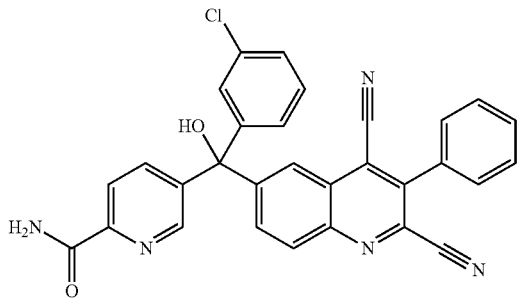 [SMILES: N#Cc1nc2ccc(C(O)(c3ccc(C(N)=O)nc3)c3cccc(Cl)c3)cc2c(C#N)c1-c1ccccc1]

The title compound was isolated from the reaction that formed Example 104. $^1$H NMR (400 MHz, MeOH-d$_4$) δ 8.64 (d, J=2.02 Hz, 1H), 8.31 (d, J=2.02 Hz, 1H), 8.28 (d, J=8.59 Hz, 1H), 8.12 (d, J=8.08 Hz, 1H), 7.94 (dd, J=2.27, 8.34 Hz, 1H), 7.68-7.73 (m, 2H), 7.63-7.67 (m, 4H), 7.45 (s, 1H), 7.36-7.40 (m, 2H), 7.23-7.28 (m, 1H); MS m/e 516.2 [M+H]$^+$.

Example 113

6-[(3-Chlorophenyl)(hydroxy)pyridin-3-ylmethyl]-2-(diethylamino)-3-phenylquinoline-4-carbonitrile•TFA

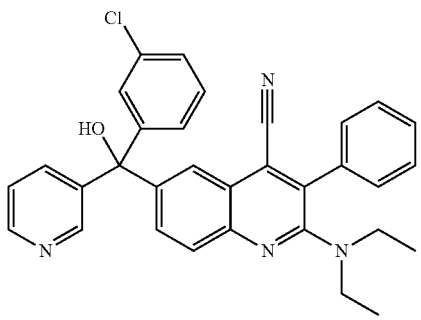 [SMILES: CCN(CC)c1nc2ccc(C(O)(c3cccnc3)c3cccc(Cl)c3)cc2c(C#N)c1-c1ccccc1]

A pressure tube containing (4-chloro-2-(diethylamino)-3-phenylquinolin-6-yl)(3-chlorophenyl)(pyridin-3-yl)methanol (30 mg, 0.040 mmol, Example 100), Pd$_2$ dba$_3$ (3.0 mg, 0.0033 mmol), 1,1'-bis(diphenylphosphino)ferrocene (dppf, 3.6 mg, 0.0065 mmol), zinc cyanide (15 mg, 0.13 mmol), and zinc nanopowder (1.0 mg, 0.015 mmol) in N,N-dimethylacetamide (0.5 mL) was purged with nitrogen for 5 min, and heated at 120° C. for 1 hour, then 100° C. for 3 hours. More Pd$_2$ dba$_3$ (3.0 mg, 0.0033 mmol) and 1,1'-bis(diphenylphosphino)ferrocene (dppf, 3.4 mg, 0.0061 mmol) were added, and the mixture was heated at 120° C. for 5 hours. The mixture was allowed to cool to room temperature and filtered through a syringe filter. The filtrate was concentrated in vacuo, EtOAc and NH$_4$OH (aqueous) were added. The organic layer was separated, and the aqueous layer was extracted with EtOAc. The combined organic layers were dried (Na$_2$SO$_4$), filtered, and concentrated. The residue was purified by reverse phase HPLC (water/acetonitrile/0.1% TFA) to give the title compound as a yellow solid. $^1$H NMR (400 MHz, MeOH-d$_4$) δ 8.76 (s, 1H), 8.68 (d, J=5.05 Hz, 1H), 8.24-8.34 (m, 1H), 7.81-7.88 (m, 3H), 7.64 (dd, J=2.02, 9.09 Hz, 1H), 7.49-7.56 (m, 5H), 7.44 (s, 1H), 7.38 (d, J=5.05 Hz, 2H), 7.22-7.27 (m, 1H), 3.24 (d, J=7.07 Hz, 4H), 0.94 (d, J=6.57 Hz, 6H); MS m/e 519.2 [M+H]$^+$.

Example 114

6-{(3-Chlorophenyl)(hydroxy)[6-(trifluoromethyl)pyridin-3-yl]methyl}-3-phenylquinoline-2,4-dicarbonitrile

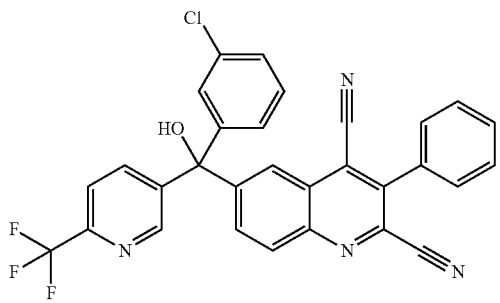 [SMILES: N#Cc1nc2ccc(C(O)(c3ccc(C(F)(F)F)nc3)c3cccc(Cl)c3)cc2c(C#N)c1-c1ccccc1]

The title compound was prepared using (3-chlorophenyl)(2,4-dichloro-3-phenylquinolin-6-yl)(6-(trifluoromethyl)pyridin-3-yl)methanol (Example 111) in place of (3-chlorophenyl)(6-chloropyridin-3-yl)(2,4-dichloro-3-phenylquinolin-6-yl)methanol according to the procedure described in Example 104. $^1$H NMR (400 MHz, CDCl$_3$) δ 8.76 (s, 1H), 8.47 (s, 1H), 8.28 (d, J=9.09 Hz, 1H), 7.95 (d, J=8.08 Hz, 1H), 7.84 (dd, J=2.02, 9.09 Hz, 1H), 7.72 (d, J=8.59 Hz, 1H), 7.60-7.68 (m, 5H), 7.32-7.44 (m, 2H), 7.30 (s, 1H), 7.14 (d, J=7.58 Hz, 1H); MS m/e 541.0 [M+H]$^+$.

Example 115

[4-Chloro-3-phenyl-2-(trifluoromethyl)quinolin-6-yl](1-methyl-1H-imidazol-5-yl)pyridin-2-ylmethanol•TFA

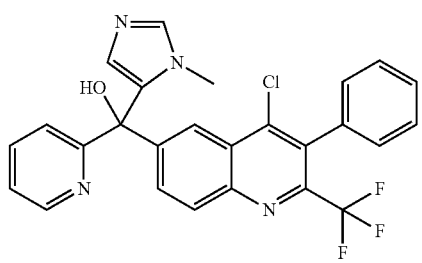 [SMILES: Cn1cncc1C(O)(c1ccc2nc(C(F)(F)F)c(-c3ccccc3)c(Cl)c2c1)c1ccccn1]

To a solution of 4-chloro-6-iodo-3-phenyl-2-(trifluoromethyl)quinoline (265 mg, 0.611 mmol, Intermediate 5, step b) in 1 mL of THF at −78° C. was added 2.0 M i-PrMgCl in THF (0.306 mL, 0.612 mmol), the clear mixture gradually turned to milky greenish. After stirring at −78° C. for 8 min, the cooling bath was removed. After stirring for 15 min, the mixture changed to grayish black slurry. The mixture was cooled to 4° C., (1-methyl-1H-imidazol-5-yl)(pyridin-2-yl)methanone (114 mg, 0.609 mmol, Intermediate 11, step b) was added in neat followed by 1.3 mL of THF. The mixture was stirred vigorously at room temperature overnight, heated at 50° C. for 40 min, and quenched with NH₄Cl (aqueous). The organic layer was separated, and the aqueous layer was extracted with EtOAc. The combined organic layers were dried (Na₂SO₄), filtered, and concentrated. The residue was purified by flash column chromatography (40 g silica gel column, 50-100% EtOAc in heptane, 5-10% MeOH in CH₂Cl₂), and then by reverse phase HPLC (water/acetonitrile/0.1% TFA) to give the title compound. ¹H NMR (400 MHz, MeOH-d₄) δ 8.97 (s, 1H), 8.58-8.65 (m, 2H), 8.28 (d, J=9.09 Hz, 1H), 8.11 (dd, J=2.02, 9.09 Hz, 1H), 7.88-7.97 (m, 1H), 7.80 (d, J=7.58 Hz, 1H), 7.48-7.55 (m, 3H), 7.38-7.46 (m, 1H), 7.26-7.34 (m, 2H), 7.11 (s, 1H), 3.63 (s, 3H); MS m/e 495.3 [M+H]⁺.

Example 116

(4-Chloro-3-phenyl-2-(trifluoromethyl)quinolin-6-yl)(4-chlorophenyl)(1-methyl-1H-imidazol-5-yl)methanol•TFA

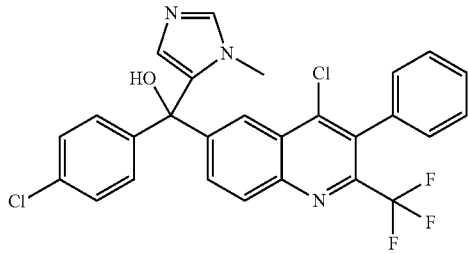 [SMILES: Cn1cncc1C(O)(c1ccc(Cl)cc1)c1ccc2nc(C(F)(F)F)c(-c3ccccc3)c(Cl)c2c1]

The title compound was prepared using 4-chloro-6-iodo-3-phenyl-2-(trifluoromethyl)quinoline (Intermediate 5, step b) and (4-chlorophenyl)(1-methyl-1H-imidazol-5-yl)methanone (Intermediate 18, step b) in place of 6-bromo-2,4-dichloro-3-phenylquinoline and di(pyridin-3-yl)methanone, respectively, according to the procedure described in Example 24. ¹H NMR (400 MHz, MeOH-d₄) δ 9.00 (s, 1H), 8.42 (d, J=2.02 Hz, 1H), 8.31 (d, J=8.59 Hz, 1H), 7.97 (dd, J=2.27, 8.84 Hz, 1H), 7.42-7.53 (m, 7H), 7.27-7.35 (m, 2H), 6.99 (s, 1H), 3.71 (s, 3H); MS m/e 528.0 [M+H]⁺.

Example 117

(4-Chlorophenyl)(4-methoxy-3-phenyl-2-(trifluoromethyl)quinolin-6-yl)(1-methyl-1H-imidazol-5-yl)methanol•TFA

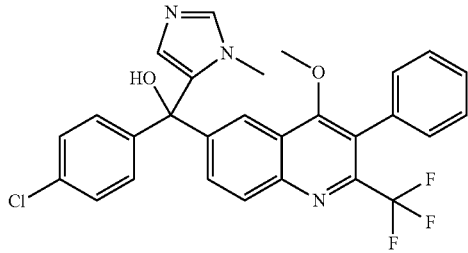 [SMILES: COc1c(-c2ccccc2)c(C(F)(F)F)nc2ccc(C(O)(c3ccc(Cl)cc3)c3cncn3C)cc12]

The title compound was prepared using (4-chloro-3-phenyl-2-(trifluoromethyl)quinolin-6-yl)(4-chlorophenyl)(1-methyl-1H-imidazol-5-yl)methanol•TFA (Example 116) in place of (3-chlorophenyl)(2,4-dichloro-3-phenylquinolin-6-yl)(pyridin-3-yl)methanol according to the procedure described in Example 79. ¹H NMR (400 MHz, MeOH-d₄) δ 8.99 (s, 1H), 8.21-8.27 (m, 2H), 7.87 (dd, J=2.02, 9.09 Hz, 1H), 7.37-7.54 (m, 9H), 6.96 (s, 1H), 3.70 (s, 3H), 3.53 (s, 3H); MS m/e 524.0 [M+H]⁺.

Example 118

6-(Hydroxy(1-methyl-1H-imidazol-5-yl)(pyridin-2-yl)methyl)-3-phenyl-2-(trifluoromethyl)quinoline-4-carbonitrile•TFA

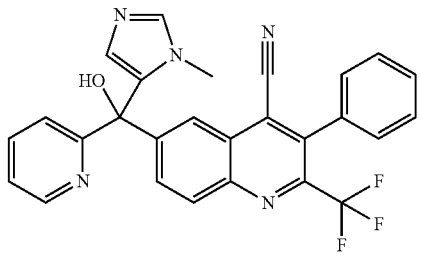 [SMILES: Cn1cncc1C(O)(c1ccc2nc(C(F)(F)F)c(-c3ccccc3)c(C#N)c2c1)c1ccccn1]

The title compound was prepared using [4-chloro-3-phenyl-2-(trifluoromethyl)quinolin-6-yl](1-methyl-1H-imidazol-5-yl)pyridin-2-ylmethanol•TFA (Example 115) in place of (3-chlorophenyl)(6-chloropyridin-3-yl)(2,4-dichloro-3-phenylquinolin-6-yl)methanol according to the procedure described in Example 104. ¹H NMR (400 MHz, MeOH-d₄) δ 8.98 (s, 1H), 8.62 (d, J=5.56 Hz, 1H), 8.51 (d, J=2.02 Hz, 1H), 8.36 (d, J=9.09 Hz, 1H), 8.21 (dd, J=2.02, 9.09 Hz, 1H), 7.91-7.96 (m, 1H), 7.84 (d, J=8.08 Hz, 1H), 7.54-7.62 (m, 3H), 7.41-7.49 (m, 3H), 7.15 (s, 1H), 3.63 (s, 3H); MS m/e 486.0 [M+H]⁺.

Example 119a (4-Chlorophenyl)(2,4-dichloro-3-phenylquinolin-6-yl)(1-methyl-1H-imidazol-5-yl)methanol

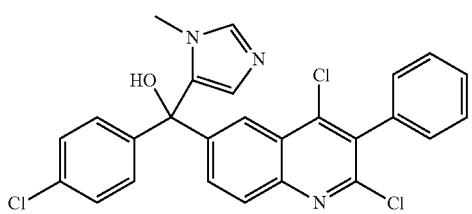 [SMILES: Cn1cncc1C(O)(c1ccc(Cl)cc1)c1ccc2nc(Cl)c(-c3ccccc3)c(Cl)c2c1]

To (4-chlorophenyl)(1-methyl-1H-imidazol-5-yl)methanone (830 mg, 3.76 mmol, Intermediate 18, step b) under an atmosphere of nitrogen was added THF (30 mL) and the mixture was heated until a solution was obtained. To 6-bromo-2,4-dichloro-3-phenylquinoline (1.21 g, 3.42 mmol, Intermediate 1, step c) under an atmosphere of nitrogen was added THF (25 mL). The resulting colorless solution was cooled in a dry ice/acetone bath. n-BuLi (1.6 M in hexane, 2.35 mL, 3.76 mmol) was added dropwise. The mixture was stirred for 5 min before addition of the THF solution of (4-chlorophenyl)(1-methyl-1H-imidazol-5-yl)methanone via cannula. The reaction mixture was stirred in the dry ice/acetone bath for 30 min, then in an ice bath for 50 min and at room temperature for 15 min, then was quenched by addition of saturated aqueous NH₄Cl solution. The mixture was diluted with water and extracted three times with EtOAc. The organic phase was dried (Na₂SO₄), filtered, and concentrated and the residue was purified by flash column chromatography (silica gel, 0-4% MeOH-DCM) to afford the title compound. ¹H NMR (400 MHz, CDCl₃) δ 8.32 (d, J=1.96 Hz, 1H), 8.02 (d, J=8.80 Hz, 1H), 7.72 (dd, J=2.20, 8.80 Hz, 1H), 7.48-7.56 (m, 3H), 7.30-7.38 (m, 7H), 6.40 (d, J=1.22 Hz, 1H), 3.39 (s, 3H); MS m/e 494.1 [M+H]⁺.

Example 119a was purified by chiral HPLC (Chiralpak AD, 100% EtOH) to give 2 pure enantiomers Example 119b and Example 119c (elution order: Example 119b first, Example 119c second). The separated enantiomers were each converted to HCl salts as follows. A solution of each in a mixture of DCM and THF was treated with 1 N HCl in Et₂O (3 equivalents) and the mixtures were concentrated.

Example 119b·HCl

¹H NMR (400 MHz, DMSO-d₆) δ 9.20 (s, 1H), 8.28 (d, J=1.96 Hz, 1H), 8.11 (d, J=8.80 Hz, 1H), 7.78-7.86 (m, 2H), 7.47-7.60 (m, 5H), 7.38-7.45 (m, 4H), 6.99 (d, J=1.47 Hz, 1H), 3.56 (s, 3H); MS m/e 494.1 [M+H]⁺.

Example 119c·HCl

¹H NMR (400 MHz, DMSO-d₆) δ 9.20 (s, 1H), 8.28 (d, J=1.96 Hz, 1H), 8.11 (d, J=8.80 Hz, 1H), 7.80-7.88 (m, 2H), 7.46-7.60 (m, 5H), 7.37-7.45 (m, 4H), 6.98 (d, J=1.22 Hz, 1H), 3.56 (s, 3H); MS m/e 494.1 [M+H]⁺.

Example 120

(2,4-Dichloro-3-phenylquinolin-6-yl)(1-methyl-1H-imidazol-5-yl)(pyrimidin-5-yl)methanol

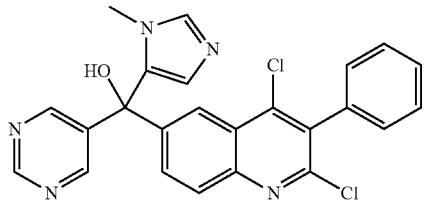 [SMILES: Cn1cncc1C(O)(c1cncnc1)c1ccc2nc(Cl)c(-c3ccccc3)c(Cl)c2c1]

THF (4.5 mL) was added to a mixture of 6-bromo-2,4-dichloro-3-phenylquinoline (117 mg, 0.333 mmol, Intermediate 1, step c) and (1-methyl-1H-imidazol-5-yl)(pyrimidin-5-yl)methanone (62.6 mg, 0.333 mmol, Intermediate 28, step b) under a nitrogen atmosphere. The resulting suspension was gently heated to form a slightly cloudy solution. The mixture was cooled in a dry ice/acetone bath. n-BuLi (1.6 M in hexane, 0.312 mL, 0.499 mmol) was added dropwise and the mixture was allowed to slowly warm to room temperature, still in the cold bath. After 1.5 hours, the reaction was quenched by addition of saturated aqueous NH₄Cl and was diluted with water. The mixture was extracted once with EtOAc, then twice with DCM. The organic phase was dried (Na₂SO₄), filtered, and concentrated. The residue was purified by flash column chromatography (silica gel, 3-6% MeOH-DCM) to afford slightly impure title compound. A dichloromethane solution of this material yielded crystals upon standing. These were triturated with DCM to afford a sample of the title compound. Additional material was obtained by combining the filtrate from the trituration with material in mixed fractions from the silica gel column and purifying by RP-HPLC (10-90% CH₃CN—H₂O, 0.1% TFA), followed by neutralization of fractions with saturated aqueous NaHCO₃ and extraction with DCM. ¹H NMR (400 MHz, CDCl₃) δ 9.13 (s, 1H), 8.77 (s, 2H), 8.36 (d, J=1.96 Hz, 1H), 8.07 (d, J=8.80 Hz, 1H), 7.73 (dd, J=2.08, 8.93 Hz, 1H), 7.47-7.57 (m, 3H), 7.30-7.38 (m, 2H), 7.23 (s, 1H), 7.00 (s, 1H), 6.26 (s, 1H), 3.37 (s, 3H); MS m/e 461.9 [M+H]⁺.

Example 121

(2,4-Dichloro-3-phenylquinolin-6-yl)(1-methyl-1H-imidazol-2-yl)(pyridazin-4-yl)methanol

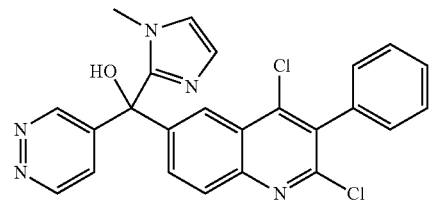 [SMILES: Cn1ccnc1C(O)(c1ccnnc1)c1ccc2nc(Cl)c(-c3ccccc3)c(Cl)c2c1]

THF (9 mL) was added to a mixture of 6-bromo-2,4-dichloro-3-phenylquinoline (228 mg, 0.645 mmol, Intermediate 1, step c) and (1-methyl-1H-imidazol-2-yl)(pyridazin-4-yl)methanone (121 mg, 0.645 mmol, Intermediate 29, step b) under a nitrogen atmosphere. The resulting suspension was gently heated to form a slightly cloudy solution. The mixture was cooled in a dry ice/acetone bath. n-BuLi (1.6 M in hexane, 0.504 mL, 0.806 mmol) was added dropwise and the mixture was stirred at −78° C. for 45 min, then moved to an ice bath and stirred for 15 min. The reaction was quenched by addition of saturated aqueous NH₄Cl and was diluted with water. The mixture was extracted three times with EtOAc. The organic phase was dried (Na₂SO₄), filtered, and concentrated. The residue was purified by flash column chromatography (silica gel, 2-6% MeOH-DCM) to afford the title compound. ¹H NMR (400 MHz, CDCl₃) δ 9.19 (br. s., 1H), 8.97 (d, J=5.38 Hz, 1H), 8.24 (d, J=1.96 Hz, 1H), 8.06 (d, J=8.80 Hz, 1H), 7.66 (dd, J=1.96, 8.80 Hz, 1H), 7.44-7.59 (m, 4H), 7.22-7.39 (m, 2H), 6.89 (s, 1H), 6.79 (s, 1H), 6.74 (br. s., 1H), 3.43 (s, 3H); MS m/e 461.9 [M+H]⁺.

Example 122

(2,4-Dichloro-3-phenylquinolin-6-yl)(1-methyl-1H-imidazol-5-yl)(pyrazin-2-yl)methanol

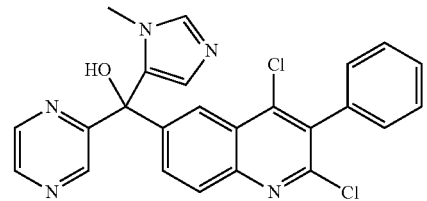 [SMILES: Cn1cncc1C(O)(c1ccc2nc(Cl)c(-c3ccccc3)c(Cl)c2c1)c1cnccn1]

The title compound was prepared using (1-methyl-1H-imidazol-5-yl)(pyrazin-2-yl)methanone (Intermediate 31) in place of (1-methyl-1H-imidazol-2-yl)(pyridazin-4-yl)methanone using the procedure described for Example 121 (gradient used for normal phase chromatography was 2-4% MeOH-DCM). $^1$H NMR (400 MHz, DMSO-$d_6$) δ 9.06 (s, 1H), 8.62 (s, 2H), 8.42 (d, J=1.71 Hz, 1H), 8.06 (d, J=8.80 Hz, 1H), 7.94 (dd, J=1.96, 8.80 Hz, 1H), 7.67 (s, 1H), 7.46-7.60 (m, 4H), 7.42 (dd, J=7.34, 11.74 Hz, 2H), 6.27 (s, 1H), 3.27 (s, 3H); MS m/e 461.9 [M+H]$^+$.

Example 123

(2,4-Dichloro-3-phenylquinolin-6-yl)(1-methyl-1H-imidazol-2-yl)(pyrazin-2-yl)methanol

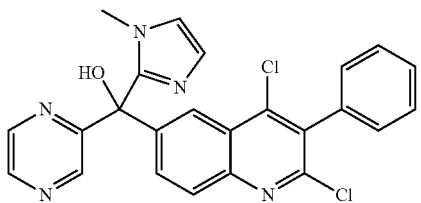 [SMILES: Cn1ccnc1C(O)(c1ccc2nc(Cl)c(-c3ccccc3)c(Cl)c2c1)c1cnccn1]

The title compound was prepared using (1-methyl-1H-imidazol-2-yl)(pyrazin-2-yl)methanone (Intermediate 30, step b) in place of (1-methyl-1H-imidazol-2-yl)(pyridazin-4-yl)methanone using the procedure described for Example 121. The gradient used for normal phase chromatography was 1-3% MeOH-DCM and an additional purification by RP-HPLC (10-90% CH$_3$CN—H$_2$O, 0.1% TFA) was required. The TFA salt obtained from RP-HPLC was converted to the free base by neutralization of fractions with saturated aqueous NaHCO$_3$ and extraction with DCM. $^1$H NMR (400 MHz, DMSO-$d_6$) δ 8.91-8.98 (m, 1H), 8.54-8.58 (m, 1H), 8.53 (dd, J=1.47, 2.45 Hz, 1H), 8.34 (d, J=1.96 Hz, 1H), 8.02 (d, J=8.80 Hz, 1H), 7.81 (dd, J=2.08, 8.93 Hz, 1H), 7.71 (s, 1H), 7.47-7.58 (m, 3H), 7.38-7.46 (m, 2H), 7.20 (d, J=0.98 Hz, 1H), 6.79 (d, J=0.98 Hz, 1H), 3.34 (s, 3H); MS m/e 461.9 [M+H]$^+$.

Example 124

(4-Chlorophenyl)(2,4-dichloro-3-phenylquinolin-6-yl)(pyrimidin-5-yl)methanol

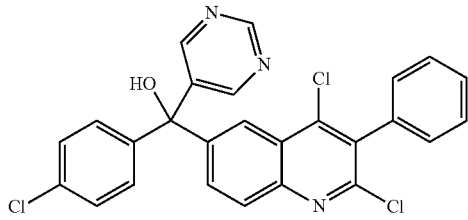 [SMILES: OC(c1ccc(Cl)cc1)(c1cncnc1)c1ccc2nc(Cl)c(-c3ccccc3)c(Cl)c2c1]

The title compound was prepared using (4-chlorophenyl)(pyrimidin-5-yl)methanone (Intermediate 32) in place of (1-methyl-1H-imidazol-2-yl)(pyridazin-4-yl)methanone using the procedure described for Example 121, with the following exception. Isolation of the product was accomplished using first RP-HPLC (10-90% CH$_3$CN—H$_2$O, 0.1% TFA), conversion to the free base by neutralization of the fractions with saturated aqueous NaHCO$_3$ and extraction with DCM, and further purification by flash column chromatography (silica gel, 40-65% EtOAc-Hept) to afford the title compound. $^1$H NMR (400 MHz, DMSO-$d_6$) δ 9.17 (s, 1H), 8.70 (s, 2H), 8.23 (d, J=1.71 Hz, 1H), 8.07 (d, J=8.80 Hz, 1H), 7.83 (dd, J=1.83, 8.93 Hz, 1H), 7.44-7.59 (m, 5H), 7.38-7.44 (m, 3H), 7.36 (d, J=8.56 Hz, 2H); MS m/e 492/493.8 [M+H]$^+$.

Example 125

(2,4-Dichloro-3-phenylquinolin-6-yl)(1-methyl-1H-imidazol-2-yl)(pyrimidin-5-yl)methanol

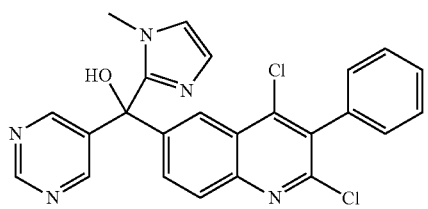 [SMILES: Cn1ccnc1C(O)(c1cncnc1)c1ccc2nc(Cl)c(-c3ccccc3)c(Cl)c2c1]

The title compound was prepared using (1-methyl-1H-imidazol-2-yl)(pyrimidin-5-yl)methanone (Intermediate 33) in place of (1-methyl-1H-imidazol-2-yl)(pyridazin-4-yl)methanone using the procedure described for Example 121, with the following exception. Isolation of the product was accomplished using first RP-HPLC (10-90% CH$_3$CN—H$_2$O, 0.1% TFA), conversion to the free base by neutralization of the fractions with saturated aqueous NaHCO$_3$ and extraction with DCM, and further purification by flash column chromatography (silica gel, 25-50% THF-EtOAc) to afford the title compound. $^1$H NMR (400 MHz, CDCl$_3$) δ 9.10 (s, 1H), 8.77 (m, 2H), 8.21 (s, 1H), 8.09 (d, J=8.80 Hz, 1H), 7.68 (d, J=8.56 Hz, 1H), 7.46-7.58 (m, 3H), 7.30-7.35 (m, 2H), 6.94 (m, 2H), 3.40 (s, 3H); MS m/e 461.9 [M+H]$^+$.

Example 126

(2,4-Dichloro-3-phenylquinolin-6-yl)(1-methyl-1H-imidazol-5-yl)(pyridazin-4-yl)methanol

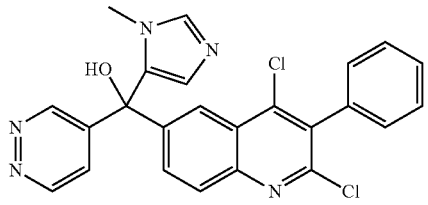 [SMILES: Cn1cncc1C(O)(c1ccnnc1)c1ccc2nc(Cl)c(-c3ccccc3)c(Cl)c2c1]

The title compound was prepared using (1-methyl-1H-imidazol-5-yl)(pyridazin-4-yl)methanone (Intermediate 35) in place of (1-methyl-1H-imidazol-2-yl)(pyridazin-4-yl)methanone using the procedure described for Example 121, with the following exceptions. The reaction time at −78° C. was 2 hours. Isolation of the product was accomplished using first RP-HPLC (10-90% CH$_3$CN—H$_2$O, 0.1% TFA), conversion to the free base by neutralization of the fractions with saturated aqueous NaHCO$_3$ and extraction with DCM, and further purification by flash column chromatography (silica gel, 1-10% MeOH-DCM) to afford the title compound. $^1$H NMR (400 MHz, DMSO-$d_6$) δ 9.29 (dd, J=1.22, 2.45 Hz, 1H), 9.24 (dd, J=1.22, 5.38 Hz, 1H), 8.26 (d, J=1.96 Hz, 1H), 8.10 (d, J=8.80 Hz, 1H), 7.82 (dd, J=2.08, 8.93 Hz, 1H), 7.77 (s, 1H), 7.65 (s, 1H), 7.46-7.60 (m, 4H), 7.36-7.46 (m, 2H), 6.30 (d, J=1.22 Hz, 1H), 3.33 (s, 3H); MS m/e 462.1 [M+H]$^+$.

Example 127

2,4-Dichloro-6-(methoxy(1-methyl-1H-imidazol-5-yl)(pyrazin-2-yl)methyl)-3-phenylquinoline•TFA

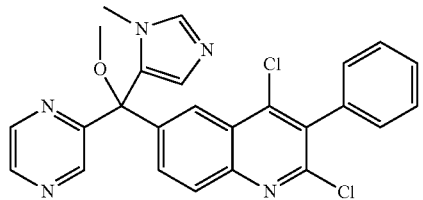 [SMILES: COC(c1ccc2nc(Cl)c(-c3ccccc3)c(Cl)c2c1)(c1cnccn1)c1cncn1C]

Sodium hydride (60% dispersion in mineral oil, 17.8 mg, 0.446 mmol) was added to a solution of (2,4-dichloro-3-phenylquinolin-6-yl)(1-methyl-1H-imidazol-5-yl)(pyrazin-2-yl)methanol (103 mg, 0.223 mmol, Example 122) in DMF (3 mL) under a nitrogen atmosphere. The reaction mixture was stirred at room temperature for 15 min. Iodomethane (0.0556 mL, 0.891 mmol) was added and the mixture was stirred for 75 min. The mixture was cooled in an ice bath and quenched by addition of water, then was extracted with EtOAc (three times). The organic phase was dried (Na$_2$SO$_4$), filtered, and concentrated. The residue was purified by RP-HPLC (10-90% CH$_3$CN—H$_2$O, 0.1% TFA) to afford the title compound. $^1$H NMR (400 MHz, DMSO-d$_6$) δ 9.17 (s, 1H), 9.05 (d, J=1.47 Hz, 1H), 8.70-8.75 (m, 1H), 8.68 (d, J=2.45 Hz, 1H), 8.47 (d, J=1.96 Hz, 1H), 8.11 (d, J=8.80 Hz, 1H), 8.03 (d, J=1.22 Hz, 1H), 7.97 (dd, J=1.96, 9.05 Hz, 1H), 7.48-7.60 (m, 3H), 7.34-7.44 (m, 2H), 3.39 (s, 3H), 3.35 (s, 3H); MS m/e 476.1 [M+H]$^+$.

Example 128

4-Chloro-6-(methoxy(1-methyl-1H-imidazol-5-yl)(pyridin-4-yl)methyl)-N,N-dimethyl-3-phenylquinolin-2-amine•TFA

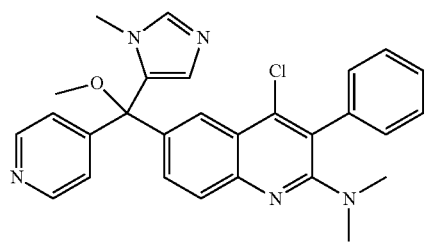 [SMILES: COC(c1ccncc1)(c1ccc2nc(N(C)C)c(-c3ccccc3)c(Cl)c2c1)c1cncn1C]

(4-chloro-2-(dimethylamino)-3-phenylquinolin-6-yl)(1-methyl-1H-imidazol-5-yl)(pyridin-4-yl)methanol•HCl (31 mg, 0.057 mmol, Example 48a•HCl) was converted to the free base by treatment with saturated aqueous NaHCO$_3$ and extraction with EtOAc (three times). The organic phase was dried (Na$_2$SO$_4$), filtered, and concentrated. A sample of the resulting free base (19.8 mg, 0.042 mmol) was dissolved in DMF (2 mL) and sodium hydride (60% dispersion in mineral oil, ca. 2 mg) was added. The resulting mixture was stirred for 15 min. Iodomethane (0.0033 mL, 0.053 mmol) was added and the mixture was stirred for 2 hours. The mixture was cooled in an ice bath and quenched by addition of water, then was extracted with EtOAc (three times). The organic phase was dried (Na$_2$SO$_4$), filtered, and concentrated. The residue was purified by RP-HPLC (10-90% CH$_3$CN—H$_2$O, 0.1% TFA) to afford the title compound. $^1$H NMR (400 MHz, DMSO-d$_6$) δ 9.25 (s, 1H), 8.69 (d, J=4.89 Hz, 2H), 8.20 (s, 1H), 7.88 (s, 1H), 7.70-7.77 (m, 4H), 7.49-7.57 (m, 2H), 7.41-7.49 (m, 1H), 7.37 (d, J=6.85 Hz, 2H), 3.38 (s, 3H), 3.24 (s, 3H), 2.65 (s, 6H); MS m/e 484.2 [M+H]$^+$.

Example 129

(2,4-Dichloro-3-phenylquinolin-6-yl)(3,5-dimethyl-isoxazol-4-yl)(6-methoxypyridin-3-yl)methanol•TFA

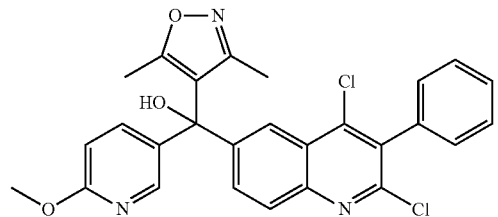 [SMILES: COc1ccc(C(O)(c2ccc3nc(Cl)c(-c4ccccc4)c(Cl)c3c2)c2c(C)noc2C)cn1]

5-Bromo-2-methoxypyridine (0.0201 mL, 0.155 mmol) was added to a solution of (2,4-dichloro-3-phenylquinolin-6-yl)(3,5-dimethylisoxazol-4-yl)methanone (47.5 mg, 0.12 mmol, Intermediate 36) in THF (2 mL) under a nitrogen atmosphere. The mixture was cooled to −78° C. before dropwise addition of n-BuLi (1.6 M in hexane, 0.0972 mL, 0.155 mmol). The mixture was stirred at −78° C. for 30 min, then at 0° C. for 30 min. The reaction was quenched by addition of saturated aqueous NH$_4$Cl and was diluted with water. The mixture was extracted three times with EtOAc. The organic phase was dried (Na$_2$SO$_4$), filtered, and concentrated. The title compound was isolated by RP-HPLC (10-90% CH$_3$CN—H$_2$O, 0.1% TFA). $^1$H NMR (400 MHz, DMSO-d$_6$) δ 8.25 (d, J=1.96 Hz, 1H), 8.09 (d, J=9.05 Hz, 1H), 8.02 (d, J=2.45 Hz, 1H), 7.88 (dd, J=2.08, 8.93 Hz, 1H), 7.70 (dd, J=2.57, 8.68 Hz, 1H), 7.47-7.59 (m, 3H), 7.39-7.47 (m, 2H), 7.03 (br. s., 1H), 6.85 (d, J=8.56 Hz, 1H), 3.84 (s, 3H), 1.81 (s, 3H), 1.70 (s, 3H); MS m/e 506.1 [M+H]$^+$.

Example 130

(4-Chlorophenyl)(2,4-dichloro-3-phenylquinolin-6-yl)(3-methylisoxazol-4-yl)methanol•TFA

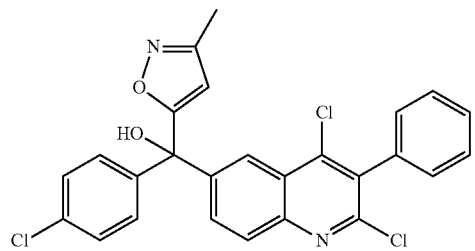 [SMILES: Cc1cc(C(O)(c2ccc(Cl)cc2)c2ccc3nc(Cl)c(-c4ccccc4)c(Cl)c3c2)on1]

(4-Chlorophenyl)magnesium bromide (1.0 M in THF, 0.222 mL, 0.222 mmol) was added dropwise to an ice-cold solution of (2,4-dichloro-3-phenylquinolin-6-yl)(3-methylisoxazol-5-yl)methanone (42.6 mg, 0.111 mmol, Intermediate 37, step b) in THF (1 mL) and the mixture was stirred at room temperature for 2 hours. The reaction was quenched by addition of saturated aqueous NH$_4$Cl and was diluted with water. The mixture was extracted three times with EtOAc. The organic phase was dried (Na$_2$SO$_4$), filtered, and concentrated. The residue was purified by RP-HPLC (10-90% CH$_3$CN—H$_2$O, 0.1% TFA) to afford the title compound. $^1$H NMR (400 MHz, DMSO-d$_6$) δ 8.26 (s, 1H), 8.08 (d, J=8.80 Hz, 1H), 7.78 (d, J=8.80 Hz, 1H), 7.37-7.65 (m, 8H), 7.31 (d, J=8.56 Hz, 2H), 6.24 (s, 1H), 2.24 (s, 3H); MS m/e 495.0 [M+H]$^+$.

Example 131

(2,4-Dichloro-3-phenylquinolin-6-yl)(6-methoxypyridin-3-yl)(3-methylisoxazol-5-yl)methanol·TFA

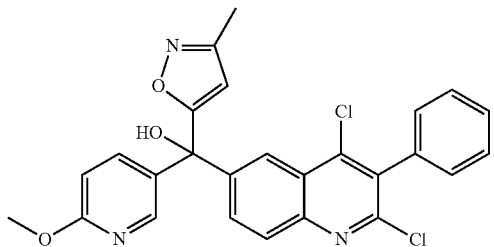 [SMILES: COc1ccc(C(O)(c2ccc3nc(Cl)c(-c4ccccc4)c(Cl)c3c2)c2cc(C)no2)cn1]

5-Bromo-2-methoxypyridine (0.0194 mL, 0.15 mmol) was added to a solution of (2,4-dichloro-3-phenylquinolin-6-yl)(3-methylisoxazol-5-yl)methanone (44.1 mg, 0.115 mmoL, Intermediate 37, step b) in THF (1 mL) under a nitrogen atmosphere. The mixture was cooled to −78° C. and n-BuLi (1.6 M in hexane, 0.0935 mL, 0.150 mmol) was added dropwise. The mixture was stirred at −78° C. for 30 min, then moved to an ice bath and stirred for 30 min. The reaction was quenched by addition of saturated aqueous NH$_4$Cl and was diluted with water. The mixture was extracted three times with EtOAc. The organic phase was dried (Na$_2$SO$_4$), filtered, and concentrated. The crude product was purified by RP-HPLC (10-90% CH$_3$CN—H$_2$O, 0.1% TFA) to afford the title compound. $^1$H NMR (400 MHz, DMSO-d$_6$) δ 8.29 (s, 1H), 8.09 (d, J=8.80 Hz, 1H), 8.01 (d, J=2.20 Hz, 1H), 7.81 (d, J=8.80 Hz, 1H), 7.46-7.64 (m, 5H), 7.42 (d, J=6.85 Hz, 2H), 6.84 (d, J=8.80 Hz, 1H), 6.27 (s, 1H), 3.85 (s, 3H), 2.24 (s, 3H); MS m/e 492.1 [M+H]$^+$.

Example 132

(2,4-Dichloro-3-phenylquinolin-6-yl)(1-methyl-1H-imidazol-5-yl)(3-methylisoxazol-5-yl)methanol·TFA

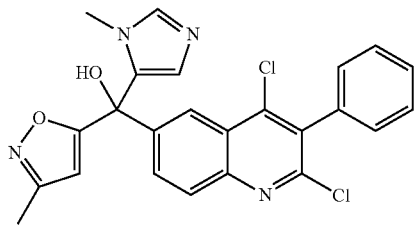 [SMILES: Cc1cc(C(O)(c2ccc3nc(Cl)c(-c4ccccc4)c(Cl)c3c2)c2cncn2C)on1]

Ethylmagnesium bromide (3 M in Et$_2$O, 0.0642 mL, 0.193 mmol) was added dropwise to a solution of 5-bromo-1-methyl-1H-imidazole (31.0 mg, 0.193 mmol) in DCM (1 mL) under a nitrogen atmosphere. The mixture was stirred at room temperature for 15 min, then was cooled to 0° C. A solution of (2,4-dichloro-3-phenylquinolin-6-yl)(3-methylisoxazol-5-yl)methanone (49.2 mg, 0.128 mmol, Intermediate 37, step b) in DCM (2 mL) was added via cannula. The mixture was stirred at room temperature for 2 hours. The reaction was quenched by addition of saturated aqueous NH$_4$Cl and was diluted with water. The mixture was extracted three times with EtOAc. The organic phase was dried (Na$_2$SO$_4$), filtered, and concentrated. The crude product was purified by RP-HPLC (10-90% CH$_3$CN—H$_2$O, 0.1% TFA) to afford the title compound. $^1$H NMR (400 MHz, DMSO-d$_6$) δ 8.99 (br. s., 1H), 8.39 (s, 1H), 8.10-8.25 (m, 2H), 7.83 (d, J=9.05 Hz, 1H), 7.47-7.63 (m, 3H), 7.36-7.47 (m, 2H), 7.27 (br. s., 1H), 6.38 (s, 1H), 3.52 (s, 3H), 2.24 (s, 3H); MS m/e 465.1 [M+H]$^+$.

Example 133

(4-Chlorophenyl)(2,4-dichloro-3-phenylquinolin-6-yl)(3,5-dimethylisoxazol-4-yl)methanol·TFA

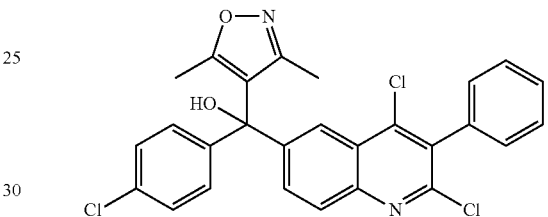

The title compound was prepared using (2,4-dichloro-3-phenylquinolin-6-yl)(3,5-dimethylisoxazol-4-yl)methanone (Intermediate 36) in place of (2,4-dichloro-3-phenylquinolin-6-yl)(3-methylisoxazol-5-yl)methanone using the procedure described for Example 130. $^1$H NMR (400 MHz, DMSO-d$_6$) δ 8.24 (s, 1H), 8.08 (d, J=8.80 Hz, 1H), 7.86 (d, J=8.80 Hz, 1H), 7.48-7.60 (m, 3H), 7.33-7.49 (m, 6H), 7.06 (br. s., 1H), 1.79 (s, 3H), 1.63 (s, 3H); MS m/e 509.3 [M+H]$^+$.

Example 134

(4-Chloro-2-(dimethylamino)-3-phenylquinolin-6-yl)(4-chlorophenyl)(3-methylisoxazol-5-yl)methanol·TFA

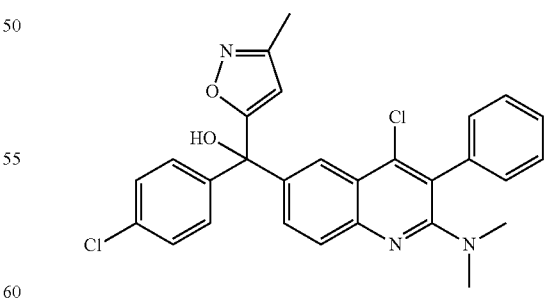

Dimethylamine (2 M in MeOH, 1 mL, 2 mmol) was added to (4-chlorophenyl)(2,4-dichloro-3-phenylquinolin-6-yl)(3-methylisoxazol-4-yl)methanol·TFA (15.5 mg, 0.0254 mmol, Example 130) and the mixture was heated in 80° C. oil bath in sealed tube for 1 day. The mixture was cooled to room temperature and was directly purified by RP-HPLC (10-90%

CH₃CN—H₂O, 0.1% TFA) to afford the title compound. ¹H NMR (400 MHz, DMSO-d₆) δ 8.04 (s, 1H), 7.75 (d, J=8.80 Hz, 1H), 7.48-7.58 (m, 3H), 7.34-7.48 (m, 6H), 7.28 (d, J=8.56 Hz, 2H), 6.19 (s, 1H), 2.67 (s, 6H), 2.23 (s, 3H); MS m/e 504.1 [M+H]⁺.

Example 135

4-Chloro-6-((4-chlorophenyl)(hydroxy)(1-methyl-1H-imidazol-5-yl)methyl)-3-phenylquinoline-2-carbonitrile

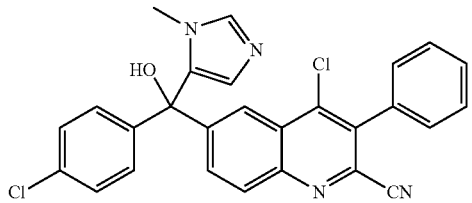 [SMILES: Cn1cncc1C(O)(c1ccc(Cl)cc1)c1ccc2nc(C#N)c(-c3ccccc3)c(Cl)c2c1]

(4-Chlorophenyl)(2,4-dichloro-3-phenylquinolin-6-yl)(1-methyl-1H-imidazol-5-yl)methanol (116 mg, 0.235 mmol, Example 119a), Pd₂dba₃ (8.6 mg, 0.0094 mmol), 1,1'-bis(diphenylphosphino)ferrocene (dppf, 10.4 mg, 0.0188 mmol), zinc cyanide (33.1 mg, 0.282 mmol), and zinc nanopowder (3.7 mg, 0.0565 mmol) were combined in a pressure tube, which was then evacuated and back-filled with nitrogen (three times). N,N-dimethylacetamide (1 mL) was added and the mixture was heated in a 120° C. oil bath for 4 hours. The mixture was allowed to cool to room temperature and was diluted with EtOAc. The mixture was washed with saturated aqueous ammonium hydroxide followed by saturated aqueous sodium chloride. The organic phase was dried (Na₂SO₄), filtered, and concentrated. The residue was partially purified by flash column chromatography (Biotage KP-NH amine-functionalized silica column, gradient 40-100% EtOAc-heptane, then 10% MeOH-DCM), followed by further purification by RP-HPLC (10-90% CH₃CN—H₂O, 0.1% TFA). Fractions containing the product were partially concentrated to remove CH₃CN, neutralized with saturated aqueous NaHCO₃, and extracted with DCM, and the organic phase was washed with water, dried over Na₂SO₄, filtered, and concentrated to afford the title compound. ¹H NMR (400 MHz, DMSO-d₆) δ 8.34 (d, J=1.96 Hz, 1H), 8.24 (d, J=8.80 Hz, 1H), 7.88 (dd, J=1.96, 8.80 Hz, 1H), 7.72 (s, 1H), 7.54-7.64 (m, 5H), 7.41-7.49 (m, 2H), 7.35 (d, J=8.56 Hz, 2H), 7.31 (s, 1H), 6.21 (d, J=0.98 Hz, 1H), 3.35 (s, 3H); MS m/e 485.1 [M+H]⁺.

Example 136

(4-Chlorophenyl)(2,4-dimethoxy-3-phenylquinolin-6-yl)(1-methyl-1H-imidazol-5-yl)methanol•TFA

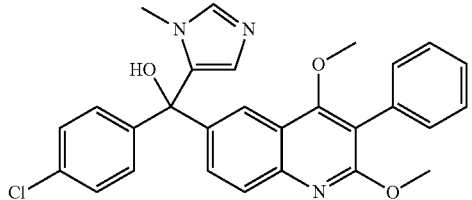 [SMILES: COc1nc2ccc(C(O)(c3ccc(Cl)cc3)c3cncn3C)cc2c(OC)c1-c1ccccc1]

A solution of sodium methoxide in MeOH (25 wt. %, 0.0924 mL, 0.404 mmol) was added to a suspension of (4-chlorophenyl)(2,4-dichloro-3-phenylquinolin-6-yl)(1-methyl-1H-imidazol-5-yl)methanol (100 mg, 0.202 mmol, Example 119a) in MeOH (0.5 mL). The mixture was heated in an 80° C. oil bath for 2.5 hours. Additional portions of sodium methoxide in MeOH (25 wt. %, 0.0924 mL, 0.404 mmol) and MeOH (0.5 mL) were added and heating was continued overnight. The reaction mixture was diluted with water and extracted with DCM (three times). The organic phase was washed with water, then was dried (Na₂SO₄), filtered, and concentrated. The residue was purified twice by RP-HPLC (10-90% CH₃CN—H₂O, 0.1% TFA) to afford the title compound. ¹H NMR (400 MHz, DMSO-d₆) δ 9.14 (s, 1H), 7.98 (d, J=2.20 Hz, 1H), 7.83 (d, J=8.80 Hz, 1H), 7.32-7.60 (m, 11H), 6.96 (s, 1H), 3.91 (s, 3H), 3.56 (s, 3H), 3.45 (s, 3H); MS m/e 486.1 [M+H]⁺.

Example 137a 6-((4-Chlorophenyl)(hydroxy)(1-methyl-1H-imidazol-5-yl)methyl)-3-phenylquinoline-2,4-dicarbonitrile

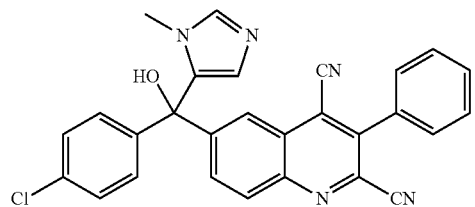 [SMILES: Cn1cncc1C(O)(c1ccc(Cl)cc1)c1ccc2nc(C#N)c(-c3ccccc3)c(C#N)c2c1]

(4-Chlorophenyl)(2,4-dichloro-3-phenylquinolin-6-yl)(1-methyl-1H-imidazol-5-yl)methanol (864 mg, 1.75 mmol, Example 119a), Pd₂dba₃ (64.0 mg, 0.0698 mmol), 1,1'-bis(diphenylphosphino)ferrocene (dppf, 77.4 mg, 0.140 mmol), zinc cyanide (246 mg, 2.10 mmol), and zinc nanopowder (27.4 mg, 0.419 mmol) were combined in a pressure tube, which was then evacuated and back-filled with nitrogen (twice). N,N-dimethylacetamide (3.5 mL) was added and the mixture was heated in a 120° C. oil bath for 22 hours. The mixture was allowed to cool to room temperature and was diluted with EtOAc and 2 N aqueous ammonium hydroxide. The mixture was filtered through Celite®. The phases of the filtrate were separated and the organic phase was washed with saturated aqueous NaCl. The aqueous extracts were back-extracted once with EtOAc. The organic phase was dried (Na₂SO₄), filtered, and concentrated. The residue was partially purified by flash column chromatography (silica gel, gradient 0-3.5% MeOH-DCM). The product was triturated with CH₃CN. Further purification was accomplished by flash column chromatography (silica gel, 20%-25% acetone-DCM) to afford the title compound. ¹H NMR (400 MHz, CDCl₃) δ 8.49 (d, J=1.71 Hz, 1H), 8.21 (d, J=9.05 Hz, 1H), 7.81 (dd, J=1.96, 9.05 Hz, 1H), 7.57-7.69 (m, 5H), 7.29-7.39 (m, 5H), 6.37 (s, 1H), 5.11 (br. s., 1H), 3.40 (s, 3H); MS m/e 476.0 [M+H]⁺.

Example 137a was purified by chiral HPLC (Chiralpak AD, 100% EtOH) to give 2 pure enantiomers (elution order: Example 137c first, Example 137b second). The separated enantiomers were each converted to HCl salts as follows. A solution of each in DCM was treated with 1 N HCl in Et₂O (3 equivalents) and the mixtures were concentrated to provide Examples 137b and 137c.

Example 137b

¹H NMR (400 MHz, DMSO-d₆) δ 9.15 (s, 1H), 8.39 (d, J=8.80 Hz, 1H), 8.26 (d, J=1.96 Hz, 1H), 8.01 (dd, J=1.96, 9.05 Hz, 1H), 7.94 (s, 1H), 7.73-7.83 (m, 2H), 7.63-7.73 (m,

3H), 7.48-7.59 (m, 2H), 7.38-7.48 (m, 2H), 7.03 (d, J=1.22 Hz, 1H), 3.56 (s, 3H); MS m/e 476.1 [M+H]⁺.

Example 137c

¹H NMR (400 MHz, DMSO-d₆) δ 9.17 (s, 1H), 8.39 (d, J=8.80 Hz, 1H), 8.26 (d, J=1.71 Hz, 1H), 8.01 (dd, J=2.08, 8.93 Hz, 1H), 7.96 (s, 1H), 7.73-7.82 (m, 2H), 7.63-7.72 (m, 3H), 7.48-7.57 (m, 2H), 7.39-7.48 (m, 2H), 7.03 (d, J=1.22 Hz, 1H), 3.56 (s, 3H); MS m/e 476.1 [M+H]⁺.

Example 138a (4-Chlorophenyl)(1-methyl-1H-imidazol-5-yl)(3-phenyl-2,4-bis(trifluoromethyl)quinolin-6-yl)methanol

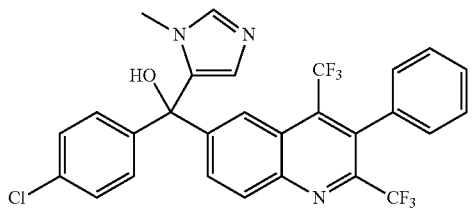 [SMILES: Cn1cncc1C(O)(c1ccc(Cl)cc1)c1ccc2nc(C(F)(F)F)c(-c3ccccc3)c(C(F)(F)F)c2c1]

Isopropylmagnesium chloride (2.0 M in THF, 0.532 mL, 1.06 mmol) was added dropwise to a solution of 6-iodo-3-phenyl-2,4-bis(trifluoromethyl)quinoline (474 mg, 1.01 mmol, Intermediate 8, step d) in THF (1 mL) at −78° C. under an argon atmosphere. The mixture was stirred at −78° C. for 5 min, then was removed from the cold bath and was stirred for 15 min. Neat (4-chlorophenyl)(1-methyl-1H-imidazol-5-yl)methanone (246 mg, 1.12 mmol, Intermediate 18, step b) was added followed by 1 mL THF to aid stirring of the thick mixture. The mixture was stirred at room temperature overnight. The reaction was quenched by addition of saturated aqueous NH₄Cl and extracted with EtOAc (three times). The organic phase was dried (Na₂SO₄), filtered, and concentrated. The residue was purified by flash column chromatography (silica gel, gradient 0-3% MeOH-DCM) to afford the title compound. ¹H NMR (400 MHz, CDCl₃) δ 8.36 (d, J=1.71 Hz, 1H), 8.29 (d, J=8.80 Hz, 1H), 7.89 (dd, J=1.59, 8.93 Hz, 1H), 7.41-7.52 (m, 3H), 7.38 (s, 1H), 7.32-7.37 (m, 4H), 7.28-7.31 (m, 2H), 6.43 (s, 1H), 3.40 (s, 3H); MS m/e 562.0 [M+H]⁺.

Example 138a was purified by chiral HPLC (Chiralpak AD, 95% heptane/5% EtOH) to give 2 enantiomers (elution order: Example 138c first, Example 138b second). The separated enantiomers were each converted to HCl salts as follows. A solution of each in DCM was treated with 1 N HCl in Et₂O (3 equivalents) and the mixtures were concentrated. One of the HCl salts required further purification; it was re-converted to the free base (saturated aqueous NaHCO₃/DCM extraction) and purified by flash column chromatography (silica gel, gradient 0-3% MeOH-DCM) to afford example 138b.

Example 138b

¹H NMR (400 MHz, CDCl₃) δ 8.32-8.39 (m, 1H), 8.28 (d, J=8.80 Hz, 1H), 7.89 (dd, J=1.96, 8.80 Hz, 1H), 7.40-7.51 (m, 3H), 7.31-7.37 (m, 5H), 7.27-7.31 (m, 2H), 6.41 (s, 1H), 3.39 (s, 3H); MS m/e 562.0 [M+H]⁺.

Example 138c

HCl Salt

¹H NMR (400 MHz, DMSO-d₆) δ 9.19 (s, 1H), 8.42 (d, J=9.05 Hz, 1H), 8.23 (br. s., 1H), 8.01 (dd, J=1.83, 8.93 Hz, 1H), 7.86 (s, 1H), 7.44-7.57 (m, 5H), 7.35-7.44 (m, 4H), 7.05 (d, J=0.98 Hz, 1H), 3.57 (s, 3H); MS m/e 562.0 [M+H]⁺.

Example 139

4-Chloro-6-((4-chlorophenyl)(1,2-dimethyl-1H-imidazol-5-yl)(hydroxy)methyl)-3-phenylquinoline-2-carbonitrile•TFA

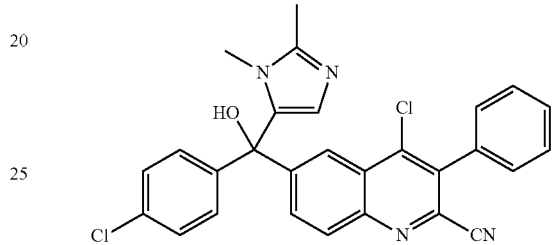

The title compound was prepared using (4-chlorophenyl)(2,4-dichloro-3-phenylquinolin-6-yl)(1,2-dimethyl-1H-imidazol-5-yl)methanol (Example 15) in place of (4-chlorophenyl)(2,4-dichloro-3-phenylquinolin-6-yl)(1-methyl-1H-imidazol-5-yl)methanol using the procedure described for Example 137a, with the following exceptions. After heating overnight, LCMS analysis showed mainly mono- rather than di-nitrile. In an attempt to convert to di-nitrile, second portions of Pd₂dba₃, dppf, and zinc cyanide (amounts equal to the initial loadings) were added, the mixture was evacuated and refilled with argon, and was again heated overnight in a 120° C. oil bath. The reaction work-up was as described for Example 137a, but the title compound was isolated by RP-HPLC (10-90% CH₃CN—H₂O, 0.1% TFA, first run; 50-80% CH₃CN—H₂O, 0.1% TFA, second run). ¹H NMR (400 MHz, CDCl₃) δ 8.35 (d, J=1.71 Hz, 1H), 8.21 (d, J=8.80 Hz, 1H), 7.87 (dd, J=1.96, 9.05 Hz, 1H), 7.52-7.63 (m, 3H), 7.41-7.48 (m, 2H), 7.36 (s, 4H), 6.50 (s, 1H), 3.49 (s, 3H), 2.54 (s, 3H); MS m/e 499.0 [M+H]⁺.

Example 140

(2,4-Dichloro-3-phenylquinolin-6-yl)(1-methyl-1H-imidazol-5-yl)(2-methylthiazol-4-yl)methanol

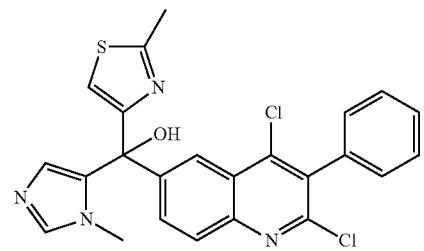 [SMILES: Cc1nc(C(O)(c2ccc3nc(Cl)c(-c4ccccc4)c(Cl)c3c2)c2cncn2C)cs1]

To a 2-necked flask containing 6-bromo-2,4-dichloro-3-phenylquinoline (200 mg, 0.57 mmol, Intermediate 1, step c)

was added THF (15 mL) to give a homogeneous clear solution. The solution was cooled to −75° C. and n-BuLi (2.5 M in hexanes, 0.20 mL, 0.50 mmol) was added which resulted in an immediate brownish homogeneous solution. After 2 min, a solution of (1-methyl-1H-imidazol-5-yl)(2-methylthiazol-4-yl)methanone (110 mg, 0.53 mmol, Intermediate 38, step b) in 2 mL of THF was added and the brown color faded to a light greenish-brown color. The mixture was maintained at −75° C. for 10 min then replaced with a ice-bath. Upon warming to 0° C. a dark purple color resulted. The mixture was quenched after 25 min with MeOH (2 mL) and saturated NH₄Cl solution and extracted with EtOAc (4×50 mL). The combined organics were washed with brine, dried over MgSO₄, filtered and concentrated to provide an amber oil. Chromatography on silica gel (20-50% acetone-DCM increasing gradient to 5% MeOH-DCM) afforded the title compound as a white solid. $^1$H NMR (500 MHz, CDCl₃) δ 8.39 (d, J=1.8 Hz, 1H), 8.06 (d, J=8.8 Hz, 1H), 7.84 (dd, J=8.8, 2.0 Hz, 1H), 7.58-7.44 (m, 3H), 7.42 (s, 1H), 7.37-7.29 (m, 2H), 6.63 (s, 1H), 6.38 (s, 1H), 3.46 (d, J=8.8 Hz, 3H), 2.71 (s, 3H). MS m/e 481.0/483.0 [M+H]$^+$.

Example 141

(2-Chloro-1-methyl-1H-imidazol-5-yl)(4-chlorophenyl)(2,4-dichloro-3-phenylquinolin-6-yl)methanol

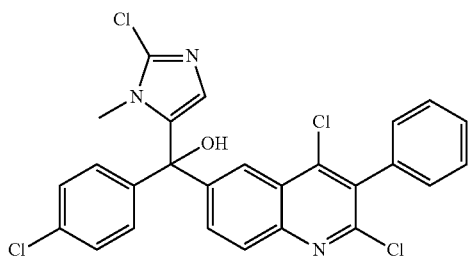 [SMILES: Cn1c(C(O)(c2ccc(Cl)cc2)c2ccc3nc(Cl)c(-c4ccccc4)c(Cl)c3c2)cnc1Cl]

To a 2-necked flask containing 6-bromo-2,4-dichloro-3-phenylquinoline (500 mg, 1.42 mmol, Intermediate 1, step c) was added THF (25 mL) to give a homogeneous clear solution. The solution was cooled −78° C. and n-BuLi (2.5 M in hexanes, 0.50 mL, 1.25 mmol) was added which resulted in an immediate brownish homogeneous solution. After 2 min, a solution of (2-chloro-1-methyl-1H-imidazol-5-yl)(4-chlorophenyl)methanone (400 mg, 1.57 mmol, Intermediate 39) in 10 mL of THF was added and the brown color faded to a light yellow color. The reaction mixture was maintained at −75° C. for 10 min then replaced with a 0° C. ice-bath. The reaction was quenched after 25 min with MeOH (2 mL) and NH₄Cl solution. The aqueous portion was extracted with EtOAc (3×50 mL). The combined organics were washed with brine, dried over MgSO₄, filtered and concentrated to provide a white solid. Chromatography on silica gel (20-30% EtOAc-DCM) afforded the title compound as a white solid. $^1$H NMR (400 MHz, CDCl₃) δ 8.31 (d, J=2.0 Hz, 1H), 8.01 (d, J=8.8 Hz, 1H), 7.68 (dd, J=8.9, 2.1 Hz, 1H), 7.58-7.46 (m, 3H), 7.41-7.28 (m, 6H), 6.22 (s, 1H), 4.23 (s, 1H), 3.37 (s, 3H), 1.62 (s, 3H). MS m/e 528.0/529.0/529.9/532.0 [M+H]$^+$.

Example 142

(2,4-Dichloro-3-phenylquinolin-6-yl)(2,6-dimethylpyridin-3-yl)(1-methyl-1H-imidazol-5-yl)methanol

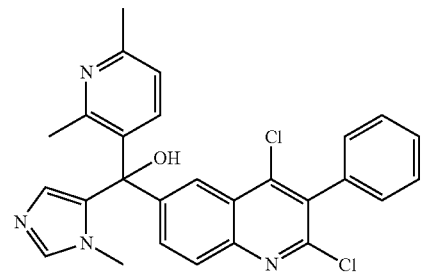 [SMILES: Cc1ccc(C(O)(c2ccc3nc(Cl)c(-c4ccccc4)c(Cl)c3c2)c2cncn2C)c(C)n1]

To a 2-necked flask containing 6-bromo-2,4-dichloro-3-phenylquinoline (450 mg, 1.27 mmol, Intermediate 1, step c) was added THF (15 mL) to give a homogeneous clear solution. The solution was cooled to −75° C. and n-BuLi (2.5 M in hexanes, 0.45 mL, 1.1 mmol) was added which resulted in an immediate brownish solution. After 2 min, a solution of (2,6-dimethylpyridin-3-yl)(1-methyl-1H-imidazol-5-yl)methanone (270 mg, 1.26 mmol, Intermediate 40, step b) in 2 mL of THF was added and the brown color faded to a lighter greenish-brown color. The mixture was maintained at −75° C. for 5 min, then replaced with a 0° C. ice-bath. The mixture was quenched after 25 min with a saturated NH₄Cl solution and extracted with EtOAc (3×50 mL). The combined organics were washed with brine, dried over MgSO₄, filtered and concentrated. Chromatography on silica gel (20-50% acetone-DCM increasing gradient to 5% MeOH-DCM) afforded the title compound as a pale yellowish solid. $^1$H NMR (500 MHz, CDCl₃) δ 8.33 (d, J=1.9 Hz, 1H), 7.99 (d, J=8.8 Hz, 1H), 7.61-7.45 (m, 4H), 7.36 (m 3H), 7.06 (d J=5.3 Hz, 1H), 6.94 (d, J=5.3 Hz, 1H), 6.20 (s, 1H), 4.33 (s, 1H), 3.50 (s, 3H), 2.52 (d, J=12.5 Hz, 3H), 2.42 (s, 3H). MS m/e 489.1/491.1 [M+H]$^+$.

Example 143

(2,4-Dichloro-3-phenylquinolin-6-yl)(2,4-dimethylthiazol-5-yl)(1-methyl-1H-imidazol-5-yl)methanol

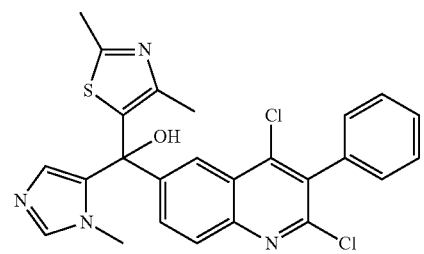 [SMILES: Cc1nc(C)c(C(O)(c2ccc3nc(Cl)c(-c4ccccc4)c(Cl)c3c2)c2cncn2C)s1]

To a 2-necked flask containing 6-bromo-2,4-dichloro-3-phenylquinoline (450 mg, 1.27 mmol, Intermediate 1, step c) was added THF (15 mL) to give a homogeneous clear solution. The solution was cooled to −75° C. and n-BuLi (2.5 M in hexanes, 0.45 mL, 1.13 mmol) was added which resulted in an immediate brownish homogeneous solution. After 2 min, a solution of (2,4-dimethylthiazol-5-yl)(1-methyl-1H-imidazol-5-yl)methanone (350 mg, 1.58 mmol, Intermediate 41, step b) in 4 mL of THF was added and the brown color faded to a light greenish-brown color. The reaction was maintained at −75° C. for 5 min then replaced with a 0° C. ice-bath. The mixture was quenched after 25 min with NH$_4$Cl solution. The aqueous portion was extracted with EtOAc (3×50 mL). The combined organics were washed with brine, dried over MgSO$_4$, filtered and concentrated to provide an amber oil. Chromatography on silica gel (20-50% acetone-DCM increasing gradient to 5% MeOH) afforded the title compound as a pale yellowish solid. $^1$H NMR (500 MHz, CDCl$_3$) δ 8.35 (d, J=1.9 Hz, 1H), 8.03 (d, J=8.8 Hz, 1H), 7.79 (dd, J=8.8, 2.1 Hz, 1H), 7.59-7.41 (m, 3H), 7.40-7.31 (m, 2H), 7.28 (d, J=6.4 Hz, 1H), 6.44 (s, 1H), 5.46 (s, 1H), 3.48 (s, 3H), 2.56 (s, 3H), 2.13 (s, 3H). MS m/e 495.0/497.0 [M+H]$^+$.

Example 144

(4-Chlorophenyl)(2,4-dichloro-3-phenylquinolin-6-yl)(1-methyl-1H-1,2,3-triazol-5-yl)methanol

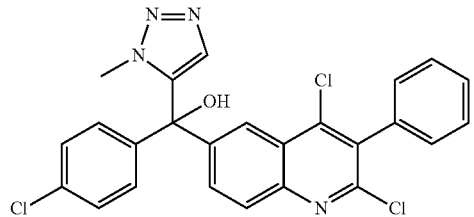 [SMILES: Cn1nncc1C(O)(c1ccc(Cl)cc1)c1ccc2nc(Cl)c(-c3ccccc3)c(Cl)c2c1]

To a 2-necked flask containing 6-bromo-2,4-dichloro-3-phenylquinoline (250 mg, 0.71 mmol, Intermediate 1, step c) was added THF (10 mL) to give a homogeneous clear solution. The solution was cooled to −78° C. and n-BuLi (2.5 M in hexanes, 0.25 mL, 0.63 mmol) was added which resulted in an immediate brownish homogeneous solution. After 2 min, a solution of (4-chlorophenyl)(1-methyl-1H-1,2,3-triazol-5-yl)methanone (180 mg, 0.811 mmol, Intermediate 42, step c) in 3 mL of THF was added and the brown color immediately faded to a light yellow color. The mixture was maintained at −75° C. for 5 min then replaced with a 0° C. ice-bath. The mixture was quenched after 35 min with a saturated NH$_4$Cl solution and extracted with EtOAc (3×50 mL). The combined organics were washed with brine, dried over MgSO$_4$, filtered and concentrated to provide a white solid. Chromatography on silica gel (5-30% EtOAc-DCM) provided the title compound as a white solid. $^1$H NMR (500 MHz, CD$_2$Cl$_2$) δ 8.26 (d, J=2.0 Hz, 1H), 8.02 (d, J=8.8 Hz, 1H), 7.68 (dd, J=8.9, 2.1 Hz, 1H), 7.58-7.46 (m, 3H), 7.41-7.23 (m, 7H), 6.98 (s, 1H), 3.82 (s, 3H). MS m/e 495.0/497.0/496.0/498.0 [M+H]$^+$.

Example 145

(4-Chlorophenyl)(2,4-dichloro-3-phenylquinolin-6-yl)(1-methyl-2-(methylthio)-1H-imidazol-5-yl)methanol

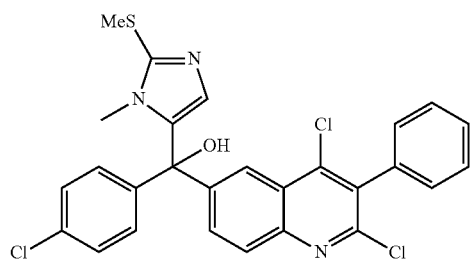 [SMILES: CSc1ncc(C(O)(c2ccc(Cl)cc2)c2ccc3nc(Cl)c(-c4ccccc4)c(Cl)c3c2)n1C]

To a 2-necked flask containing 6-bromo-2,4-dichloro-3-phenylquinoline (255 mg, 0.72 mmol, Intermediate 1, step c) was added THF (10 mL) to give a homogeneous clear solution. The solution was cooled to −75° C. and n-BuLi (2.5 M in hexanes, 0.28 mL, 0.69 mmol) was added which resulted in an immediate brownish homogeneous solution. After 2 min, a solution of (4-chlorophenyl)(1-methyl-2-(methylthio)-1H-imidazol-5-yl)methanone (US patent application 20050250948) (210 mg, 0.787 mmol) in 4 mL of THF was added and the brown color immediately faded to a light green-yellow color. The reaction mixture was maintained at −75° C. for 5 min then replaced with a 0° C. ice-bath. The reaction mixture was quenched after 35 min with a saturated NH$_4$Cl solution and extracted with EtOAc (3×50 mL). The combined organics were washed with brine, dried over MgSO$_4$, filtered and concentrated to provide a white solid. The crude material was triturated with DCM and MeOH (~5:1) to afford the title compound as a white solid. $^1$H NMR (500 MHz, MeOD) δ 8.27 (d, J=1.8 Hz, 1H), 8.00 (d, J=8.9 Hz, 1H), 7.87 (dd, J=8.9, 2.1 Hz, 1H), 7.59-7.42 (m, 3H), 7.42-7.27 (m, 6H), 6.30 (s, 1H), 3.41 (s, 3H), 2.53 (s, 3H). MS m/e 540.0/541.0/544.0 [M+H]$^+$.

Example 146

(2,4-Dichloro-3-phenylquinolin-6-yl)(1-methyl-1H-imidazol-5-yl)(2-methylbenzo[d]oxazol-5-yl)methanol

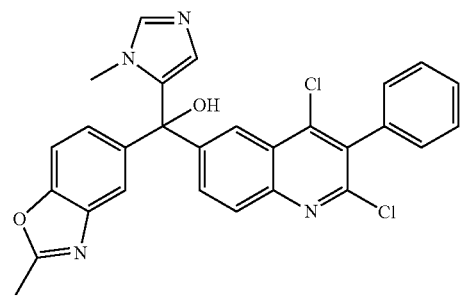 [SMILES: Cc1nc2cc(C(O)(c3ccc4nc(Cl)c(-c5ccccc5)c(Cl)c4c3)c3cncn3C)ccc2o1]

To a 2-necked flask containing 6-bromo-2,4-dichloro-3-phenylquinoline (255 mg, 0.720 mmol, Intermediate 1, step c) was added THF (10 mL) to give a homogeneous clear solution. The solution was cooled to −75° C. and n-BuLi (2.5 M in hexanes, 0.28 mL, 0.69 mmol) was added which resulted in an immediate brownish homogeneous solution. After 2 min, a solution of (1-methyl-1H-imidazol-5-yl)(2-methylbenzo[d]oxazol-5-yl)methanone (175 mg, 0.781 mmol, Intermediate 43, step b) in 5 mL of THF was added and the brown color immediately became a darker brown suspension. The reaction was maintained at −75° C. for 5 min then replaced with a 0° C. ice-bath. As the reaction warmed up, the dark brown suspension became lighter in color and more homogeneous. After 10 min, the reaction mixture became an orangish homogeneous solution. The mixture was quenched after 3 hours with saturated NH$_4$Cl solution and extracted with EtOAc (3×50 mL). The combined organics were washed with brine, dried over MgSO$_4$, filtered and concentrated. Chromatography on silica gel (3-5% MeOH-DCM increasing gradient to 2 M NH$_3$-MeOH-DCM) provided the title compound as an off white solid. $^1$H NMR (500 MHz, CDCl$_3$) δ 8.34 (d, J=1.9 Hz, 1H), 7.98 (d, J=8.8 Hz, 1H), 7.75 (dd, J=8.9, 2.0 Hz, 1H), 7.61 (d, J=1.6 Hz, 1H), 7.56-7.46 (m, 3H), 7.39 (d, J=8.5 Hz, 1H), 7.36-7.27 (m, 4H), 6.34 (s, 1H), 3.38 (s, 3H), 2.62 (s, 3H). MS m/e 515.0/517.0 [M+H]⁺.

Example 147

(4-Chlorophenyl)(2,4-dichloro-3-phenylquinolin-6-yl)(1-(3-methoxypropyl)-1H-imidazol-5-yl)methanol

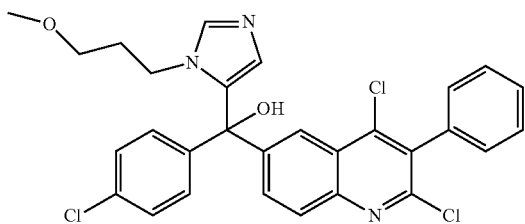 [SMILES: COCCCn1cncc1C(O)(c1ccc(Cl)cc1)c1ccc2nc(Cl)c(-c3ccccc3)c(Cl)c2c1]

To a 2-necked flask containing 6-bromo-2,4-dichloro-3-phenylquinoline (255 mg, 0.72 mmol, Intermediate 1, step c) was added THF (10 mL) to give a homogeneous clear solution. The solution was cooled to −75° C. and n-BuLi (2.5 M in hexanes, 0.26 mL, 0.65 mmol) was added which resulted in an immediate orange-brown homogeneous solution. After 2 min, a solution of (4-chlorophenyl)(1-(3-methoxypropyl)-1H-imidazol-5-yl)methanone (230 mg, 0.825 mmol) in 4 mL of THF was added and the orange-brown color immediately faded to a light greenish-yellow solution then to a light orangish solution. The reaction was maintained at −75° C. for 5 min then replaced with a 0° C. ice-bath. After 30 min the ice-bath was removed and the reaction was stirred at 22° C. The reaction mixture was quenched after 1 hours with saturated NH₄Cl solution, and extracted with EtOAc (3×50 mL). The combined organics were washed with brine, dried over MgSO₄, filtered and concentrated. Chromatography on silica gel (10-25% acetone-DCM) provided the title compound as a white amorphous solid. ¹HNMR (500 MHz, CD₂Cl₂) δ 8.28 (d, J=1.9 Hz, 1H), 7.98 (d, J=8.8 Hz, 1H), 7.75 (dd, J=8.8, 2.0 Hz, 1H), 7.60-7.44 (m, 4H), 7.44-7.23 (m, 6H), 6.22 (s, 1H), 5.72 (s, 1H), 5.36-5.22 (m, 2H), 3.79 (t, J=6.9 Hz, 2H), 3.31-3.12 (m, 5H), 1.97-1.74 (m, 2H). MS m/e 552.1/554.1 [M+H]⁺.

Example 148

(2,4-Dichloro-3-phenylquinolin-6-yl)(1-methyl-1H-imidazol-5-yl)(quinolin-4-yl)methanol

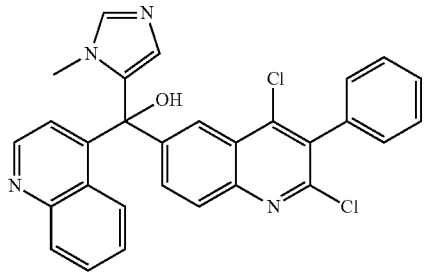 [SMILES: Cn1cncc1C(O)(c1ccc2nc(Cl)c(-c3ccccc3)c(Cl)c2c1)c1ccnc2ccccc12]

To a 2-necked flask containing 6-bromo-2,4-dichloro-3-phenylquinoline (250 mg, 0.71 mmol, Intermediate 1, step c) was added THF (8 mL) to give a homogeneous clear solution. The solution was cooled to −75° C. and n-BuLi (2.5 M in hexanes, 0.26 mL, 0.65 mmol) was added which resulted in an immediate orange homogeneous solution. After 2 min, a solution of (1-methyl-1H-imidazol-5-yl)(quinolin-4-yl)methanone (190 mg, 0.800 mmol, Intermediate 44, step b) in 3 mL of THF was added and an immediate color change to a greenish-brown mixture resulted. The reaction was maintained at −75° C. for 5 min then replaced with a 0° C. ice-bath. The reaction was quenched after 45 min with saturated NH₄Cl solution and extracted with EtOAc (3×50 mL). The combined organics were washed with brine, dried over MgSO₄, filtered and concentrated. Chromatography on silica gel (30% acetone-DCM increasing gradient to 10% MeOH-DCM) provided the title compound as a white solid. ¹H NMR (500 MHz, CDCl₃) δ 8.82 (d, J=4.6 Hz, 1H), 8.48 (d, J=1.6 Hz, 1H), 8.26 (d, J=8.5 Hz, 1H), 8.14 (d, J=8.4 Hz, 1H), 7.97 (d, J=8.8 Hz, 1H), 7.70-7.60 (m, 2H), 7.58-7.43 (m, 3H), 7.43-7.30 (m, 4H), 6.99 (d, J=4.5 Hz, 1H), 6.21 (s, 1H), 5.11 (s, 1H), 3.51 (s, 3H). MS m/e 511.0/512.0/513.0/514.0/515.0 [M+H]⁺.

Example 149

(2,4-Dichloro-3-phenylquinolin-6-yl)(2,4-dimethylthiazol-5-yl)(1-methyl-1H-1,2,3-triazol-5-yl)methanol

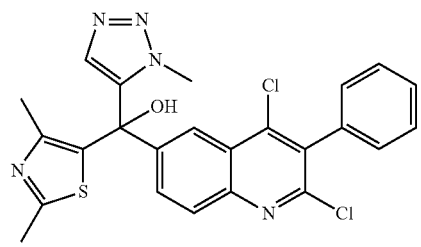 [SMILES: Cc1nc(C)c(C(O)(c2ccc3nc(Cl)c(-c4ccccc4)c(Cl)c3c2)c2cnnn2C)s1]

To a 2-necked flask containing 6-bromo-2,4-dichloro-3-phenylquinoline (250 mg, 0.710 mmol, Intermediate 1, step c) was added THF (10 mL) to give a homogeneous clear solution. The solution was cooled to −75° C. and n-BuLi (2.5 M in hexanes, 0.28 mL, 0.70 mmol) was added which resulted in an immediate orange homogeneous solution. After 2 min, a solution of 2,4-dimethylthiazol-5-yl)(1-methyl-1H-1,2,3-triazol-5-yl)methanone (200 mg, 0.897 mmol, Intermediate 45, step b) in 7 mL of THF was added. After 5 min the dry-ice bath was replaced with a 0° C. ice-bath. The reaction was quenched after 45 min with NH₄Cl solution, extracted with EtOAc (3×50 mL). The combined organic layer was washed with brine, dried over MgSO₄, filtered and concentrated. Chromatography on silica gel (10% EtOAc-DCM, 5% MeOH-DCM) provided the title compound as a light tan solid. ¹H NMR (500 MHz, CDCl₃) δ 8.32 (d, J=2.0 Hz, 1H), 8.09 (d, J=8.9 Hz, 1H), 7.73 (dd, J=8.9, 2.2 Hz, 1H), 7.58-7.46

(m, 3H), 7.33 (m, 2H), 7.20 (s, 1H), 4.38 (s, 1H), 3.94 (s, 3H), 2.58 (s, 3H), 2.16 (s, 3H). MS m/e 496.0/498.0 [M+H]⁺.

Example 150

6-((2,4-Dimethylthiazol-5-yl)(hydroxy)(1-methyl-1H-1,2,3-triazol-5-yl)methyl)-3-phenylquinoline-2,4-dicarbonitrile

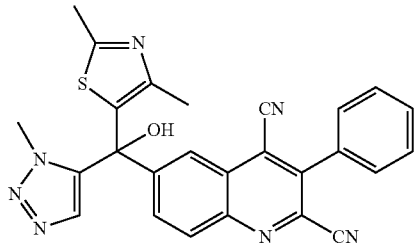 [SMILES: Cc1nc(C)c(C(O)(c2ccc3nc(C#N)c(-c4ccccc4)c(C#N)c3c2)c2cnnn2C)s1]

Similar to the procedure described in the Eur. J. Org. Chem. (2008), 563. To a large microwave vial was added (2,4-dichloro-3-phenylquinolin-6-yl)(2,4-dimethylthiazol-5-yl) (1-methyl-1H-1,2,3-triazol-5-yl)methanol (100 mg, 0.200 mmol, Example 149), zinc cyanide (75 mg, 0.64 mmol), 2-dicyclohexylphosphino-2',4',6'-triisopropylbiphenyl (X-Phos, 25 mg, 0.52 mmol), zinc powder (2 mg, 0.031 mmol), Pd₂(dba)₃ (60 mg, 0.66 mmol) followed by N,N-dimethylacetamide (3 mL, degassed with N₂ for 10 min). The vial was sealed and evacuated. The mixture was heated to 120° C. in an oil bath. After 1.5 hours, the mixture was filtered while still warm through Celite® and rinsed with EtOAc. The light yellow effluent was concentrated and the N,N-dimethylacetamide was partially removed under high vacuum. The crude material was chromatographed on silica gel (3-8% MeOH-DCM) to provide the product along with residual DMA, which after trituration with Et₂O and hexane gave the title compound as a pale yellow foam. ¹H NMR (500 MHz, CDCl₃) δ 8.54 (s, 1H), 8.27 (d, J=8.9 Hz, 1H), 7.81 (d, J=9.0 Hz, 1H), 7.71-7.54 (m, 5H), 7.12 (s, 1H), 6.10 (s, 1H), 3.97 (s, 3H), 2.58 (d, J=18.6 Hz, 3H), 2.14 (s, 3H). MS m/e 478.1/479.1 [M+H]⁺.

Example 151

(4-Chloro-3-phenyl-2-(pyridin-3-yl)quinolin-6-yl)(4-chlorophenyl)(pyridin-3-yl)methanol

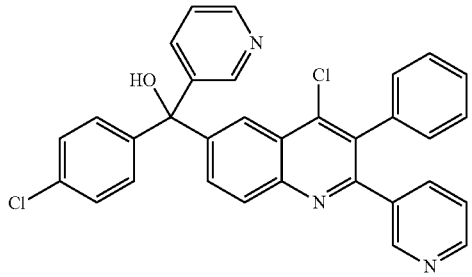 [SMILES: OC(c1ccc(Cl)cc1)(c1cccnc1)c1ccc2nc(-c3cccnc3)c(-c3ccccc3)c(Cl)c2c1]

A mixture of (4-chlorophenyl)(2,4-dichloro-3-phenylquinolin-6-yl)(pyridin-3-yl)methanol (75 mg, 0.15 mmol, Example 17), 3-(4,4,5,5-tetramethyl-1,3,2-dioxaborolan-2-yl)pyridine (37 mg, 0.18 mmol), PdCl₂(dppf) (11 mg, 0.015 mmol) and K₂CO₃ (42 mg, 0.30 mmol) in 10 mL of dioxane was combined with 2 mL of water and heated to 70° C. After 3 hours, the reaction mixture was cooled to room temperature, diluted with EtOAc, and washed with water. The organic phase was dried over Na₂SO₄, filtered and concentrated. The residue was purified on an ISCO using 0-10% methanol in ethyl acetate and lyophilized to give the title compound as a white solid. ¹H NMR (400 MHz, CDCl₃) δ=8.60 (s, 1H), 8.55 (d, J=4.0 Hz, 1H), 8.45 (d, J=3.5 Hz, 1H), 8.27-8.34 (m, 2H), 8.15 (d, J=8.6 Hz, 1H), 7.73 (dd, J=8.6, 2.0 Hz, 2H), 7.58 (d, J=7.6 Hz, 1H), 7.28-7.36 (m, 8H), 7.08-7.16 (m, 3H); MS m/e 534.8 [M+H]⁺.

Example 152

(4-Chloro-3-phenyl-2-(pyrimidin-5-yl)quinolin-6-yl)(4-chlorophenyl)(pyridin-3-yl)methanol

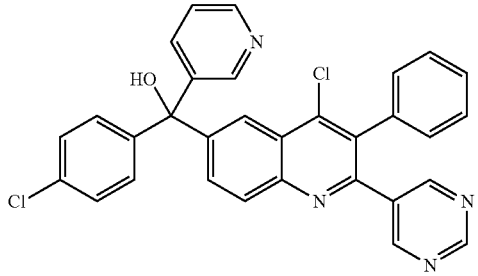 [SMILES: OC(c1ccc(Cl)cc1)(c1cccnc1)c1ccc2nc(-c3cncnc3)c(-c3ccccc3)c(Cl)c2c1]

A mixture of (4-chlorophenyl)(2,4-dichloro-3-phenylquinolin-6-yl)(pyridin-3-yl)methanol (75 mg, 0.15 mmol, Example 17), pyrimidin-5-ylboronic acid (23 mg, 0.18 mmol), PdCl₂(dppf) (11 mg, 0.015 mmol) and K₂CO₃ (42 mg, 0.30 mmol) in 10 mL dioxane was combined with 2 mL of water and heated to 70° C. After 3 hours, the reaction mixture was cooled to room temperature, diluted with EtOAc, and washed with water. The organic phase was dried over Na₂SO₄, filtered and concentrated. The residue was purified on an ISCO using 0-10% methanol in ethyl acetate and lyophilized to give the title compound as a white solid. ¹H NMR (400 MHz, CDCl₃) δ=9.06 (s, 1H), 8.64 (s, 2H), 8.60 (d, J=2.0 Hz, 1H), 8.57 (d, J=3.0 Hz, 1H), 8.35 (d, J=2.0 Hz, 1H), 8.17 (d, J=8.6 Hz, 1H), 7.69-7.78 (m, 2H), 7.27-7.42 (m, 8H), 7.19 (dd, J=6.3, 2.8 Hz, 2H); MS m/e 535.8 [M+H]⁺.

Example 153a (4-Chlorophenyl)(2,4-dichloro-3-(2-chlorophenyl) quinolin-6-yl)(1-methyl-1H-imidazol-5-yl)methanol

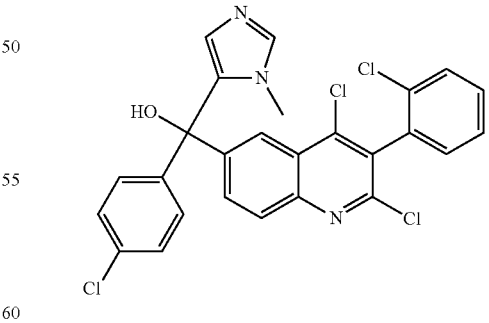

n-BuLi (2.5 M) (1.8 mL, 4.47 mmol) was added to a solution of 6-bromo-2,4-dichloro-3-(2-chlorophenyl)quinoline (1.6 g, 4.2 mmol, Intermediate 2, step c) in THF (10 mL) at −70° C., and stirred at −60° C.~−50° C. for 1 hour. Then (4-chlorophenyl)(1-methyl-1H-imidazol-5-yl)methanone (0.75 g, 3.4 mmol, Intermediate 18, step b) in THF (50 mL)

was added and stirred at −60° C.~−50° C. for an additional 30 min before the mixture was warmed to 40° C. and stirred for 12 hours. The reaction was quenched by adding water at room temperature and stirred for 15 min, concentrated and extracted with EtOAc (3×20 mL). The combined organic phase was concentrated and purified by silica gel column chromatography (eluted by MeOH/DCM=1/200 to 1/40) and recrystallization from EtOAc to give the title compound as a white solid. $^1$H NMR (300 MHz, CD$_3$OD): δ 8.29-8.27 (m, 1H), 8.04 (d, J=9.0 Hz, 1H), 7.92-7.89 (m, 1H), 7.70 (s, 1H), 7.62-7.59 (m, 1H), 7.52-7.48 (m, 2H), 7.39-7.36 (m, 5H), 3.48 (s, 3H); MS m/e [M+H]$^+$=528.

Example 153a was purified by chiral HPLC [Chiralcel OJ, 95% CO$_2$/5% (MeOH+0.2% isopropylamine)→60% CO$_2$/40% (MeOH+0.2% isopropylamine)] to give 4 diastereomers (elution order: Example 153b first, Example 153c third, Example 153d fourth) which were each further purified by C18 HPLC (20% to 100% CH$_3$CN, with 0.1% TFA throughout) to provide, after lyophilization, the TFA salts as Examples 153b, 153c, and 153d.

Example 153b $^1$H NMR (400 MHz, MeOH-d$_4$) δ 8.97 (s, 1H), 8.36 (d, J=2.02 Hz, 1H), 8.09 (d, J=8.59 Hz, 1H), 7.89 (dd, J=2.27, 8.84 Hz, 1H), 7.61 (d, J=7.58 Hz, 1H), 7.34-7.56 (m, 8H), 6.96 (s, 1H), 3.70 (s, 3H); MS m/e 527.7 [M+H]$^+$.

Example 153c $^1$H NMR (400 MHz, MeOD) δ 9.00 (s, 1H), 8.31 (d, J=1.71 Hz, 1H), 8.10 (d, J=8.80 Hz, 1H), 7.93 (dd, J=1.83, 8.93 Hz, 1H), 7.58-7.65 (m, 1H), 7.40-7.57 (m, 6H), 7.37 (dd, J=1.83, 7.21 Hz, 1H), 6.94-7.02 (m, 1H), 3.71 (s, 3H); MS m/e 527.7 [M+H]$^+$.

Example 153d $^1$H NMR (400 MHz, MeOH-d$_4$) δ 8.99 (s, 1H), 8.37 (d, J=2.02 Hz, 1H), 8.09 (d, J=9.09 Hz, 1H), 7.89 (dd, J=2.02, 9.09 Hz, 1H), 7.61 (d, J=7.58 Hz, 1H), 7.34-7.58 (m, 7H), 6.97 (s, 1H), 3.71 (s, 3H); MS m/e 528.0 [M+H]$^+$.

Example 154

(2,4-Dichloro-8-fluoro-3-phenylquinolin-6-yl)(1-methyl-1H-imidazol-5-yl)(pyridin-3-yl)methanol•TFA

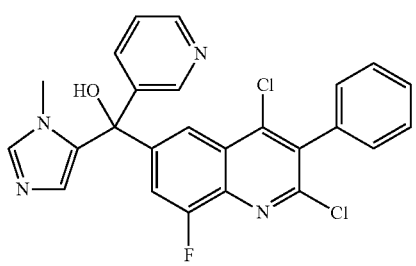 [SMILES: Cn1cncc1C(O)(c1cccnc1)c1cc(F)c2nc(Cl)c(-c3ccccc3)c(Cl)c2c1]

A solution of 3-iodopyridine (24.6 mg, 0.12 mmol) in DCM (0.25 mL) was stirred at room temperature while iPrMgCl—LiCl (0.1 mL, 1.2 M in THF, 0.12 mmol) was added dropwise over ~30 sec under argon. After ~10 min at room temperature, the yellow solution was added dropwise over ~30 sec at room temperature to a mixture of (2,4-dichloro-8-fluoro-3-phenylquinolin-6-yl)(1-methyl-1H-imidazol-5-yl)methanone (25.7 mg, 0.0642 mmol, Intermediate 46, step c) in LaCl$_3$·2LiCl (0.126 mL, 0.56 M in THF, 0.0706 mmol). The reaction was then stirred at 40° C. for 45 min, quenched with 1 M NaHCO$_3$ (2 mL) and extracted with EtOAc (2×4 mL). The combined organic layers were dried (Na$_2$SO$_4$), filtered, and concentrated. The residue was purified by C18 HPLC (20% to 100% CH$_3$CN, with 0.1% TFA throughout) to provide, after lyophilization, the title compound as a white solid. $^1$H NMR (400 MHz, MeOH-d$_4$) δ 9.02 (s, 1H), 8.68 (s, 1H), 8.64 (d, J=4.55 Hz, 1H), 8.11 (s, 1H), 7.98 (d, J=9.09 Hz, 1H), 7.71 (dd, J=2.02, 11.12 Hz, 1H), 7.48-7.63 (m, 4H), 7.32-7.38 (m, 2H), 7.13 (s, 1H), 3.72 (s, 3H); MS m/e 479.1 [M+H]$^+$.

Example 155

(2,4-Dichloro-8-fluoro-3-phenylquinolin-6-yl)(1-methyl-1H-imidazol-5-yl)(pyridin-4-yl)methanol•TFA

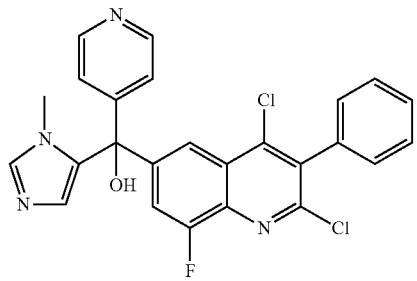 [SMILES: Cn1cncc1C(O)(c1ccncc1)c1cc(F)c2nc(Cl)c(-c3ccccc3)c(Cl)c2c1]

A slurry of (2,4-dichloro-8-fluoro-3-phenylquinolin-6-yl)(1-methyl-1H-imidazol-5-yl)methanone (33.2 mg, 0.083 mmol, Intermediate 46, step c) and 4-iodopyridine (33.3 mg, 0.162 mmol) in THF (0.5 mL) was stirred at ~−70° C. while n-BuLi (0.0627 mL, 2.59 M in hexane, 0.162 mmol) was added dropwise under argon over 1 min. The resulting peach-colored slurry was immediately removed from the ~−70° C. bath and stirred at ambient conditions. After 15 min, the dark homogeneous solution was quenched with 1 M NaHCO$_3$ (1 mL) and extracted with EtOAc (1×6 mL). The organic layer was dried (Na$_2$SO$_4$), filtered, and concentrated. The residue was purified by C18 HPLC (30% to 90% CH$_3$CN, with 0.1% TFA throughout) to provide, after lyophilization, the title compound as a white solid. $^1$H NMR (400 MHz, MeOH-d$_4$) δ 8.96 (s, 1H), 8.66 (d, J=5.56 Hz, 2H), 8.12 (s, 1H), 7.72 (d, J=11.12 Hz, 1H), 7.47-7.64 (m, 5H), 7.35 (d, J=7.58 Hz, 2H), 7.13 (s, 1H), 3.69 (s, 3H); MS m/e 479.1 [M+H]$^+$.

Example 156

(2,4-Dichloro-8-methyl-3-phenylquinolin-6-yl)(1-methyl-1H-imidazol-5-yl)(6-methylpyridin-3-yl)methanol•TFA

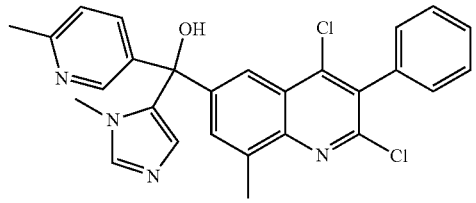 [SMILES: Cc1ccc(C(O)(c2cc(C)c3nc(Cl)c(-c4ccccc4)c(Cl)c3c2)c2cncn2C)cn1]

A solution of 5-bromo-2-methylpyridine (20.7 mg, 0.12 mmol) in THF (0.25 mL) was stirred on an ice bath while iPrMgCl—LiCl (0.1 mL, 1.2 M in THF, 0.12 mmol) was added dropwise over ~15 sec under argon. After stirring at room temperature for 1-2 min, the dark yellow solution was stirred at 55° C. for 15 min. The dark red amber reaction was then cooled to room temperature and added in one portion over ~5 sec to a slurry of (2,4-dichloro-8-methyl-3-phenylquinolin-6-yl)(1-methyl-1H-imidazol-5-yl)methanone (32.1 mg, 0.081 mmol, Intermediate 48, step b) in THF (0.16 mL) at room temperature. After stirring for 1-2 min at room temperature, the light amber reaction was stirred at 55° C. for 22 min, and was then cooled to room temperature, quenched with 5 M $NH_4Cl$ (1 mL) and extracted with EtOAc (2×3 mL). The combined organic layers were dried ($Na_2SO_4$), filtered, and concentrated. The residue was purified by C18 HPLC (20% to 100% $CH_3CN$, with 0.1% TFA throughout) to provide, after lyophilization, the title compound as a white solid. $^1$H NMR (400 MHz, MeOH-$d_4$) δ 9.00 (s, 1H), 8.57 (d, J=2.02 Hz, 1H), 8.17 (d, J=2.02 Hz, 1H), 8.01 (dd, J=2.27, 8.34 Hz, 1H), 7.73 (s, 1H), 7.45-7.62 (m, 4H), 7.29-7.37 (m, 2H), 7.09 (s, 1H), 3.71 (s, 3H), 2.77 (s, 3H), 2.65 (s, 3H); MS m/e 489.1 [M+H]$^+$.

Example 157

(2,4-Dichloro-8-methyl-3-phenylquinolin-6-yl)(6-methylpyridin-3-yl)(1H-pyrrol-3-yl)methanol•TFA

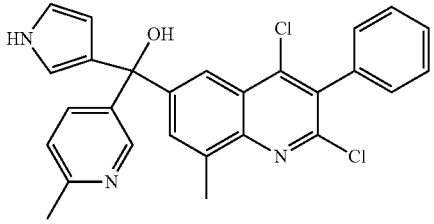 [SMILES: Cc1ccc(C(O)(c2cc[nH]c2)c2cc(C)c3nc(Cl)c(-c4ccccc4)c(Cl)c3c2)cn1]

A pale yellow mixture of (2,4-dichloro-8-methyl-3-phenylquinolin-6-yl)(6-methylpyridin-3-yl)methanone (31.5 mg, 0.0773 mmol, Intermediate 47: step c) and 3-bromo-1-(triisopropylsilyl)-1H-pyrrole (30.6 mg, 0.101 mmol) in THF (0.36 mL) was stirred at −70° C. under argon while n-BuLi (0.0589 mL, 1.59 M in hexane, 0.0936 mmol) was added dropwise over ~30 sec. The reaction immediately turned dark brown and was stirred for an additional 5 min at −70° C. before transferring it to an ice bath. The resulting dark solution was stirred at 0° C. for 6 min, removed from the ice bath and stirred at ambient temperature for 5 min, and the homogeneous amber red solution was then quenched with 5 M $NH_4Cl$ (1 mL) and extracted with EtOAc (2×3 mL). The combined organic layers were dried ($Na_2SO_4$), filtered, and concentrated. The residue was dissolved in THF (0.6 mL) and treated with TBAF (0.116 mL, 1 M in THF, 0.116 mmol) in one portion at room temperature, and stirred at room temperature under air for 30 min. The reaction was then partitioned with 1 M $NaHCO_3$ (3 mL) and EtOAc (3 mL), and the aqueous layer was extracted with EtOAc (1×3 mL). The combined organic layers were dried ($Na_2SO_4$), and concentrated. The residue was purified by C18 HPLC (20% to 100% $CH_3CN$, with 0.1% TFA throughout) to provide, after lyophilization, the title compound as a yellow solid. $^1$H NMR (400 MHz, DMSO-$d_6$) δ 10.85 (s, 1H), 8.60 (s, 1H), 8.19 (s, 1H), 8.09 (br. s., 1H), 7.75 (s, 1H), 7.45-7.59 (m, 3H), 7.31- 7.45 (m, 3H), 6.82 (s, 1H), 6.74 (br. s., 1H), 6.36 (s, 1H), 5.98 (s, 1H), 2.65 (s, 3H), 2.61 (s, 3H); MS m/e 474.1 [M+H]$^+$.

Example 158

(2,4-Dichloro-8-methyl-3-phenylquinolin-6-yl)(6-methylpyridin-3-yl)(3-methylthiophen-2-yl)methanol

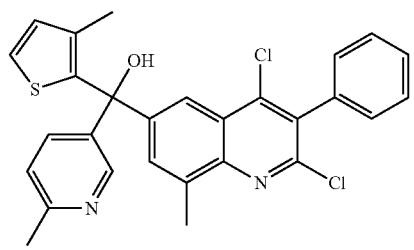 [SMILES: Cc1ccc(C(O)(c2cc(C)c3nc(Cl)c(-c4ccccc4)c(Cl)c3c2)c2sccc2C)cn1]

A yellow mixture of (2,4-dichloro-8-methyl-3-phenylquinolin-6-yl)(6-methylpyridin-3-yl)methanone (35 mg, 0.0859 mmol, Intermediate 47, step c) and 2-bromo-3-methylthiophene (25.2 mg, 0.142 mmol) in THF (0.52 mL) was stirred at ~−70° C. under argon while n-BuLi (0.0811 mL, 1.59 M in hexane, 0.129 mmol) was added dropwise over 1.5 min. The reddish-amber reaction was stirred for an additional 15 min at ~−70° C. before transferring it to an ice bath. The resulting solution was stirred at 0° C. for 5 min, and was then quenched with 5 M $NH_4Cl$ (1 mL) and extracted with EtOAc (2×3 mL). The combined yellow organic layers were dried ($Na_2SO_4$), filtered, and concentrated. The residue was purified by C18 HPLC (20% to 100% $CH_3CN$, with 0.1% TFA throughout) and then, after neutralization, further purified with flash chromatography with a 2% EtOAc/heptane to 100% EtOAc gradient to yield the title compound as a white powder. $^1$H NMR (400 MHz, MeOH-$d_4$) δ 8.38-8.46 (m, 1H), 8.08 (s, 1H), 7.78 (s, 1H), 7.73 (dd, J=2.08, 8.19 Hz, 1H), 7.43-7.57 (m, 3H), 7.26-7.38 (m, 3H), 7.22 (d, J=5.13 Hz, 1H), 6.93 (d, J=5.13 Hz, 1H), 2.73 (s, 3H), 2.54 (s, 3H), 1.97 (s, 3H); MS m/e 505.0 [M+H]$^+$.

Example 159

(2,4-Dichloro-8-methyl-3-phenylquinolin-6-yl)(1-methyl-1H-imidazol-5-yl)(2-methylpyridin-4-yl)methanol•TFA

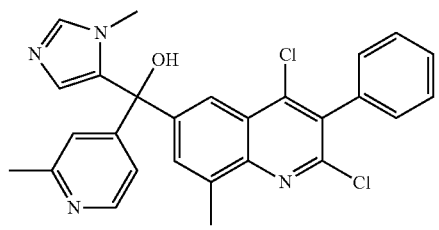 [SMILES: Cc1cc(C(O)(c2cc(C)c3nc(Cl)c(-c4ccccc4)c(Cl)c3c2)c2cncn2C)ccn1]

A yellow mixture of (2,4-dichloro-8-methyl-3-phenylquinolin-6-yl)(1-methyl-1H-imidazol-5-yl)methanone (35 mg, 0.0883 mmol, Intermediate 48, step b) and 4-bromo-2-methylpyridine (27.2 mg, 0.158 mmol) in THF (0.52 mL) was stirred at ~−70° C. under argon while n-BuLi (0.0833 mL, 1.59 M in hexane, 0.132 mmol) was added dropwise over 1.5 min. The reddish-amber reaction was stirred for an additional 15 min at ~−70° C. before transferring it to an ice bath. The resulting dark solution was stirred at 0° C. for 5 min, and was then quenched with 1 mL 5 M NH₄Cl and extracted with EtOAc (2×3 mL). The combined yellow organic layers were dried (Na₂SO₄), filtered, and concentrated. The residue was purified by C18 HPLC (20% to 100% CH₃CN, with 0.1% TFA throughout) to provide, after lyophilization, the title compound as a light peach-colored solid. ¹H NMR (400 MHz, MeOH-d₄) δ 9.04 (s, 1H), 8.64 (d, J=5.87 Hz, 1H), 8.25 (s, 1H), 7.85 (s, 1H), 7.77 (br. s., 2H), 7.44-7.58 (m, 3H), 7.32 (d, J=6.60 Hz, 2H), 7.21 (s, 1H), 3.70 (s, 3H), 2.77 (s, 3H), 2.71 (s, 3H); MS m/e 489.1 [M+H]⁺.

Example 160

(2,4-Dichloro-8-methyl-3-phenylquinolin-6-yl)(1-methyl-1H-imidazol-5-yl)(2-(trifluoromethyl)pyridin-4-yl)methanol•TFA

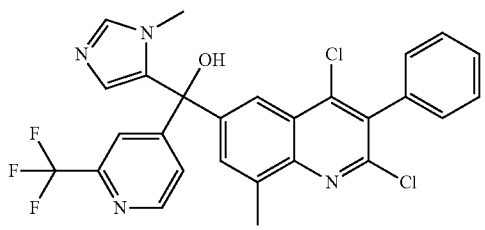 [SMILES: Cc1cc(C(O)(c2ccnc(C(F)(F)F)c2)c2cncn2C)cc2c(Cl)c(-c3ccccc3)c(Cl)nc12]

A yellow mixture of (2,4-dichloro-8-methyl-3-phenylquinolin-6-yl)(1-methyl-1H-imidazol-5-yl)methanone (35 mg, 0.0883 mmol, Intermediate 48, step b) and 4-bromo-2-(trifluoromethyl)pyridine (29.9 mg, 0.132 mmol) in THF (0.52 mL) was treated essentially as described for Example 159 to provide, after HPLC purification, the title compound as a white solid. ¹H NMR (400 MHz, MeOH-d₄) δ 9.02 (s, 1H), 8.78 (d, J=5.13 Hz, 1H), 8.16 (s, 1H), 8.01 (s, 1H), 7.76 (s, 1H), 7.66 (d, J=4.65 Hz, 1H), 7.45-7.57 (m, 3H), 7.33 (d, J=6.36 Hz, 2H), 7.13 (s, 1H), 3.66-3.73 (m, 3H), 2.78 (s, 3H); MS m/e 543.2 [M+H]⁺.

Example 161

(4-Chlorophenyl)(2,4-dichloro-7-fluoro-3-phenylquinolin-6-yl)(1-methyl-1H-imidazol-5-yl)methanol•TFA

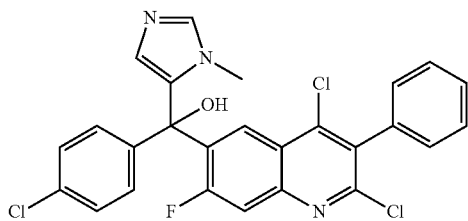 [SMILES: Cn1cncc1C(O)(c1ccc(Cl)cc1)c1cc2c(Cl)c(-c3ccccc3)c(Cl)nc2cc1F]

A mixture of 6-bromo-2,4-dichloro-7-fluoro-3-phenylquinoline (35.3 mg, 0.0951 mmol, Intermediate 6) and (4-chlorophenyl)(1-methyl-1H-imidazol-5-yl)methanone (31.2 mg, 0.141 mmol, Intermediate 18, step b) in THF (0.38 mL) was stirred at ~−70° C. under argon while n-BuLi (0.0838 mL, 1.59 M in hexane, 0.133 mmol) was added dropwise over 1.5 min. The reddish-amber reaction was stirred for an additional 2 hours at ~−70° C., and was then removed from the cold bath and stirred under ambient conditions for 40 min. The reaction was then quenched with 5 M NH₄Cl (1 mL) and extracted with EtOAc (2×3 mL). The combined organic layers were dried (Na₂SO₄), filtered, and concentrated. The residue was purified by C18 HPLC (20% to 100% CH₃CN, with 0.1% TFA throughout) to provide, after lyophilization, the title compound. ¹H NMR (400 MHz, MeOH-d₄) δ 8.96 (s, 1H), 8.53 (d, J=8.08 Hz, 1H), 7.79 (d, J=12.13 Hz, 1H), 7.39-7.59 (m, 7H), 7.30-7.38 (m, 2H), 7.18 (s, 1H), 3.76 (s, 3H); MS m/e 512.1 [M+H]⁺.

Example 162

(2,4-Dichloro-5-fluoro-3-phenylquinolin-6-yl)(1-methyl-1H-imidazol-5-yl)(pyridin-4-yl)methanol•TFA

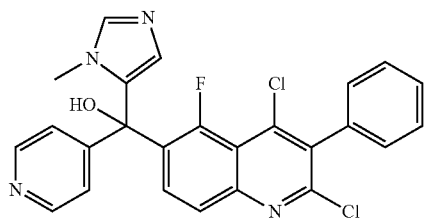 [SMILES: Cn1cncc1C(O)(c1ccncc1)c1ccc2nc(Cl)c(-c3ccccc3)c(Cl)c2c1F]

A mixture of 6-bromo-2,4-dichloro-5-fluoro-3-phenylquinoline (35.8 mg, 0.0965 mmol, Intermediate 7) and (1-methyl-1H-imidazol-5-yl)(pyridin-4-yl)methanone (26.9 mg, 0.144 mmol, Intermediate 9, step b) in THF (0.38 mL) was treated essentially as described for Example 161 to provide, after HPLC purification, the title compound. ¹H NMR (400 MHz, MeOH-d₄) δ 9.01 (s, 1H), 8.66 (d, J=6.06 Hz, 2H), 8.06-8.15 (m, 1H), 8.00 (d, J=9.60 Hz, 1H), 7.64 (d, J=5.05 Hz, 2H), 7.44-7.57 (m, 3H), 7.27-7.34 (m, 2H), 7.25 (s, 1H), 3.78 (s, 3H); MS m/e 479.1 [M+H]⁺.

Example 163

(4-Chlorophenyl)(2,4-dichloro-5-fluoro-3-phenylquinolin-6-yl)(1-methyl-1H-imidazol-5-yl)methanol•TFA

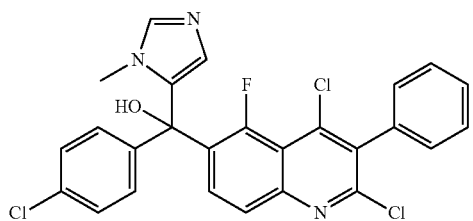 [SMILES: Cn1cncc1C(O)(c1ccc(Cl)cc1)c1ccc2nc(Cl)c(-c3ccccc3)c(Cl)c2c1F]

A mixture of 6-bromo-2,4-dichloro-5-fluoro-3-phenylquinoline (36.1 mg, 0.0973 mmol, Intermediate 7) and (4-chlorophenyl)(1-methyl-1H-imidazol-5-yl)methanone (32.2 mg, 0.146 mmol, Intermediate 18, step b) in THF (0.38 mL) was treated essentially as described for Example 159, except the reaction was stirred for 2 hours at ~−70° C., and was then allowed to warm to room temperature over 40 min. HPLC purification as described in Example 159 provided the title compound. ¹H NMR (400 MHz, MeOH-d₄) δ 8.96 (s, 1H), 8.00-8.09 (m, 1H), 7.92-8.00 (m, 1H), 7.47-7.57 (m, 3H), 7.45 (s, 4H), 7.27-7.35 (m, 2H), 7.11 (s, 1H), 3.76 (s, 3H); MS m/e 512.1 [M+H]⁺.

Example 164

(1-Methyl-1H-imidazol-5-yl)(3-phenyl-2,4-bis(trifluoromethyl)quinolin-6-yl)(pyridin-4-yl)methanol•TFA

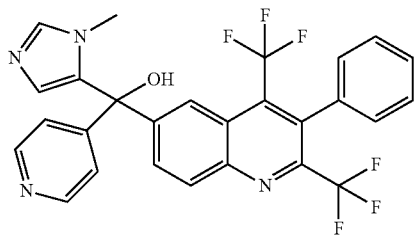 [SMILES: Cn1cncc1C(O)(c1ccncc1)c1ccc2nc(C(F)(F)F)c(-c3ccccc3)c(C(F)(F)F)c2c1]

A −71° C. solution of 6-bromo-3-phenyl-2,4-bis(trifluoromethyl)quinoline (69.8 mg, 0.166 mmol, Intermediate 8, step c) in THF (0.6 mL) was treated with n-BuLi (0.125 mL, 1.59 M in hexane, 0.199 mmol) dropwise via syringe under argon over the course of 1 min. After 10 min a solution of (1-methyl-1H-imidazol-5-yl)(pyridin-4-yl)methanone (26.9 mg, 0.144 mmol, Intermediate 9, step b) in THF (1.2 mL) was added dropwise over 1 min to provide a rust colored opaque mixture. This was stirred at −70° C. and was allowed to warm to room temperature overnight (15 hrs) as the cold bath expired. The homogeneous amber reaction was then quenched with 5 M NH₄Cl (0.5 mL) in one portion at 0° C. and partitioned with 4 mL of EtOAc and 1 mL of 5 M NaCl. The organic layer was dried (Na₂SO₄), filtered, and concentrated, and the residue was purified by C18 HPLC (20% to 100% CH₃CN, with 0.1% TFA throughout) to provide, after lyophilization, the title compound as a white solid. ¹H NMR (400 MHz, MeOH-d₄) δ 9.08 (s, 1H), 8.75 (d, J=5.38 Hz, 2H), 8.43 (d, J=8.31 Hz, 2H), 8.07 (d, J=9.05 Hz, 1H), 7.79 (d, J=5.14 Hz, 2H), 7.42-7.54 (m, 3H), 7.33 (d, J=7.09 Hz, 2H), 7.21 (s, 1H), 3.71 (s, 3H); MS m/e 529.2 [M+H]⁺.

Example 165

(3-Chlorophenyl)(3-phenyl-2,4-bis(trifluoromethyl)quinolin-6-yl)(pyridin-3-yl)methanol•TFA

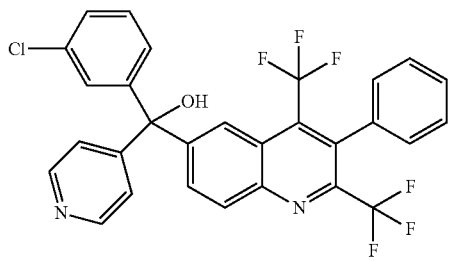 [SMILES: OC(c1ccncc1)(c1cccc(Cl)c1)c1ccc2nc(C(F)(F)F)c(-c3ccccc3)c(C(F)(F)F)c2c1]

A −71° C. solution of 6-bromo-3-phenyl-2,4-bis(trifluoromethyl)quinoline (70.1 mg, 0.167 mmol, Intermediate 8, step c) and (3-chlorophenyl)(pyridin-3-yl)methanone (41.2 mg, 0.189 mmol) in THF (1.8 mL) was treated dropwise with n-BuLi (0.126 mL, 1.59 M in hexane, 0.2 mmol) via syringe under argon over 1 min, and the light reddish-amber homogeneous solution was stirred at −71° C. while the cold bath was allowed to expire. The resulting homogeneous light amber solution was quenched with 5 M NH₄Cl (0.5 mL) in one portion at 0° C. and partitioned with EtOAc (4 mL) and 5 M NaCl (1 mL). The organic layer was dried (Na₂SO₄), filtered, and concentrated, and the residue was purified by C18 HPLC (20% to 100% CH₃CN, with 0.1% TFA throughout) to provide, after lyophilization, the title compound as an off-white powder. ¹H NMR (400 MHz, MeOH-d₄) δ 8.88 (s, 1H), 8.79 (d, J=5.56 Hz, 1H), 8.47 (d, J=9.09 Hz, 1H), 8.37 (d, J=8.59 Hz, 1H), 8.29 (s, 1H), 7.94-8.03 (m, 2H), 7.38-7.53 (m, 6H), 7.33 (d, J=7.07 Hz, 2H), 7.28 (dd, J=2.53, 6.57 Hz, 1H); MS m/e 558.9 [M+H]⁺.

Example 166

3-((3-Chlorophenyl)(hydroxy)(3-phenyl-2,4-bis(trifluoromethyl)quinolin-6-yl)methyl)pyridine 1-oxide•TFA

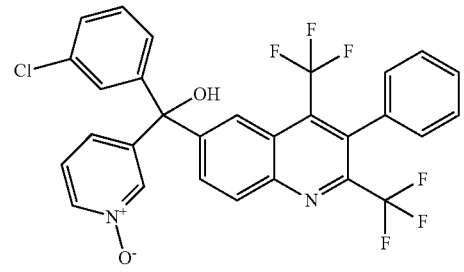 [SMILES: [O-][n+]1cccc(C(O)(c2cccc(Cl)c2)c2ccc3nc(C(F)(F)F)c(-c4ccccc4)c(C(F)(F)F)c3c2)c1]

(3-Chlorophenyl)(3-phenyl-2,4-bis(trifluoromethyl)quinolin-6-yl)(pyridin-3-yl)methanol (99.7 mg, 0.157 mmol, crude Example 165) was dissolved in DCM (0.75 mL), treated with mCPBA (37.9 mg, 71.4% w/w, 0.157 mmol), and stirred under air (capped) at 40° C. for 1 hour. The reaction was concentrated and the residue was purified by C18 HPLC (20% to 100% CH₃CN, with 0.1% TFA throughout) to provide, after lyophilization, the title compound as a white solid. ¹H NMR (400 MHz, MeOH-d₄) δ 8.40 (s, 1H), 8.31-8.39 (m, 2H), 8.25 (s, 1H), 8.00 (dd, J=2.02, 9.09 Hz, 1H), 7.58 (d, J=3.54 Hz, 2H), 7.38-7.53 (m, 6H), 7.33 (d, J=7.07 Hz, 2H), 7.26 (dt, J=2.40, 4.29 Hz, 1H); MS m/e 575.1 [M+H]⁺.

Example 167

Phenyl(3-phenyl-2,4-bis(trifluoromethyl)quinolin-6-yl)(piperidin-4-yl)methanol•TFA

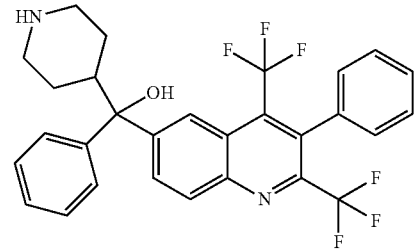 [SMILES: OC(c1ccccc1)(c1ccc2nc(C(F)(F)F)c(-c3ccccc3)c(C(F)(F)F)c2c1)C1CCNCC1]

The precursor of the title compound was prepared essentially as described for Example 164, using tert-butyl 4-benzoylpiperidine-1-carboxylate (commercial; e.g., Matrix Scientific) in place of (1-methyl-1H-imidazol-5-yl)(pyridin-4-yl)methanone to provide, after heptanes/acetone flash chromatography, tert-butyl 4-(hydroxy(phenyl)(3-phenyl-2,4-bis(trifluoromethyl)quinolin-6-yl)methyl)piperidine-1-carboxylate as a clear yellow oil.

A yellow solution of the above product (90 mg, 0.143 mmol) in DCM (1 mL) was treated with TFA (0.218 mL, 2.85 mmol) and stirred at room temperature for 45 min. The reaction was then diluted with DCM (10 mL) and neutralized with dropwise addition of 10 M NaOH (0.285 mL, 2.85 mmol) with swirling (aqueous pH>10). The aqueous layer was extracted with DCM (1×4 mL), and the combined organic layers were dried ($Na_2SO_4$), filtered, and concentrated to provide 71.4 mg of crude title compound. 23.3 mg of this was purified by C18 HPLC (20% to 100% $CH_3CN$, with 0.1% TFA throughout) to provide, after lyophilization, the title compound as a white powder. $^1$H NMR (400 MHz, MeOH-$d_4$) δ 8.64 (br. s., 1H), 8.23 (d, J=9.09 Hz, 1H), 8.07 (d, J=9.09 Hz, 1H), 7.64 (d, J=7.58 Hz, 2H), 7.41-7.53 (m, 3H), 7.28-7.41 (m, 4H), 7.20-7.28 (m, 1H), 3.34-3.50 (m, 2H), 2.98-3.22 (m, 3H), 1.92 (d, J=11.62 Hz, 1H), 1.71-1.87 (m, 2H), 1.53 (d, J=14.65 Hz, 1H); MS m/e 531.2 [M+H]$^+$.

Example 168

(1-Ethylpiperidin-4-yl)(phenyl)(3-phenyl-2,4-bis(trifluoromethyl)quinolin-6-yl)methanol•TFA

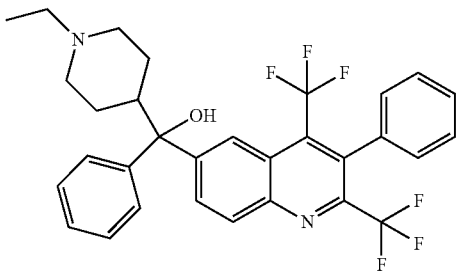 [SMILES: CCN1CCC(C(O)(c2ccccc2)c2ccc3nc(C(F)(F)F)c(-c4ccccc4)c(C(F)(F)F)c3c2)CC1]

A solution of phenyl(3-phenyl-2,4-bis(trifluoromethyl)quinolin-6-yl)(piperidin-4-yl)methanol (24.3 mg, 0.0458 mmol, Example 167 free base) in DCM (0.5 mL) and HOAc (5.2 uL, 0.092 mmol) was treated with acetaldehyde (0.010 mL, 0.18 mmol) followed by NaBH(OAc)$_3$ at room temperature and was stirred at room temperature for 40 min. The reaction was then partitioned with 2 M $K_2CO_3$ (2 mL) and the aqueous layer extracted with DCM (1×5 mL). The combined organic layers were dried ($Na_2SO_4$), filtered, and concentrated. The residue was purified by C18 HPLC (20% to 100% $CH_3CN$, with 0.1% TFA throughout) to provide, after lyophilization, the title compound as a white solid. $^1$H NMR (400 MHz, MeOH-$d_4$) δ 8.63 (br. s., 1H), 8.24 (d, J=9.09 Hz, 1H), 8.03-8.10 (m, 1H), 7.64 (d, J=7.58 Hz, 2H), 7.41-7.53 (m, 3H), 7.37 (t, J=7.83 Hz, 2H), 7.28-7.34 (m, 2H), 7.21-7.28 (m, 1H), 3.60 (br. s., 1H), 3.53 (br. s., 1H), 2.93-3.20 (m, 5H), 1.79-2.02 (m, 3H), 1.59 (d, J=15.16 Hz, 1H), 1.32 (t, J=7.33 Hz, 3H); MS m/e 559.2 [M+H]$^+$.

Example 169a 1-(4-(Hydroxy(phenyl)(3-phenyl-2,4-bis(trifluoromethyl)quinolin-6-yl)methyl)piperidin-1-yl)ethanone

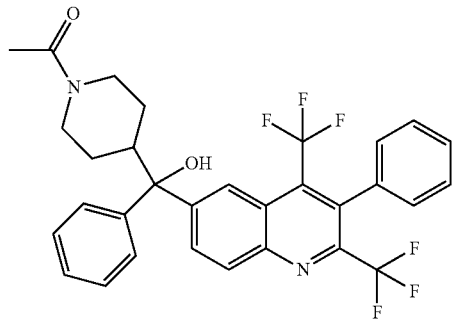 [SMILES: CC(=O)N1CCC(C(O)(c2ccccc2)c2ccc3nc(C(F)(F)F)c(-c4ccccc4)c(C(F)(F)F)c3c2)CC1]

A ~–70° C. solution of 6-iodo-3-phenyl-2,4-bis(trifluoromethyl)quinoline (754 mg, 1.61 mmol, Intermediate 8, step d) in THF (1.4 mL) was treated with iPrMgCl (0.784 mL, 2.06 M in THF, 1.61 mmol) dropwise via syringe under argon over the course of 3 min to provide a light amber solution. After 9 min, the opaque yellow slurry was removed from the cold bath and stirred under ambient conditions for 4 min. A solution of 1-(4-benzoylpiperidin-1-yl)ethanone (442 mg, 1.91 mmol, Intermediate 27) in THF (0.3 mL) was added to the olive drab slurry rapidly dropwise over ~15 sec, and the homogeneous brown solution was stirred at room temperature overnight. The light amber solution was then quenched with 5 M $NH_4Cl$ (1 mL) and extracted with 2-methoxy-2-methylpropane (1×10 mL, 1×2 mL), and the combined organic layers were dried ($Na_2SO_4$), filtered, and concentrated. The residue was flash chromatographed using 50% acetone/heptane (isocratic elution), and impure fractions were additionally flash chromatographed using 90% EtOAc/heptanes (isocratic elution) to afford the title compound as an off-white foam. $^1$H NMR (400 MHz, CDCl$_3$) δ 8.52 (d, J=10.11 Hz, 1H), 8.24 (dd, J=5.56, 9.09 Hz, 1H), 7.94 (t, J=8.84 Hz, 1H), 7.54 (t, J=7.33 Hz, 2H), 7.41-7.51 (m, 3H), 7.33-7.41 (m, 2H), 7.28 (br. s., 3H), 4.71 (d, J=7.58 Hz, 1H), 3.86 (br. s., 1H), 3.00-3.21 (m, 1H), 2.74-2.89 (m, 1H), 2.52-2.69 (m, 1H), 2.44-2.52 (m, 1H; $D_2O$-exch), 2.05 (d, J=2.02 Hz, 3H), 1.69-1.84 (m, 1H), 1.31-1.55 (m, 3H); MS m/e 573.0 [M+H]$^+$.

Example 169a was purified by chiral HPLC (Chiralpak AD, 90% heptane/10% EtOH) to give 2 enantiomers (elution order: Example 169b first, Example 169c second) that were each further purified with a silica plug (DCM→$CH_3CN$ to remove non-volatile aliphatics) to provide, after lyophilization, Examples 169b and 169c.

Example 169b $^1$H NMR (400 MHz, CDCl$_3$) δ 8.52 (d, J=10.10 Hz, 1H), 8.24 (dd, J=5.31, 8.84 Hz, 1H), 7.89-7.98 (m, 1H), 7.54 (t, J=7.33 Hz, 2H), 7.41-7.51 (m, 3H), 7.37 (td, J=4.29, 7.71 Hz, 2H), 7.28 (br. s., 3H), 4.72 (d, J=7.58 Hz, 1H), 3.78-3.93 (m, 1H), 3.01-3.20 (m, 1H), 2.81 (tt, J=3.16, 11.75 Hz, 1H), 2.50-2.68 (m, 1H), 2.37 (d, J=2.53 Hz, 1H), 2.06 (s, 3H), 1.70-1.82 (m, 1H), 1.29-1.54 (m, 3H); MS m/e 573.3 [M+H]$^+$.

Example 169c

¹H NMR (400 MHz, CDCl₃) δ 8.52 (d, J=9.60 Hz, 1H), 8.24 (dd, J=5.05, 9.09 Hz, 1H), 7.88-7.99 (m, 1H), 7.54 (t, J=7.33 Hz, 2H), 7.41-7.50 (m, 3H), 7.37 (td, J=4.29, 7.71 Hz, 2H), 7.28 (br. s., 3H), 4.74 (d, J=12.63 Hz, 1H), 3.83 (d, J=15.16 Hz, 1H), 3.01-3.22 (m, 1H), 2.81 (tt, J=3.35, 11.81 Hz, 1H), 2.56-2.70 (m, 1H), 2.35 (d, J=3.03 Hz, 1H), 2.06 (s, 3H), 1.76 (br. s., 1H), 1.28-1.53 (m, 3H); MS m/e 573.2 [M+H]⁺.

Example 170

Phenyl(3-phenyl-2,4-bis(trifluoromethyl)quinolin-6-yl)(pyridin-3-yl)methanol

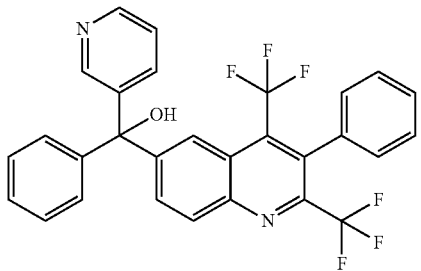 [SMILES: OC(c1ccccc1)(c1cccnc1)c1ccc2nc(C(F)(F)F)c(-c3ccccc3)c(C(F)(F)F)c2c1]

A ~−70° C. solution of 6-bromo-3-phenyl-2,4-bis(trifluoromethyl)quinoline (66.8 mg, 0.159 mmol, Intermediate 8, step c) in THF (0.9 mL) was treated dropwise with n-BuLi (0.12 mL, 1.59 M, 0.191 mmol) via syringe under argon over 1 min. After stirring for less than 1 min, the dark homogeneous solution was treated with a solution of phenyl(pyridin-3-yl)methanone (32.0 mg, 0.175 mmol, Aldrich) in THF (0.6 mL) over 2 min, and the resulting dark amber solution was stirred at ~−70° C. while the cold bath was allowed to expire over 4 hours. The amber solution was then partitioned with 5 M NH₄Cl (2 mL) and EtOAc (5 mL), and the organic layer was dried (Na₂SO₄), filtered, and concentrated. The residue was purified by C18 HPLC (20% to 100% CH₃CN, with 0.1% TFA throughout) to provide, after lyophilization, the title compound as a white solid. ¹H NMR (400 MHz, MeOH-d₄) δ 8.87 (s, 1H), 8.78 (d, J=5.38 Hz, 1H), 8.47 (d, J=8.07 Hz, 1H), 8.27-8.39 (m, 2H), 7.92-8.05 (m, 2H), 7.26-7.54 (m, 10H); MS m/e 568.0 [M+H]⁺.

Example 171

(2,4-Dichloro-3-phenylquinolin-6-yl)(pyridin-3-yl)(4-(trifluoromethyl)phenyl)methanol•TFA

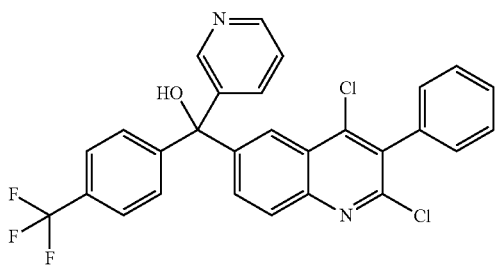 [SMILES: OC(c1ccc(C(F)(F)F)cc1)(c1cccnc1)c1ccc2nc(Cl)c(-c3ccccc3)c(Cl)c2c1]

A mixture of 6-bromo-2,4-dichloro-3-phenylquinoline (0.051 g, 0.144 mmol, Intermediate 1, step c) and commercially available pyridin-3-yl(4-(trifluoromethyl)phenyl)methanone (Rieke) (0.036 g, 0.144 mmol) in THF (5 mL) was stirred at −78° C. A solution of t-butyllithium [1.6M in heptanes](0.181 mL) was added dropwise. After 20 minutes, the reaction was warmed to room temperature. Water was added and the product was extracted with ethyl acetate, dried with sodium sulfate, filtered, and evaporated in vacuo. The crude material was purified via reverse phase HPLC eluting with a gradient (H₂O/acetonitrile/0.1% TFA) to give the title compound. ¹H NMR, 400 MHz (MeOH-d₄) δ: 8.78 (d, J=2.7 Hz, 1H), 8.64-8.74 (m, 1H), 8.24-8.33 (m, 2H), 8.05 (d, J=8.8 Hz, 1H), 7.86 (dd, J=8.9, 2.1 Hz, 1H), 7.78-7.83 (m, 1H), 7.73 (d, J=8.6 Hz, 2H), 7.60 (d, J=8.3 Hz, 2H), 7.47-7.57 (m, 3H), 7.30-7.37 (m, 2H); MS m/e 525 [M+H]⁺.

Example 172

(4-Chloro-3-phenyl-2-(trifluoromethyl)quinolin-6-yl)(1-methyl-1H-imidazol-5-yl)(6-(trifluoromethyl)pyridin-3-yl)methanol•TFA

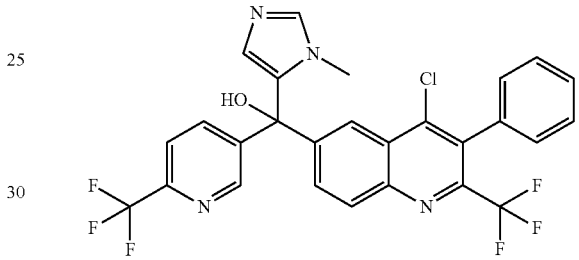

The title compound was prepared using (1-methyl-1H-imidazol-5-yl)(6-(trifluoromethyl)pyridin-3-yl)methanone (Intermediate 15, step c) and 6-bromo-4-chloro-3-phenyl-2-(trifluoromethyl)quinoline (Intermediate 34, step b) in place of di(pyridin-3-yl)methanone and 6-bromo-2,4-dichloro-3-phenylquinoline, respectively, according to the procedure described in Example 24. ¹H NMR (400 MHz, MeOH-d₄) δ 9.06 (s, 1H), 8.86 (d, J=2.53 Hz, 1H), 8.51 (d, J=2.02 Hz, 1H), 8.35 (d, J=8.59 Hz, 1H), 8.12 (dd, J=2.02, 8.08 Hz, 1H), 7.97 (dd, J=2.02, 9.09 Hz, 1H), 7.91 (d, J=8.08 Hz, 1H), 7.46-7.57 (m, 3H), 7.27-7.36 (m, 2H), 7.17 (s, 1H), 3.72 (s, 3H); MS m/e 563.1 [M+H]⁺.

Example 173a 6-(Hydroxy(1-methyl-1H-imidazol-5-yl)(6-(trifluoromethyl)pyridin-3-yl)methyl)-3-phenyl-2-(trifluoromethyl)quinoline-4-carbonitrile•TFA

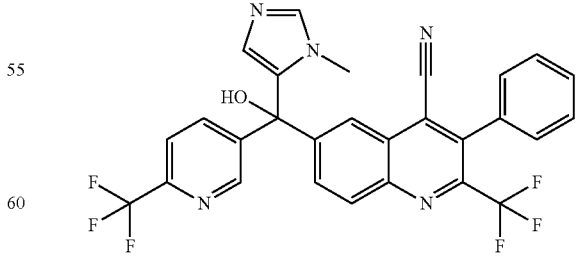

A pressure tube containing (4-chloro-3-phenyl-2-(trifluoromethyl)quinolin-6-yl)(1-methyl-1H-imidazol-5-yl)(6-(trifluoromethyl)pyridin-3-yl)methanol•TFA (101 mg, 0.128 mmol, Example 172), Pd₂dba₃ (12 mg, 0.013 mmol), dicyclohexyl(2',4',6'-triisopropyl-[1,1'-biphenyl]-2-yl)phosphine (X-Phos, 6.3 mg, 0.013 mmol), zinc cyanide (10 mg, 0.085 mmol), and zinc nanopowder (2.5 mg, 0.038 mmol) in N,N-dimethylacetamide (1 mL) was purged with nitrogen for 5 min, and then heated at 120° C. for 2.5 hours. The mixture was allowed to cool to room temperature and filtered through a syringe filter. The filtrate was concentrated in vacuo, and EtOAc and NH$_4$OH (aqueous) were added. The organic layer was separated, and the aqueous layer was extracted with EtOAc. The combined organic layers were dried (Na$_2$SO$_4$), filtered, and concentrated. The residue was purified by reverse phase HPLC (water/acetonitrile/0.1% TFA) to give the title compound as a white solid. $^1$H NMR (400 MHz, MeOD-d$_4$) δ 9.06 (s, 1H), 8.87 (d, J=2.02 Hz, 1H), 8.38-8.47 (m, 2H), 8.14 (dd, J=2.27, 8.34 Hz, 1H), 8.05 (dd, J=2.02, 9.09 Hz, 1H), 7.91 (d, J=8.08 Hz, 1H), 7.52-7.62 (m, 3H), 7.47 (d, J=6.06 Hz, 2H), 7.19 (s, 1H), 3.72 (s, 3H); MS m/e 554.1 [M+H]

Example 173a was neutralized by partitioning between NaHCO$_3$ (aqueous) and DCM. The organic layer was dried, filtered, concentrated, and purified by chiral HPLC (Chiralpak AD, 80% heptane/20% EtOH) to give two pure enantiomers (elution order: Example 173b first, Example 173c second).

Example 173b $^1$H NMR (400 MHz, CDCl$_3$) δ 8.79 (s, 1H), 8.50 (s, 1H), 8.29 (d, J=9.09 Hz, 1H), 7.94 (d, J=8.08 Hz, 1H), 7.77 (dd, J=2.02, 9.09 Hz, 1H), 7.67 (d, J=8.08 Hz, 1H), 7.50-7.62 (m, 3H), 7.34-7.45 (m, 2H), 7.21-7.24 (m, 1H), 6.28 (br. s., 1H), 3.37 (s, 3H); MS m/e 554.2 [M+H]$^+$.

Example 173c $^1$H NMR (400 MHz, CDCl$_3$) δ 8.79 (s, 1H), 8.51 (d, J=2.02 Hz, 1H), 8.29 (d, J=9.09 Hz, 1H), 7.94 (d, J=8.08 Hz, 1H), 7.72-7.80 (m, 1H), 7.67 (d, J=8.08 Hz, 1H), 7.51-7.61 (m, 3H), 7.39 (t, J=5.81 Hz, 2H), 7.22 (s, 1H), 6.21-6.30 (m, 1H), 3.37 (s, 3H); MS m/e 554.2 [M+H]$^+$.

Example 174a (4-Methoxy-3-phenyl-2-(trifluoromethyl)quinolin-6-yl)(1-methyl-1H-imidazol-5-yl)(6-(trifluoromethyl)pyridin-3-yl)methanol•TFA

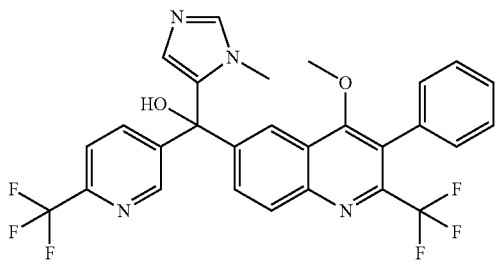 [SMILES: COc1c(-c2ccccc2)c(C(F)(F)F)nc2ccc(C(O)(c3ccc(C(F)(F)F)nc3)c3cncn3C)cc12]

A mixture of (4-chloro-3-phenyl-2-(trifluoromethyl)quinolin-6-yl)(1-methyl-1H-imidazol-5-yl)(6-(trifluoromethyl)pyridin-3-yl)methanol•TFA (78 mg, 0.099 mmol, Example 172) and 0.5 M NaOMe in MeOH (0.46 mL, 0.23 mmol) in a sealed tube was heated at 70° C. for 7 hours. More 0.5 M NaOMe in MeOH (0.33 mL, 0.17 mmol) was added and the mixture was heated at the same temperature for another hour. The solvent was evaporated, and DMSO was added. After filtering through a syringe filter, the filtrate was purified by reverse phase HPLC (water/acetonitrile/0.1% TFA) to give the title compound as a white solid. $^1$H NMR (400 MHz, MeOD-d$_4$) δ 9.07 (s, 1H), 8.86 (d, J=2.02 Hz, 1H), 8.34 (d, J=2.53 Hz, 1H), 8.27 (d, J=8.59 Hz, 1H), 8.13 (dd, J=2.02, 8.08 Hz, 1H), 7.84-7.95 (m, 2H), 7.46-7.56 (m, 3H), 7.35-7.45 (m, 2H), 7.15 (s, 1H), 3.72 (s, 3H), 3.55 (s, 3H); MS m/e 559.2 [M+H]$^+$.

Example 174a was neutralized by partitioning between NaHCO$_3$ (aqueous) and DCM. The organic layer was dried, filtered, concentrated, and purified by chiral HPLC (Chiralpak AD, 80% heptane/20% EtOH) to give two pure enantiomers (elution order: Example 174b first, Example 174c second).

Example 174b $^1$H NMR (400 MHz, CDCl$_3$) δ 8.85 (s, 1H), 8.14-8.28 (m, 2H), 7.92 (d, J=7.58 Hz, 1H), 7.78 (d, J=9.09 Hz, 1H), 7.64 (d, J=8.08 Hz, 1H), 7.42-7.52 (m, 3H), 7.36 (d, J=4.04 Hz, 3H), 6.31 (br. s., 1H), 3.48 (s, 3H), 3.36 (s, 3H); MS m/e 559.2 [M+H]$^+$.

Example 174c $^1$H NMR (400 MHz, CDCl$_3$) δ 8.85 (s, 1H), 8.15-8.28 (m, 2H), 7.93 (d, J=8.08 Hz, 1H), 7.78 (d, J=9.09 Hz, 1H), 7.65 (d, J=8.08 Hz, 1H), 7.41-7.53 (m, 3H), 7.32-7.40 (m, 3H), 6.30-6.45 (m, 1H), 3.48 (s, 3H), 3.39 (s, 3H); MS m/e 559.2 [M+H]$^+$.

Example 175a 3-(3-Fluorophenyl)-6-((4-fluorophenyl)(hydroxy)(1-methyl-1H-imidazol-5-yl)methyl)-8-methylquinoline-2,4-dicarbonitrile

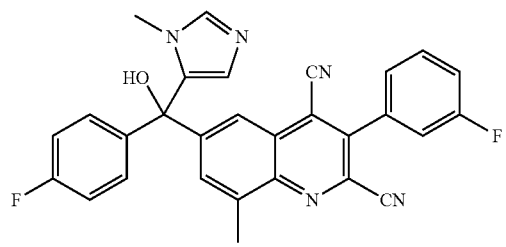 [SMILES: Cc1cc(C(O)(c2ccc(F)cc2)c2cncn2C)cc2c(C#N)c(-c3cccc(F)c3)c(C#N)nc12]

A round bottom flask was charged with (2,4-dichloro-3-(3-fluorophenyl)-8-methylquinolin-6-yl)(4-fluorophenyl)(1-methyl-1H-imidazol-5-yl)methanol (646 mg, 1.27 mmol, Example 190), ZnCN$_2$ (193 mg, 1.65 mmol), Pd$_2$dba$_3$ (116 mg, 0.127 mmol), zinc nanopowder (16.6 mg, 0.254 mmol), and dicyclohexyl(2',4',6'-triisopropyl-[1,1'-biphenyl]-2-yl)phosphine (X-Phos, 62.3 mg, 0.127 mmol). The flask was evacuated and re-filled with argon (three cycles). Dimethylacetamide (6.5 mL, degassed by bubbling argon through for 30 min) was then added and the mixture was heated at 120° C. for 1.5 hours. The mixture was cooled to room temperature and was filtered through Celite®, washing with EtOAc. The filtrate was washed sequentially with 2 M aqueous NH$_4$OH, water, and saturated aqueous NaCl. The organic phase was dried (Na$_2$SO$_4$), filtered, and concentrated. LCMS analysis indicated incomplete conversion, so the crude product was resubjected to the reaction conditions as above for 2 additional hours, then was worked-up as above. The residue was purified by flash column chromatography (silica gel, 10-40% CH₃CN in [2% conc. aqueous NH₄OH in DCM, aqueous phase removed], column run twice) to afford the title compound as a yellow foam.

Example 175a was purified by chiral HPLC (Chiralcel OD, 80% heptane/20% EtOH) to give 2 enantiomers (elution order: Example 175b first, Example 175c second). The enantiomers were then further purified on plug silica gel columns (0-5% MeOH-DCM).

Example 175b $^1$H NMR (400 MHz, CHLOROFORM-d) δ 8.29 (d, J=1.47 Hz, 1H), 7.69 (s, 1H), 7.57-7.67 (m, 1H), 7.30-7.45 (m, 6H), 7.04-7.12 (m, 2H), 6.43 (s, 1H), 4.47 (br. s., 1H), 3.42 (s, 3H), 2.80 (s, 3H). MS m/e 492.1 [M+H]⁺.

Example 175c $^1$H NMR (400 MHz, CHLOROFORM-d) δ 8.28 (d, J=1.47 Hz, 1H), 7.68 (d, J=0.98 Hz, 1H), 7.62 (td, J=5.62, 7.95 Hz, 1H), 7.29-7.46 (m, 6H), 7.01-7.15 (m, 2H), 6.40 (d, J=0.98 Hz, 1H), 4.69 (br. s., 1H), 3.41 (s, 3H), 2.79 (s, 3H). MS m/e 492.1 [M+H]⁺.

Example 176a 3-(3-Fluorophenyl)-6-(hydroxy(1-methyl-1H-imidazol-5-yl)(6-(trifluoromethyl)pyridin-3-yl)methyl)-8-methylquinoline-2,4-dicarbonitrile

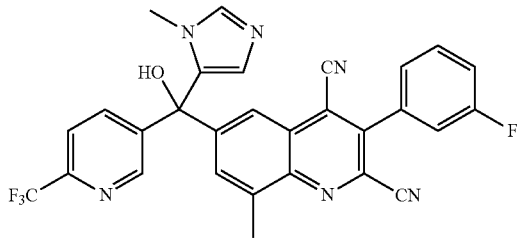 [SMILES: Cc1cc(C(O)(c2ccc(C(F)(F)F)nc2)c2cncn2C)cc2c(C#N)c(-c3cccc(F)c3)c(C#N)nc12]

A round bottom flask was charged with (2,4-dichloro-3-(3-fluorophenyl)-8-methylquinolin-6-yl)(1-methyl-1H-imidazol-5-yl)(6-(trifluoromethyl)pyridin-3-yl)methanol (586 mg, 1.04 mmol, Example 191), ZnCN₂ (306 mg, 2.61 mmol), Pd₂dba₃ (143 mg, 0.157 mmol), zinc nanopowder (20.5 mg, 0.313 mmol), and dicyclohexyl(2',4',6'-triisopropyl-[1,1'-biphenyl]-2-yl)phosphine (X-Phos, 102.6 mg, 0.209 mmol). The flask was evacuated and re-filled with argon (three cycles). Dimethylacetamide (5.4 mL, degassed by bubbling argon through for 30 min) was then added and the mixture was heated at 120° C. for 4.5 hours. The mixture was cooled to room temperature and was filtered through Celite®, washing with EtOAc. The filtrate was washed sequentially with 2 M aqueous NH₄OH, water, and saturated aqueous NaCl. The organic phase was dried (Na₂SO₄), filtered, and concentrated. The residue was purified by flash column chromatography (silica gel, 45-60% CH₃CN in [2% conc. aqueous NH₄OH in DCM, aqueous phase removed]) to afford the title compound as a yellow foam.

Example 176a was purified by chiral HPLC (Chiralcel OD, 90% heptane/10% EtOH, 0.2% isopropylamine throughout) to give 2 enantiomers (elution order: Example 176b first, Example 176c second). The enantiomers were then further purified on plug silica gel columns (0-5% MeOH-DCM).

Example 176b $^1$H NMR (400 MHz, CHLOROFORM-d) δ 8.78 (d, J=1.96 Hz, 1H), 8.34 (d, J=1.71 Hz, 1H), 7.96 (dd, J=1.96, 8.31 Hz, 1H), 7.58-7.75 (m, 3H), 7.29-7.44 (m, 3H), 7.25 (s, 1H), 6.91 (s, 1H), 6.28 (d, J=0.98 Hz, 1H), 3.38 (s, 3H), 2.79 (s, 3H). MS m/e 543.2 [M+H]⁺.

Example 176c $^1$H NMR (400 MHz, CHLOROFORM-d) δ 8.78 (d, J=2.20 Hz, 1H), 8.34 (d, J=1.47 Hz, 1H), 7.96 (dd, J=1.96, 8.07 Hz, 1H), 7.59-7.74 (m, 3H), 7.30-7.43 (m, 3H), 7.26 (s, 1H), 6.79 (br. s., 1H), 6.29 (d, J=0.98 Hz, 1H), 3.39 (s, 3H), 2.79 (s, 3H). MS m/e 543.2 [M+H]⁺.

Example 177a (4-Chloro-3-(3-fluorophenyl)-2-methoxy-8-methylquinolin-6-yl)(1-methyl-1H-imidazol-5-yl)(6-(trifluoromethyl)pyridin-3-yl)methanol

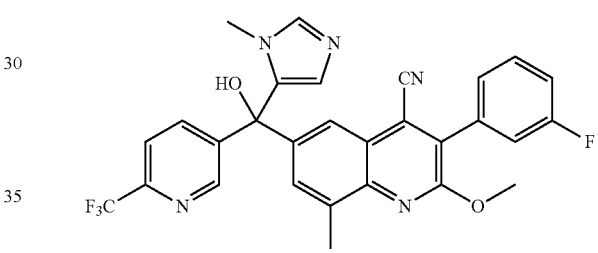

n-BuLi (1.6 M in hexane, 2.19 mL, 3.50 mmol) was added over approximately 1 min to a solution of 6-bromo-4-chloro-3-(3-fluorophenyl)-2-methoxy-8-methylquinoline (1.40 g, 3.68 mmol, Intermediate 52) in THF (5 mL) under argon at −78° C. After 1 min, a solution of (1-methyl-1H-imidazol-5-yl)(6-(trifluoromethyl)pyridin-3-yl)methanone (939 mg, 3.68 mmol, Intermediate 15, step c) in 5 mL THF under argon was added via cannula. The resulting mixture was stirred at −78° C. for 10 min, then transferred to an ice water bath and stirred 30 min. The reaction was quenched by addition of saturated aqueous NH₄Cl, diluted with water and extracted with EtOAc (3×). The organic phase was dried (Na₂SO₄), filtered, and concentrated. The residue was purified by flash column chromatography (silica gel, 45-60% CH₃CN in [2% conc. aqueous NH₄OH in DCM, aqueous phase removed]) to afford the title compound as a white foam.

Example 177a was purified by chiral HPLC (Chiralcel OD, 90% heptane/10% EtOH, 0.2% isopropylamine throughout) to give 2 enantiomers (elution order: Example 177b first, Example 177c second). The enantiomers were then further purified on plug silica gel columns (0-5% MeOH-DCM).

Example 177b $^1$H NMR (400 MHz, CHLOROFORM-d) δ 8.83 (d, J=1.96 Hz, 1H), 8.04 (d, J=1.71 Hz, 1H), 7.93 (dd, J=1.96, 8.31 Hz, 1H), 7.67 (d, J=8.31 Hz, 1H), 7.39-7.51 (m, 2H), 7.33 (s, 1H), 7.09-7.20 (m, 2H), 7.06 (dt, J=1.96, 9.54 Hz, 1H), 6.37 (d, J=0.98 Hz, 1H), 5.08 (s, 1H), 4.02 (s, 3H), 3.40 (s, 3H), 2.68 (s, 3H). MS m/e 557.1 [M+H]+.

Example 177c $^1$H NMR (400 MHz, CHLOROFORM-d) δ 8.83 (d, J=1.96 Hz, 1H), 8.04 (d, J=1.96 Hz, 1H), 7.93 (dd, J=1.96, 8.07 Hz, 1H), 7.67 (d, J=8.07 Hz, 1H), 7.39-7.51 (m, 2H), 7.33 (s, 1H), 7.09-7.20 (m, 2H), 7.02-7.09 (m, 1H), 6.37 (d, J=1.22 Hz, 1H), 5.11 (s, 1H), 4.02 (s, 3H), 3.39 (s, 3H), 2.68 (s, 3H). MS m/e 557.2 [M+H]+.

Example 178a (4-Chloro-3-(3-fluorophenyl)-2-methoxy-8-methylquinolin-6-yl)(4-fluorophenyl)(1-methyl-1H-imidazol-5-yl)methanol

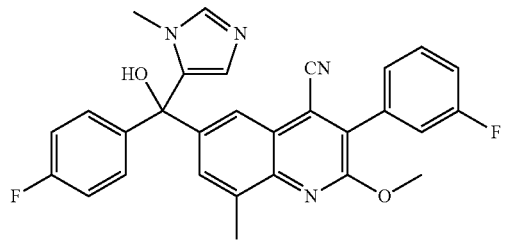 [SMILES: COc1nc2c(C)cc(C(O)(c3ccc(F)cc3)c3cncn3C)cc2c(C#N)c1-c1cccc(F)c1]

The title compound was prepared using (4-fluorophenyl)(1-methyl-1H-imidazol-5-yl)methanone (Intermediate 49, step b) in place of (1-methyl-1H-imidazol-5-yl)(6-(trifluoromethyl)pyridin-3-yl)methanone using the procedure described for Example 177a, with the exception that twice as much THF (10 mL) was required to dissolve the starting ketone.

Example 178a was purified by chiral HPLC (Chiralpak AD, 80% CO$_2$/20% iPrOH+0.2% isopropylamine) to give 2 enantiomers (elution order: Example 178b first, Example 178c second). The enantiomers were then further purified by reverse-phase HPLC (40-100% CH$_3$CN—H$_2$O, 0.2% ammonium bicarbonate).

Example 178b $^1$H NMR (400 MHz, CHLOROFORM-d) δ 7.99 (d, J=1.96 Hz, 1H), 7.48 (d, J=1.22 Hz, 1H), 7.41-7.47 (m, 2H), 7.32-7.39 (m, 2H), 7.10-7.18 (m, 2H), 7.01-7.10 (m, 3H), 6.45 (s, 1H), 4.03 (s, 3H), 3.43 (s, 3H), 3.32 (s, 1H), 2.69 (s, 3H). MS m/e 506.1 [M+H]+.

Example 178c $^1$H NMR (400 MHz, CHLOROFORM-d) δ 7.99 (d, J=1.96 Hz, 1H), 7.41-7.51 (m, 3H), 7.33-7.40 (m, 2H), 7.10-7.21 (m, 2H), 7.00-7.10 (m, 3H), 6.45 (s, 1H), 4.03 (s, 3H), 3.43 (s, 3H), 3.34 (s, 1H), 2.69 (s, 3H). MS m/e 506.1 [M+H]+.

Example 179a 3-(3-Fluorophenyl)-6-(hydroxy(1-methyl-1H-imidazol-5-yl)(6-(trifluoromethyl)pyridin-3-yl)methyl)-2-methoxy-8-methylquinoline-4-carbonitrile

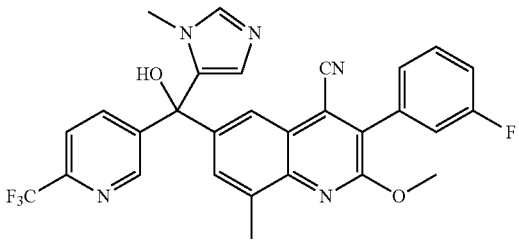 [SMILES: COc1nc2c(C)cc(C(O)(c3ccc(C(F)(F)F)nc3)c3cncn3C)cc2c(C#N)c1-c1cccc(F)c1]

A round bottom flask was charged with (4-chloro-3-(3-fluorophenyl)-2-methoxy-8-methylquinolin-6-yl)(1-methyl-1H-imidazol-5-yl)(6-(trifluoromethyl)pyridin-3-yl)methanol (701 mg, 1.26 mmol, Example 177a), ZnCN$_2$ (266 mg, 2.27 mmol), Pd$_2$dba$_3$ (173 mg, 0.189 mmol), zinc nanopowder (25 mg, 0.378 mmol), and dicyclohexyl(2',4',6'-triisopropyl-[1,1'-biphenyl]-2-yl)phosphine (X-Phos, 124 mg, 0.252 mmol). The flask was evacuated and re-filled with argon (three cycles). Dimethylacetamide (6.5 mL, degassed by bubbling argon through for 30 min) was then added and the mixture was heated at 120° C. for 4 hours. The mixture was cooled to room temperature and was filtered through Celite®, washing with EtOAc. The filtrate was washed sequentially with 2 M aqueous NH$_4$OH, water, and saturated aqueous NaCl. The organic phase was dried (Na$_2$SO$_4$), filtered, and concentrated. The residue was purified by flash column chromatography (silica gel, 45-60% CH$_3$CN in [2% conc. aqueous NH$_4$OH in DCM, aqueous phase removed]) to afford the title compound as a yellow foam.

Example 179a was purified by chiral HPLC (Chiralpak IC, 80% CO$_2$/20% iPrOH+0.2% isopropylamine) to give 2 enantiomers (elution order: Example 179b first, Example 179c second). The enantiomers were then further purified by reverse-phase HPLC (35-100% CH$_3$CN—H$_2$O, 0.25% ammonium bicarbonate). To convert the enantiomers to their succinate salts, they were dissolved in EtOH, solutions of 1.05 equivalents succinic acid in EtOH were added, and the mixtures were concentrated.

Example 179b•Succinic Acid $^1$H NMR (400 MHz, DMSO-d$_6$) δ 11.84 (br. s., 2H), 8.79 (d, J=1.71 Hz, 1H), 7.95-8.03 (m, 1H), 7.89-7.95 (m, 1H), 7.86 (d, J=1.71 Hz, 1H), 7.76 (s, 1H), 7.67 (d, J=0.98 Hz, 1H), 7.60 (td, J=6.11, 7.95 Hz, 1H), 7.42-7.55 (m, 3H), 7.38 (td, J=2.32, 8.86 Hz, 1H), 6.26 (s, 1H), 4.02 (s, 3H), 3.36 (s, 3H), 2.68 (s, 3H), 2.41 (s, 4H). MS m/e 548.3 [M+H]+.

Example 179c•Succinic Acid $^1$H NMR (400 MHz, DMSO-d$_6$) δ 12.23 (br. s., 2H), 8.79 (s, 1H), 7.95-8.02 (m, 1H), 7.89-7.95 (m, 1H), 7.86 (s, 1H), 7.76 (s, 1H), 7.67 (s, 1H), 7.55-7.65 (m, 1H), 7.47-7.55 (m, 2H), 7.45 (d, J=7.58 Hz, 1H), 7.38 (td, J=2.57, 8.62 Hz, 1H), 6.26 (s, 1H), 4.02 (s, 3H), 3.36 (s, 3H), 2.68 (s, 3H), 2.41 (s, 4H). MS m/e 548.3 [M+H]$^+$.

Example 180a 3-(3-Fluorophenyl)-6-((4-fluorophenyl)(hydroxy)(1-methyl-1H-imidazol-5-yl)methyl)-2-methoxy-8-methylquinoline-4-carbonitrile

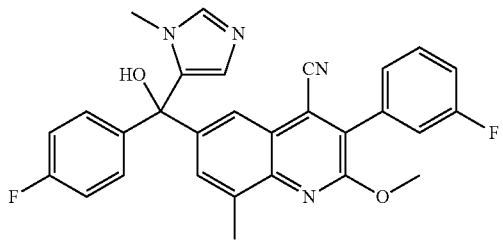 [SMILES: COc1nc2c(C)cc(C(O)(c3ccc(F)cc3)c3cncn3C)cc2c(C#N)c1-c1cccc(F)c1]

The title compound was prepared using (4-chloro-3-(3-fluorophenyl)-2-methoxy-8-methylquinolin-6-yl)(4-fluorophenyl)(1-methyl-1H-imidazol-5-yl)methanol (Example 178a) in place of (4-chloro-3-(3-fluorophenyl)-2-methoxy-8-methylquinolin-6-yl)(1-methyl-1H-imidazol-5-yl)(6-(trifluoromethyl)pyridin-3-yl)methanol using the procedure described for Example 179a.

Example 180a was purified by chiral HPLC (Chiralpak IC, 75% CO$_2$/25% iPrOH+0.2% isopropylamine) to give 2 enantiomers (elution order: Example 180b first, Example 180c second). The enantiomers were then further purified by reverse-phase HPLC (35-100% CH$_3$CN—H$_2$O, 0.25% ammonium bicarbonate). To convert the enantiomers to their succinate salts, they were dissolved in EtOH, solutions of 1.05 equivalents succinic acid in EtOH were added, and the mixtures were concentrated.

Example 180b•Succinic Acid $^1$H NMR (400 MHz, DMSO-d$_6$) δ 12.21 (br. s., 2H), 7.80 (d, J=1.47 Hz, 1H), 7.69 (s, 1H), 7.65 (d, J=0.98 Hz, 1H), 7.60 (td, J=6.11, 8.07 Hz, 1H), 7.48-7.55 (m, 1H), 7.45 (d, J=8.07 Hz, 1H), 7.29-7.41 (m, 3H), 7.20 (t, J=8.93 Hz, 2H), 7.07 (s, 1H), 6.15 (s, 1H), 4.02 (s, 3H), 3.35 (s, 3H), 2.67 (s, 3H), 2.41 (s, 4H). MS m/e 497.2 [M+H]$^+$.

Example 180c•Succinic Acid $^1$H NMR (400 MHz, DMSO-d$_6$) δ 12.20 (br. s., 2H), 7.80 (d, J=1.71 Hz, 1H), 7.69 (s, 1H), 7.65 (s, 1H), 7.60 (td, J=6.11, 7.95 Hz, 1H), 7.48-7.55 (m, 1H), 7.45 (d, J=7.83 Hz, 1H), 7.30-7.41 (m, 3H), 7.15-7.24 (m, 2H), 7.07 (s, 1H), 6.16 (d, J=0.98 Hz, 1H), 4.02 (s, 3H), 3.35 (s, 3H), 2.67 (s, 3H), 2.42 (s, 4H). MS m/e 497.2 [M+H]$^+$.

Example 181a 1-(4-(Hydroxy(1-methyl-1H-imidazol-5-yl)(3-phenyl-2,4-bis(trifluoromethyl)quinolin-6-yl)methyl)piperidin-1-yl)ethanone

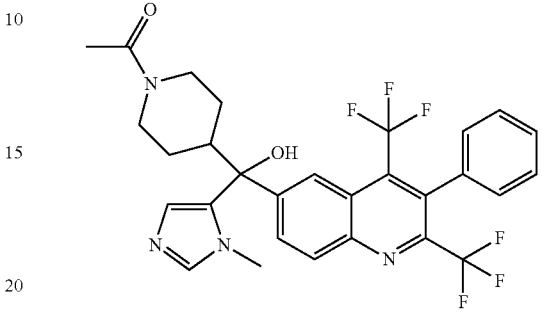

A ~–70° C. solution of 6-iodo-3-phenyl-2,4-bis(trifluoromethyl)quinoline (150 mg, 0.322 mmol; Intermediate 8, step d) in THF (0.322 mL) was treated with iPrMgCl (2.06 M in THF; 0.156 mL, 0.322 mmol) dropwise via syringe under argon over the course of 30 sec to provide a light amber solution that became a yellow opaque slurry within 2 min. After 8 additional min the reaction was removed from the cold bath and stirred on a room temperature water bath for 10 min, at which point solid 1-(4-(1-methyl-1H-imidazole-5-carbonyl)piperidin-1-yl)ethanone (90.9 mg, 0.386 mmol; Intermediate 53, step c) was added in one portion and the reaction quickly evacuated and flushed with argon four times. After 5 min, additional THF (2.6 mL) was added to aid the dissolution of the ketone, and the reaction became an opaque easily stirred tan slurry within 30 min. After 110 min, the reaction was quenched with D$_2$O (0.2 mL) and partitioned with 5 M NH$_4$Cl (1 mL) and heptane (1 mL), and the organic layer was dried (Na$_2$SO$_4$), filtered, and concentrated. The residue was flash chromatographed using a DCM to 9:1 DCM/MeOH gradient to provide the title compound as a white powder.

Example 181a was purified by chiral HPLC (Chiralpak OD, 100% EtOH) to give 2 enantiomers (elution order: Example 181b first, Example 181c second). To convert the enantiomers to their succinate salts, they were dissolved in CH$_3$CN, treated with 1.0 equivalent of 0.1 M succinic acid in 95:5 v/v CH$_3$CN/water to provide homogeneous solutions, frozen (with water added as necessary to ensure complete freezing), and lyophilized.

Example 181b•Succinic Acid $^1$H NMR (400 MHz, MeOH) (two conformers) δ 8.50 (m, 1H), 8.27 (d, J=9.09 Hz, 1H), 7.82 (d, J=8.59 Hz, 1H), 7.62 (s, 1H), 7.42-7.53 (m, 3H), 7.39 (s, 1H), 7.34 (d, J=6.57 Hz, 2H), 4.64 (d, J=13.64 Hz, ~0.5H), 4.44 (d, J=12.63 Hz, ~0.5H), 4.03 (d, J=13.3 Hz, ~0.5H), 3.83 (d, J=13.3 Hz, ~0.5H), 3.36 (s, ~1.5H), 3.35 (s, ~1.5H), 3.29 (m, ~0.5H; partially obscured by CD$_3$OD), 3.05 (td, J=2.53, 13.14 Hz, ~0.5H), 2.63-2.84 (m, ~1.5H), 2.56 (s, 4H), 2.54 (m, ~0.5H, partially obscured by succinic acid), 2.29 (m, 1H), 2.07 (s, ~1.5H), 2.02 (s, ~1.5H), 1.06-1.57 (m, 3H). MS m/e 577.2 [M+H]$^+$.

Example 181c•Succinic Acid

¹H NMR (400 MHz, MeOH) (two conformers) δ 8.50 (m, 1H), 8.27 (d, J=8.59 Hz, 1H), 7.82 (d, J=8.59 Hz, 1H), 7.62 (s, 1H), 7.41-7.54 (m, 3H), 7.38 (s, 1H), 7.33 (d, J=6.57 Hz, 2H), 4.64 (d, J=13.14 Hz, 1H), 4.44 (d, J=13.64 Hz, 1H), 4.03 (d, J=13.3 Hz, ~0.5H), 3.83 (d, J=13.3 Hz, ~0.5H), 3.36 (s, ~1.5H), 3.35 (s, ~1.5H), 3.28 (m, ~0.5H; partially obscured by CD$_3$OD), 3.05 (td, J=2.53, 13.14 Hz, ~0.5H), 2.63-2.84 (m, ~1.5H), 2.56 (s, 4H), 2.53 (m, ~0.5H, partially obscured by succinic acid), 2.29 (m, 1H), 2.07 (s, ~1.5H), 2.02 (s, ~1.5H), 1.06-1.57 (m, 3H). MS m/e 577.2 [M+H]$^+$.

Example 182

Bis(1-methyl-1H-1,2,3-triazol-5-yl)(3-phenyl-2,4-bis(trifluoromethyl)quinolin-6-yl)methanol

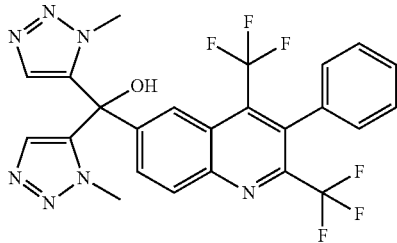 [SMILES: Cn1nncc1C(O)(c1ccc2nc(C(F)(F)F)c(-c3ccccc3)c(C(F)(F)F)c2c1)c1cnnn1C]

A ~−70° C. solution of 6-iodo-3-phenyl-2,4-bis(trifluoromethyl)quinoline (152 mg, 0.326 mmol; Intermediate 8, step d) in THF (0.322 mL) was treated with iPrMgCl (2.06 M in THF; 0.158 mL, 0.326 mmol) dropwise via syringe under argon over the course of 30 sec to provide an amber solution that became a yellow opaque slurry within 2 min. After 2 additional min the dark yellow opaque slurry was removed from the cold bath and immediately treated rapidly dropwise with a pre-formed solution of bis(1-methyl-1H-1,2,3-triazol-5-yl)methanone (74.2 mg, 0.386 mmol; Intermediate 57) in THF (2.6 mL) over 45 sec. The reaction was stirred at room temperature for 3 hours and was then quenched with 5 M NH$_4$Cl (1 mL). The aqueous layer was extracted with MTBE (1×3 mL), and the combined organic layers were dried (Na$_2$SO$_4$), filtered, and concentrated. The residue was dry load flash chromatographed with a heptane to 80% EtOAc/heptane gradient to provide the title compound as a white solid. ¹H NMR (400 MHz, DMSO-d6) δ 8.45 (d, J=8.59 Hz, 1H), 8.29 (br. s., 1H), 8.21 (s, 1H), 7.87 (d, J=9.09 Hz, 1H), 7.40-7.56 (m, 5H), 7.29 (s, 2H), 3.87 (s, 6H). MS m/e 534.2 [M+H]$^+$.

Example 183a (4-Chloro-2-methoxy-8-methyl-3-(4-(trifluoromethoxy)phenyl)quinolin-6-yl)(1-methyl-1H-imidazol-5-yl)(6-(trifluoromethyl)pyridin-3-yl)methanol•TFA

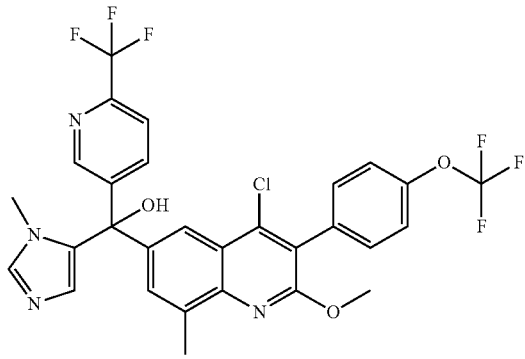 [SMILES: COc1nc2c(C)cc(C(O)(c3ccc(C(F)(F)F)nc3)c3cncn3C)cc2c(Cl)c1-c1ccc(OC(F)(F)F)cc1]

n-Butyllithium (2.0 mL, 3.202 mmol) was added to a −78° C. mixture of 6-bromo-4-chloro-2-methoxy-8-methyl-3-(4-(trifluoromethoxy)phenyl)quinoline (1.1 g, 2.463 mmol, Intermediate 58, step d) and (1-methyl-1H-imidazol-5-yl)(6-(trifluoromethyl)pyridin-3-yl)methanone (0.691 g, 2.709 mmol, Intermediate 15, step c) in dry THF (25 mL) over a 2 min period. After complete addition stirring was continued at −78° C. for 10 min then the reaction was warmed up to 0° C. and stirred for 1 hour. Saturated NH$_4$Cl was added and the reaction mixture slowly warmed to room temperature. Water was added and the layers were separated. The aqueous layer was extracted with EtOAc. The combined organic extracts was dried (Na$_2$SO$_4$), filtered, evaporated in vacuo and chromatographed (DCM/10% MeOH in EtOAc) to provide product. Further purification using reverse phase HPLC provided the TFA salt of the title compound. MS (ESI) 623.1

Example 183a was purified by chiral HPLC (Diacel OD column, eluent A: 2% isopropylamine in 2-propanol/eluent B: acetonitrile, 80 mL/min, 240 nm wavelength) to give two pure enantiomers (elution order: Example 183b first, Example 183c second).

Example 183b

¹H NMR (CHLOROFORM-d) δ: 8.83 (s, 1H), 8.02 (s, 1H), 7.94 (d, J=8.1 Hz, 1H), 7.68 (d, J=8.1 Hz, 1H), 7.27-7.54 (m, 6H), 6.46 (s, 1H), 4.02 (s, 3H), 3.42 (s, 3H), 2.68 (s, 3H). mass calc'd for C$_{29}$H$_{21}$ClF$_6$N$_4$O$_3$, 622.95. m/z found, 623.2.

Example 183c

¹H NMR (CHLOROFORM-d) δ: 8.82 (s, 1H), 8.03 (d, J=2.0 Hz, 1H), 7.93 (d, J=8.1 Hz, 1H), 7.67 (d, J=8.1 Hz, 1H), 7.47 (s, 1H), 7.28-7.44 (m, 5H), 6.42 (br. s., 1H), 4.02 (s, 3H), 3.41 (s, 3H), 2.68 (s, 3H). mass calc'd for C$_{29}$H$_{21}$ClF$_6$N$_4$O$_3$, 622.95. m/z found, 623.2.

Example 184a 3-(4-Fluorophenyl)-6-(hydroxy(1-methyl-1H-imidazol-5-yl)(6-(trifluoromethyl)pyridin-3-yl)methyl)-8-methylquinoline-2,4-dicarbonitrile

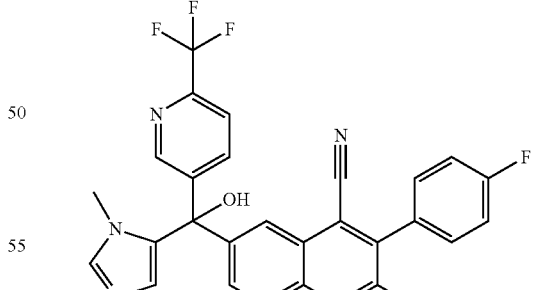

Zinc cyanide (172 mg, 1.463 mmol), Zn nanopowder (4.6 mg, 0.070 mmol), Pd$_2$(dba)$_3$ (137 mg, 0.15 mmol) and X-Phos (57 mg, 0.12 mmol) were combined in a microwave tube, sealed, evacuated and filled with nitrogen (3×). A solution of (2,4-dichloro-3-(4-fluorophenyl)-8-methylquinolin-6-yl)(1-methyl-1H-imidazol-5-yl)(6-(trifluoromethyl)pyridin-3-yl)methanol (259 mg, 0.461 mmol, Example 192) in dry DMA was then added to the tube and the resulting mixture was again evacuated and filled with nitrogen (3×). The tube was then placed in a 120° C. oil bath for 2.5 hours, cooled to room temperature overnight, diluted with EtOAc, stirred for 20 min then filtered through a Celite® plug. The crude product mixture was diluted with sat'd NH$_4$Cl and layers were separated. The EtOAc extract was dried over Na$_2$SO$_4$, filtered, evaporated in vacuo and chromatographed (DCM/10% MeOH, gradient). The product was further purified by reverse phase HPLC to provide the title compound as a white solid. MS (ESI) 614.2

Example 184a was purified by chiral HPLC (Chiralpak OD-H column, eluent 80:20 Heptane/EtOH, 80 mL/min, 263 nm wavelength) to give two pure enantiomers (elution order: Example 184b first, Example 184c second).

Example 184b $^1$H NMR (CHLOROFORM-d) δ: 8.79 (d, J=2.0 Hz, 1H), 8.32 (s, 1H), 7.92-8.04 (m, 1H), 7.71 (d, J=8.1 Hz, 1H), 7.55-7.67 (m, 3H), 7.30-7.43 (m, 3H), 6.40 (s, 1H), 5.59 (br. s., 1H), 3.40 (s, 3H), 2.80 (s, 3H) mass calc'd for C$_{29}$H$_{18}$F$_4$N$_6$O, 542.49. m/z found 543.1.

Example 184c $^1$H NMR (CHLOROFORM-d) δ: 8.79 (s, 1H), 8.31 (s, 1H), 7.97 (d, J=8.1 Hz, 1H), 7.71 (d, J=8.1 Hz, 1H), 7.53-7.67 (m, 3H), 7.30-7.43 (m, 3H), 6.42 (s, 1H), 5.46 (br. s., 1H), 3.40 (s, 3H), 2.80 (s, 3H) mass calc'd for C$_{29}$H$_{18}$F$_4$N$_6$O, 542.49. m/z found 543.1.

Example 185a (1-Methyl-1H-imidazol-5-yl)(3-phenyl-2,4-bis(trifluoromethyl)quinolin-6-yl)(pyridin-2-yl)methanol

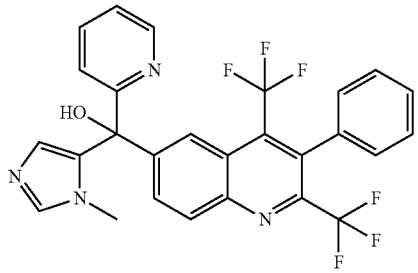 [SMILES: Cn1cncc1C(O)(c1ccc2nc(C(F)(F)F)c(-c3ccccc3)c(C(F)(F)F)c2c1)c1ccccn1]

A solution of n-BuLi (2.5 M in hexanes, 0.10 mL, 0.25 mmol) was added dropwise by syringe to a solution of 6-iodo-3-phenyl-2,4-bis(trifluoromethyl)quinoline (122 mg, 0.261 mmol, Intermediate 8, step d) in dry THF (4.5 mL) in a dry ice-acetone bath. After 2 min, a solution of (1-methyl-1H-imidazol-5-yl)(pyridin-2-yl)methanone (0.0540 g, 0.288 mmol, Intermediate 11, step b) in dry THF (0.25 mL) was added dropwise. The reaction mixture was stirred for 5 min in a dry ice-acetone bath, then the reaction flask was placed into an ice-water bath. After 5 min, the mixture was warmed to room temperature and the reaction was quenched with methanol and water. The mixture was partitioned between water and ethyl acetate. The separated aqueous phase was further extracted with ethyl acetate. The organic phase was dried (Na$_2$SO$_4$), filtered, and concentrated. The crude product was purified by reverse-phase chromatography (acetonitrile w/0.05% TFA in water). Saturated sodium bicarbonate was used to form the free-base product, which was extracted with DCM and concentrated to provide the title compound as a white solid. $^1$H NMR (500 MHz, CDCl$_3$) δ 8.66 (d, J=4.4 Hz, 1H), 8.32 (d, J=8.9 Hz, 1H), 8.26 (d, J=2.0 Hz, 1H), 8.05 (dd, J=8.9, 1.8 Hz, 1H), 7.75 (td, J=7.7, 1.7 Hz, 1H), 7.51 (s, 1H), 7.49-7.40 (m, 3H), 7.35 (dd, J=7.0, 5.3 Hz, 1H), 7.28 (s, 1H), 7.22 (d, J=7.9 Hz, 1H), 6.72 (s, 1H), 6.39 (s, 1H), 3.44 (s, 3H). MS m/e 529.2 [M+H]$^+$.

Example 185a was purified by chiral HPLC (ChiralPak OD, 80:20 heptane/ethanol) to give two pure enantiomers, Example 185b and Example 185c (elution order: Example 185b first, Example 185c second).

Example 185b $^1$H NMR (400 MHz, CD$_3$OD) δ 8.60 (d, J=4.2 Hz, 1H), 8.47 (s, 1H), 8.32 (d, J=8.9 Hz, 1H), 8.17 (d, J=8.9 Hz, 1H), 8.01 (s, 1H), 7.88 (t, J=7.8 Hz, 1H), 7.66 (d, J=8.0 Hz, 1H), 7.46 (dd, J=14.7, 7.3 Hz, 3H), 7.41-7.36 (m, 1H), 7.33 (d, J=6.9 Hz, 2H), 6.57 (s, 1H), 3.47 (s, 3H). MS m/e 529.2 [M+H]$^+$.

Example 185c $^1$H NMR (400 MHz, MeOD) δ 8.60 (d, J=4.2 Hz, 1H), 8.47 (s, 1H), 8.32 (d, J=8.9 Hz, 1H), 8.17 (d, J=9.0 Hz, 1H), 8.02 (s, 1H), 7.88 (t, J=6.9 Hz, 1H), 7.67 (d, J=7.9 Hz, 1H), 7.53-7.41 (m, 3H), 7.39 (dd, J=6.9, 5.1 Hz, 1H), 7.33 (d, J=6.8 Hz, 2H), 6.56 (s, 1H), 3.47 (s, 3H). MS m/e 529.2 [M+H]$^+$.

Example 186a (2-Azetidin-1-yl-4-chloro-3-phenylquinolin-6-yl)(1-methyl-1H-imidazol-5-yl)[6-(trifluoromethyl)pyridin-3-yl]methanol

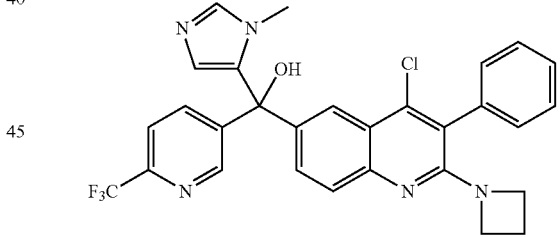

To a 5 mL sealed tube was added (2,4-dichloro-3-phenylquinolin-6-yl)(1-methyl-1H-imidazol-5-yl)[6-(trifluoromethyl)pyridin-3-yl]methanol (200 mg, 0.38 mmol, 1 equivalent, Example 109), azetidine (108 mg, 1.89 mmol, 5 equivalents) and dimethylformamide (2 mL). The reaction vessel was sealed and heated in a 100° C. oil bath. After two days, the vessel was cooled and contents transferred to a reparatory funnel with ethyl acetate dilution. The organic phase was extracted with saturated, aqueous ammonium chloride solution and deionized water. The organic phase was separated, dried over magnesium sulfate, filtered and evaporated to dryness under reduced pressure. The crude material was purified via reverse phase chromatography using acetonitrile with ammonium hydroxide in water as eluent to provide racemic (2-azetidin-1-yl-4-chloro-3-phenylquinolin-6-yl)(1-methyl-1H-imidazol-5-yl) [6-(trifluoromethyl) pyridin-3-yl]methanol. MS (ESI): mass calcd. for $C_{29}H_{23}ClF_3N_5O$, 549.15. m/z found, 550.3 [M+H]$^+$. $^1$H NMR (600 MHz, MeOD) δ 8.76 (d, J=2.0 Hz, 1H), 8.04-7.97 (m, 2H), 7.83 (d, J=8.2 Hz, 1H), 7.78-7.70 (m, 2H), 7.58 (dd, J=8.9, 2.2 Hz, 1H), 7.51-7.41 (m, 3H), 7.33 (d, J=7.8 Hz, 2H), 6.33 (s, 1H), 3.72-3.61 (m, 4H), 3.48 (s, 3H), 2.10-2.02 (m, 2H).

Racemic (2-azetidin-1-yl-4-chloro-3-phenylquinolin-6-yl)(1-methyl-1H-imidazol-5-yl)[6-(trifluoromethyl)pyridin-3-yl]methanol was purified on a chiralcel OD column (20 um, Diacel) with methanol to provide two enantiomers (elution order: Example 186b first, Example 186c second).

Example 186b

MS (ESI): mass calcd. for $C_{29}H_{23}ClF_3N_5O$, 549.15. m/z found, 550.3 [M+H]$^+$. $^1$H NMR (600 MHz, MeOD) δ 8.76 (d, J=2.0 Hz, 1H), 8.02 (d, J=2.0 Hz, 1H), 8.00 (dd, J=8.2, 2.0 Hz, 1H), 7.82 (d, J=8.2 Hz, 1H), 7.76-7.71 (m, 2H), 7.58 (dd, J=8.9, 2.2 Hz, 1H), 7.48-7.41 (m, 3H), 7.34-7.29 (m, 2H), 6.33 (s, 1H), 3.69-3.62 (m, 4H), 3.48 (s, 3H), 2.09-2.00 (m, 2H).

Example 186c

MS (ESI): mass calcd. for $C_{29}H_{23}ClF_3N_5O$, 549.15. m/z found, 550.3 [M+H]$^+$. $^1$H NMR (600 MHz, MeOD) δ 8.76 (d, J=2.0 Hz, 1H), 8.02 (d, J=2.1 Hz, 1H), 8.00 (dd, J=8.3, 2.0 Hz, 1H), 7.83 (d, J=8.2 Hz, 1H), 7.77-7.71 (m, 2H), 7.58 (dd, J=8.9, 2.2 Hz, 1H), 7.50-7.41 (m, 3H), 7.32 (dd, J=5.8, 1.9 Hz, 2H), 6.33 (d, J=1.1 Hz, 1H), 3.66 (t, J=7.1 Hz, 4H), 3.48 (s, 3H), 2.09-2.00 (m, 2H).

Example 187

(4-Chlorophenyl)(2,4-dichloro-3-(3-chlorophenyl)quinolin-6-yl)(1-methyl-1H-imidazol-5-yl)methanol

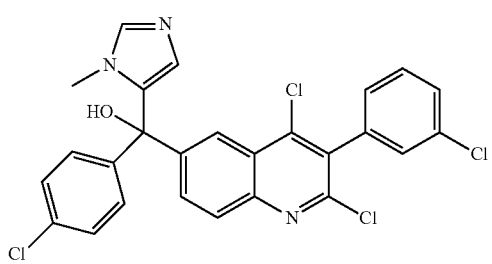 [SMILES: Cn1cncc1C(O)(c1ccc(Cl)cc1)c1ccc2nc(Cl)c(-c3cccc(Cl)c3)c(Cl)c2c1]

A solution of n-BuLi (1.6 M in hexanes, 2.41 mL, 3.9 mmol) was added to 6-bromo-2,4-dichloro-3-(3-chlorophenyl)quinoline (1.0 g, 2.6 mmol, Intermediate 60, step c) in THF (10 mL) at −70° C. under nitrogen. The mixture was stirred at −70° C. for 45 min before addition of (4-chlorophenyl)(1-methyl-1H-imidazol-5-yl)methanone (0.85 g, 3.9 mmol, Intermediate 18, step b). The mixture was stirred at −70° C. for 1 hour, then brought to −50° C. and quenched by addition of water. The mixture was extracted with EtOAc. The organic phase was dried (Na$_2$SO$_4$), filtered, and concentrated. The residue was purified by flash column chromatography (silica gel, DCM/MeOH/NH$_4$OH, 97/3/0.1) to afford the title compound. MS m/e 530.2 [M+H]$^+$.

Example 188

(4-Chlorophenyl)[2,4-dichloro-3-(pyridin-2-yl)quinolin-6-yl](1-methyl-1H-imidazol-4-yl)methanol

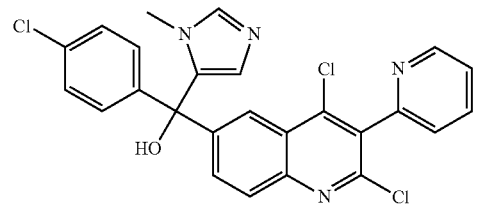 [SMILES: Cn1cncc1C(O)(c1ccc(Cl)cc1)c1ccc2nc(Cl)c(-c3ccccn3)c(Cl)c2c1]

Into a 100-mL round-bottom flask were placed, under nitrogen, a solution of 6-bromo-2,4-dichloro-3-(pyridin-2-yl)quinoline (380 mg, 1.07 mmol, 1.20 equivalents, Intermediate 61, step c) in tetrahydrofuran (10 mL). This was followed by the addition of n-BuLi (3 M in hexane, 0.43 mL, 1.28 mmol, 1.40 equivalents) dropwise with stirring at −78° C. In 30 min a solution of (4-chlorophenyl)(1-methyl-1H-imidazol-5-yl)methanone (199 mg, 0.90 mmol, 1.00 equivalents, Intermediate 18, step b) in tetrahydrofuran (10 ml) was added dropwise. The resulting solution was allowed to warm to room temperature and stirred for an additional 2 hours. The reaction was then quenched with 10 mL of NH$_4$Cl and then concentrated under vacuum. The crude product (200 mg) was purified by Prep-HPLC (45-65% MeOH in water, 0.05% TFA) to yield the title compound as a white solid. $^1$H NMR (300 MHz, CHLOROFORM-d+D$_2$O, mixture of rotamers, ratio 1.0:1, single rotamer peaks marked * where separated) δ 8.75 (br. s., 2H), 8.50 (br. s., 2H), 8.33-8.44 (m, 1H)*, 8.18-8.33 (m, 1H)*, 8.03-8.15 (m, 2H), 7.90-8.02 (m, 2H), 7.70-7.86 (m, 2H), 7.44-7.59 (m, 4H), 7.31-7.44 (m, 6H), 6.58-6.79 (m, 2H), 3.59 (br. s., 6H); MS m/e 495 [M+H]$^+$.

Example 189

(4-Chlorophenyl)(2,4-dichloro-3-(pyridin-3-yl)quinolin-6-yl)(1-methyl-1H-imidazol-5-yl)methanol

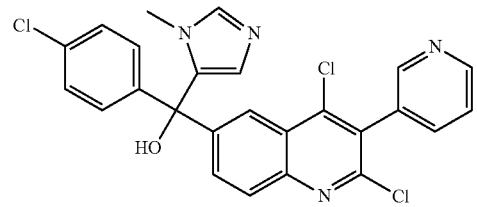 [SMILES: Cn1cncc1C(O)(c1ccc(Cl)cc1)c1ccc2nc(Cl)c(-c3cccnc3)c(Cl)c2c1]

Into a 100-mL round-bottom flask were placed, under nitrogen, a solution of 6-bromo-2,4-dichloro-3-(pyridin-3-yl)quinoline (160 mg, 0.45 mmol, 1.00 equivalent, Intermediate 51, step c) in tetrahydrofuran (10 mL). This was followed by the addition of t-BuLi (0.85 mL, 3.00 equivalents, 1.6 M in hexane) dropwise with stirring at −78° C. In 30 min a solution of (4-chlorophenyl)(1-methyl-1H-imidazol-5-yl)methanone (121 mg, 0.55 mmol, 1.20 equivalents, Intermediate 18, step b) in tetrahydrofuran (10 mL) was added dropwise. The resulting solution was allowed to warm to −40° C.

for an additional 30 min, followed by stirring at room temperature overnight. The reaction was then quenched with 10 mL of NH₄Cl, and extracted with 3×10 mL of ethyl acetate. The combined organic layer was dried over anhydrous sodium sulfate, filtered, and concentrated under vacuum. The crude product (400 mg) was purified by Prep-HPLC (22-44% acetonitrile in water, 0.05% TFA) to yield the title compound as an off-white solid. ¹H NMR (400 MHz, MeOD, mixture of rotamers, ratio 1:0.8, minor rotamer peaks marked *) δ 9.03 (s, 2H), 8.73-8.82 (m, 2H), 8.70 (s, 1H), 8.59-8.67 (m, 1H)*, 8.31-8.44 (m, 2H), 8.04-8.17 (m, 4H), 7.89-8.02 (m, 2H), 7.69-7.83 (m, 2H), 7.37-7.58 (m, 8H), 6.95-7.04 (m, 2H), 3.75 (s, 3H)*, 3.73 (s, 3H); MS m/e 495 [M+H]⁺.

Example 190

(2,4-Dichloro-3-(3-fluorophenyl)-8-methylquinolin-6-yl)(4-fluorophenyl)(1-methyl-1H-imidazol-5-yl)methanol

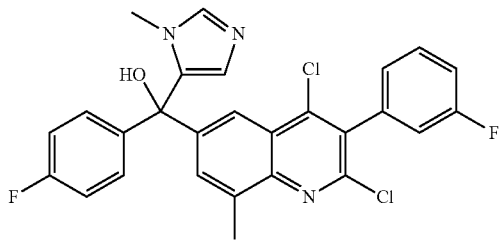

A round bottom flask was charged with 6-bromo-2,4-dichloro-3-(3-fluorophenyl)-8-methylquinoline (1.00 g, 2.60 mmol, Intermediate 50, step c) and (4-fluorophenyl)(1-methyl-1H-imidazol-5-yl)methanone (583 mg, 2.86 mmol, Intermediate 49, step b) and was evacuated and re-filled with argon (three times). THF (20 mL) was added, and the solution was cooled in a dry ice acetone bath for 2 minutes. At this point the mixture began to turn cloudy and n-BuLi (1.6 M in hexane, 2.11 mL, 3.38 mmol) was added over about 1 minute. The mixture was stirred at −78° C. for 10 minutes, then in an ice water bath for 1 hour. The reaction was quenched by addition of saturated aqueous NH₄Cl, diluted with water and extracted with EtOAc (3×). The organic phase was dried (Na₂SO₄), filtered, and concentrated. The residue was purified by flash column chromatography (silica gel, 30-60% acetone-DCM) to afford slightly impure title compound as an off-white solid. ¹H NMR (400 MHz, CHLOROFORM-d) δ 8.09 (s, 1H), 7.60 (s, 1H), 7.44-7.55 (m, 1H), 7.30-7.39 (m, 3H), 7.15-7.23 (m, 1H), 7.01-7.12 (m, 4H), 6.40 (s, 1H), 4.00 (br. s., 1H), 3.40 (s, 3H), 2.74 (s, 3H). MS m/e 510.1 [M+H]⁺.

Example 191

(2,4-Dichloro-3-(3-fluorophenyl)-8-methylquinolin-6-yl)(1-methyl-1H-imidazol-5-yl)(6-(trifluoromethyl)pyridin-3-yl)methanol

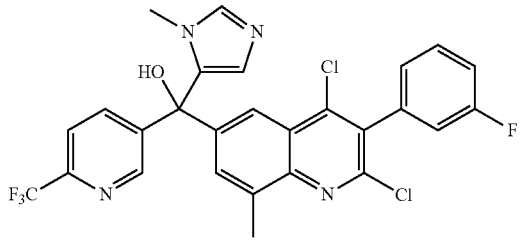 [SMILES: Cc1cc(C(O)(c2ccc(C(F)(F)F)nc2)c2cncn2C)cc2c(Cl)c(-c3cccc(F)c3)c(Cl)nc12]

n-BuLi (1.6 M in hexane, 1.91 mL, 3.05 mmol) was added over approximately 1 minute to a solution of 6-bromo-2,4-dichloro-3-(3-fluorophenyl)-8-methylquinoline (1.23 g, 3.20 mmol, Intermediate 50, step c) in THF (10 mL) under argon at −78° C. After 1 minute, a solution of (1-methyl-1H-imidazol-5-yl)(6-(trifluoromethyl)pyridin-3-yl)methanone (817 mg, 3.20 mmol, Intermediate 15, step c) in 10 mL THF under argon was added via cannula. The resulting mixture was stirred at −78° C. for 10 minutes, then transferred to an ice water bath and stirred 1 hour. The reaction was quenched by addition of saturated aqueous NH₄Cl, diluted with water and extracted with EtOAc (3×). The organic phase was dried (Na₂SO₄), filtered, and concentrated. The residue was purified by flash column chromatography (silica gel, 45-60% CH₃CN in [2% conc. aqueous NH₄OH in DCM, aqueous phase removed]) to afford the title compound as a cream colored solid. ¹H NMR (400 MHz, CHLOROFORM-d) δ 8.83 (s, 1H), 8.14 (dd, J=1.83, 7.46 Hz, 1H), 7.92 (d, J=8.31 Hz, 1H), 7.65 (d, J=8.31 Hz, 1H), 7.57-7.62 (m, 1H), 7.44-7.53 (m, 1H), 7.20 (td, J=2.20, 8.31 Hz, 1H), 7.09 (t, J=6.60 Hz, 1H), 7.01-7.07 (m, 1H), 6.29 (d, J=0.98 Hz, 1H), 6.02 (br. s., 1H), 3.37 (s, 3H), 2.74 (s, 3H). MS m/e 561.2 [M+H]⁺.

Example 192

(2,4-Dichloro-3-(4-fluorophenyl)-8-methylquinolin-6-yl)(1-methyl-1H-imidazol-5-yl)(6-(trifluoromethyl)pyridin-3-yl)methanol

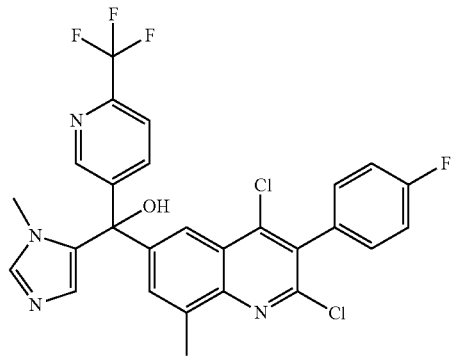 [SMILES: Cc1cc(C(O)(c2ccc(C(F)(F)F)nc2)c2cncn2C)cc2c(Cl)c(-c3ccc(F)cc3)c(Cl)nc12]

n-Butyllithium (0.78 mL, 1.249 mmol) was added to a −78° C. mixture of 6-bromo-2,4-dichloro-3-(4-fluorophenyl)-8-methylquinoline (0.37 g, 0.961 mmol, Intermediate 59, step c) and (1-methyl-1H-imidazol-5-yl)(6-(trifluoromethyl)pyridin-3-yl)methanone (0.27 g, 1.057 mmol, Intermediate 15, step c) in dry THF (10 mL) over a 2 min period. After complete addition stirring was continued at −78° C. for 10 min then the reaction was warmed up to 0° C. and stirred for 1 hour. Saturated NH₄Cl was added and the reaction mixture slowly warmed to room temperature. Water was added and the layers were separated. The aqueous layer was extracted with EtOAc. The combined organic extracts were dried over Na₂SO₄, filtered, evaporated in vacuo and chromatographed (EtOAc/DCM gradient) to provide the title compound. ¹H NMR (CHLOROFORM-d) δ: 8.84 (d, J=2.0 Hz, 1H), 8.14 (d, J=2.0 Hz, 1H), 7.92 (d, J=2.0 Hz, 1H), 7.66 (d, J=8.6 Hz, 1H), 7.60 (s, 1H), 7.26-7.38 (m, 3H), 7.16-7.25 (m, 2H), 6.37 (s, 1H), 3.81 (s, 1H), 3.39 (s, 3H), 2.75 (s, 3H); MS (ESI) 561.1.

In Vitro Biological Data
ThermoFluor® Assay

ThermoFluor® is a fluorescence based assay that estimates ligand binding affinities by measuring the effect of a ligand on protein thermal stability (Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) High-density miniaturized thermal shift assays as a general strategy for drug discovery. *J Biomol Screen* 6, 429-40, and Matulis, D., Kranz, J. K., Salemme, F. R., and Todd, M. J. (2005) Thermodynamic stability of carbonic anhydrase: measurements of binding affinity and stoichiometry using ThermoFluor. *Biochemistry* 44, 5258-66). This approach is applicable to a wide variety of systems, and rigorous in theoretical interpretation through quantitation of equilibrium binding constants ($K_D$).

In a ThermoFluor® experiment where protein stability is monitored as the temperature is steadily increased, an equilibrium binding ligand causes the midpoint of an unfolding transition ($T_m$) to occur at a higher temperature. The shift in the melting point described as a $\Delta T_m$ is proportional to the concentration and affinity of the ligand. The compound potency may be compared as a rank order of either $\Delta T_m$ values at a single compound concentration or in terms of $K_D$ values, estimated from concentration response curves.

RORγt ThermoFluor® Assay Construct

For the RORγt construct used in the ThermoFluor® assay, numbering for the nucleotide sequences was based on the reference sequence for human RORγt, transcript variant 2, NCBI Accession: NM_001001523.1 (SEQ ID NO:1). Nucleotides 850-1635 (SEQ ID NO:2) coding for the wild type human RORγt ligand binding domain (RORγt LBD) were cloned into the pHIS1 vector, a modified pET *E. coli* expression vector (Accelagen, San Diego), containing an in-frame N-terminal His-tag and a TurboTEV protease cleavage site (ENLYFQG, SEQ ID NO:3) upstream of the cloned insert sequence. The amino acid sequence for the RORγt construct used in the Thermofluor assay is shown as SEQ ID NO:4.

ThermoFluor® experiments were carried out using instruments owned by Janssen Research and Discovery, L.L.C. through its acquisition of 3-Dimensional Pharmaceuticals, Inc. 1,8-ANS (Invitrogen) was used as a fluorescent dye. Protein and compound solutions are dispensed into black 384-well polypropylene PCR microplates (Abgene) and overlayed with silicone oil (1 µL Fluka, type DC 200) to prevent evaporation.

Bar-coded assay plates are robotically loaded onto a thermostatically controlled PCR-type thermal block and then heated at a typical ramp-rate of 1° C./min for all experiments. Fluorescence was measured by continuous illumination with UV light (Hamamatsu LC6) supplied via fiber optic and filtered through a band-pass filter (380-400 nm; >6 OD cutoff). Fluorescence emission of the entire 384-well plate was detected by measuring light intensity using a CCD camera (Sensys, Roper Scientific) filtered to detect 500±25 nm, resulting in simultaneous and independent readings of all 384 wells. Images were collected at each temperature, and the sum of the pixel intensity in a given area of the assay plate was recorded versus temperature. Reference wells contained RORγt without compounds, and the assay conditions were as follows:

0.065 mg/mL RORγt
60 µM 1,8-ANS
100 mM Hepes, pH 7.0
10 mM NaCl
2.5 mM GSH
0.002% Tween-20

Project compounds were arranged in a pre-dosed mother plate (Greiner Bio-one) wherein compounds are serially diluted in 100% DMSO by 1:2 from a high concentration of 10 mM over 12 columns within a series (column 12 is a reference well containing DMSO, no compound).

The compounds were robotically dispensed directly into assay plates (1×=46 mL) using a Hummingbird capillary liquid handling instrument (Digilab). Following compound dispense, protein and dye in buffer was added to achieve the final assay volume of 3 µL, followed by 1 µL of silicone oil.

The binding affinity was estimated as described previously (Matulis, D., Kranz, J. K., Salemme, F. R., and Todd, M. J. (2005) Thermodynamic stability of carbonic anhydrase: measurements of binding affinity and stoichiometry using ThermoFluor®. *Biochemistry* 44, 5258-66) using the following thermodynamic parameters of protein unfolding:

Reference RORγt $T_m$: 47.8° C.
$\Delta H_{(Tm)}$=115 kcal/mol
$\Delta C_{p(Tm)}$=3 kcal/mol Cell Based Biological Data
RORγt Reporter Assay A reporter assay was used to test functional activity of RORγt modulatory compounds on transcriptional activation driven by the RORγt LBD. Cells used in the assay were co-transfected with two constructs. The first construct, pBIND-RORγt LBD, contained the wild type human RORγt LBD fused to the DNA binding domain of the GAL4 protein. The second construct, pGL4.31 (Promega Cat no. C935A), contained multiple GAL4 responsive DNA elements upstream of firefly luciferase. To generate a background control, cells were similarly co-transfected with two constructs, but in the first construct the AF2 amino acid motif in the RORγt LBD was changed from LYKELF (SEQ ID NO:5) to LFKELF (SEQ ID NO:6). The AF2 mutation has been shown to prevent co-activator binding to the RORγt LBD, thus preventing transcription of firefly luciferase. The mutant construct was called pBIND-RORγt-AF2.

For the RORγt constructs used in the reporter assay, numbering for the nucleotide sequences was also based on the reference sequence for human RORγt, transcript variant 2, NCBI Accession: NM_001001523.1 (SEQ ID NO:1). For the wild type human RORγt LBD construct, pBIND-RORγt LBD, nucleotides 850-1635 (SEQ ID NO:2) coding for the wild type human RORγt LBD were cloned into EcoRI and NotI sites in the pBIND vector (Promega cat. No E245A). The pBIND vector contains the GAL4 DNA Binding Domain (GAL4 DBD) and the *renilla* luciferase gene under control of the SV40 promoter. *Renilla* luciferase expression serves as a control for transfection efficiency and cell viability. For the background control construct, pBIND-RORγt-AF2, the AF2 domain of RORγt LBD was mutated using the Quik Change II Site Directed Mutagenesis System (Stratagene Cat. No. 200519). The nucleotide sequence coding for the RORγt LBD sequence with the mutated AF2 domain is shown as SEQ ID NO:7. The amino acid sequences for the wild type RORγt LBD and RORγt LBD with the mutated AF2 domain are shown as SEQ ID NO:8 and SEQ ID NO:9, respectively.

The reporter assay was performed by transiently transfecting HEK293T cells with 5 ng of pBIND-RORγt LBD or pBIND-RORγt LBD-AF2 and 5 µg pGL4.31 (Promega Cat no. C935A) using Fugene 6 (Invitrogen Cat no. E2691) at a 1:6 ratio of DNA:Fugene 6 in a T-75 flask in which cells were at least 80% confluent. Twenty four hours after bulk transfection, cells were plated into 96-well plates at 50,000 cells/well in phenol-red free DMEM containing 5% Lipid Reduced FCS and Pen/Strep. Six hours after plating, cells were treated with compounds for 24 hours. Media was removed and cells were lysed with 50 μL 1× Glo Lysis Buffer (Promega). Dual Glo Luciferase Reagent (50 μL/well) was then added and firefly luciferase luminescence was read on an Envision after a ten minute incubation. Finally, Stop and Glo reagent (50 μL/well) was added and *renilla* luciferase luminescence was read on an Envision after a ten minute incubation. To calculate the effect of compounds on RORγt activity, the ratio of firefly to *renilla* luciferase was determined and plotted against compound concentration. Agonist compounds increase RORγt-driven luciferase expression, and antagonist or inverse agonist compounds decrease luciferase expression.

Human Th17 Assay

The human Th17 assay tests the effect of RORγt modulatory compounds on IL-17 production by CD4 T cells under conditions which favor Th17 differentiation. Total CD4+ T cells were isolated from the peripheral blood mononuclear cells (PBMC) of healthy donors using a CD4+ T cell isolation kit II, following the manufacturer's instructions (Miltenyi Biotec). Cells were resuspended in a medium of RPMI-1640 supplemented with 10% fetal bovine serum, penicillin, streptomycin, glutamate, and β-mercaptoethanol and were added to 96-well plates at $1.5 \times 10^5$ per 100 μL per well. 50 μL of compound at titrated concentrations in DMSO were added into each well at final DMSO concentration at 0.2%. Cells were incubated for 1 hour, then 50 μL of Th17 cell differentiation medium was added to each well. The final concentrations of antibodies and cytokines (R&D Systems) in differentiation medium were: $3 \times 10^6$/mL anti-CD3/CD28 beads (prepared using human T cell activation/expansion kit, Miltenyi Biotec), 10 μg/mL anti-IL4, 10 μg/mL anti-IFNγ, 10 ng/mL IL1β, 10 ng/mL IL23, 50 ng/mL IL6, 3 ng/mL TGFβ and 20 U/mL IL2. Cells were cultured at 37° C. and 5% $CO_2$ for 3 days. Supernatants were collected and the accumulated IL-17 in culture was measured by using MULTI-SPOT® Cytokine Plate following manufacture's instruction (Meso Scale Discovery). The plate was read using Sector Imager 6000, and IL-17 concentration was extrapolated from the standard curve. The IC50s were determined by GraphPad.

TABLE 1

| Example Number | ThermoFluor® Assay, Kd (μM) | RORγt reporter Assay, IC50 (μM) | RORγt reporter Assay, % inhibition @ 6 μM | Human Th17 Assay, $IC_{50}$ (μM) |
|---|---|---|---|---|
| 1 | 0.96 | 1 | 93 | ND |
| 2 | 0.076 | 0.13 | 100 | 0.62, ~0.7 |
| 3 | 1.5 | 2.1 | 84 | ND |
| 4 | 3.3 | 3.2 | 97 | ND |
| 5 | 21 | 0.38 | 79 | ND |
| 6 | 0.074 | 0.24 | 90 | ~6 |
| 7 | 5.3 | 1.2 | 83 | ND |
| 8 | 4.3 | 2.7 | 78 | ND |
| 9 | 7.1 | 6.1 | 70 | ND |
| 10 | 0.029 | 0.15 | 98 | 0.59 |
| 11 | 1.1 | 4.2 | 75 | ND |
| 12 | 0.022 | ~0.1 | 103 | 0.33 |
| 13 | 0.015 | 0.085 | 106 | 0.53 |
| 14 | 0.45 | 0.82 | 101 | ND |
| 15 | 0.19 | 0.6 | 106 | ND |
| 16 | 0.013 | 0.05 | 105 | 0.13 |
| 17 | 0.21 | 0.27 | 102 | 0.94 |
| 18 | 9.5 | >6 | 17 | ND |
| 19 | 9.1 | >6 | 13 | ND |
| 20 | 0.13 | 0.33 | 104 | 0.52 |
| 21 | 0.12 | 0.86 | 91 | ~0.9 |
| 22 | 0.075 | 0.22 | 104 | 0.44 |
| 23 | 0.23 | 0.8 | 89 | ND |
| 24 | 0.024 | 0.079 | 104 | 0.32, ~0.2 |
| 25 | 0.065 | 0.094, ~0.09 | 99 | 0.34 |
| 26 | 1.3 | 0.7 | 100 | 2.8 |
| 27 | 8.3 | 4.2 | 75 | ND |
| 28 | 0.23 | ~0.2 | 99 | 4, ~1 |
| 29 | 0.18 | 0.26 | 95 | 2.8 |
| 30 | 0.033 | ~0.3 | 93 | ~1 |
| 31 | 5.6 | 2.1 | 67 | ND |
| 32 | 0.33 | 0.094 | 97 | 0.86 |
| 33 | 3.3 | 2 | 78 | ND |
| 34 | 0.033 | 0.047, <0.05 | 100 | 0.14 |
| 35 | 0.33 | 0.34 | 97 | 0.77 |
| 36 | 2 | 0.29 | 98 | 1.6 |
| 37 | 0.2 | 0.19 | 91 | ~1 |
| 38 | 0.037 | 0.11, <0.05 | 98 | 0.27 |
| 39 | 2.5 | 1.6 | 86 | ND |
| 40 | 0.018 | 0.047, <0.05 | 100 | 0.056 |
| 41 | 0.023 | 0.11, ~0.1 | 98 | 0.2 |
| 42 | 1.4 | ~2 | 91 | ND |
| 43 | 1.6 | 1.1 | 99 | ND |
| 44 | 0.33 | 0.17 | 97 | 0.55 |
| 45 | 2.9 | 1.6 | 75 | ND |
| 46 | 4 | 2 | 94 | ND |
| 47 | 0.023 | 0.11 | 101 | 0.32 |
| 48a | 0.004 | 0.0075, <0.05, ~0.009 | 105 | 0.019 |
| 48b | 0.29 | 0.62 | 101 | ND |
| 48c | 0.0019 | 0.01 | 105 | ND |
| 49 | 0.038 | 0.14 | 103 | 0.41 |
| 50 | 0.005 | 0.007, ~0.009, <0.05 | 105 | 0.036 |

TABLE 1-continued

| Example Number | ThermoFluor ® Assay, Kd (μM) | RORγt reporter Assay, IC50 (μM) | RORγt reporter Assay, % inhibition @ 6 μM | Human Th17 Assay, $IC_{50}$ (μM) |
|---|---|---|---|---|
| 51 | 1.8 | ~4 | 75 | ND |
| 52 | 1.3 | ~3 | 80 | ND |
| 53 | 0.95 | ~2 | 61 | ND |
| 54 | 0.039 | 0.15 | 97 | 0.36 |
| 55 | 0.33 | 0.82 | 92 | ND |
| 56 | 0.04 | 0.17 | 91 | 0.24 |
| 57 | 0.055 | 0.16 | 90 | 0.28 |
| 58 | 2.2 | ~6 | 40 | ND |
| 59 | 4.4 | ~6 | 37 | ND |
| 60 | 1.3 | ~1 | 86 | ND |
| 61 | 1.8 | 2 | 80 | ND |
| 62 | 0.42 | 0.25 | 98 | 0.7 |
| 63 | 0.015 | 0.0086 | 106 | 0.063 |
| 64 | 0.5 | ~4 | 87 | ND |
| 65 | 0.2 | 0.16 | 103 | 0.19 |
| 66 | 0.0017 | 0.01 | 105 | 0.059 |
| 67 | 0.00063 | 0.013 | 104 | 0.027 |
| 68 | 0.0039 | 0.0058 | 103 | 0.048 |
| 69 | 0.3 | 0.15 | 99 | 0.61 |
| 70 | 0.77 | 0.047 | 95 | 0.63 |
| 71 | 0.31 | 0.082 | 94 | 0.69 |
| 72 | 8.5 | ~2 | 83 | ND |
| 73 | 0.018 | 0.36 | 88 | 1.2 |
| 74 | 0.005 | 0.025 | 92 | 0.11 |
| 75 | 0.42 | ~2 | 88 | ND |
| 76 | 0.0023 | 0.0049 | 100 | 0.04 |
| 77 | 1.1 | ~4 | 75 | ND |
| 78 | 0.27 | ~2 | 92 | ND |
| 79 | 0.51 | 1.2 | 73 | ND |
| 80 | 0.055 | 0.025 | 89 | 0.12 |
| 81 | 0.17 | 0.32 | 93 | ND |
| 82 | 0.56 | ~4 | 71 | ND |
| 83 | 4.2 | >6 | −3 | ND |
| 84 | 1.4 | 0.89 | 73 | 1.3 |
| 85 | 0.13 | 0.64 | 92 | ND |
| 86 | 0.0053 | 0.021 | 103 | 0.037 |
| 87 | 0.00011 | 0.0053 | 105 | ~0.002 |
| 88 | 0.0096 | 0.037 | 100 | 0.068 |
| 89 | 0.034 | 0.16 | 99 | 0.3 |
| 90 | 0.091 | 0.3 | 96 | 0.8 |
| 91 | 0.22 | 0.2 | 97 | ND |
| 92 | 0.044 | 0.12 | 100 | 0.15 |
| 93 | 1.2 | >6 | 49 | ND |
| 94 | 2.4 | >6 | 43 | ND |
| 95 | 0.023 | 0.5 | 98 | >6 |
| 96 | 0.029 | 0.37 | 98 | >6 |
| 97 | 0.053 | 0.58 | 100 | ND |
| 98 | 0.036 | 0.35 | 98 | 0.3 |
| 99 | 0.002 | 0.011, <0.05 | 100 | 0.026 |
| 100 | 0.35 | 0.16 | 95 | 0.15 |
| 101 | 2.5 | 0.64 | 94 | ND |
| 102 | 0.041 | 0.14 | 104 | 0.15 |
| 103 | 1.4 | 2.2 | 85 | ND |
| 104 | 0.03 | 0.039 | 100 | 0.043 |
| 105 | 0.039 | 0.15 | 101 | 0.19 |
| 106 | 1.3 | 2.3 | 75 | ND |
| 107 | 0.065 | 0.059 | 101 | 0.039 |
| 108 | 0.33 | 1.1 | 90 | ND |
| 109 | 0.031 | 0.18 | 100 | ND |
| 110 | 0.0064 | 0.082 | 101 | ND |
| 111 | 0.64 | 1.0, ~2 | 77 | ND |
| 112 | 0.12 | 0.38 | 100 | 0.48 |
| 113 | 1.8 | 0.086 | 101 | 0.25 |
| 114 | 0.61 | 0.74 | 104 | ND |
| 115 | 0.45 | 0.13 | 105 | 0.48 |
| 116 | 0.057 | 0.12 | 110 | 0.1 |
| 117 | 0.16 | 0.65 | 98 | ND |
| 118 | 0.36 | 0.37 | 94 | ND |
| 119a | 0.16 | 0.26 | 101 | 1.8 |
| 119b | 5.7 | ~6, >6 | 58 | 15, ~6 |
| 119c | 0.032 | 0.22 | 100 | 0.7 |
| 120 | 0.13 | 0.17 | 98 | 0.4 |
| 121 | 1.7 | ~2 | 72 | ND |
| 122 | 0.25 | 0.47 | 91 | 0.5 |
| 123 | 2.2 | ~6 | 70 | ND |
| 124 | 0.12 | 0.22 | 100 | 0.92 |
| 125 | 0.65 | 1 | 66 | ND |

TABLE 1-continued

| Example Number | ThermoFluor ® Assay, Kd (μM) | RORγt reporter Assay, IC50 (μM) | RORγt reporter Assay, % inhibition @ 6 μM | Human Th17 Assay, $IC_{50}$ (μM) |
|---|---|---|---|---|
| 126 | 0.021 | 0.22 | 97 | ND |
| 127 | 0.99 | 1.6 | 88 | ND |
| 128 | 0.097 | 0.14 | 98 | 0.24 |
| 129 | 0.0062 | 0.16 | 100 | 0.08 |
| 130 | 0.17 | 0.58 | 97 | ND |
| 131 | 0.026 | 0.091 | 100 | 0.21 |
| 132 | 0.016 | 0.048 | 103 | 0.13 |
| 133 | 1.5 | >6 | 41 | ND |
| 134 | 0.29 | 0.52 | 96 | 1.1 |
| 135 | 0.051 | 0.11 | 101 | 0.13 |
| 136 | 0.57 | ~2 | 97 | ND |
| 137a | 0.055 | 0.24 | 105 | 0.3 |
| 137b | 0.02 | 0.053 | 103 | 0.069 |
| 137c | 1.8 | ~2 | 81 | ND |
| 138a | 0.0095 | 0.11 | 97 | 0.23 |
| 138b | 0.0087 | 0.082 | 102 | 0.057 |
| 138c | 0.7 | 0.42 | 92 | 0.79 |
| 139 | 0.061 | 0.31 | 102 | 0.35 |
| 140 | 0.56 | 0.32 | 105 | 1.8 |
| 141 | 0.62 | 0.21 | 99 | 1.2 |
| 142 | 0.0076 | 0.092 | 105 | 0.14 |
| 143 | 0.0011 | 0.01 | 104 | 0.02 |
| 144 | 0.26 | 0.52 | 102 | ND |
| 145 | 2.1 | 0.25 | 93 | 1.2 |
| 146 | 0.077 | 0.13 | 112 | ND |
| 147 | 1.1 | 1.3 | 97 | ND |
| 148 | 0.00049 | 0.0055 | 101 | ND |
| 149 | 0.0035 | 0.02 | 106 | ND |
| 150 | 0.0083 | 0.04 | 98 | ND |
| 151 | 5 | 2.2 | 85 | ND |
| 152 | 0.77 | 0.35 | 97 | 1.2 |
| 153a | 0.071 | 0.23, ~0.4 | 96 | 0.48, ~0.7 |
| 153b | 0.27 | 0.69 | 93 | 1.6 |
| 153c | 0.019 | 0.14 | 96 | 0.25 |
| 153d | 3.5 | 1.5 | 75 | ND |
| 154 | 0.12 | 0.97 | 90 | 1.9 |
| 155 | 0.068 | 0.11 | 96 | ND |
| 156 | 0.057 | 0.32 | 98 | ND |
| 157 | 2.8 | ND | ND | ND |
| 158 | 2 | 0.49 | 79 | >6 |
| 159 | 0.0012 | 0.017 | 93 | 0.075 |
| 160 | 0.0061 | 0.12 | 97 | 0.69 |
| 161 | 0.078 | 0.17 | 104 | 0.36 |
| 162 | 0.2 | 0.91 | 92 | ND |
| 163 | 1.2 | 1.4 | 87 | ND |
| 164 | 0.0012 | 0.018 | 98 | 0.026 |
| 165 | 0.0024 | 0.048 | 98 | 0.097 |
| 166 | 0.036 | 0.18 | 103 | 0.15 |
| 167 | 0.4 | >6 | 62 | ND |
| 168 | 3.3 | ~6 | 71 | ND |
| 169a | 0.0081 | 0.072 | 96 | 0.066 |
| 169b | 0.003 | 0.0038 | 94 | 0.027 |
| 169c | 0.052 | 0.1 | 96 | 0.11 |
| 170 | 0.0042 | 0.035 | 98 | 0.096 |
| 171 | 0.14 | 0.32 | 85 | 0.3 |
| 172 | 0.0046 | 0.14 | 96 | ND |
| 173a | 0.017 | 0.049 | 103 | ND |
| 173b | 0.26 | 0.56 | 100 | ND |
| 173c | 0.0047 | 0.085 | 95 | 0.13 |
| 174a | ND | ND | ND | ND |
| 174b | 0.014 | 0.19 | 93 | 0.57 |
| 174c | 0.87 | 1.8 | 99 | ND |
| 175a | ND | ND | ND | ND |
| 175b | 8.2 | 2.1 | 76 | ND |
| 175c | 0.064 | 0.14 | 95 | 0.11 |
| 176a | ND | ND | ND | ND |
| 176b | 3.4 | 1.5 | 94 | ND |
| 176c | 0.068 | 0.32 | 95 | 0.31 |
| 177a | ND | ND | ND | ND |
| 177b | 0.022 | 0.4 | 83 | 0.2 |
| 177c | 1.3 | 0.36 | 98 | 2.5 |
| 178a | ND | ND | ND | ND |
| 178b | 21 | 0.61 | 72 | ND |
| 178c | 0.029 | 0.035 | 96 | 0.045 |
| 179a | ND | ND | ND | ND |
| 179b | 6.6 | 1.3 | 98 | ND |
| 179c | 0.063 | 0.48 | 96 | ~1 |

TABLE 1-continued

| Example Number | ThermoFluor ® Assay, Kd (μM) | RORγt reporter Assay, IC50 (μM) | RORγt reporter Assay, % inhibition @ 6 μM | Human Th17 Assay, IC$_{50}$ (μM) |
|---|---|---|---|---|
| 180a | ND | ND | ND | ND |
| 180b | 67 | 1.9, ~3 | 80 | ~5 |
| 180c | 0.093 | 0.17 | 99 | 0.097 |
| 181a | 0.016 | 0.14 | 101 | ND |
| 181b | 0.027 | 0.062 | 99 | 0.12 |
| 181c | 0.023 | 0.053 | 105 | 0.16 |
| 182 | 0.0015 | 0.015, ~0.0006 | 94 | 0.007 |
| 183a | 0.0093 | >6 | 26 | ND |
| 183b | 0.0037 | >6 | 34 | 1.2 |
| 183c | 0.19 | 0.36 | 73 | 0.87 |
| 184a | ND | ND | ND | ND |
| 184b | 2.5 | 3 | 99 | ND |
| 184c | 0.041 | 0.26 | 97 | 0.7 |
| 185a | 0.074 | 0.2 | 100 | ND |
| 185b | 0.029 | 0.13 | 103 | 0.096 |
| 185c | 0.76 | 0.81 | 91 | ND |
| 186a | 0.032 | 0.1 | 106 | ND |
| 186b | 0.18 | 0.35 | 103 | 0.57 |
| 186c | 0.006 | ~0.05 | 103 | 0.017 |
| 187 | 0.1 | 0.58, ~6 | 73 | >6 |
| 188 | 0.62 | 1.7 | 87 | ND |
| 189 | 0.94 | 1.9 | 92 | ND |
| 190 | ND | ND | ND | ND |
| 191 | ND | ND | ND | ND |
| 192 | ND | ND | ND | ND |

All data shown in Table 1 is either the value of one data point or the average of more than one data point. In cases where more than one value is shown in a table cell, values with qualifiers such as ~, > or < shown on the right side of the table cell could not be included in the averaging calculation for the value shown on the left side of the table cell.

ND—no data

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All documents cited herein are incorporated by reference.

What is claimed is:

1. The compounds of Formula I:

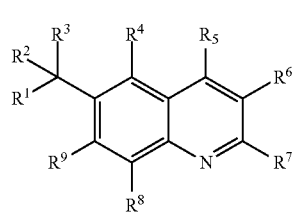

Formula I wherein:

R¹ is pyrrolyl, pyrazolyl, imidazolyl, triazolyl, thiazolyl, pyridyl, pyridyl N-oxide, pyrazinyl, pyrimidinyl, pyridazyl, piperidinyl, quinazolinyl, cinnolinyl, benzothiazolyl, indazolyl, tetrahydropyranyl, tetrahydrofuranyl, furanyl, phenyl, oxazolyl, isoxazolyl, thiophenyl, benzoxazolyl, benzimidazolyl, indolyl, thiadiazolyl, oxadiazolyl or quinolinyl; wherein said pyridyl, pyridyl N-oxide, pyrazinyl, pyrimidinyl, pyridazyl, piperidinyl, quinazolinyl, cinnolinyl, benzothiazolyl, indazolyl, imidazolyl, phenyl, thiophenyl, benzoxazolyl, benzimidazolyl, indolyl, quinolinyl, and pyrazolyl are optionally substituted with $C(O)C_{(1-4)}$ alkyl, $C(O)NH_2$, $C(O)NHC_{(1-2)}$alkyl, $C(O)N(C_{(1-2)}$ alkyl)$_2$, NHC(O)C$_{(1-4)}$alkyl, NHSO$_2$C$_{(1-4)}$alkyl, C$_{(1-4)}$ alkyl, CF$_3$, CH$_2$CF$_3$, Cl, F, —CN, OC$_{(1-4)}$alkyl, N(C$_{(1-4)}$alkyl)$_2$, —(CH$_2$)$_3$OCH$_3$, SC$_{(1-4)}$alkyl, OH, CO$_2$H, CO$_2$C$_{(1-4)}$alkyl, C(O)CF$_3$, SO$_2$CF$_3$, OCF$_3$, OCHF$_2$, SO$_2$CH$_3$, SO$_2$NH$_2$, SO$_2$NHC$_{(1-2)}$alkyl, SO$_2$N (C$_{(1-2)}$alkyl)$_2$, C(O)NHSO$_2$CH$_3$, or OCH$_2$OCH$_3$; and optionally substituted with up to two additional substituents independently selected from the group consisting of Cl, C$_{(1-2)}$alkyl, SCH$_3$, OC$_{(1-2)}$alkyl, CF$_3$, —CN, and F; and wherein said triazolyl, oxazolyl, isoxazolyl, pyrrolyl, and thiazolyl are optionally substituted with up to two substituents independently selected from the group consisting of SO$_2$CH$_3$, SO$_2$NH$_2$, C(O)NH$_2$, —CN, OC$_{(1-2)}$alkyl, (CH$_2$)$_{(2-3)}$OCH$_3$, SCH$_3$, CF$_3$, F, Cl, and C$_{(1-2)}$alkyl; and said thiadiazolyl and oxadiazolyl are optionally substituted with C$_{(1-2)}$alkyl; and said pyridyl, pyridyl-N-oxide, pyrimidinyl, pyridazyl, and pyrazinyl are optionally substituted with up to three additional substituents independently selected from the group consisting of C(O)NHC$_{(1-2)}$alkyl, C(O)N(C$_{(1-2)}$alkyl)$_2$, NHC(O)C$_{(1-4)}$alkyl, NHSO$_2$C$_{(1-4)}$alkyl, C(O)CF$_3$, SO$_2$CF$_3$, SO$_2$NHC$_{(1-2)}$alkyl, SO$_2$N(C$_{(1-2)}$alkyl)$_2$, C(O)NHSO$_2$CH$_3$, SO$_2$CH$_3$, SO$_2$NH$_2$, C(O)NH$_2$, —CN, OC$_{(1-4)}$alkyl, (CH$_2$)$_{(2-3)}$OCH$_3$, SC$_{(1-4)}$alkyl, CF$_3$, F, Cl, and C$_{(1-4)}$alkyl;

R$^2$ is triazolyl, pyridyl, pyridyl-N-oxide, pyrazolyl, pyrimidinyl, oxazolyl, isoxazolyl, N-acetyl piperidinyl, 1-H-piperidinyl, N-Boc-piperidinyl, N—C$_{(1-3)}$alkyl-piperidinyl, thiazolyl, pyridazyl, pyrazinyl, 1-(3-methoxypropyl)-imidazolyl, thiadiazolyl, oxadiazolyl, or imidazolyl; wherein said imidazolyl is optionally substituted with up to three additional substituents independently selected from the group consisting of C$_{(1-2)}$alkyl, SCH$_3$, OC$_{(1-2)}$alkyl, CF$_3$, —CN, F, and Cl; and said pyridyl, pyridyl-N-oxide, pyrimidinyl, pyridazyl, and pyrazinyl, are optionally substituted with up to three additional substituents independently selected from the group consisting of SO$_2$CH$_3$, SO$_2$NH$_2$, C(O)NH$_2$, —CN, OC$_{(1-2)}$alkyl, (CH$_2$)$_{(2-3)}$OCH$_3$, SCH$_3$, CF$_3$, F, Cl, or C$_{(1-2)}$alkyl; and said triazolyl, thiazolyl, oxazolyl and isoxazolyl are optionally substituted with up to two substituents independently selected from the group consisting of SO$_2$CH$_3$, SO$_2$NH$_2$, C(O)NH$_2$, —CN, OC$_{(1-2)}$alkyl, (CH$_2$)$_{(2-3)}$OCH$_3$, SCH$_3$, CF$_3$, F, Cl, and C$_{(1-2)}$alkyl; and said thiadiazolyl and oxadiazolyl are optionally substituted with C$_{(1-2)}$alkyl; and said pyrazolyl is optionally substituted with up to three CH$_3$ groups;

R$^3$ is H, OH, OCH$_3$, or NH$_2$;

R$^4$ is H, or F;

R$^5$ is H, Cl, —CN, CF$_3$, SC$_{(1-4)}$alkyl, OC$_{(1-4)}$alkyl, OH, C$_{(1-4)}$alkyl, N(CH$_3$)OCH$_3$, NH(C$_{(1-4)}$alkyl), N(C$_{(1-4)}$ alkyl)$_2$, or 4-hydroxy-piperidinyl;

R$^6$ is pyridyl, pyrimidinyl, pyridazyl, pyrazinyl, thiazolyl, isothiazolyl, furanyl, thiophenyl, oxazolyl, isoxazolyl, imidazolyl, pyrazolyl, pyrrolyl, triazolyl, oxadiazolyl, thiadiazolyl, or phenyl, any of which is optionally substituted with up to two substituents independently selected from the group consisting of piperidinyl, pyrrolidinyl, azetidinyl, pyrazolyl, triazolyl, imidazolyl, —CN, C$_{(1-4)}$alkyl, OC$_{(1-4)}$alkyl, C(O)C$_{(1-4)}$alkyl, CO$_2$H, CO$_2$C$_{(1-4)}$alkyl, NH$_2$, NHC$_{(1-2)}$alkyl, N(C$_{(1-2)}$ alkyl)$_2$, SONH$_2$, SON(CH$_3$)2, SO$_2$NH$_2$, SO$_2$NHC$_{(1-2)}$ alkyl, SO$_2$N(C$_{(1-2)}$alkyl)$_2$, SCH$_3$, OCH$_2$CF$_3$, SO$_2$CH$_3$, CF$_3$, Cl, F, OH, and OCF$_3$;

R$^7$ is H, Cl, —CN, C$_{(1-4)}$alkyl, OC$_{(1-4)}$alkylCF$_3$, OCF$_3$, OCHF$_2$, OCH$_2$CH$_2$OC$_{(1-4)}$alkyl, CF$_3$, SCH$_3$, C$_{(1-4)}$ alkylNA$^1$A$^2$, CH$_2$OC$_{(2-3)}$alkylNA$^1$A$^2$, NA$^1$A$^2$, C(O) NA$^1$A$^2$, CH$_2$NHC$_{(2-3)}$alkylNA$^1$A$^2$, CH$_2$N(CH$_3$)C$_{(2-3)}$ alkylNA$^1$A$^2$, NHC$_{(2-3)}$alkylNA$^1$A$^2$, N(CH$_3$)C$_{(2-4)}$ alkylNA$^1$A$^2$, OC$_{(2-4)}$alkylNA$^1$A$^2$, OC$_{(1-4)}$alkyl, OCH$_2$-(1-methyl)-imidazol-2-yl, phenyl, thiophenyl, furyl, pyrazolyl, imidazolyl, pyridyl, pyridazyl, pyrazinyl, or pyrimidinyl; wherein said phenyl, thiophenyl, furyl, pyrazolyl, imidazolyl, pyridyl, pyridazyl, pyrazinyl, and pyrimidinyl are optionally substituted with up to three substituents independently selected from the group consisting of F, Cl, CH$_3$, CF$_3$, and OCH$_3$;

A$^1$ is H, or C$_{(1-4)}$alkyl;

A$^2$ is H, C$_{(1-4)}$alkyl, C$_{(1-4)}$alkylOC$_{(1-4)}$alkyl, C$_{(1-4)}$alkylOH, C(O)C$_{(1-4)}$alkyl, or OC$_{(1-4)}$alkyl; or A$^1$ and A$^2$ may be taken together with their attached nitrogen to form a ring selected from the group consisting of:

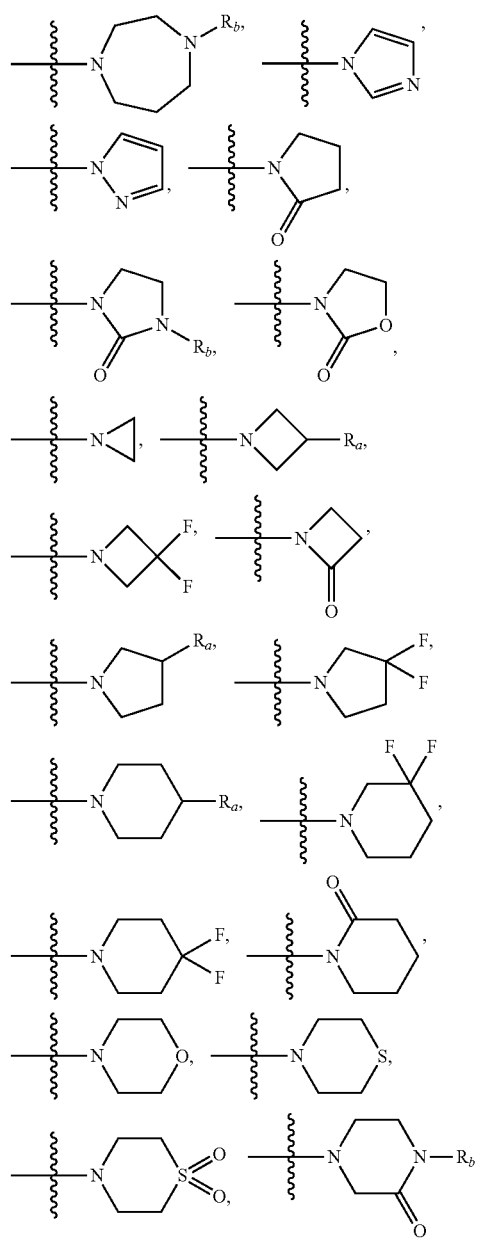

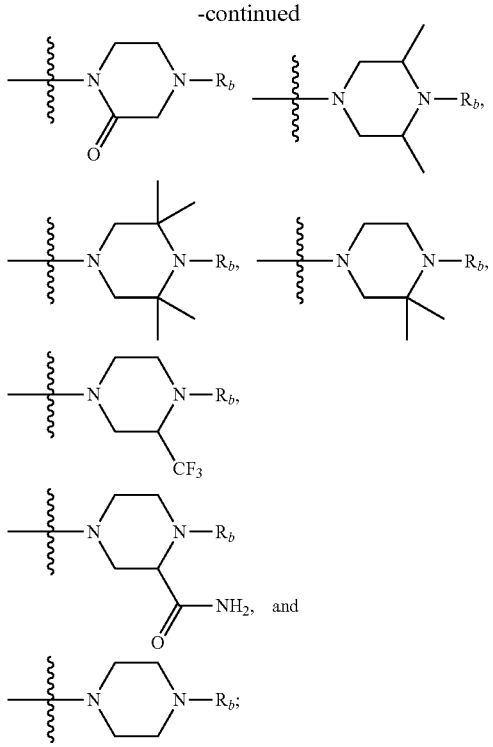

$R^a$ is H, $OC_{(1-4)}$alkyl, $CH_2OH$, $NH(CH_3)$, $N(CH_3)_2$, $NH_2$, $CH_3$, F, $CF_3$, $SO_2CH_3$, or OH;

$R_b$ is H, $CO_2C(CH_3)_3$, $C_{(1-4)}$alkyl, $C(O)C_{(1-4)}$alkyl, $SO_2C_{(1-4)}$alkyl, $CH_2CH_2CF_3$, $CH_2CF_3$, $CH_2$-cyclopropyl, phenyl, $CH_2$-phenyl, or $C_{(3-6)}$cycloalkyl;

$R^8$ is H, $C_{(1-3)}$alkyl, $OC_{(1-3)}$alkyl, $CF_3$, $NH_2$, $NHCH_3$, —CN, or F;

$R^9$ is H, or F;

and pharmaceutically acceptable salts thereof;

provided that (4-chloro-3-phenylquinolin-6-yl)(1-methyl-1H-imidazol-5-yl)(pyridin-3-yl)methanamine, (4-chlorophenyl)(2,4-dichloro-3-(2-chlorophenyl)quinolin-6-yl)(1-methyl-1H-imidazol-2-yl)methanol, (2,4-dichloro-3-phenylquinolin-6-yl)(oxazol-2-yl)(phenyl)methanol, (4-chlorophenyl)(2,4-dichloro-3-phenylquinolin-6-yl)(2-methyl-4-(trifluoromethyl)thiazol-5-yl)methanol, (4-chloro-3-phenylquinolin-6-yl)(1-methyl-1H-imidazol-5-yl)(pyridin-4-yl)methanamine, (4-chlorophenyl)(3-(2,6-dichlorophenyl)quinolin-6-yl)(1-methyl-1H-imidazol-5-yl)methanol, (4-chloro-3-phenylquinolin-6-yl)(2-(dimethylamino)pyridin-4-yl)(1-methyl-1H-imidazol-2-yl)methanol, 4-(2-((4-chloro-6-((4-chlorophenyl)(hydroxy)(1-methyl-1H-imidazol-5-yl)methyl)-3-phenylquinolin-2-yl)oxy)ethyl)thiomorpholine 1,1-dioxide, 1-(2-((4-chloro-6-((4-chlorophenyl)(hydroxy)(1-methyl-1H-imidazol-5-yl)methyl)-3-phenylquinolin-2-yl)oxy)ethyl)pyrrolidin-2-one, (2-chloro-4-(dimethylamino)-3-phenylquinolin-6-yl)(pyridin-2-yl)(pyridin-4-yl)methanol, (4-chloro-3-phenylquinolin-6-yl)(2-fluoropyridin-4-yl)(1-methyl-1H-imidazol-2-yl)methanol, (4-chloro-2-(1-methyl-1H-pyrazol-4-yl)-3-phenylquinolin-6-yl)(4-chlorophenyl)(pyridin-3-yl)methanol, (2,4-dichloro-3-phenylquinolin-6-yl)di(pyridin-2-yl)methanol, 6-((3-chlorophenyl)(hydroxy)(2-(trifluoromethyl)pyridin-4-yl)methyl)-3-phenylquinoline-2-carbonitrile, (2,4-dichloro-8-methyl-3-phenylquinolin-6-yl)(1-methyl-1H-imidazol-4-yl)(6-methylpyridin-3-yl)methanol, (4-methoxy-3-phenyl-2-(trifluoromethyl)quinolin-6-yl)(1-methyl-1H-imidazol-5-yl)(pyridin-2-yl)methanol, (4-chlorophenyl)(2,4-dichloro-3-(2-chlorophenyl)quinolin-6-yl)(1-methyl-1H-imidazol-2-yl)methanol and (2,4-dichloro-3-phenylquinolin-6-yl)(phenyl)(pyridin-2-yl)methanol are excluded from the claim.

2. The compounds of claim 1, wherein:

$R^1$ is pyrrolyl, pyrazolyl, imidazolyl, triazolyl, thiazolyl, pyridyl, pyridyl N-oxide, pyrazinyl, pyrimidinyl, pyridazyl, piperidinyl, tetrahydropyranyl, phenyl, oxazolyl, isoxazolyl, thiophenyl, benzoxazolyl, or quinolinyl; wherein said piperidinyl, imidazolyl, phenyl, thiophenyl, benzoxazolyl, pyrazolyl, pyridyl, pyridyl N-oxide, pyrazinyl, pyrimidinyl, pyridazyl, or quinolinyl are optionally substituted with $C(O)C_{(1-4)}$alkyl, $C(O)NH_2$, $C_{(1-4)}$alkyl, $CF_3$, $CH_2CF_3$, Cl, F, —CN, $OC_{(1-4)}$alkyl, $N(C_{(1-4)}alkyl)_2$, —$(CH_2)_3OCH_3$, $SC_{(1-4)}$alkyl, OH, $CO_2H$, $CO_2C_{(1-4)}$alkyl, $OCF_3$, $OCHF_2$, $SO_2CH_3$, $SO_2NH_2$, or $OCH_2OCH_3$; and optionally substituted with up to two additional substituents independently selected from the group consisting of Cl, $C_{(1-2)}$alkyl, $SCH_3$, $OC_{(1-2)}$alkyl, $CF_3$, —CN, and F; and wherein said triazolyl, oxazolyl, isoxazolyl, pyrrolyl, and thiazolyl are optionally substituted with up to two substituents independently selected from the group consisting of $SO_2CH_3$, $SO_2NH_2$, $C(O)NH_2$, —CN, $OC_{(1-2)}$alkyl, $(CH_2)_{(2-3)}OCH_3$, $SCH_3$, $CF_3$, F, Cl, and $C_{(1-2)}$alkyl; and said pyridyl, and pyridyl-N-oxide are optionally substituted with up to three additional substituents independently selected from the group consisting of $SO_2CH_3$, $SO_2NH_2$, $C(O)NH_2$, —CN, $OC_{(1-4)}$alkyl, $(CH_2)_{(2-3)}OCH_3$, $SC_{(1-4)}$alkyl, $CF_3$, F, Cl, and $C_{(1-4)}$alkyl;

$R^2$ is 1-methyl triazolyl, pyridyl, pyridyl-N-oxide, 1-methyl pyrazolyl, pyrimidinyl, oxazolyl, isoxazolyl, N-acetyl piperidinyl, 1-H-piperidinyl, N-Boc-piperidinyl, N—$C_{(1-3)}$alkyl-piperidinyl, thiazolyl, pyridazyl, pyrazinyl, 1-(3-methoxypropyl)-imidazolyl, or 1-$C_{(1-2)}$alkyl imidazolyl; wherein said 1-$C_{(1-2)}$alkyl imidazolyl is optionally substituted with up to two additional substituents independently selected from the group consisting of $C_{(1-2)}$alkyl, $SCH_3$, $OC_{(1-2)}$alkyl, $CF_3$, —CN, F, and Cl; and said pyridyl, and pyridyl-N-oxide are optionally substituted with up to three additional substituents independently selected from the group consisting of $SO_2CH_3$, $SO_2NH_2$, $C(O)NH_2$, —CN, $OC_{(1-2)}$alkyl, $(CH_2)_{(2-3)}OCH_3$, $SCH_3$, $CF_3$, F, Cl, and $C_{(1-2)}$alkyl; and said thiazolyl, oxazolyl and isoxazolyl are optionally substituted with up to two substituents independently selected from the group consisting of $SO_2CH_3$, $SO_2NH_2$, $C(O)NH_2$, —CN, $OC_{(1-2)}$alkyl, $(CH_2)_{(2-3)}OCH_3$, $SCH_3$, $CF_3$, F, Cl, and $C_{(1-2)}$alkyl; and said 1-methyl pyrazolyl is optionally substituted with up to two additional $CH_3$ groups;

$R^6$ is pyridyl, pyrimidinyl, pyridazyl, pyrazinyl, or phenyl, any of which is optionally substituted with —CN, $CH_3$, $OC_{(1-4)}$alkyl, $N(C_{(1-2)}alkyl)_2$, $SONH_2$, $SON(CH_3)2$, $OCH_2CF_3$, $SO_2CH_3$, $CF_3$, Cl, F, or $OCF_3$;

$R^7$ is H, Cl, —CN, $C_{(1-4)}$alkyl, $OC_{(1-4)}$alkylCF$_3$, $OCH_2CH_2OC_{(1-4)}$alkyl, $CF_3$, $SCH_3$, $CH_2NA^1A^2$, $CH_2OC_{(2-3)}$alkylNA$^1$A$^2$, $NA^1A^2$, $C(O)NA^1A^2$, $N(CH_3)C_{(2-4)}$alkylNA$^1$A$^2$, $OC_{(2-4)}$alkylNA$^1$A$^2$, $OC_{(1-4)}$alkyl, $OCH_2$-(1-methyl)-imidazol-2-yl, furyl, pyrazolyl, imidazolyl, pyridyl, pyridazyl, pyrazinyl, or pyrimidinyl; wherein said imidazolyl or pyrazolyl is optionally substituted with one $CH_3$ group;

$A^1$ is H, or $C_{(1-4)}$alkyl;
$A^2$ is H, $C_{(1-4)}$alkyl, $C_{(1-4)}$alkylO$C_{(1-4)}$alkyl, $C_{(1-4)}$alkylOH, C(O)$C_{(1-4)}$alkyl, or O$C_{(1-4)}$alkyl; or $A^1$ and $A^2$ may be taken together with their attached nitrogen to form a ring selected from the group consisting of:

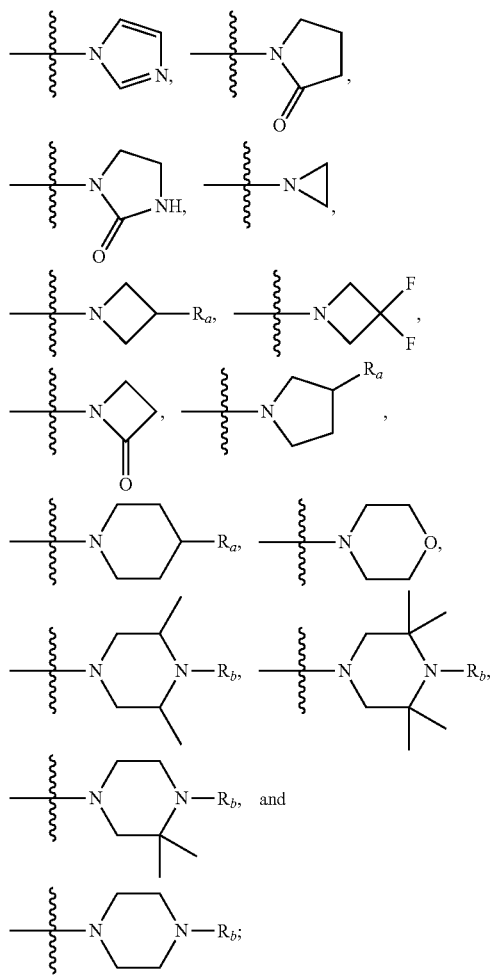

$R_a$ is H, O$C_{(1-4)}$alkyl, CH$_2$OH, NH(CH$_3$), N(CH$_3$)$_2$, NH$_2$, CH$_3$, F, or OH;
$R_b$ is H, CO$_2$C(CH$_3$)$_3$, $C_{(1-4)}$alkyl, C(O)$C_{(1-4)}$alkyl, SO$_2$$C_{(1-4)}$alkyl, CH$_2$CH$_2$CF$_3$, CH$_2$CF$_3$, CH$_2$-cyclopropyl, phenyl, CH$_2$-phenyl, or $C_{(3-6)}$cycloalkyl;
$R^8$ is H, CH$_3$, OCH$_3$, or F;
and pharmaceutically acceptable salts thereof.

3. The compounds of claim 2, wherein:
$R^1$ is pyrrolyl, pyrazolyl, imidazolyl, triazolyl, thiazolyl, pyridyl, pyridyl N-oxide, pyrazinyl, pyrimidinyl, pyridazyl, piperidinyl, tetrahydropyranyl, phenyl, oxazolyl, isoxazolyl, thiophenyl, benzoxazolyl, or quinolinyl; wherein said piperidinyl, pyridyl, pyridyl N-oxide, imidazolyl, phenyl, thiophenyl, benzoxazolyl, and pyrazolyl are optionally substituted with C(O)$C_{(1-4)}$alkyl, C(O)NH$_2$, $C_{(1-4)}$alkyl, CF$_3$, CH$_2$CF$_3$, Cl, F, —CN, O$C_{(1-4)}$alkyl, N(C$_{(1-4)}$alkyl)$_2$, —(CH$_2$)$_3$OCH$_3$, S$C_{(1-4)}$alkyl, OH, CO$_2$H, CO$_2$$C_{(1-4)}$alkyl, OCF$_3$, OCHF$_2$, SO$_2$CH$_3$, SO$_2$NH$_2$, or OCH$_2$OCH$_3$; and optionally substituted with up to two additional substituents independently selected from the group consisting of Cl, OCH$_3$, and CH$_3$; and wherein said triazolyl, oxazolyl, isoxazolyl, and thiazolyl are optionally substituted with one or two CH$_3$ groups;

$R^2$ is 1-methyl triazolyl, pyridyl, pyridyl-N-oxide, 1-methyl pyrazolyl, pyrimidinyl, pyrazinyl, oxazolyl, isoxazolyl, N-acetyl piperidinyl, 1-H-piperidinyl, N-Boc-piperidinyl, N—$C_{(1-2)}$alkyl-piperidinyl, thiazolyl, pyridazyl, 1-(3-methoxypropyl)-imidazolyl, or 1-$C_{(1-2)}$alkyl imidazolyl; wherein said 1-$C_{(1-2)}$alkyl imidazolyl is optionally substituted with up to two additional CH$_3$ groups, or one substituent selected from the group consisting of SCH$_3$, and Cl; and said pyridyl, and pyridyl-N-oxide are optionally substituted with up to two subsituents independently selected from the group consisting of SO$_2$CH$_3$, SO$_2$NH$_2$, C(O)NH$_2$, —CN, OCH$_3$, CF$_3$, Cl, and CH$_3$; and said thiazolyl, oxazolyl and isoxazolyl are optionally substituted with up to two CH$_3$ groups; and said 1-methyl pyrazolyl is optionally substituted with up to two additional CH$_3$ groups;

$R^6$ is pyridyl or phenyl, either of which is optionally substituted with —CN, CH$_3$, OCH$_3$, N(CH$_3$)$_2$, SONH$_2$, SO$_2$CH$_3$, CF$_3$, Cl, F, or OCF$_3$;

$R^7$ is H, Cl, —CN, $C_{(1-4)}$alkyl, O$C_{(1-4)}$alkylCF$_3$, OCH$_2$CH$_2$O$C_{(1-4)}$alkyl, CF$_3$, SCH$_3$, NA$^1$A$^2$, C(O)NA$^1$A$^2$, N(CH$_3$)$C_{(2-4)}$alkylNA$^1$A$^2$, O$C_{(2-4)}$alkylNA$^1$A$^2$, O$C_{(1-4)}$alkyl, OCH$_2$-(1-methyl)-imidazol-2-yl, imidazolyl, furyl, pyrazolyl, pyridyl, or pyrimidinyl; wherein said imidazolyl or pyrazolyl is optionally substituted with one CH$_3$ group;

$A^{1is}$ H, or $C_{(1-4)}$alkyl;
$A^2$ is H, $C_{(1-4)}$alkyl, $C_{(1-4)}$alkylO$C_{(1-4)}$alkyl, $C_{(1-4)}$alkylOH, C(O)$C_{(1-4)}$alkyl, or O$C_{(1-4)}$alkyl; or $A^1$ and $A^2$ may be taken together with their attached nitrogen to form a ring selected from the group consisting of:

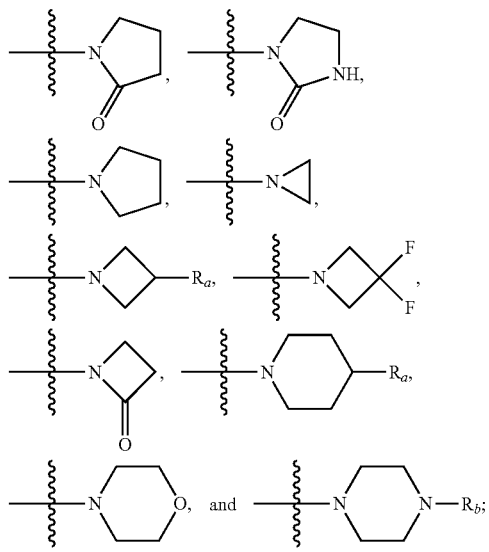

$R_a$ is H, F, O$C_{(1-4)}$alkyl, or OH;
$R_b$ is $C_{(1-4)}$alkyl, C(O)CH$_3$, or phenyl;
and pharmaceutically acceptable salts thereof;
provided that (4-chloro-3-phenylquinolin-6-yl)(1-methyl-1H-imidazol-5-yl)(pyridin-3-yl)methanamine, (4-chlorophenyl)(2,4-dichloro-3-(2-chlorophenyl)quinolin-6-yl)(1-methyl-1H-imidazol-2-yl)methanol, (2,4-dichloro-3-phenylquinolin-6-yl)(oxazol-2-yl)(phenyl)methanol, (4-chloro-3-phenylquinolin-6-yl)(1-methyl-1H-imidazol-5-yl)(pyridin-4-yl)methanamine, (4-chlorophenyl)(3-(2,6- dichlorophenyl)quinolin-6-yl)(1-methyl-1H-imidazol-5-yl) methanol, (4-chloro-3-phenylquinolin-6-yl)(2-(dimethylamino)pyridin-4-yl)(1-methyl-1H-imidazol-2-yl) methanol, 4-(2-((4-chloro-6-((4-chlorophenyl)(hydroxy)(1-methyl-1H-imidazol-5-yl)methyl)-3-phenylquinolin-2-yl)oxy)ethyl)thiomorpholine 1,1-dioxide, 1-(2-((4-chloro-6-((4-chlorophenyl)(hydroxy)(1-methyl-1H-imidazol-5-yl) methyl)-3-phenylquinolin-2-yl)oxy)ethyl)pyrrolidin-2-one, (2-chloro-4-(dimethylamino)-3-phenylquinolin-6-yl)(pyridin-2-yl)(pyridin-4-yl)methanol, (4-chloro-3-phenylquinolin-6-yl)(2-fluoropyridin-4-yl)(1-methyl-1H-imidazol-2-yl) methanol, (4-chloro-2-(1-methyl-1H-pyrazol-4-yl)-3-phenylquinolin-6-yl)(4-chlorophenyl)(pyridin-3-yl) methanol, (2,4-dichloro-3-phenylquinolin-6-yl)di(pyridin-2-yl)methanol, 6-((3-chlorophenyl)(hydroxy)(2-(trifluoromethyl)pyridin-4-yl)methyl)-3-phenylquinoline-2-carbonitrile, (2,4-dichloro-8-methyl-3-phenylquinolin-6-yl)(1-methyl-1H-imidazol-4-yl)(6-methylpyridin-3-yl) methanol, (4-methoxy-3-phenyl-2-(trifluoromethyl) quinolin-6-yl)(1-methyl-1H-imidazol-5-yl)(pyridin-2-yl) methanol, (4-chlorophenyl)(2,4-dichloro-3-(2-chlorophenyl)quinolin-6-yl)(1-methyl-1H-imidazol-2-yl) methanol and (2,4-dichloro-3-phenylquinolin-6-yl)(phenyl) (pyridin-2-yl)methanol are excluded from the claim.

4. The compounds of claim 3, wherein:

$R^1$ is pyrrolyl, pyrazolyl, imidazolyl, triazolyl, thiazolyl, pyridyl, pyridyl N-oxide, pyrazinyl, pyrimidinyl, pyridazyl, piperidinyl, tetrahydropyranyl, phenyl, oxazolyl, isoxazolyl, thiophenyl, benzoxazolyl, or quinolinyl; wherein said piperidinyl, pyridyl, pyridyl N-oxide, imidazolyl, phenyl, thiophenyl, benzoxazolyl, and pyrazolyl are optionally substituted with $SO_2CH_3$, $C(O)CH_3$, $C(O)NH_2$, $CH_3$, $CH_2CH_3$, $CF_3$, Cl, F, —CN, $OCH_3$, $N(CH_3)_2$, —$(CH_2)_3OCH_3$, $SCH_3$, OH, $CO_2H$, $CO_2C(CH_3)_3$, or $OCH_2OCH_3$; and optionally substituted with up to two additional substituents independently selected from the group consisting of Cl, $OCH_3$, and $CH_3$; and wherein said triazolyl, oxazolyl, isoxazolyl, and thiazolyl are optionally substituted with one or two $CH_3$ groups;

$R^2$ is 1-methyl-1,2,3-triazolyl, pyridyl, pyridyl-N-oxide, 1-methyl pyrazol-4-yl, pyrimidin-5-yl, pyridazyl, pyrazin-2-yl, isoxazolyl, N-acetyl piperidinyl, 1-H-piperidinyl, N-Boc-piperidinyl, N—$C_{(1-2)}$alkyl-piperidinyl, thiazol-5-yl, 1-(3-methoxypropyl)-imidazol-5-yl, or 1-$C_{(1-2)}$alkyl imidazol-5-yl; wherein said 1-$C_{(1-2)}$ alkyl imidazol-5-yl is optionally substituted with up to two additional $CH_3$ groups, or one substituent selected from the group consisting of $SCH_3$, and Cl; and said pyridyl, and pyridyl-N-oxide are optionally substituted with up to two substituents independently selected from the group consisting of $C(O)NH_2$, —CN, $OCH_3$, $CF_3$, Cl, and $CH_3$; and said thiazol-5-yl, and said isoxazolyl are optionally substituted with up to two $CH_3$ groups; and said 1-methyl pyrazol-4-yl is optionally substituted with up to two additional $CH_3$ groups;

$R^5$ is H, Cl, —CN, $CF_3$, $SCH_3$, $OC_{(1-3)}$alkyl, OH, $C_{(1-4)}$ alkyl, $N(CH_3)OCH_3$, $NH(C_{(1-2)}alkyl)$, $N(C_{(1-2)}alkyl)_2$, or 4-hydroxy-piperidinyl;

$R^6$ is pyridyl or phenyl, either of which is optionally substituted with Cl, F, $CF_3$, $SO_2CH_3$, —CN, or $OCF_3$;

$R^7$ is H, Cl, —CN, $C_{(1-4)}$alkyl, $OCH_2CF_3$, $OCH_2CH_2OCH_3$, $CF_3$, $SCH_3$, $NA^1A^2$, $C(O)NHCH_3$, $N(CH_3)CH_2CH_2NA^1A^2$, $OCH_2CH_2NA^1A^2$, $OC_{(1-3)}$ alkyl, $OCH_2$-(1-methyl)-imidazol-2-yl, imidazol-2-yl, fur-2-yl, pyrazol-4-yl, pyrid-3-yl, or pyrimidin-5-yl;

wherein said imidazolyl or pyrazolyl is optionally substituted with one $CH_3$ group;

$A^1$ is H, or $C_{(1-4)}$alkyl;

$A^2$ is H, $C_{(1-4)}$alkyl, $C_{(1-4)}$alkylO$C_{(1-4)}$alkyl, $C_{(1-4)}$alkylOH, $C(O)C_{(1-2)}$alkyl, $OCH_3$; or $A^1$ and $A^2$ may be taken together with their attached nitrogen to form a ring selected from the group consisting of:

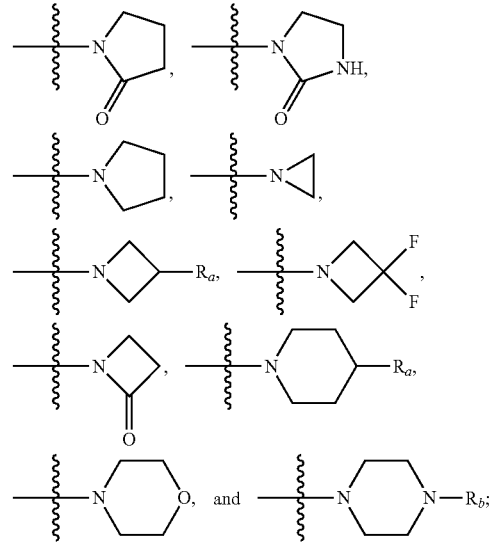

$R_a$ is H, F, $OCH_3$, or OH;

$R_b$ is $CH_3$, or phenyl;

and pharmaceutically acceptable salts thereof;

provided that (4-chloro-3-phenylquinolin-6-yl)(1-methyl-1H-imidazol-5-yl)(pyridin-3-yl)methanamine, (4-chlorophenyl)(2,4-dichloro-3-(2-chlorophenyl)quinolin-6-yl)(1-methyl-1H-imidazol-2-yl)methanol, (4-chloro-3-phenylquinolin-6-yl)(1-methyl-1H-imidazol-5-yl)(pyridin-4-yl)methanamine, (4-chlorophenyl)(3-(2,6-dichlorophenyl) quinolin-6-yl)(1-methyl-1H-imidazol-5-yl)methanol, (4-chloro-3-phenylquinolin-6-yl)(2-(dimethylamino)pyridin-4-yl)(1-methyl-1H-imidazol-2-yl)methanol, 4-(2-((4-chloro-6-((4-chlorophenyl)(hydroxy)(1-methyl-1H-imidazol-5-yl)methyl)-3-phenylquinolin-2-yl)oxy)ethyl) thiomorpholine 1,1-dioxide, 1-(2-((4-chloro-6-((4-chlorophenyl)(hydroxy)(1-methyl-1H-imidazol-5-yl) methyl)-3-phenylquinolin-2-yl)oxy)ethyl)pyrrolidin-2-one, (2-chloro-4-(dimethylamino)-3-phenylquinolin-6-yl)(pyridin-2-yl)(pyridin-4-yl)methanol, (4-chloro-3-phenylquinolin-6-yl)(2-fluoropyridin-4-yl)(1-methyl-1H-imidazol-2-yl) methanol, (4-chloro-2-(1-methyl-1H-pyrazol-4-yl)-3-phenylquinolin-6-yl)(4-chlorophenyl)(pyridin-3-yl) methanol, (2,4-dichloro-3-phenylquinolin-6-yl)di(pyridin-2-yl)methanol, 6-((3-chlorophenyl)(hydroxy)(2-(trifluoromethyl)pyridin-4-yl)methyl)-3-phenylquinoline-2-carbonitrile, (2,4-dichloro-8-methyl-3-phenylquinolin-6-yl) (1-methyl-1H-imidazol-4-yl)(6-methylpyridin-3-yl) methanol, (4-methoxy-3-phenyl-2-(trifluoromethyl) quinolin-6-yl)(1-methyl-1H-imidazol-5-yl)(pyridin-2-yl) methanol, (4-chlorophenyl)(2,4-dichloro-3-(2-chlorophenyl)quinolin-6-yl)(1-methyl-1H-imidazol-2-yl) methanol and (2,4-dichloro-3-phenylquinolin-6-yl)(phenyl) (pyridin-2-yl)methanol are excluded from the claim.

5. The compounds of claim 4 wherein:

$R^1$ is pyrrolyl, triazolyl, imidazolyl, thiazolyl, pyridyl, pyridyl N-oxide, pyrazinyl, pyrimidinyl, pyridazyl, piperidinyl, phenyl, isoxazolyl, thiophenyl, benzoxazolyl, pyrazolyl or quinolinyl; wherein said piperidinyl, pyridyl, imidazolyl, phenyl, thiophenyl, benzoxazolyl, and pyrazolyl are optionally substituted with C(O)CH$_3$, C(O)NH$_2$, CH$_3$, CH$_2$CH$_3$, CF$_3$, Cl, F, —CN, OCH$_3$, N(CH$_3$)$_2$, —(CH$_2$)$_3$OCH$_3$, SCH$_3$, OH, CO$_2$H, CO$_2$C(CH$_3$)$_3$, or OCH$_2$OCH$_3$; and optionally substituted with up to two additional CH$_3$ groups, or one additional chloro group; and wherein said triazolyl, isoxazolyl, and thiazolyl are optionally substituted with one or two CH$_3$ groups;

$R^2$ is 1-methyl-1,2,3-triazolyl, pyridyl, pyridyl-N-oxide, 1-methyl pyrazol-4-yl, pyrimidin-5-yl, pyridazyl, pyrazin-2-yl, isoxazol-4-yl, isoxazol-5-yl, N-acetyl piperidin-3-yl, N-acetyl piperidin-4-yl, 1-H-piperidin-3-yl, 1-H-piperidin-4-yl, N-Boc-piperidin-3-yl, N-Boc-piperidin-4-yl, N—C$_{(1-2)}$alkyl-piperidin-3-yl, N—C$_{(1-2)}$alkyl-piperidin-4-yl, thiazol-5-yl, 1-(3-methoxypropyl)-imidazol-5-yl, or 1-C$_{(1-2)}$alkyl imidazol-5-yl; wherein said 1-C$_{(1-2)}$alkyl imidazol-5-yl is optionally substituted with up to two additional CH$_3$ groups, or one substituent selected from the group consisting of SCH$_3$, and Cl; and said pyridyl is optionally substituted with up to two subsitutents selected from the group consisting of C(O)NH$_2$, —CN, OCH$_3$, CF$_3$, Cl, and CH$_3$; and said thiazol-5-yl, isoxazol-4-yl, and isoxazol-5-yl are optionally substituted with up to two CH$_3$ groups; and said 1-methyl pyrazol-4-yl is optionally substituted with up to two additional CH$_3$ groups;

$R^6$ is pyridyl or phenyl, wherein said phenyl is optionally substituted with Cl, F, CF$_3$, SO$_2$CH$_3$, or OCF$_3$;

$R^7$ is H, Cl, —CN, C$_{(1-3)}$alkyl, OCH$_2$CF$_3$, OCH$_2$CH$_2$OCH$_3$, CF$_3$, SCH$_3$, NA$^1$A$^2$, N(CH$_3$)CH$_2$CH$_2$N(CH$_3$)$_2$, OCH$_2$CH$_2$NH$_2$, OCH$_2$CH$_2$—N-aziridinyl, OCH$_2$CH$_2$NHC(O)CH$_3$, OC$_{(1-3)}$alkyl, OCH$_2$-(1-methyl)-imidazol-2-yl, pyrid-3-yl, or pyrimidin-5-yl;

$A^1$ is H, or C$_{(1-4)}$alkyl;

$A^2$ is H, C$_{(1-4)}$alkyl, C$_{(1-4)}$alkylOC$_{(1-4)}$alkyl, C$_{(1-4)}$alkylOH, C(O)C$_{(1-2)}$alkyl, or OCH$_3$; or A and A$^2$ may be taken together with their attached nitrogen to form a ring selected from the group consisting of:

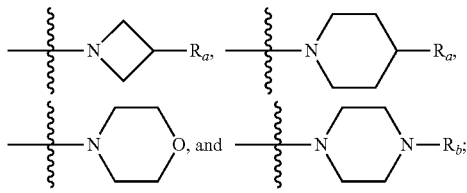

$R_a$ is H, OCH$_3$, or OH;
$R_b$ is CH$_3$, or phenyl;
$R^8$ is H, CH$_3$, or F;

and pharmaceutically acceptable salts thereof;

provided that (4-chloro-3-phenylquinolin-6-yl)(1-methyl-1H-imidazol-5-yl)(pyridin-3-yl)methanamine, (4-chlorophenyl)(2,4-dichloro-3-(2-chlorophenyl)quinolin-6-yl)(1-methyl-1H-imidazol-2-yl)methanol, (4-chloro-3-phenylquinolin-6-yl)(1-methyl-1H-imidazol-5-yl)(pyridin-4-yl)methanamine, (4-chlorophenyl)(3-(2,6-dichlorophenyl)quinolin-6-yl)(1-methyl-1H-imidazol-5-yl)methanol, (4-chloro-3-phenylquinolin-6-yl)(2-(dimethylamino)pyridin-4-yl)(1-methyl-1H-imidazol-2-yl)methanol, (2-chloro-4-(dimethylamino)-3-phenylquinolin-6-yl)(pyridin-2-yl) (pyridin-4-yl)methanol, (4-chloro-3-phenylquinolin-6-yl)(2-fluoropyridin-4-yl)(1-methyl-1H-imidazol-2-yl)methanol, (2,4-dichloro-3-phenylquinolin-6-yl)di(pyridin-2-yl)methanol, 6-((3-chlorophenyl)(hydroxy)(2-(trifluoromethyl)pyridin-4-yl)methyl)-3-phenylquinoline-2-carbonitrile, (2,4-dichloro-8-methyl-3-phenylquinolin-6-yl)(1-methyl-1H-imidazol-4-yl)(6-methylpyridin-3-yl)methanol, (4-methoxy-3-phenyl-2-(trifluoromethyl)quinolin-6-yl)(1-methyl-1H-imidazol-5-yl)(pyridin-2-yl)methanol, (4-chlorophenyl)(2,4-dichloro-3-(2-chlorophenyl)quinolin-6-yl)(1-methyl-1H-imidazol-2-yl)methanol and (2,4-dichloro-3-phenylquinolin-6-yl)(phenyl)(pyridin-2-yl)methanol are excluded from the claim.

6. The compounds of claim 5, wherein:

$R^1$ is pyrrolyl, triazolyl, imidazolyl, thiazolyl, pyridyl, pyrazinyl, pyrimidinyl, pyridazyl, piperidinyl, phenyl, isoxazolyl, thiophenyl, benzoxazolyl, or quinolinyl; wherein said piperidinyl, pyridyl, phenyl, thiophenyl, and benzoxazolyl, are optionally substituted with C(O) CH$_3$, CH$_3$, CF$_3$, Cl, F, OCH$_3$, N(CH$_3$)$_2$, OH, or OCH$_2$OCH$_3$; and optionally substituted with CH$_3$; and wherein said triazolyl, imidazolyl, isoxazolyl, and thiazolyl are optionally substituted with one or two CH$_3$ groups;

$R^5$ is H, Cl, —CN, CF$_3$, OC$_{(1-3)}$alkyl, OH, C$_{(1-4)}$alkyl, NH(CH$_3$), N(C$_{(1-2)}$alkyl)$_2$, or 4-hydroxy-piperidinyl;

$R^6$ is phenyl, or pyridyl, wherein said phenyl is optionally substituted with Cl, F, or OCF$_3$;

$R^7$ is H, Cl, —CN, C$_{(1-2)}$alkyl, CF$_3$, NA$^1$A$^2$, N(CH$_3$)CH$_2$CH$_2$N(CH$_3$)$_2$, OC$_{(1-3)}$alkyl, pyrid-3-yl, or pyrimidin-5-yl;

$A^1$ is C$_{(1-2)}$alkyl;

$A^2$ is C$_{(1-4)}$alkyl, or CH$_2$CH$_2$OCH$_3$; or A$^1$ and A$^2$ may be taken together with their attached nitrogen to form a ring selected from the group consisting of:

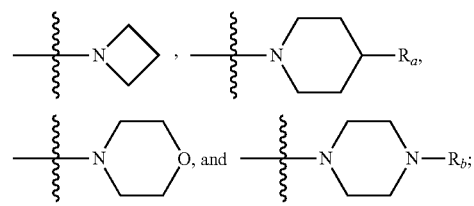

$R_a$ is OCH$_3$, or OH;
$R_b$ is CH$_3$, or phenyl;

and pharmaceutically acceptable salts thereof.

7. A compound of claim 1 selected from the group consisting of:

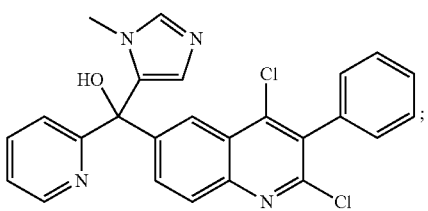

261
-continued
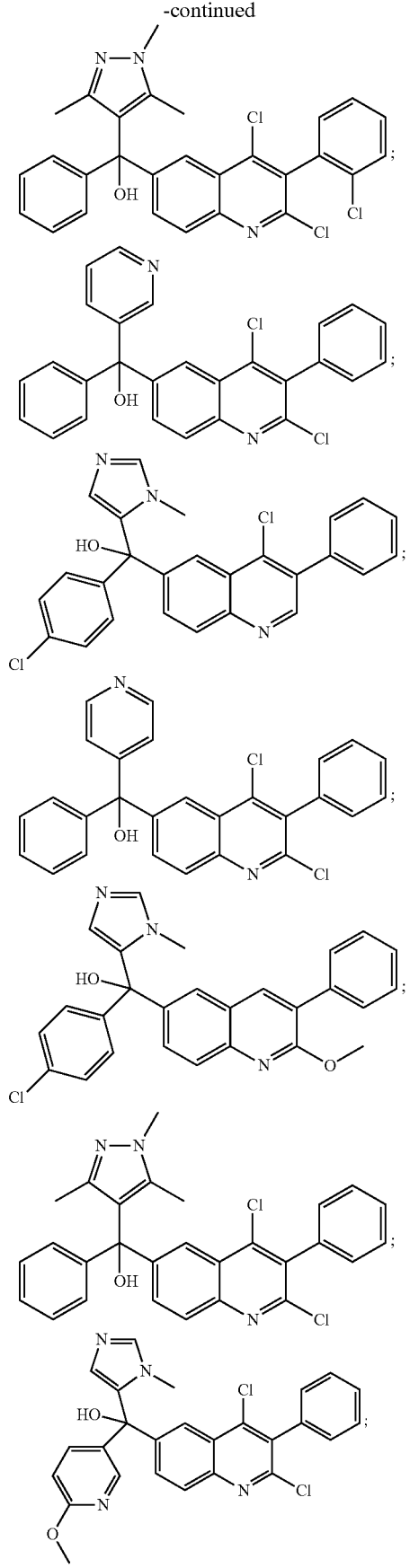
262
-continued
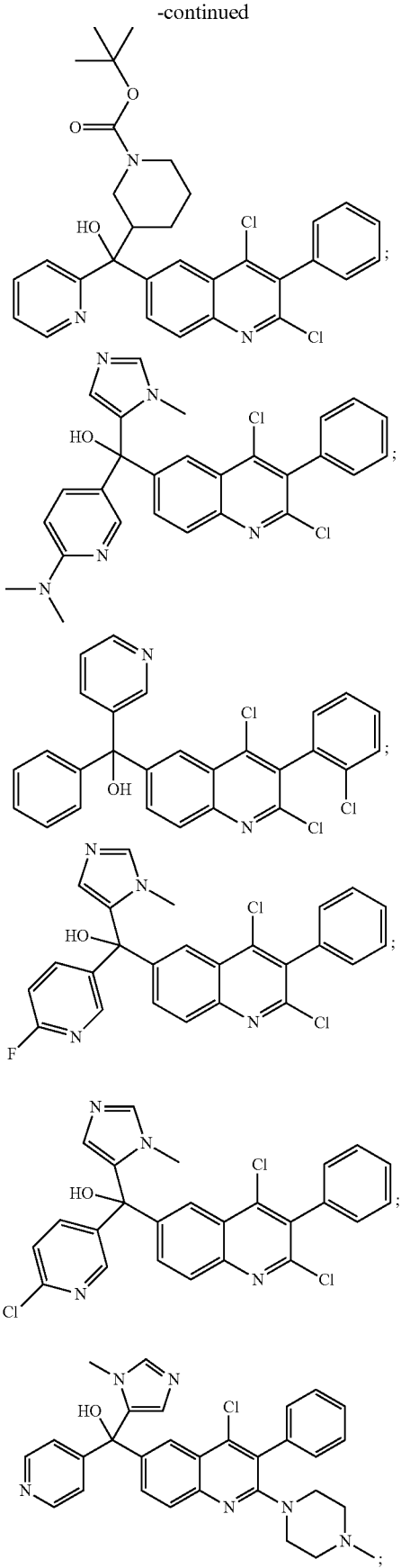

-continued
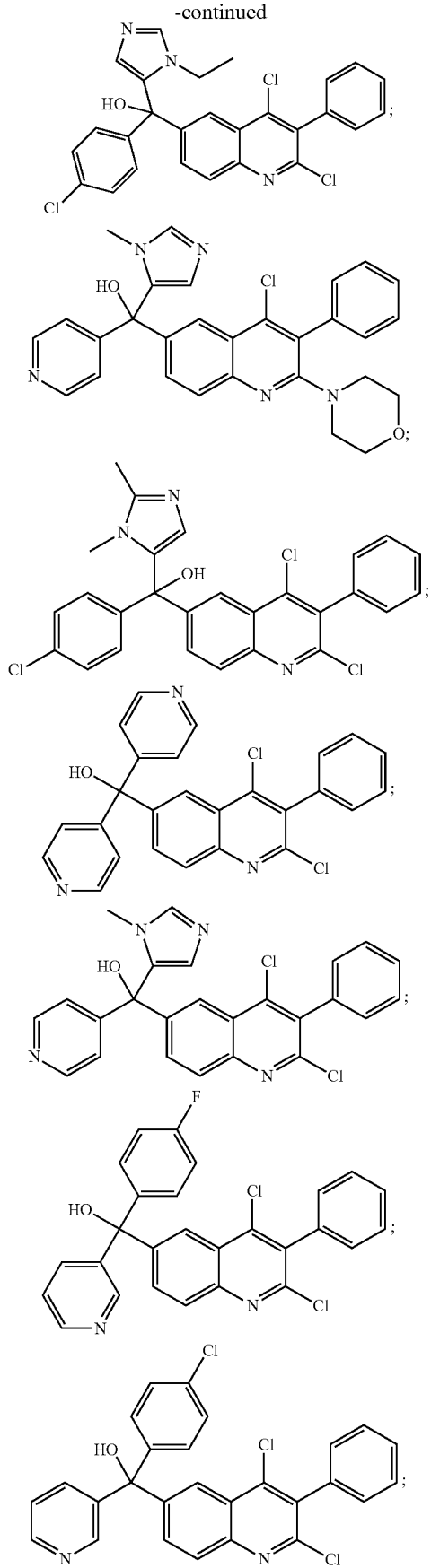
-continued
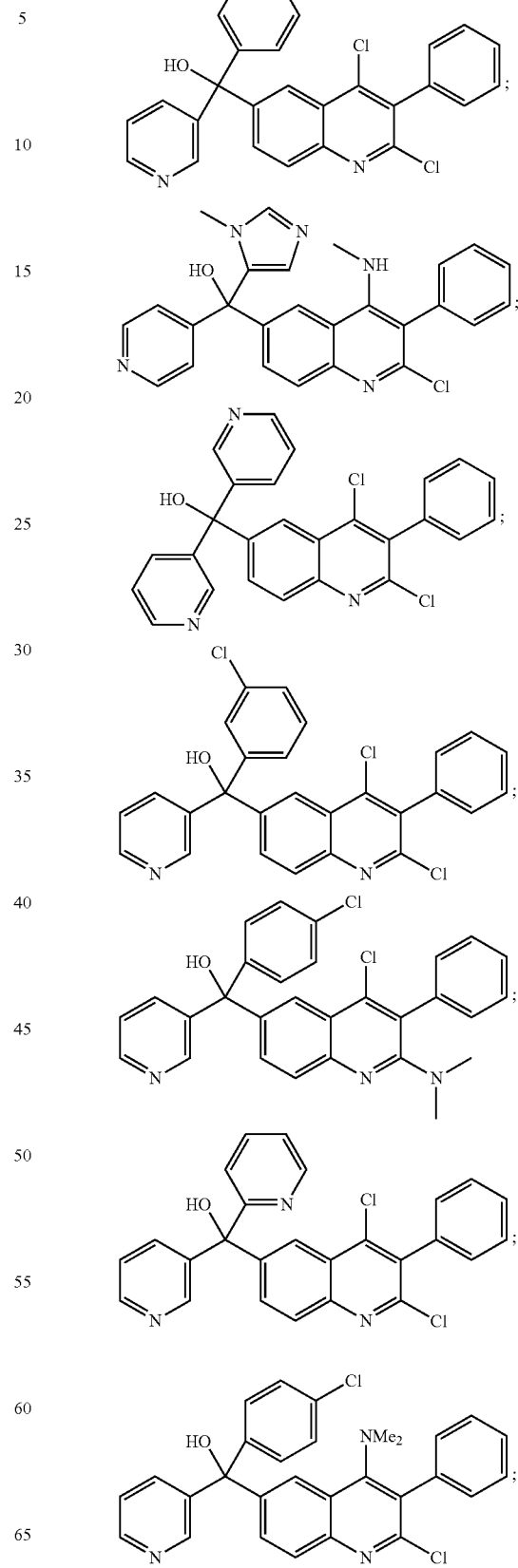

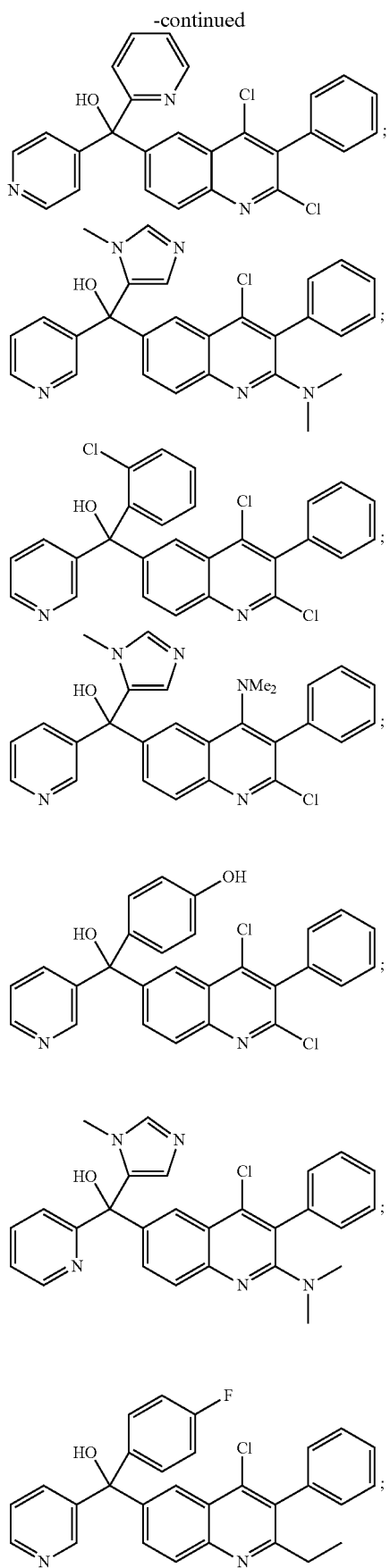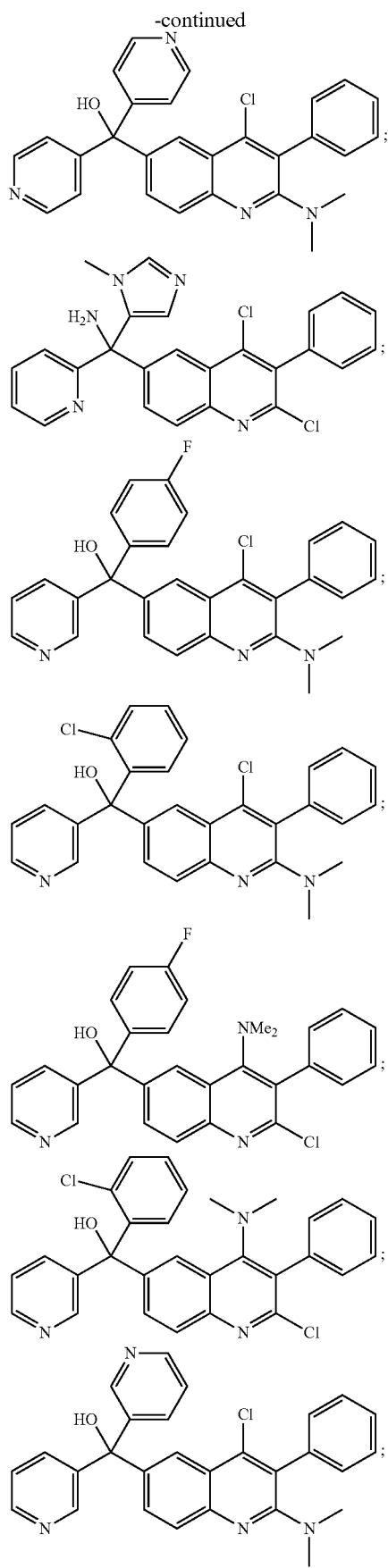

-continued
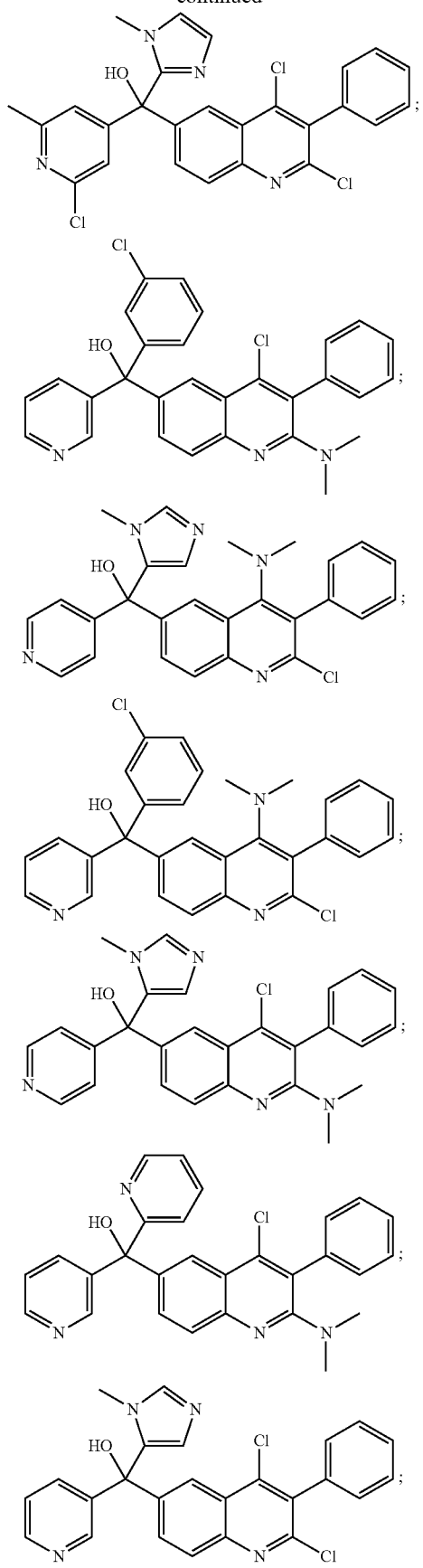
-continued
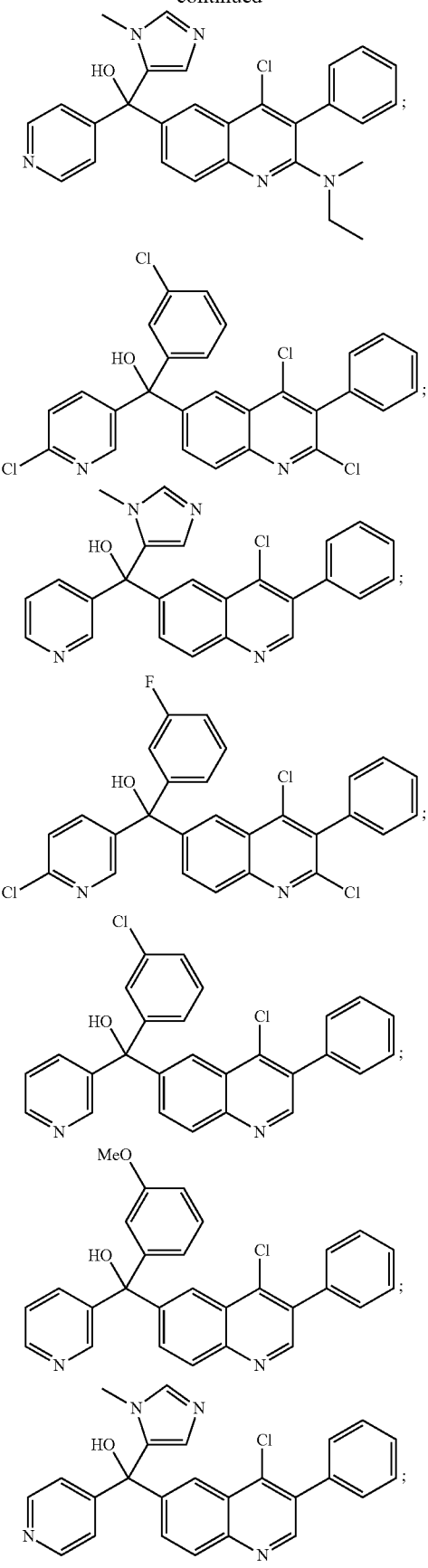

269
-continued
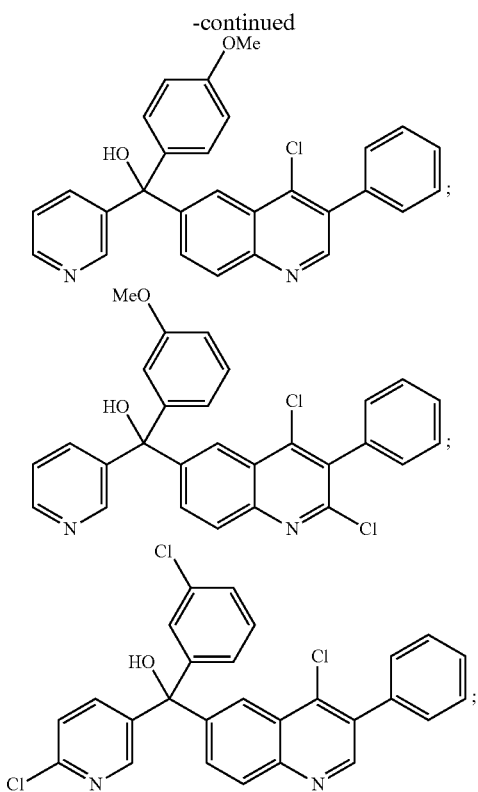
270
-continued
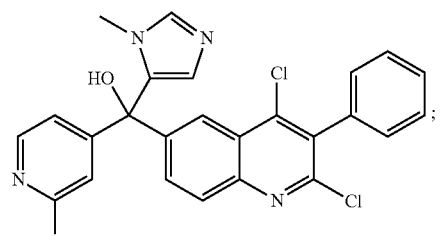
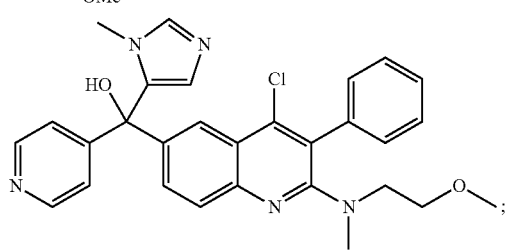
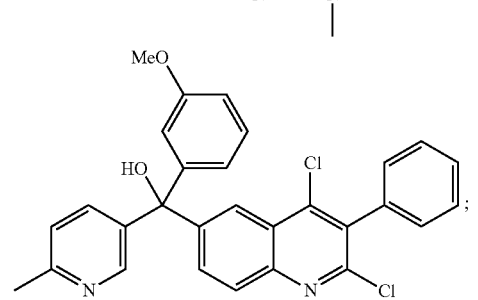
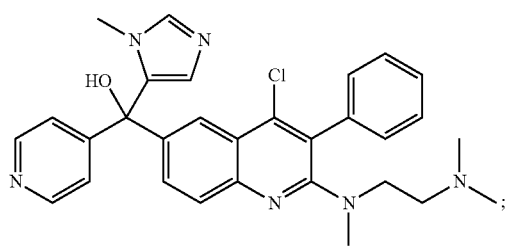
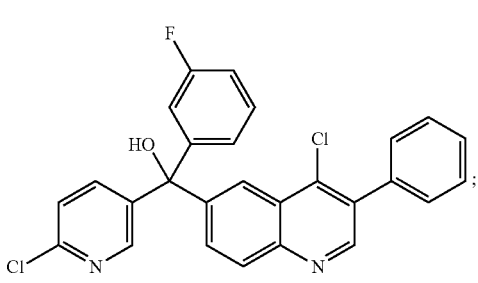
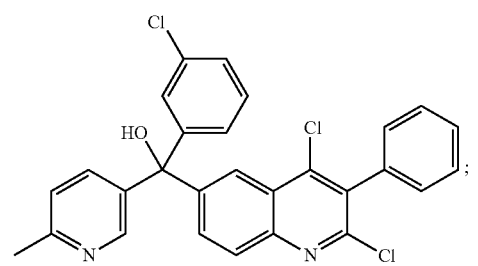
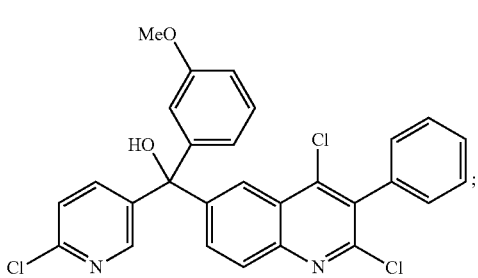

-continued
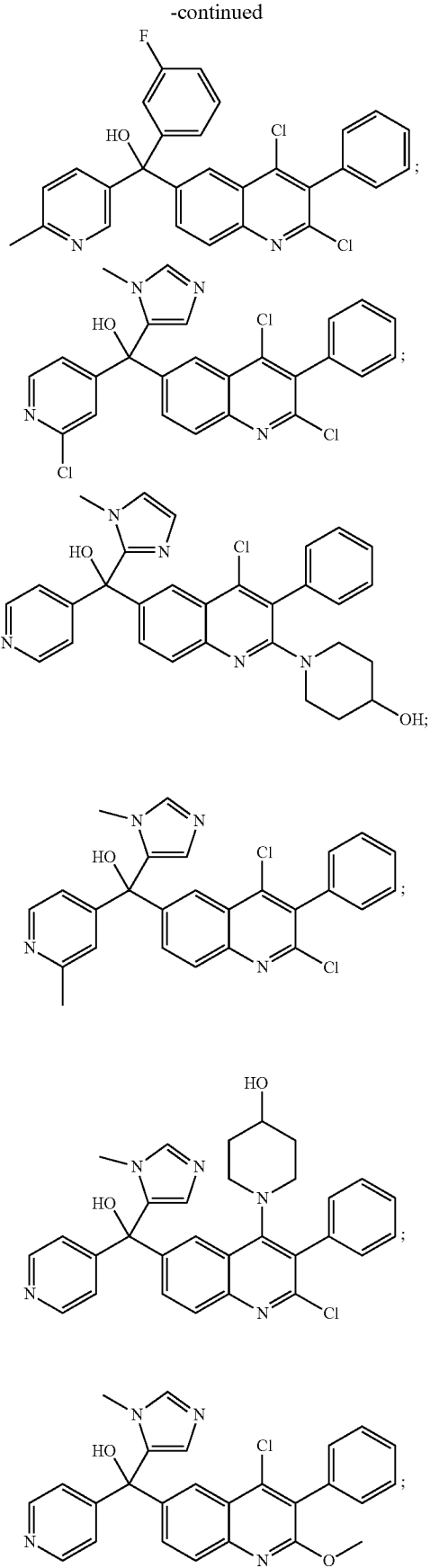
-continued
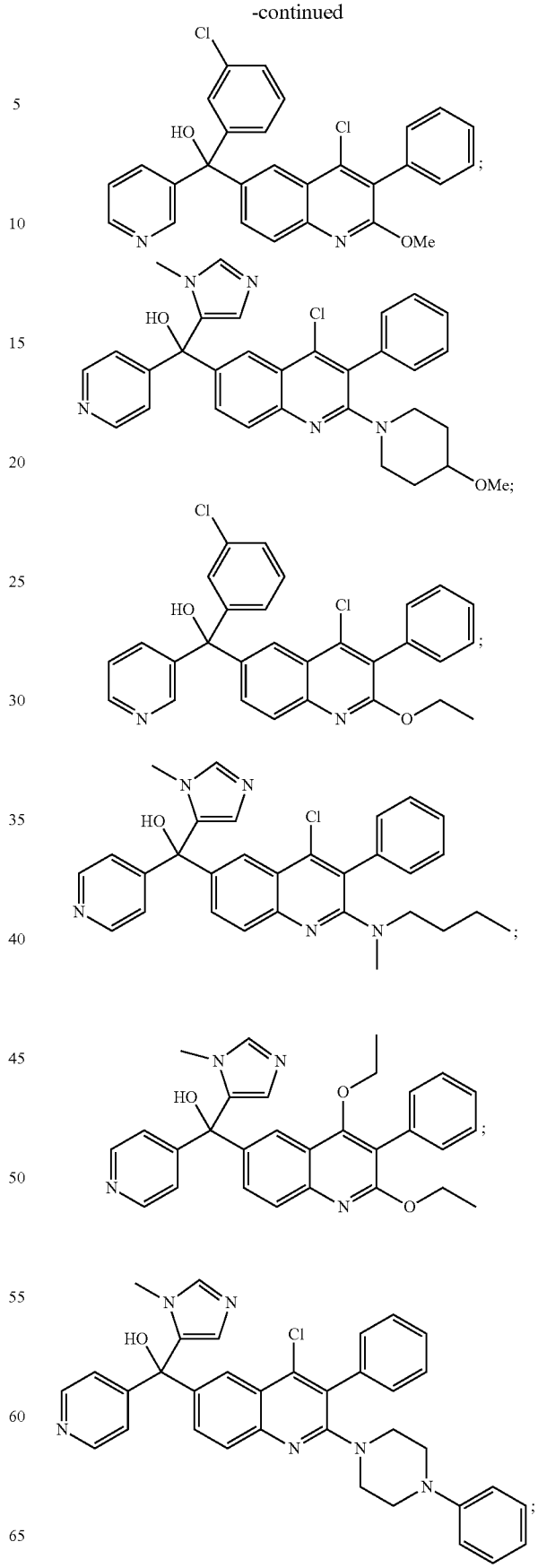

273
-continued
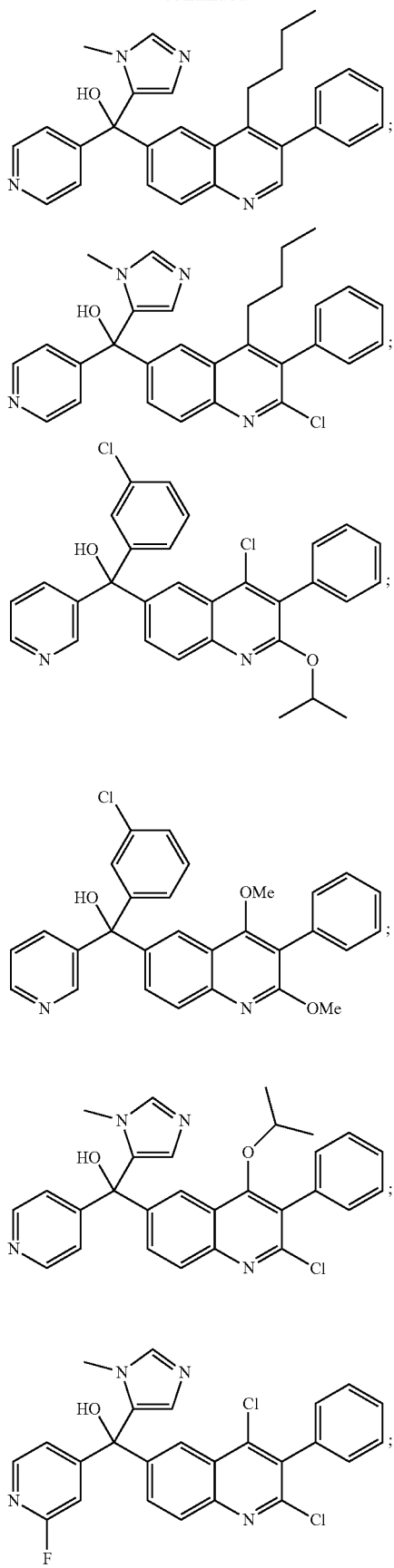
274
-continued
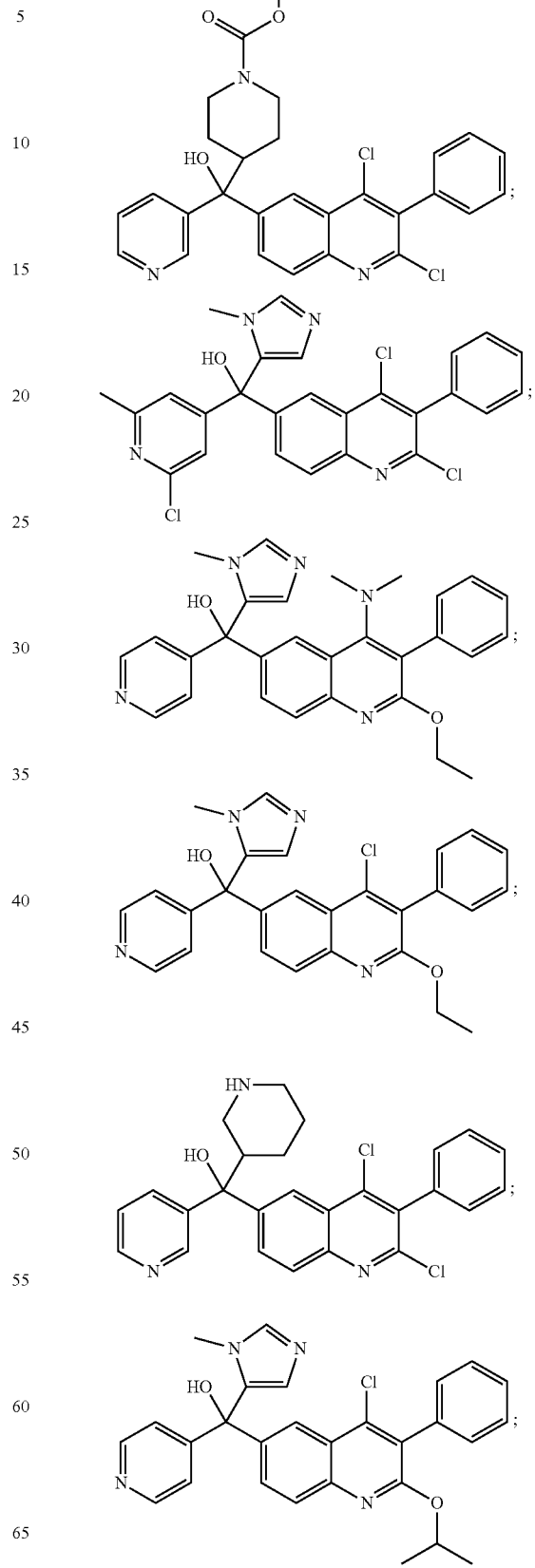

275
-continued
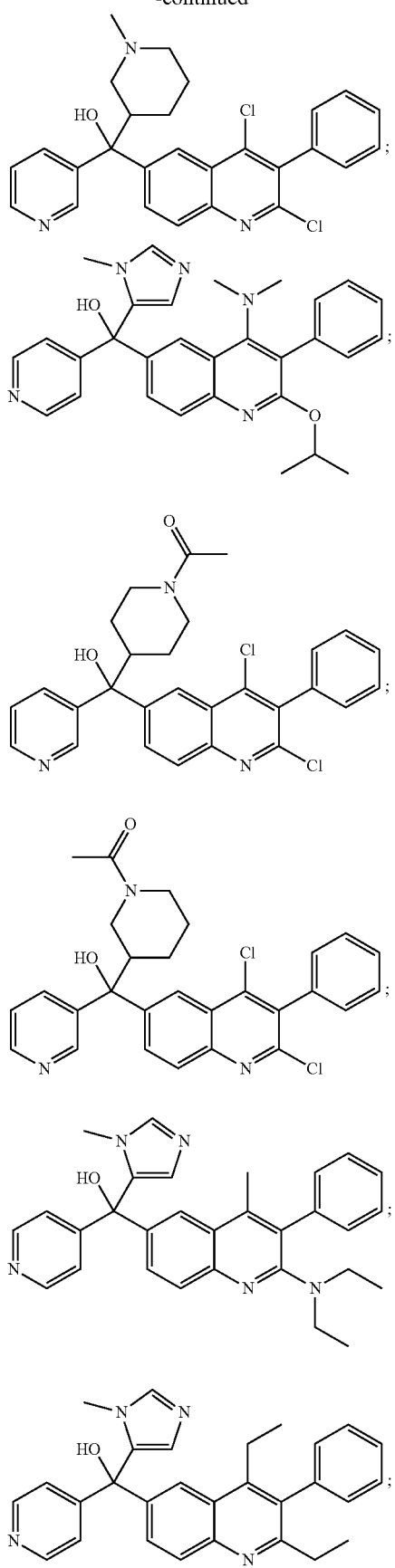
276
-continued
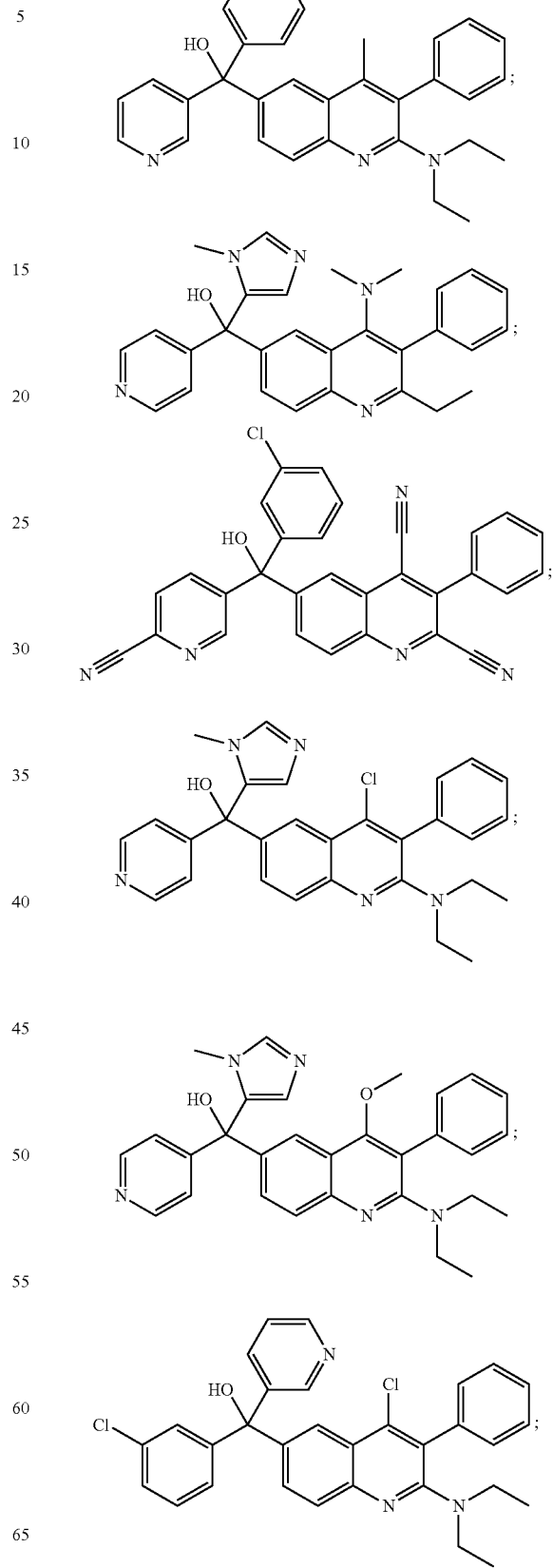

277
-continued
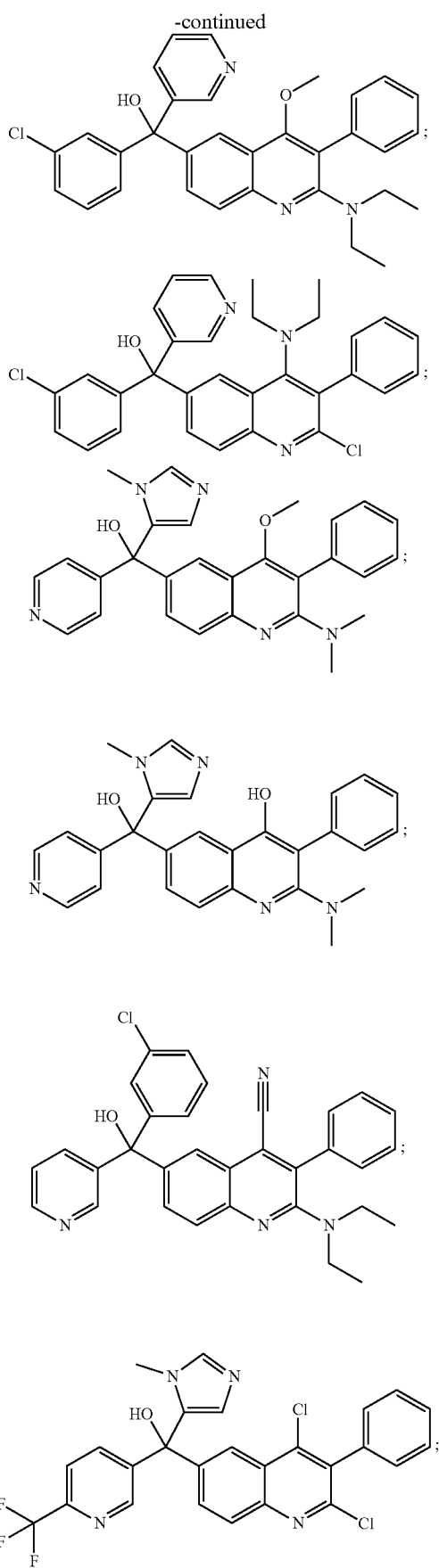
278
-continued
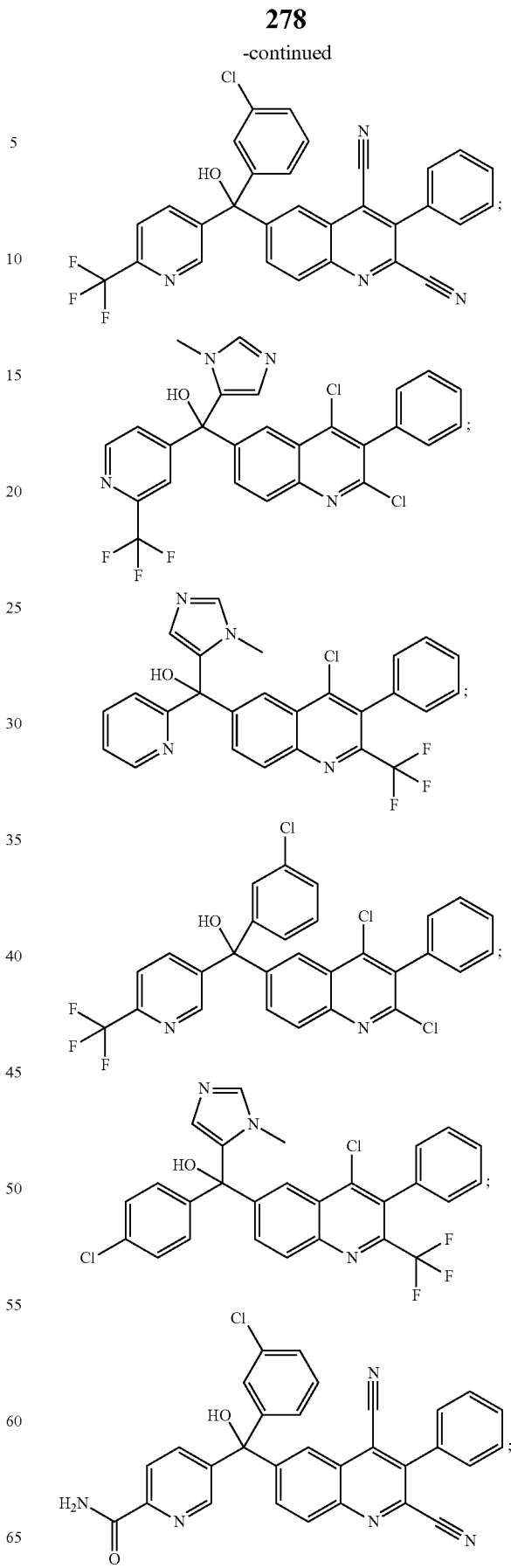

279
-continued
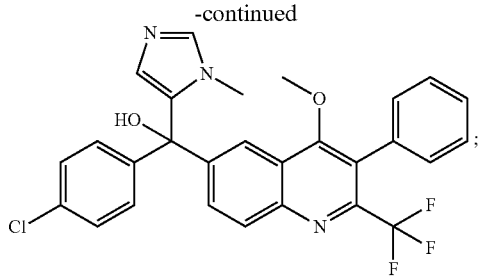
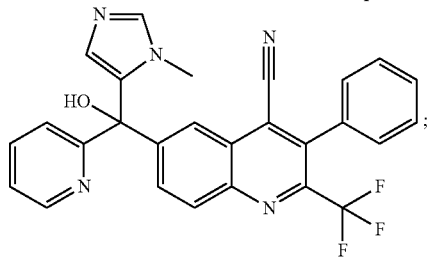
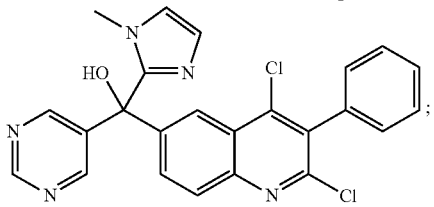
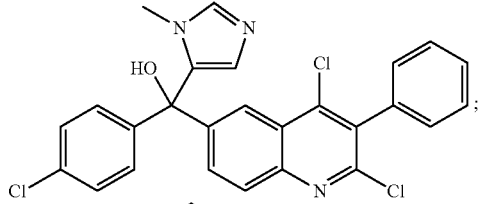
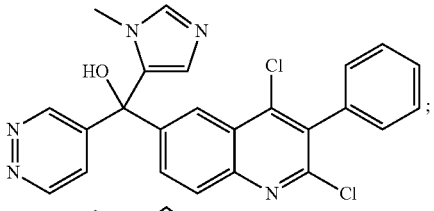
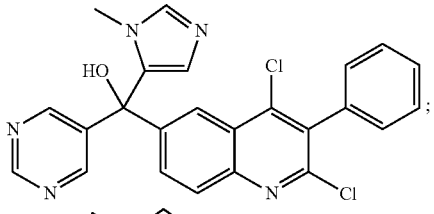
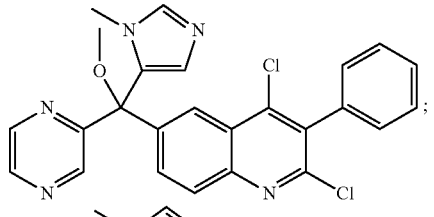
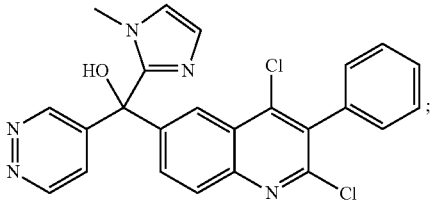
280
-continued
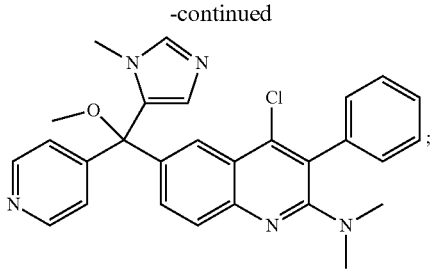
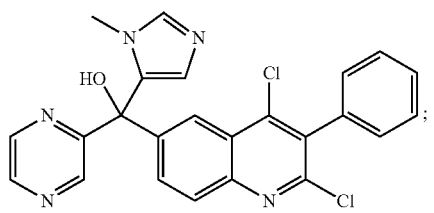
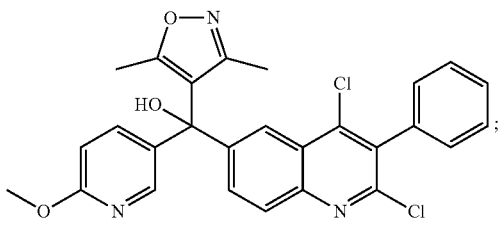
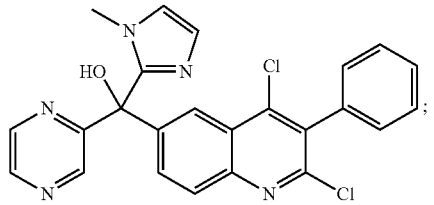
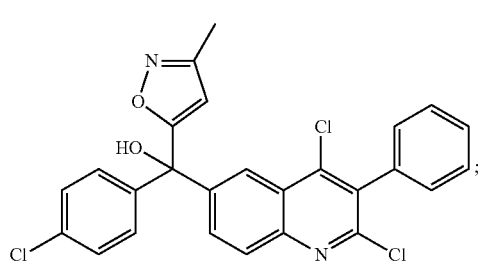
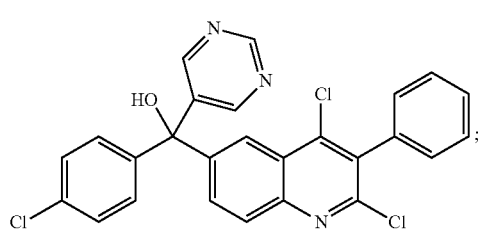
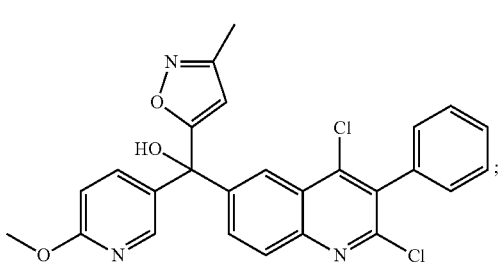

281
-continued
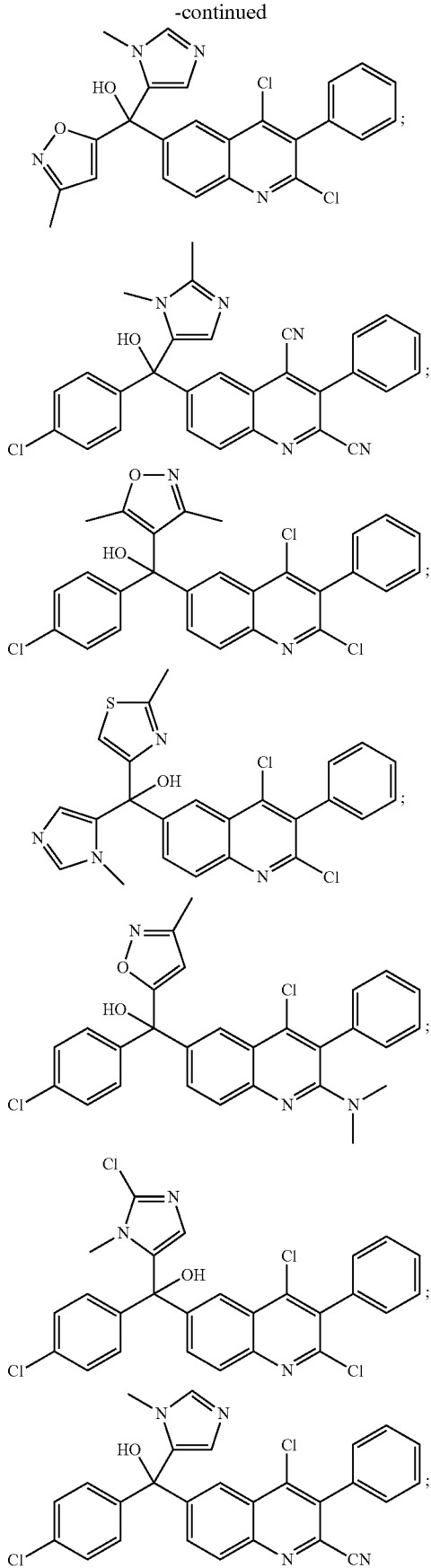
282
-continued
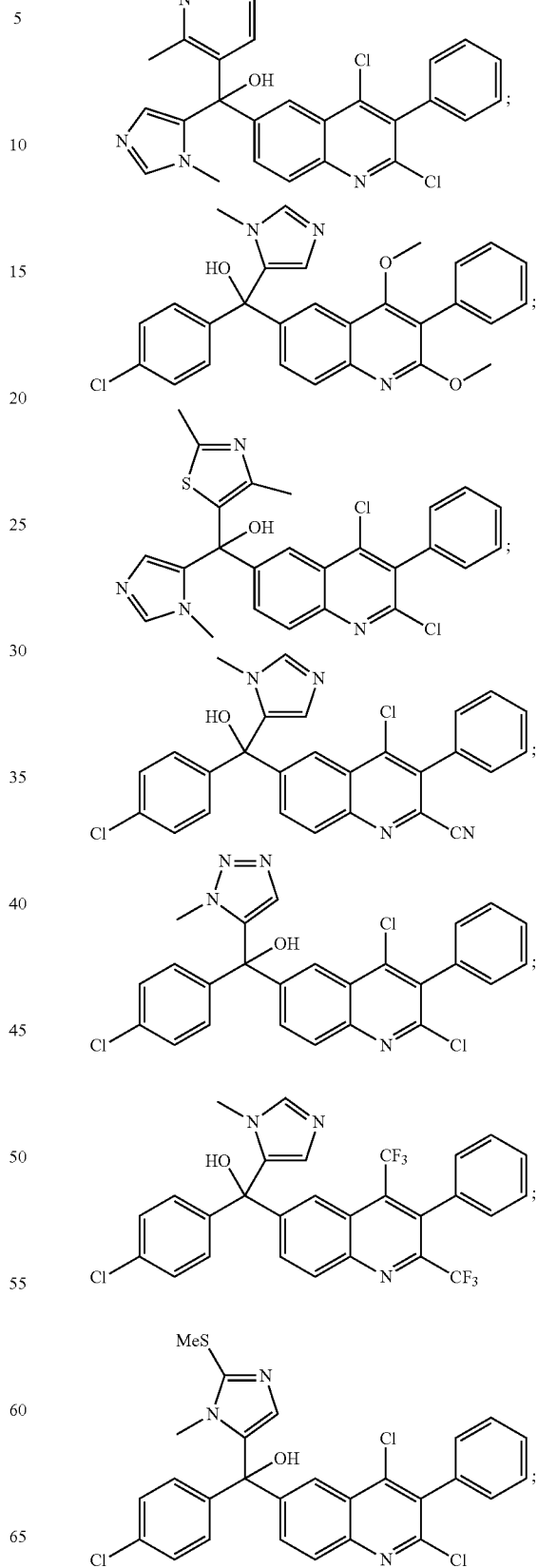

-continued
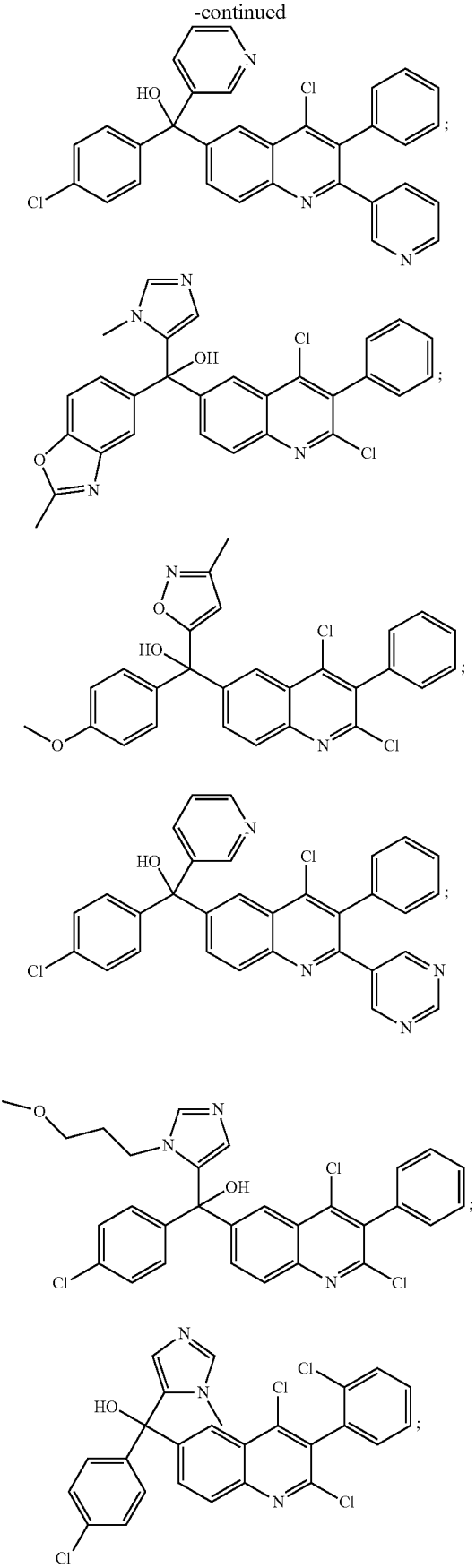
-continued
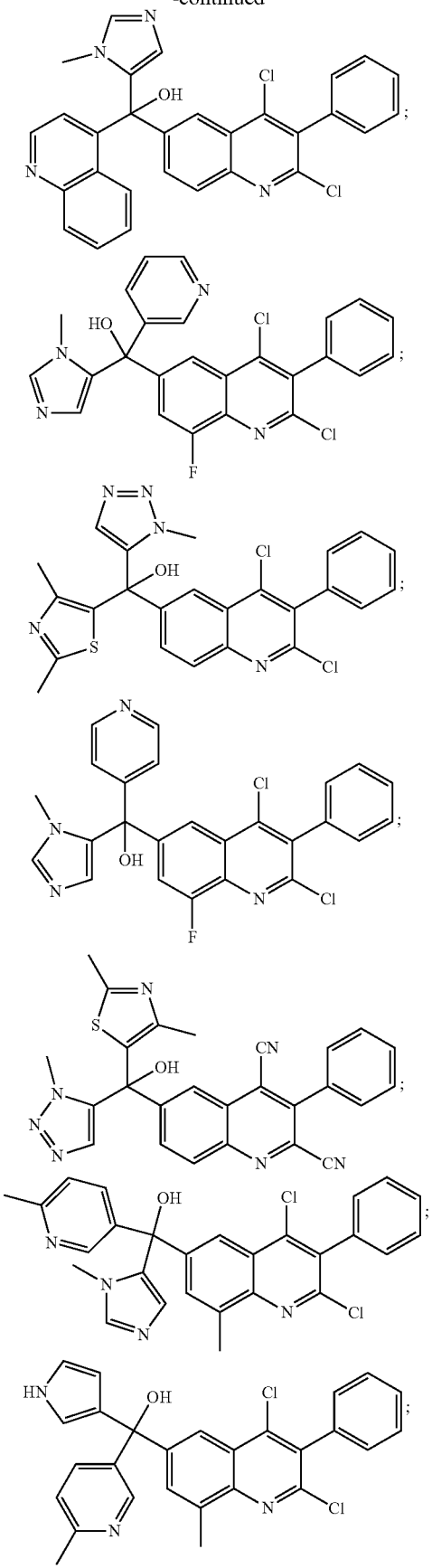

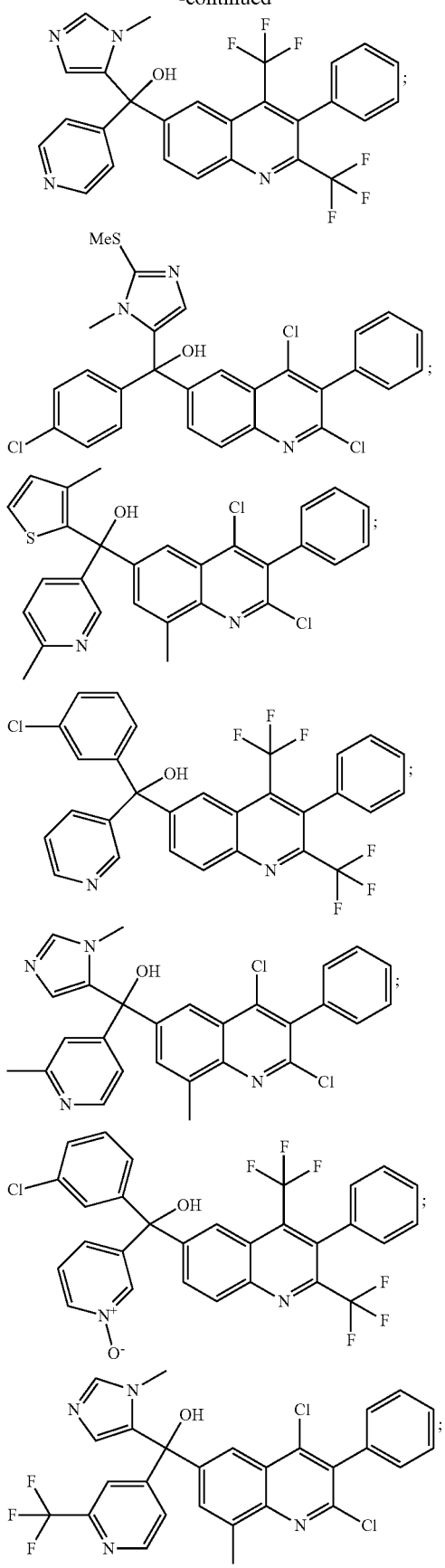
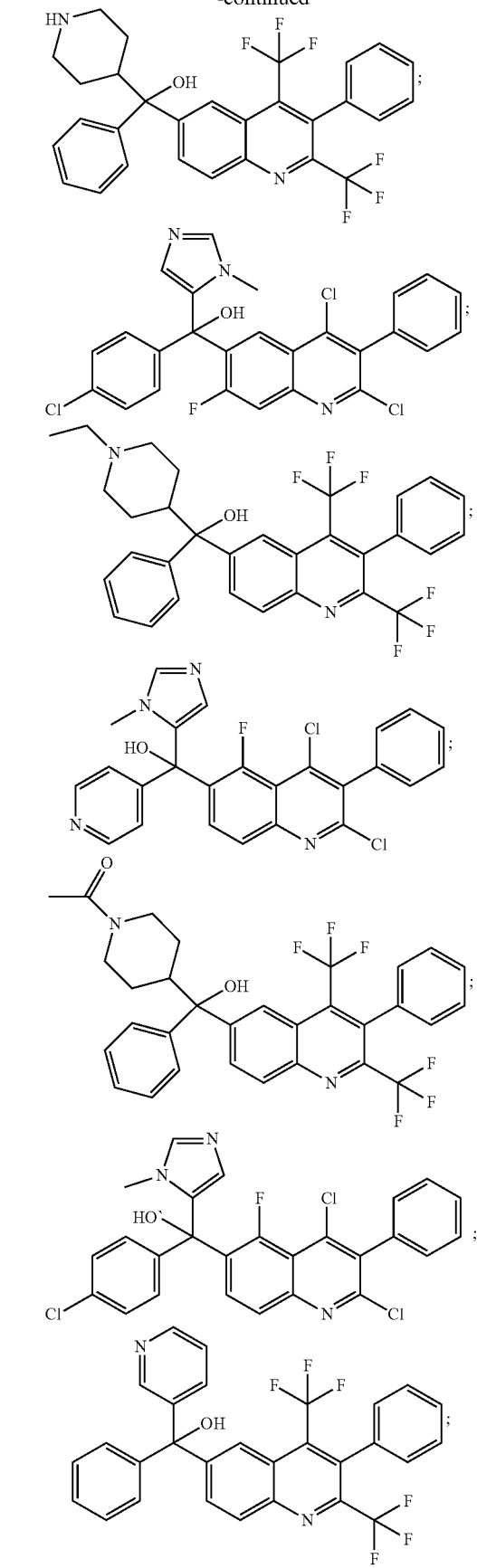

-continued
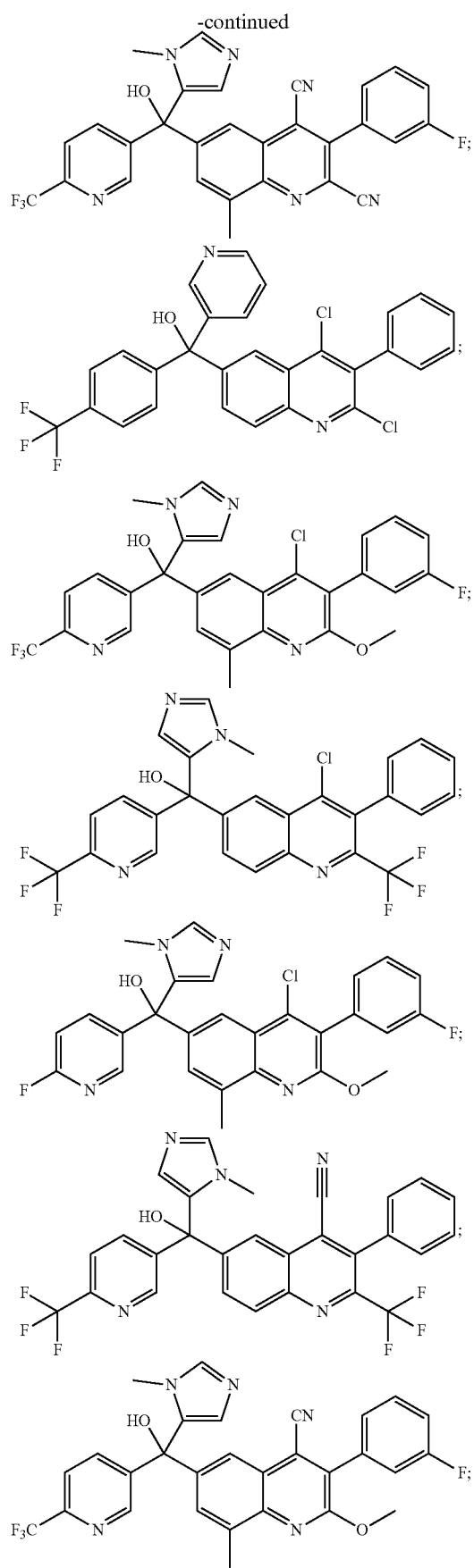
-continued
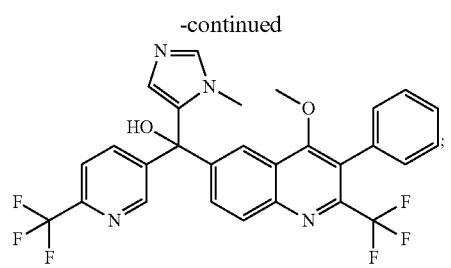
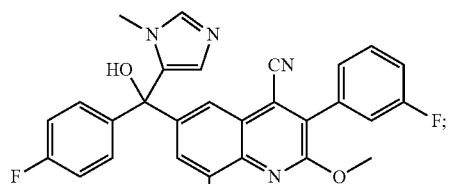
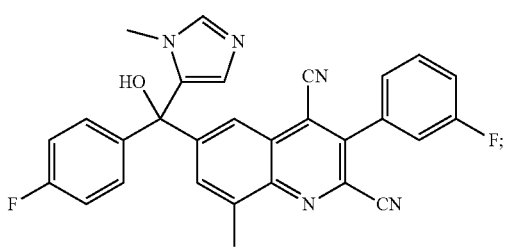
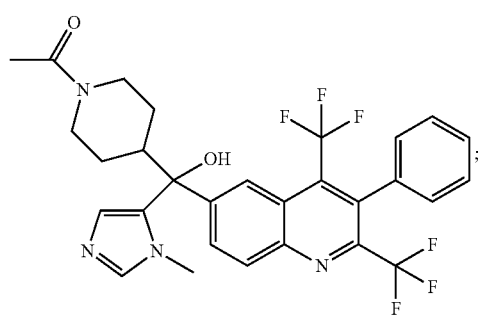
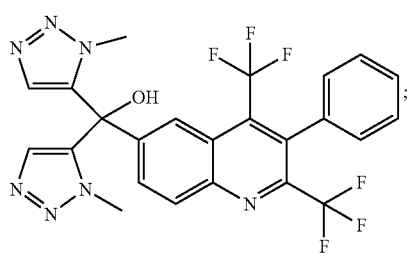
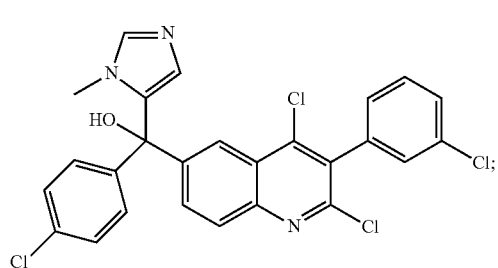

-continued

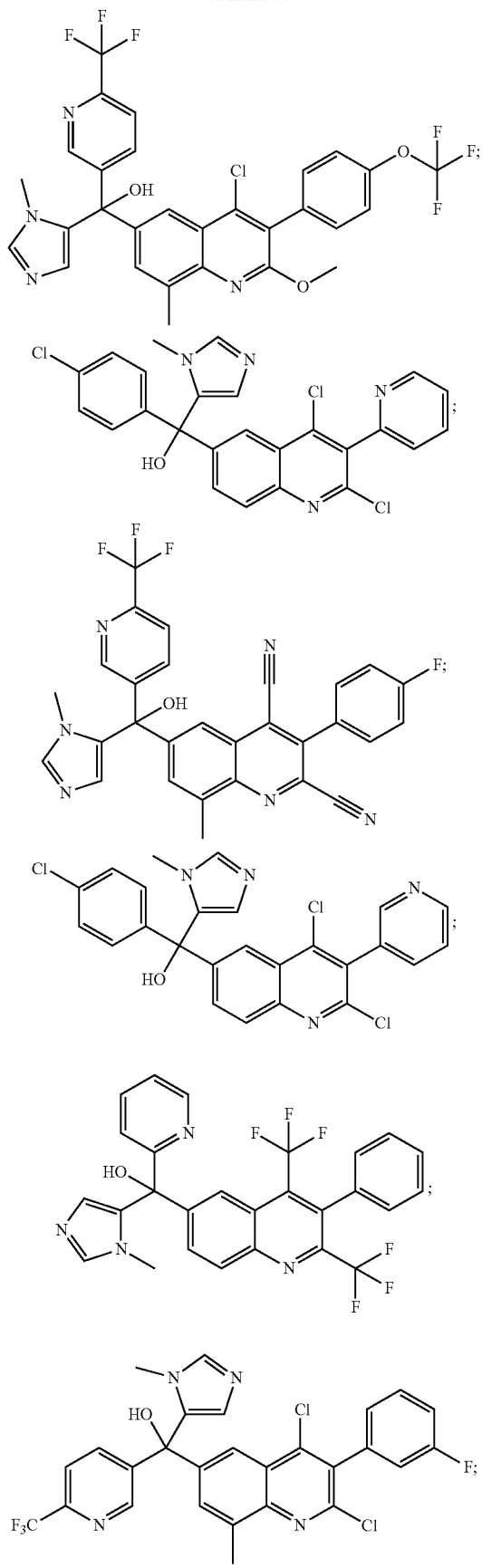

-continued

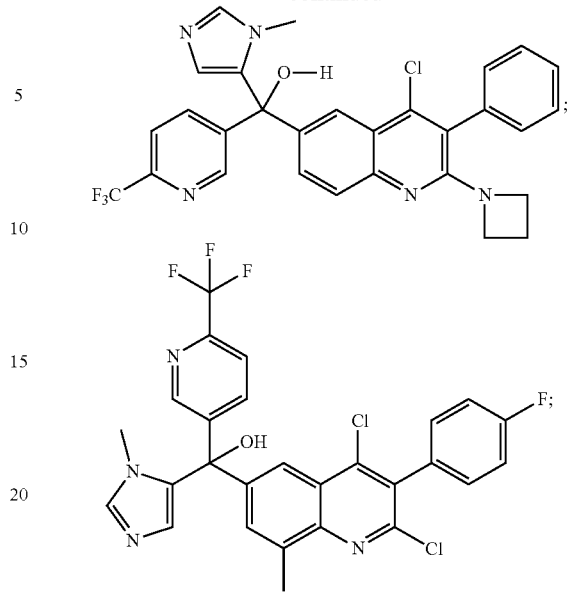

and pharmaceutically acceptable salts thereof.

8. A pharmaceutical composition, comprising a compound of claim 1 and a pharmaceutically acceptable carrier.

9. A pharmaceutical composition made by mixing a compound of claim 1 and a pharmaceutically acceptable carrier.

10. A process for making a pharmaceutical composition comprising mixing a compound of claim 1 and a pharmaceutically acceptable carrier.

11. A method for treating or ameliorating a RORγt mediated inflammatory syndrome, disorder or disease comprising administering to a subject in need thereof an effective amount of a compound of claim 1, wherein the disease is selected from the group consisting of: rheumatoid arthritis, psoriasis, chronic obstructive pulmonary disorder, psoriatic arthritis, ankylosing spondylitis, Crohn's disease, neutrophilic asthma, steroid resistant asthma, multiple sclerosis, systemic lupus erythematosus, and ulcerative colitis.

12. The method of claim 11, wherein the disease is psoriasis.

13. The method of claim 11, wherein the disease is rheumatoid arthritis.

14. The method of claim 11, wherein the disease is ulcerative colitis.

15. The method of claim 11, wherein the disease is Crohn's disease.

16. The method of claim 11, wherein the disease is multiple sclerosis.

17. The method of claim 11, wherein the disease is neutrophilic asthma.

18. The method of claim 11, wherein the disease is steroid resistant asthma.

19. The method of claim 11, wherein the disease is psoriatic arthritis.

20. The method of claim 11, wherein the disease is ankylosing spondylitis.

21. The method of claim 11, wherein the disease is systemic lupus erythematosus.

22. The method of claim 11, wherein the disease is chronic obstructive pulmonary disorder.

23. A method of treating or ameliorating a syndrome, disorder or disease, in a subject in need thereof comprising administering to the subject an effective amount of a compound of claim 1 or composition or medicament thereof in a combination therapy with one or more anti-inflammatory agents, or immunosuppressive agents, wherein said syndrome, disorder or disease is selected from the group consisting of: rheumatoid arthritis, and psoriasis.

24. A method for treating or ameliorating a RORγt mediated inflammatory syndrome, disorder or disease comprising administering to a subject in need thereof an effective amount of a compound of claim 7, wherein the disease is selected from the group consisting of: rheumatoid arthritis and psoriasis.

25. A method of inhibiting production of interleukin-17, comprising administering to a subject in need thereof an effective amount of a compound of claim 1.

* * * * *

```
                         SEQUENCE LISTING

<160> NUMBER OF SEQ ID NOS: 9

<210> SEQ ID NO 1
<211> LENGTH: 3054
<212> TYPE: DNA
<213> ORGANISM: Homo sapiens

<400> SEQUENCE: 1
agagagctag gtgcagagct tcaggctgag gcgctgctga gagggcctcg ccccgcctct     60
gccgccagct gcaccccact cctggaccac cccctgctga gaaggacagg gagccaaggc    120
cggcagagcc aaggctcagt catgagaaca caaattgaag tgatcccttg caaaatctgt    180
ggggacaagt cgtctgggat ccactacggg gttatcacct gtgaggggtg caagggcttc    240
ttccgccgga gccagcgctg taacgcggcc tactcctgca cccgtcagca gaactgcccc    300
atcgaccgca ccagccgaaa ccgatgccag cactgccgcc tgcagaaatg cctggcgctg    360
ggcatgtccc gagatgctgt caagttcggc cgcatgtcca agaagcagag ggacagcctg    420
catgcagaag tgcagaaaca gctgcagcag cggcaacagc agcaacagga accagtggtc    480
aagacccctc cagcagggc caaggagca gataccctca cctacacctt ggggctccca    540 gacggcagc tgccctggg ctcctcgcct gacctgcctg aggcttctgc ctgtcccct    600 ggcctcctga aagcctcagg ctctgggccc tcatattcca caacttggc caaggcaggg    660 ctcaatgggg cctcatgcca ccttgaatac agccctgagc ggggcaaggc tgagggcaga    720
gagagcttct atagcacagg cagccagctg acccctgacc gatgtggact tcgttttgag    780
```

```
gaacacaggc atcctgggct tggggaactg ggacagggcc cagacagcta cggcagcccc    840
agtttccgca gcacaccgga ggcaccctat gcctccctga cagagataga gcacctggtg    900
cagagcgtct gcaagtccta cagggagaca tgccagctgc ggctggagga cctgctgcgg    960
cagcgctcca acatcttctc ccgggaggaa gtgactggct accagaggaa gtccatgtgg   1020
gagatgtggg aacggtgtgc ccaccacctc accgaggcca ttcagtacgt ggtggagttc   1080
gccaagaggc tctcaggctt tatggagctc tgccagaatg accagattgt gcttctcaaa   1140
gcaggagcaa tggaagtggt gctggttagg atgtgccggg cctacaatgc tgacaaccgc   1200
acggtctttt tgaaggcaa atacggtggc atggagctgt tccgagcctt gggctgcagc   1260
gagctcatca gctccatctt tgacttctcc cactccctaa gtgccttgca ctttccgag    1320 gatgagattg ccctctacac agcccttgtt ctcatcaatg cccatcggcc agggctccaa   1380
gagaaaagga agtagaaca gctgcagtac aatctggagc tggcctttca tcatcatctc   1440
tgcaagactc atcgccaaag catcctggca aagctgccac ccaaggggaa gcttcggagc   1500
ctgtgtagcc agcatgtgga aaggctgcag atcttccagc acctccaccc catcgtggtc   1560
caagccgctt tccctccact ctacaaggag ctcttcagca ctgaaaccga gtcacctgtg   1620
gggctgtcca agtgacctgg aagagggact ccttgcctct ccctatggcc tgctggccca   1680
cctccctgga ccccgttcca ccctcaccct tttcctttcc catgaaccct ggagggtggt   1740
ccccaccagc tctttggaag tgagcagatg ctgcggctgg cttctgtca gcaggccggc    1800 ctggcagtgg gacaatcgcc agagggtggg gctggcagaa caccatctcc agcctcagct   1860
ttgacctgtc tcatttccca tattccttca cacccagctt ctggaaggca tggggtggct   1920
gggatttaag gacttctggg ggaccaagac atcctcaaga aaacaggggc atccagggct   1980
ccctggatga atagaatgca attcattcag aagctcagaa gctaagaata agcctttgaa   2040
atacctcatt gcatttccct ttgggcttcg gcttgggag atggatcaag ctcagagact    2100
ggcagtgaga gcccagaagg acctgtataa aatgaatctg gagctttaca ttttctgcct   2160
ctgccttcct cccagctcag caaggaagta tttgggcacc ctacccttta cctggggtct   2220
aaccaaaaat ggatgggatg aggatgagag gctggagata attgttttat gggatttggg   2280
tgtgggacta gggtacaatg aaggccaaga gcatctcaga catagagtta aaactcaaac   2340
ctcttatgtg cactttaaag atagacttta ggggctggca caaatctgat cagagacaca   2400
tatccataca caggtgaaac acatacagac tcaacagcaa tcatgcagtt ccagagacac   2460
atgaacctga cacaatctct cttatccttg aggccacagc ttggaggagc ctagaggcct   2520
caggggaaag tcccaatcct gagggaccct cccaaacatt tccatggtgc tccagtccac   2580
tgatcttggg tctggggtga tccaaatacc accccagctc cagctgtctt ctaccactag   2640
aagacccaag agaagcagaa gtcgctcgca ctggtcagtc ggaaggcaag atcagatcct   2700
ggaggacttt cctggcctgc ccgccagccc tgctcttgtt gtggagaagg aagcagatgt   2760
gatcacatca ccccgtcatt gggcaccgct gactccagca tggaggacac cagggagcag   2820
ggcctgggcc tgtttcccca gctgtgatct tgcccagaac ctctcttggc ttcataaaca   2880
gctgtgaacc ctcccctgag ggattaacag caatgatggg cagtcgtgga gttgggggg    2940 ttggggggtgg gattgtgtcc tctaagggga cgggttcatc tgagtaaaca taaacccccaa  3000 cttgtgccat tctttataaa atgatttta aggcaaaaaa aaaaaaaaaa aaaa           3054
```

<210> SEQ ID NO 2
<211> LENGTH: 786
<212> TYPE: DNA
<213> ORGANISM: Homo sapiens

<400> SEQUENCE: 2

```
agcacaccgg aggcacccta tgcctccctg acagagatag agcacctggt gcagagcgtc      60
tgcaagtcct acagggagac atgccagctg cggctggagg acctgctgcg gcagcgctcc     120
aacatcttct cccggggagga agtgactggc taccagagga agtccatgtg ggagatgtgg    180
gaacggtgtg cccaccacct caccgaggcc attcagtacg tggtggagtt cgccaagagg    240
ctctcaggct ttatggagct ctgccagaat gaccagattg tgcttctcaa agcaggagca    300
atggaagtgg tgctggttag gatgtgccgg gcctacaatg ctgacaaccg cacggtcttt    360
tttgaaggca aatacggtgg catggagctg ttccgagcct gggctgcag cgagctcatc     420
agctccatct ttgacttctc ccactcccta agtgccttgc actttccga ggatgagatt     480
gccctctaca cagcccttgt tctcatcaat gcccatcggc agggctcca agagaaaagg     540
aaagtagaac agctgcagta caatctggag ctggcctttc atcatcatct ctgcaagact    600
catcgccaaa gcatcctggc aaagctgcca cccaagggga agcttcggag cctgtgtagc    660
cagcatgtgg aaaggctgca gatcttccag cacctccacc ccatcgtggt ccaagccgct    720
ttccctccac tctacaagga gctcttcagc actgaaaccg agtcacctgt ggggctgtcc    780
aagtga                                                                786
```

<210> SEQ ID NO 3
<211> LENGTH: 7
<212> TYPE: PRT
<213> ORGANISM: Artificial Sequence
<220> FEATURE:
<223> OTHER INFORMATION: TurboTEV protease cleavage site

<400> SEQUENCE: 3

```
Glu Asn Leu Tyr Phe Gln Gly
1               5
```

<210> SEQ ID NO 4
<211> LENGTH: 283
<212> TYPE: PRT
<213> ORGANISM: Artificial Sequence
<220> FEATURE:
<223> OTHER INFORMATION: Construct used in the Thermofluor assay

<400> SEQUENCE: 4

```
Met Ala His His His His His His Ala Gly Gly Ala Glu Asn Leu Tyr
1               5                   10                  15

Phe Gln Gly Ala Met Asp Ser Thr Pro Glu Ala Pro Tyr Ala Ser Leu
            20                  25                  30

Thr Glu Ile Glu His Leu Val Gln Ser Val Cys Lys Ser Tyr Arg Glu
        35                  40                  45

Thr Cys Gln Leu Arg Leu Glu Asp Leu Leu Arg Gln Arg Ser Asn Ile
    50                  55                  60

Phe Ser Arg Glu Glu Val Thr Gly Tyr Gln Arg Lys Ser Met Trp Glu
65                  70                  75                  80

Met Trp Glu Arg Cys Ala His His Leu Thr Glu Ala Ile Gln Tyr Val
                85                  90                  95
```

-continued

```
Val Glu Phe Ala Lys Arg Leu Ser Gly Phe Met Glu Leu Cys Gln Asn
            100                 105                 110
Asp Gln Ile Val Leu Leu Lys Ala Gly Ala Met Glu Val Leu Val
        115                 120                 125
Arg Met Cys Arg Ala Tyr Asn Ala Asp Asn Arg Thr Val Phe Phe Glu
130                 135                 140
Gly Lys Tyr Gly Gly Met Glu Leu Phe Arg Ala Leu Gly Cys Ser Glu
145                 150                 155                 160
Leu Ile Ser Ser Ile Phe Asp Phe Ser His Ser Leu Ser Ala Leu His
                165                 170                 175
Phe Ser Glu Asp Glu Ile Ala Leu Tyr Thr Ala Leu Val Leu Ile Asn
            180                 185                 190
Ala His Arg Pro Gly Leu Gln Glu Lys Arg Lys Val Glu Gln Leu Gln
        195                 200                 205
Tyr Asn Leu Glu Leu Ala Phe His His His Leu Cys Lys Thr His Arg
210                 215                 220
Gln Ser Ile Leu Ala Lys Leu Pro Pro Lys Gly Lys Leu Arg Ser Leu
225                 230                 235                 240
Cys Ser Gln His Val Glu Arg Leu Gln Ile Phe Gln His Leu His Pro
                245                 250                 255
Ile Val Val Gln Ala Ala Phe Pro Pro Leu Tyr Lys Glu Leu Phe Ser
            260                 265                 270
Thr Glu Thr Glu Ser Pro Val Gly Leu Ser Lys
        275                 280

<210> SEQ ID NO 5
<211> LENGTH: 6
<212> TYPE: PRT
<213> ORGANISM: Homo sapiens

<400> SEQUENCE: 5

Leu Tyr Lys Glu Leu Phe
1               5

<210> SEQ ID NO 6
<211> LENGTH: 6
<212> TYPE: PRT
<213> ORGANISM: Artificial Sequence
<220> FEATURE:
<223> OTHER INFORMATION: mutated AF2 domain

<400> SEQUENCE: 6

Leu Phe Lys Glu Leu Phe
1               5

<210> SEQ ID NO 7
<211> LENGTH: 786
<212> TYPE: DNA
<213> ORGANISM: Artificial Sequence
<220> FEATURE:
<223> OTHER INFORMATION: LBD with mutated AF2 domain

<400> SEQUENCE: 7
agcacaccgg aggcacccta tgcctccctg acagagatag agcacctggt gcagagcgtc      60
tgcaagtcct acagggagac atgccagctg cggctggagg acctgctgcg gcagcgctcc     120
aacatcttct cccggagga agtgactggc taccagagga agtccatgtg ggagatgtgg     180
gaacggtgtg cccaccacct caccgaggcc attcagtacg tggtggagtt cgccaagagg     240
```

-continued

```
ctctcaggct ttatggagct ctgccagaat gaccagattg tgcttctcaa agcaggagca    300
atggaagtgg tgctggttag gatgtgccgg gcctacaatg ctgacaaccg cacggtcttt    360
tttgaaggca aatacggtgg catggagctg ttccgagcct gggctgcag cgagctcatc     420 agctccatct ttgacttctc ccactcccta agtgccttgc acttttccga ggatgagatt    480
gccctctaca cagcccttgt tctcatcaat gcccatcggc cagggctcca agagaaaagg    540
aaagtagaac agctgcagta caatctggag ctggcctttc atcatcatct ctgcaagact    600
catcgccaaa gcatcctggc aaagctgcca cccaagggga agcttcggag cctgtgtagc    660
cagcatgtgg aaaggctgca gatcttccag cacctccacc ccatcgtggt ccaagccgct    720
ttccctccac tcttcaagga gctcttcagc actgaaaccg agtcacctgt ggggctgtcc    780
aagtga                                                              786
```

```
<210> SEQ ID NO 8
<211> LENGTH: 261
<212> TYPE: PRT
<213> ORGANISM: Homo sapiens

<400> SEQUENCE: 8
```

Ser Thr Pro Glu Ala Pro Tyr Ala Ser Leu Thr Glu Ile Glu His Leu
1               5                   10                  15

Val Gln Ser Val Cys Lys Ser Tyr Arg Glu Thr Cys Gln Leu Arg Leu
            20                  25                  30

Glu Asp Leu Leu Arg Gln Arg Ser Asn Ile Phe Ser Arg Glu Glu Val
        35                  40                  45

Thr Gly Tyr Gln Arg Lys Ser Met Trp Glu Met Trp Glu Arg Cys Ala
    50                  55                  60

His His Leu Thr Glu Ala Ile Gln Tyr Val Val Glu Phe Ala Lys Arg
65                  70                  75                  80

Leu Ser Gly Phe Met Glu Leu Cys Gln Asn Asp Gln Ile Val Leu Leu
                85                  90                  95

Lys Ala Gly Ala Met Glu Val Val Leu Val Arg Met Cys Arg Ala Tyr
            100                 105                 110

Asn Ala Asp Asn Arg Thr Val Phe Phe Glu Gly Lys Tyr Gly Gly Met
        115                 120                 125

Glu Leu Phe Arg Ala Leu Gly Cys Ser Glu Leu Ile Ser Ser Ile Phe
    130                 135                 140

Asp Phe Ser His Ser Leu Ser Ala Leu His Phe Ser Glu Asp Glu Ile
145                 150                 155                 160

Ala Leu Tyr Thr Ala Leu Val Leu Ile Asn Ala His Arg Pro Gly Leu
                165                 170                 175

Gln Glu Lys Arg Lys Val Glu Gln Leu Gln Tyr Asn Leu Glu Leu Ala
            180                 185                 190

Phe His His His Leu Cys Lys Thr His Arg Gln Ser Ile Leu Ala Lys
        195                 200                 205

Leu Pro Pro Lys Gly Lys Leu Arg Ser Leu Cys Ser Gln His Val Glu
    210                 215                 220

Arg Leu Gln Ile Phe Gln His Leu His Pro Ile Val Val Gln Ala Ala
225                 230                 235                 240

Phe Pro Pro Leu Tyr Lys Glu Leu Phe Ser Thr Glu Thr Glu Ser Pro
                245                 250                 255

Val Gly Leu Ser Lys
            260

```
<210> SEQ ID NO 9
<211> LENGTH: 261
<212> TYPE: PRT
<213> ORGANISM: Artificial Sequence
<220> FEATURE:
<223> OTHER INFORMATION: LBD with mutated AF2 domain

<400> SEQUENCE: 9

Ser Thr Pro Glu Ala Pro Tyr Ala Ser Leu Thr Glu Ile Glu His Leu
1               5                   10                  15

Val Gln Ser Val Cys Lys Ser Tyr Arg Glu Thr Cys Gln Leu Arg Leu
            20                  25                  30

Glu Asp Leu Leu Arg Gln Arg Ser Asn Ile Phe Ser Arg Glu Glu Val
        35                  40                  45

Thr Gly Tyr Gln Arg Lys Ser Met Trp Glu Met Trp Glu Arg Cys Ala
    50                  55                  60

His His Leu Thr Glu Ala Ile Gln Tyr Val Val Glu Phe Ala Lys Arg
65                  70                  75                  80

Leu Ser Gly Phe Met Glu Leu Cys Gln Asn Asp Gln Ile Val Leu Leu
                85                  90                  95

Lys Ala Gly Ala Met Glu Val Val Leu Val Arg Met Cys Arg Ala Tyr
            100                 105                 110

Asn Ala Asp Asn Arg Thr Val Phe Phe Glu Gly Lys Tyr Gly Gly Met
        115                 120                 125

Glu Leu Phe Arg Ala Leu Gly Cys Ser Glu Leu Ile Ser Ser Ile Phe
    130                 135                 140

Asp Phe Ser His Ser Leu Ser Ala Leu His Phe Ser Glu Asp Glu Ile
145                 150                 155                 160

Ala Leu Tyr Thr Ala Leu Val Leu Ile Asn Ala His Arg Pro Gly Leu
                165                 170                 175

Gln Glu Lys Arg Lys Val Glu Gln Leu Gln Tyr Asn Leu Glu Leu Ala
            180                 185                 190

Phe His His His Leu Cys Lys Thr His Arg Gln Ser Ile Leu Ala Lys
        195                 200                 205

Leu Pro Pro Lys Gly Lys Leu Arg Ser Leu Cys Ser Gln His Val Glu
    210                 215                 220

Arg Leu Gln Ile Phe Gln His Leu His Pro Ile Val Val Gln Ala Ala
225                 230                 235                 240

Phe Pro Pro Leu Phe Lys Glu Leu Phe Ser Thr Glu Thr Glu Ser Pro
                245                 250                 255

Val Gly Leu Ser Lys
            260
```